US011753397B2

(12) United States Patent
Henderson et al.

(10) Patent No.: US 11,753,397 B2
(45) Date of Patent: Sep. 12, 2023

(54) CEREBLON BINDERS FOR THE DEGRADATION OF IKAROS

(71) Applicant: C4 Therapeutics, Inc., Watertown, MA (US)

(72) Inventors: James A. Henderson, Weston, MA (US); Gesine Kerstin Veits, Somerville, MA (US); Minsheng He, Watertown, MA (US); Christopher G. Nasveschuk, Stoneham, MA (US); Andrew J. Phillips, Arlington, MA (US); Andrew Charles Good, Watertown, MA (US)

(73) Assignee: C4 Therapeutics, Inc., Watertown, MA (US)

( * ) Notice: Subject to any disclaimer, the term of this patent is extended or adjusted under 35 U.S.C. 154(b) by 0 days.

(21) Appl. No.: 17/031,550

(22) Filed: Sep. 24, 2020

(65) Prior Publication Data

US 2021/0009559 A1   Jan. 14, 2021

Related U.S. Application Data

(63) Continuation of application No. PCT/US2019/024094, filed on Mar. 26, 2019.
(Continued)

(51) Int. Cl.
*C07D 401/14* (2006.01)

(52) U.S. Cl.
CPC .................. *C07D 401/14* (2013.01)

(58) Field of Classification Search
CPC ..................................... C07D 401/14
See application file for complete search history.

(56) References Cited

U.S. PATENT DOCUMENTS

| 5,635,517 A | 6/1997 | Muller et al. |
| 6,045,501 A | 4/2000 | Elsayed et al. |

(Continued)

FOREIGN PATENT DOCUMENTS

| BR | PI1100318 A2 | 5/2013 |
| CN | 103421061 A | 12/2013 |

(Continued)

OTHER PUBLICATIONS

US, 2019/0076539, A1, U.S. Appl. No. 16/186,333, Phillips et al., Mar. 14, 2019.

(Continued)

*Primary Examiner* — Brian E McDowell
(74) *Attorney, Agent, or Firm* — Knowles Intellectual Property Strategies, LLC

(57) ABSTRACT

The invention provides cereblon binders of Formulas:

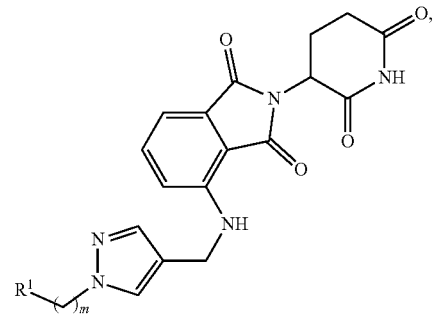

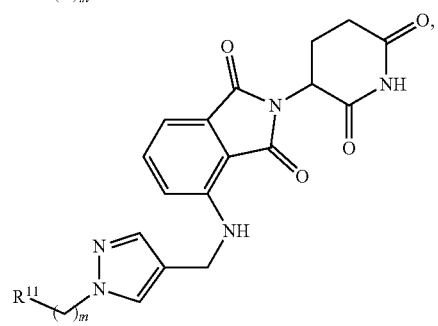

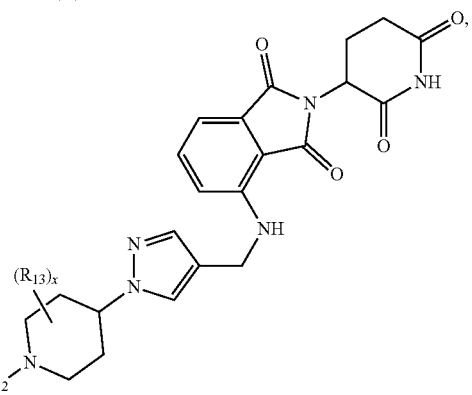

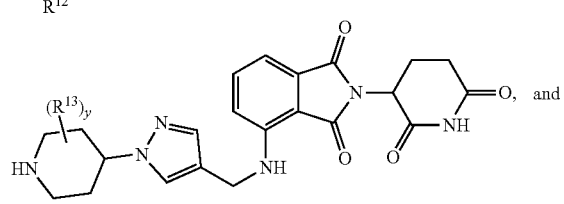

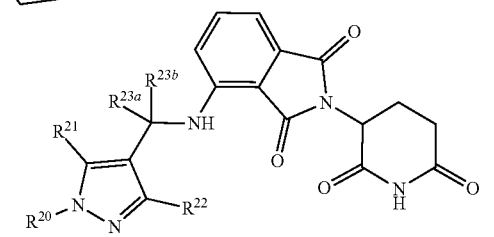

or pharmaceutically acceptable salts thereof, for the degradation of Ikaros or Aiolos by the ubiquitin proteasome pathway along with their use in therapeutic applications to treat medical disorders including, but not limited to cancer.

19 Claims, No Drawings

Related U.S. Application Data

(60) Provisional application No. 62/648,238, filed on Mar. 26, 2018.

(56) References Cited

U.S. PATENT DOCUMENTS

| | | |
|---|---|---|
| 6,306,663 B1 | 10/2001 | Kenten et al. |
| 6,315,720 B1 | 11/2001 | Williams et al. |
| 6,395,754 B1 | 5/2002 | Muller et al. |
| 6,561,976 B2 | 5/2003 | Elsayed et al. |
| 6,561,977 B2 | 5/2003 | Williams et al. |
| 6,755,784 B2 | 6/2004 | Williams et al. |
| 6,869,399 B2 | 3/2005 | Williams et al. |
| 6,908,432 B2 | 6/2005 | Elsayed et al. |
| 7,041,298 B2 | 5/2006 | Deshaies et al. |
| 7,141,018 B2 | 11/2006 | Williams et al. |
| 7,208,157 B2 | 4/2007 | Deshaies et al. |
| 7,230,012 B2 | 6/2007 | D-Angio et al. |
| 7,820,697 B2 | 10/2010 | Man Hon-Wah et al. |
| 7,874,984 B2 | 1/2011 | Elsayed et al. |
| 7,959,566 B2 | 6/2011 | Williams et al. |
| 8,204,763 B2 | 6/2012 | Elsayed et al. |
| 8,315,886 B2 | 11/2012 | Williams et al. |
| 8,589,188 B2 | 11/2013 | Elsayed et al. |
| 8,626,531 B2 | 1/2014 | Williams et al. |
| 8,673,939 B2 | 3/2014 | Zeldis |
| 8,735,428 B2 | 5/2014 | Zeldis |
| 8,741,929 B2 | 6/2014 | Zeldis |
| 8,828,427 B2 | 9/2014 | Tutino et al. |
| 9,056,120 B2 | 6/2015 | Zeldis |
| 9,101,621 B2 | 8/2015 | Zeldis |
| 9,101,622 B2 | 8/2015 | Zeldis |
| 9,125,915 B2 | 9/2015 | Miyoshi et al. |
| 9,249,161 B2 | 2/2016 | Albrecht et al. |
| 10,351,568 B2 | 7/2019 | Finley et al. |
| 11,185,543 B2 | 11/2021 | Alexander et al. |
| 2001/0006973 A1 | 7/2001 | Man et al. |
| 2002/0045643 A1 | 4/2002 | Muller et al. |
| 2004/0220144 A1 | 11/2004 | Zeldis |
| 2006/0069067 A1 | 3/2006 | Bhatnagar et al. |
| 2013/0190340 A1 | 7/2013 | Hedstrom et al. |
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0274738 A1 | 10/2015 | Gray et al. |
| 2015/0291562 A1 | 10/2015 | Crew et al. |
| 2016/0016966 A1 | 1/2016 | Amans et al. |
| 2016/0022642 A1 | 1/2016 | Crews et al. |
| 2016/0045607 A1 | 2/2016 | Crew et al. |
| 2016/0046661 A1 | 2/2016 | Gray et al. |
| 2016/0058872 A1 | 3/2016 | Crew et al. |
| 2016/0176916 A1 | 6/2016 | Bradner et al. |
| 2016/0214972 A1 | 7/2016 | Jin et al. |
| 2016/0272639 A1 | 9/2016 | Crew et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2018/0015087 A1 | 1/2018 | Liu et al. |
| 2018/0085465 A1 | 3/2018 | Bradner et al. |

FOREIGN PATENT DOCUMENTS

| | | |
|---|---|---|
| WO | WO 1998/011111 A1 | 3/1998 |
| WO | WO 2002/059106 A1 | 8/2002 |
| WO | WO 2006/102557 A2 | 9/2006 |
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |
| WO | WO 2008/12203 8 A1 | 10/2008 |
| WO | WO 2009/042177 A1 | 4/2009 |
| WO | WO 2009/139880 A1 | 11/2009 |
| WO | WO 2009/145899 A1 | 12/2009 |
| WO | WO 2010/053732 A1 | 5/2010 |
| WO | WO 2010/107485 A1 | 9/2010 |
| WO | WO 2011/097218 A1 | 8/2011 |
| WO | WO 2011/143669 A2 | 11/2011 |
| WO | WO 2012/079022 A1 | 6/2012 |
| WO | WO 2012/178208 A2 | 12/2012 |
| WO | WO 2013/059215 A1 | 4/2013 |
| WO | WO 2013/106646 A2 | 7/2013 |
| WO | WO 2013/170147 A1 | 11/2013 |
| WO | WO 2014/145887 A1 | 9/2014 |
| WO | WO 2015/085172 A2 | 6/2015 |
| WO | WO 2015/160845 A1 | 10/2015 |
| WO | WO 2016/065139 A1 | 4/2016 |
| WO | WO 2016/105518 A1 | 6/2016 |
| WO | WO 2016/118666 A1 | 7/2016 |
| WO | WO 2016/146985 A1 | 9/2016 |
| WO | WO 2016/149668 A1 | 9/2016 |
| WO | WO 2016/169989 A1 | 10/2016 |
| WO | WO 2016/191178 A1 | 12/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/030814 A1 | 2/2017 |
| WO | WO 2017/079267 A1 | 5/2017 |
| WO | WO 2017/161119 A1 | 9/2017 |
| WO | WO 2017/176708 A1 | 10/2017 |
| WO | WO 2017/176957 A1 | 10/2017 |
| WO | WO 2017/176958 A1 | 10/2017 |
| WO | WO 2017/180417 A1 | 10/2017 |
| WO | WO 2017/197036 A1 | 11/2017 |
| WO | WO 2017/197046 A1 | 11/2017 |
| WO | WO 2017/197051 A1 | 11/2017 |
| WO | WO 2017/197055 A1 | 11/2017 |
| WO | WO 2017/197056 A1 | 11/2017 |
| WO | WO 2017/197240 A1 | 11/2017 |
| WO | WO 2017/201069 A1 | 11/2017 |
| WO | WO 2017/201449 A1 | 11/2017 |
| WO | WO 2018/023029 A1 | 2/2018 |
| WO | WO 2018/051107 A1 | 3/2018 |
| WO | WO 2018/052945 A1 | 3/2018 |
| WO | WO 2018/052949 A1 | 3/2018 |
| WO | WO 2018/053354 A1 | 3/2018 |
| WO | WO 2018/071606 A1 | 4/2018 |
| WO | WO 2018/085247 A1 | 5/2018 |
| WO | WO 2018/102067 A2 | 6/2018 |
| WO | WO 2018/102725 A1 | 6/2018 |
| WO | WO 2018/118598 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/140809 A1 | 8/2018 |
| WO | WO 2018/144649 A1 | 8/2018 |
| WO | WO 2018/169777 A1 | 9/2018 |
| WO | WO 2018/183411 A1 | 10/2018 |
| WO | WO 2018/189554 A1 | 10/2018 |
| WO | WO 2018/191199 A1 | 10/2018 |
| WO | WO 2019/060693 A1 | 3/2019 |
| WO | WO 2019/060742 A1 | 3/2019 |
| WO | WO 2019/140387 A1 | 7/2019 |
| WO | WO 2019/152440 A1 | 8/2019 |
| WO | WO 2019/165229 A1 | 8/2019 |
| WO | WO 2019/199816 A1 | 10/2019 |
| WO | WO 2019/213005 A1 | 11/2019 |
| WO | WO 2020/006262 A1 | 1/2020 |
| WO | WO 2020/006264 A1 | 1/2020 |
| WO | WO 2020/006265 A1 | 1/2020 |
| WO | WO 2020/010227 A1 | 1/2020 |
| WO | WO 2020/023851 A1 | 1/2020 |
| WO | WO 2020/041331 A1 | 2/2020 |
| WO | WO 2020/051564 A1 | 3/2020 |
| WO | WO 2020/081450 A1 | 4/2020 |

OTHER PUBLICATIONS

US, 2020/0308171, A1, U.S. Appl. No. 16/903,237, Jaeschke et al., Oct. 1, 2020.

(56) References Cited

OTHER PUBLICATIONS

US, 2020/0361930, A1, U.S. Appl. No. 16/984,987, Duplessis et al., Nov. 19, 2020.
US, 2021/0009559, A1, U.S. Appl. No. 17/031,550, Henderson et al, Jan. 14, 2021.
US, 2021/0070763, A1, U.S. Appl. No. 17/103,621, Naveschuk et al, Mar. 11, 2021.
US, 2021/0106688, A1, U.S. Appl. No. 16/882,236, Phillips et al., Apr. 15, 2021.
US, 2021/0198256, A1, U.S. Appl. No. 17/192,634, Nasveschuk et al, Jul. 1, 2021.
US, U.S. Appl. No. 17/351,935, filed Jun. 18, 2021, Phillips et al.
US, U.S. Appl. No. 17/465,583, filed Sep. 2, 2021, Nasveschuk et al.
US, U.S. Appl. No. 17/498,617, filed Oct. 11, 2021, Henderson et al.
Matyskiela, Mary E. et al.; "A Cereblon Modulator (CC-220) with Improved Degradation of Ikaros and Aiolos," Journal of Medicinal Chemistry, DOI: 10.1021/acs.jmedchem.6b01921, J. Med. Chem. 2018, 61, 535-542, ACS Publications, 2017.
Rok, Frlan et al.; "Evaluation of US 2016/0115161A1: Isoindoline compounds and methods of their use," Expert Opinion on Therapeutic Patents, 27:6, 637-641, 2017.
Agafonov Roman et al., EMBO Poster Presentation "Quantitative and high throughput method for measuring complex formation between target proteins and E3 ubiquitin ligase", Sep. 16, 2017.
Bartlett, et al. "The evolution of thalidomide and its IMiD derivatives as anticancer agents." Nat Rev Cancer 2004, 4(4):312-322.
Berndsen et al. "New insights into ubiquitin E3 ligase mechanism" Nat. Struct. Mol. Biol. 2014, 21:301-307.
Bondeson et al. "Catalytic in vivo protein knockdown by small-molecule PROTACs" Nature Chemical Biology 2015, 11:611-617.
Buckley et al. "HaloPROTACS: Use of Small Molecule PROTACS to Induce Degradation of HaloTag Fusion Proteins" ACS Chemical Biology 2015, 10:1831-1837.
Buckley et al. "Small-Molecule Control of Intracellular Protein Levels through Modulation of the Ubiquitin Proteasome System" Angewandte Reviews, 2014, 53:2312-2330.
Buckley et al. "Targeting the Von Hippel-Lindau E3 Ubiquitin Ligase Using Small Molecules to Disrupt the Vhl/Hif-1 alpha Interaction" J. Am. Chem. Soc. 2012, 134:4465-4468.
Burkhard et al. "Synthesis and Stability of Oxetane Analogs of Thalidomide and Lenalidomide" Organic Letters 2013, 15(7):4312-4315.
Chamberlain et al. "Structure of the human cereblon-DDB1-lenalidomide complex reveals basis for responsiveness to thalidomide analogs" Nature Structural and Molecule Biology, 2014, 21(9):803-809.
Chang, X. and Stewart, K. A. "What is the functional role of the thalidomide binding protein cereblon?" Int J Biochem Mol Bio. 2011, 2(3):287-294.
Contino-Pepin, et al., "Preliminary biological evaluations of new thalidomide analogues for multiple sclerosis application", Bioorganic & Medicinal Chemistry Letters, 2009, 19(3), 878-881.
Corson et al. "Design and applications of bifunctional small molecules: Why two heads are better than one" ACS Chemical Biology 2008, 3(11): 677-692.
Crews, C. M. "Targeting the undruggable proteome: the small molecules of my dreams" Chemistry and Biology 2010, 17(6):551-555.
Deshaies et al. "Ring domain E3 ubiquitin ligases." Ann. Rev. Biochem. 2009, 78:399-434.
Elam W.A., et al., Poster Presentation titled "Application of Biophysical Techniques to the Targeted Protein Degradation Therapeutic Strategy", Sep. 24, 2017.
Faden et al. "Generic tools for conditionally altering protein abundance and phenotypes on demain" Biol. Chem. 2014, 395(7-8):737-762.
Fan, Y. and Lu, D. "The Ikaros family of zinc-finger proteins", Acta Pharmaceutica Sinica B, 2016, 6(6), 513-521.
Fischer et al. "Structure of the DDB1-CRBN E3 ubiquitin ligase in complex with thalidomide" Nature 2014, 512:49-53.
Fischer et al. "The Molecular Basis of CRL4DDB2/CSA Ubiquitin Ligase Architecture, Targeting, and Activation," Cell 2011, 147:1024-103 9.
Fisher S., Presentation titled "Targeted protein degradation", Targeted Protein Degradation Summit, Boston, MA, Oct. 24-25, 2018.
Fisher et al., "Targeted protein degradation and the enzymology of degraders", Current Opinion of Chemical Biology, 2018, 44, 47-55.
Georgopoulos, K. et al. "Ikaros, an early lymphoid-specific transcription factor and a putative mediator for T cell commitment", Science, 1992, 258(5083), 802-812.
Gosink et al. "Redirecting the Specificity of Ubiquitination by Modifying Ubiquitin-Conjugating Enzymes" Proc. Natl. Acad. Sci. USA 1995, 92:9117-9121.
Gustafson et al. "Small-Molecule-Mediated Degradation of the Androgen Receptor through Hydrophobic Tagging" Angewandte Chemie 2015, 54:9659-9662.
Henderson C., Presentation titled "Development of AchillesTAG degradation systems and their application to control CAR-T activity", ChemBio in the hub, Cambridge, MA. Oct. 22, 2018.
Hines et al. "Posttranslational protein knockdown couple to receptor tyrosine kinase activation with phosphoPROTACs" PNAS 2013, 110(22):8942-8947.
International Search Report and Written opinion for PCT/US2019/024094 dated May 17, 2019.
Ito et al., "Identification of a Primary Target of thalidomide teratogenicity", Science, 2010, 327(5971), 1345-1350, XP0055062167.
Itoh et al. "Protein knockdown using methyl bestatin-ligand hybrid molecules: design and synthesis of inducers of ubiquitination-mediated degradation of cellular retinoic acid-binding proteins" Journal of the American Chemical Society 2010, 132(16), 5820-5826.
Jacques et al. "Differentiation of anti-inflammatory and antitumorigenic properties of stabilized enantiomers of thalidomide analogs" PNAS 2015, 112(12): E1471-E1479.
John, L. B., and Ward, A.C., "The Ikaros gene family: transcriptional regulators of hematopoiesis and immunity", Mol Immunol, 2011, 48, 1272-1278.
Kronke et al. "Lenalidomide Causes Selective Degradation of IKZF1 and IKZF3 in Multiple Myeloma Cells" Science 2014, 343(6168):301-305.
Kronke et al. "Lenalidomide induces ubiquitination and degradation of CDK1 [alpha] in del(5q) MDS" Nature 2015, 523(7559):183-188.
Lai et al. "Modular PROTAC Design for the Degradation of Oncogenic BCR-ABL" Angewandte Chemie International Edition 2016, 55:807-810.
Lee et al. "Targeted Degradation of the Aryl Hydrocarbon Receptor by the PROTAC Approach: A Useful Chemical Genetic Tool" ChemBioChem 2007, 8:2058-2062.
Li et al. "Genome-wide and functional annotation of human E3 ubiquitin ligases identifies MULAN, a mitochondrial E3 that regulates the organelle's dynamics and signaling" PLOS One 2008, 3:1487.
Liu et al. "Design and biological characterization of hybrid compounds of curcumin and thalidomide for multiple myeloma" Organic and Biomolecular Chemistry 2013, 11:4757.
Lu et al. "Hijacking the E3 Ubiquitin Ligase Cereblon to Efficiently Target BRD4" Chemistry and Biology 2015, 22(6):755-763.
Lu et al. "The myeloma drug lenalidomide promotes the cereblon-dependent destruction of Ikaros proteins" Science 2014, 343:305-309.
Martiniani, R. et al., "Biological activity of lenalidomide and its underlying therapeutic effects in multiple myeloma", Adv Hematol., 2012, 2012, 842945.
Nasveschuk C., Presentation titled "Advances in the Medicinal Chemistry of Targeted Protein Degradation", Aug. 7, 2018.
Nawaz et al. "Proteasome-Dependent Degradation of the Human Estrogen Receptor" Proc. Natl. Acad. Sci. USA 1999, 96:1858-1862.

(56) References Cited

OTHER PUBLICATIONS

Neklesa et al. "Small-molecule hydrophobic tagging-induced degradation of HaloTag fusion proteins." Nat Chem Biol 2011, 7(8):538-543.
Patel, J., Poster Presentation titled "Diverse Utility of Targeted Protein Degradation at C4 Therapeutics", Sep. 17, 2017.
Perdomo, J. et al., "Eos and Pegasus, two members of the Ikaros family of proteins with distinct DNA binding activities: J", Biol Chem., 2000, 275(49), 38347-38354.
Phillips A., Presentation titled "Small molecule driven targeted protein degradation", ChemBio in the hub, Cambridge, MA. Oct. 22, 2018.
Phillips A., Presentation titled "Targeted Protein Degradation", Applied Pharmaceutical Chemistry, Cambridge, MA. Apr. 5, 2018.
Raina et al. "Chemical Inducers of Targeted Protein Degradation" Journal of Biological Chemistry 2010, 285:11057-11060.
Rodriguez-Gonzalez et al. "Targeting steroid hormone receptors for ubiquitination and degradation in breast and prostate cancer" Oncogene 2008, 27:7201-7211.
Ruchelman et al. "Isosteric analogs of lenalidomide and pomalidomide: Synthesis and biological activity" Bioorganic and Medicinal Chemistry Letters 2012, 23:360-365.
Sakamoto et al. "Development of Protacs to Target Cancer-Promoting Proteins for Ubiquitination and Degradation" Molecular and Cellular Proteomics 2003, 2(12):1350-1357.
Sakamoto et al. "Protacs: chimeric molecules that target proteins to the Skp1-Cullin-F box complex for ubiquitination and degradation" PNAS 2001, 98(15):8554-8559.
Schmitt, C. et al., "Aiolos and Ikaros: regulators of lymphocyte development, homeostasis and lymphoproliferation", Apoptosis, 2002, 7, 277-284.
Schneekloth et al. "Chemical approaches to controlling intracellular protein degradation" Chembiochem 2005, 6(1):40-46.
Schneekloth et al. "Chemical Genetic Control of Protein Levels: Selective in Vivo Targeted Degradation" Journal of the American Chemical Society 2004, 126(12):3748-3754.
Schneekloth et al. "Targeted Intracellular Protein Degradation Induced by a Small Molecule: En Route to Chemical Proteomics" Bioorganic and Medicinal Chemistry Letters 2008, 18:5904-5908.
Shoji, et al., "Modified DNA Aptamer That Binds the (R)-Isomer of a Thalidomide Derivative with High Enantioselectivity", J. Am. Chem. Soc., 2007, 129, 1456-1464.
Smith et al. "Targeted Intracellular Protein Degradation Induced by a Small Molecule: En Route to Chemical Proteomics" Bioorg. Med. Chem. Lett. 2008, 18(22):5904-5908.
Spratt et al. "RBRE3 ubiquitin ligases: new structures, new insights, new questions." Biochem. 2014, 458:421-437.
Terpos, E. et al., "Pomalidomide: a novel drug to treat relapsed and refractory multiple myeloma", Oncotargets and Therapy, 2013, 6, 531.
Toure et al. "Small-Molecule PROTACs: New Approaches to Protein Degradation" Angewandte Chemie International Edition 2016, 55:1966-1973.
Vassilev et al. "In Vivo Activation of the P53 Pathway by Small-Molecule Antagonists of MDM2" Science 2004, 303:844-848.
Vieux Ellen et al., Poster Presentation titled "Measuring Small Molecule Induced Ubiquitination of Proteins", EMBO, Sep. 18, 2017.
Wang et al. "Roles of F-box proteins in cancer." Nat. Rev. Cancer 2014, 14:233-347.
Winandy, S. et al., "A dominant mutation in the Ikaros gene leads to rapid development of leukemia and lymphoma", Cell, 1995, 83, 289-299.
Winter et al. "Phthalimide conjugation as a strategy for in vivo target protein degradation" Science 2015, 348(6241):1376-1381.
Yoshida, T. and Georgopoulos, K., "Ikaros fingers on lymphocyte differentiation", Int J Hematol, 2014, 100(3), 220-229.
Zengerle et al. "Selective Small Molecule Induced Degradation of the BET Bromodomain Protein BRD4" ACS Chem. Biol. 2015, 10:1770-1777.
Zhou et al. "Harnessing the Ubiquitination Machinery to Target the Degradation of Specific Cellular Proteins" Molecular Cell 2000, 6:751-756.
Zeid Rhamy, Oral Presentation "Targeted protein degradation as a novel therapeutic approach", Gordon Research Conference Jun. 29, 2017.
US, 2022/0098194, A1, U.S. Appl. No. 17/541,035, Nasveschuk et al., Mar. 31, 2022.
US, 2022/0289738, A1, U.S. Appl. No. 17/576,582, Norcross et al., Sep. 15, 2022.
US, 2023/0060334, A1, U.S. Appl. No. 17/901,775, Nasveschuk et al, Mar. 2, 2023.
US, U.S. Appl. No. 17/524,558, filed Nov. 11, 2021, Phillips et al.
US, U.S. Appl. No. 17/723,199, filed Apr. 18, 2022, Henderson et al.
US, U.S. Appl. No. 17/843,769, filed Jun. 17, 2022, Nasveschuk et al.
US, U.S. Appl. No. 17/878,753, filed Aug. 1, 2022, Henderson et al.
US, U.S. Appl. No. 17/959,144, filed Oct. 3, 2022, Phillips et al.
US, U.S. Appl. No. 17/965,569, filed Oct. 13, 2022 Nasveschuk et al.
US, U.S. Appl. No. 18/079,815, filed Dec. 12, 2022, Phillips et al.
US, U.S. Appl. No. 18/084,380, filed Dec. 19, 2022, Nasveschuk et al.
US, U.S. Appl. No. 18/100,992, filed Jan. 24, 2023, Nasveschuk et al.
US, U.S. Appl. No. 18/105,735, filed Feb. 3, 2023, Henderson et al.
US, U.S. Appl. No. 18/106,893, filed Feb. 7, 2023, Proia et al.
US, U.S. Pat. No. 10,646,575, B2, U.S. Appl. No. 16/186,339, Phillips et al., May 12, 2020.
US, U.S. Appl. No. 10,660,968, B2, U.S. Appl. No. 16/186,334, Phillips et al., May 26, 2020.
US, U.S. Pat. No. 10,849,982, B2, U.S. Appl. No. 16/186,341, Phillips et al., Dec. 1, 2020.
US, U.S. Pat. No. 10,905,768, B2, U.S. Appl. No. 16/872,225, Phillips et al., Feb. 2, 2021.
US, 2020/0140456, A1, 16/721,650, Phillips et al., May 7, 2020.
US, 2020/0207764, A1, U.S. Appl. No. 16/809,325, Norcross et al., Jul. 2, 2020.
US, 2020/0207783, A1, U.S. Appl. No. 16/809,336, Norcross et al., Jul. 2, 2020.
US, 2020/0207733, A1, U.S. Appl. No. 16/809,345, Norcross et al., Jul. 2, 2020.
US, 2021/0032245, A1, U.S. Appl. No. 17/072,896, Nasveschuk et al, Feb. 4, 2021.
U.S. Appl. No. 16/874,475, filed May 15, 2020, Phillips et al.
U.S. Appl. No. 16/882,236, filed May 22, 2020, Phillips et al.
U.S. Appl. No. 17/103,621, filed Nov. 24, 2020, Nasveschuk et al.
U.S. Appl. No. 17/107,781, filed Nov. 30, 2020, Phillips et al.
U.S. Appl. No. 17/121,389, filed Dec. 14, 2020, Phillips et al.
U.S. Appl. No. 17/164,446, filed Feb. 1, 2021, Phillips et al.
U.S. Appl. No. 17/192,634, filed Mar. 4, 2021, Nasveschuk et al.

CEREBLON BINDERS FOR THE DEGRADATION OF IKAROS

CROSS-REFERENCE TO RELATED APPLICATIONS

This application is a continuation of International Application No. PCT/US2019/024094, filed in the International Patent Cooperation Treaty, U.S. Receiving Office on Mar. 26, 2019, which claims the benefit of U.S. Provisional Application 62/648,238, filed Mar. 26, 2018. The entirety of these applications are hereby incorporated by reference herein for all purposes.

FIELD OF THE INVENTION

The invention provides cereblon binders for the degradation of Ikaros or Aiolos by the ubiquitin proteasome pathway for therapeutic applications as described further herein.

BACKGROUND

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

The Ikaros family is a series of zinc-finger protein transcription factors that are important for certain physiological processes, particularly lymphocyte development (see Fan, Y. and Lu, D. "The Ikaros family of zinc-finger proteins" Acta Pharmaceutica Sinica B, 2016, 6:513-521). Ikaros was first discovered in 1992 (see Georgopoulos, K. et al. "Ikaros, an early lymphoid-specific transcription factor and a putative mediator for T cell commitment" Science, 1992, 258:802-812), and over the subsequent two decades four additional homologs have been identified: Helios, Aiolos, Eos, and Pegasus (see John, L. B., and Ward, A. C. The Ikaros gene family: transcriptional regulators of hematopoiesis and immunity" Mol Immunol, 2011, 48:1272-1278). Each homolog gene can produce several protein isoforms through alternative splicing, theoretically allowing for the generation of a large number of protein complexes through different combinations of the various homologs. Highly conserved among members of this family is a set of two $Cys_2His_2$ zinc finger motifs at the C-terminus that mediates protein interactions among various members of the protein family. Up to four zinc finger motifs at the N-terminus are present for recognition of DNA sequences; with the number of these N-terminal zinc fingers varying due to alternative splicing. Isoforms without these N-terminal zinc fingers show a dominant negative effect on transcriptional activation (see Winandy, S. et al. "A dominant mutation in the Ikaros gene leads to rapid development of leukemia and lymphoma" Cell, 1995, 83:289-299). The distribution of various members of the Ikaros protein family within the body varies significantly. Ikaros, Helios, and Aiolos are mainly present in lymphoid cells and their corresponding progenitors, with Ikaros additionally being detected in the brain, and Ikaros and Helios being detected in erythroid cells. Eos and Pegasus are more widely spread, being found in skeletal muscle, the liver, the brain, and the heart (see Perdomo, J. et al. "Eos and Pegasus, two members of the Ikaros family of proteins with distinct DNA binding activities: J Biol Chem, 2000, 275:38347-38354; Schmitt, C. et al. "Aiolos and Ikaros: regulators of lymphocyte development, homeostasis and lymphoproliferation" Apoptosis, 2002, 7:277-284; Yoshida, T. and Georgopoulos, K. "Ikaros fingers on lymphocyte differentiation" Int J Hematol, 2014, 100:220-229).

Ikaros is important for proper lymphocyte development. Deletion of the exons encoding the first three N-terminal zinc fingers leads to mice lacking T-cells, B-cells, natural killer (NK) cells, and their progenitors. Genetic alterations in Ikaros are correlated with a poor outcome in the treatment of acute lymphoblastic leukemia (ALL). Ikaros and Aiolos are involved in the proliferation of multiple myeloma cells, suggesting a potential role in malignancy.

The drug thalidomide and its analogs lenalidomide and pomalidomide have garnered interest as immunomodulators and antineoplastics, especially in multiple myeloma (see Martiniani, R. et al. "Biological activity of lenalidomide and its underlying therapeutic effects in multiple myeloma" Adv Hematol, 2012, 2012:842945; and Terpos, E. et al. "Pomalidomide: a novel drug to treat relapsed and refractory multiple myeloma" Oncotargets and Therapy, 2013, 6:531). While the exact therapeutic mechanism of action of thalidomide, lenalidomide and pomalidomide is unknown, the compounds are used in the treatment of some cancers including multiple myeloma. There are also clinical and preclinical studies related to the treatment of renal cell carcinoma, glioblastoma, prostate cancer, melanoma, colorectal cancer, crohns disease, rheumatoid arthritis, Behcet's syndrome, breast cancer, head and neck cancer, ovarian cancer, chronic heart failure, graft-versus-host disease, and tuberculous meningitis.

Thalidomide and its analogues have been found to bind to the ubiquitin ligase cereblon and redirect its ubiquitination activity (see Ito, T. et al. "Identification of a primary target of thalidomide teratogenicity" Science, 2010, 327:1345). Cereblon forms part of an E3 ubiquitin ligase complex which interacts with damaged DNA binding protein 1, forming an E3 ubiquitin ligase complex with Cullin 4 and the E2-binding protein ROC1 (known as RBX1) where it functions as a substrate receptor to select proteins for ubiquitination. The binding of lenalidomide to cereblon facilitates subsequent binding of cereblon to Ikaros and Aiolos, leading to their ubiquitination and degradation by the proteasome (see Lu, G. et al. "The myeloma drug lenalidomide promotes the cereblon-dependent destruction of Ikaros proteins" Science, 2014, 343:305-309; Krönke, J. et al. "Lenalidomide causes selective degradation of IKZF1 and IKZF3 in multiple myeloma cells" Science, 2014, 343:301-305).

The disclosure that thalidomide binds to the cereblon E3 ubiquitin ligase led to research to investigate incorporating thalidomide and certain derivatives into compounds for the targeted destruction of proteins. Celgene has disclosed imids for similar uses, including those in U.S. Pat. Nos. 6,045,501; 6,315,720; 6,395,754; 6,561,976; 6,561,977; 6,755,784; 6,869,399; 6,908,432; 7,141,018; 7,230,012; 7,820,697; 7,874,984; 7,959,566; 8,204,763; 8,315,886; 8,589,188; 8,626,531; 8,673,939; 8,735,428; 8,741,929; 8,828,427; 9,056,120; 9,101,621; and 9,101,622.

The Regents of the University of Michigan have also filed patent applications that disclose imids for the treatment of diseases, including WO 2017/176958 titled "Monofunctional Intermediates for Ligand-Dependent Target Protein Degradation", which describes compounds that function as immunomodulators or monofunctional synthetic intermediates to prepare small-molecule drug conjugates for protein degradation. WO 2017/176957 and WO 2017/180417 which are also assigned to the Regents of the University of Michigan describe specific small-molecule protein degraders.

Patent filings in this area include those that use the ability of cereblon to direct degradation to targeted proteins by attaching a cereblon ligand and a protein targeting ligand with a covalent linker. WO 2016/105518 and WO 2017/007612 titled "Methods to Induce Targeted Protein Degradation Through Bifunctional Molecules" are assigned to Dana-Farber Cancer Institute and describe compounds capable of binding to an E3 ubiquitin ligase and a target protein for degradation.

Patent applications filed by C4 Therapeutics, Inc., that describe compounds capable of binding to an E3 ubiquitin ligase and a target protein for degradation include: WO 2017/197051 titled "Amine-Linked C3-Glutarimide Degronimers for Target Protein Degradation"; WO 2017/197055 titled "Heterocyclic Degronimers for Target Protein Degradation"; WO 2017/197036 titled "Spirocyclic Degronimers for Target Protein Degradation"; WO 2017/197046 titled "C3-Carbon Linked Glutarimide Degronimers for Target Protein Degradation"; and WO 2017/197056 titled "Bromodomain Targeting Degronimers for Target Protein Degradation."

Arvinas, Inc. has filed a patent application that describes some compounds comprising a protein degradation moiety covalently bound to a linker and a targeting ligand, U.S. Patent Publication No. 2015/0291562 assigned to Arvinas, Inc. and titled "Imide-Based Modulators of Proteolysis and Associated Methods of Use." In particular, the specification discloses protein degrading compounds that incorporate certain small molecules that can bind to an E3 ubiquitin ligase. Other patent applications filed by Arvinas that describe protein degrading compounds include: WO 2015/160845; WO 2016/118666; WO 2016/149668; WO 2016/197032; WO 2016/197114; WO 2017/030814; and WO 2017/176708.

It is an object of the present invention to provide new compounds, methods, and compositions that are useful for the treatment of medical disorders that are mediated by Ikaros.

SUMMARY OF THE INVENTION

New compounds are provided, along with their uses and manufacture that bind cereblon. It is believed that binding of the disclosed compounds to cereblon results in increased interactions of cereblon with Ikaros or Aiolos, leading to their subsequent ubiquitination and degradation in the proteasome. Decreased levels of Ikaros or Aiolos leads to changes in transcriptional regulation of their downstream proteins. The selected compounds are found to be both potent binders of cereblon as well as showing potent inhibition of multiple myeloma cell proliferation as compared to pomalidomide.

A selected compound disclosed herein, its pharmaceutically acceptable salt, or its pharmaceutically acceptable composition can be used to treat a disorder mediated by Ikaros or Aiolos, for example, a hematopoietic malignancy such as multiple myeloma, leukemia, acute myeloid leukemia, acute lymphoblastic leukemia, chronic lymphoblastic leukemia, a myelodysplastic syndrome, or other target indications. Therefore, in some embodiments a method to treat a host (typically a human) with a disorder mediated by Ikaros or Aiolos, is provided that includes administering an effective amount of the disclosed compound or its pharmaceutically acceptable salt described herein to the host, optionally as a pharmaceutically acceptable composition. The compounds can also be used to achieve immunomodulation or reduce angiogenesis.

In one aspect, the compound of the present invention is selected from Formula I:

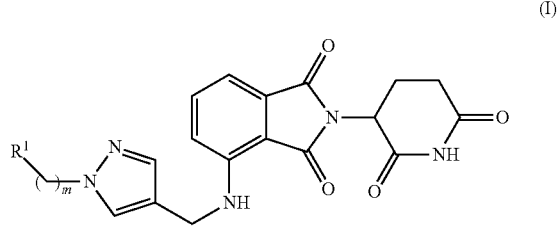

(I)

or a pharmaceutically acceptable salt, N-oxide, isotopic derivative, or prodrug thereof, optionally in a pharmaceutically acceptable carrier to form a composition;

wherein:

$R^1$ is selected from:

a. haloalkyl (typically $C_1$-$C_6$haloalkyl) and alkyl (typically $C_1$-$C_6$alkyl); either of which is optionally substituted with 1, 2, 3, or 4 substituents independently selected from aryl, cycloalkyl (typically $C_1$-$C_6$cycloalkyl or $C_5$-$C_9$ multicyclic fused, bridged, or spiro cycloalkyl), heteroaryl, —$SO_2R^5$, —$NR^2$—C(O)—$R^3$, —C(O)$OR^4$, and —C(O)—$R^3$; wherein when the haloalkyl or alkyl group has two or more carbons it can additionally be optionally substituted with 1, 2, 3, or 4 substituents independently selected from —OC(O)—$R^3$, —$NR^4R^4$, and —$OR^4$, wherein these additional substituents are not on the carbon alpha to the pyrazole;

b. cycloalkyl (typically $C_3$-$C_6$ monocyclic cycloalkyl or $C_5$-$C_9$ multicyclic fused, bridged, or spiro cycloalkyl) and aryl; either of which is optionally substituted with 1, 2, 3, or 4 substituents independently selected from alkyl (typically $C_1$-$C_6$alkyl), alkenyl (typically $C_2$-$C_6$alkenyl), alkynyl (typically $C_2$-$C_6$alkynyl), halogen (for example, F, Cl, Br, or I), cyano, heteroaryl, aryl, cycloalkyl (typically $C_3$-$C_6$ monocyclic cycloalkyl or $C_5$-$C_9$ multicyclic fused, bridged, or spiro cycloalkyl), heterocycle, —$NR^2R^2$, —$OR^2$, —$N^2$—C(O)—$R^3$, —O—C(O)—$R^3$, and —C(O)—$R^3$;

c. heteroaryl optionally substituted with 1, 2, 3, or 4 substituents independently selected from alkyl (typically $C_1$-$C_6$alkyl), alkenyl (typically $C_2$-$C_6$alkenyl), halogen, cyano, heteroaryl, aryl, cycloalkyl (typically $C_3$-$C_6$ monocyclic cycloalkyl or $C_5$-$C_9$ multicyclic fused, bridged, or spiro cycloalkyl), —$NR^4R^4$, —$OR^4$, —$NR^2$—C(O)—$R^3$, —O—C(O)—$R^3$, and —C(O)—$R^3$; wherein the heteroaryl group is only substituted such that no N—O or N—N bonds are formed, for example pyrazole cannot be substituted with $OR^4$ on the nitrogen atom;

d. heterocycle (typically $C_3$-$C_7$ monocyclic heterocycle or $C_7$-$C_{11}$ multicyclic heterocycle containing 1, 2, or 3 heteroatoms selected from N, O, and S) substituted with 1, 2, 3, or 4 substituents independently selected from alkyl (typically $C_1$-$C_6$alkyl), alkenyl (typically $C_2$-$C_6$alkenyl), alkynyl (typically $C_2$-$C_6$alkynyl), halogen, cyano, heteroaryl, aryl, cycloalkyl (typically $C_3$-$C_6$ monocyclic cycloalkyl or $C_5$-$C_9$ multicyclic fused, bridged, or spiro cycloalkyl), heterocycle (typically $C_3$-$C_7$ monocyclic heterocycle or $C_7$-$C_{11}$ multicyclic heterocycle containing 1, 2, or 3 heteroatoms selected from N, O, and S), —$NR^2R^2$, —$OR^2$, —$NR^2$—C(O)—$R^3$, —O—C(O)—$R^3$, —C(O)—$R^3$, —$SO_2R^5$, —C(O)—$R^5$, and $R^5$; wherein the heterocycle group is only substituted such that no N—O or N—N bonds are formed, for example piperidine cannot be substituted with $OR^2$ on the nitrogen atom;

e. $(CR^4R^2)$—$(CR^2R^2)_o$-heterocycle (typically $C_3$-$C_7$ monocyclic heterocycle or $C_7$-$C_{11}$ multicyclic heterocycle containing 1, 2, or 3 heteroatoms selected from N, O, and S) optionally substituted with 1, 2, 3, or 4 substituents independently selected from alkyl (typically $C_1$-$C_6$alkyl), alkenyl (typically $C_2$-$C_6$alkenyl), alkynyl (typically $C_2$-$C_6$alkynyl), halogen, cyano, heteroaryl, aryl, cycloalkyl (typically $C_3$-$C_6$ monocyclic cycloalkyl or $C_5$-$C_9$ multicyclic fused, bridged, or spiro cycloalkyl), heterocycle (typically $C_3$-$C_7$ monocyclic heterocycle or $C_7$-$C_{11}$ multicyclic heterocycle containing 1, 2, or 3 heteroatoms selected from N, O, and S), —$NR^2R^2$, —$OR^2$, —$NR^2$—C(O)—$R^3$, —O—C(O)—$R^3$, —C(O)—$R^3$, —$SO_2R^5$, —C(O)—$R^5$, and $R^5$; wherein the heterocycle group is only substituted such that no N—O or N—N bonds are formed, for example piperidine cannot be substituted with $OR^2$ on the nitrogen atom; and f. bicyclic heterocycle or multicyclic heterocycle, typically with 5, 6, 7, 8, 9, 10, 11, 12, 13, 14, 15, or 16 carbon atoms and 1, 2, or 3 heteroatoms selected from N, O, and S, optionally substituted with 1, 2, 3, or 4 substituents independently selected from alkyl (typically $C_1$-$C_6$alkyl), alkenyl (typically $C_2$-$C_6$alkenyl), alkynyl (typically $C_2$-$C_6$alkynyl), halogen, cyano, heteroaryl, aryl, cycloalkyl (typically $C_3$-$C_6$ monocyclic cycloalkyl or $C_5$-$C_9$ multicyclic fused, bridged, or spiro cycloalkyl), heterocycle (typically $C_3$-$C_7$ monocyclic heterocycle or $C_7$-$C_{11}$ multicyclic heterocycle containing 1, 2, or 3 heteroatoms selected from N, O, and S), —$NR^2R^2$, —$OR^2$, —$NR^2$—C(O)—$R^3$, —O—C(O)—$R^3$, —C(O)—$R^3$, —$SO_2R^5$, —C(O)—$R^5$, and $R^5$; wherein the bicyclic heterocycle group is only substituted such that no N—O or N—N bonds are formed, for example piperidine cannot be substituted with $OR^2$ on the nitrogen atom;

$R^2$ at each instance is independently selected from hydrogen, alkyl (typically $C_1$-$C_6$alkyl), alkenyl (typically $C_2$-$C_6$alkenyl), alkynyl (typically $C_2$-$C_6$alkynyl), aryl, heterocycle (typically $C_3$-$C_7$ monocyclic heterocycle or $C_7$-$C_{11}$ multicyclic heterocycle containing 1, 2, or 3 heteroatoms selected from N, O, and S), heteroaryl, and cycloalkyl (typically $C_3$-$C_6$ monocyclic cycloalkyl or $C_5$-$C_9$ multicyclic fused, bridged, or spiro cycloalkyl);

$R^3$ is selected from hydrogen, alkyl (typically $C_1$-$C_6$alkyl), alkenyl (typically $C_2$-$C_6$alkenyl), alkynyl (typically $C_2$-$C_6$alkynyl), haloalkyl (typically $C_1$-$C_6$haloalkyl), cycloalkyl (typically $C_3$-$C_6$ monocyclic cycloalkyl or $C_5$-$C_9$ multicyclic fused, bridged, or spiro cycloalkyl), aryl, heterocycle (typically $C_3$-$C_7$ monocyclic heterocycle or $C_7$-$C_{11}$ multicyclic heterocycle containing 1, 2, or 3 heteroatoms selected from N, O, and S), heteroaryl, —$NR^2R^2$, and —$OR^4$;

$R^4$ at each instance is independently selected from hydrogen, alkyl (typically $C_1$-$C_6$alkyl), alkenyl (typically $C_2$-$C_6$alkenyl), cycloalkyl (typically $C_3$-$C_6$ monocyclic cycloalkyl or $C_5$-$C_9$ multicyclic fused, bridged, or spiro cycloalkyl), haloalkyl (typically $C_1$-$C_6$haloalkyl), aryl, heterocycle (typically $C_3$-$C_7$ monocyclic heterocycle or $C_7$-$C_{11}$ multicyclic heterocycle containing 1, 2, or 3 heteroatoms selected from N, O, and S), heteroaryl, and alkynyl (typically $C_2$-$C_6$alkynyl);

$R^5$ is selected from hydrogen, alkyl (typically $C_1$-$C_6$alkyl), alkenyl (typically $C_2$-$C_6$alkenyl), alkynyl (typically $C_2$-$C_6$alkynyl), haloalkyl (typically $C_1$-$C_6$haloalkyl), cycloalkyl (typically $C_3$-$C_6$ monocyclic cycloalkyl or $C_5$-$C_9$ multicyclic fused, bridged, or spiro cycloalkyl), heteroaryl, heterocycle (typically $C_3$-$C_7$ monocyclic heterocycle or $C_7$-$C_{11}$ multicyclic heterocycle containing 1, 2, or 3 heteroatoms selected from N, O, and S), aryl, —O-cycloalkyl (typically $C_3$-$C_6$ monocyclic cycloalkyl or $C_5$-$C_9$ multicyclic fused, bridged, or spiro cycloalkyl), —O-aryl, —O—heteroaryl, —O-heterocycle (typically $C_3$-$C_7$ monocyclic heterocycle or $C_7$-$C_{11}$ multicyclic heterocycle containing 1, 2, or 3 heteroatoms selected from N, O, and S), —O-alkyl (typically $C_1$-$C_6$alkyl), —$NR^2$-cycloalkyl (typically $C_3$-$C_6$ monocyclic cycloalkyl or $C_5$-$C_9$ multicyclic fused, bridged, or spiro cycloalkyl), —$NR^2$-aryl, —$NR^2$-heteroaryl, —$NR^2$-heterocycle (typically $C_3$-$C_7$ monocyclic heterocycle or $C_7$-$C_{11}$ multicyclic heterocycle containing 1, 2, or 3 heteroatoms selected from N, O, and S), —$NR^2$-alkyl (typically $C_1$-$C_6$alkyl), —$CH_2$-cycloalkyl (typically $C_3$-$C_6$ monocyclic cycloalkyl or $C_5$-$C_9$ multicyclic fused, bridged, or spiro cycloalkyl), —$CH_2$-aryl, —$CH_2$-heteroaryl, —$CH_2$-heterocycle (typically $C_3$-$C_7$ monocyclic heterocycle or $C_7$-$C_{11}$ multicyclic heterocycle containing 1, 2, or 3 heteroatoms selected from N, O, and S), —$OR^2$, and —$NR^2R^2$; each of which except for hydrogen is optionally substituted with 1, 2, 3, or 4 substituents independently selected from alkyl (typically $C_1$-$C_6$alkyl), alkenyl (typically $C_2$-$C_6$alkenyl), alkynyl (typically $C_2$-$C_6$alkynyl), haloalkyl, cycloalkyl (typically $C_3$-$C_6$ monocyclic cycloalkyl or $C_5$-$C_9$ multicyclic fused, bridged, or spiro cycloalkyl), heterocycle (typically $C_3$-$C_7$ monocyclic heterocycle or $C_7$-$C_{11}$ multicyclic heterocycle containing 1, 2, or 3 heteroatoms selected from N, O, and S), aryl, heteroaryl, cyano, halogen, —$OR^2$, and —$NR^2R^2$; and m and o are independently selected from 0, 1, 2, 3, 4, and 5.

In another embodiment, $R^1$ is -alkyl-OH (for example —($C_1$-$C_6$alkyl)-OH) wherein the OH is not on the terminal carbon atom. For example, in this embodiment $R^1$ can be

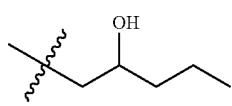 [SMILES: *CC(O)CCC]

but cannot be

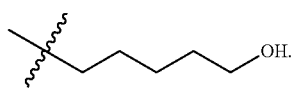 [SMILES: *CCCCCO]

In another embodiment, R¹ is -alkyl-OH (for example —($C_1$-$C_6$alkyl)-OH), wherein the alkyl group is substituted with 1, 2, 3, or 4 substituents independently selected from aryl, cycloalkyl, heterocycle, —$NR^2$—C(O)—$R^3$, and —C(O)—$R^3$.

In another embodiment R¹ is —$C_2$-$C_6$haloalkyl-OH.

In another embodiment R¹ is selected from:

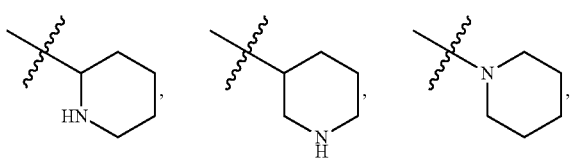

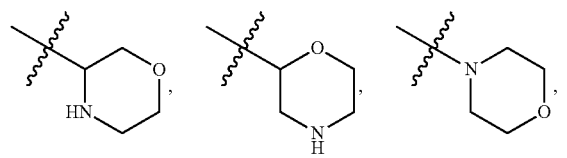

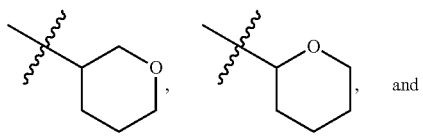

In another embodiment R¹ is selected from:

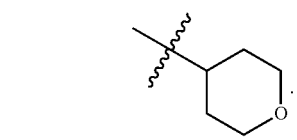

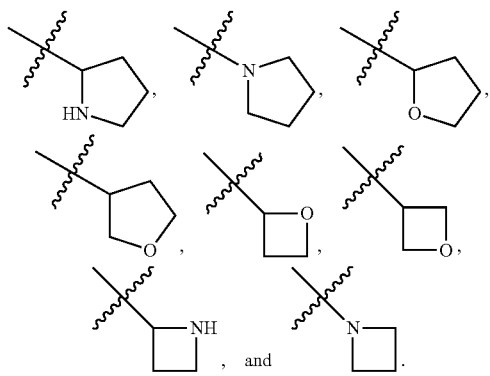

In another embodiment R¹ is selected from:

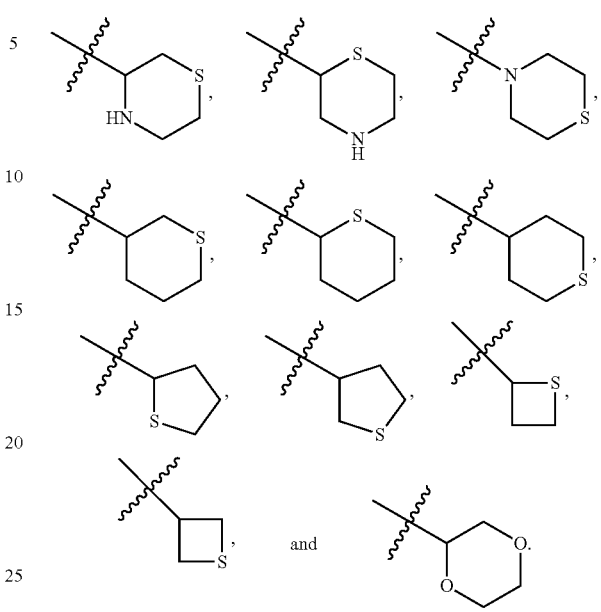

In another embodiment, R¹ is

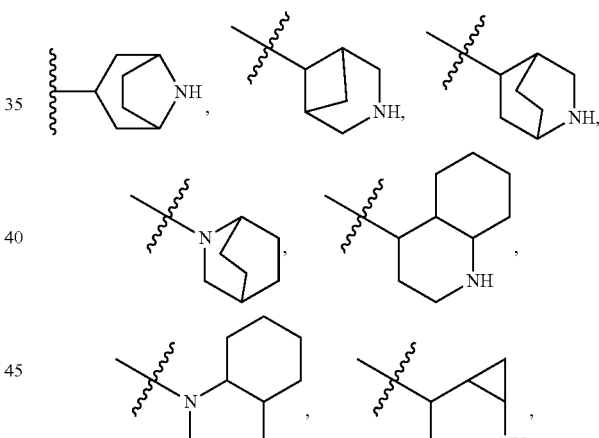

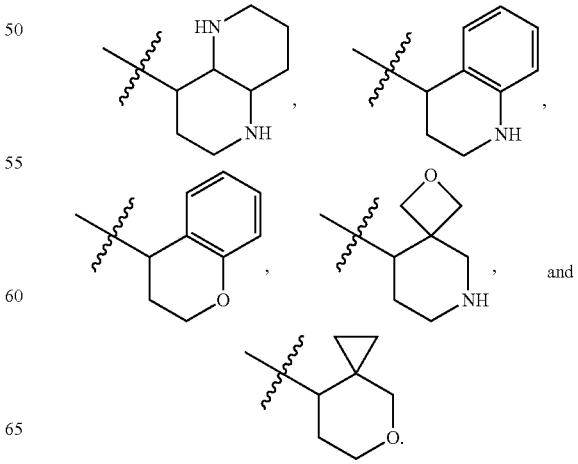

In another embodiment, R¹ is selected from:

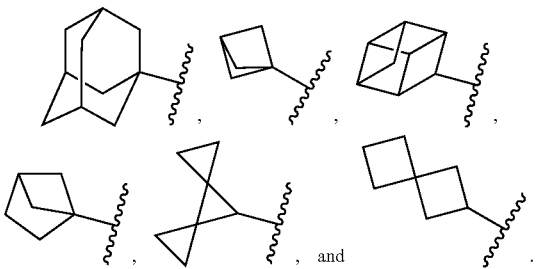

, and

In one embodiment Formula I is:

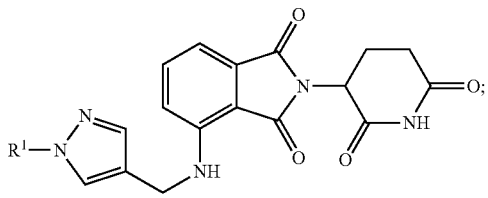

or a pharmaceutically acceptable salt, N-oxide, isotopic derivative, or prodrug thereof, optionally in a pharmaceutically acceptable carrier to form a composition.

In one embodiment, the compound of Formula I is:

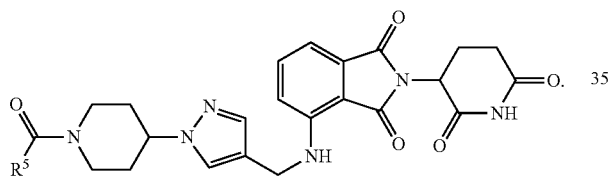

In one embodiment, the compound of Formula I is:

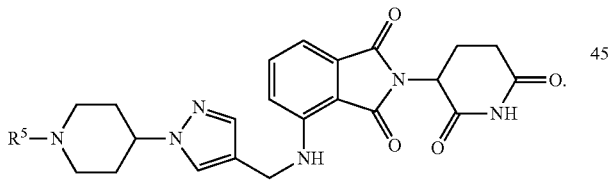

In another aspect, the compound is selected from Formula II

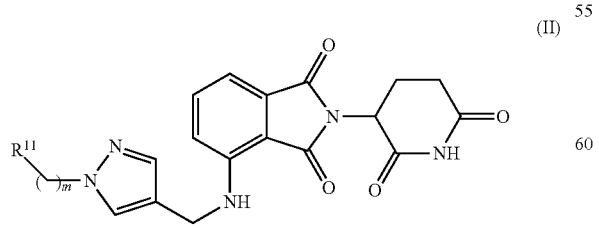

(II)

or a pharmaceutically acceptable salt, N-oxide, isotopic derivative, or prodrug thereof, optionally in a pharmaceutically acceptable carrier to form a composition;

wherein:
$R^{11}$ is selected from
  a. haloalkyl (typically $C_1$-$C_6$ haloalkyl) and alkyl (typically $C_1$-$C_6$ alkyl); each of which is optionally substituted with 1, 2, 3, or 4 substituents independently selected from —NR²—C(O)—R³, —O—C(O)—R³, and —C(O)—R³; wherein when the haloalkyl or alkyl group has two or more carbons it can additionally be optionally substituted with 1, 2, 3, or 4 substituents independently selected from —OC(O)—R³, —NR⁴R⁴, and —OR₄, wherein these additional substituents are not on the carbon alpha to the pyrazole;
  b. cycloalkyl (typically $C_3$-$C_6$ monocyclic cycloalkyl or $C_5$-$C_9$ multicyclic fused, bridged, or spiro cycloalkyl), heteroaryl, and aryl; each of which is optionally substituted with 1, 2, 3, or 4 substituents independently selected from alkyl (typically $C_1$-$C_6$ alkyl), alkenyl (typically $C_2$-$C_6$ alkenyl), halogen (for example, F, Cl, Br, or I), cyano, heteroaryl, aryl, cycloalkyl, —NR⁴R⁴, —OR⁴, —NR²—C(O)—R³, —O—C(O)—R³, and —C(O)—R³;
  c. —(CR²R²)ₙ-heterocycle (typically $C_3$-$C_7$ monocyclic heterocycle or $C_7$-$C_{11}$ multicyclic heterocycle containing 1, 2, or 3 heteroatoms selected from N, O, and S) substituted with 1, 2, 3, or 4 substituents independently selected from alkyl (typically $C_1$-$C_6$ alkyl), alkenyl (typically $C_2$-$C_6$ alkenyl), halogen, cyano, heteroaryl, aryl, cycloalkyl (typically $C_3$-$C_6$ monocyclic cycloalkyl or $C_5$-$C_9$ multicyclic fused, bridged, or spiro cycloalkyl), —NR⁴R⁴, —OR⁴, —N²—C(O)—R³, —O—C(O)—R³, —C(O)—R³, and —SO₂R⁵; wherein the heterocycle group is only substituted such that no N—O or N—N bonds are formed, for example piperidine cannot be substituted with OR⁴ on the nitrogen atom; and
  d. bicyclic heterocycle optionally substituted with 1, 2, 3, or 4 substituents independently selected from alkyl (typically $C_1$-$C_6$ alkyl), alkenyl (typically $C_2$-$C_6$ alkenyl), alkynyl (typically $C_2$-$C_6$ alkynyl), halogen, cyano, heteroaryl, aryl, cycloalkyl (typically $C_3$-$C_6$ monocyclic cycloalkyl or $C_5$-$C_9$ multicyclic fused, bridged, or spiro cycloalkyl), heterocycle (typically $C_3$-$C_7$ monocyclic heterocycle or $C_7$-$C_{11}$ multicyclic heterocycle containing 1, 2, or 3 heteroatoms selected from N, O, and S), —NR²R², —OR², —NR²—C(O)—R³, —O—C(O)—R³, —C(O)—R³, —SO₂R⁵, —C(O)—R⁵, and R⁵; wherein the bicyclic heterocycle group is only substituted such that no N—O or N—N bonds are formed, for example piperidine cannot be substituted with OR⁴ on the nitrogen atom;

n is 0, 1, 2, 3, or 4; and
wherein the remaining variables are as defined herein.
In one embodiment Formula II is:

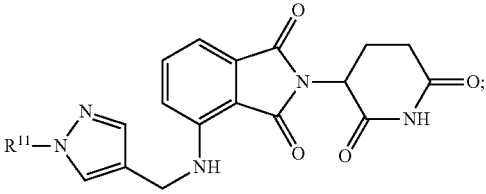

or a pharmaceutically acceptable salt, N-oxide, isotopic derivative, or prodrug thereof, optionally in a pharmaceutically acceptable carrier to form a composition.

In another aspect, the compound is selected from Formula III:

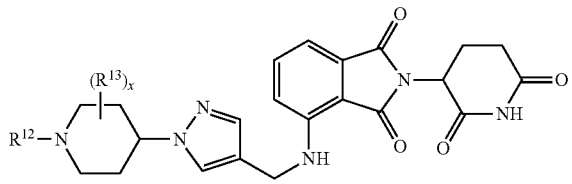

(III)

or a pharmaceutically acceptable salt, N-oxide, isotopic derivative, or prodrug thereof, optionally in a pharmaceutically acceptable carrier to form a composition;
wherein
x is 0, 1, 2, 3, 4, 5, or 6;
$R^{12}$ is selected from alkyl (typically $C_1$-$C_6$alkyl), haloalkyl (typically $C_1$-$C_6$haloalkyl), alkenyl (typically $C_2$-$C_6$alkenyl), alkynyl (typically $C_2$-$C_6$alkynyl), heteroaryl, aryl, cycloalkyl (typically $C_3$-$C_6$ monocyclic cycloalkyl or $C_5$-$C_9$ multicyclic fused, bridged, or spiro cycloalkyl), heterocycle (typically $C_3$-$C_7$ monocyclic heterocycle or $C_7$-$C_{11}$ multicyclic heterocycle containing 1, 2, or 3 heteroatoms selected from N, O, and S), —C(O)—$R^3$, —SO$_2$$R^5$, and —C(O)—$R^5$; and
$R^{13}$ at each instance is independently selected from alkyl (typically $C_1$-$C_6$alkyl), alkenyl (typically $C_2$-$C_6$alkenyl), alkynyl (typically $C_2$-$C_6$alkynyl), halogen, cyano, heteroaryl, aryl, cycloalkyl (typically $C_3$-$C_6$ monocyclic cycloalkyl or $C_5$-$C_9$ multicyclic fused, bridged, or spiro cycloalkyl), heterocycle (typically $C_3$-$C_7$ monocyclic heterocycle or $C_7$-$C_{11}$ multicyclic heterocycle containing 1, 2, or 3 heteroatoms selected from N, O, and S), —NR$^2$$R^2$, —OR$^2$, —NR$^2$—C(O)—$R^3$, —O—C(O)—$R^3$, —C(O)—$R^3$, —SO$_2$$R^5$, —C(O)—$R^5$, and $R^5$; and two $R^{13}$s may together with the carbon(s) to which they are attached be replaced with a spiro or fused, heterocycle or carbocycle ring, or two $R^{13}$s may together with the carbon to which they are attached be replaced with a aryl ring; and
wherein the remaining variables are as defined herein.

In one embodiment $R^{12}$ is selected from alkyl, alkenyl, haloalkyl, heteroaryl, aryl, cycloalkyl, —C(O)—$R^3$, and —SO$_2$$R^5$.

In one embodiment $R^{13}$ at each instance is independently selected from alkyl, alkenyl, halogen, cyano, heteroaryl, aryl, cycloalkyl, —NR$^2$—C(O)—$R^3$, —O—C(O)—$R^3$, —C(O)—$R^3$, and —SO$_2$$R^5$.

Non-limiting examples of compounds of Formula III include:

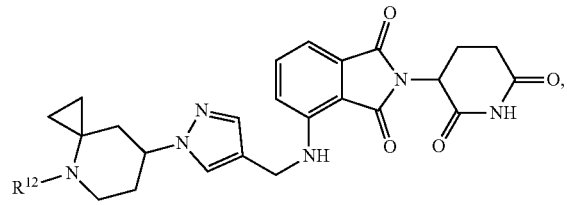

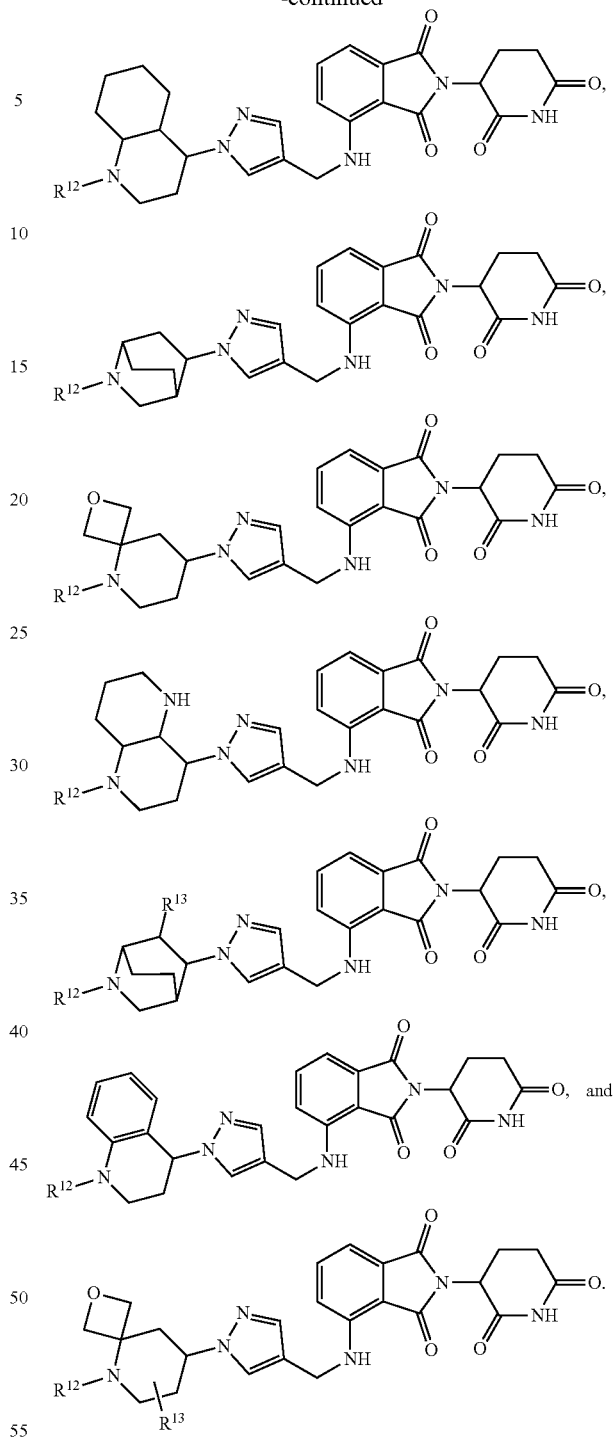

In one embodiment the compound of Formula III is selected from:

or a pharmaceutically acceptable salt, N-oxide, isotopic derivative, or prodrug thereof, optionally in a pharmaceutically acceptable carrier to form a composition.

In another aspect, the compound is selected from Formula IV:

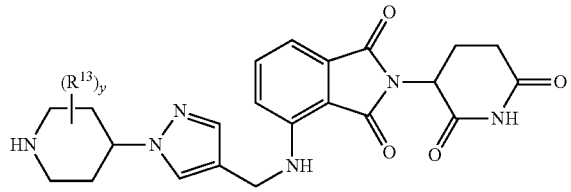

(IV)

or a pharmaceutically acceptable salt, N-oxide, isotopic derivative, or prodrug thereof, optionally in a pharmaceutically acceptable carrier to form a composition;

wherein y is 1, 2, 3, 4, 5, or 6; and wherein the remaining variables are as defined herein.

In one embodiment the compound of Formula IV is selected from:

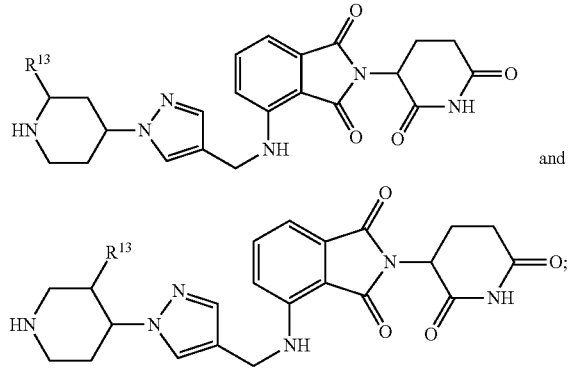

and or a pharmaceutically acceptable salt, N-oxide, isotopic derivative, or prodrug thereof, optionally in a pharmaceutically acceptable carrier to form a composition.

In one embodiment the compound of Formula IV is selected from:

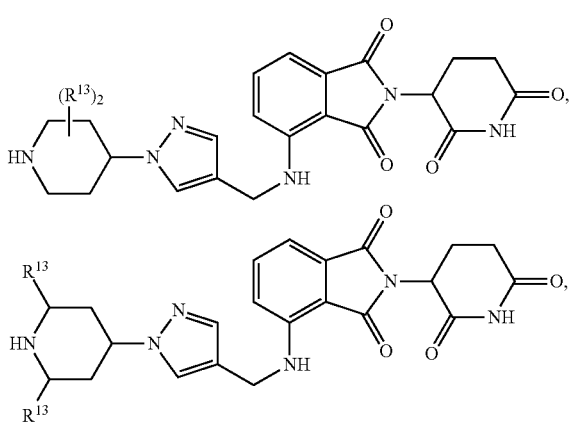

-continued

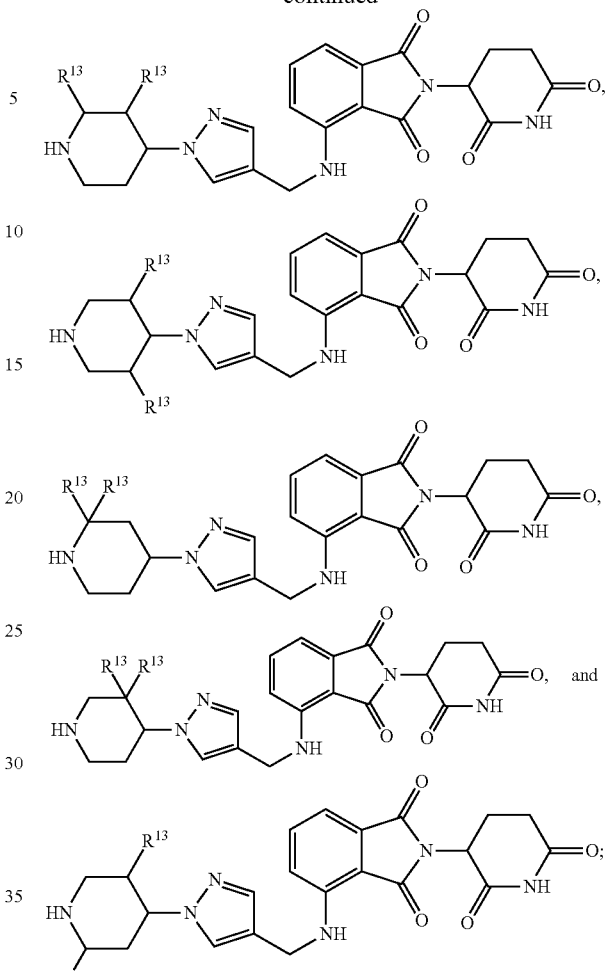

or a pharmaceutically acceptable salt, N-oxide, isotopic derivative, or prodrug thereof, optionally in a pharmaceutically acceptable carrier to form a composition.

In an alternative aspect, a compound is provided of Formula V:

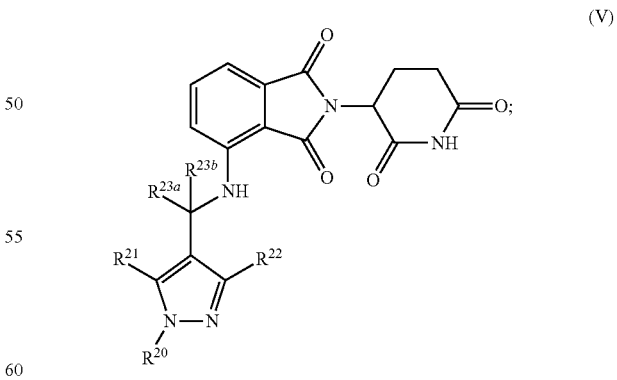

(V)

or a pharmaceutically acceptable salt, N-oxide, isotopic derivative, or prodrug thereof, optionally in a pharmaceutically acceptable carrier to form a composition;

wherein:

$R^{20}$ is heterocycle (typically $C_3$-$C_7$ monocyclic heterocycle or $C_7$-$C_{11}$ multicyclic heterocycle containing 1, 2, or 3 heteroatoms selected from N, O, and S) substituted with 1, 2, 3, or 4 substituents independently selected from alkyl (typically $C_1$-$C_6$alkyl), alkenyl (typically $C_2$-$C_6$alkenyl), alkynyl (typically $C_2$-$C_6$alkynyl), halogen, cyano, heteroaryl, aryl, cycloalkyl (typically $C_3$-$C_6$ monocyclic cycloalkyl or $C_5$-$C_9$ multicyclic fused, bridged, or spiro cycloalkyl), heterocycle (typically $C_3$-$C_7$ monocyclic heterocycle or $C_7$-$C_{11}$ multicyclic heterocycle containing 1, 2, or 3 heteroatoms selected from N, O, and S), —$NR^2R^2$, —$OR^2$, —$NR^2$—C(O)—$R^{24}$, —O—C(O)—$R^{24}$, —C(O)—$R^{24}$, —$SO_2R^{24}$, and $R^{24}$; wherein the heterocycle group is only substituted such that no N—O or N—N bonds are formed, for example piperidine cannot be substituted with $OR^2$ on the nitrogen atom;

$R^{21}$ and $R^{22}$ are independently selected from hydrogen, alkyl (typically $C_1$-$C_6$alkyl), cycloalkyl (typically $C_3$-$C_6$ monocyclic cycloalkyl or $C_5$-$C_9$ multicyclic fused, bridged, or spiro cycloalkyl), alkenyl (typically $C_2$-$C_6$alkenyl), alkynyl (typically $C_2$-$C_6$alkynyl), —($C_2$-$C_6$alkenylene)-cycloalkyl (typically $C_3$-$C_6$ monocyclic cycloalkyl or $C_5$-$C_9$ multicyclic fused, bridged, or spiro cycloalkyl), —($C_2$-$C_6$alkynylene)-cycloalkyl (typically $C_3$-$C_6$ monocyclic cycloalkyl or $C_5$-$C_9$ multicyclic fused, bridged, or spiro cycloalkyl), halogen, and cyano;

$R^{23a}$ and $R^{23b}$ are independently selected from hydrogen, alkyl (typically $C_1$-$C_6$alkyl), cycloalkyl (typically $C_3$-$C_6$ monocyclic cycloalkyl or $C_5$-$C_9$ multicyclic fused, bridged, or spiro cycloalkyl), and —($C_1$-$C_6$alkylene)-$NR^2R^2$;

or $R^{21}$ and $R^{23a}$ are joined together with the carbons to which they are attached to form a 5- to 6-membered carbocyclic ring;

or $R^{22}$ and $R^{23a}$ are joined together with the carbons to which they are attached to form a 5- to 6-membered carbocyclic ring;

$R^{24}$ is selected at each occurrence from alkyl (typically $C_1$-$C_6$alkyl), alkenyl (typically $C_2$-$C_6$alkenyl), alkynyl (typically $C_2$-$C_6$alkynyl), haloalkyl (typically $C_1$-$C_6$haloalkyl), cycloalkyl (typically $C_3$-$C_6$ monocyclic cycloalkyl or $C_5$-$C_9$ multicyclic fused, bridged, or spiro cycloalkyl), heteroaryl, heterocycle (typically $C_3$-$C_7$ monocyclic heterocycle or $C_7$-$C_{11}$ multicyclic heterocycle containing 1, 2, or 3 heteroatoms selected from N, O, and S), aryl, —O-cycloalkyl (typically $C_3$-$C_6$ monocyclic cycloalkyl or $C_5$-$C_9$ multicyclic fused, bridged, or spiro cycloalkyl), —O-aryl, —O-heteroaryl, —O-heterocycle (typically $C_3$-$C_7$ monocyclic heterocycle or $C_7$-$C_{11}$ multicyclic heterocycle containing 1, 2, or 3 heteroatoms selected from N, O, and S), —O-alkyl (typically $C_1$-$C_6$alkyl), —$NR^2$-cycloalkyl (typically $C_3$-$C_6$ monocyclic cycloalkyl or $C_5$-$C_9$ multicyclic fused, bridged, or spiro cycloalkyl), —$NR^2$-aryl, —$NR^2$-heteroaryl, —$NR^2$-heterocycle (typically $C_3$-$C_7$ monocyclic heterocycle or $C_7$-$C_{11}$ multicyclic heterocycle containing 1, 2, or 3 heteroatoms selected from N, O, and S), —$NR^2$-alkyl (typically $C_1$-$C_6$alkyl), —$CH_2$-cycloalkyl (typically $C_3$-$C_6$ monocyclic cycloalkyl or $C_5$-$C_9$ multicyclic fused, bridged, or spiro cycloalkyl), —$CH_2$-aryl, —$CH_2$-heteroaryl, —$CH_2$-heterocycle (typically $C_3$-$C_7$ monocyclic heterocycle or $C_7$-$C_{11}$ multicyclic heterocycle containing 1, 2, or 3 heteroatoms selected from N, O, and S), —$OR^2$, and —$NR^2R^2$; wherein each $R^{24}$ is optionally substituted with 1, 2, 3, or 4 groups independently selected from $R^{25}$; and $R^{25}$ is selected at each occurrence from: alkyl (typically $C_1$-$C_6$alkyl); alkenyl (typically $C_2$-$C_6$alkenyl); alkynyl (typically $C_2$-$C_6$alkynyl); haloalkyl (typically $C_1$-$C_6$haloalkyl); cycloalkyl (typically $C_3$-$C_6$ monocyclic cycloalkyl or $C_5$-$C_9$ multicyclic fused, bridged, or spiro cycloalkyl); heterocycle (typically $C_3$-$C_7$ monocyclic heterocycle or $C_7$-$C_{11}$ multicyclic heterocycle containing 1, 2, or 3 heteroatoms selected from N, O, and S); aryl optionally substituted with 1, 2, or 4 groups independently selected from alkyl, alkoxy, or halogen; heteroaryl optionally substituted with 1, 2, or 3 groups independently selected from alkyl, alkoxy, or halogen; —$CH_2$-cycloalkyl (typically $C_3$-$C_6$ monocyclic cycloalkyl or $C_5$-$C_9$ multicyclic fused, bridged, or spiro cycloalkyl); —$CH_2$-aryl optionally substituted with 1, 2, or 3 groups independently selected from alkyl, alkoxy, or halogen; —$CH_2$-heteroaryl optionally substituted with 1, 2, or 3 groups independently selected from alkyl, alkoxy, or halogen; —$CH_2$-heterocycle (typically $C_3$-$C_7$ monocyclic heterocycle or $C_7$-$C_{11}$ multicyclic heterocycle containing 1, 2, or 3 heteroatoms selected from N, O, and S); —$CH_2$—NH—C(O) $CH_3$; —C(O)-cycloalkyl (typically $C_3$-$C_6$ monocyclic cycloalkyl or $C_5$-$C_9$ multicyclic fused, bridged, or spiro cycloalkyl); —C(O)-aryl optionally substituted with 1, 2, or 3 groups independently selected from alkyl, alkoxy, or halogen; —C(O)-heteroaryl optionally substituted with 1, 2, or 3 groups independently selected from alkyl, alkoxy, or halogen; —C(O)-heterocycle (typically $C_3$-$C_7$ monocyclic heterocycle or $C_7$-$C_{11}$ multicyclic heterocycle containing 1, 2, or 3 heteroatoms selected from N, O, and S); —C(O)-alkyl (typically $C_1$-$C_6$alkyl); —($C_2$-$C_6$alkenylene)-aryl; —($C_2$-$C_6$alkynylene)-aryl; —($C_2$-$C_6$alkenylene)-cycloalkyl (typically $C_3$-$C_6$ monocyclic cycloalkyl or $C_5$-$C_9$ multicyclic fused, bridged, or spiro cycloalkyl); —($C_2$-$C_6$alkynylene)-cycloalkyl (typically $C_3$-$C_6$ monocyclic cycloalkyl or $C_5$-$C_9$ multicyclic fused, bridged, or spiro cycloalkyl); —C(O)—($C_1$-$C_6$alkylene)-O-alkyl; —C(O)—($C_1$-$C_6$alkylene)-aryl; cyano; halogen; —$OR^2$; and —$NR^2R^2$; or two $R^{25}$ groups may join together with the atoms to which they are attached to form a 3- to 7-membered carbocyclic ring;

and all other variables are as defined herein.

In an alternative aspect, a compound is provided of Formula VI:

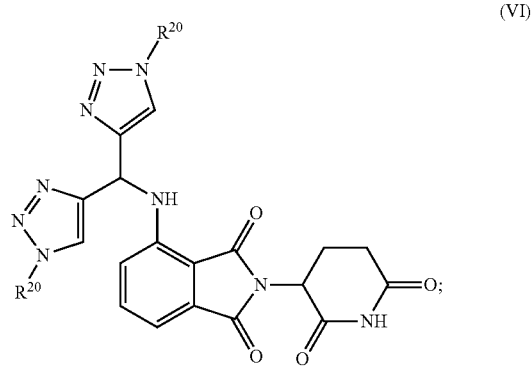

(VI)

or a pharmaceutically acceptable salt, N-oxide, isotopic derivative, or prodrug thereof, optionally in a pharmaceutically acceptable carrier to form a composition;

wherein all variables are defined as herein.

In one embodiment the compounds described herein bind to cereblon, increasing the interaction between cereblon and Ikaros or Aiolos and leading to the subsequent ubiquitination and degradation in the proteasome of the protein.

In one embodiment, therefore, based on this discovery, compounds and methods are presented for the treatment of a patient with a disorder mediated by Ikaros or Aiolos. Ikaros or Aiolos are targeted for selective degradation that includes administering an effective amount of a selected compound as described herein alone or in combination to a patient (typically a human) in need thereof, optionally in a pharmaceutically acceptable carrier to form a composition. In one embodiment, the disorder is a lymphoid disorder. In one embodiment, the disorder is a leukemia. In one embodiment, the disorder is a lymphoid leukemia. In one embodiment, the disorder is a lymphoblastic leukemia. In one embodiment, the disorder is a hematological malignancy, for example multiple myeloma, a myelodysplastic syndrome such as 5q-syndrome, acute lymphoblastic leukemia, chronic lymphocytic leukemia, Hodgkin's lymphoma, non-Hodgkin's lymphoma, or chronic lymphocytic leukemia.

In another embodiment, a selected compound of the present invention is administered to achieve immunomodulation or to reduce angiogenesis.

In other embodiments, compounds and methods are presented for the treatment of a disorder which can be treated by thalidomide, pomalidomide, or lenalidomide. Non-limiting examples of disorders that may be treated by thalidomide, pomalidomide, or lenalidomide include, but are not limited to, benign growth, neoplasm, tumor, cancer, abnormal cellular proliferation, immune disorder, inflammatory disorder, graft-versus-host rejection, viral infection, bacterial infection, an amyloid-based proteinopathy, a proteinopathy, or a fibrotic disorder. Further, other disorders are described below which can be treated with an effective amount of a compound described herein.

In certain embodiments any of the compounds described herein have at least one desired isotopic substitution of an atom, at an amount above the natural abundance of the isotope, i.e., enriched. In one embodiment, the compound includes a deuterium or multiple deuterium atoms.

Other features and advantages of the present invention will be apparent from the following detailed description and claims.

Thus, the present invention includes at least the following features:
(a) a selected compound as described herein, or a pharmaceutically acceptable salt, isotopic derivative (including the deuterated derivative), or prodrug thereof;
(b) a compound as described herein, or a pharmaceutically acceptable salt, isotopic derivative (including the deuterated derivative), or prodrug thereof for the treatment of a disorder that is mediated by Ikaros or Aiolos;
(c) use of a compound as described herein in an effective amount in the treatment of a patient, typically a human, with any of the disorders described herein, including those mediated by Ikaros or Aiolos;
(d) use of a compound as described herein or a pharmaceutically acceptable salt, isotopic derivative (including a deuterated derivative), or prodrug thereof in the manufacture of a medicament for the treatment of a medical disorder sensitive to the compound, as further described herein;
(e) a method of manufacturing a medicament for the treatment of a disorder in a host characterized in that the compound as described herein is used in the manufacture;
(f) a compound as described herein, or a pharmaceutically acceptable salt, isotopic derivative (including a deuterated derivative), or prodrug thereof that is useful in the treatment of cancer in a host, including any of the cancers described herein;
(g) use of the compound as described herein, or a pharmaceutically acceptable salt, isotopic derivative (including a deuterated derivative), or prodrug thereof in the manufacture of a medicament for the treatment of cancer, including any of the cancers described herein;
(h) a method of manufacturing a medicament for the therapeutic use of treating a cancer, including any of the cancers described herein, characterized in that a compound as described herein is used in the manufacture;
(i) a compound as described herein, or a pharmaceutically acceptable salt, isotopic derivative (including a deuterated derivative), or prodrug thereof that is useful in the treatment of a tumor in a host, including any of the tumors described herein;
(j) use of the compound as described herein, or a pharmaceutically acceptable salt, isotopic derivative (including a deuterated derivative), or prodrug thereof in the manufacture of a medicament for the treatment of a tumor, including any of the cancers described herein;
(k) a method of manufacturing a medicament for the therapeutic use of treating a tumor, including any of the tumors described herein, characterized in that a compound as described herein is used in the manufacture;
(l) a compound as described herein, or a pharmaceutically acceptable salt, isotopic derivative (including a deuterated derivative), or prodrug thereof that is useful in the treatment of an immune, autoimmune, or inflammatory disorder in a host;
(m) use of the compound as described herein, or a pharmaceutically acceptable salt, isotopic derivative (including a deuterated derivative), or prodrug thereof in the manufacture of a medicament for the treatment of an immune, autoimmune, or inflammatory disorder;
(n) a method of manufacturing a medicament for the therapeutic use of treating an immune, autoimmune, or inflammatory disorder, characterized in that a compound as described herein is used in the manufacture;
(o) a compound as described herein, or a pharmaceutically acceptable salt, isotopic derivative (including a deuterated derivative), or prodrug thereof that is useful in the treatment of a hematological malignancy such as multiple myeloma, leukemia, lymphoblastic leukemia, chronic lymphocytic leukemia, Hodgkin's lymphoma, non-Hodgkin's lymphoma, or chronic lymphocytic leukemia;
(p) use of the compound as described herein, or a pharmaceutically acceptable salt, isotopic derivative (including a deuterated derivative), or prodrug thereof in the manufacture of a medicament for the treatment of a hematological malignancy multiple myeloma, leukemia, lymphoblastic leukemia, chronic lymphocytic leukemia, Hodgkin's lymphoma, non-Hodgkin's lymphoma, or chronic lymphocytic leukemia;
(q) a method of manufacturing a medicament for the therapeutic use of treating a hematological malignancy such as multiple myeloma, leukemia, lymphoblastic leukemia, chronic lymphocytic leukemia, Hodgkin's lymphoma, non-Hodgkin's lymphoma, or chronic lymphocytic leukemia, characterized in that a compound as described herein is used in the manufacture;
(r) a pharmaceutical composition comprising an effective host-treating amount of a compound as described herein or a pharmaceutically salt, isotopic derivative, or prodrug thereof with a pharmaceutically acceptable carrier or diluent;

(s) a compound as described herein as a mixture of enantiomers or diastereomers (as relevant), including as a racemate;

(t) a compound as described herein in enantiomerically or diastereomerically (as relevant) enriched form, including an isolated enantiomer or diastereomer (i.e. greater than 85, 90, 95, 97, or 99% pure); and (u) a process for the preparation of therapeutic products that contain an effective amount of a compound as described herein.

DETAILED DESCRIPTION OF THE INVENTION

I. Definitions

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice and testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Compounds are described using standard nomenclature. Unless defined otherwise, all technical and scientific terms used herein have the same meaning as is commonly understood by one of skill in the art to which this invention belongs.

In one embodiment of each compound described herein, the compound may be in the form of a racemate, enantiomer, mixture of enantiomers, diastereomer, mixture of diastereomers, tautomer, N-oxide, or isomer, such as a rotamer, as if each is specifically described unless specifically excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds described herein with at least one desired isotopic substitution of an atom, at an amount above the natural abundance of the isotope, i.e., enriched. Isotopes are atoms having the same atomic number but different mass numbers, i.e., the same number of protons but a different number of neutrons. If isotopic substitutions are used, the common replacement is at least one deuterium for hydrogen.

More generally, examples of isotopes that can be incorporated into compounds of the invention include isotopes of hydrogen, carbon, nitrogen, oxygen, fluorine, and chlorine such as $^2H$ $^3H$, $^{11}C$, $^{13}C$, $^{11}C$, $^{15}N$, $^{17}O$, $^{18}O$, $^{18}F$, $^{35}S$, and $^{36}Cl$ respectively. In one non-limiting embodiment, isotopically labelled compounds can be used in metabolic studies (with, for example $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. Additionally, any hydrogen atom present in the compound of the invention may be substituted with an $^{18}F$ atom, a substitution that may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively, or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any compound described herein. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compounds of the present invention may form a solvate with a solvent (including water). Therefore, in one non-limiting embodiment, the invention includes a solvated form of the compounds described herein. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C═O)NH$_2$ is attached through carbon of the keto (C═O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. In one non-limiting embodiment, the alkenyl contains from 2 to about 12 carbon atoms, more generally from 2 to about 6 carbon atoms or from 2 to about 4 carbon atoms. In certain embodiments the alkenyl is $C_2$, $C_2$-$C_3$, $C_2$-$C_4$, $C_2$-$C_5$, or $C_2$-$C_6$. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. In one non-limiting embodiment, the alkynyl contains from 2 to about 12 carbon atoms, more generally from 2 to about 6 carbon atoms or from 2 to about 4 carbon atoms. In certain embodiments the alkynyl is $C_2$, $C_2$-$C_3$, $C_2$-$C_4$, $C_2$-$C_5$, or $C_2$-$C_6$. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

"Halo" and "Halogen" is independently fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

As used herein, "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more cycloalkyl or heterocycle groups wherein the radical or point of attachment is on the aryl ring, and in such instances, the number of carbon atoms continue to designate the number of carbon atoms in the aryl ring system. The one or more fused cycloalkyl or heterocycle groups can be a 4 to 7-membered saturated or partially unsaturated cycloalkyl or heterocycle groups.

The term "heterocycle" denotes and partially saturated heteroatom-containing ring radicals, wherein there are 1, 2, 3, or 4 heteroatoms independently selected from nitrogen, sulfur, boron, silicone, and oxygen. Heterocyclic rings may comprise monocyclic 3-10 membered rings, as well as 5-16 membered bicyclic ring systems (which can include bridged, fused, and spiro-fused bicyclic ring systems). It does not include rings containing —O—O—, —O—S— or —S—S— portions. Examples of saturated heterocycle groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocycle radicals include but are not limited to, dihydrothienyl, dihydropyranyl, dihydrofuryl, and dihydrothiazolyl. Examples of partially saturated and saturated heterocycle groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-lH-lλ'-benzo[d]isothiazol-6-yl, dihydropyranyl, dihydrofuryl and dihydrothiazolyl.

"Heterocycle" also includes groups wherein the heterocyclic radical is fused/condensed with an aryl or carbocycle radical, wherein the point of attachment is the heterocycle ring. "Heterocycle" also includes groups wherein the heterocyclic radical is substituted with an oxo group

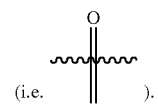

(i.e. ).

For example a partially unsaturated condensed heterocyclic group containing 1 to 5 nitrogen atoms, for example, indoline or isoindoline; a partially unsaturated condensed heterocyclic group containing 1 to 2 oxygen atoms and 1 to 3 nitrogen atoms; a partially unsaturated condensed heterocyclic group containing 1 to 2 sulfur atoms and 1 to 3 nitrogen atoms; and a saturated condensed heterocyclic group containing 1 to 2 oxygen or sulfur atoms.

The term "bicyclic heterocycle" denotes a heterocycle as defined herein wherein there is one bridged, fused, or spirocyclic portion of the heterocycle. The bridged, fused, or spirocyclic portion of the heterocycle can be a carbocycle, heterocycle, or aryl group as long as a stable molecule results. Unless excluded by context the term "heterocycle" includes bicyclic heterocycles. Bicyclic heterocycle includes groups wherein the fused heterocycle is substituted with an oxo group. Non-limiting examples of bicyclic heterocycles include:

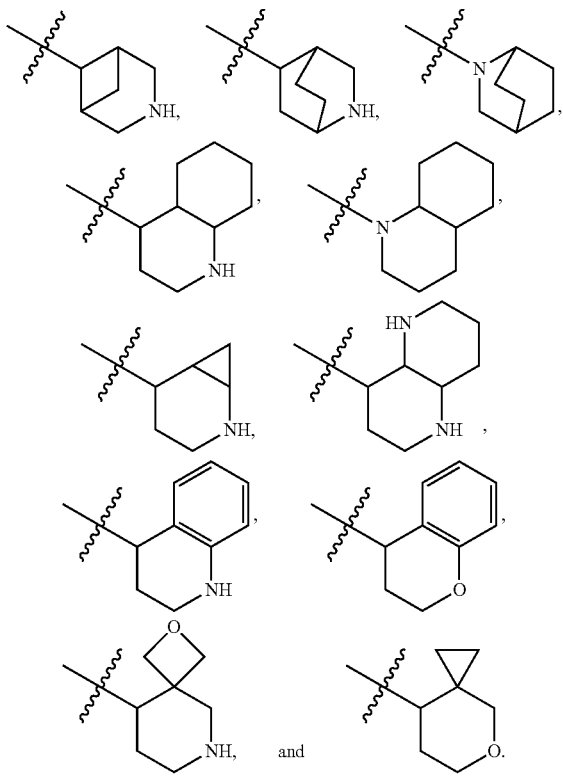

The term "heteroaryl" denotes stable aromatic ring systems that contain 1, 2, 3, or 4 heteroatoms independently selected from O, N, and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. In one embodiment the "heteroaryl" group is a 8, 9, or 10 membered bicyclic ring system. Examples of 8, 9, or 10 membered bicyclic heteroaryl groups include benzofurazanyl, benzothiophenyl, benzothiazolyl, benzoxazolyl, quinazolinyl, quinoxalinyl, naphthyridinyl, quinolinyl, isoquinolinyl, benzofuranyl, indolyl, indazolyl, and benzotriazolyl.

As used herein, "carbocyclic", "carbocycle" or "cycloalkyl" includes a saturated or partially unsaturated (i.e., not aromatic) group containing all carbon ring atoms and from 3 to 14 ring carbon atoms ("$C_{3-14}$ cycloalkyl") and zero heteroatoms in the non-aromatic ring system. In some embodiments, a cycloalkyl group has 3 to 10 ring carbon atoms ("$C_{3-10}$ cycloalkyl"). In some embodiments, a cycloalkyl group has 3 to 9 ring carbon atoms ("$C_{3-9}$ cycloalkyl"). In some embodiments, a cycloalkyl group has 3 to 8 ring carbon atoms ("$C_{3-8}$ cycloalkyl"). In some embodiments, a cycloalkyl group has 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{3-6}$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_3$), cyclohexenyl ($C_6$), cyclohexadienyl ($C_6$), and the like. Exemplary $C_{3-8}$ cycloalkyl groups include, without limitation, the aforementioned $C_{3-6}$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), and the like. Exemplary $C_{3-10}$ cycloalkyl groups include, without limitation, the aforementioned $C_{3-8}$ cycloalkyl groups as well as cyclononyl ($C_9$), cyclononenyl ($C_9$), cyclodecyl ($C_{10}$), cyclodecenyl ($C_{10}$), and the like. As the foregoing examples illustrate, in certain embodiments, the cycloalkyl group can be saturated or can contain one or more carbon-carbon double bonds. The term "cycloalkyl" also includes ring systems wherein the cycloalkyl ring, as defined above, is fused with one heterocycle, aryl or heteroaryl ring wherein the point of attachment is on the cycloalkyl ring, and in such instances, the number of carbons continue to designate the number of carbons in the carbocyclic ring system. The term "cycloalkyl" also includes ring systems wherein the cycloalkyl ring, as defined above, has a spirocyclic heterocycle, aryl or heteroaryl ring wherein the point of attachment is on the cycloalkyl ring, and in such instances, the number of carbons continue to designate the number of carbons in the carbocyclic ring system. The term "cycloalkyl" also includes bicyclic or polycyclic fused, bridged, or spiro ring systems that contain from 5 to 14 carbon atoms and zero heteroatoms in the non-aromatic ring system. Representative examples of "cycloalkyl" include, but are not limited to,

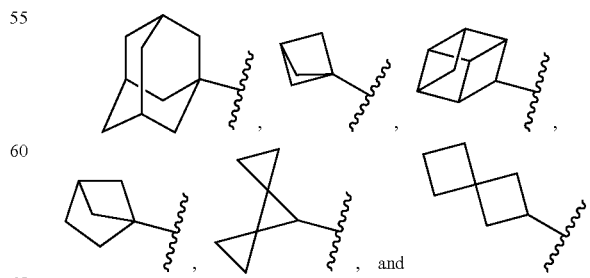

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein, means an amount which provides a therapeutic or prophylactic benefit.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Parenteral" administration of a compound includes, e.g., subcutaneous (s.c.), intravenous (i.v.), intramuscular (i.m.), or intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and the maximum number of amino acids present within the protein or peptide's sequence is typically comparable to that found in nature. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "pharmaceutical compositions" is a composition comprising at least one active agent such as a selected active compound as described herein, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, a "pharmaceutically acceptable salt" is a derivative of the disclosed compound in which the parent compound is modified by making inorganic and organic, acid or base addition salts thereof with a biologically acceptable lack of toxicity. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences*, 17th ed., Mack Publishing Company, Easton, Pa., p. 1418 (1985).

The term "carrier" means a diluent, excipient, or vehicle that an active agent is used or delivered in.

A "pharmaceutically acceptable excipient" means an excipient that is useful in preparing a pharmaceutical composition/combination that is generally safe, and neither biologically nor otherwise inappropriate for administration to a host, typically a human. In one embodiment, an excipient is used that is acceptable for veterinary use.

A "patient" or "host" or "subject" is a human or non-human animal in need of treatment, in an alternative embodiment prevention, of any of the disorders as specifically described herein, for example that is modulated by a natural (wild-type) or modified (non-wild type) protein that can be degraded according to the present invention, resulting in a therapeutic effect. Typically, the host is a human. A "host" may alternatively refer to for example, a mammal, primate (e.g., human), cow, sheep, goat, horse, dog, cat, rabbit, rat, mice, fish, bird and the like.

A "therapeutically effective amount" of a pharmaceutical composition/combination of this invention means an amount effective, when administered to a host, to provide a therapeutic benefit such as an amelioration of symptoms or reduction or diminution of the disease itself.

Throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

II. Compounds

Embodiments of "Alkyl"

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

Embodiments of "Haloalkyl"

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.
In one embodiment "haloalkyl" has one carbon and one halogen.
In one embodiment "haloalkyl" has one carbon and two halogens.
In one embodiment "haloalkyl" has one carbon and three halogens.
In one embodiment "haloalkyl" has two carbons.
In one embodiment "haloalkyl" has three carbons.
In one embodiment "haloalkyl" has four carbons.
In one embodiment "haloalkyl" has five carbons.
In one embodiment "haloalkyl" has six carbons.

Non-limiting examples of "haloalkyl" include:

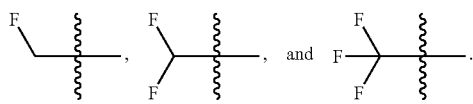

Additional non-limiting examples of "haloalkyl" include:

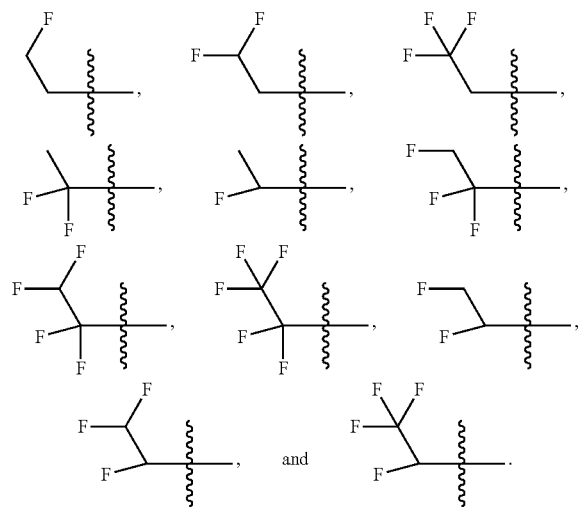

Additional non-limiting examples of "haloalkyl" include:

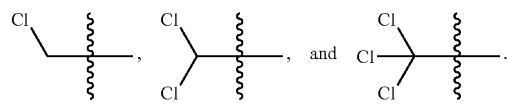

Additional non-limiting examples of "haloalkyl" include:

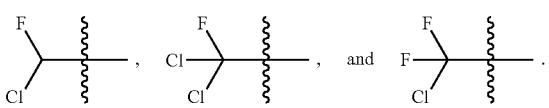

Embodiments of "Aryl"

In one embodiment "aryl" is a 6 carbon aromatic group (phenyl).

In one embodiment "aryl" is a 10 carbon aromatic group (napthyl).

In one embodiment "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example

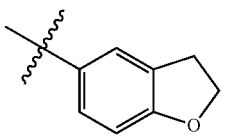

is an "aryl" group.

However,

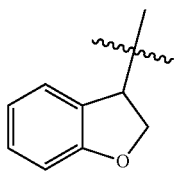 [SMILES: *C1COc2ccccc21]

is a "heterocycle" group.

In one embodiment "aryl" is a 6 carbon aromatic group fused to a cycloalkyl wherein the point of attachment is the aryl ring. Non-limiting examples of "aryl" include dihydroindene and tetrahydronaphthalene wherein the point of attachment for each group is on the aromatic ring.

For example

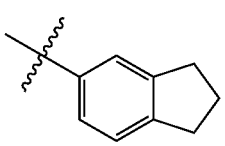 [SMILES: *c1ccc2c(c1)CCC2]

is an "aryl" group.

However,

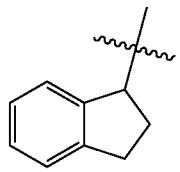 [SMILES: *C1CCc2ccccc21]

is a "cycloalkyl" group.

Embodiments of "Heteroaryl"

In one embodiment "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

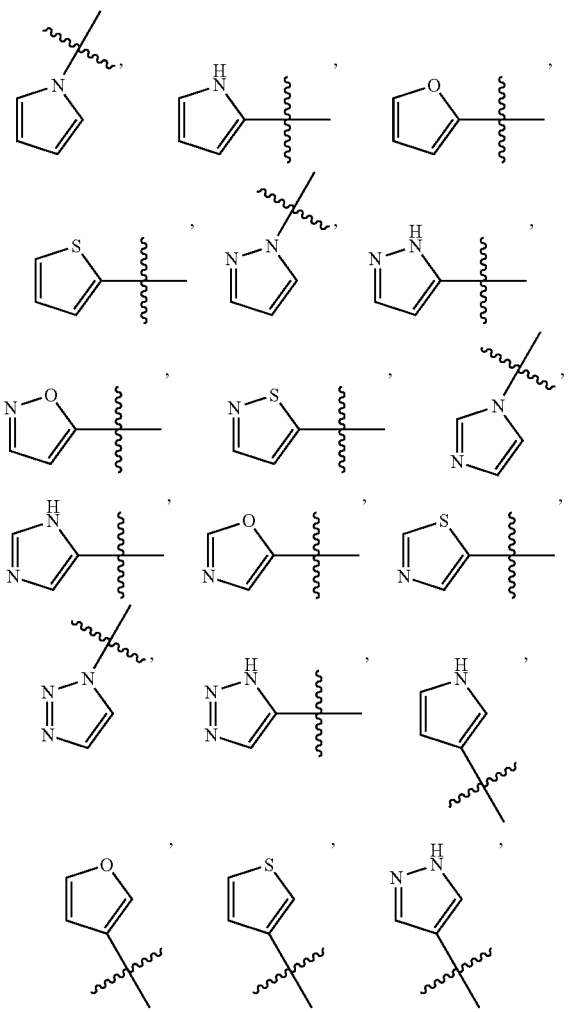

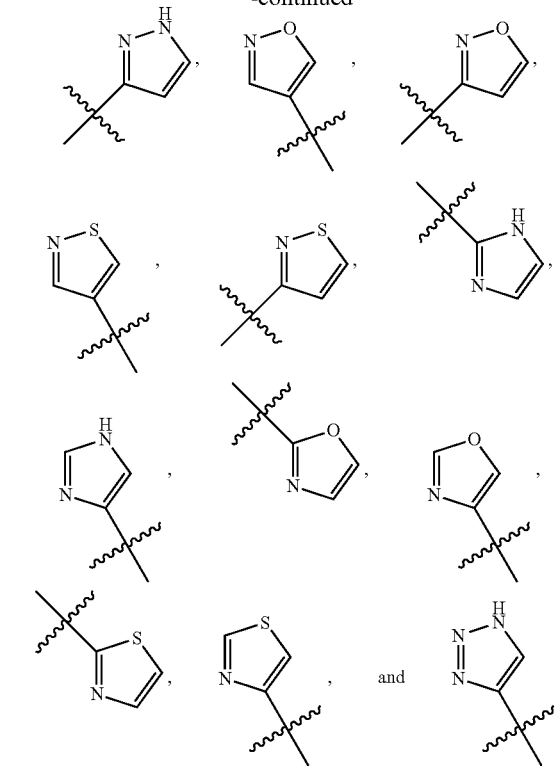

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

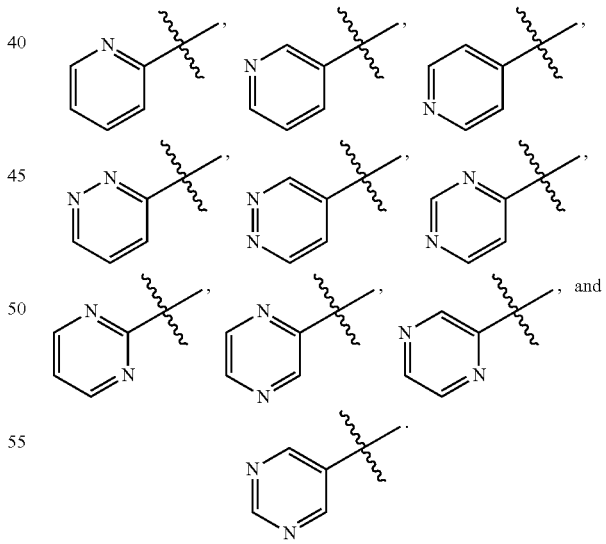

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

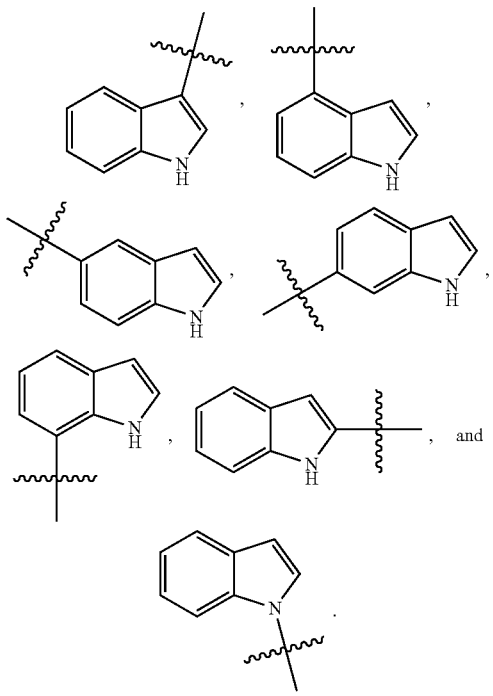

Additional non-limiting examples of "heteroaryl" groups that are bicyclic include:

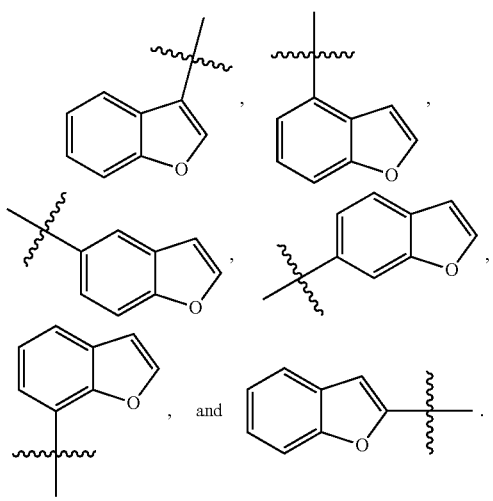

Additional non-limiting examples of "heteroaryl" groups that are bicyclic include:

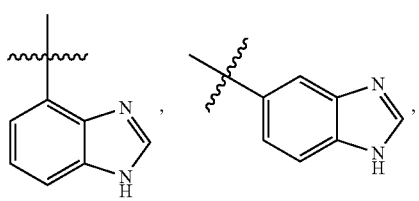

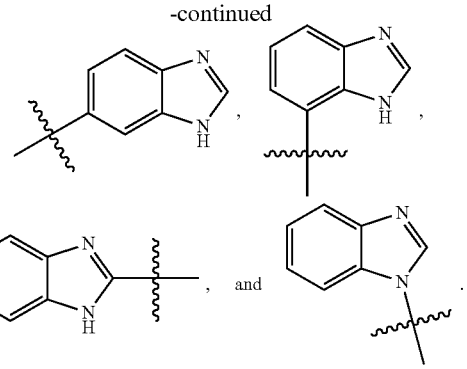

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

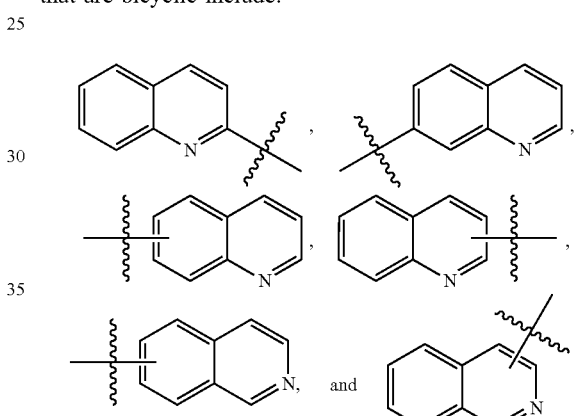

Embodiments of "Cycloalkyl"

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment "cycloalkyl" has three carbons.

In one embodiment "cycloalkyl" has four carbons.

In one embodiment "cycloalkyl" has five carbons.

In one embodiment "cycloalkyl" has six carbons.

In one embodiment "cycloalkyl" has seven carbons.

In one embodiment "cycloalkyl" has eight carbons.

In one embodiment "cycloalkyl" has nine carbons.

In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Additional non-limiting examples of "cycloalkyl" include dihydro-indene and tetrahydronaphthalene wherein the point of attachment for each group is on the cycloalkyl ring.

For example,

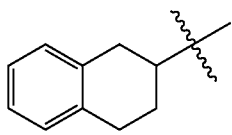 [SMILES: *C1CCc2ccccc2C1]

is an "cycloalkyl" group.

However,

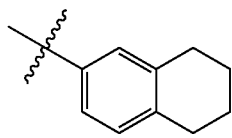 [SMILES: *c1ccc2c(c1)CCCC2]

is an "aryl" group.

Additional examples of "cycloalkyl" groups include

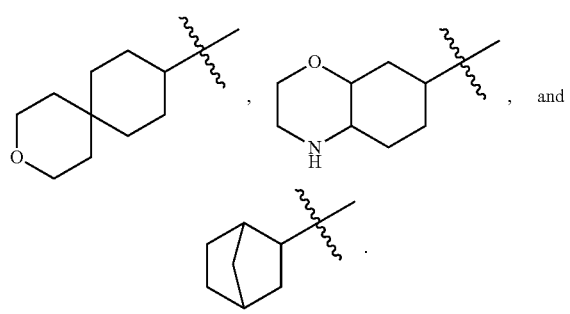

Embodiments of "Heterocycle"

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocyclic ring.

For example,

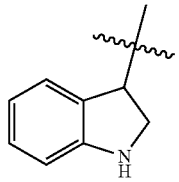 [SMILES: *C1CNc2ccccc21]

is a "heterocycle" group.

However,

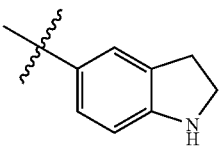 [SMILES: *c1ccc2c(c1)CCN2]

is an "aryl" group.

Non-limiting examples of "heterocycle" also include:

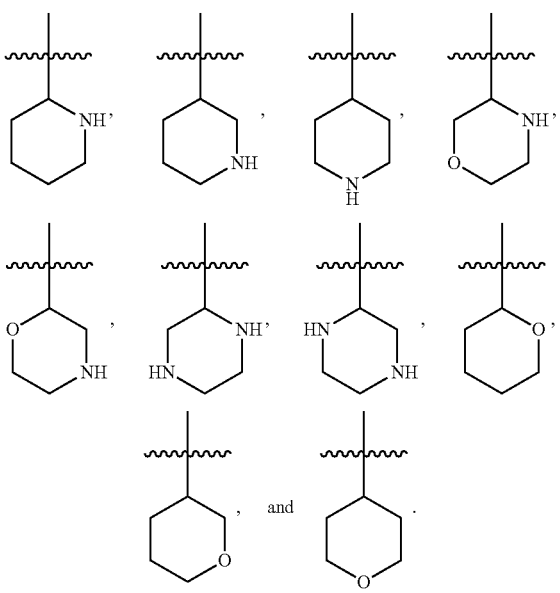

Additional non-limiting examples of "heterocycle" include:

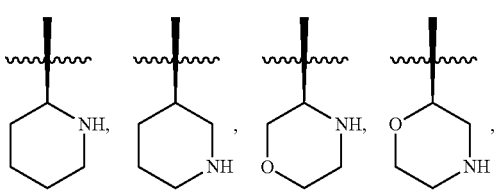

-continued

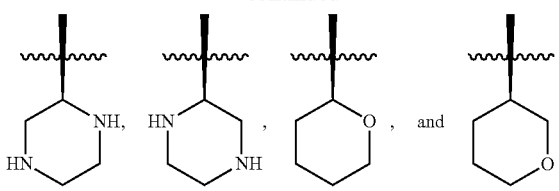

Additional non-limiting examples of "heterocycle" include:

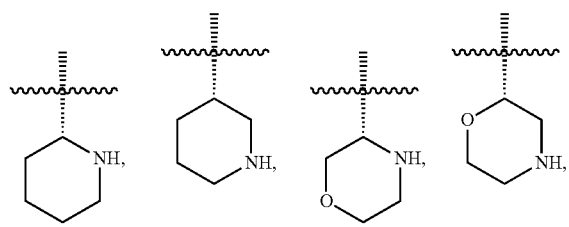

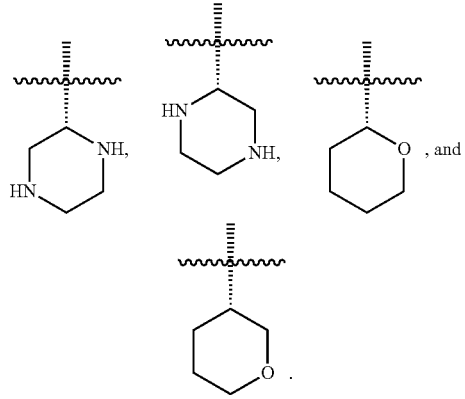

Non-limiting examples of "heterocycle" also include:

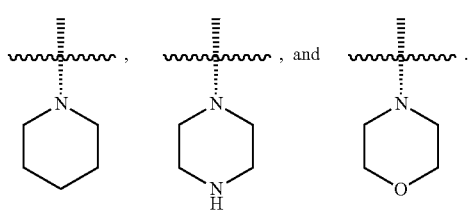

Non-limiting examples of "heterocycle" also include:

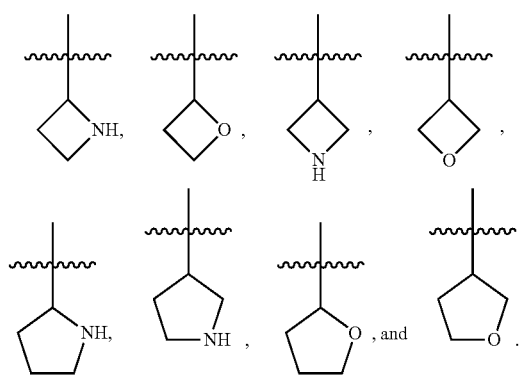

Additional non-limiting examples of "heterocycle" include:

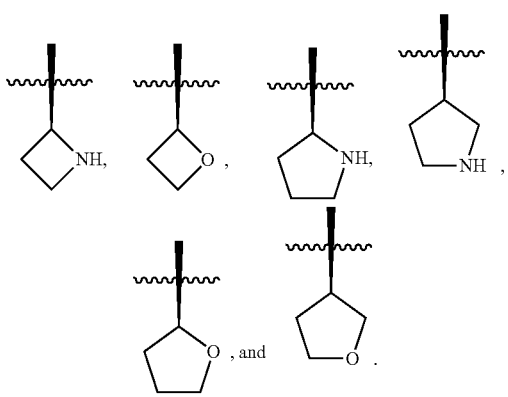

Additional non-limiting examples of "heterocycle" include:

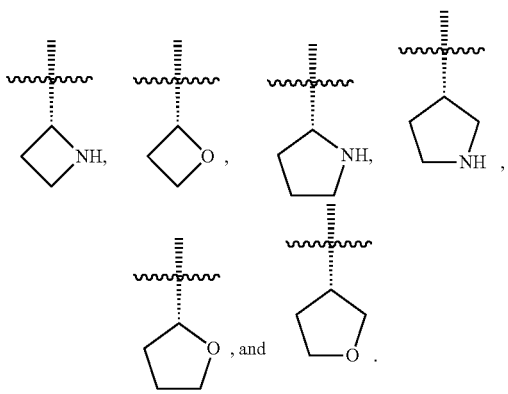

Optional Substituents

In one embodiment a group described herein that can be substituted with 1, 2, 3, or 4 substituents is substituted with one substituent.

In one embodiment a group described herein that can be substituted with 1, 2, 3, or 4 substituents is substituted with two substituents.

In one embodiment a group described herein that can be substituted with 1, 2, 3, or 4 substituents is substituted with three substituents.

In one embodiment a group described herein that can be substituted with 1, 2, 3, or 4 substituents is substituted with four substituents.

Embodiments of $R^1$

In one embodiment $R^1$ is selected from haloalkyl and alkyl; each of which is optionally substituted with 1, 2, 3, or 4 substituents independently selected from aryl, cycloalkyl, heterocycle —NR$^2$—C(O)—R$^3$, —O—C(O)—R$^3$, and —C(O)—R$^3$.

In one embodiment $R^1$ is selected from cycloalkyl and aryl; each of which is optionally substituted with 1, 2, 3, or 4 substituents independently selected from alkyl, alkenyl, alkynyl, halogen, cyano, heteroaryl, aryl, cycloalkyl, heterocycle, —NR$^2$R$^2$, —OR$^2$, —NR$^2$—C(O)—R$^3$, —O—C(O)—R$^3$, and —C(O)—R$^3$.

In one embodiment R¹ is selected from heteroaryl optionally substituted with 1, 2, 3, or 4 substituents independently selected from alkyl, alkenyl, halogen, cyano, heteroaryl, aryl, cycloalkyl, —NR⁴R⁴, —OR⁴, —NR²—C(O)—R³, —O—C(O)—R³, and —C(O)—R³.

In one embodiment R¹ is selected from alkenyl which is optionally substituted with 1, 2, 3, or 4 substituents independently selected from alkyl, alkenyl, alkynyl, halogen, cyano, heteroaryl, aryl, cycloalkyl, heterocycle, —NR²R², —OR², —NR²—C(O)—R³, —O—C(O)—R³, and —C(O)—R³.

In one embodiment R¹ is heterocycle substituted with 1, 2, 3, or 4 substituents independently selected from alkyl, alkenyl, alkynyl, halogen, cyano, heteroaryl, aryl, cycloalkyl, heterocycle, —NR²R², —OR², —NR²—C(O)—R³, —O—C(O)—R³, —C(O)—R³, —SO₂R⁵, —C(O)—R⁵, and R⁵.

In one embodiment R¹ is bicyclic heterocycle.
In one embodiment R¹ is alkyl.
In one embodiment R¹ is haloalkyl.
In one embodiment R¹ is cycloalkyl.
In one embodiment R¹ is aryl.
In one embodiment R¹ is phenyl.
In one embodiment R¹ is heteroaryl.
In one embodiment R¹ is alkenyl.
In one embodiment R¹ is heterocycle substituted with 1 alkyl substituent.
In one embodiment R¹ is heterocycle substituted with 2 alkyl substituents.
In one embodiment R¹ is heterocycle substituted with 1 substituent selected from —C(O)—R³, —SO₂R⁵, and —C(O)—R⁵.
In one embodiment R¹ is heterocycle substituted with 1 substituent selected from —C(O)—R³.
In one embodiment R¹ is heterocycle substituted with 1 substituent selected from —SO₂R⁵.
In one embodiment R¹ is heterocycle substituted with 1 substituent selected from —C(O)—R⁵.

In one embodiment, R¹ is selected from:

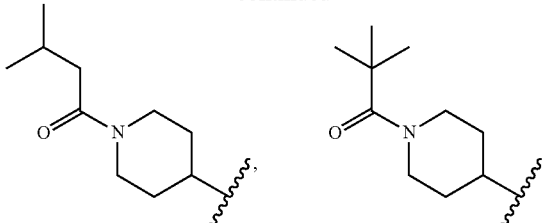
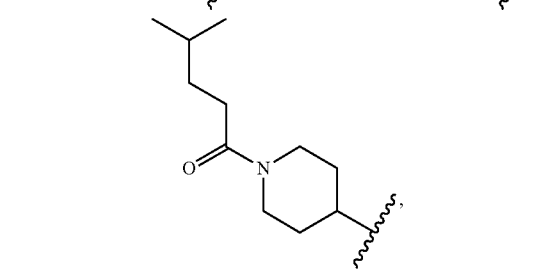
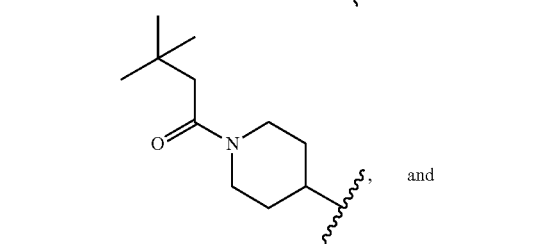
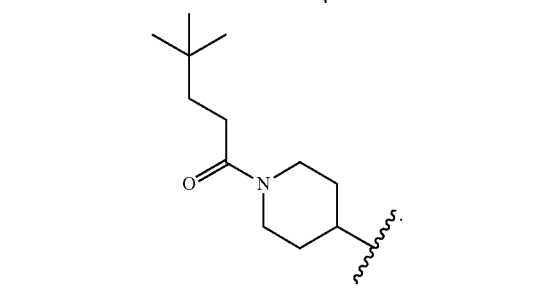

In one embodiment, R¹ is selected from:

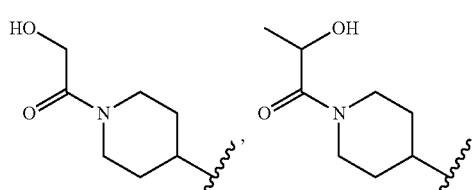
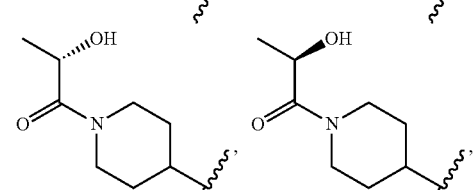
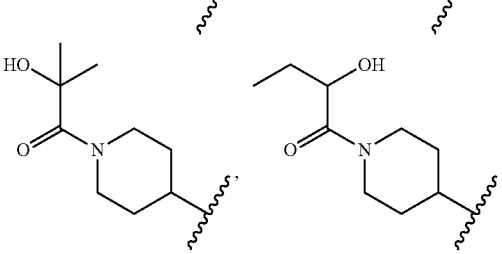

-continued
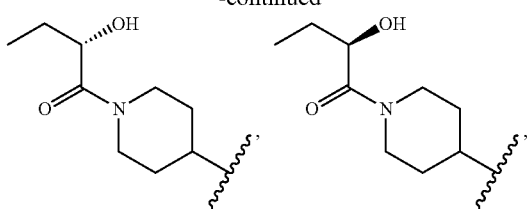
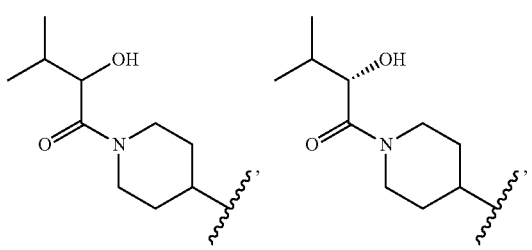
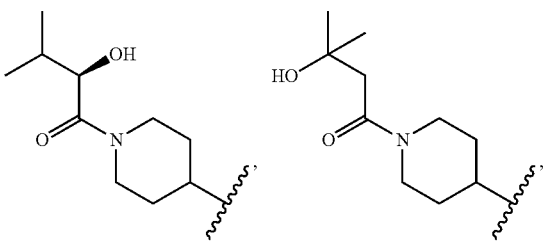
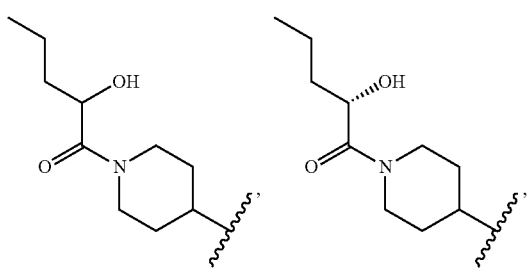
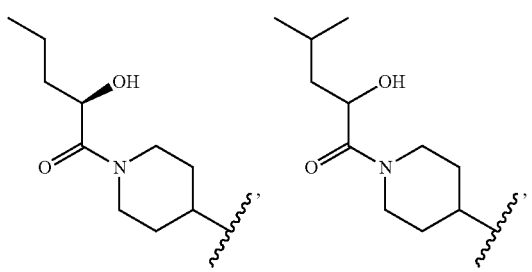
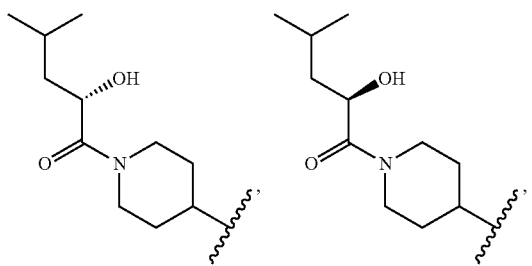
-continued
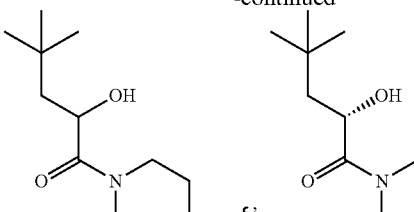
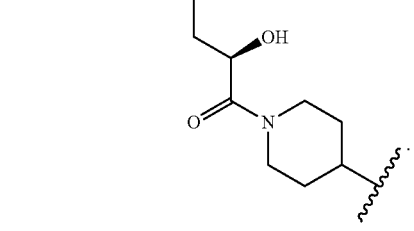
In one embodiment, R¹ is selected from:
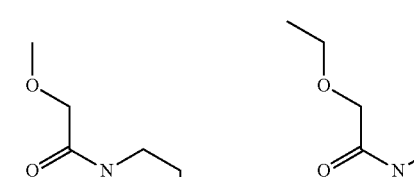
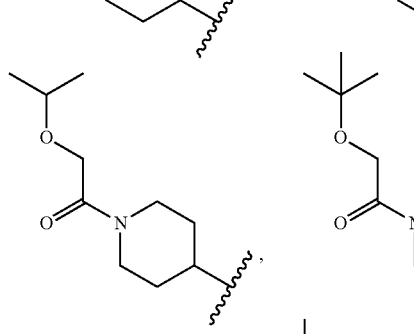
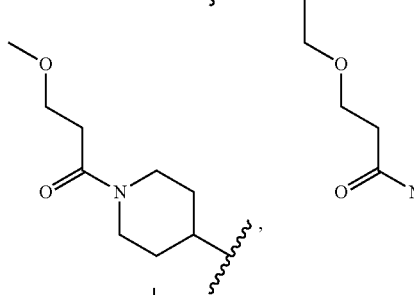
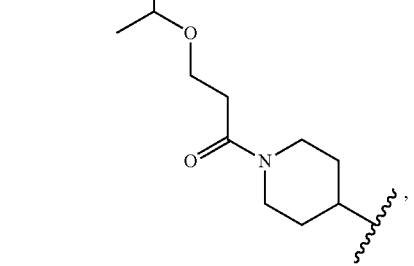

-continued
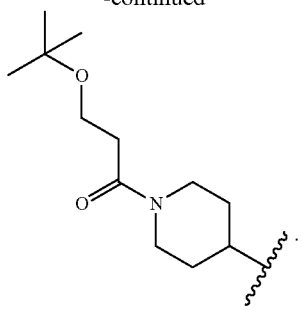
In one embodiment, R¹ is
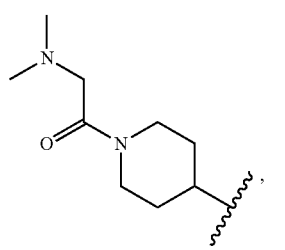 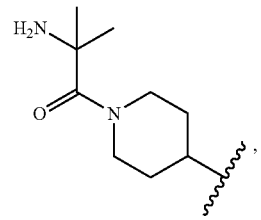
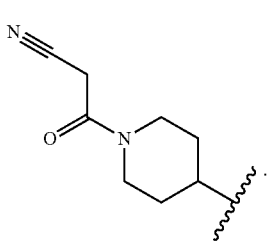 [SMILES: *C1CCN(C(=O)CC#N)CC1]
In one embodiment, R¹ is
In one embodiment, R¹ is selected from:
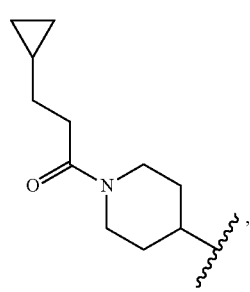 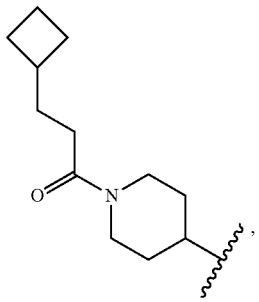
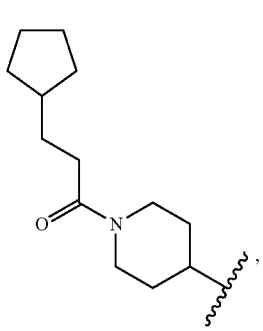 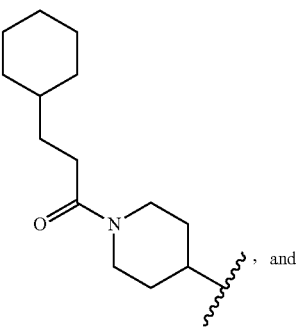, and
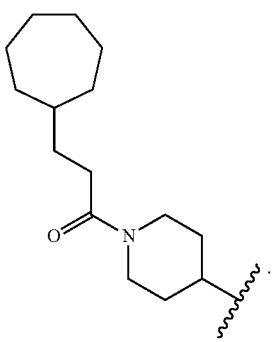
In one embodiment, R¹ is selected from:
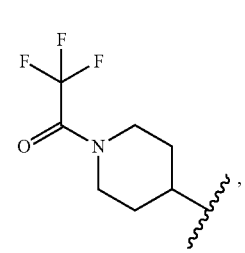 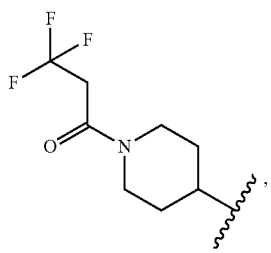
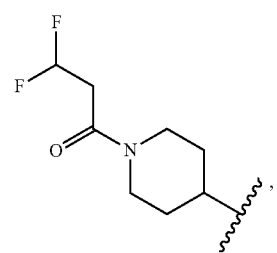 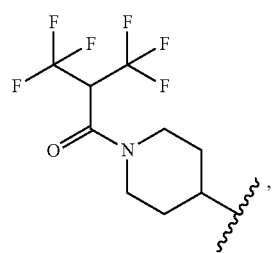

-continued
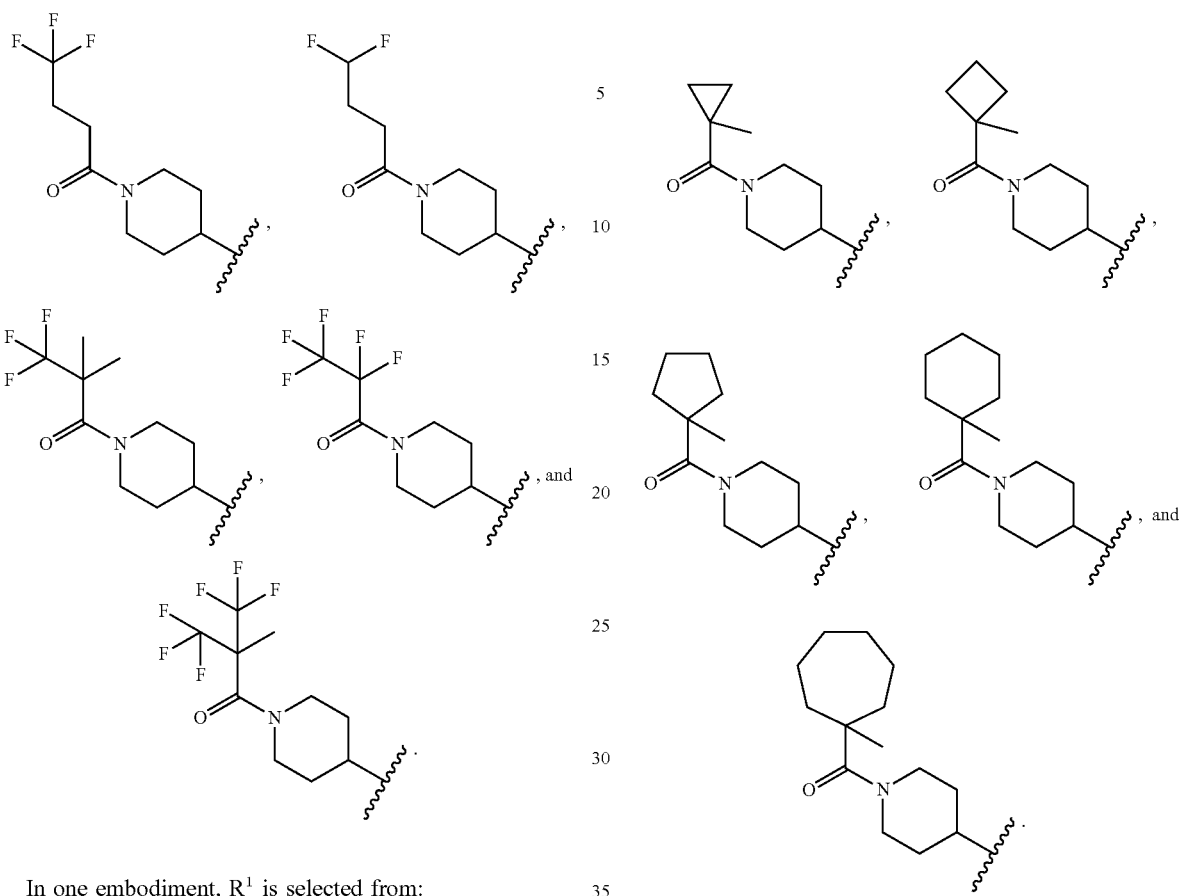
In one embodiment, R¹ is selected from:
In one embodiment, R¹ is selected from:
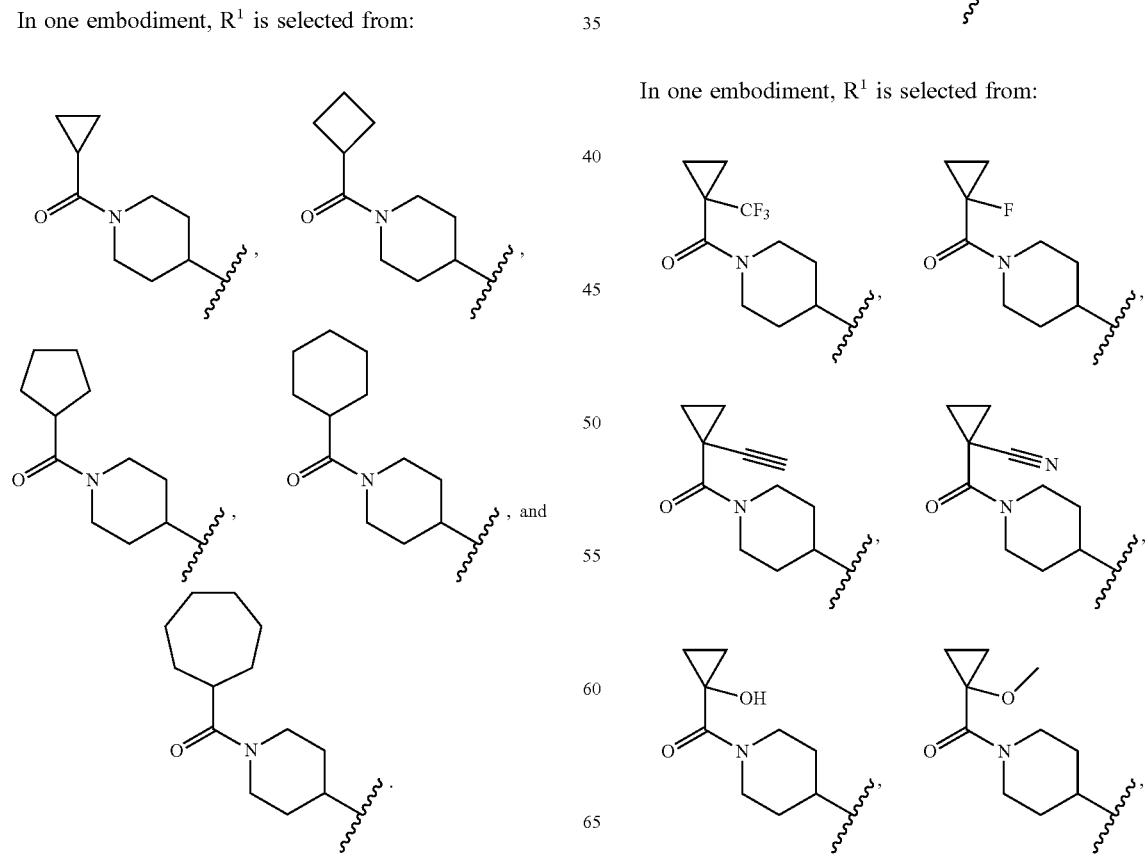
In one embodiment, R¹ is selected from:

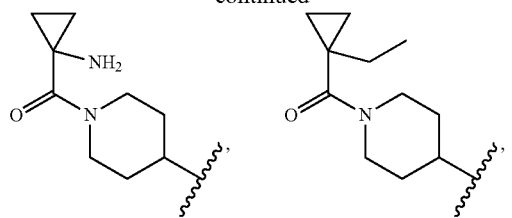
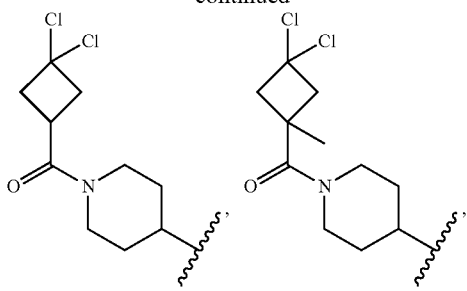
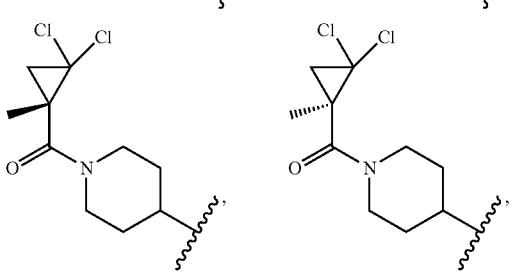
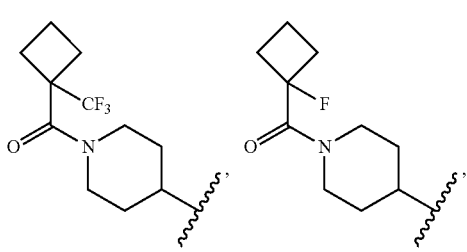
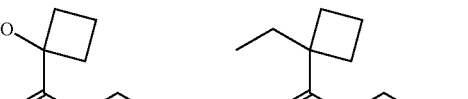
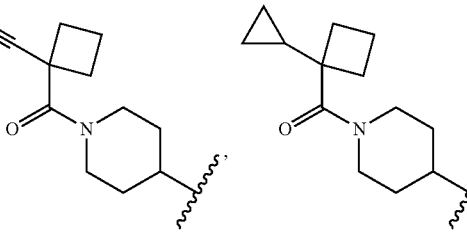
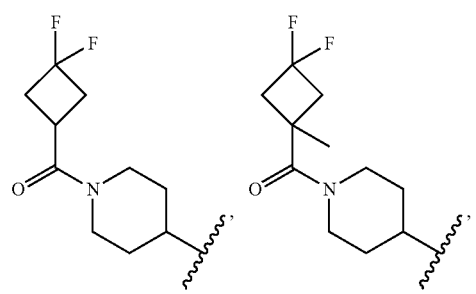
and
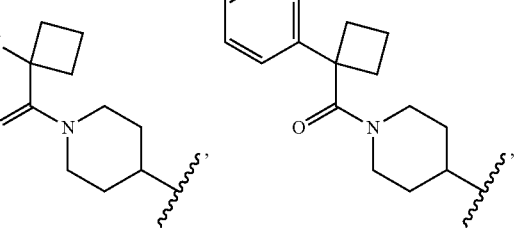
In one embodiment, R¹ is selected from:

-continued
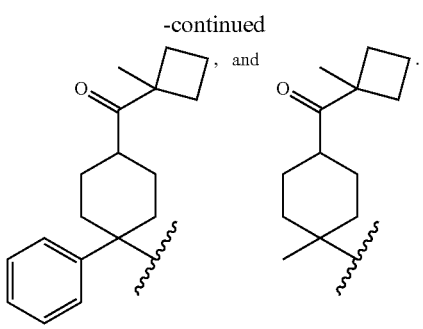
In one embodiment, R¹ is selected from:
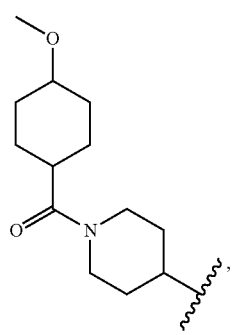
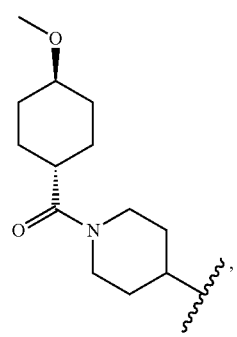
, and
In one embodiment, R¹ is selected from:
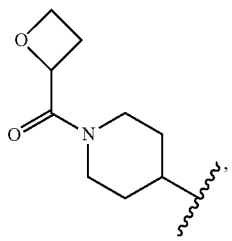 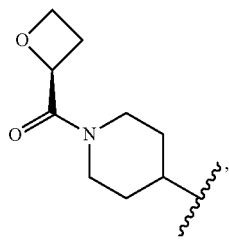
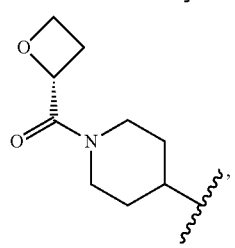 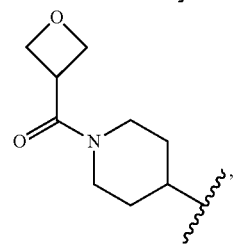
-continued
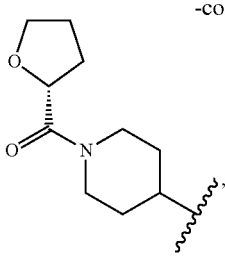 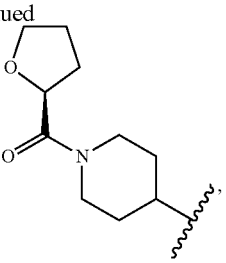
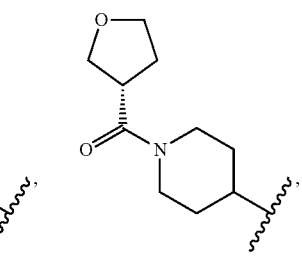
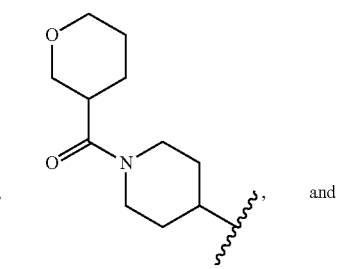
and
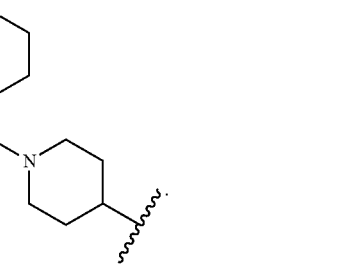
In one embodiment, R¹ is selected from:
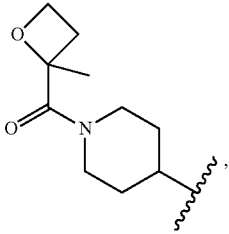 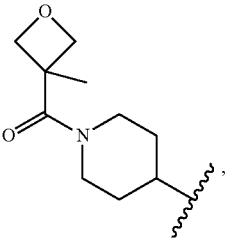
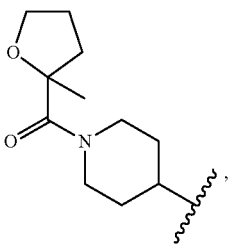 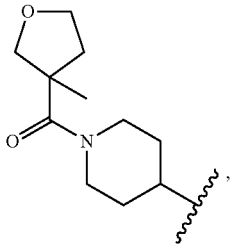

49
-continued
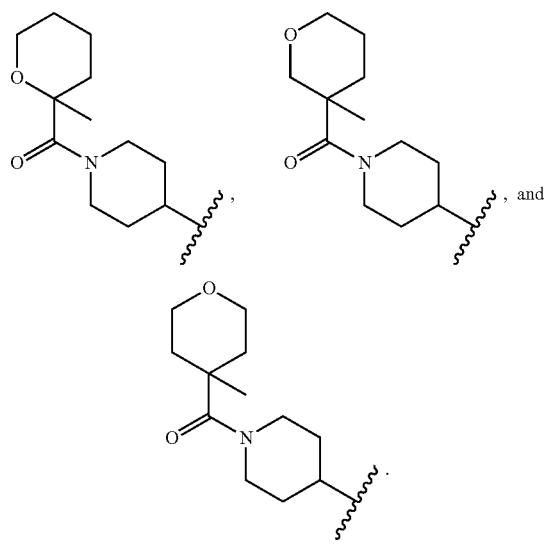
In one embodiment, R¹ is selected from:
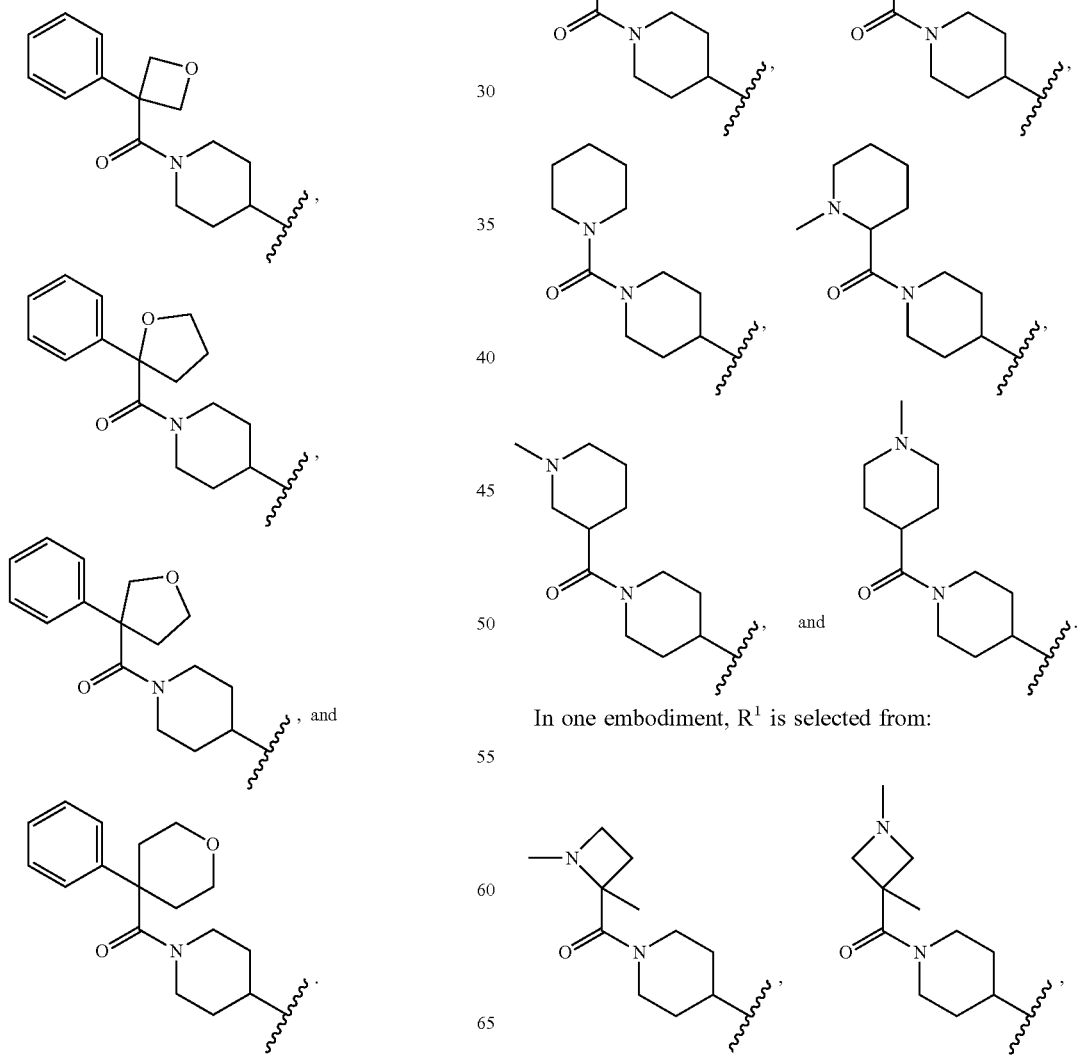
In one embodiment, R¹ is selected from:
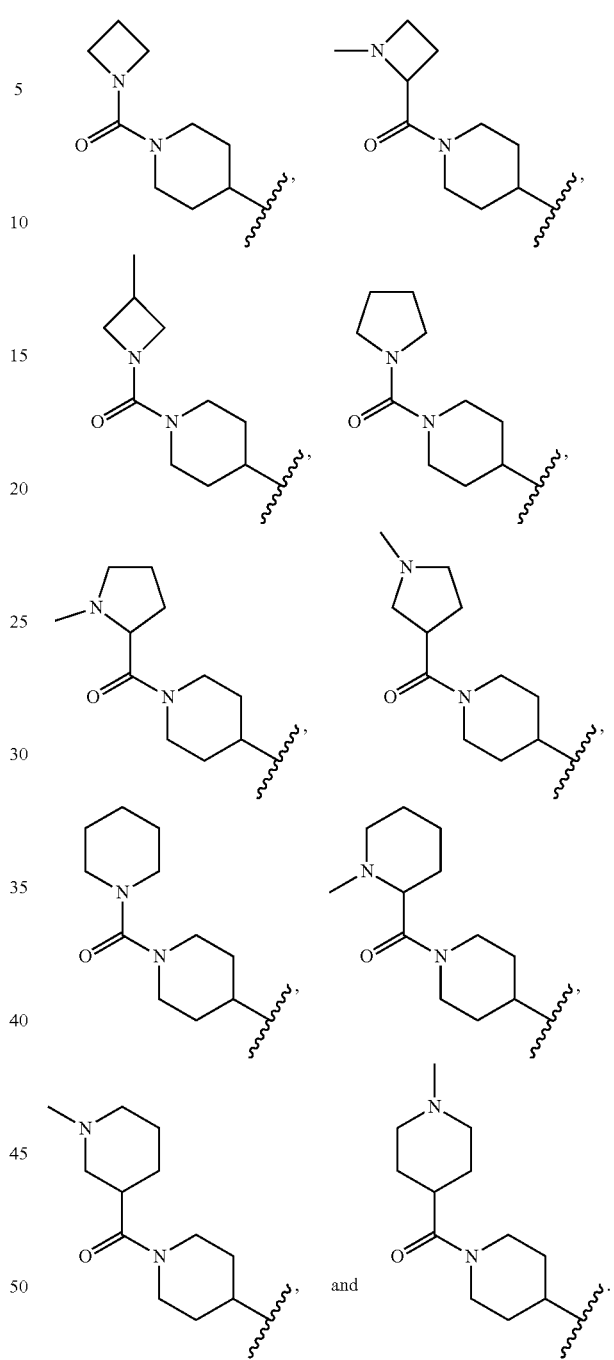
In one embodiment, R¹ is selected from:
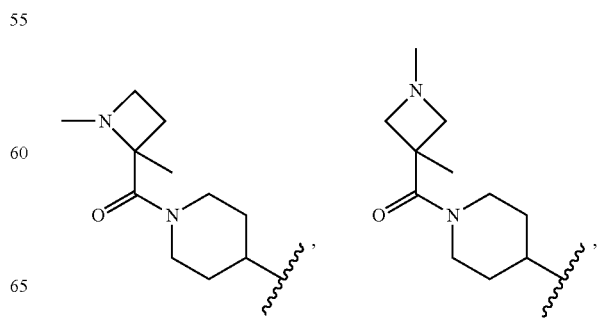

-continued
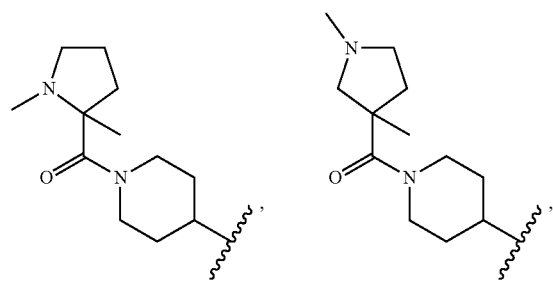
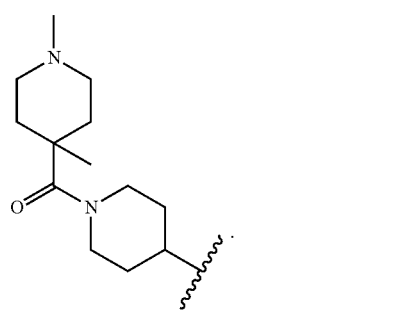
In one embodiment, $R^1$ is
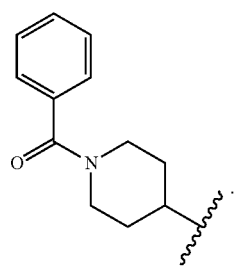 [SMILES: *C1CCN(C(=O)c2ccccc2)CC1]
In one embodiment, $R^1$ is selected from:
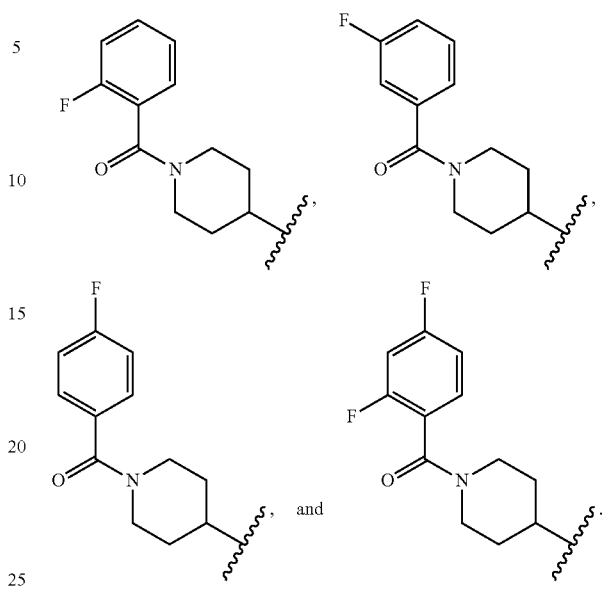
In one embodiment, $R^1$ is
In one embodiment, $R^1$ is selected from In one embodiment, R¹ is selected from
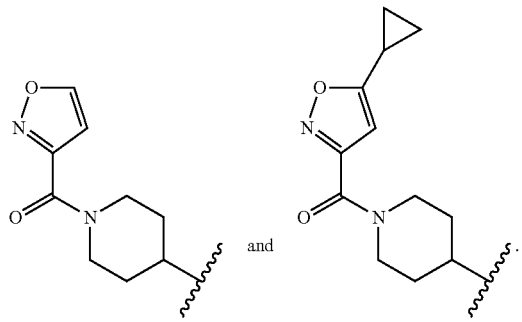 [SMILES: *C1CCN(C(=O)c2ccon2)CC1 ; *C1CCN(C(=O)c2cc(C3CC3)on2)CC1] and
In one embodiment, R¹ is
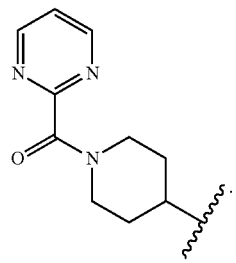 [SMILES: *C1CCN(C(=O)c2ncccn2)CC1]
In on embodiment, R¹ is
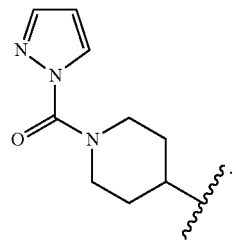 [SMILES: *C1CCN(C(=O)n2cccn2)CC1]
In one embodiment, R¹ is.
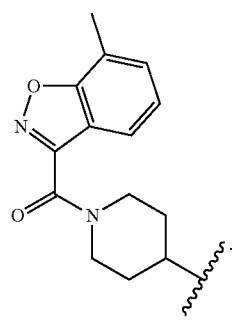 [SMILES: *C1CCN(C(=O)c2noc3c(C)cccc23)CC1]
In one embodiment, R¹ is
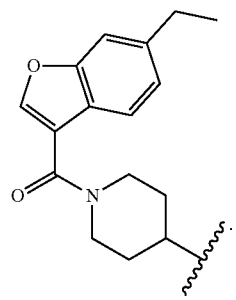 [SMILES: *C1CCN(C(=O)c2coc3cc(CC)ccc23)CC1]
In one embodiment, R¹ is
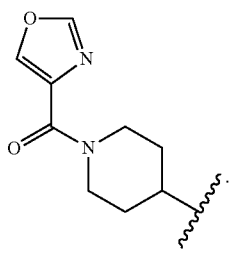 [SMILES: *C1CCN(C(=O)c2cocn2)CC1]
In one embodiment, R¹ is
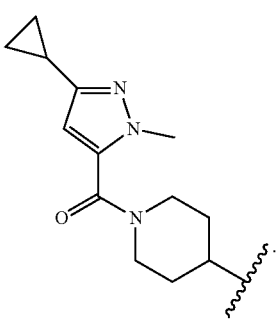 [SMILES: *C1CCN(C(=O)c2cc(C3CC3)nn2C)CC1]
In one embodiment, R¹ is selected from:
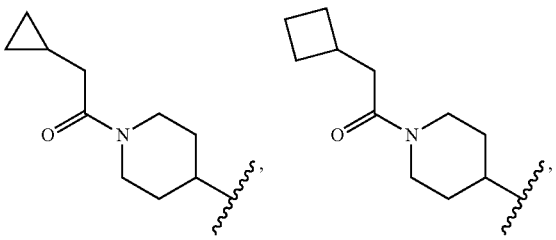
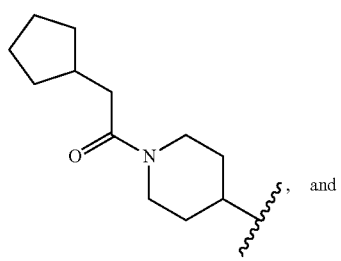, and
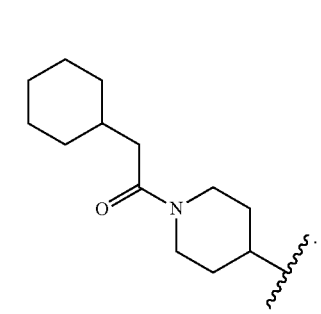

In one embodiment, R¹ is selected from:
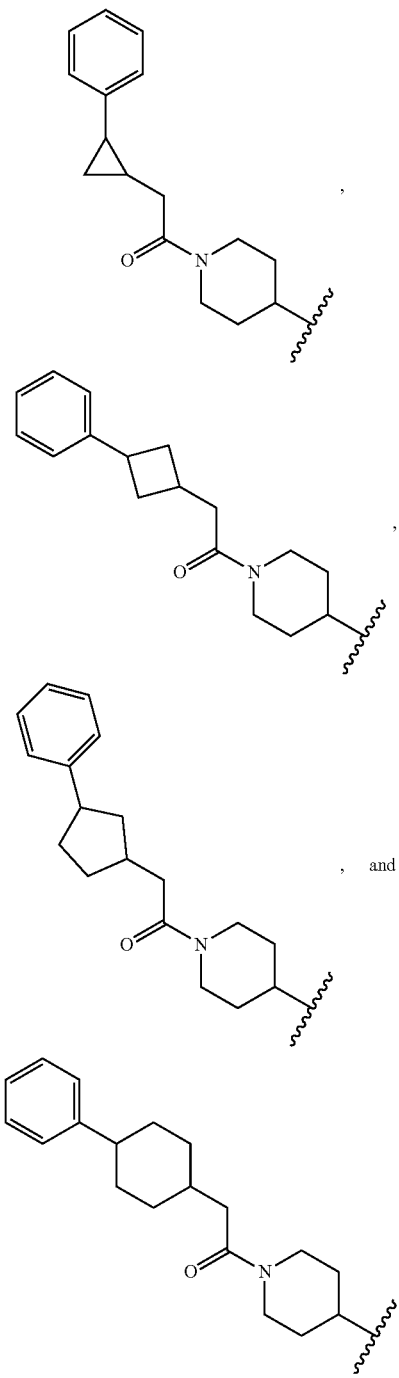
, and
In one embodiment, R¹ is
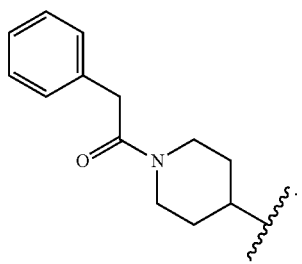 [SMILES: *C1CCN(C(=O)Cc2ccccc2)CC1]
In one embodiment, R¹ is selected from:
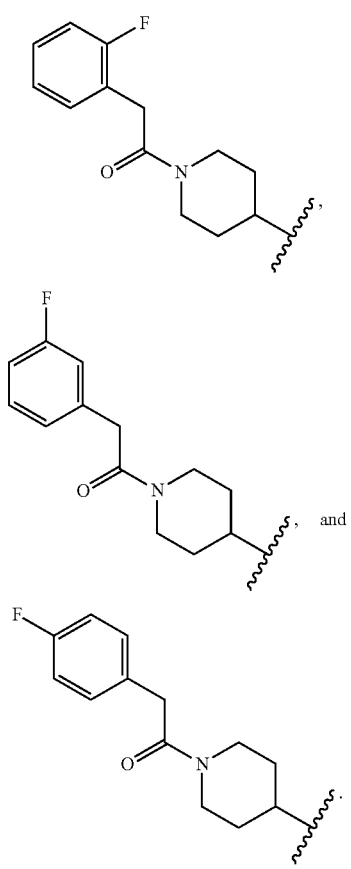 [SMILES: *C1CCN(C(=O)Cc2ccccc2F)CC1 ; *C1CCN(C(=O)Cc2cccc(F)c2)CC1 ; *C1CCN(C(=O)Cc2ccc(F)cc2)CC1]
, and
In one embodiment, R¹ is selected from:
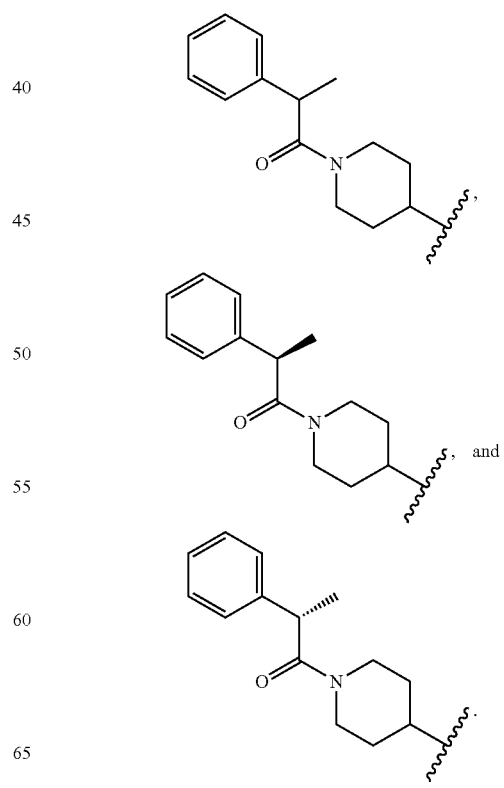
, and In one embodiment, R¹ is
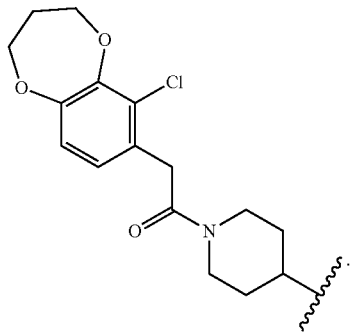 [SMILES: *C1CCN(C(=O)Cc2ccc3c(c2Cl)OCCCO3)CC1]
In one embodiment, R¹ is selected from:
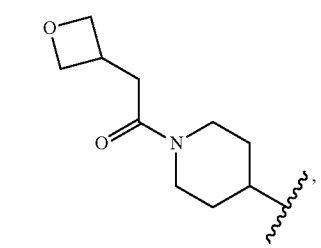
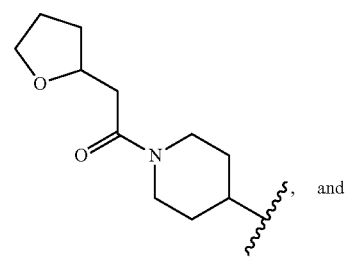
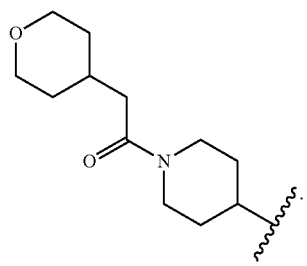
In one embodiment, R¹ is selected from:
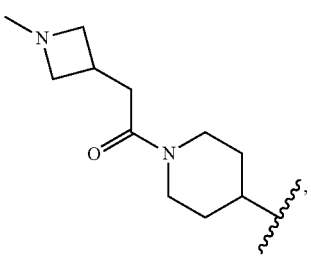
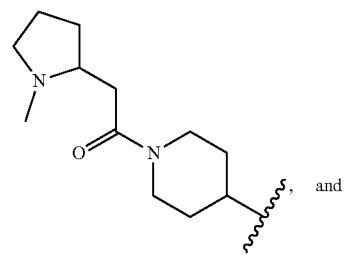
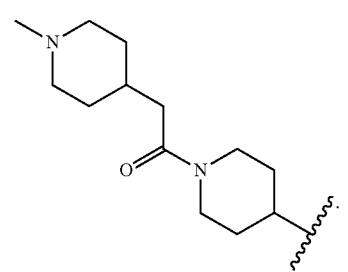
In one embodiment, R¹ is
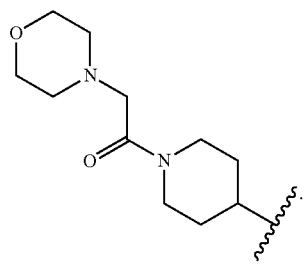 [SMILES: *C1CCN(C(=O)CN2CCOCC2)CC1]
In one embodiment, R¹ is selected from:
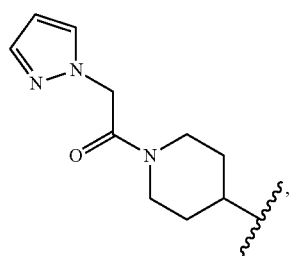
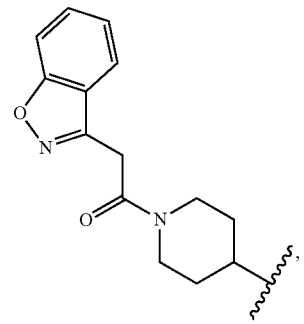

-continued
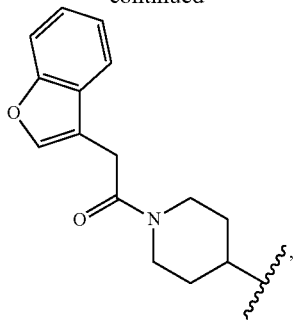
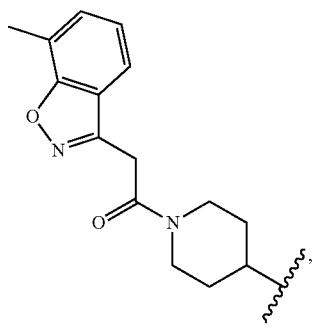
In one embodiment, R¹ is selected from:
-continued
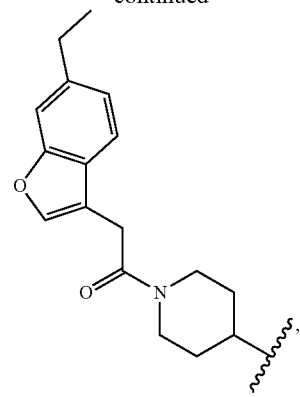
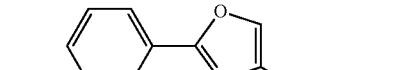
In one embodiment, R¹ is selected from:

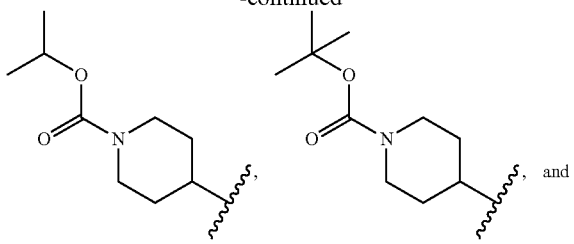, and
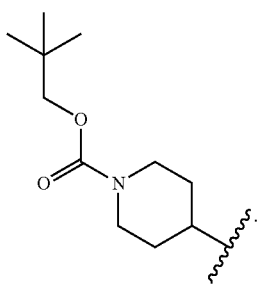
In one embodiment, $R^1$ is selected from
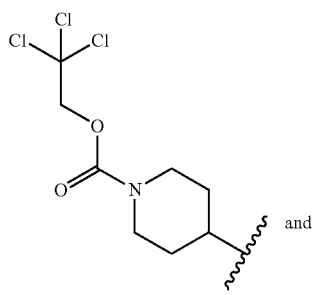 and
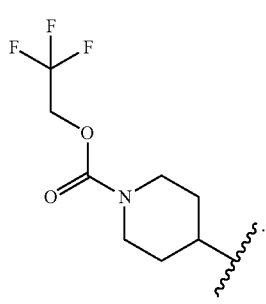
In one embodiment, $R^1$ is
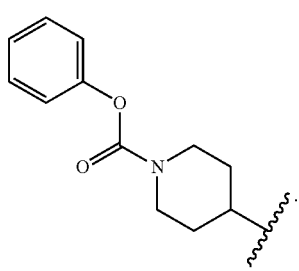
In one embodiment, $R^1$ is
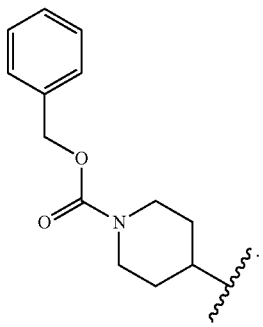 [SMILES: *C1CCN(C(=O)OCc2ccccc2)CC1]
In one embodiment, $R^1$ is selected from:
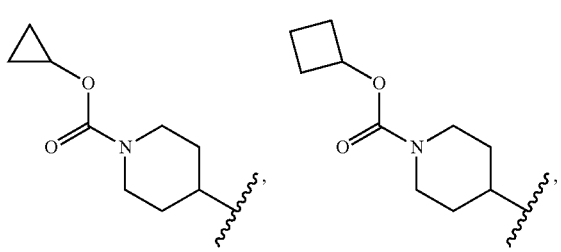,
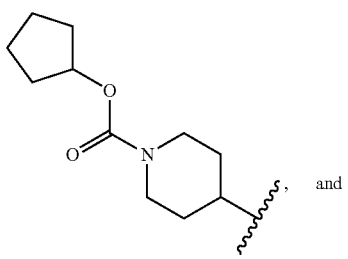, and
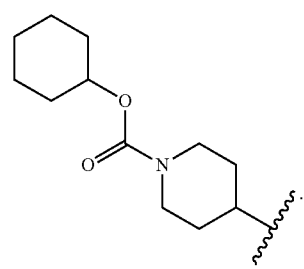
In one embodiment, $R^1$ is selected from:
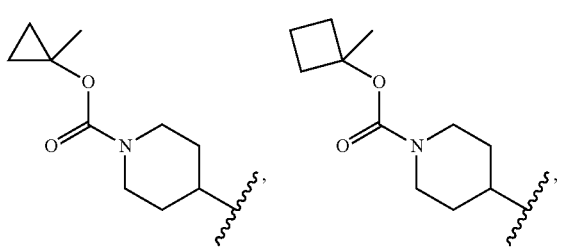, -continued
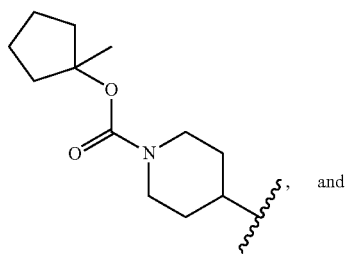, and
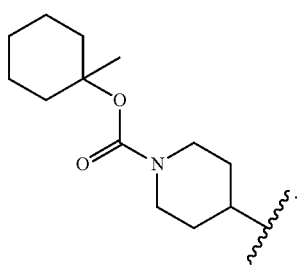.
In one embodiment, R¹ is selected from:
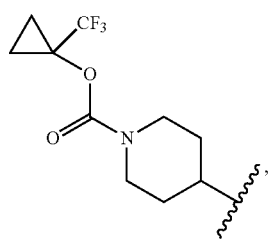, 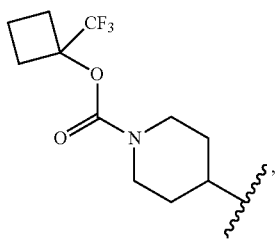,
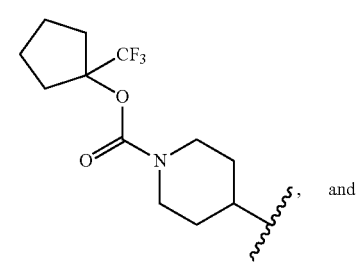, and
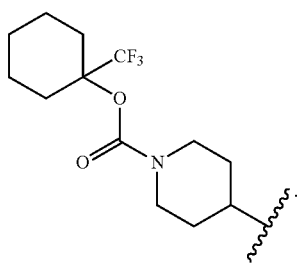.
In one embodiment, R¹ is selected from:
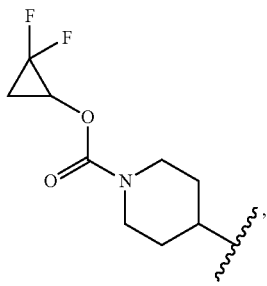,
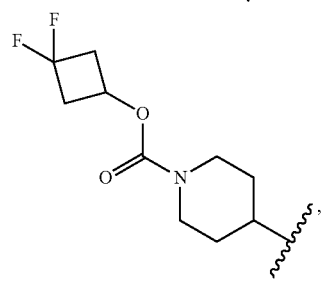,
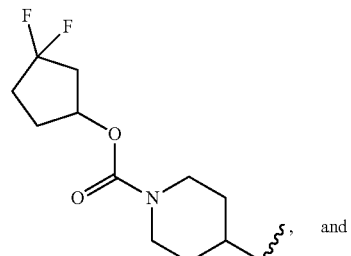, and
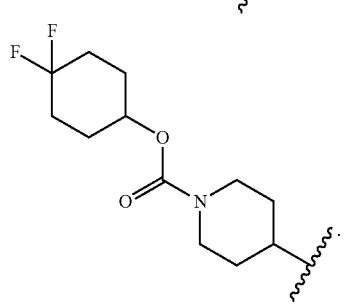.
In one embodiment, R¹ is selected from:
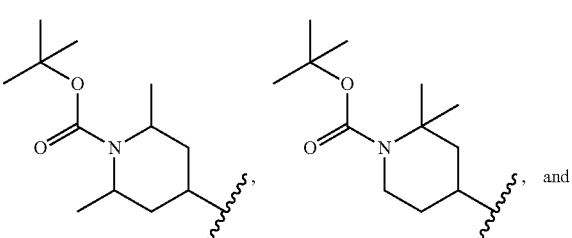, and
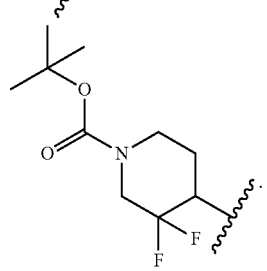.

In one embodiment, R¹ is selected from:
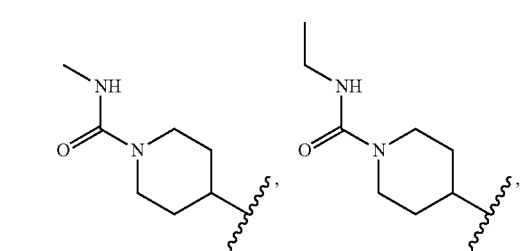
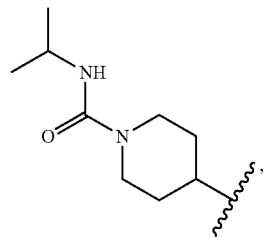
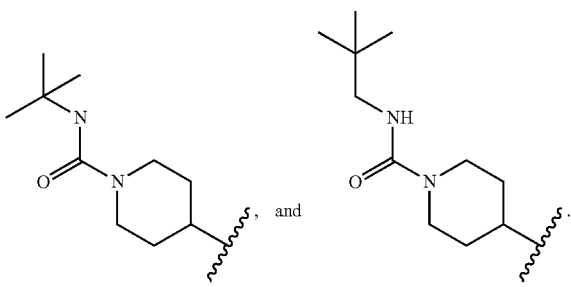
In one embodiment, R¹ is selected from:
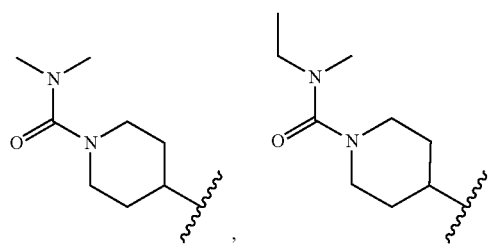
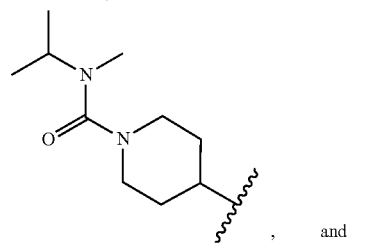
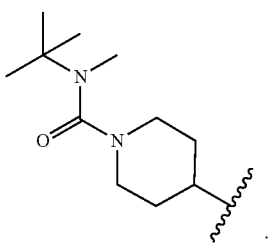
In one embodiment, R¹ is
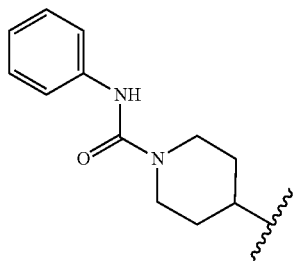
In one embodiment, R¹ is
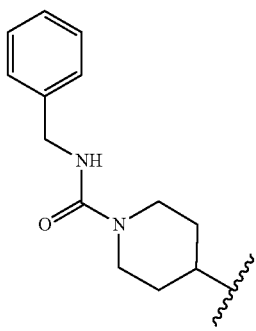
In one embodiment R¹ is selected from:
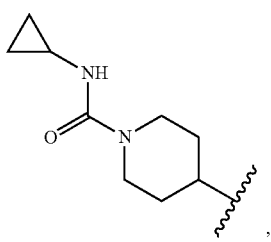
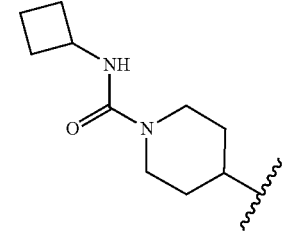
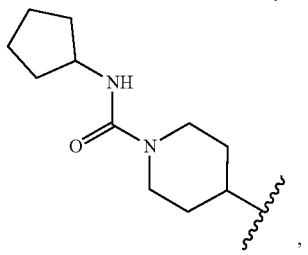, and
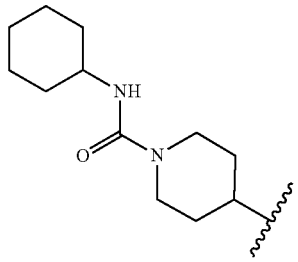

In one embodiment, R¹ is selected from:
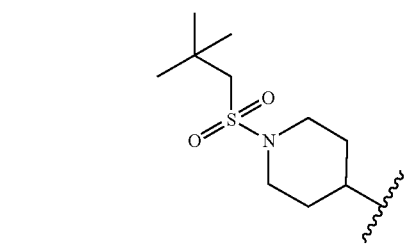
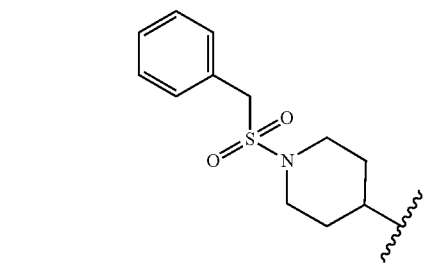
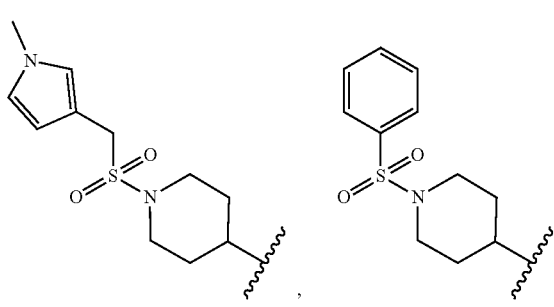
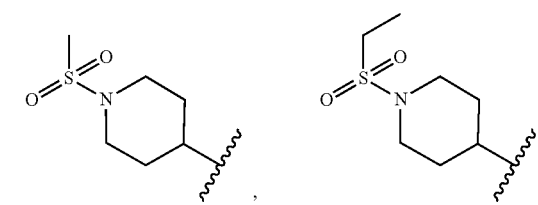
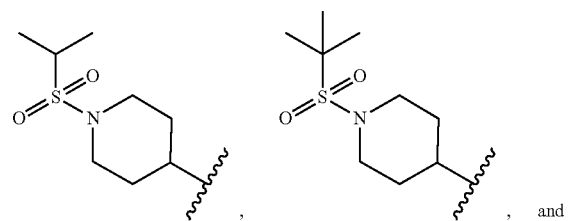
,  and
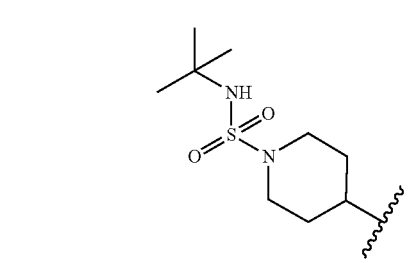
.
In one embodiment, R¹ is.
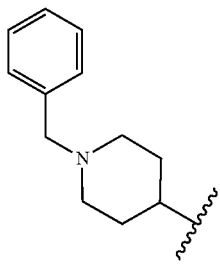
.
In one embodiment, R¹ is selected from:
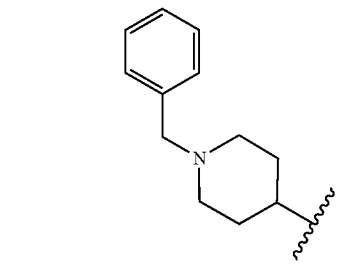
,
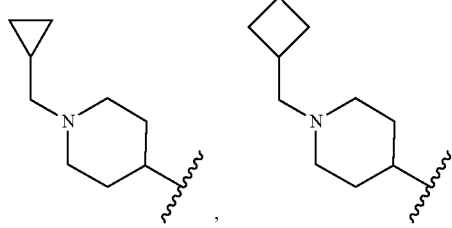
, and
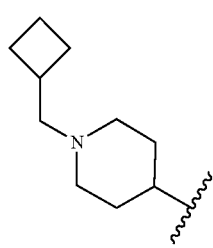
.
In one embodiment, R¹ is selected from:
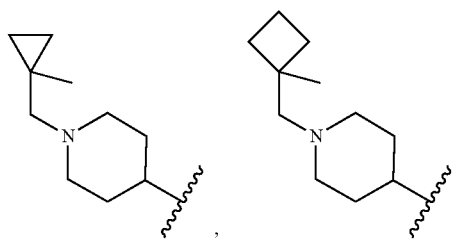
,
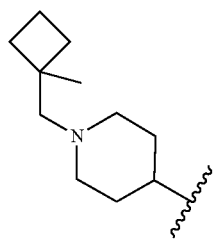
,
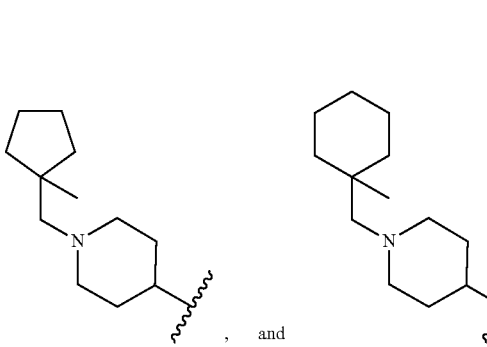
, and
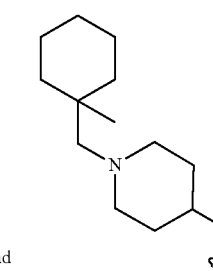
, In one embodiment, R¹ is selected from:
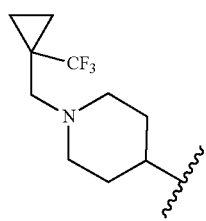 , 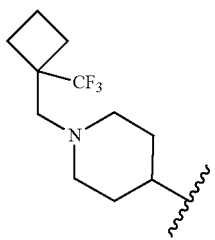 ,
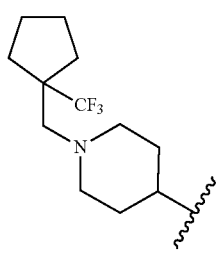 , and 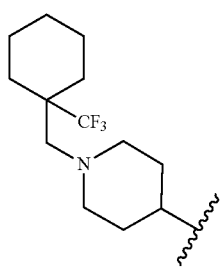 .
In one embodiment, R¹ is selected from:
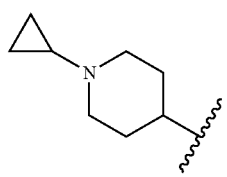 , 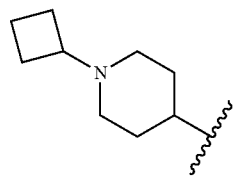 ,
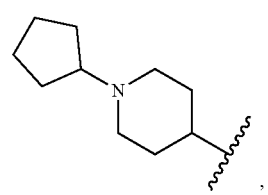 , and
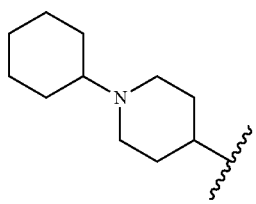 .
In one embodiment, R¹ is selected from:
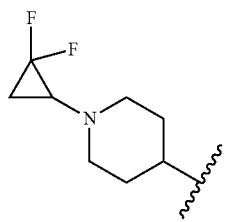 , 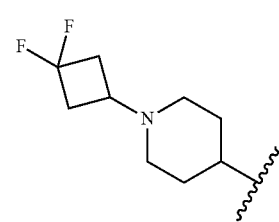 ,
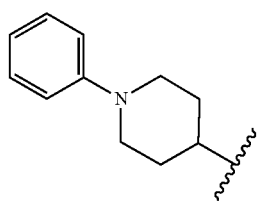 ,
and
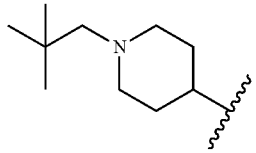 .
In one embodiment, R¹ is selected from:
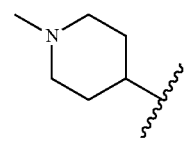 , 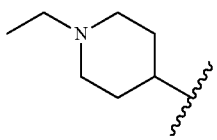 ,
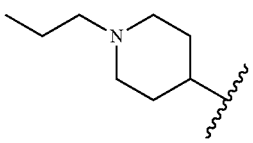 , 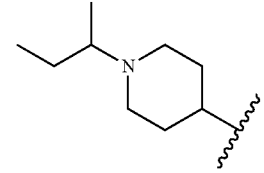 ,
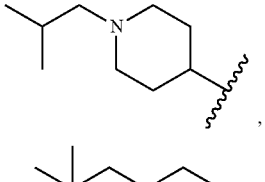 , and
In one embodiment, R¹ is In one embodiment, R¹ is selected from:
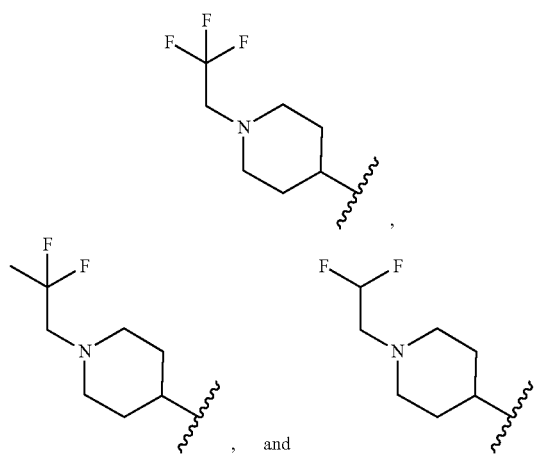
, and
In one embodiment, R¹ is
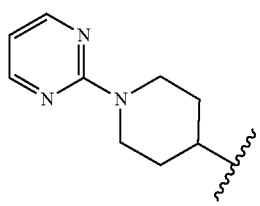
In one embodiment, R¹ is selected from:
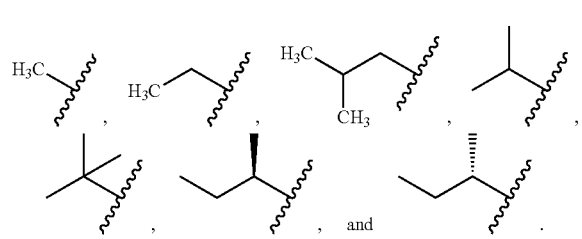
In one embodiment, R¹ is selected from:
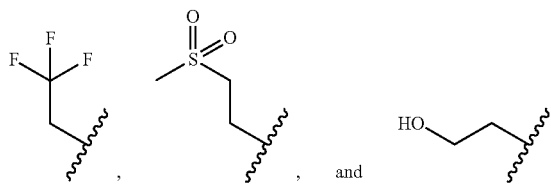
In one embodiment, R¹ is selected from:
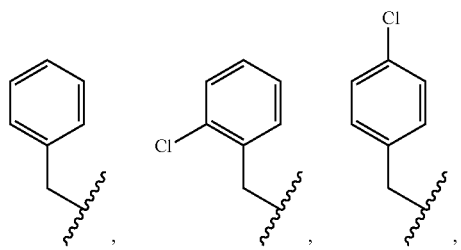
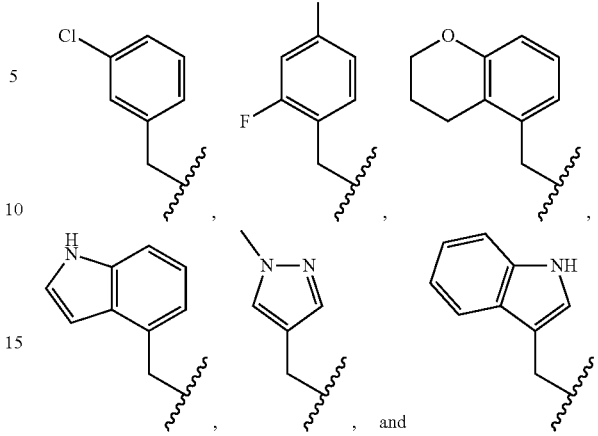
, and
In one embodiment, R¹ is selected from:
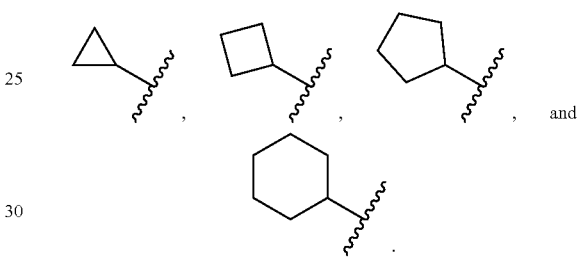
In one embodiment, R¹ is selected from
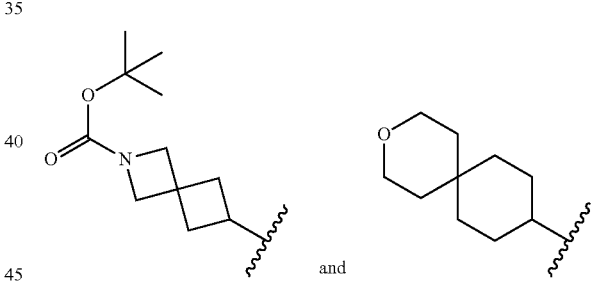
and
In one embodiment, R¹ is selected from
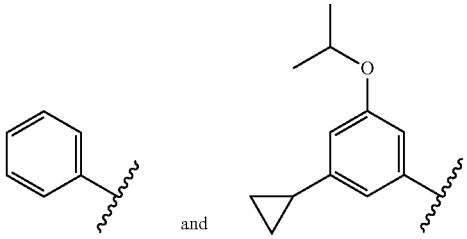
and
In one embodiment, R¹ is
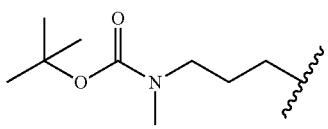

In one embodiment, R¹ is selected from:
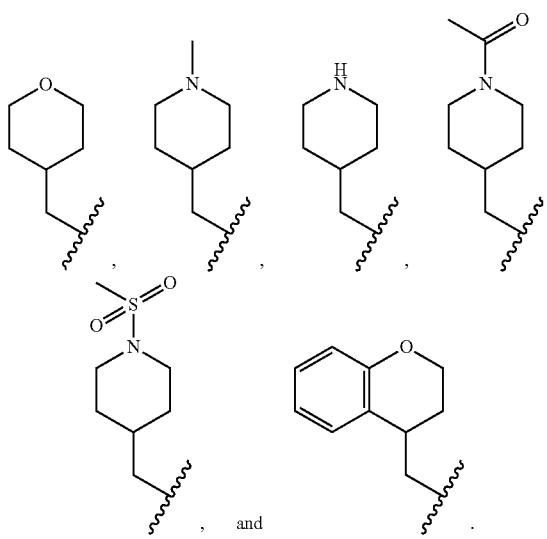
, and .
In one embodiment, R¹ is
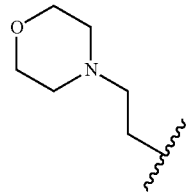
.
In one embodiment, R¹ is selected from
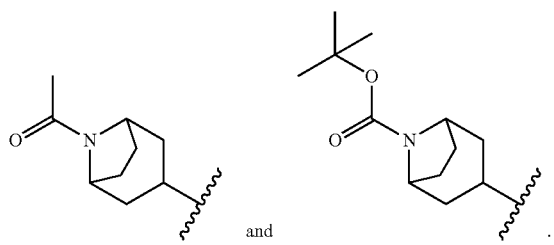 [SMILES: *C1CC2CCC(C1)N2C(C)=O ; *C1CC2CCC(C1)N2C(=O)OC(C)(C)C]
and .
In one embodiment, R¹ is
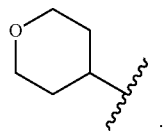 [SMILES: *C1CCOCC1]
.
In one embodiment, R¹ is selected from:
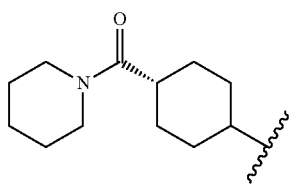
,
-continued
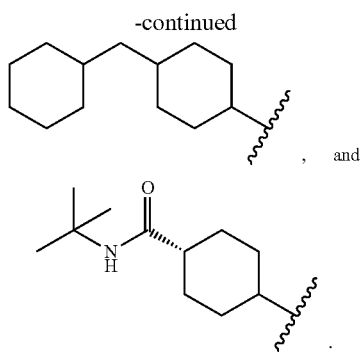
, and .
In one embodiment, R¹ is selected from:
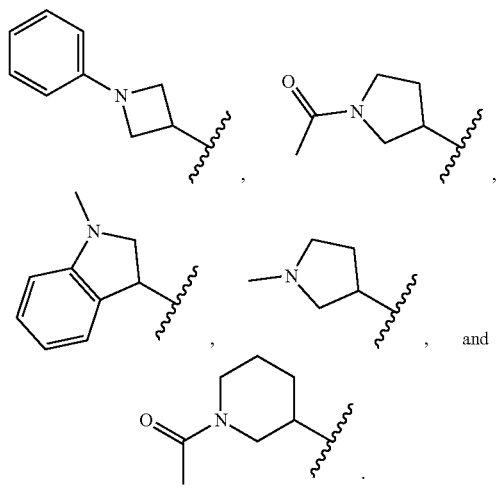
, , , and .
In one embodiment, R¹ is
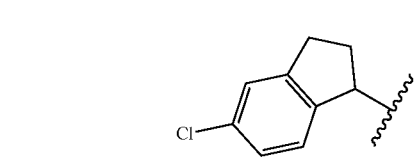
.
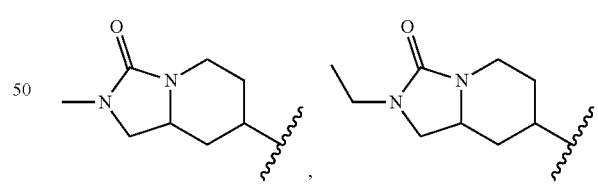
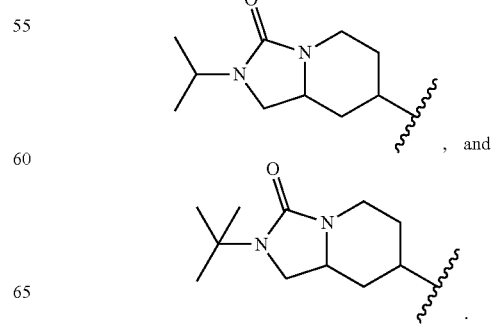

In one embodiment, R¹ is selected from:

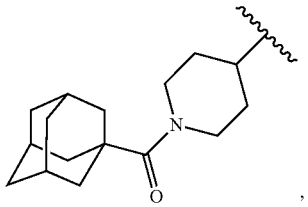
,

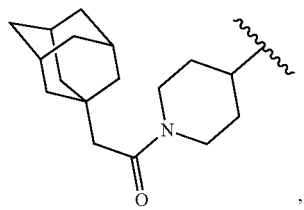
,

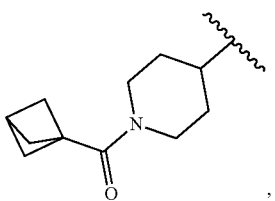
,

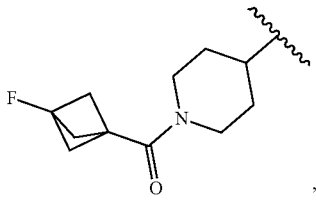
,

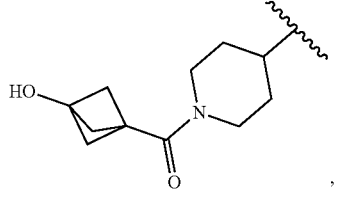
,

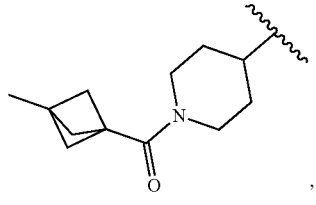
,

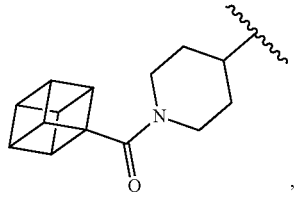
,

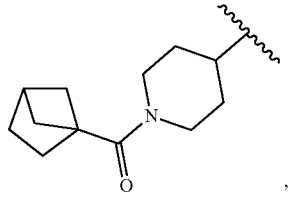
,

-continued

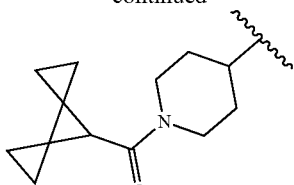
,

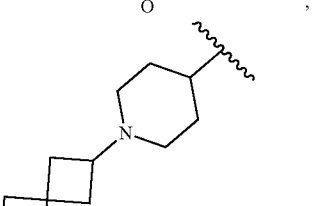
, and

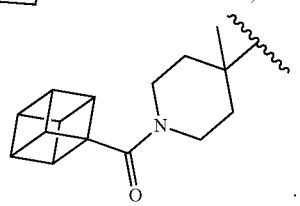
.

Embodiments of y and x

In one embodiment y is 1. In one embodiment y is 2. In one embodiment y is 3. In one embodiment y is 4. In one embodiment y is 5. In one embodiment y is 6. In one embodiment y is 2, 3, 4, 5, or 6. In one embodiment y is 2, 3, 4, or 5.

In one embodiment x is 0. In one embodiment x is 1. In one embodiment x is 2. In one embodiment x is 3. In one embodiment x is 4. In one embodiment x is 5. In one embodiment x is 6. In one embodiment x is 0, 1, 2, 3, or 4. In one embodiment x is 1, 2, 3, 4, 5, or 6.

Additional Embodiments

In one embodiment R² at each instance is independently selected from hydrogen, alkyl, alkenyl, alkynyl, aryl, and cycloalkyl; R³ is selected from alkyl, alkenyl, alkynyl, haloalkyl, cycloalkyl, —NR²R², and —OR⁴, and R⁴ at each instance is independently selected from alkyl, alkenyl, haloalkyl, and alkynyl.

In one embodiment R² at each instance is independently selected from hydrogen, alkyl, alkenyl, alkynyl, aryl, and cycloalkyl.

In one embodiment R³ is selected from alkyl, alkenyl, alkynyl, haloalkyl, cycloalkyl, —NR²R², and —OR⁴.

In one embodiment R⁴ at each instance is independently selected from alkyl, alkenyl, haloalkyl, and alkynyl.

Non-Limiting Examples of Compounds of Formula I

In one embodiment the compound of Formula I is selected from:

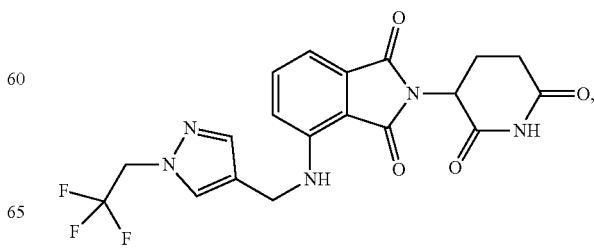

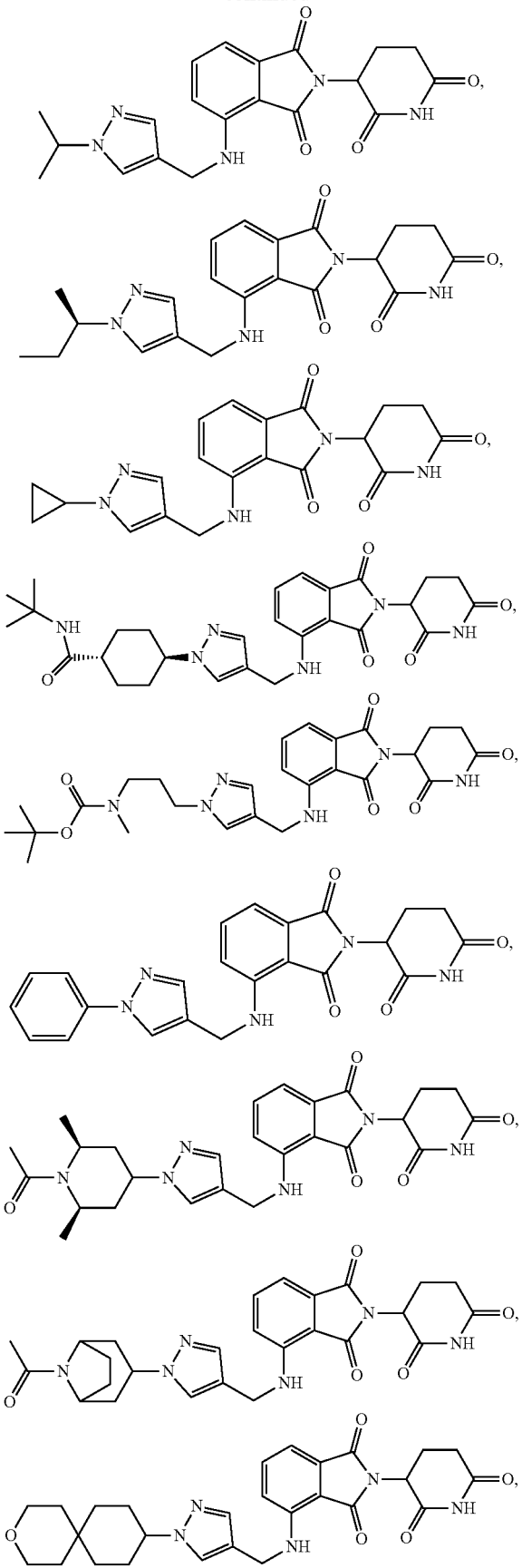
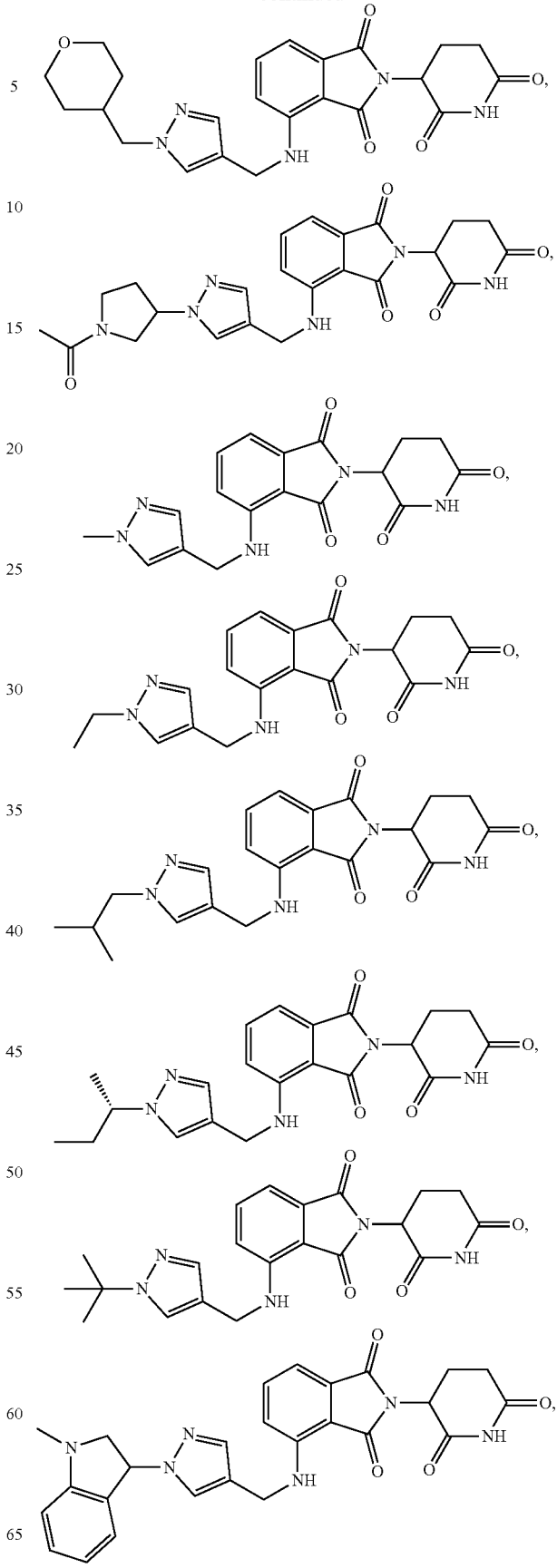

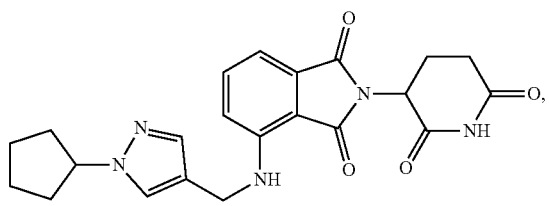
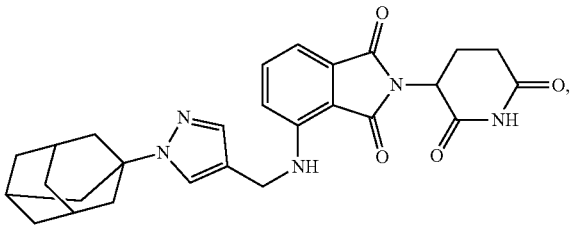
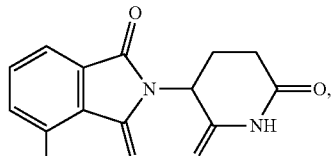
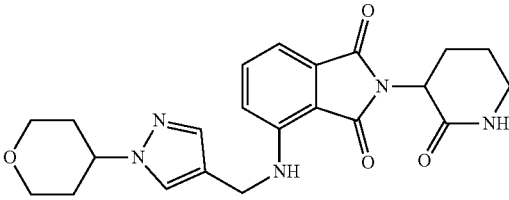
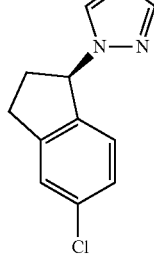
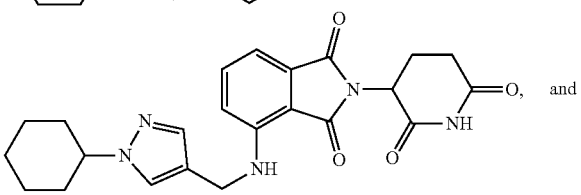
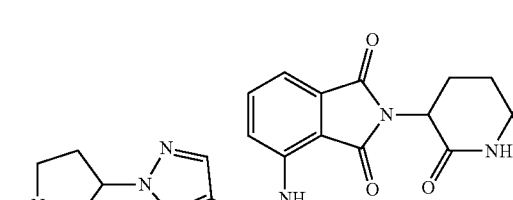
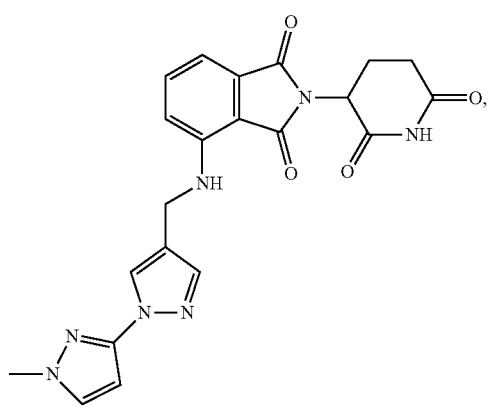
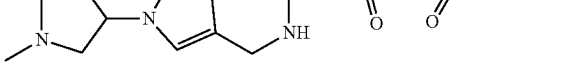
In one embodiment the compound of Formula I is selected from:
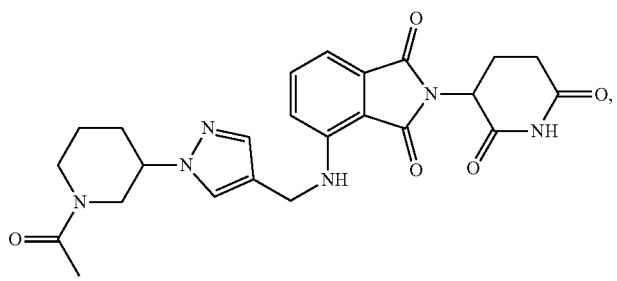
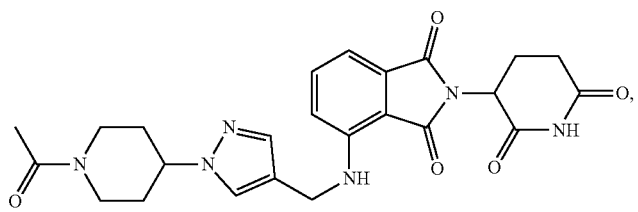

-continued
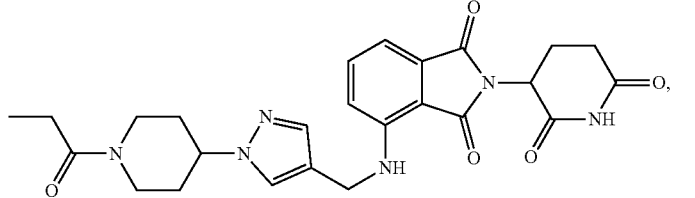
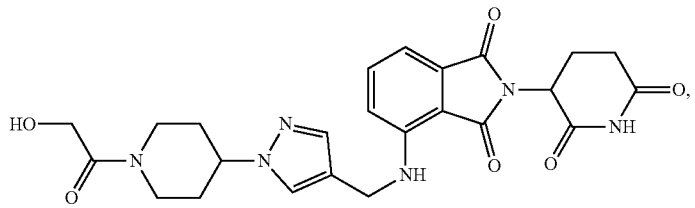
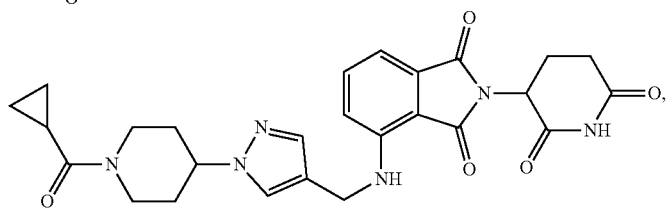
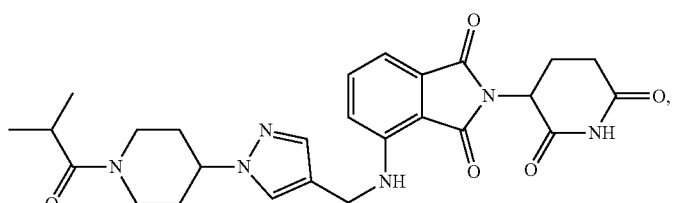
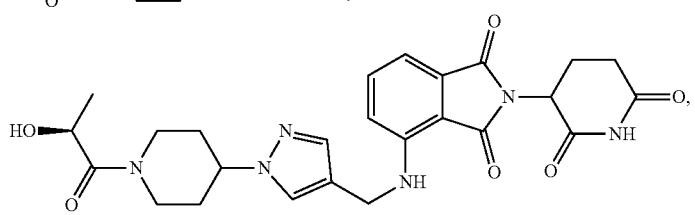
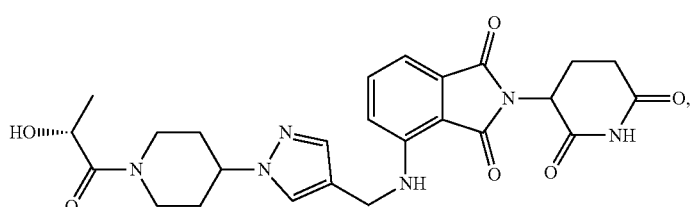
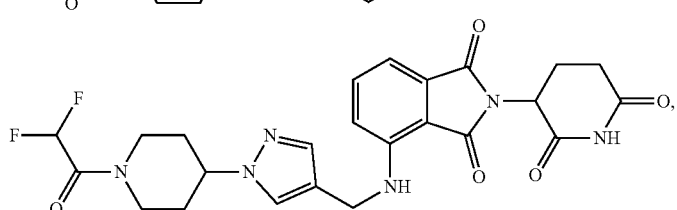
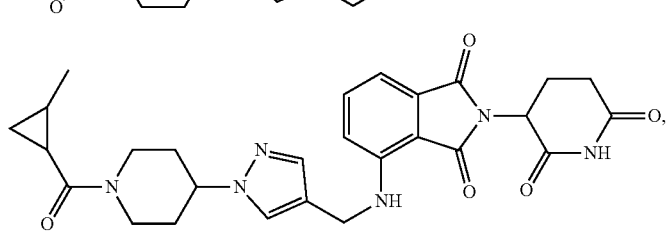

-continued
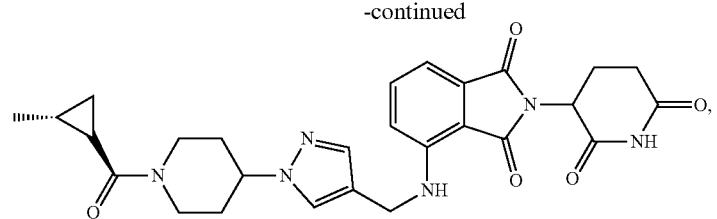
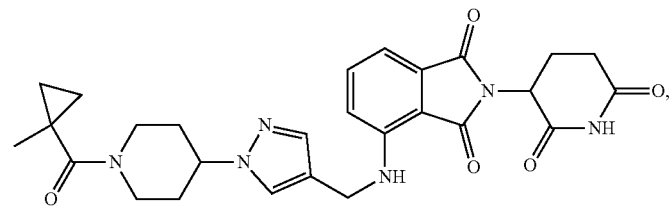
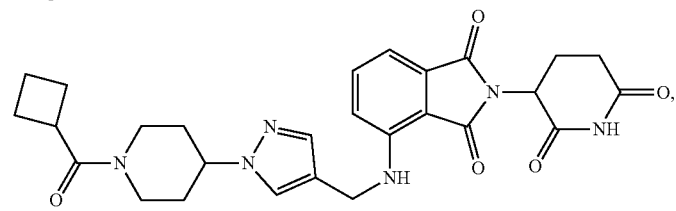
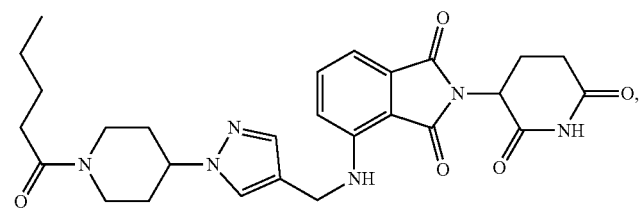
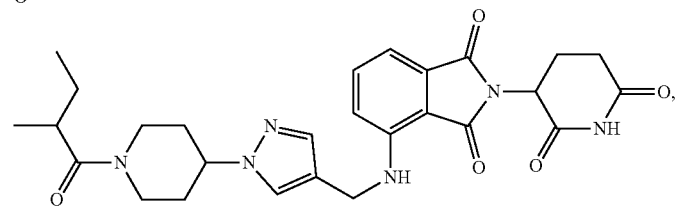
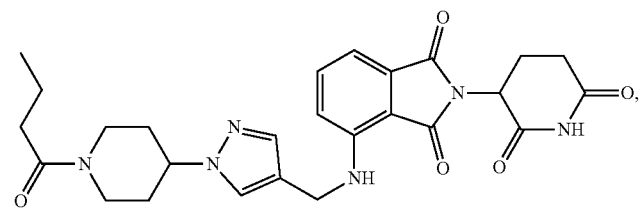
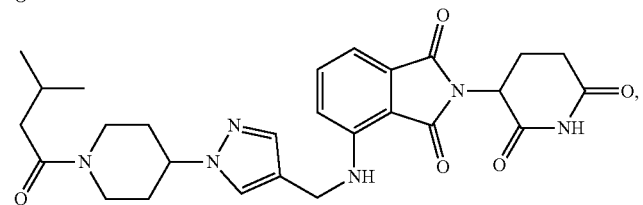
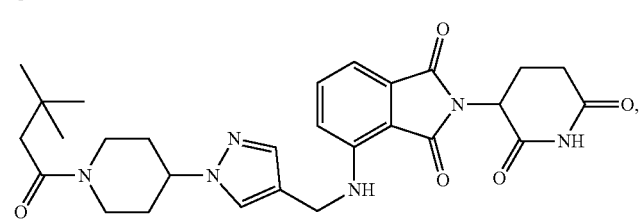

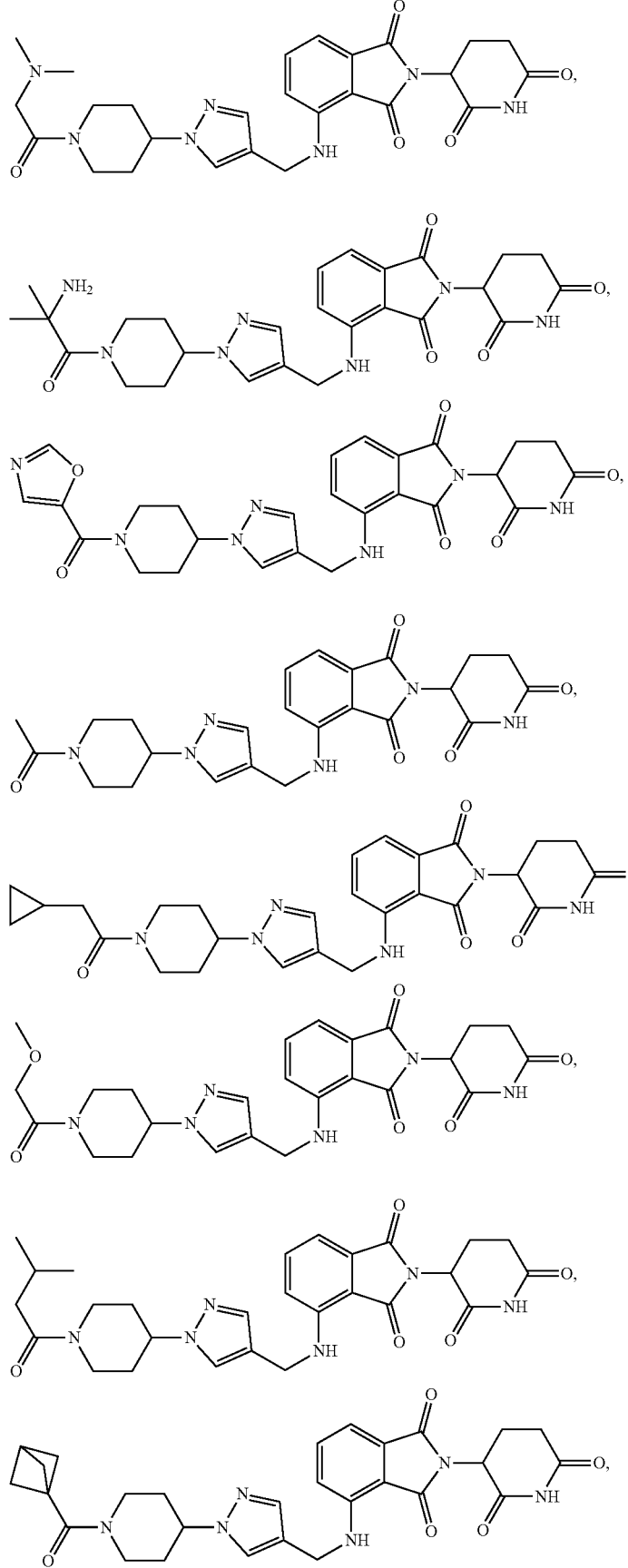

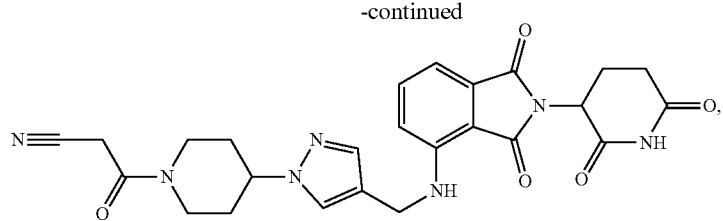
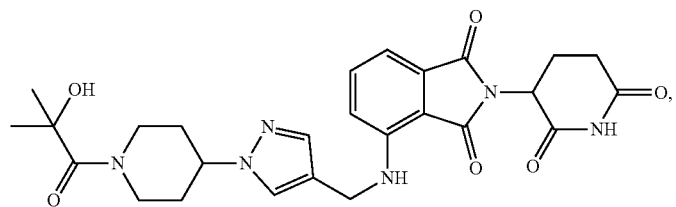
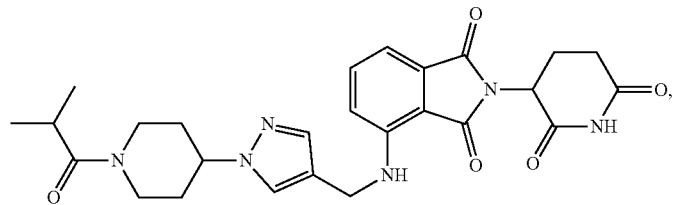
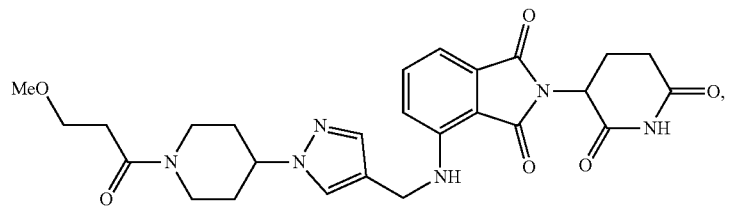
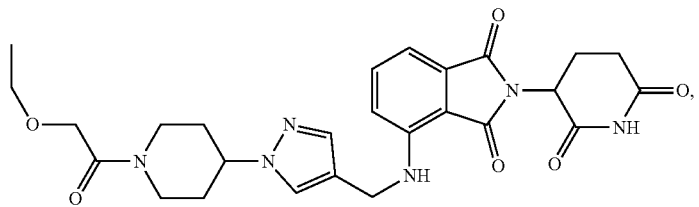
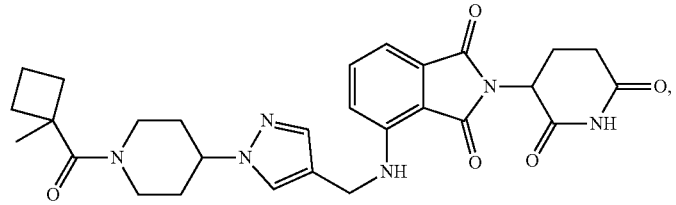
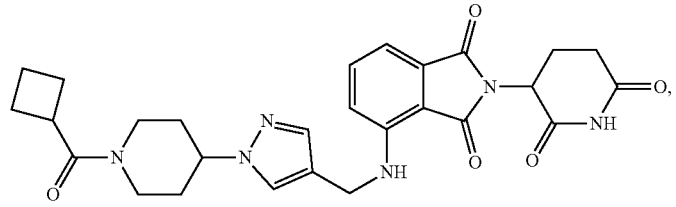
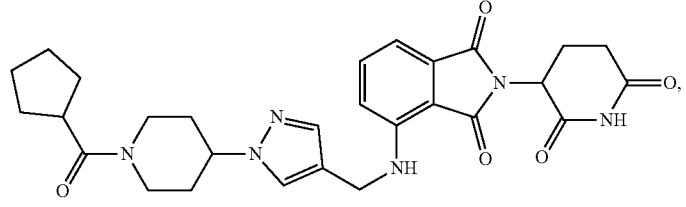

-continued
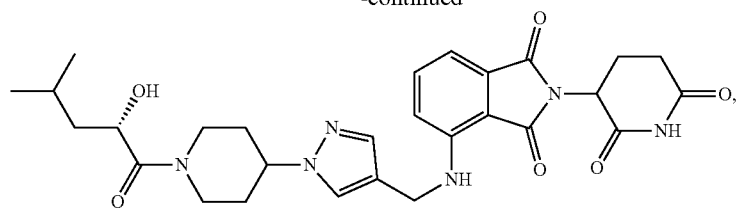
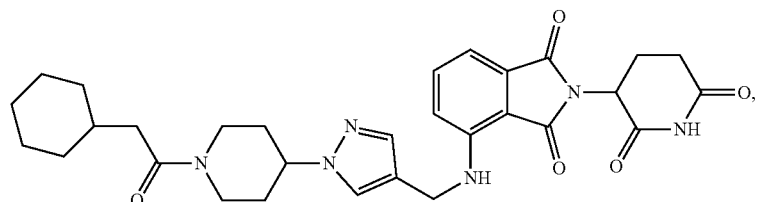
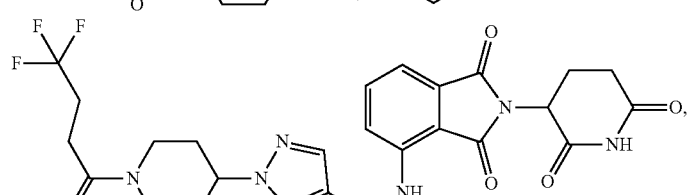
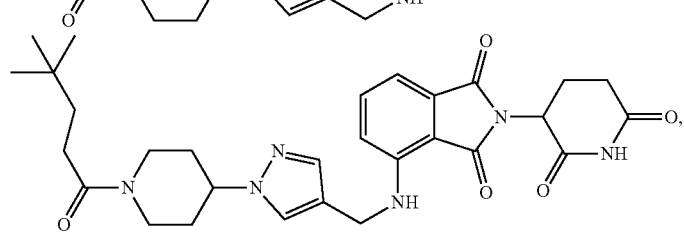
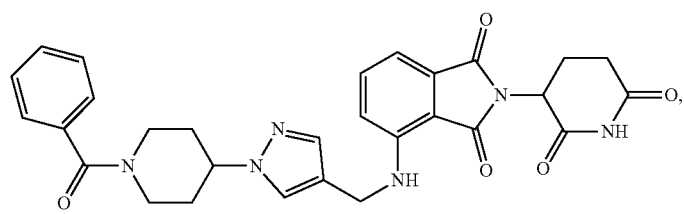
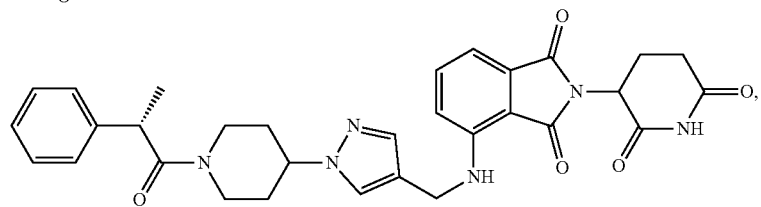
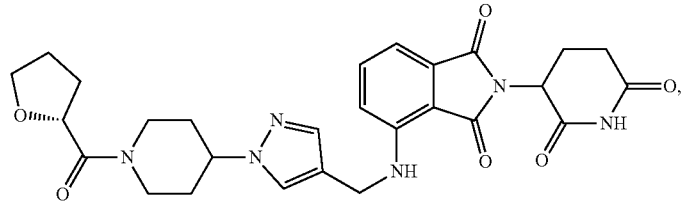
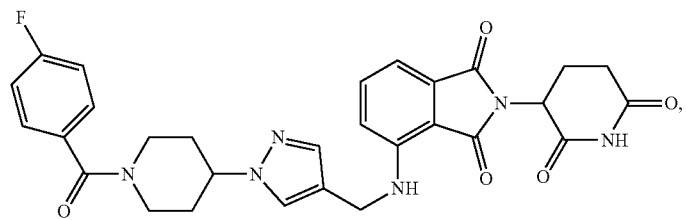

-continued
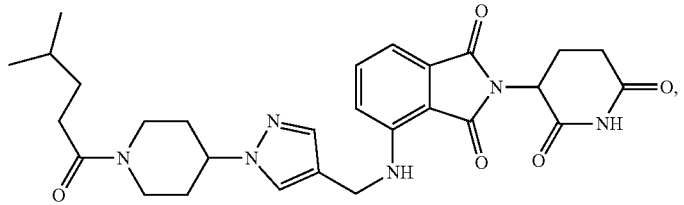
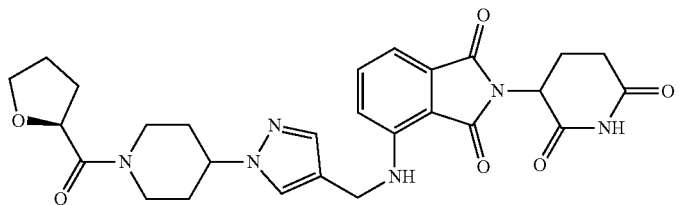
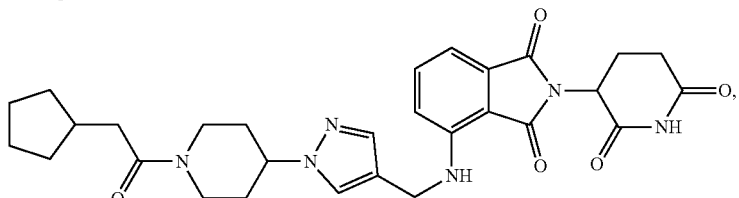
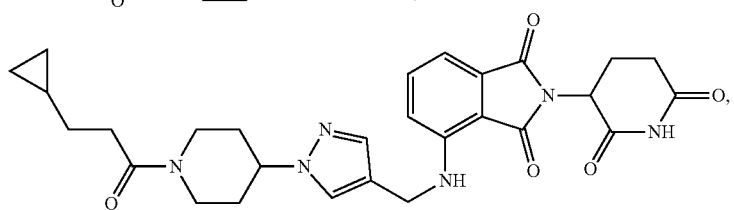
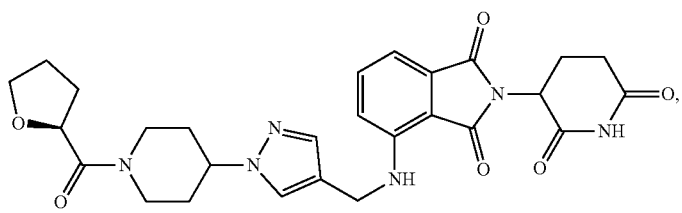
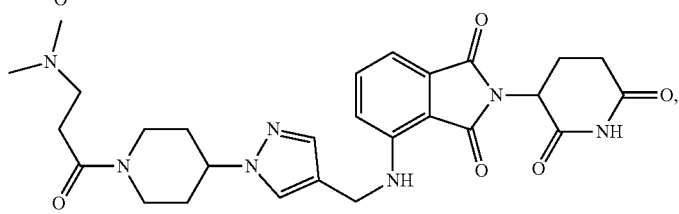
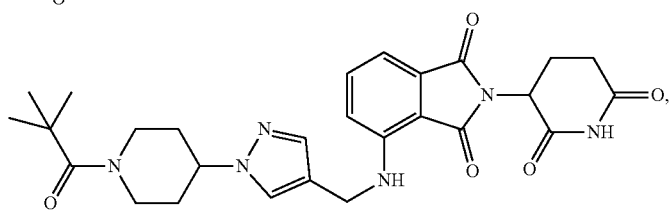
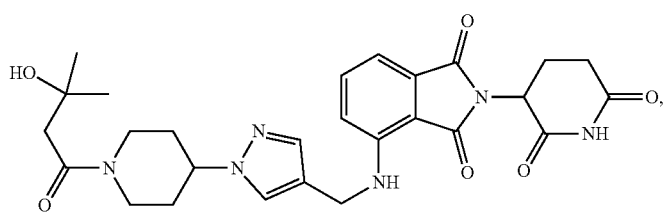

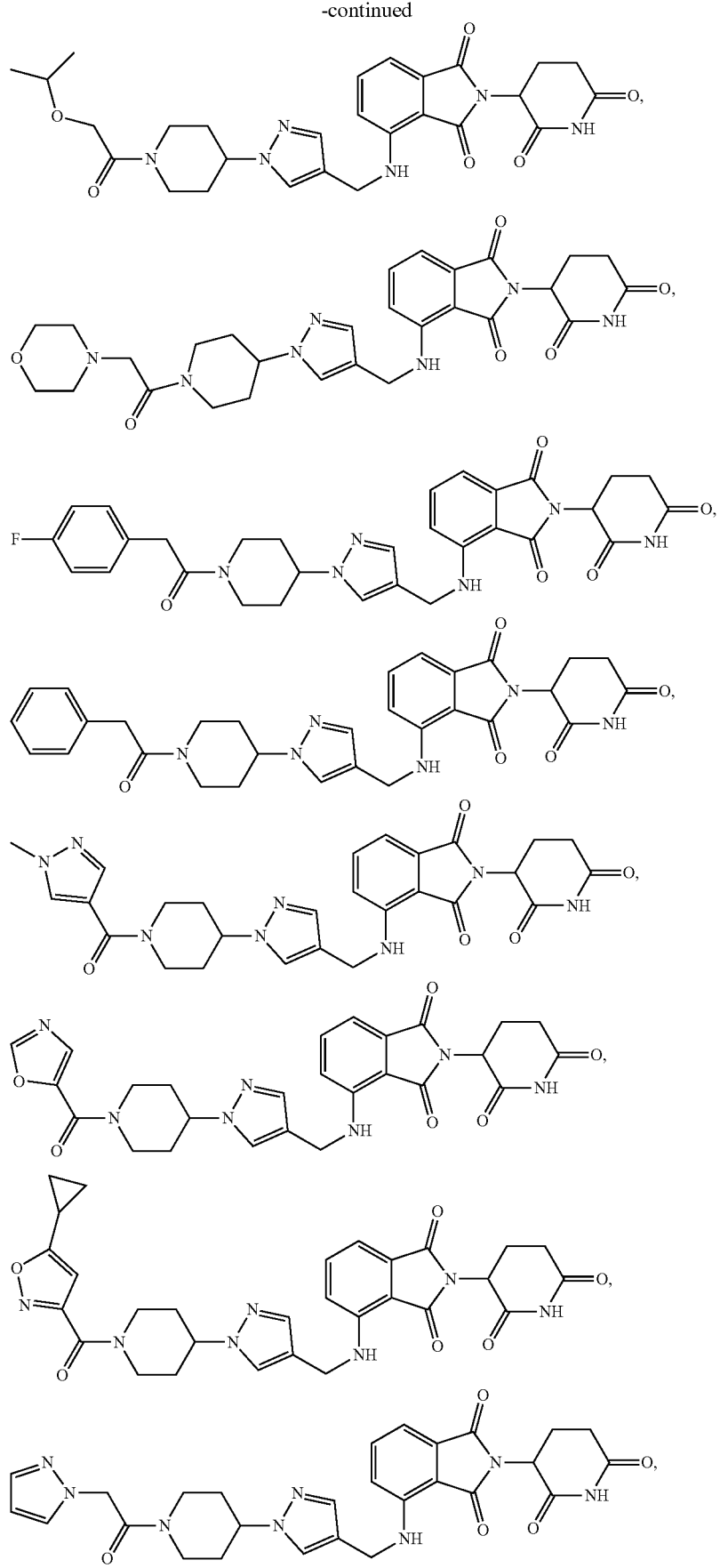

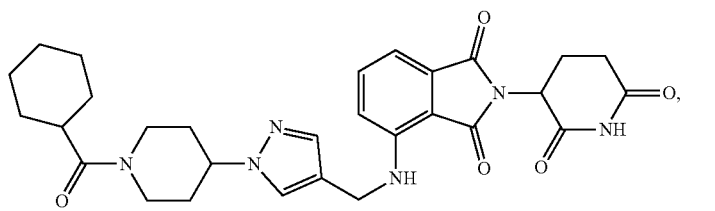
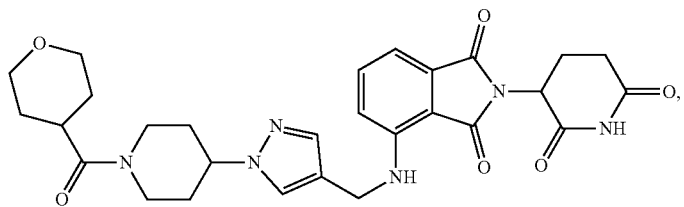
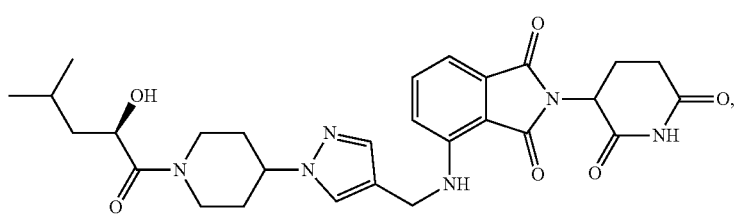
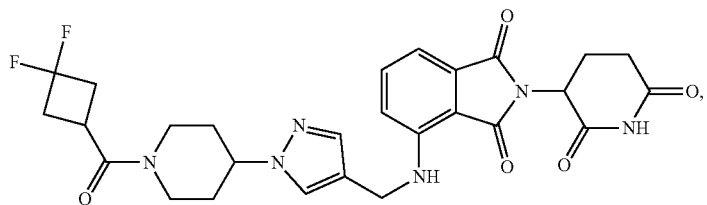
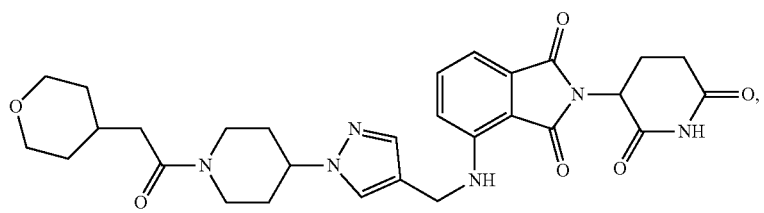
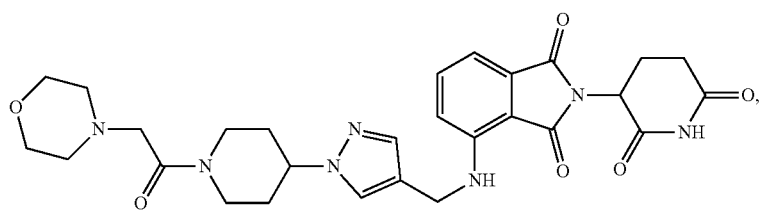
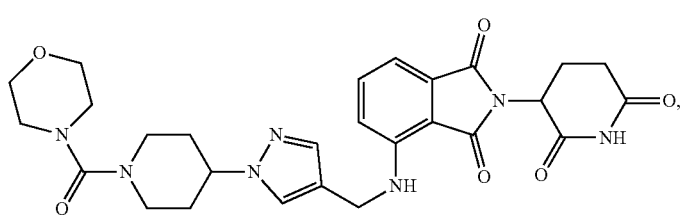
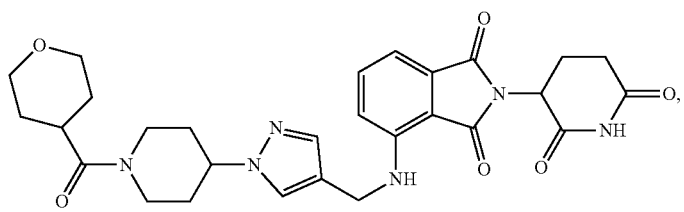

-continued
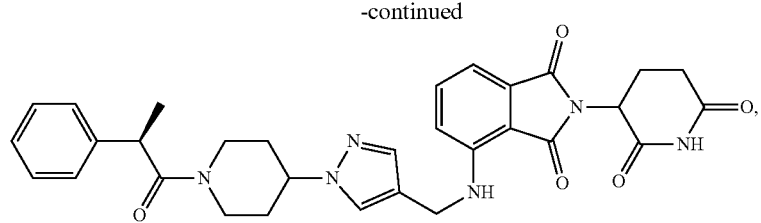
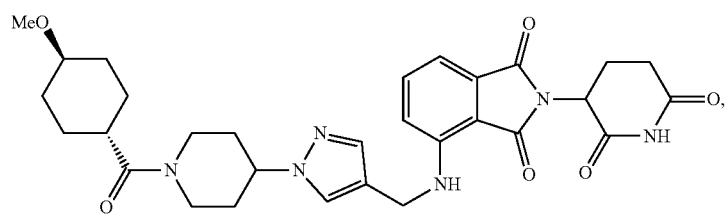
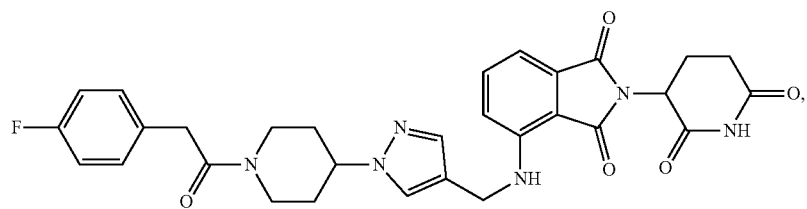
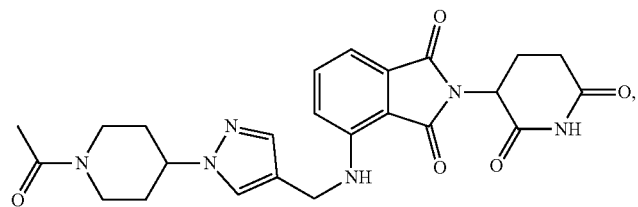
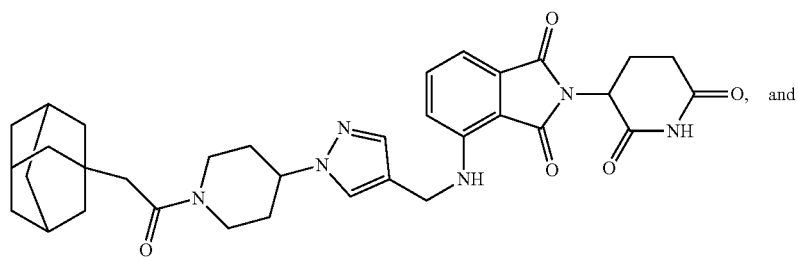
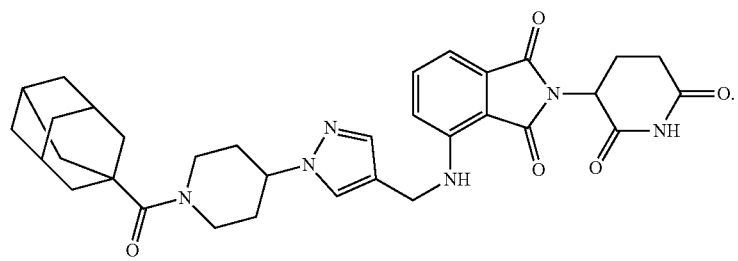

In another embodiment the compound of Formula I is selected from:
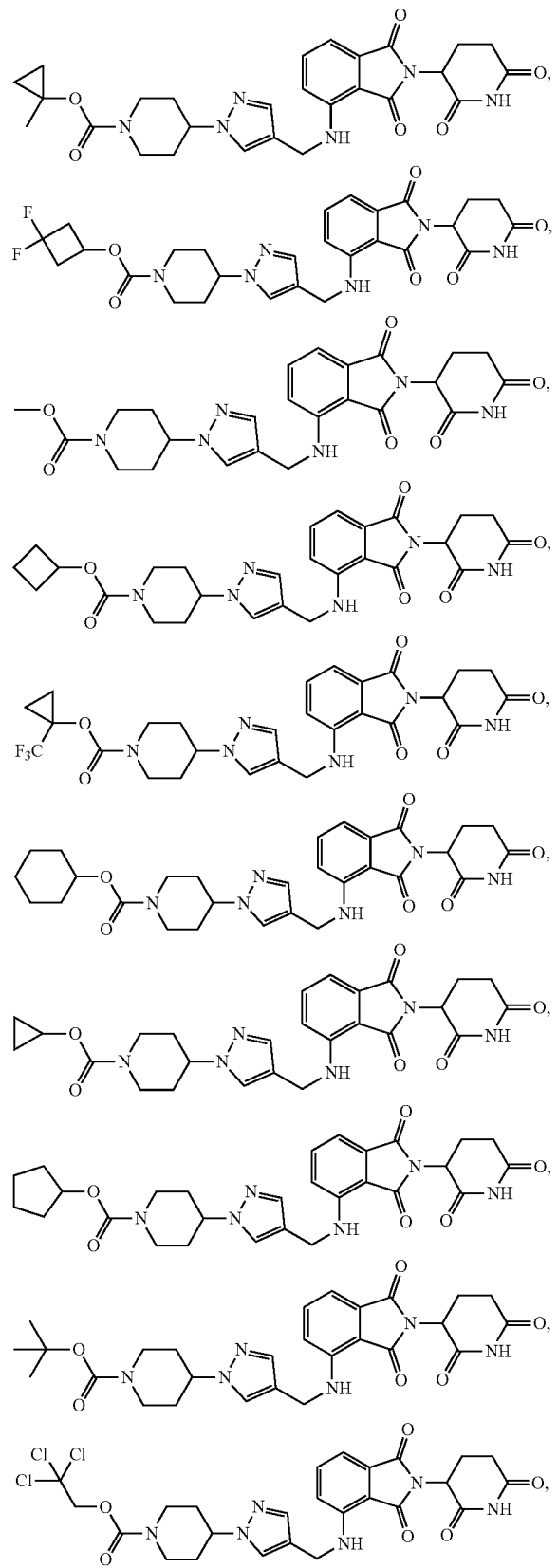
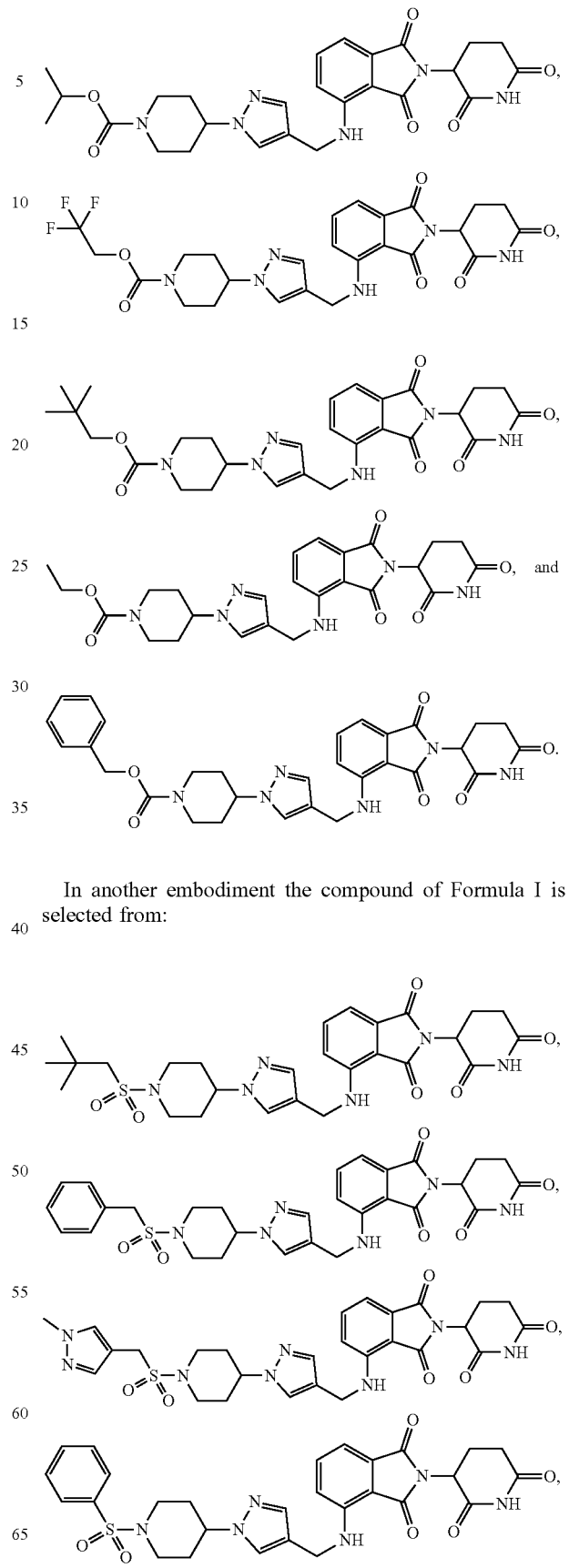
In another embodiment the compound of Formula I is selected from:

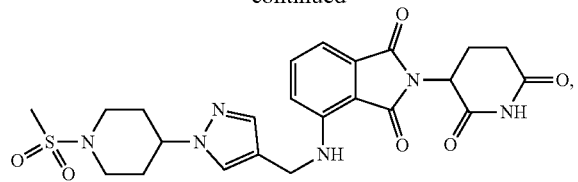

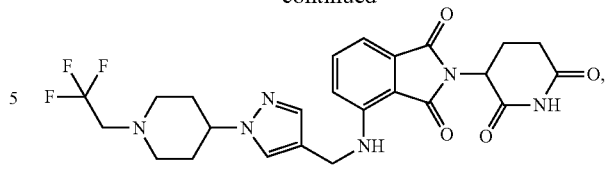
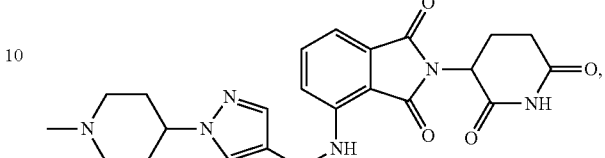
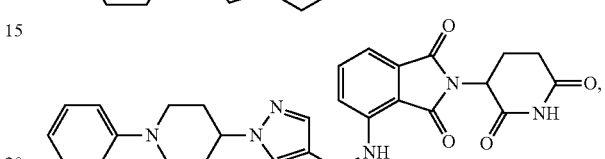
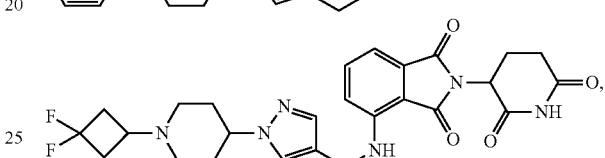
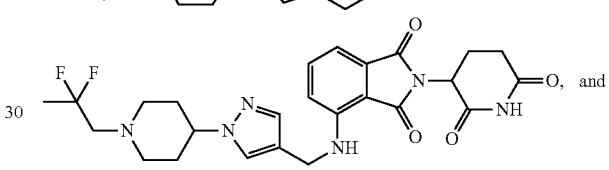
In another embodiment the compound of Formula I is selected from:
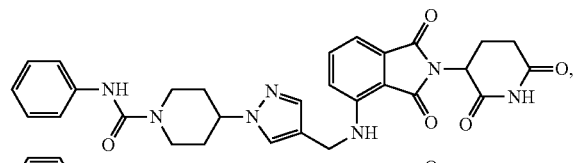
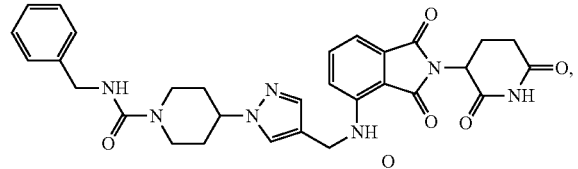
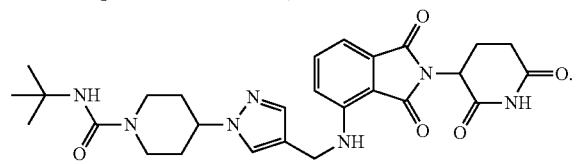
In another embodiment the compound of Formula I is selected from:
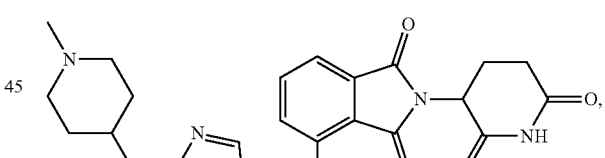
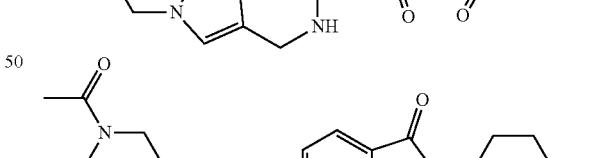
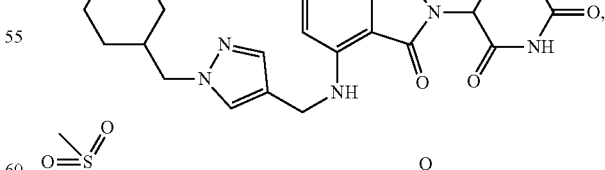
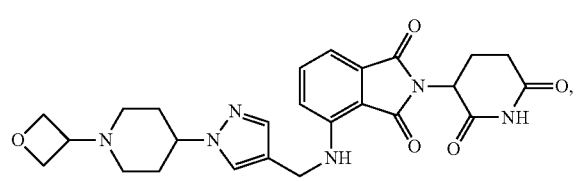

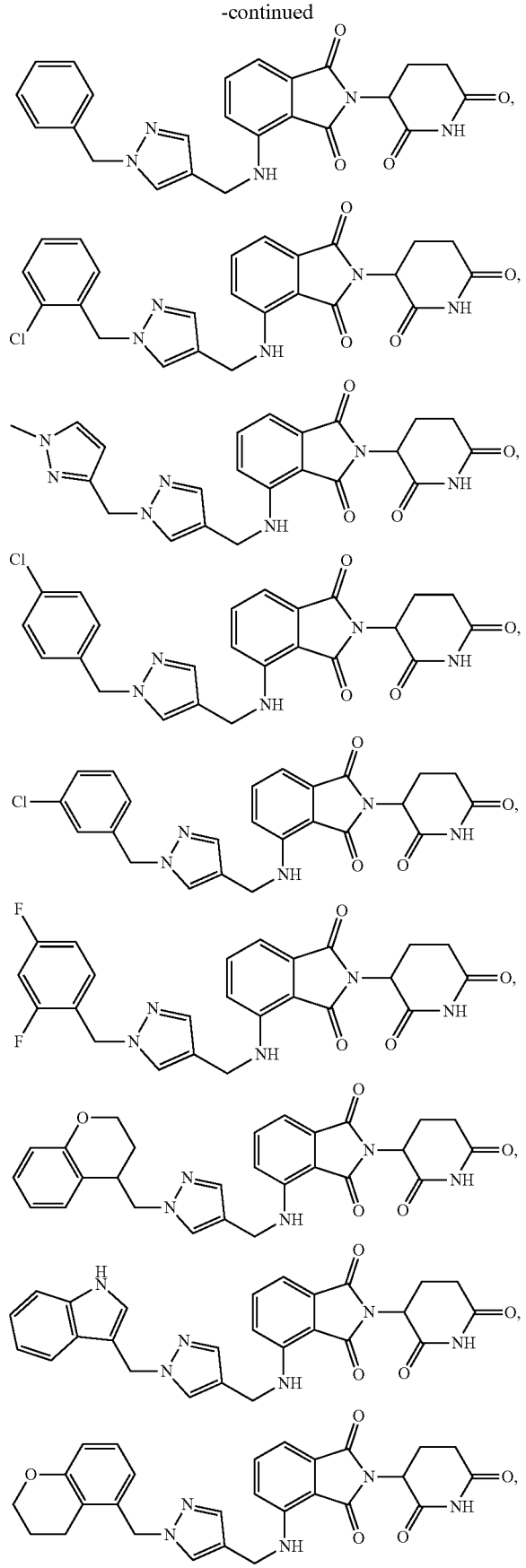
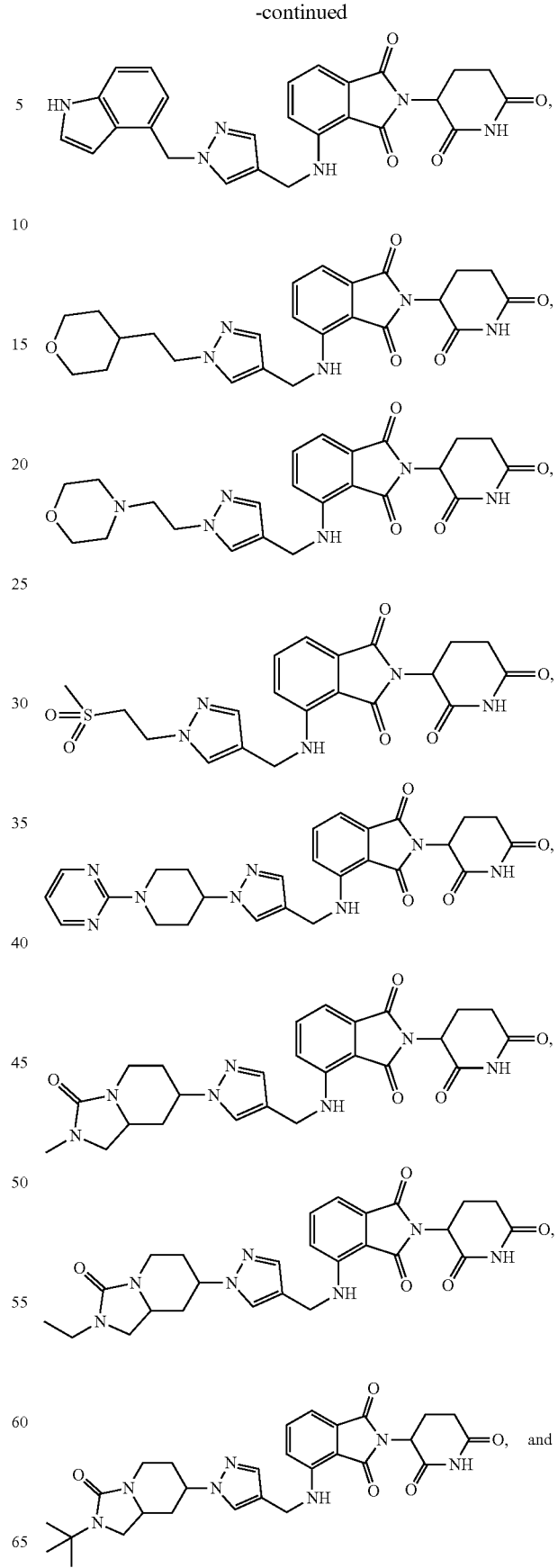

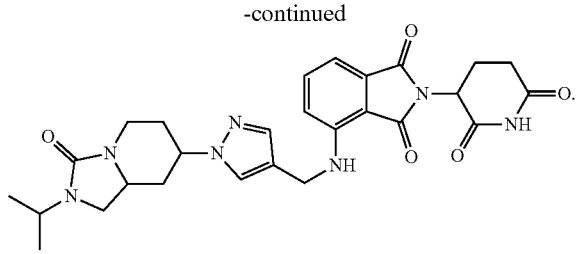
In an alternative embodiment the compound of Formula I is selected from:
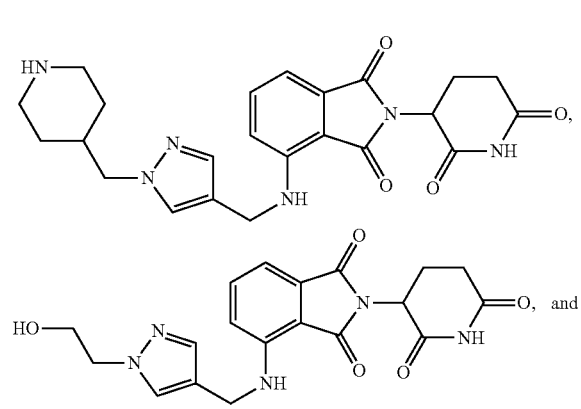
In an alternative embodiment, the compound of Formula I is selected from:
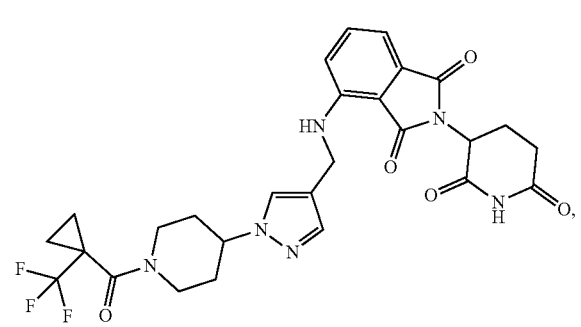
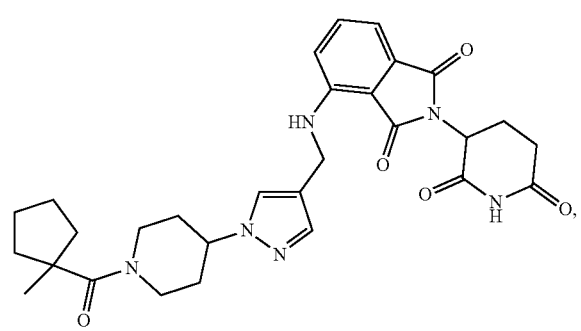
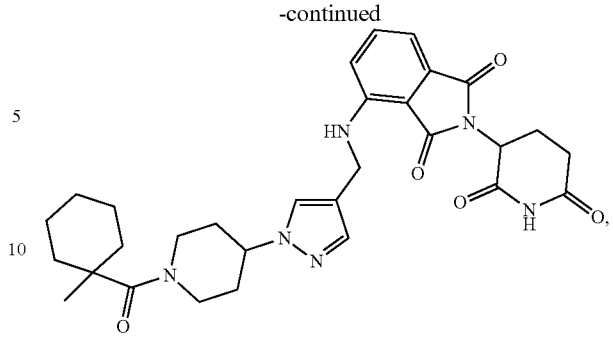
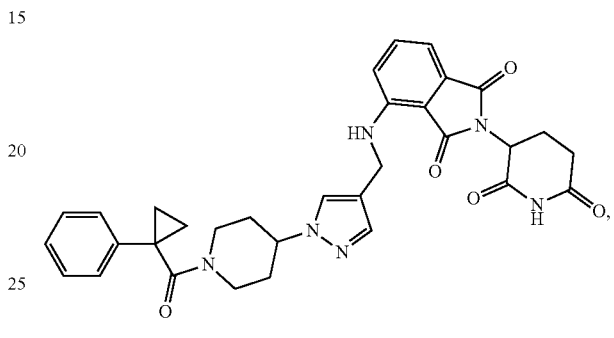
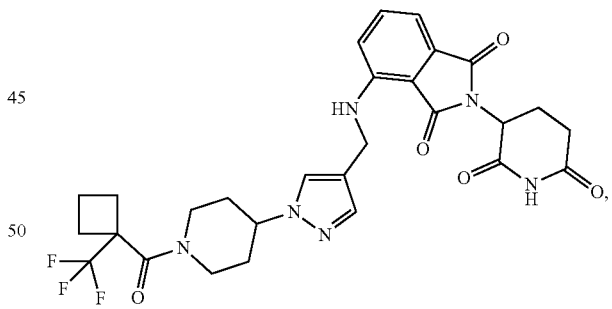
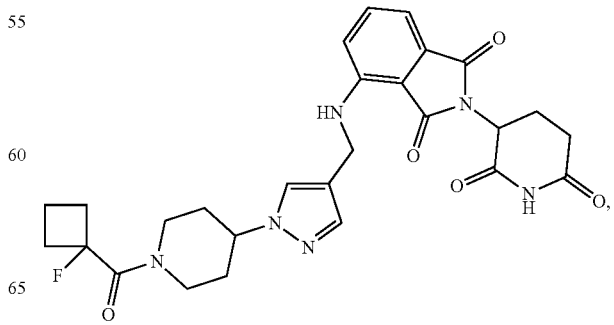

107
-continued
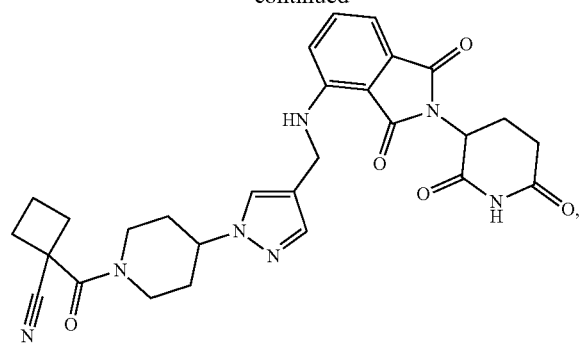
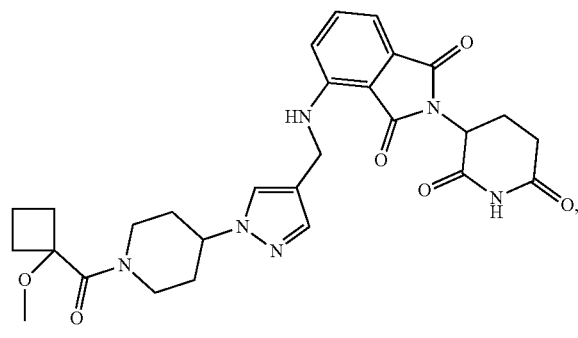
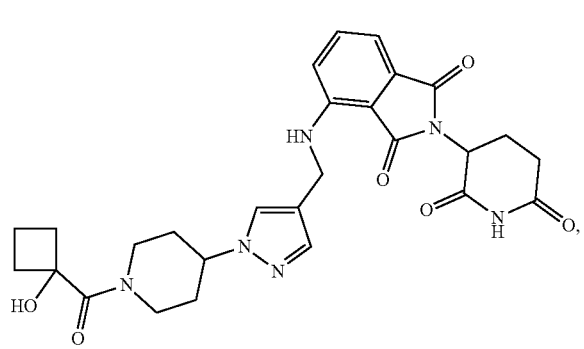
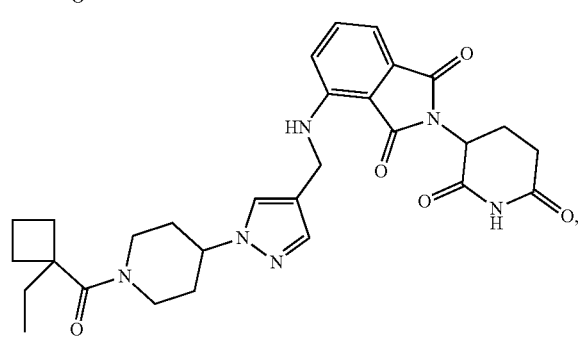
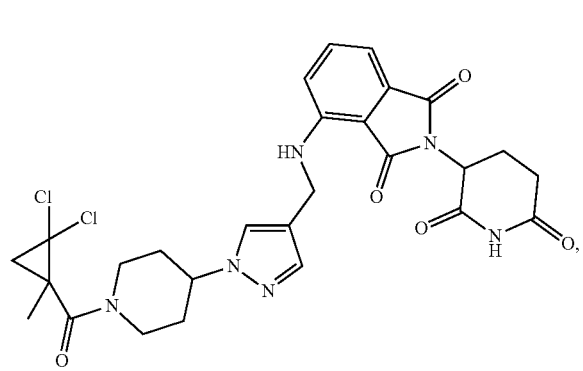
108
-continued
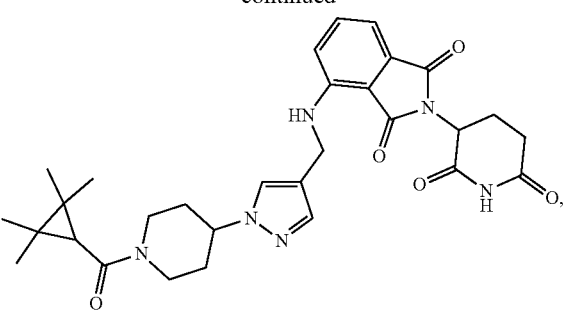
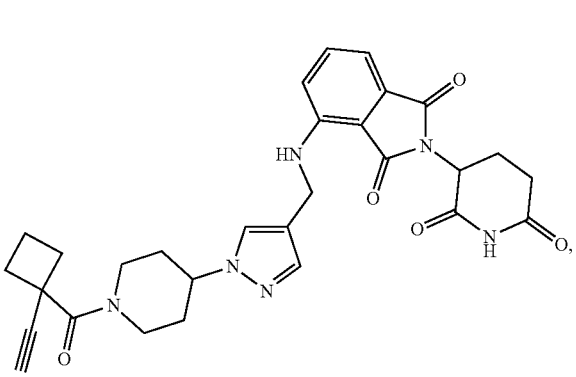
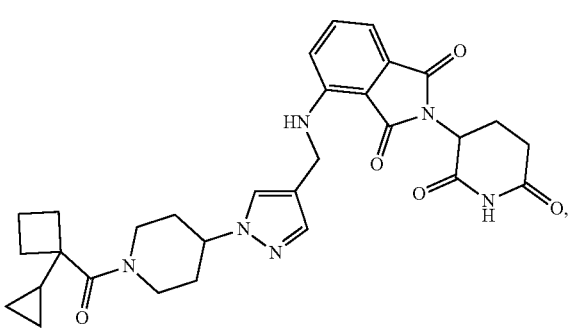
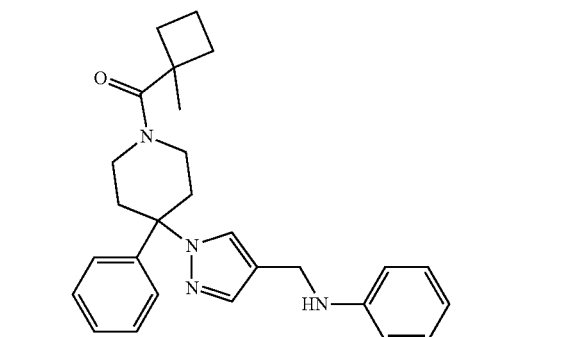
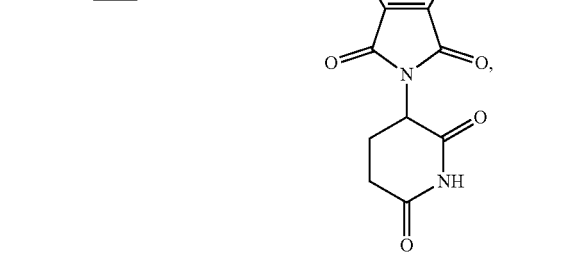

-continued
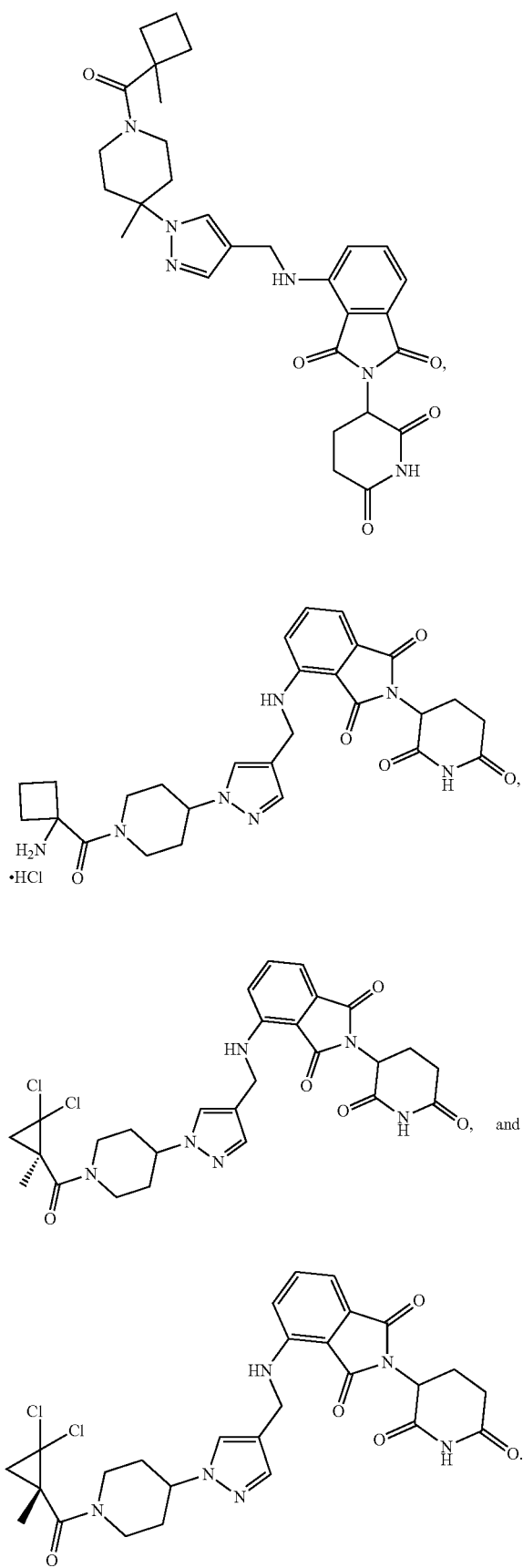
In an alternative embodiment, the compound of Formula I is selected from:
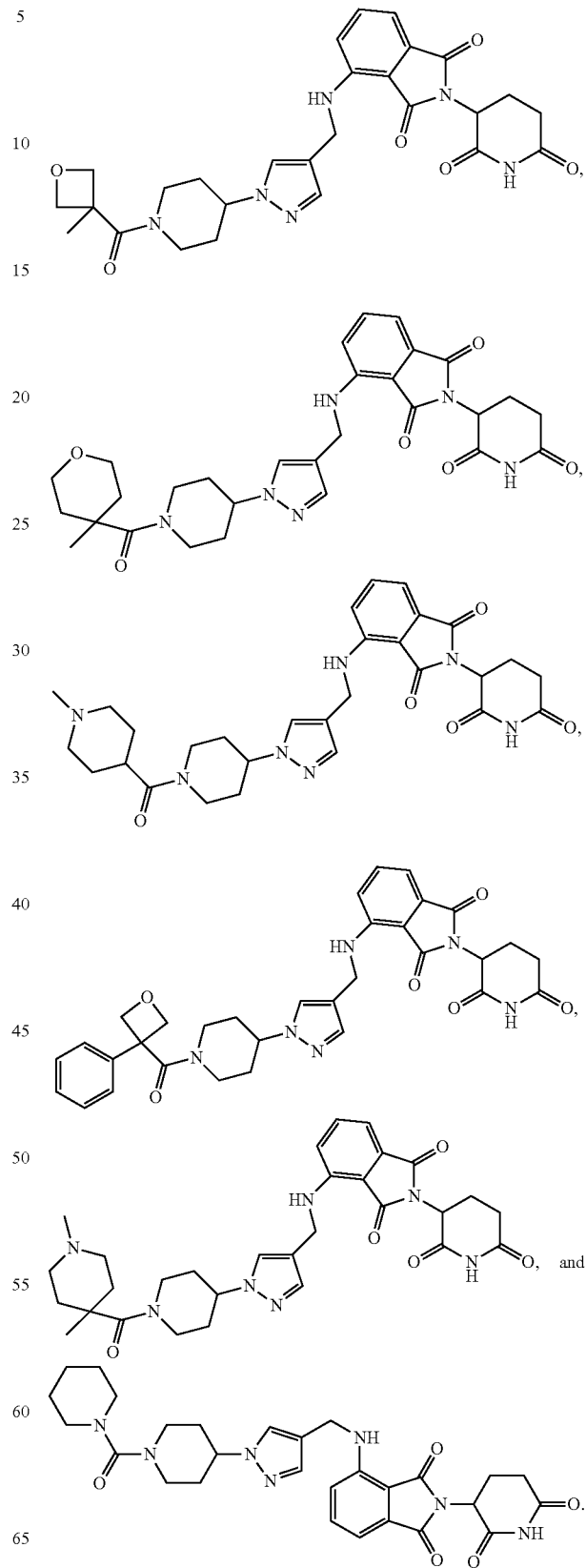

In an alternative embodiment, the compound of Formula I is selected from:
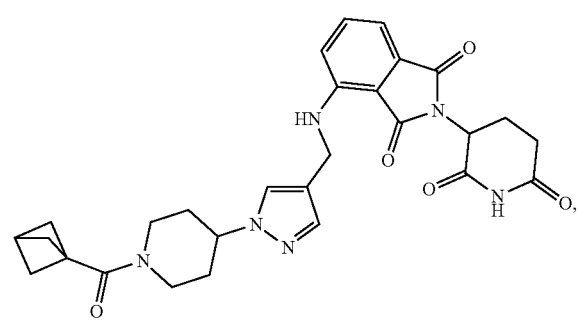
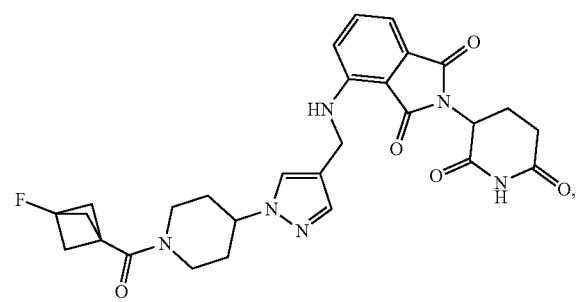
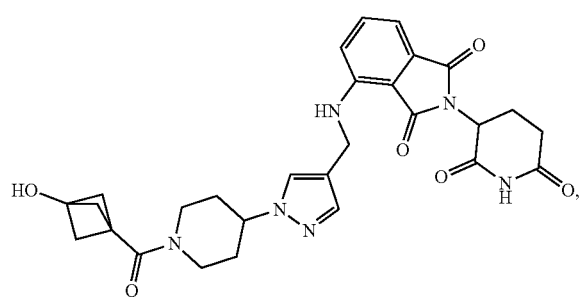
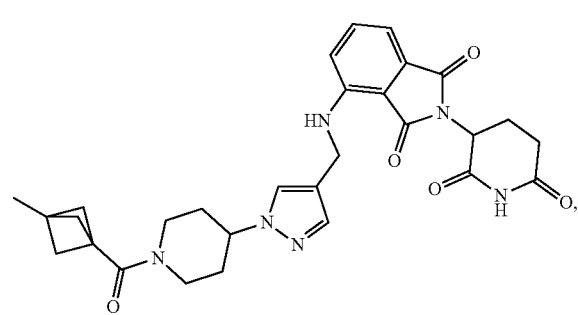
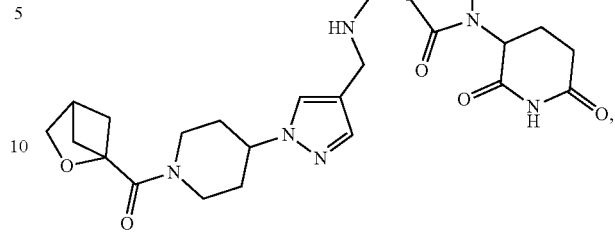
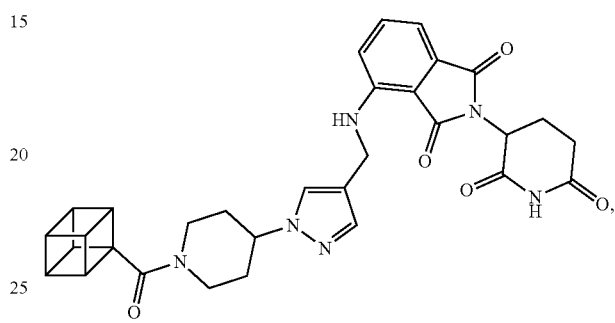
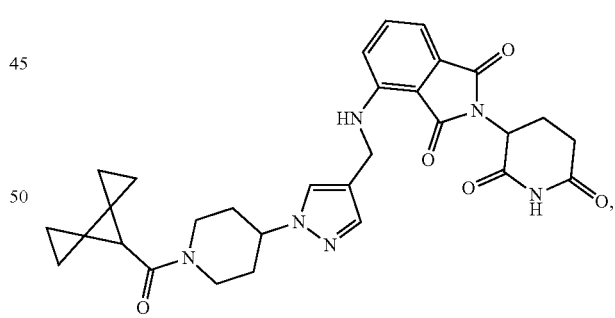
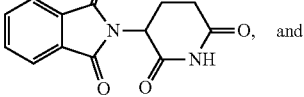

113
-continued
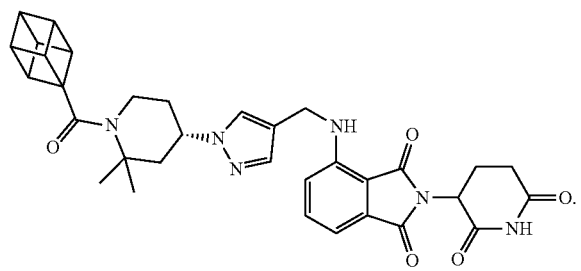
In an alternative embodiment, Compound I is selected from:
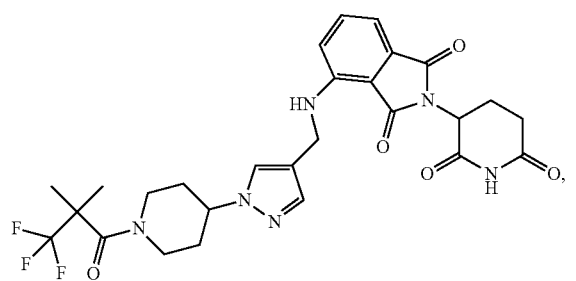
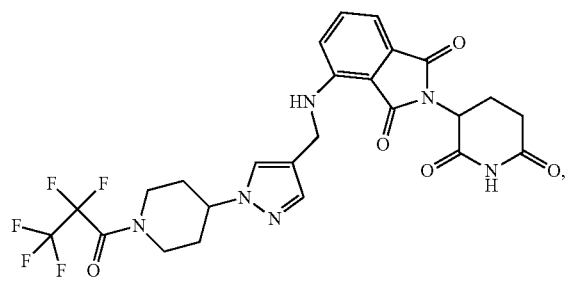
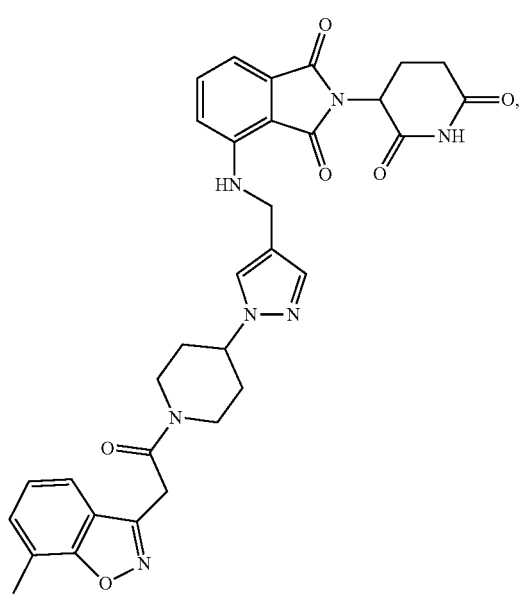
114
-continued
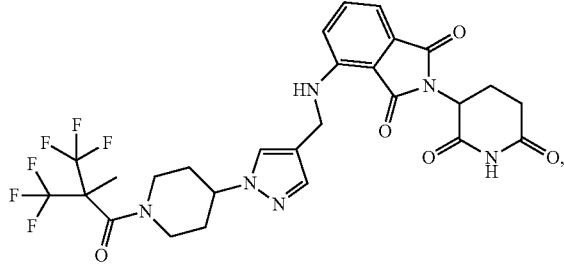
and
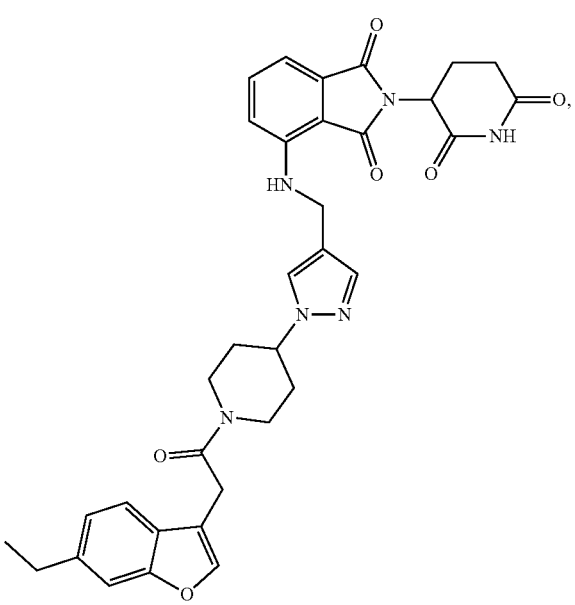
In an alternative embodiment, the compound of Formula I is selected from:

-continued
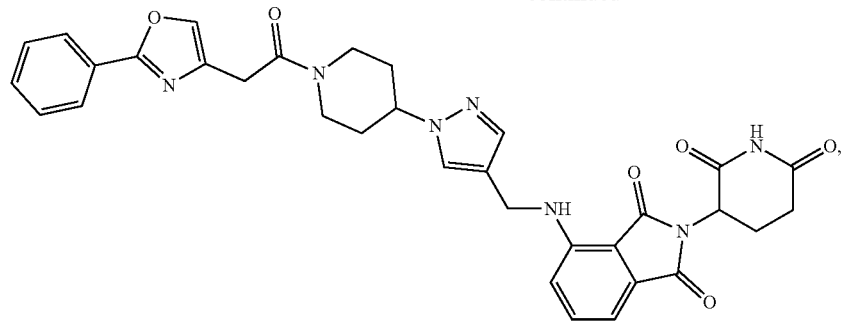
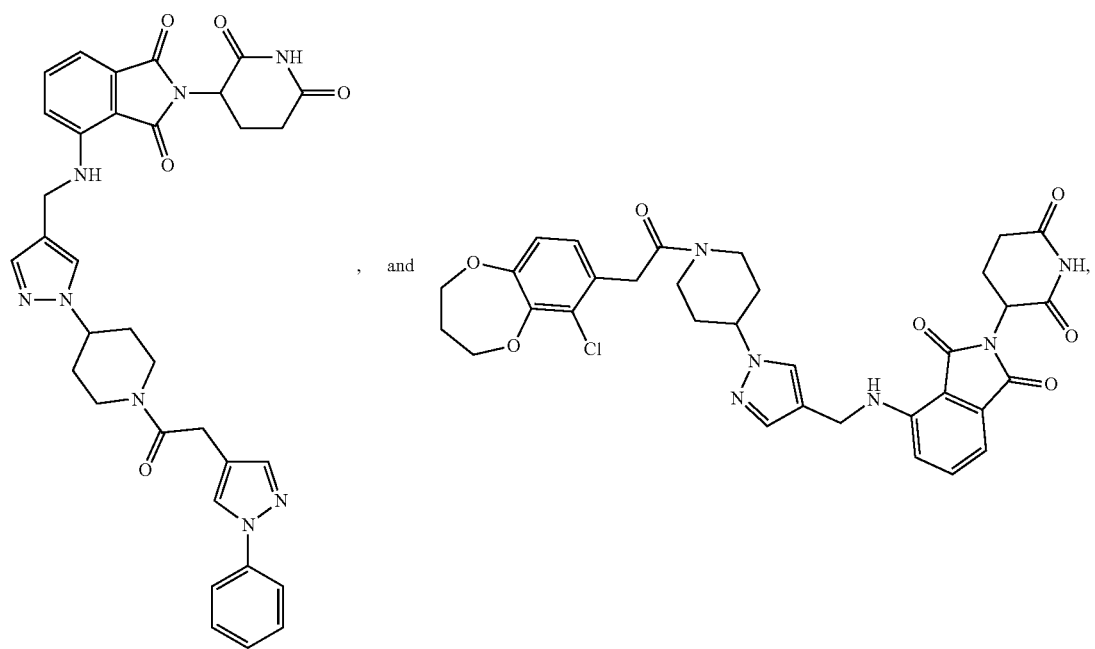
, and
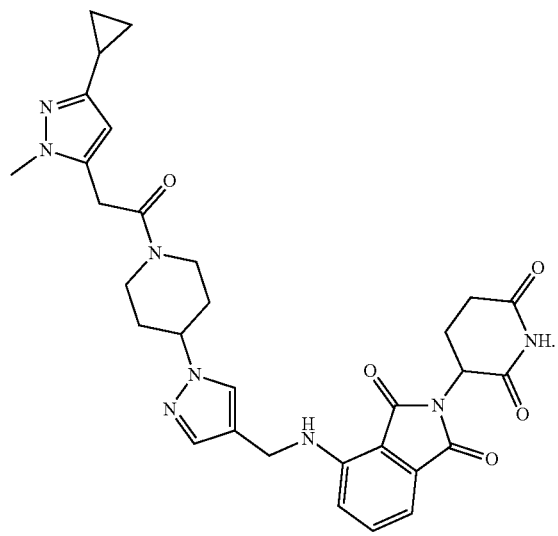 [SMILES: Cn1nc(C2CC2)cc1CC(=O)N1CCC(n2cc(CNc3cccc4c3C(=O)N(C3CCC(=O)NC3=O)C4=O)cn2)CC1]

In an alternative embodiment, the compound of Formula I is selected from:
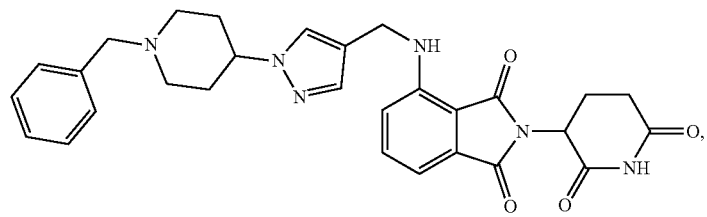
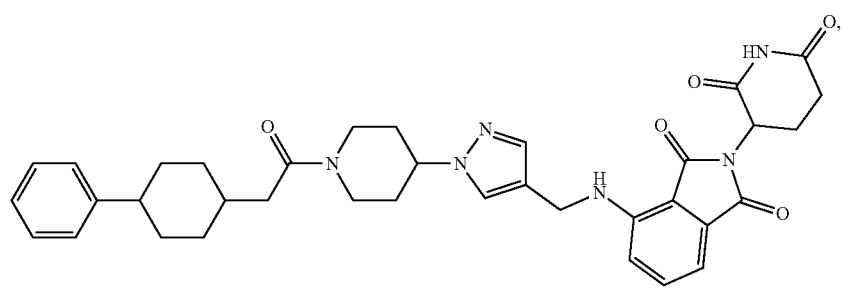
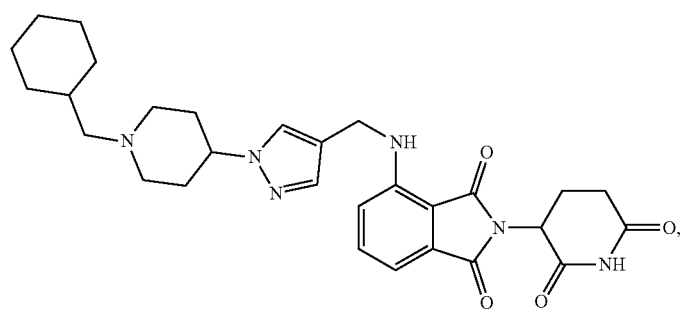
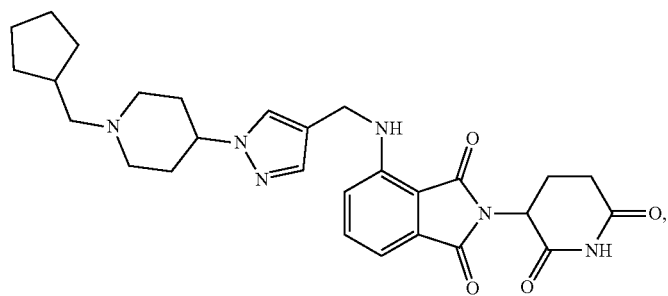
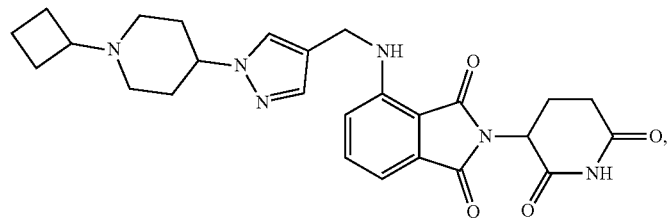

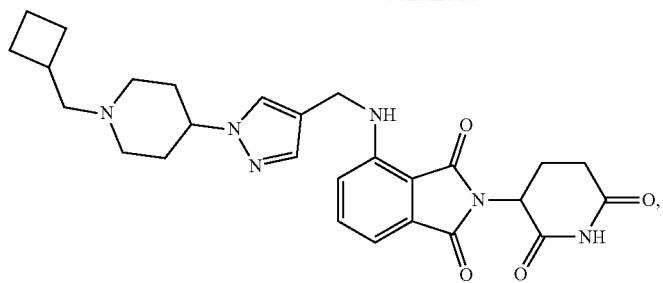
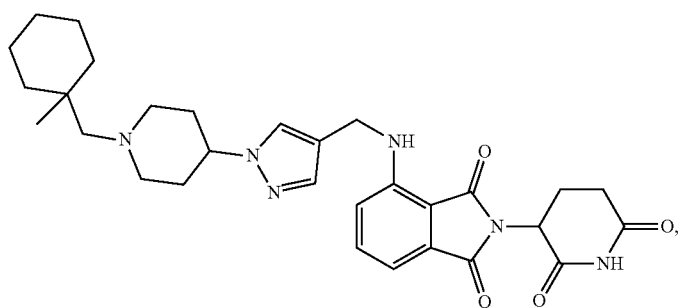
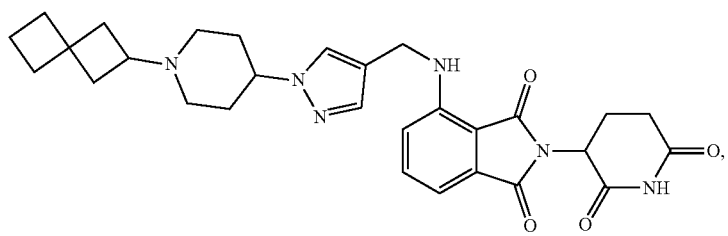
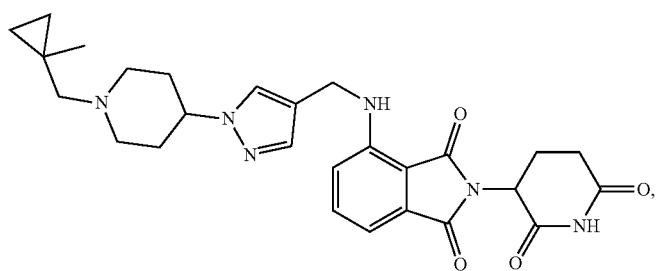
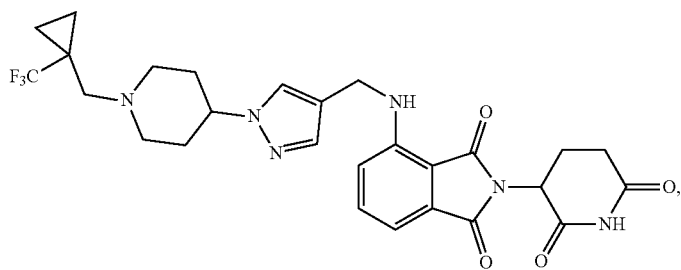

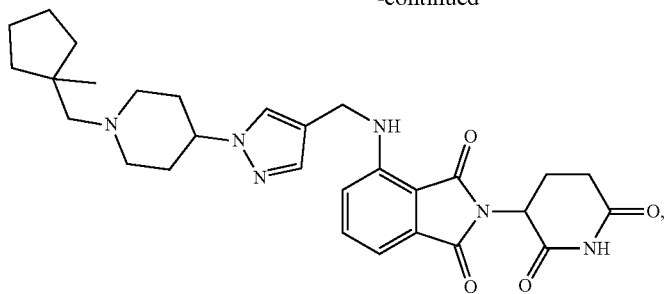
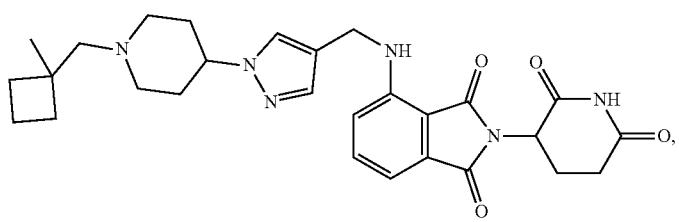
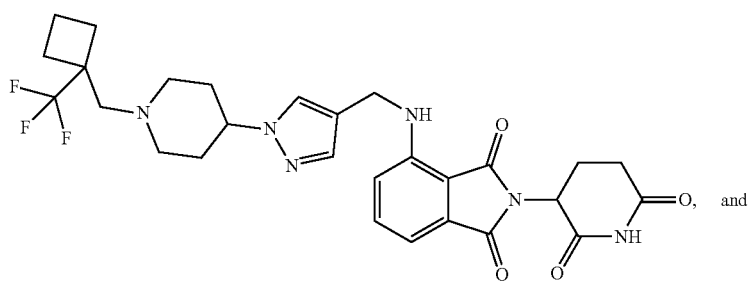
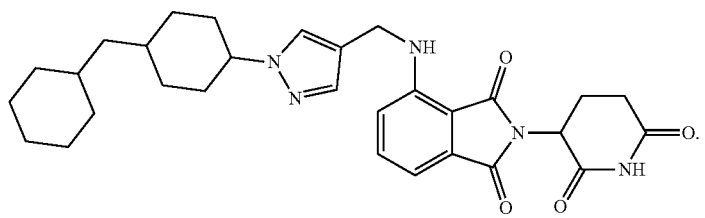
In an alternative embodiment, the compound of Formula I is selected from:
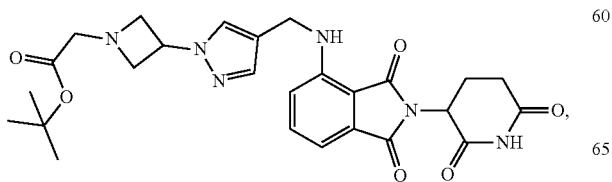

-continued

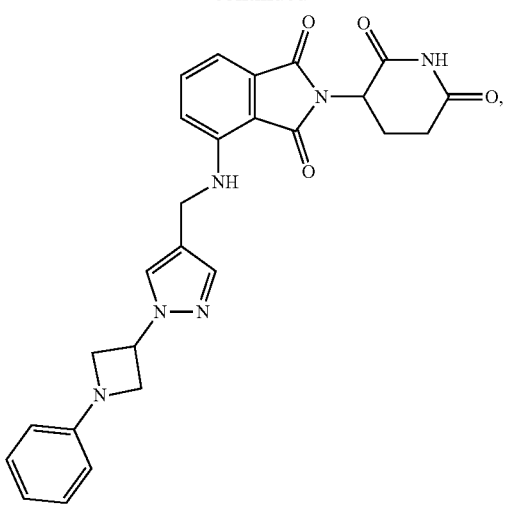

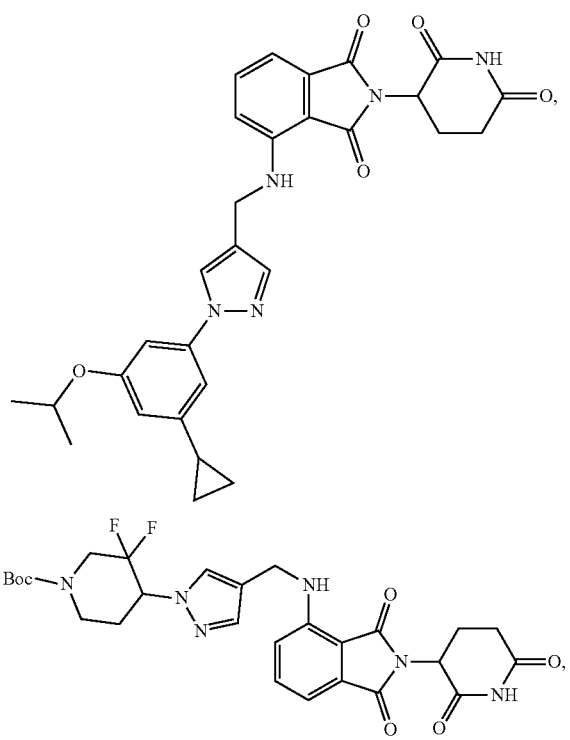

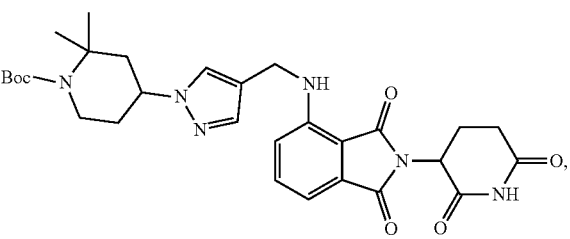

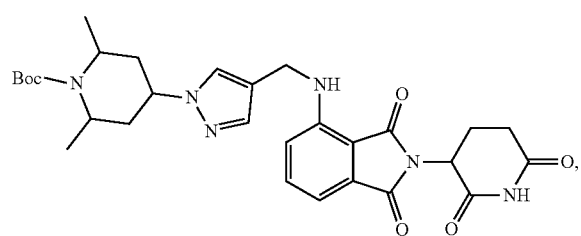

-continued

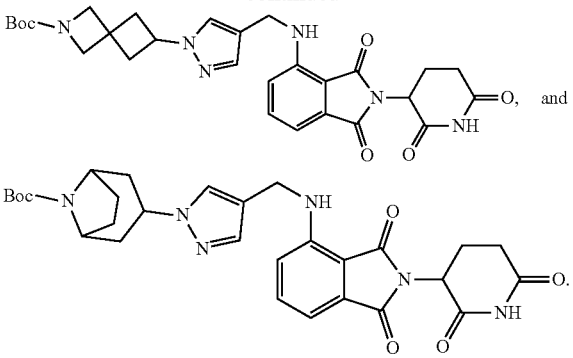

In another embodiment the compound of Formula I is selected from:

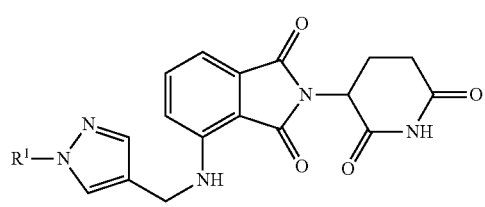

(I)

or a pharmaceutically acceptable salt, N-oxide, isotopic derivative, or prodrug thereof, optionally in a pharmaceutically acceptable carrier to form a composition;
wherein:
$R^1$ is selected from alkenyl and alkynyl; each of which is substituted with 1, 2, 3, or 4 substituents independently selected from alkyl, alkenyl, alkynyl, halogen, cyano, heteroaryl, aryl, cycloalkyl, heterocycle, —$NR^2R^2$, —$OR^2$, —$NR^2$—C(O)—$R^3$, —O—C(O)—$R^3$, and —C(O)—$R^3$; wherein the alkenyl group can be unsubstituted;
$R^2$ at each instance is independently selected from hydrogen, alkyl, alkenyl, alkynyl, aryl, and cycloalkyl; and
$R^3$ is selected from alkyl, alkenyl, alkynyl, haloalkyl, cycloalkyl, —$NR^2R^2$, and —$OR^4$.

In another embodiment the compound of Formula II is selected from:

(II)

or a pharmaceutically acceptable salt, N-oxide, isotopic derivative, or prodrug thereof, optionally in a pharmaceutically acceptable carrier to form a composition;
wherein:
$R^{11}$ is selected from alkenyl and alkynyl; each of which is substituted with 1, 2, 3, or 4 substituents independently selected from alkyl, alkenyl, alkynyl, halogen, cyano, heteroaryl, aryl, cycloalkyl, heterocycle, —$NR^2R^2$, —OR², —NR²—C(O)—R³, —O—C(O)—R³, and —C(O)—R³; wherein the alkenyl group can be unsubstituted;
wherein the remaining variables are as defined herein.
Embodiments of R²⁰
In one embodiment, R²⁰ is selected from:
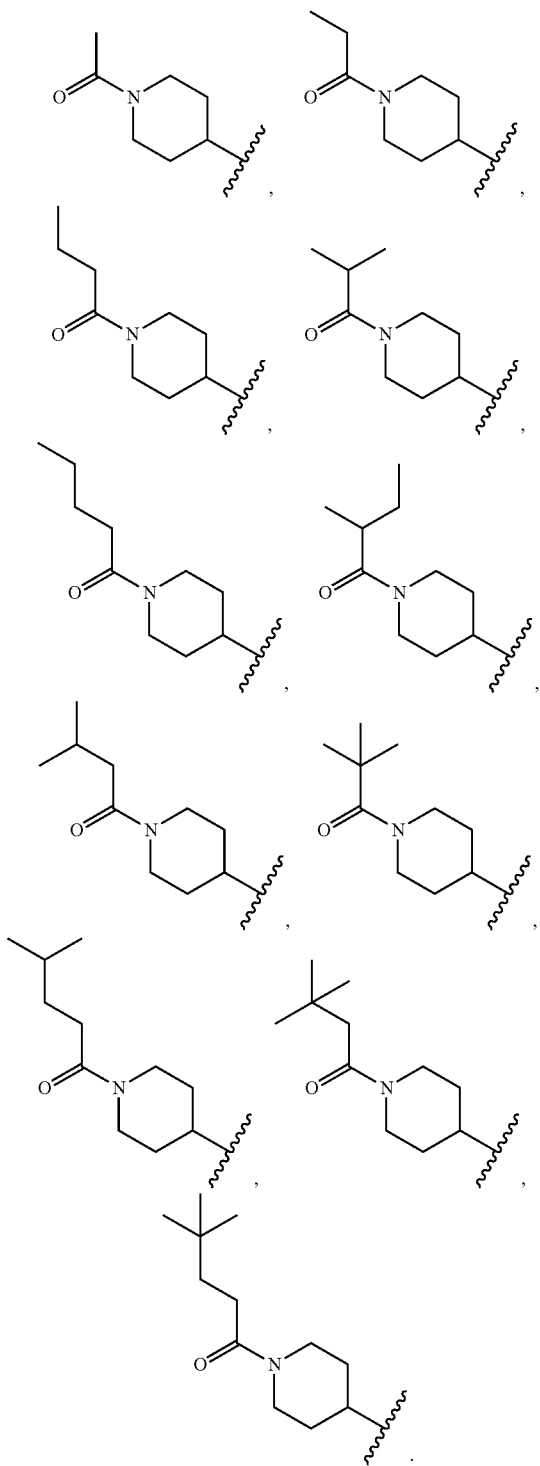
In one embodiment, R² is selected from:
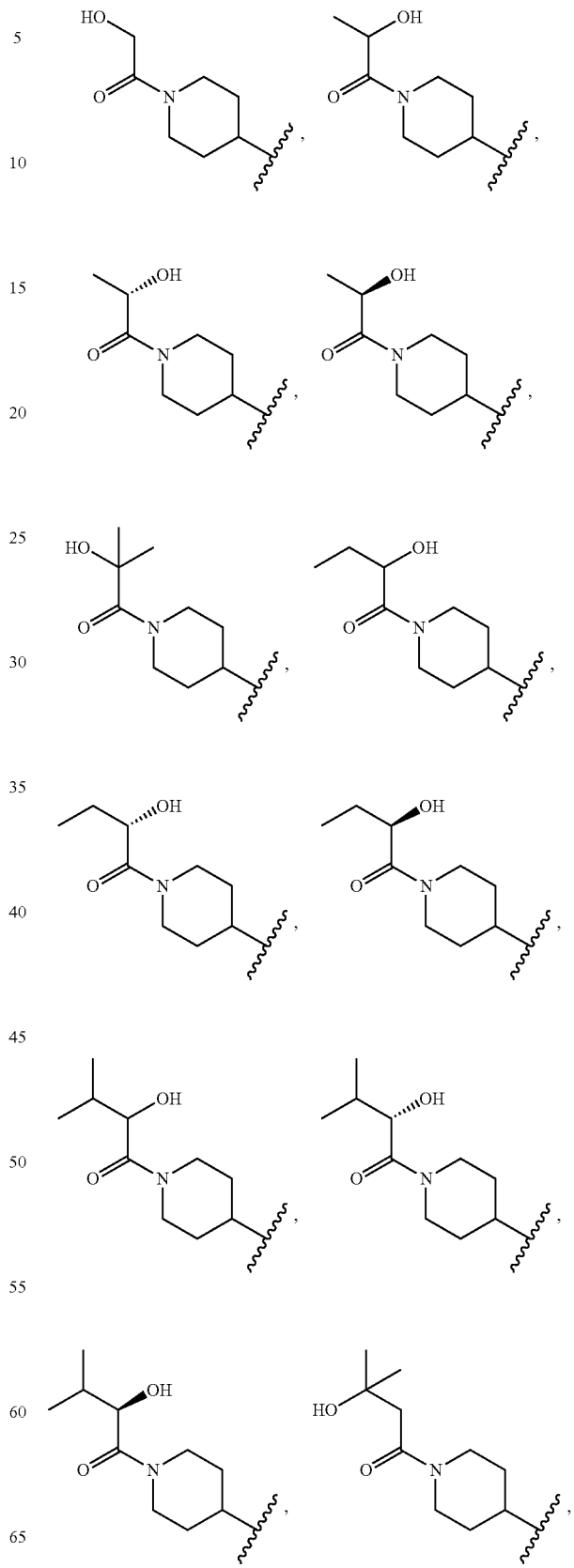

-continued
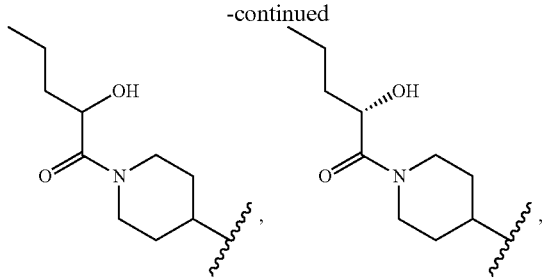
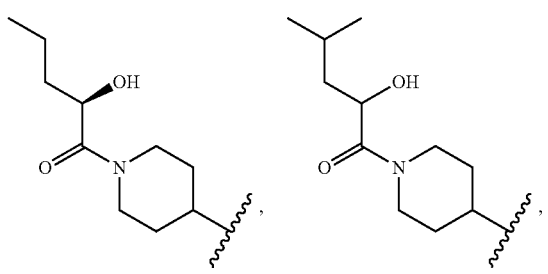
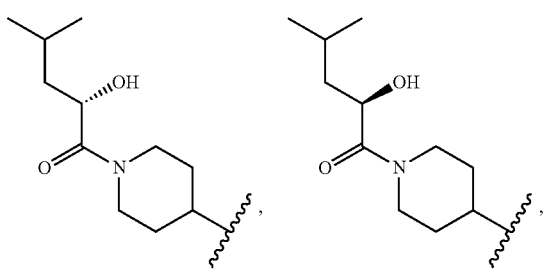
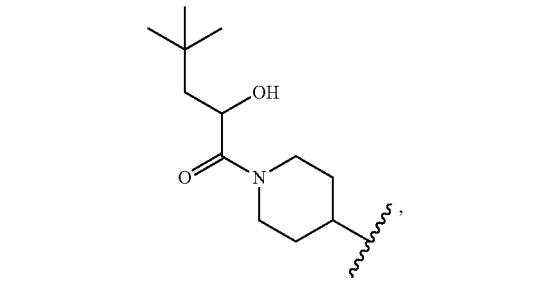
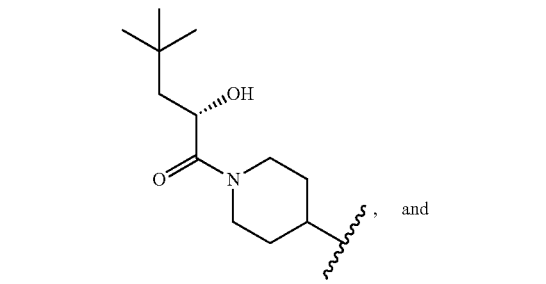, and
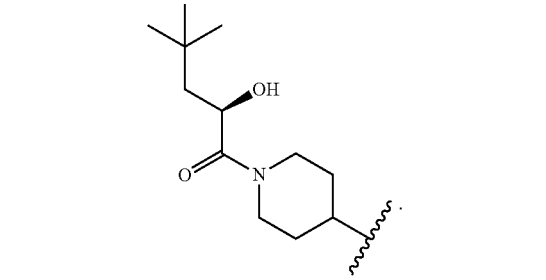.
In one embodiment, R$^{20}$ is selecte from:
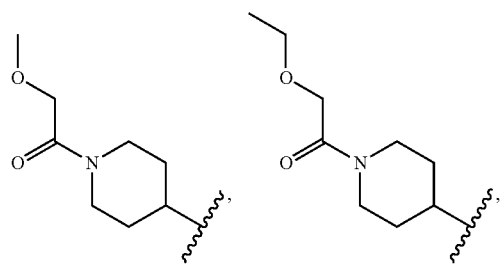
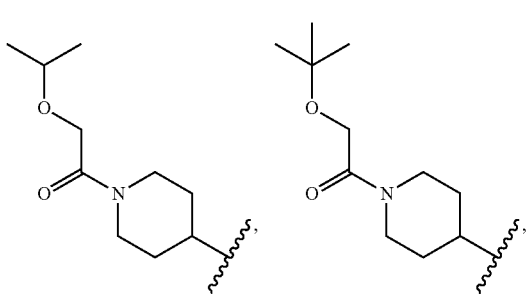
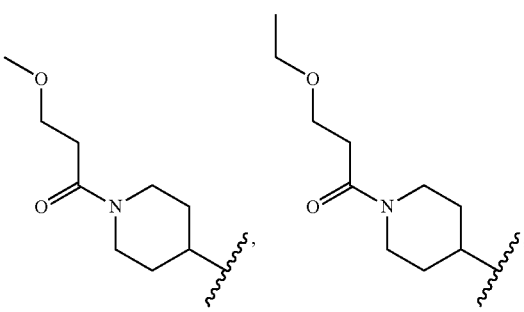
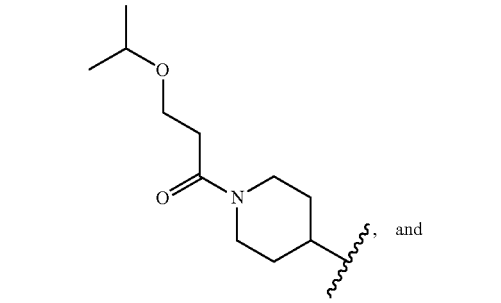, and
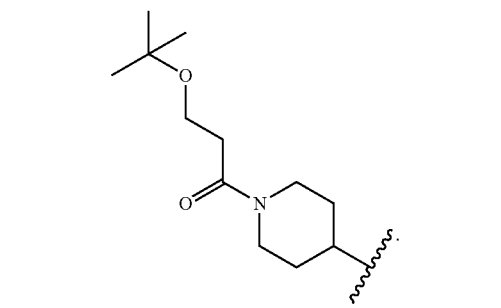.

In one embodiment, $R^{20}$ is selected from:
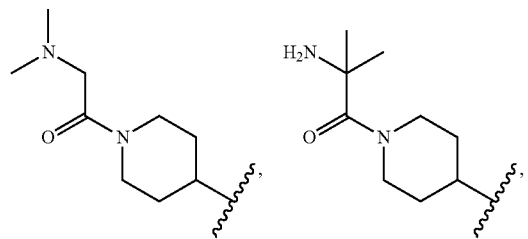
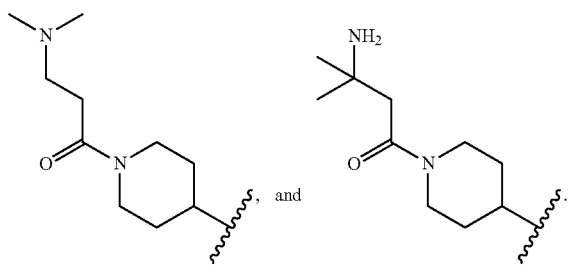
In one embodiment, $R^{20}$ is
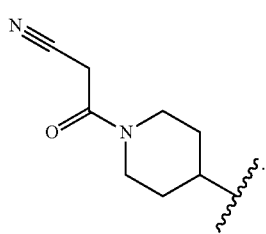 [SMILES: *C1CCN(C(=O)CC#N)CC1]
In one embodiment, $R^{20}$ is selected from:
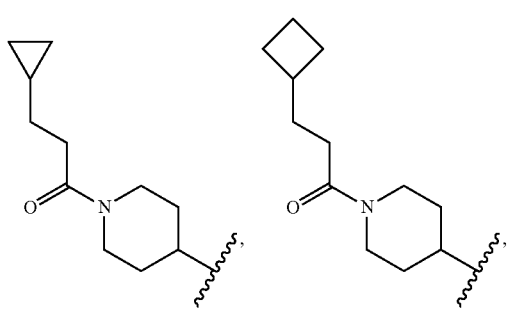
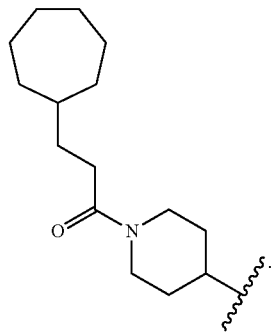
In one embodiment, $R^{20}$ is selected from:
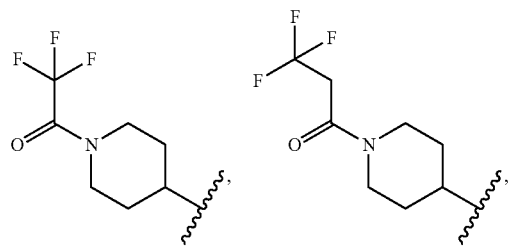
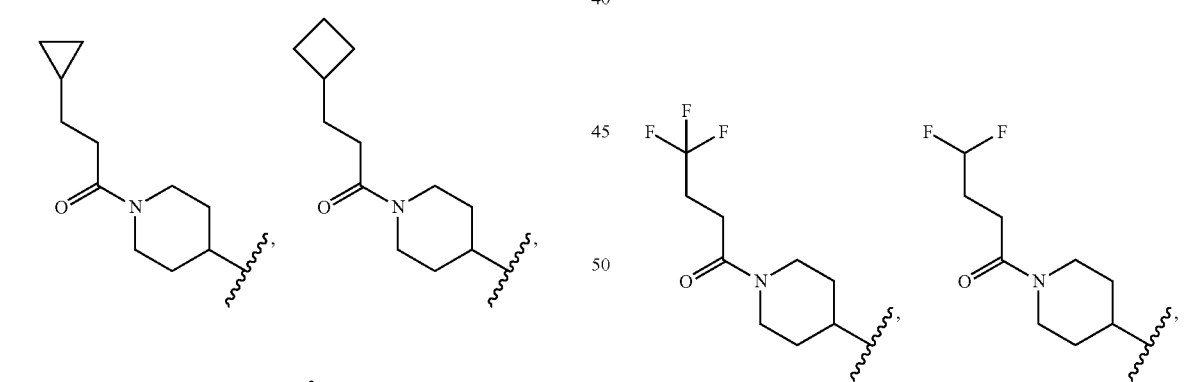
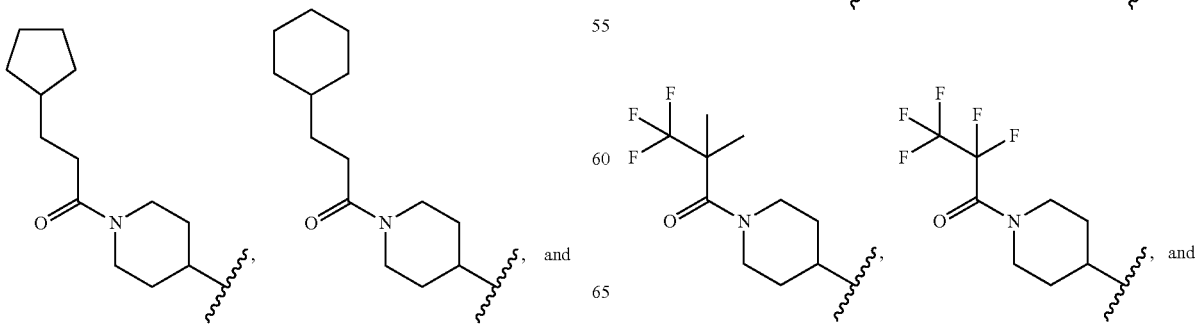

-continued
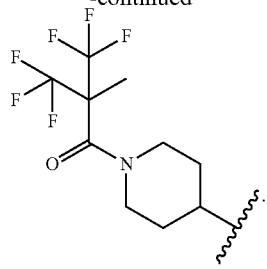
In one embodiment, $R^{20}$ is selected from:
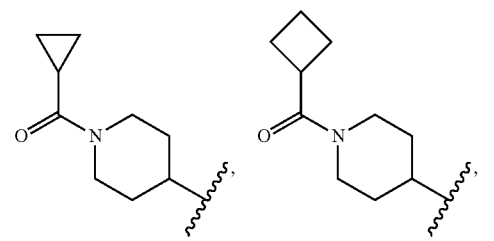
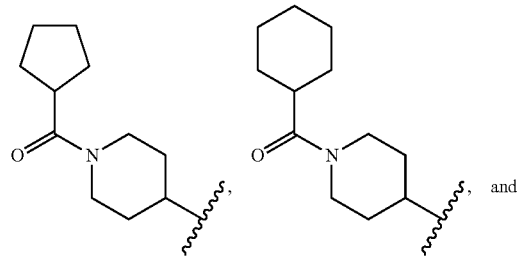
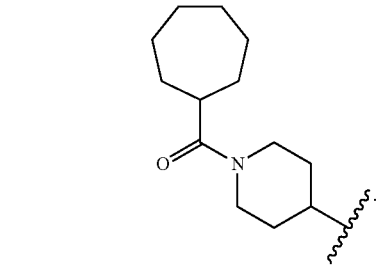
In one embodiment, $R^{20}$ is selected from:
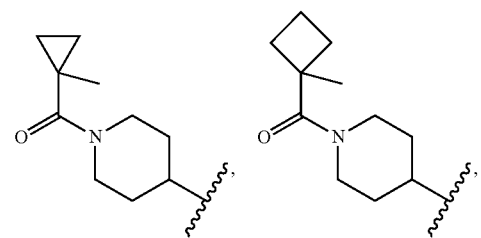
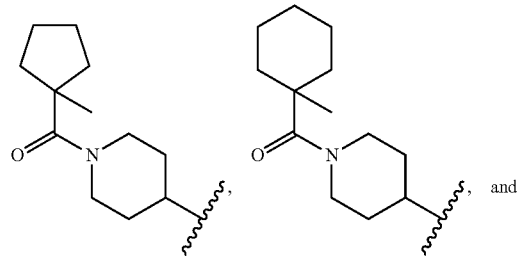
-continued
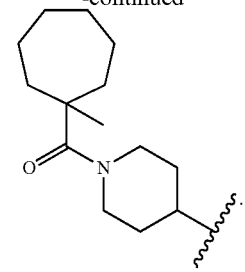
In one embodiment, $R^{20}$ is selected from:
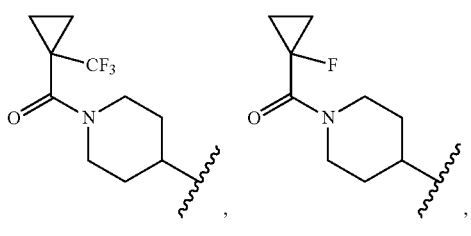
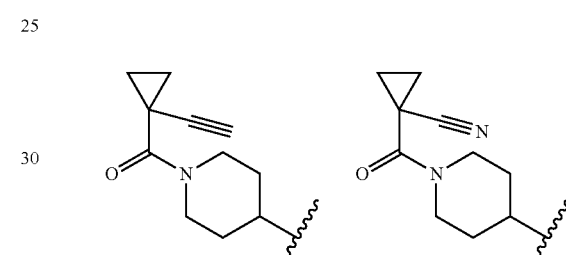
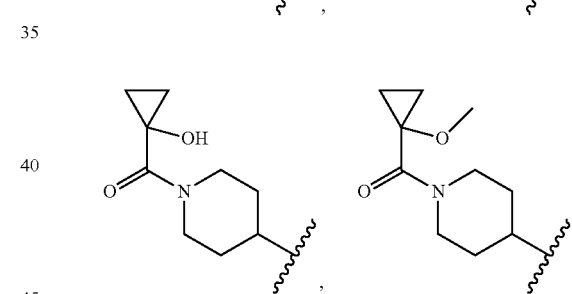
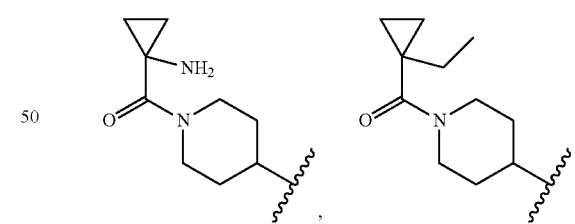
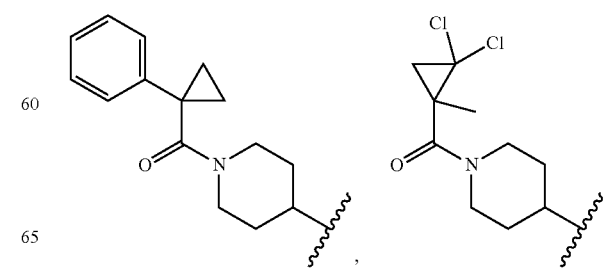

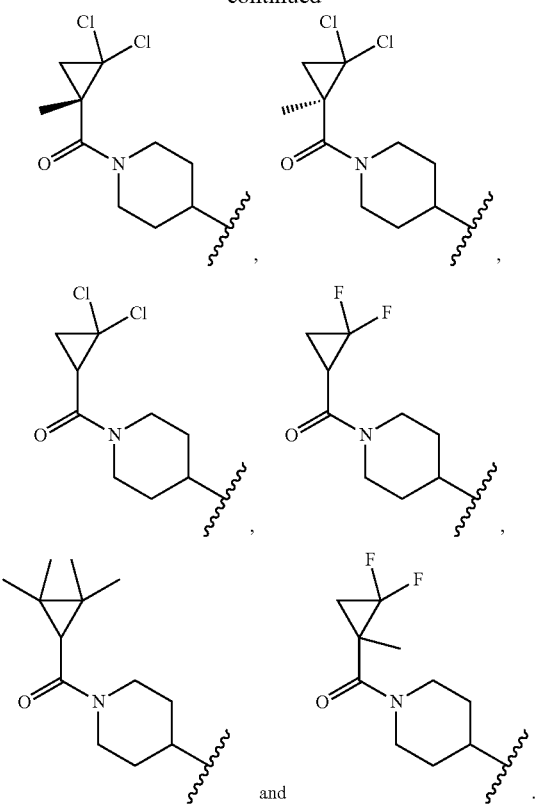
In one embodiment, R²⁰ is selected from:
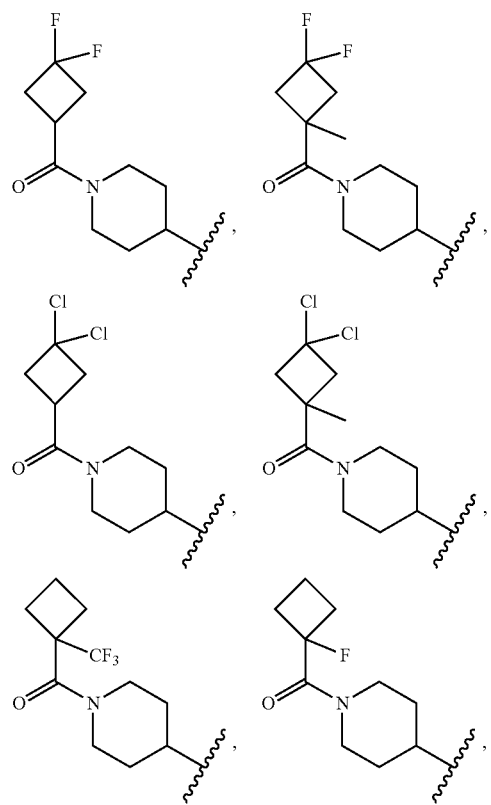
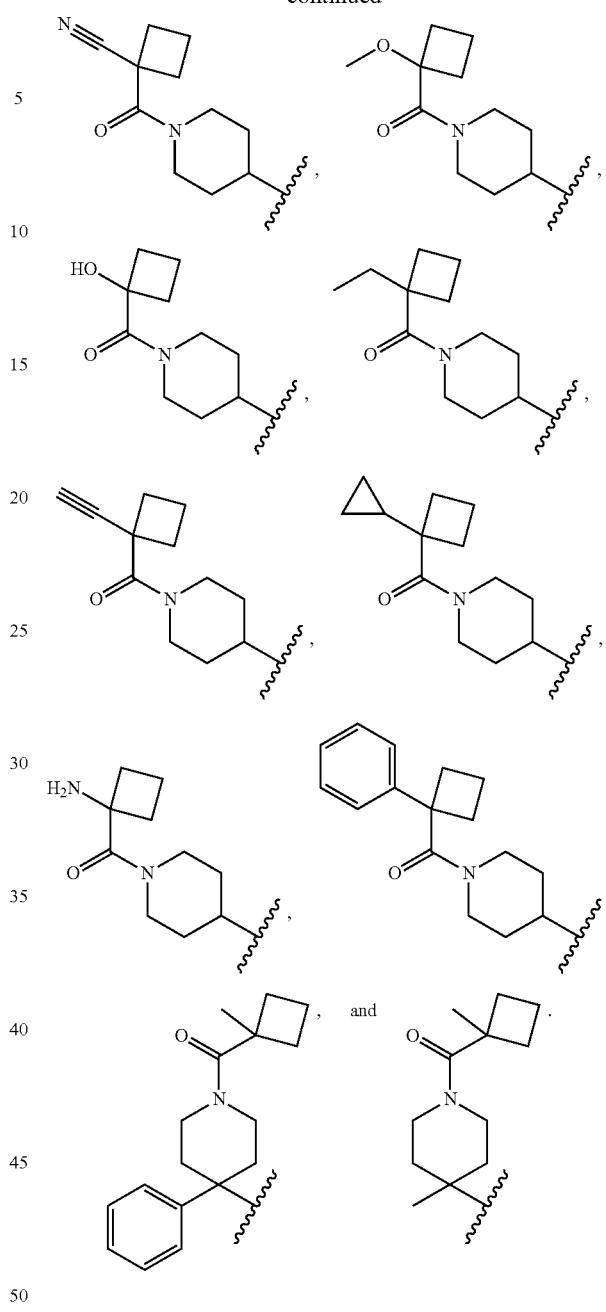
In one embodiment, R²⁰ is selected from:
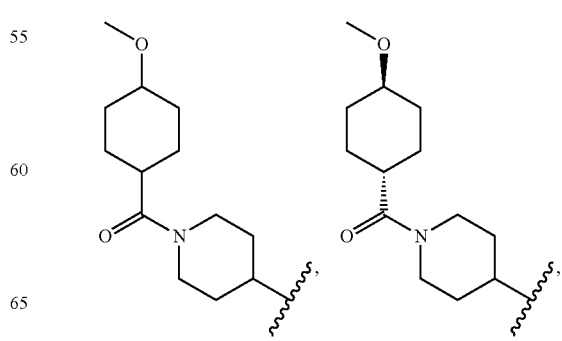

-continued
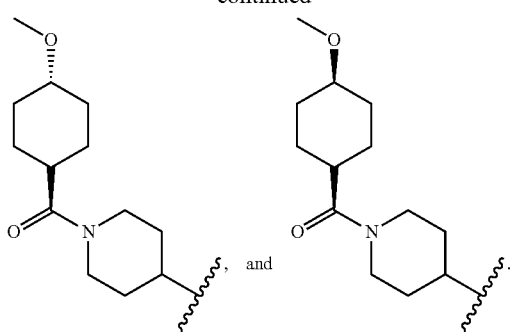, and
In one embodiment, R²⁰ is selected from:
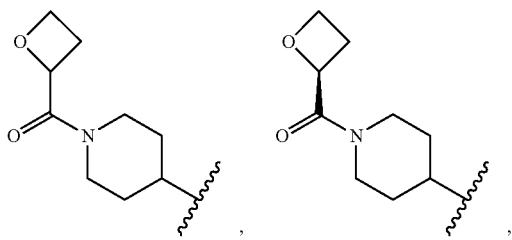,
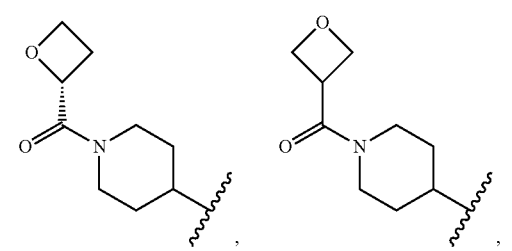,
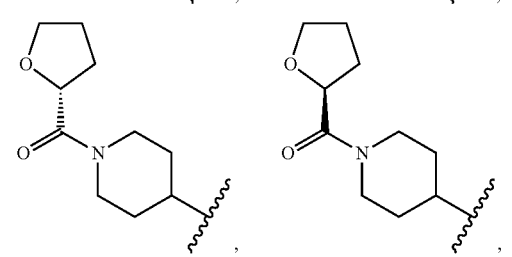,
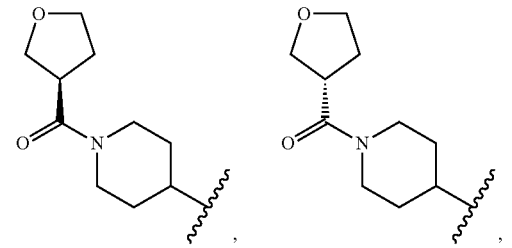,
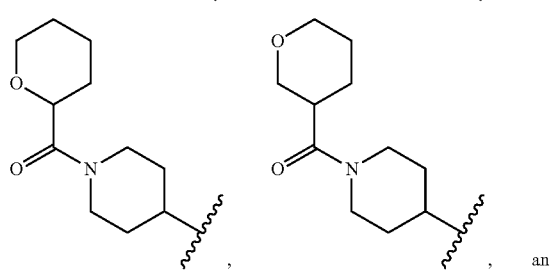, and
-continued
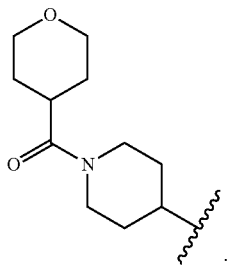.
In one embodiment, R²⁰ is selected from:
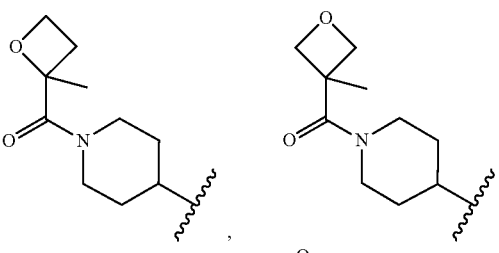,
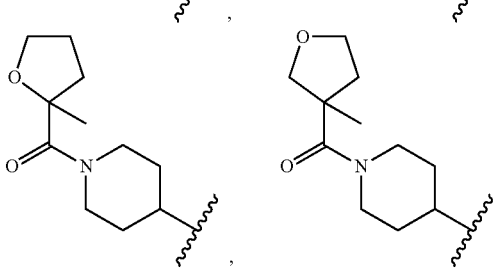,
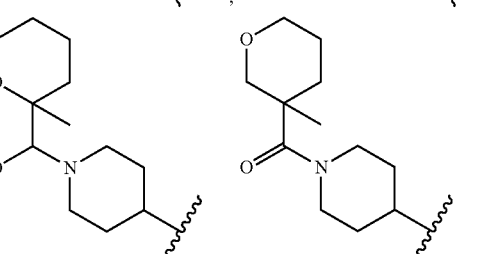,
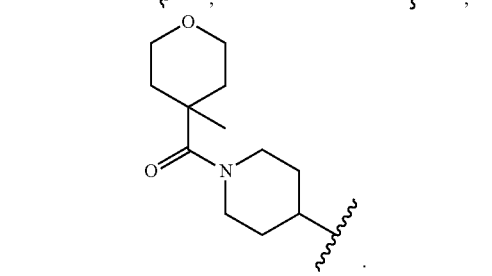, and
In one embodiment, R²⁰ is selected from:
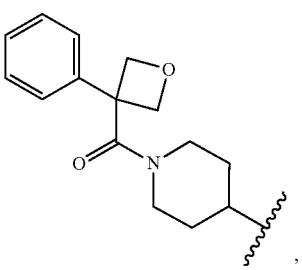, -continued
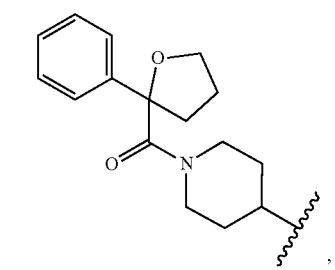
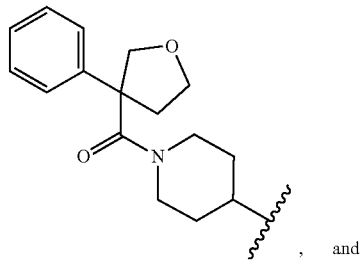
, and
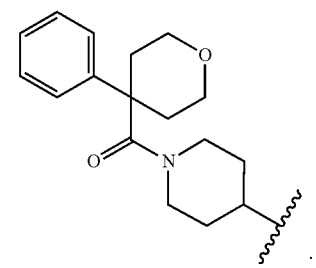
In one embodiment, $R^{20}$ is selected from:
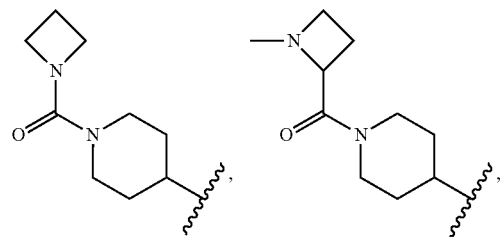
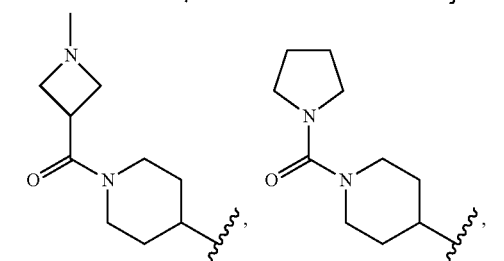
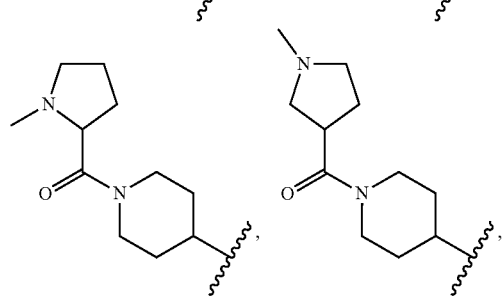
-continued
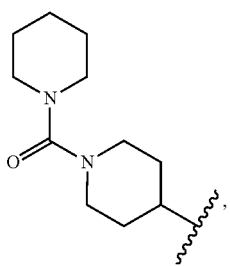 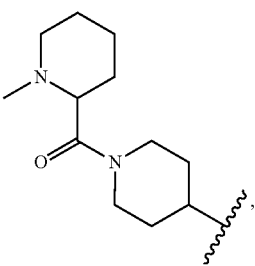
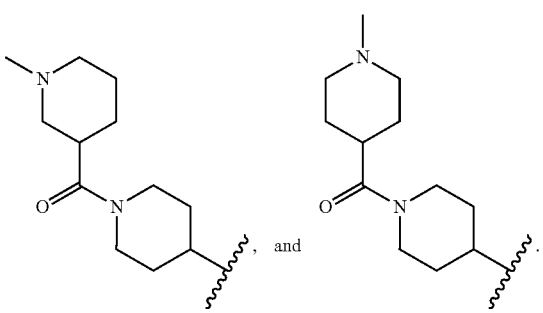
, and
In one embodiment, $R^{20}$ is selected from:
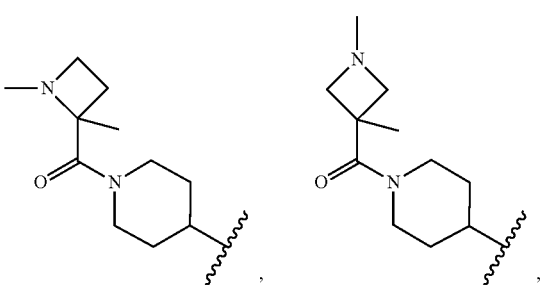
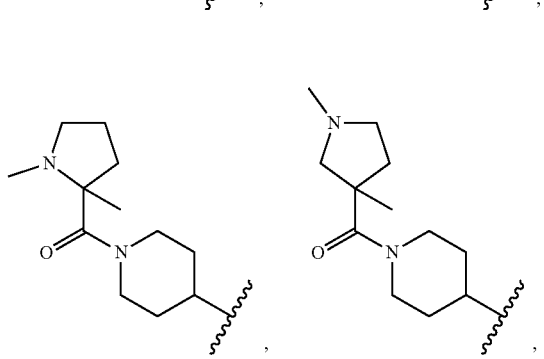
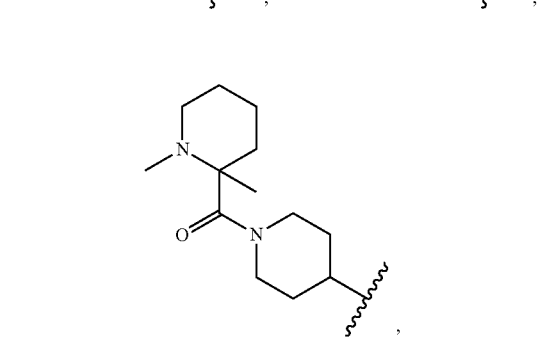

-continued
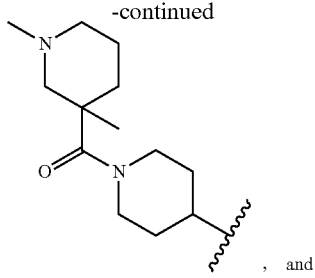
, and
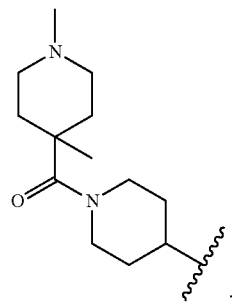
.
In one embodiment, R[20] is
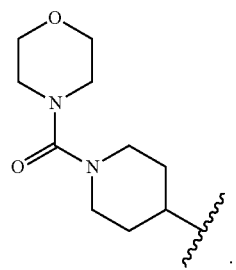 [SMILES: *C1CCN(C(=O)N2CCOCC2)CC1]
In one embodiment, R[20] is
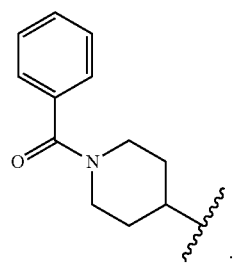 [SMILES: *C1CCN(C(=O)c2ccccc2)CC1]
In one embodiment, R[20] is selected from:
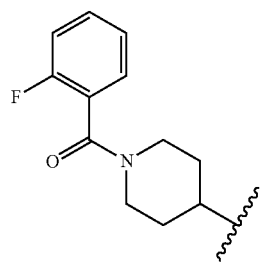
,
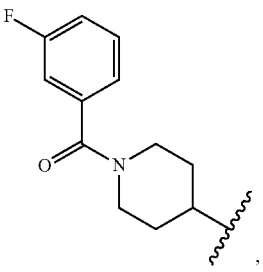
,
-continued
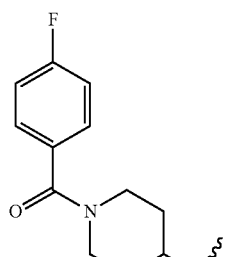
, and
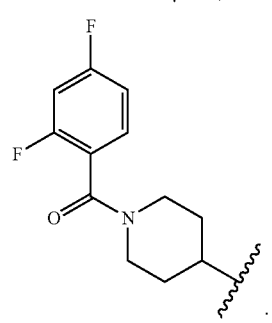
.
In one embodiment, R[20] is
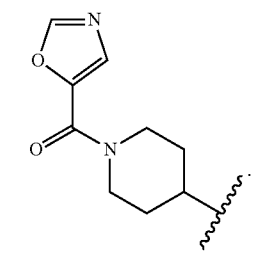 [SMILES: *C1CCN(C(=O)c2cnco2)CC1]
.
In one embodiment, R[20] is selected from
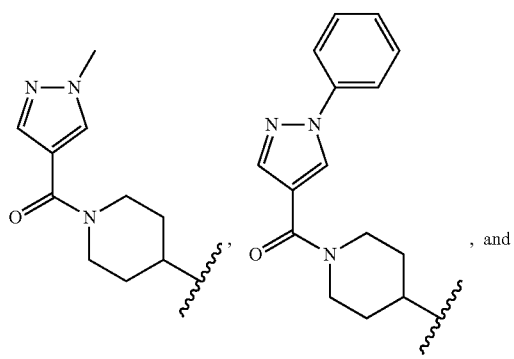
, and
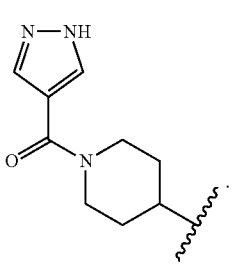
.

In one embodiment, $R^{20}$ is selected from
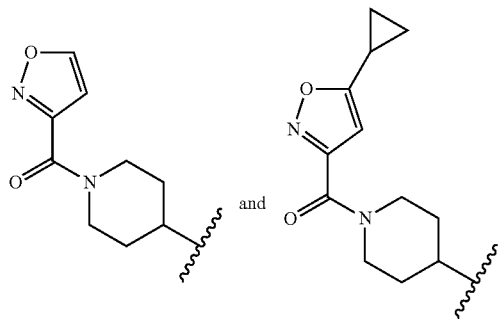 and .
In one embodiment, $R^{20}$ is
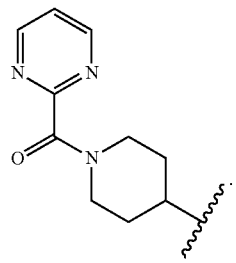
In one embodiment, $R^{20}$ is
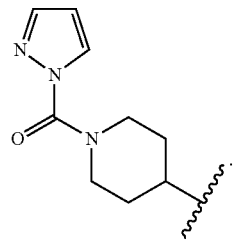 [SMILES: *C1CCN(C(=O)n2cccn2)CC1]
In on embodiment, $R^{20}$ is
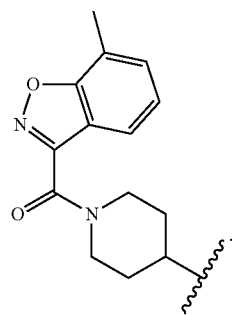 [SMILES: *C1CCN(C(=O)c2noc3c(C)cccc23)CC1]
In one embodiment, $R^{20}$ is
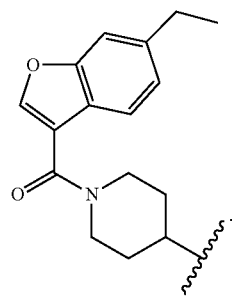 [SMILES: *C1CCN(C(=O)c2coc3cc(CC)ccc23)CC1]
In one embodiment, $R^{20}$ is
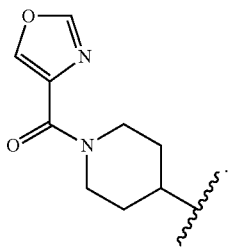 [SMILES: *C1CCN(C(=O)c2cocn2)CC1]
In one embodiment, $R^{20}$ is
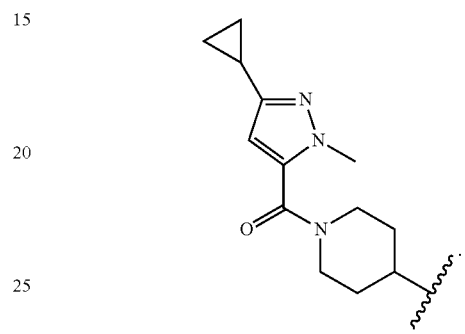
In one embodiment, $R^{20}$ is selected from:
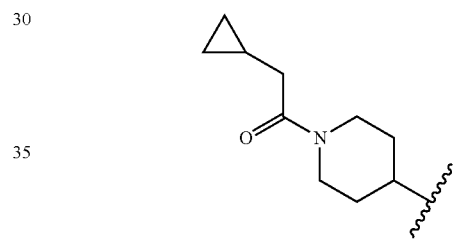,
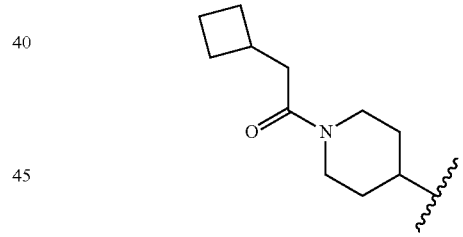,
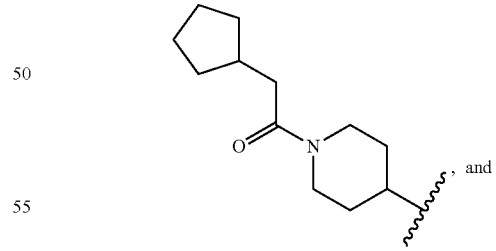, and
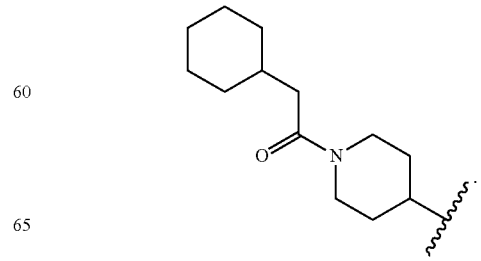

In one embodiment, $R^{20}$ is selected from:
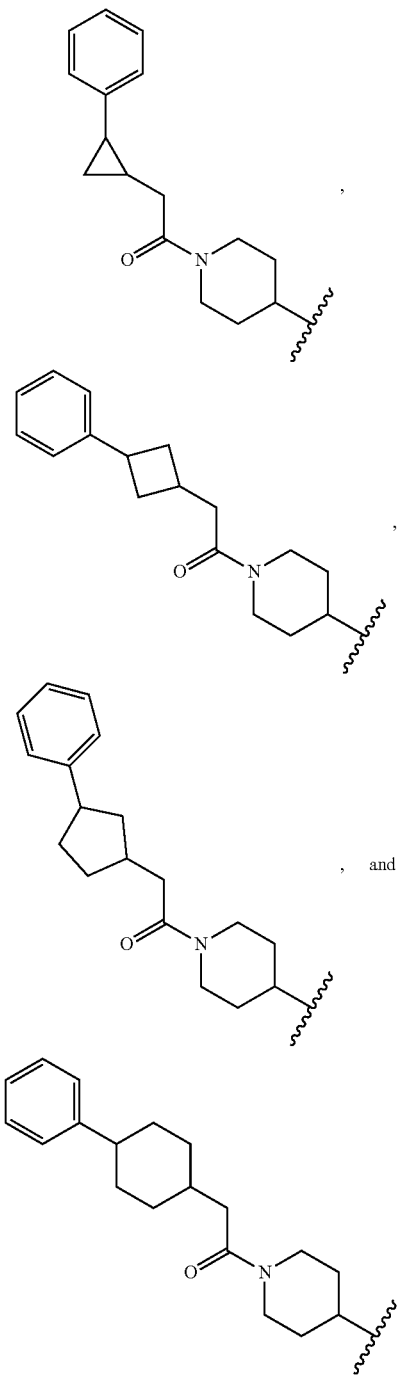
In one embodiment, $R^{20}$ is
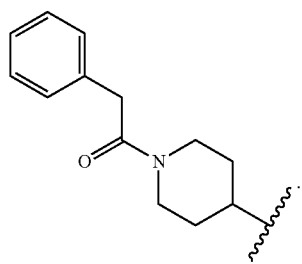 [SMILES: *C1CCN(C(=O)Cc2ccccc2)CC1]
In one embodiment, $R^{20}$ is selected from:
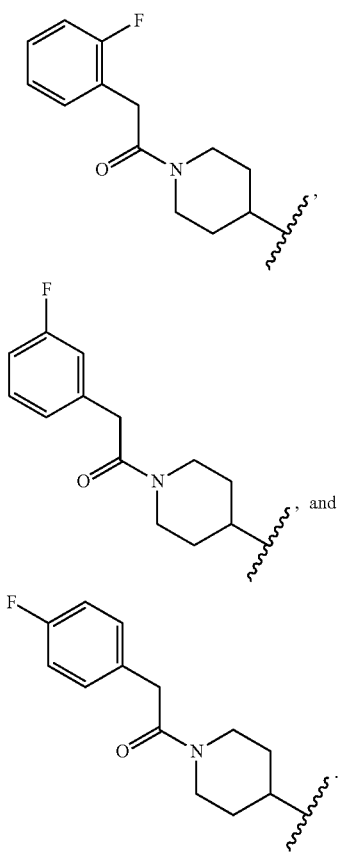
In one embodiment, $R^{20}$ is selected from:
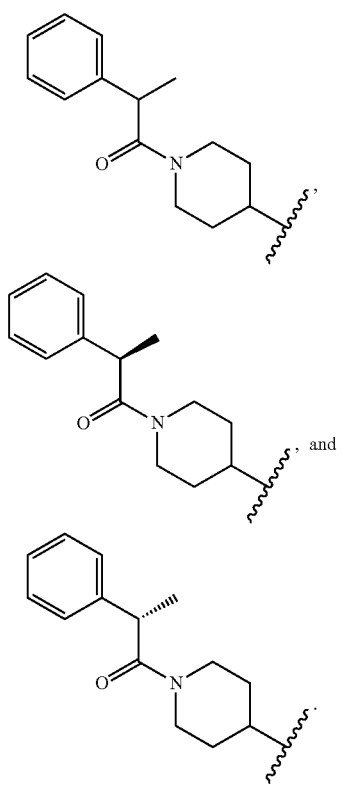

In one embodiment, $R^{20}$ is
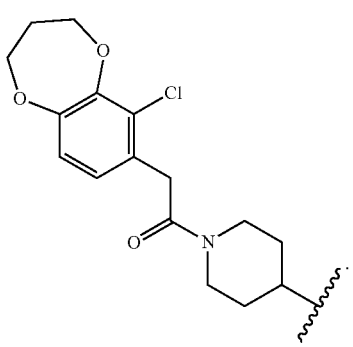 [SMILES: *C1CCN(C(=O)Cc2ccc3c(c2Cl)OCCCO3)CC1]
In one embodiment, $R^{20}$ is selected from:
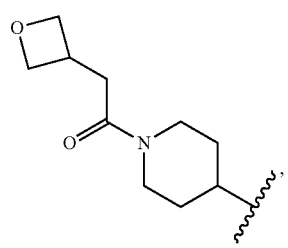
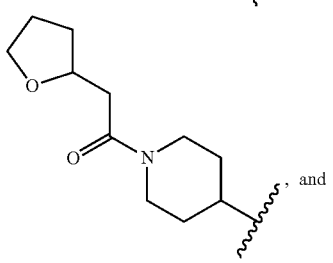
, and
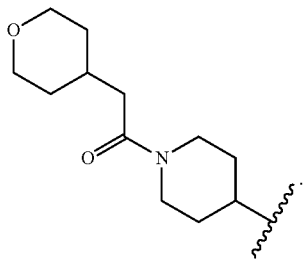
.
In one embodiment, $R^{20}$ is selected from:
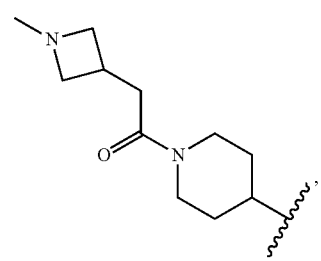
,
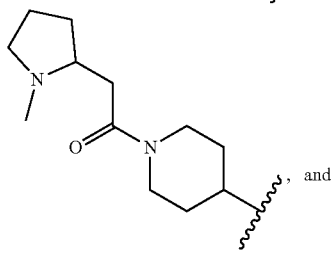
, and
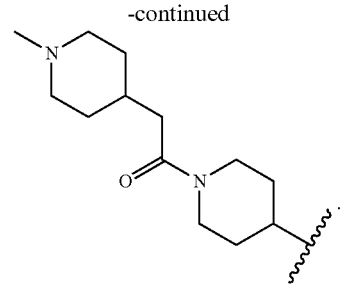
.
In one embodiment, $R^{20}$ is
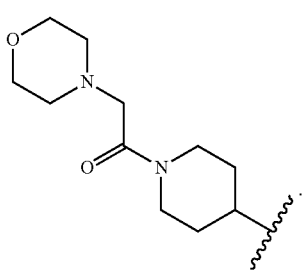 [SMILES: *C1CCN(C(=O)CN2CCOCC2)CC1 ; "."]
.
In one embodiment, $R^{20}$ is selected from:
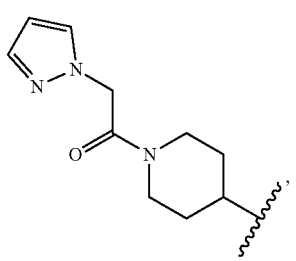
,
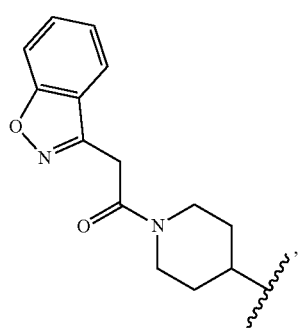
,
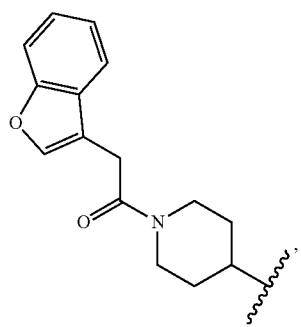
, 147
-continued
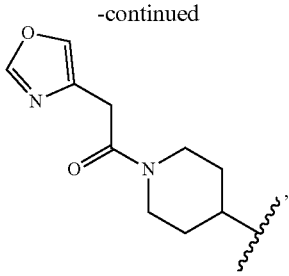
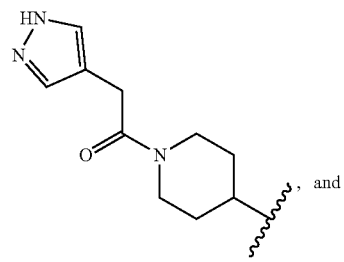, and
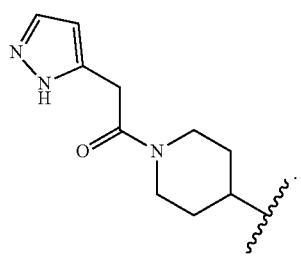.
In one embodiment, R$^{20}$ is selected from:
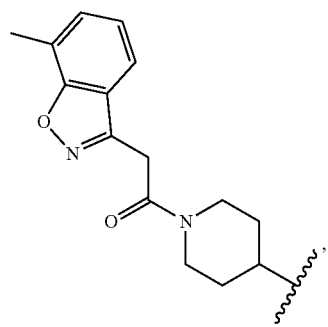
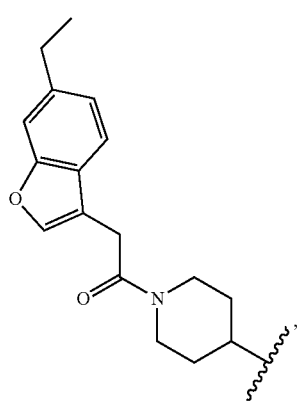
148
-continued
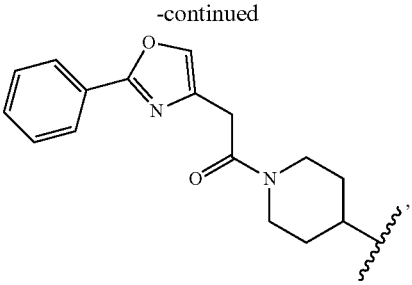
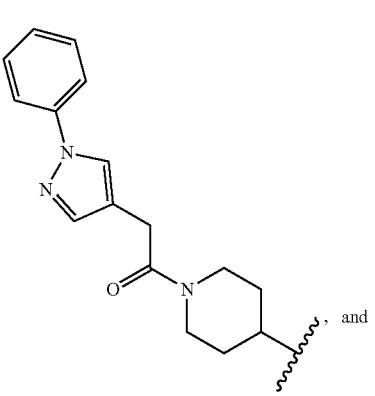, and
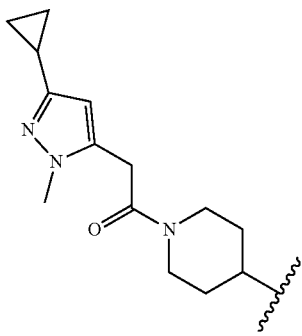
In one embodiment, R$^{20}$ is selected from:
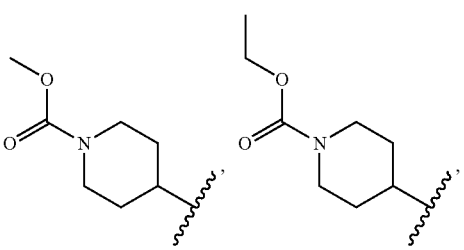
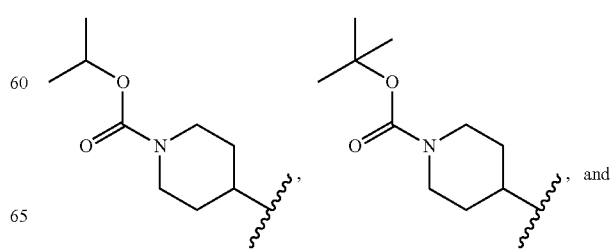, and -continued
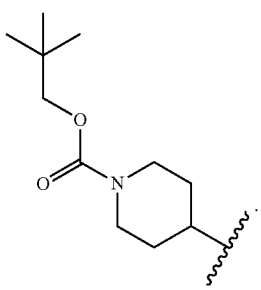
In one embodiment, R$^{20}$ is selected from
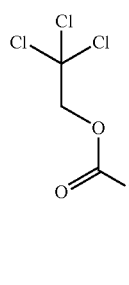 and 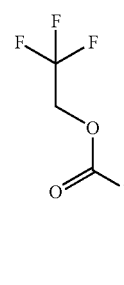
In one embodiment, R$^{20}$ is
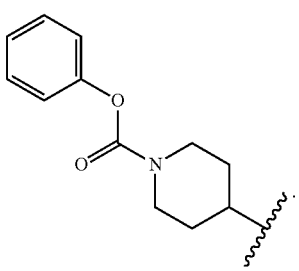 [SMILES: *C1CCN(C(=O)Oc2ccccc2)CC1 ; "."]
In one embodiment, R$^{20}$ is
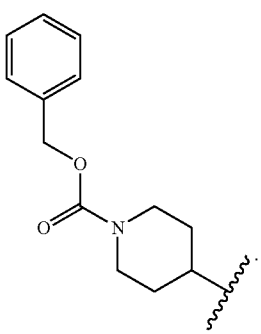 [SMILES: *C1CCN(C(=O)OCc2ccccc2)CC1 ; "."]
In one embodiment, R$^{20}$ is selected from:
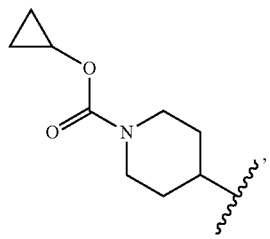 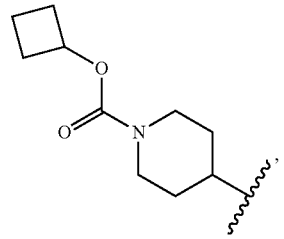
-continued
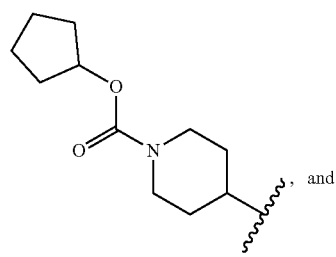, and
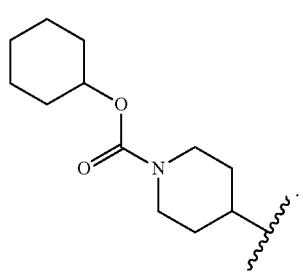
In one embodiment, R$^{20}$ is selected from:
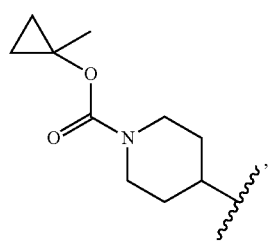 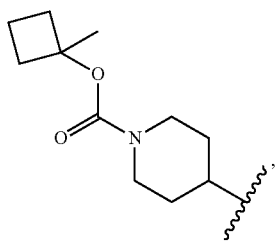
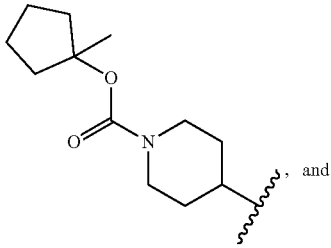, and
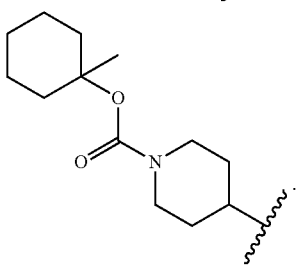
In one embodiment, R$^{20}$ is selected from:
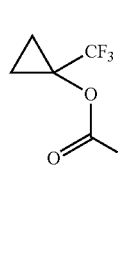 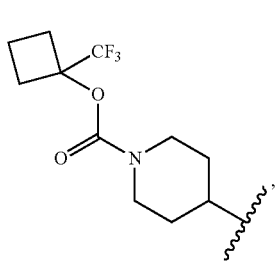

-continued
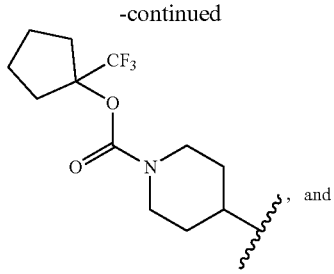, and
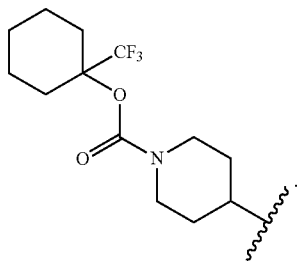.
In one embodiment, R²⁰ is selected from:
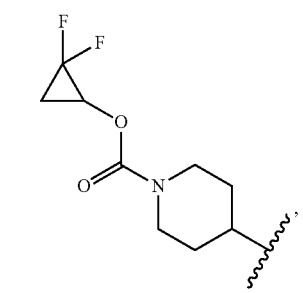,
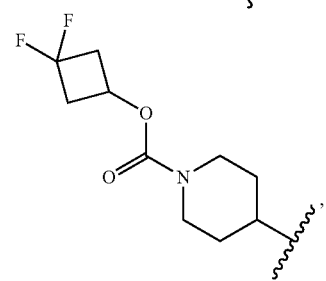,
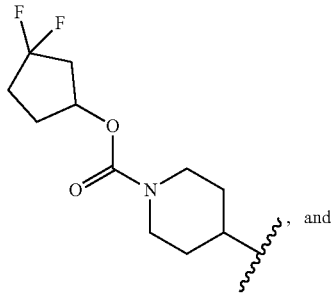, and
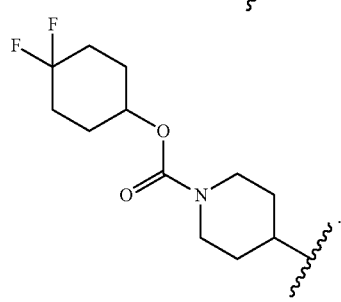.
In one embodiment, R²⁰ is selected from:
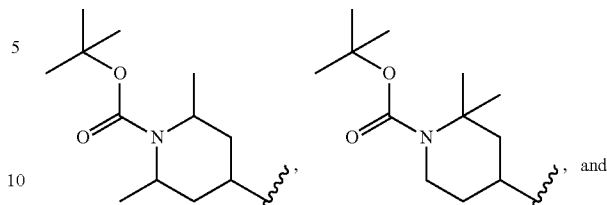, and
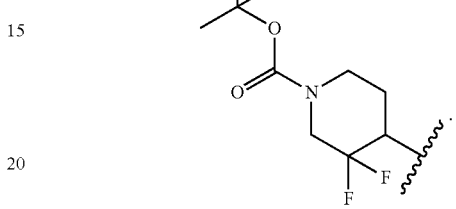.
In one embodiment, R²⁰ is selected from:
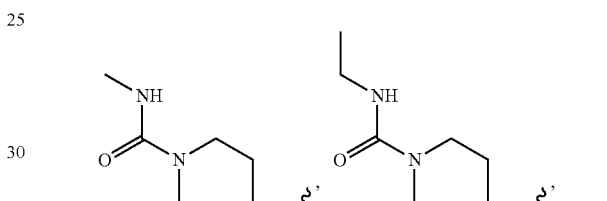,
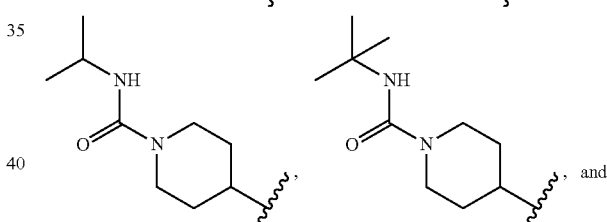, and
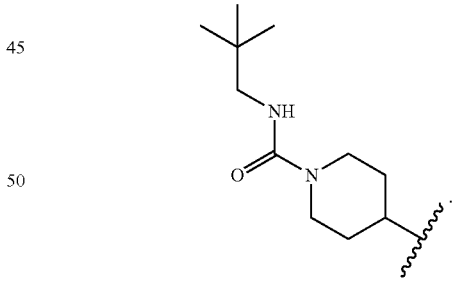.
In one embodiment, R²⁰ is selected from:
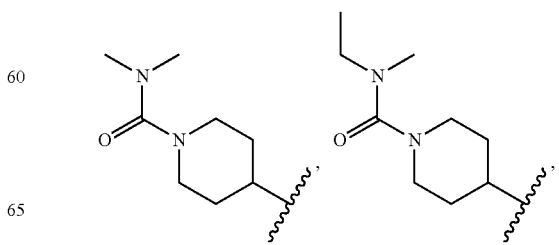,

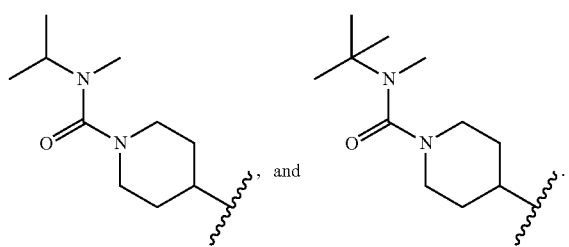, and 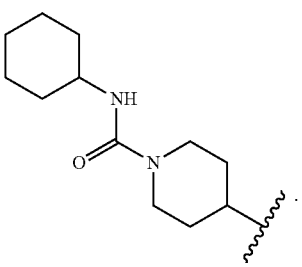.
In one embodiment, R²⁰ is
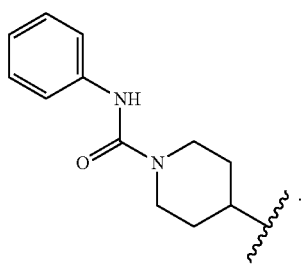 [SMILES: *C1CCN(C(=O)Nc2ccccc2)CC1]
In one embodiment, R²⁰ is
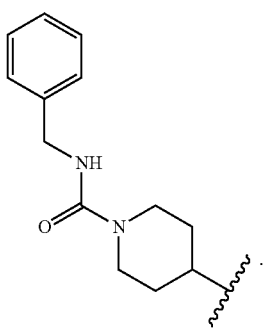 [SMILES: *C1CCN(C(=O)NCc2ccccc2)CC1]
In one embodiment, R²⁰ is selected from:
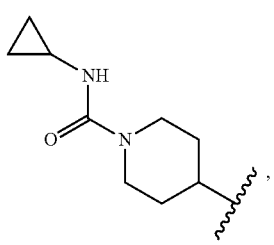, 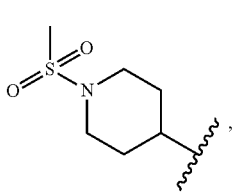,
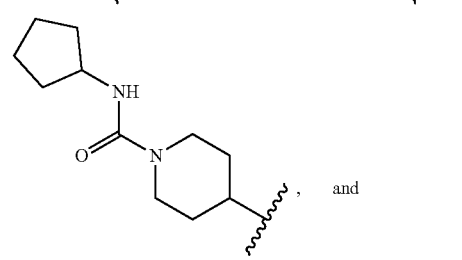, and
In one embodiment, R²⁰ is selected from:
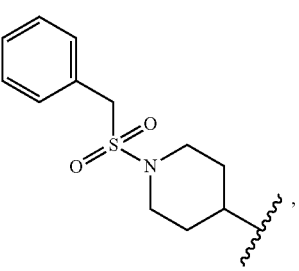,
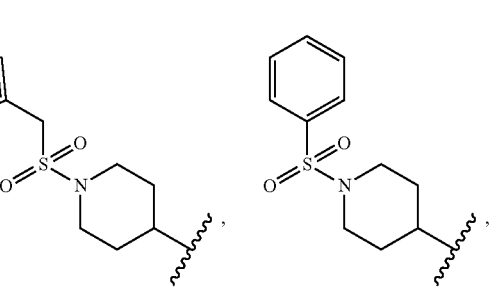,
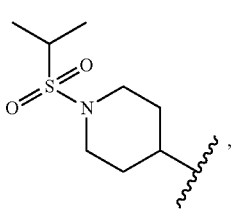, 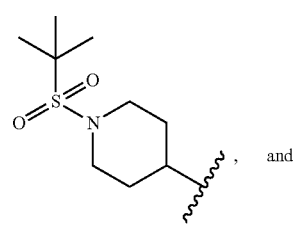, and

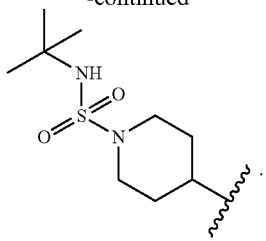
In one embodiment, $R^{20}$ is
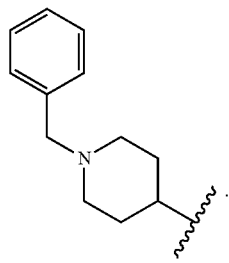 [SMILES: *C1CCN(Cc2ccccc2)CC1]
In one embodiment, $R^{20}$ is selected from:
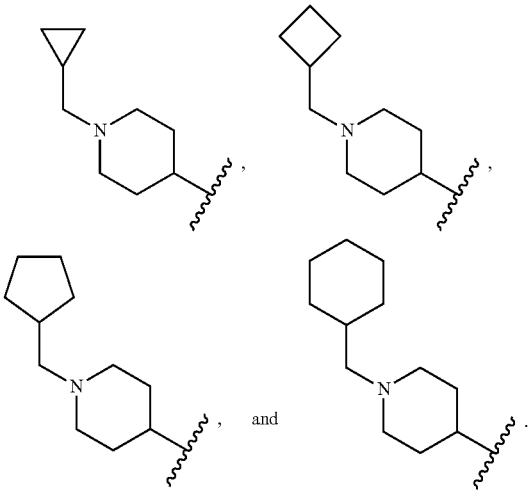
In one embodiment, $R^{20}$ is selected from:
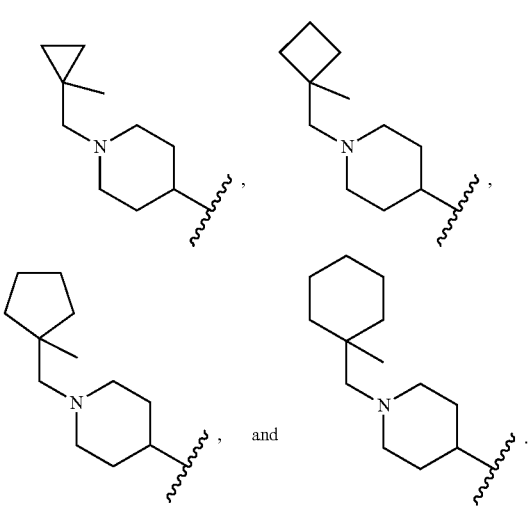
In one embodiment, $R^{20}$ is selected from:
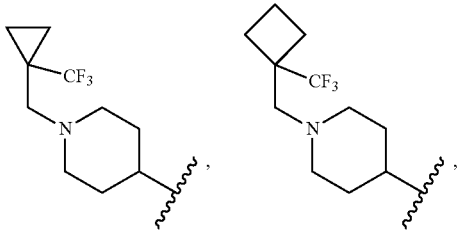
In one embodiment, $R^{20}$ is selected from:
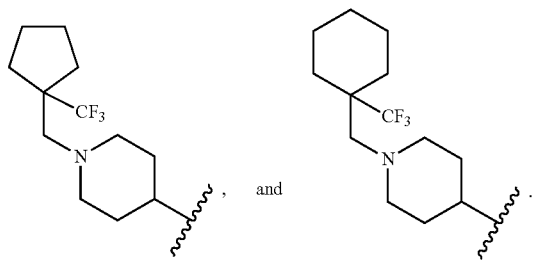
In one embodiment, $R^{20}$ is selected from:
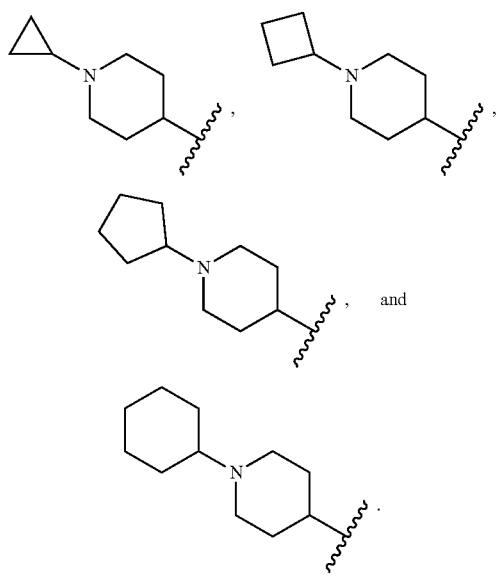
In one embodiment, $R^{20}$ is selected from:
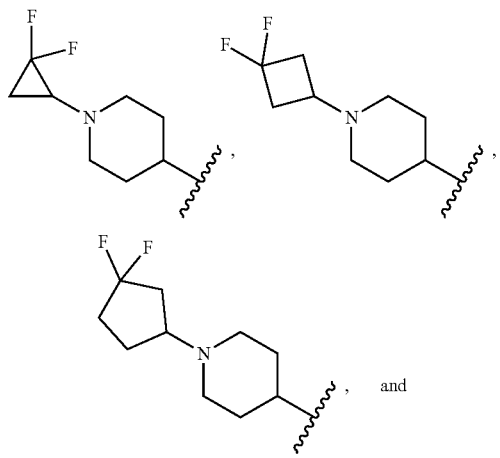

-continued
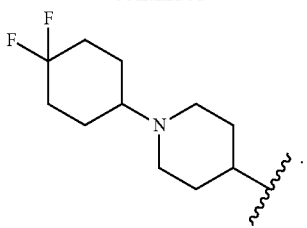
In one embodiment, R$^{20}$ is selected from:
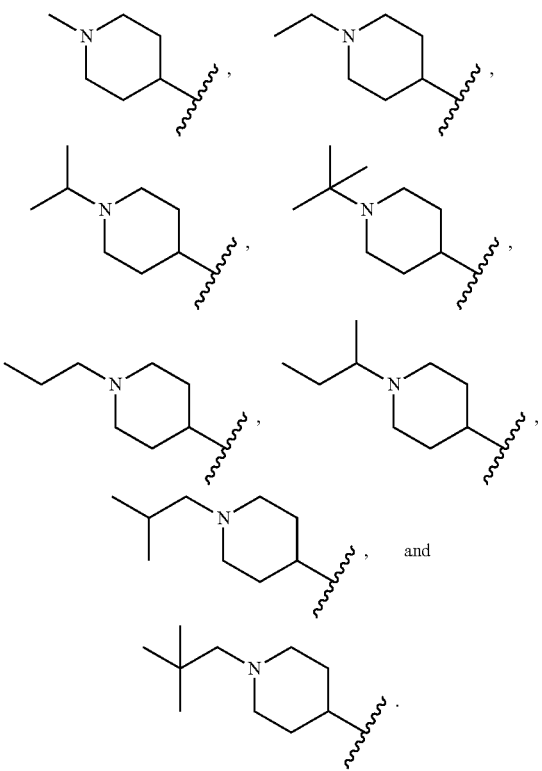
In one embodiment, R$^{20}$ is
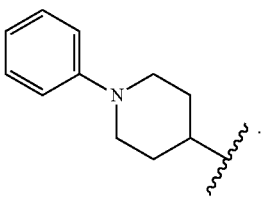 [SMILES: *C1CCN(c2ccccc2)CC1]
In one embodiment, R$^{20}$ is selected from:
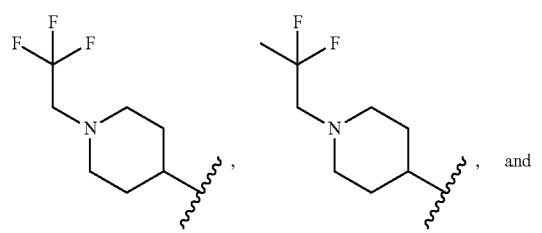
-continued
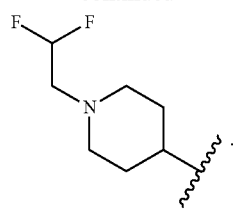
In one embodiment, R$^{20}$ is
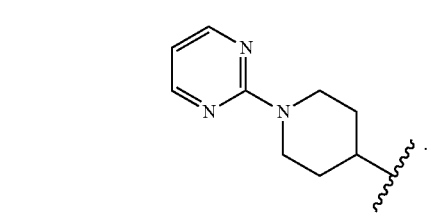 [SMILES: *C1CCN(c2ncccn2)CC1]
In one embodiment, R$^{20}$ is selected from:
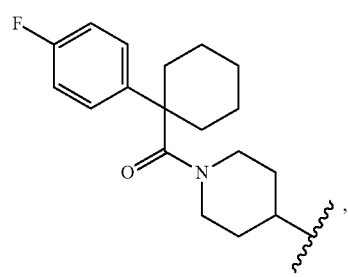
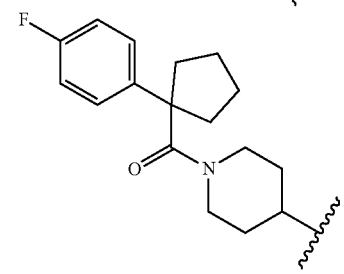
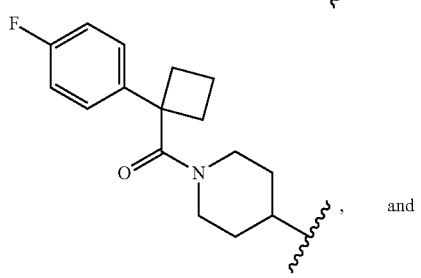
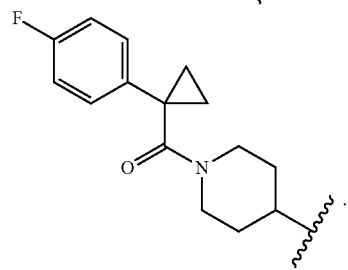

In one embodiment, $R^{20}$ is selected from:
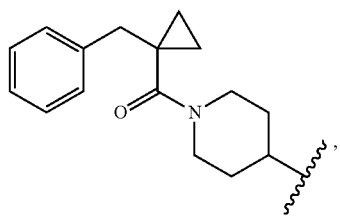,
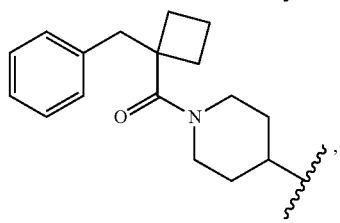,
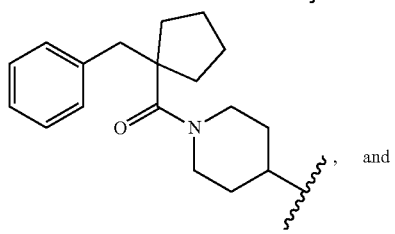, and
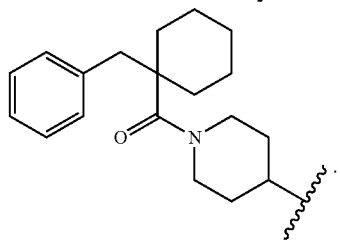.
In one embodiment, $R^{20}$ is selected from:
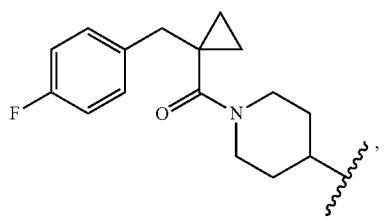,
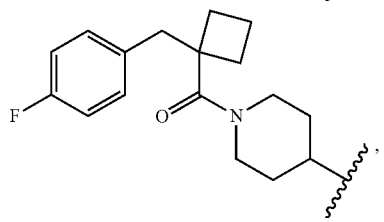,
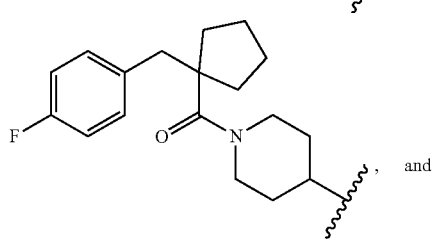, and
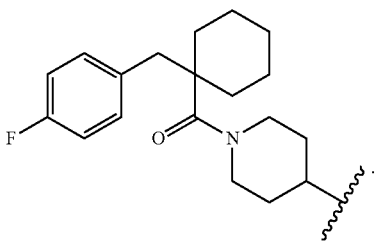.
In one embodiment, $R^{20}$ is
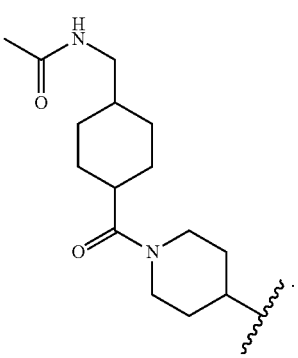 [SMILES: *C1CCN(C(=O)C2CCC(CNC(C)=O)CC2)CC1]
In one embodiment, $R^{20}$ is selected from:
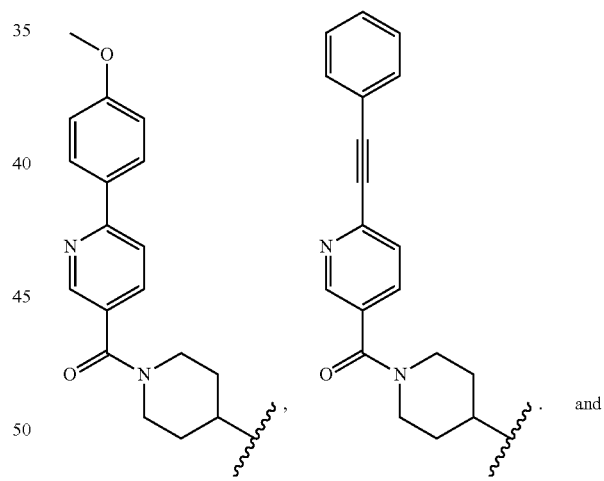, and
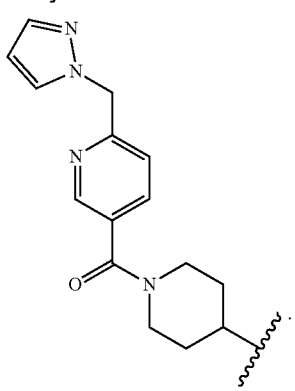.

In one embodiment, $R^{20}$ is selected from:
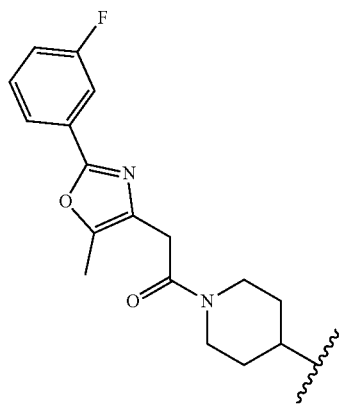
and
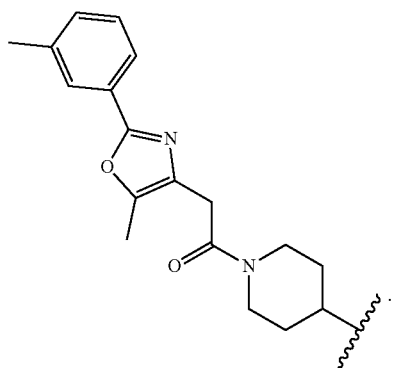
.
In one embodiment, $R^{20}$ is
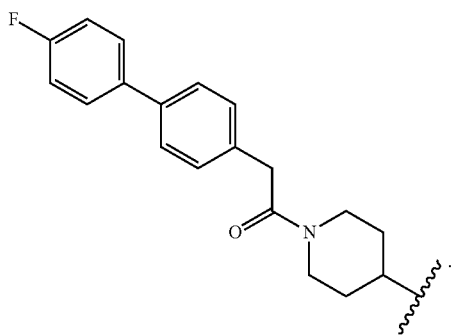 [SMILES: *C1CCN(C(=O)Cc2ccc(-c3ccc(F)cc3)cc2)CC1]
.
In one embodiment, $R^{20}$ is selected from:
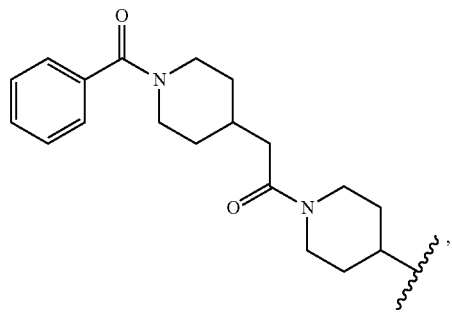
,
-continued
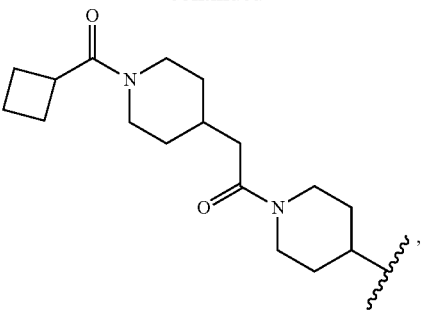
,
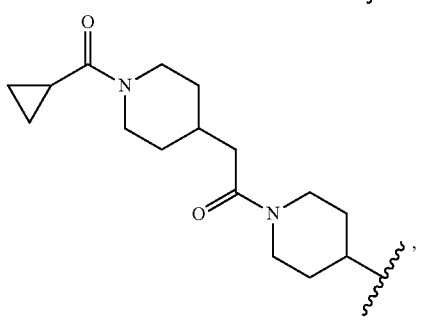
,
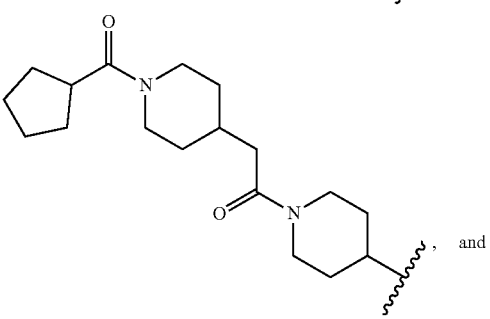
, and
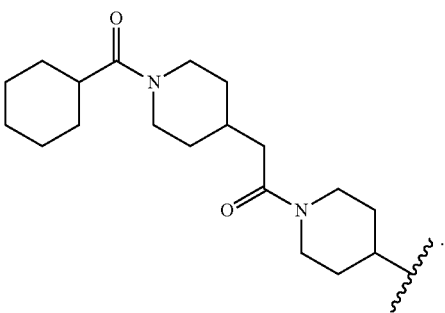
.
In one embodiment, $R^{20}$ is selected from:
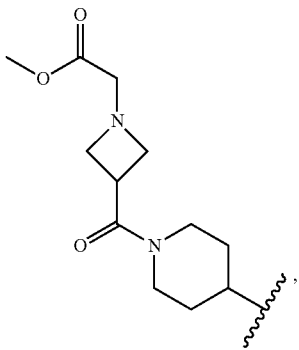
, -continued
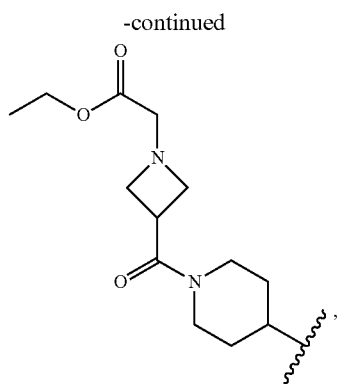
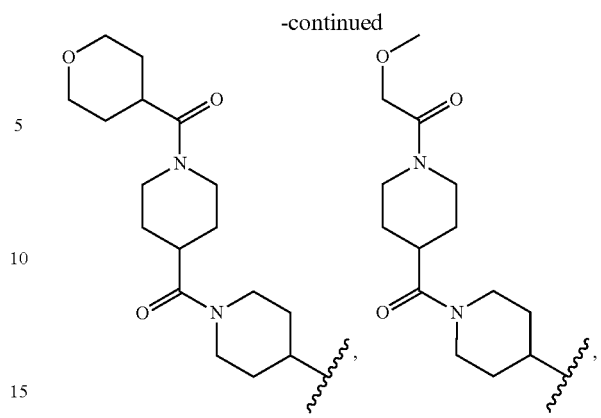
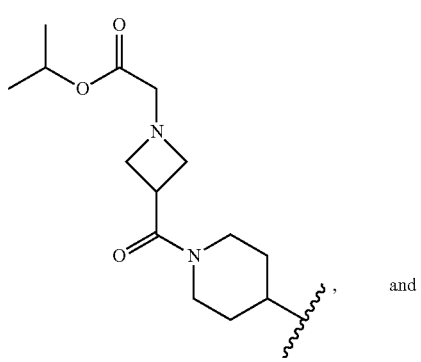
and
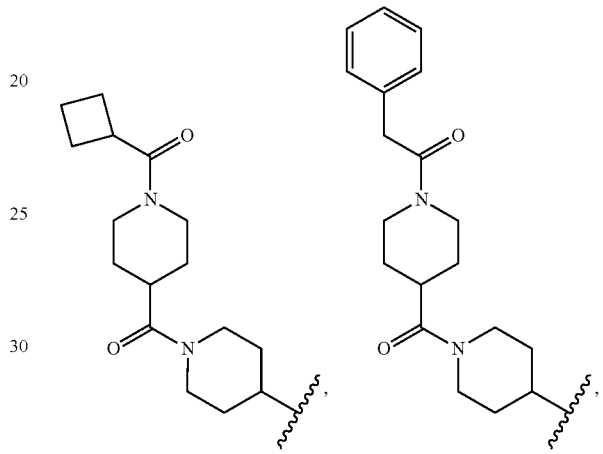
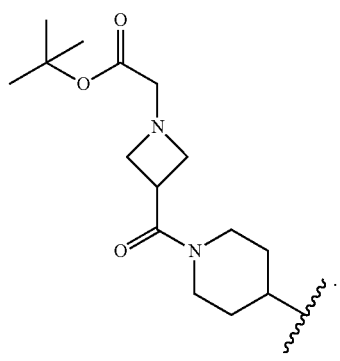
.
In one embodiment, R[20] is selected from:
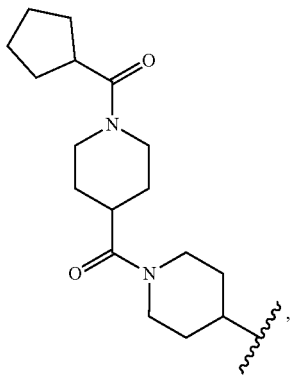
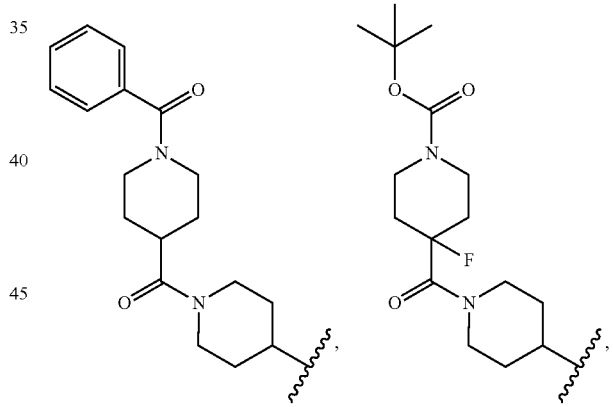
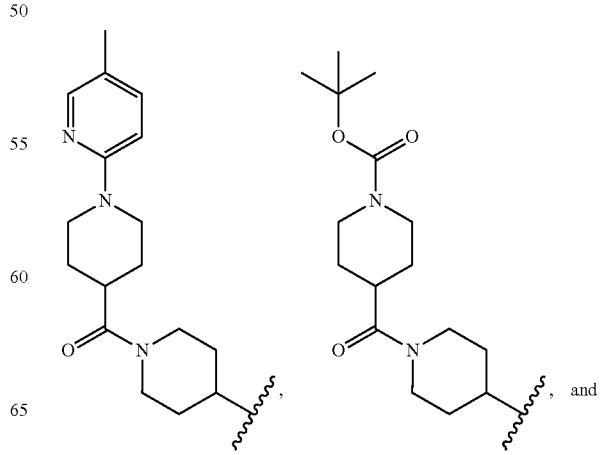
, and

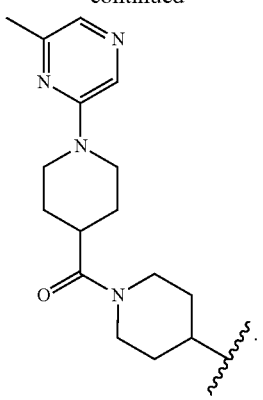
In one embodiment,
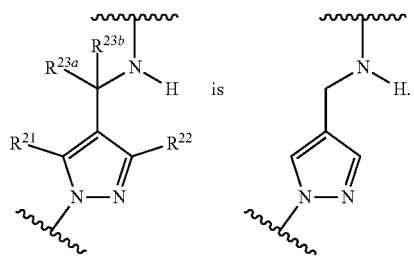 is
In one embodiment,
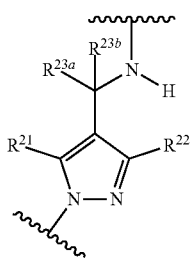
is selected from:
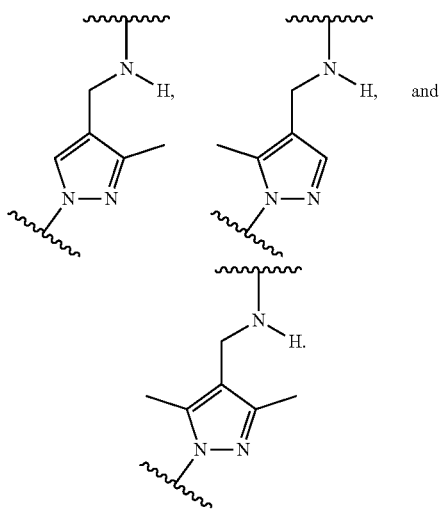
In one embodiment,
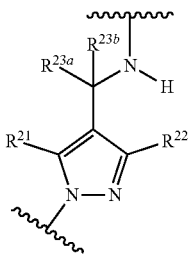
is selected from:
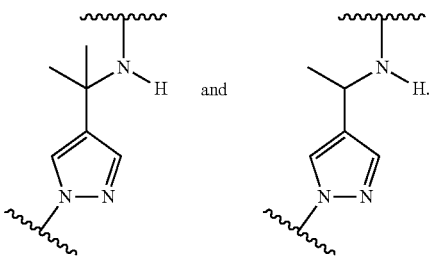
In one embodiment,
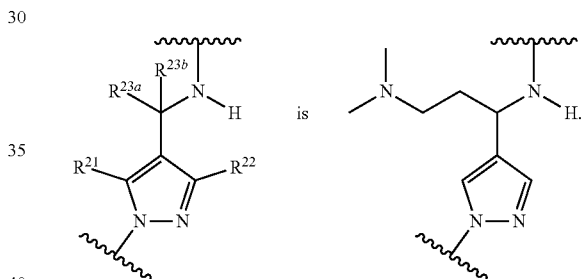
In one embodiment,
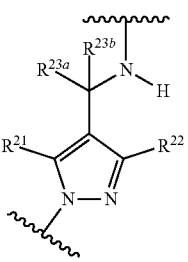
is selected from:
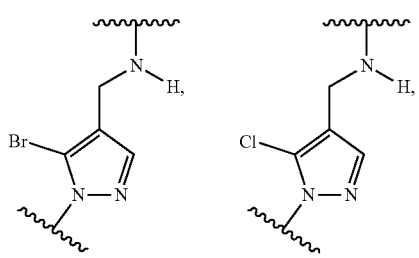

-continued
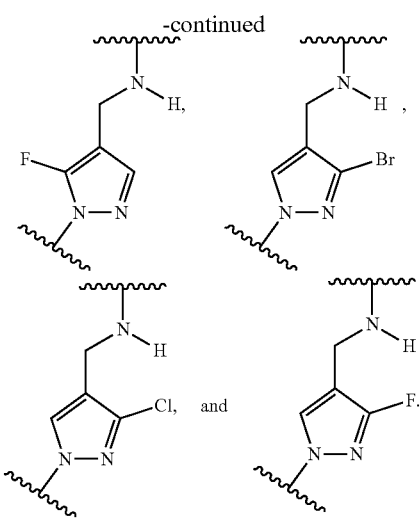
In one embodiment,
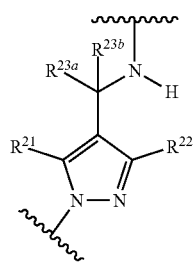
is selected from:
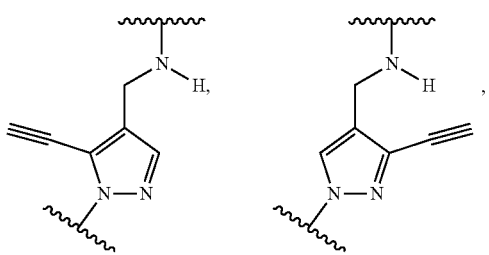
-continued
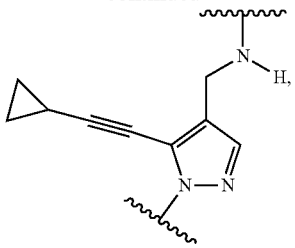
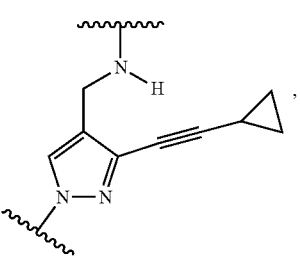
Non-Limiting Examples of Compounds of Formula V
In one embodiment, a compound of Formula V is selected from:
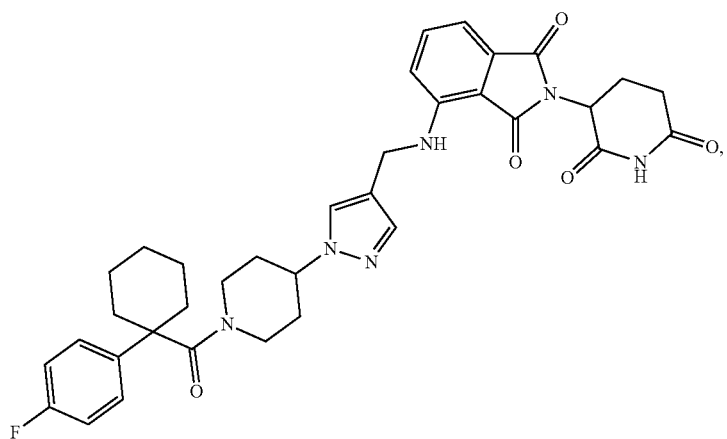

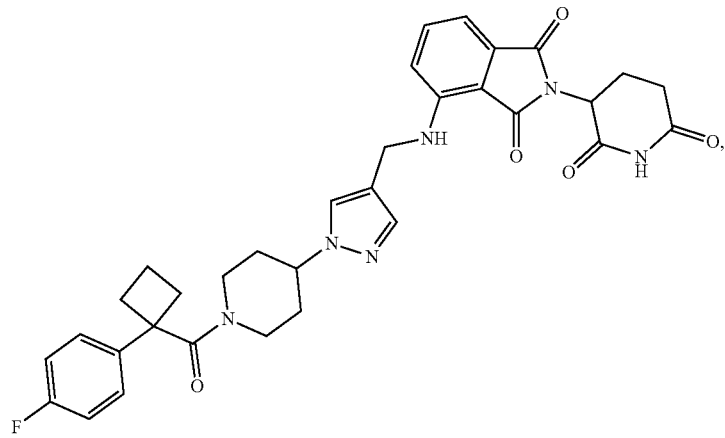
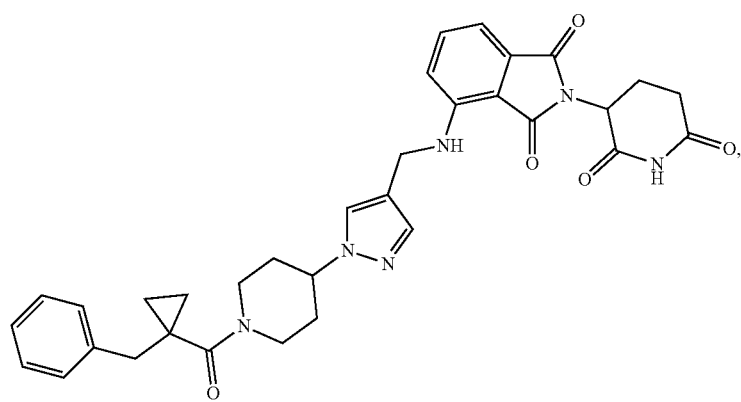
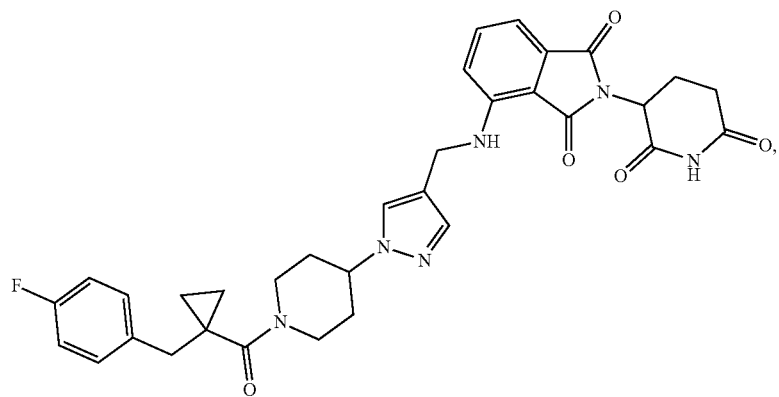
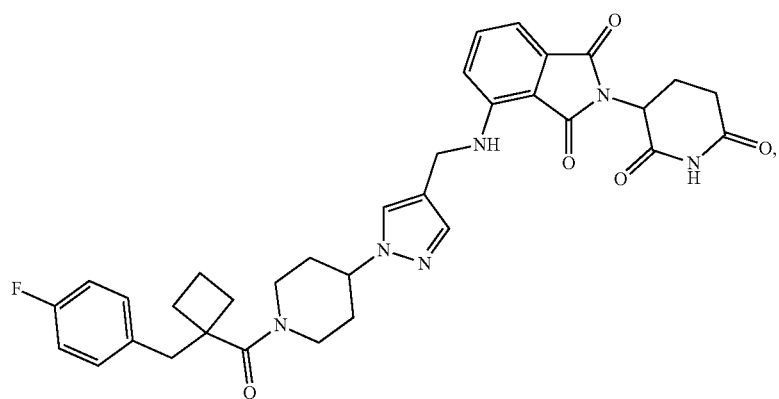

-continued
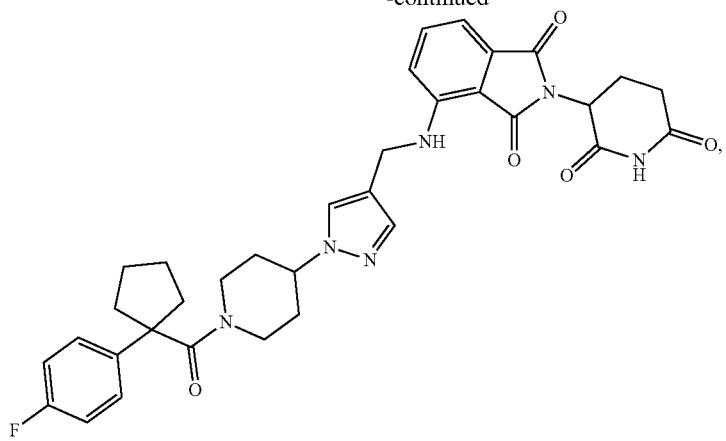
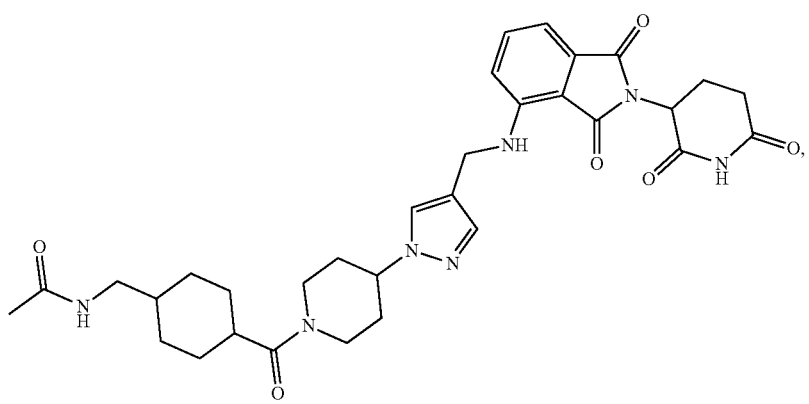
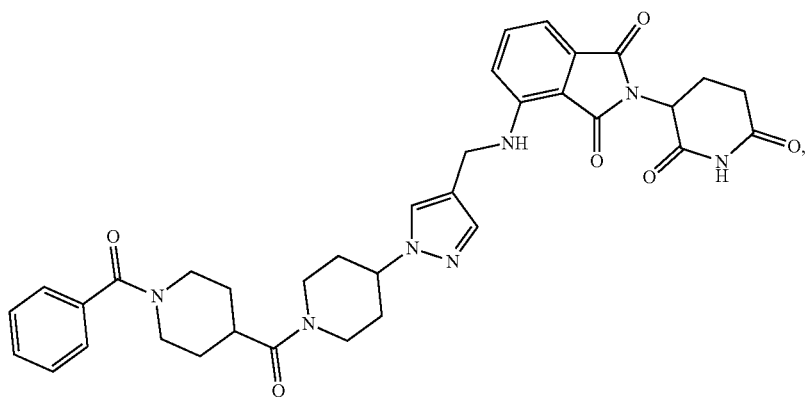
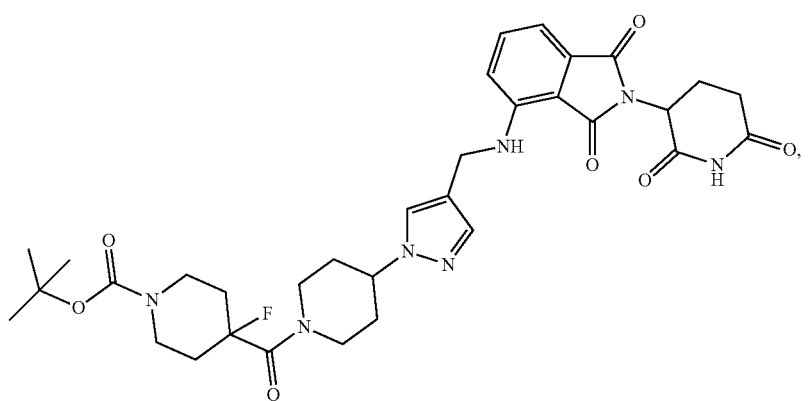

-continued
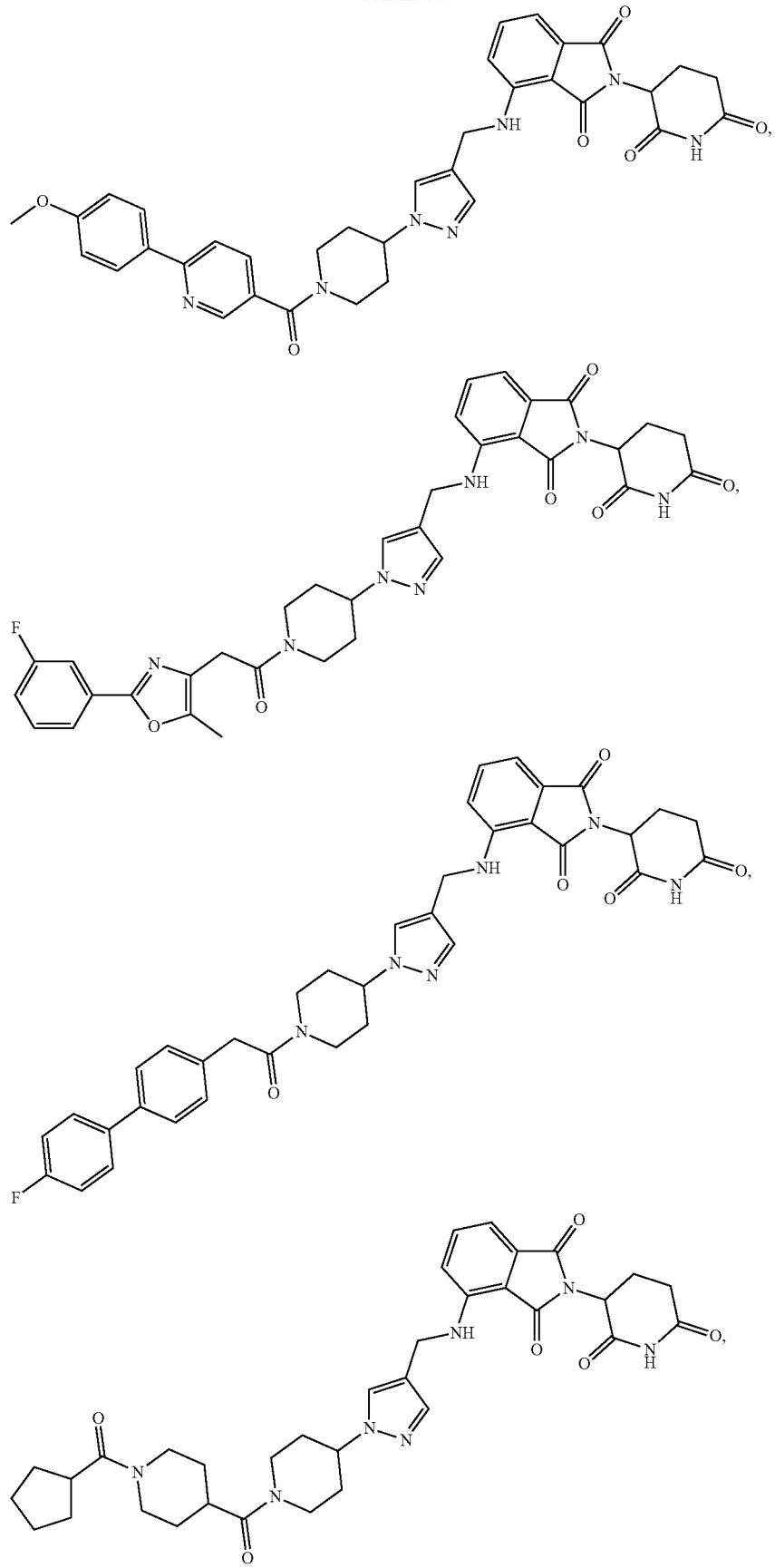

-continued
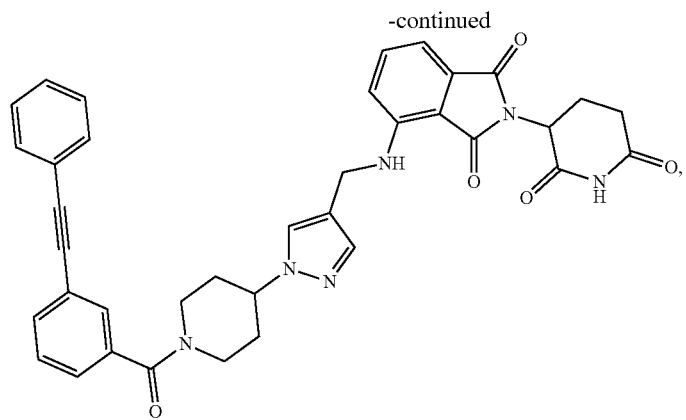
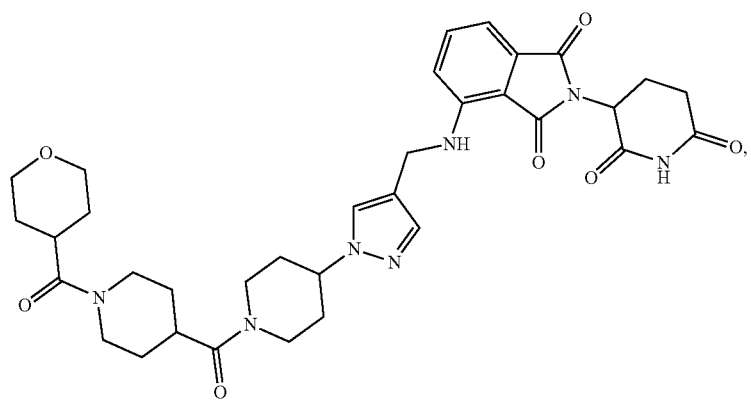
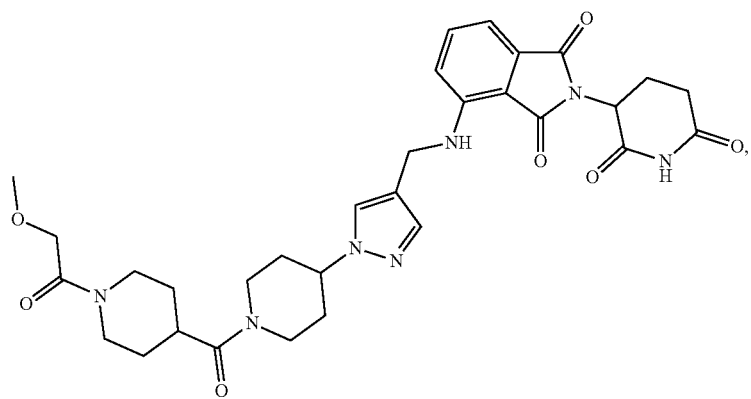
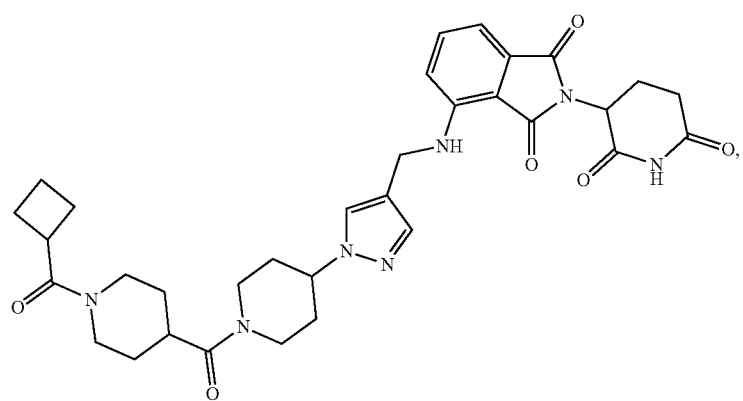

-continued
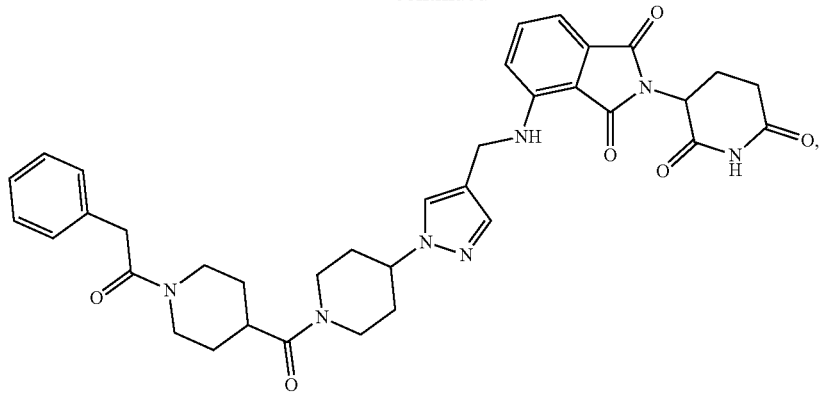
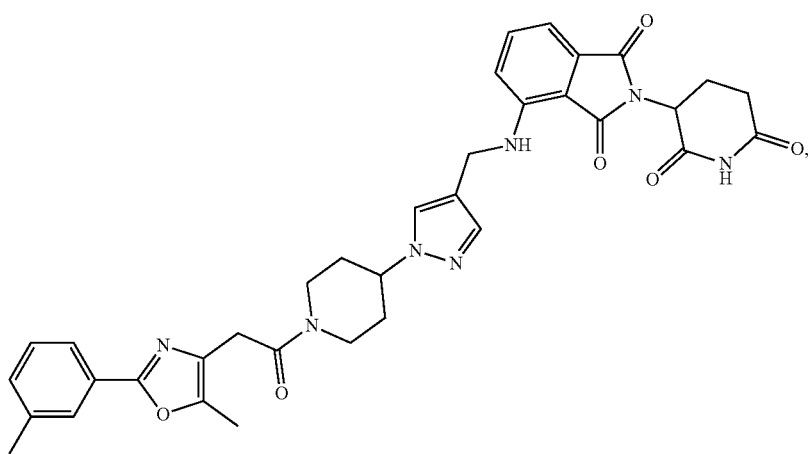
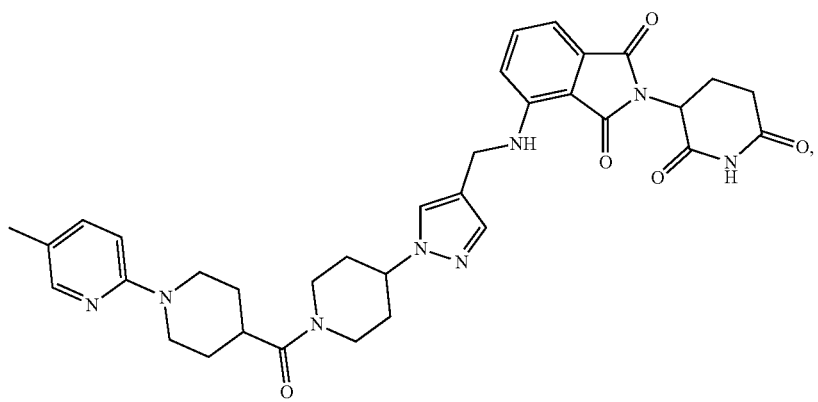
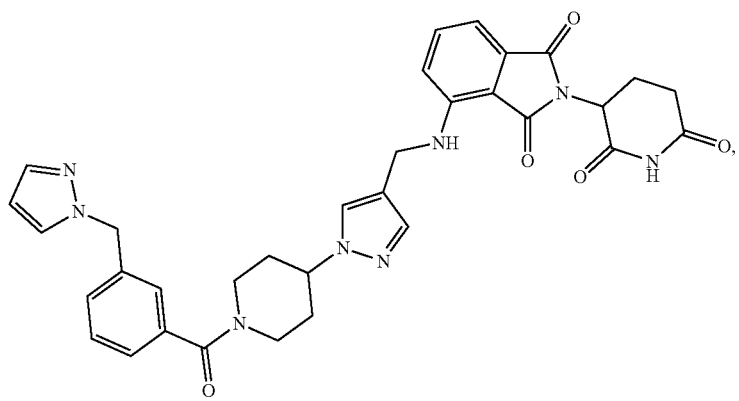

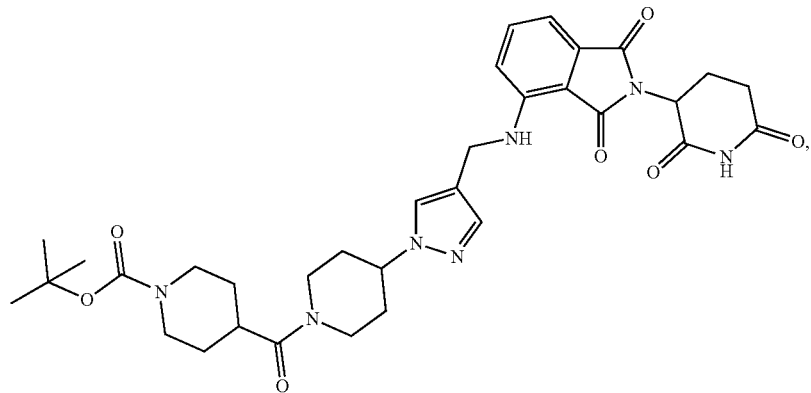
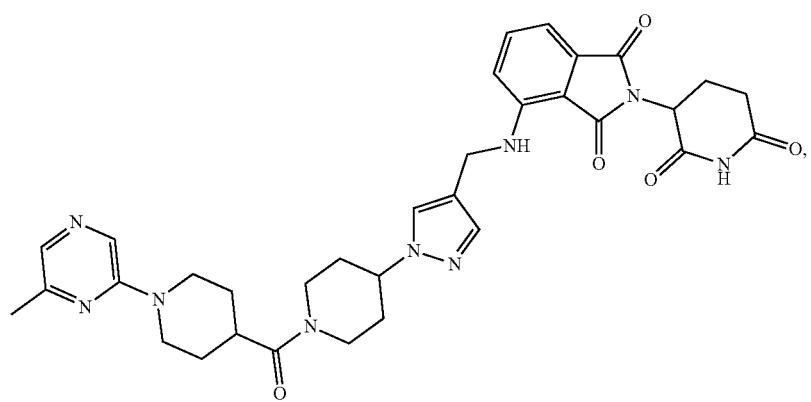
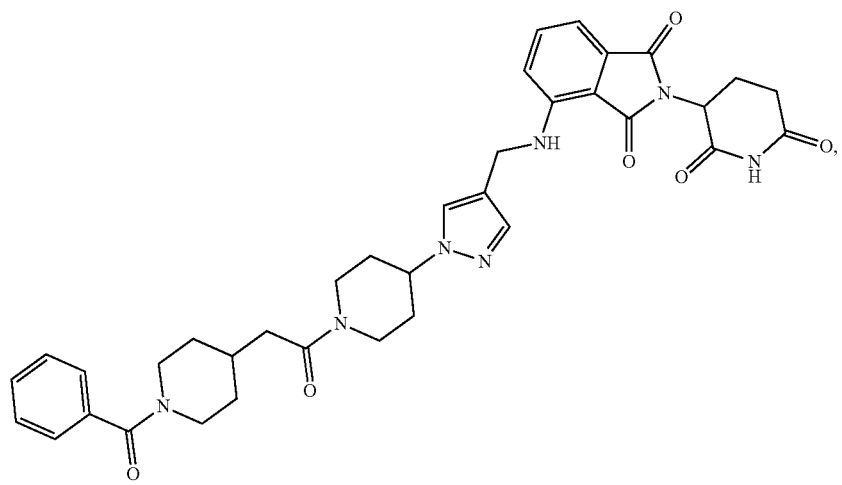

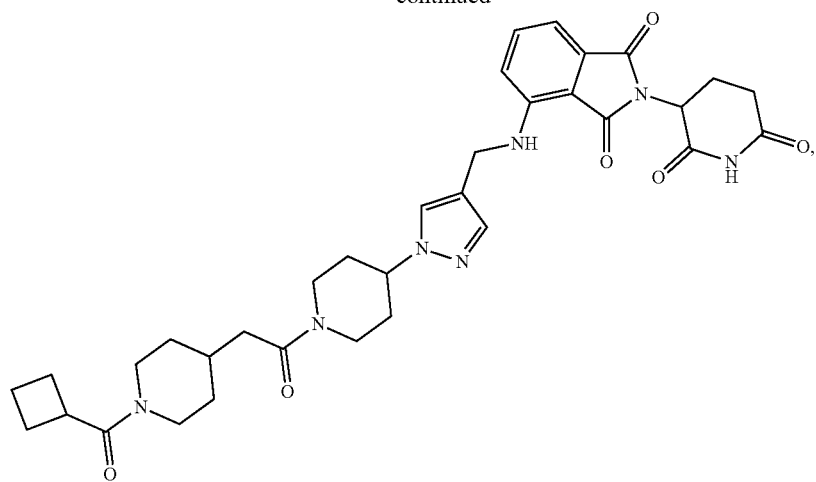
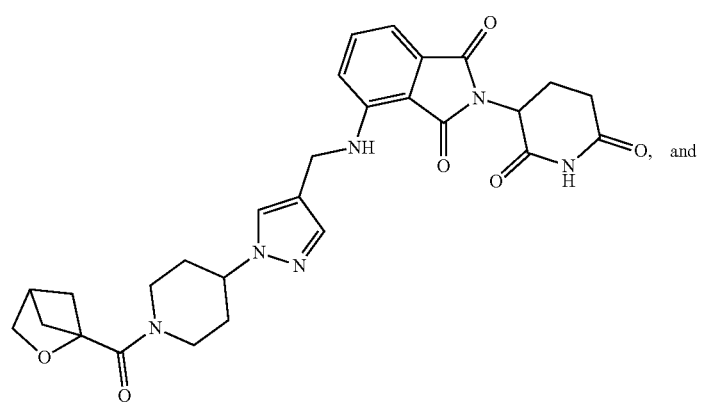
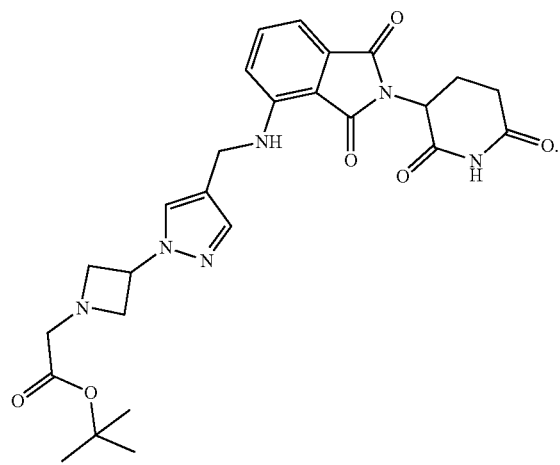

In one embodiment, a compound of Formula V is selected from:
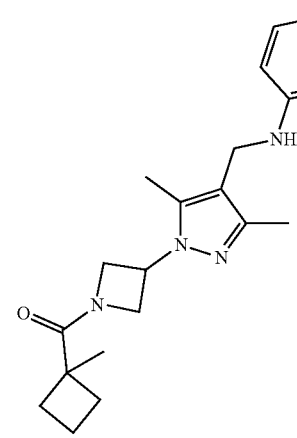 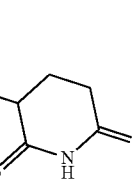
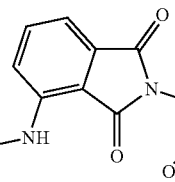
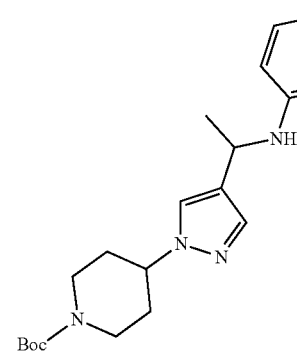 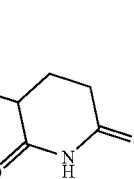
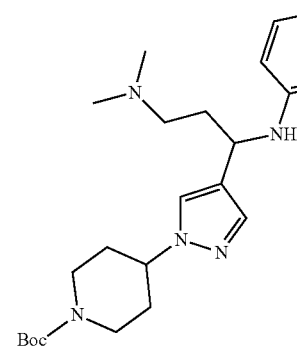 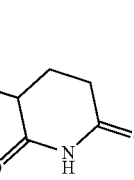
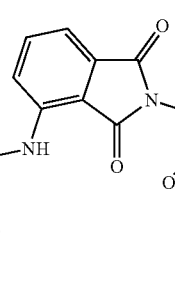
 
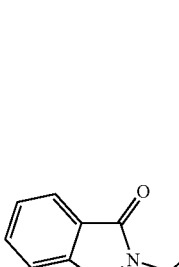
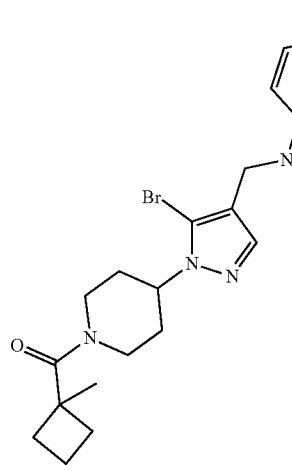 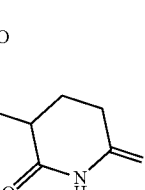
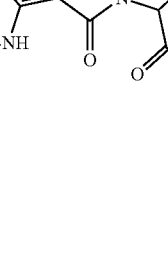
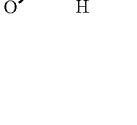, and
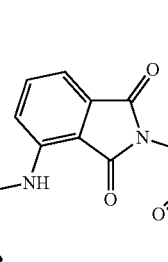.

III. Methods of Treatment

Any of the compounds described herein can be used in an effective amount to treat a host, including a human, in need thereof, optionally in a pharmaceutically acceptable carrier to treat any of the disorders described herein. In certain embodiments, the method comprises administering an effective amount of the active compound or its salt as described herein, optionally including a pharmaceutically acceptable excipient, carrier, or adjuvant (i.e., a pharmaceutically acceptable composition), optionally in combination or alternation with another bioactive agent or combination of agents.

In one embodiment a compound of Formula I is used to treat a disorder described herein.

In one embodiment a compound of Formula II is used to treat a disorder described herein.

In one embodiment a compound of Formula III is used to treat a disorder described herein.

In one embodiment a compound of Formula IV is used to treat a disorder described herein.

In one embodiment, a compound of Formula V is used to treat a disorder described herein.

In one embodiment, a compound of Formula VI is used to treat a disorder described herein.

In one embodiment the disorder treated by a compound of the present invention is an immunomodulatory disorder. In one embodiment the disorder treated by a compound of the present invention is mediated by angiogenesis. In one embodiment the disorder treated by a compound of the present invention is related to the lymphatic system.

In one embodiment a compound of the present invention pharmaceutical salt thereof, optionally in a pharmaceutical composition as described herein is used to degrade Ikaros or Aiolos, which is a mediator of the disorder affecting the patient, such as a human. The control of protein level afforded by any of the compounds of the present invention provides treatment of a disease state or condition, which is modulated through Ikaros or Aiolos by lowering the level of that protein in the cell, e.g., cell of a patient, or by lowering the level of downstream proteins in the cell. In certain embodiments, the method comprises administering an effective amount of the compound as described herein, optionally including a pharmaceutically acceptable excipient, carrier, adjuvant (i.e., a pharmaceutically acceptable composition), optionally in combination or alternation with another bioactive agent or combination of agents.

In one embodiment, a compound of the present invention is used to treat a disorder treatable by thalidomide, pomalidimide, or lenalidomide. Non-limiting examples of disorders that may be treated by thalidomide, pomalidimide, or lenalidomide include benign growth, neoplasm, tumor, cancer, abnormal cellular proliferation, immune disorder, inflammatory disorder, graft-versus-host rejection, viral infection, bacterial infection, an amyloid-based proteinopathy, a proteinopathy, or a fibrotic disorder.

The term "disease state" or "condition" when used in connection with any of the compounds is meant to refer to any disease state or condition that is mediated by Ikaros or Aiolos, such as cellular proliferation, or by proteins that are downstream of the Ikaros or Aiolos, and where degradation of such protein in a patient may provide beneficial therapy or relief of symptoms to a patient in need thereof. In certain instances, the disease state or condition may be cured. In an alternative embodiment "disease state" or "condition" refers to a disorder that lenalidomide, pomalidamide, or thalidomide is used to treat.

In one embodiment, a compound or its corresponding pharmaceutically acceptable salt, isotopic derivative, or prodrug as described herein can be used in an effective amount to treat a host, for example a human, with a lymphoma or lymphocytic or myelocytic proliferation disorder or abnormality. For example, a compound as described herein can be administered to a host suffering from a Hodgkin Lymphoma or a Non-Hodgkin Lymphoma. For example, the host can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); diffuse small-cleaved cell lymphoma (DSCCL); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; Langerhans cell histiocytosis; or Waldenstrom's Macroglobulinemia.

In another embodiment, a compound or its corresponding pharmaceutically acceptable salt, isotopic derivative, or prodrug as described herein can be used in an effective amount to treat a host, for example a human, with a Hodgkin lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

In another embodiment, a compound or its corresponding pharmaceutically acceptable salt, isotopic derivative, or prodrug as described herein can be used in an effective amount to treat a host, for example a human, with an immunomodulatory condition. Non-limiting examples of immunomodulatory conditions include: arthritis, lupus, celiac disease, Sjogren's syndrome, polymyalgia rheumatia, multiple sclerosis, ankylosing spondylitis, type 1 diabetes, alopecia areata, vasculitis, and temporal arteritis.

In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

Abnormal proliferation of B-cells, T-cells, and/or NK cells can result in a wide range of diseases such as cancer, proliferative disorders and inflammatory/immune diseases. A host, for example a human, afflicted with any of these disorders can be treated with an effective amount of a compound as described herein to achieve a decrease in symptoms (palliative agent) or a decrease in the underlying disease (a disease modifying agent).

In one embodiment, a compound or its corresponding pharmaceutically acceptable salt, isotopic derivative, or prodrug as described herein can be used in an effective amount to treat a host, for example a human, with a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; diffuse poorly differentiated lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In one embodiment, a compound or its corresponding pharmaceutically salt, isotopic derivative, or prodrug as described herein can be used in an effective amount to treat a host, for example a human, with a T-cell or NK-cell lymphoma such as, but not limited to: anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sezary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In one embodiment, a compound or its corresponding pharmaceutically acceptable salt, isotopic derivative, or prodrug as described herein can be used to treat a host, for example a human, with leukemia. For example, the host may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); large granular lymphocytic leukemia; or Adult T-cell chronic leukemia. In one embodiment, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

A compound or its pharmaceutically acceptable salt, isotopic analog, or prodrug as described herein can be used in an effective amount to treat a host, for example a human, with a proliferative condition such as myeloproliferative disorder (MPD), polycythemia vera (PV), essential thrombocythemia (ET), myeloid metaplasia with myelofibrosis (MMM), chronic myelomonocytic leukemia (CMML), hypereosinophilic syndrome (HES), system mast cell disease (SMCD), and the like. In another embodiment, a compound provided herein is useful for the treatment of primary myelofibrosis, post-polycythemia vera myelofibrosis, post-essential thrombocythemia myelofibrosis, and secondary acute myelogenous leukemia.

In one embodiment, a compound or its pharmaceutically acceptable salt, isotopic analog, or prodrug as described herein can be used in an effective amount to treat a host, for example a human, with a myelodysplastic syndrome (MDS) such as, but not limited to: refractory cytopenia with uni-lineage dysplasia, refractory anemia with ring sideroblasts (RARS), refractory anemia with ring sideroblasts-thrombocytosis (RARS-t), refractory cytopenia with multilineage dyslplasia (RCMD) including RCMD with multilineage dysplasia and ring sideroblasts (RCMD-RS), Refractory amenias with excess blasts I (RAEB-I) and II (RAEB-II), 5q-syndrome, refractory cytopenia of childhood, and the like.

In one embodiment a compound of the present invention can provide a therapeutic effect either by direct degradation of the Ikaros or Aiolos or by changing the transcriptional regulation of a protein downstream of the Ikaros or Aiolos.

The term "neoplasia" or "cancer" is used to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma. In one embodiment the disorder is adenoid cystic carcinoma. In one embodiment the disorder is NUT midline carcinoma.

In another embodiment, a compound or its pharmaceutically acceptable salt, isotopic derivative or prodrug as described herein can be used in an effective amount to treat a host, for example a human, with an autoimmune disorder. Examples include, but are not limited to: Acute disseminated encephalomyelitis (ADEM); Addison's disease; Agammaglobulinemia; Alopecia areata; Amyotrophic lateral sclerosis (Also Lou Gehrig's disease; Motor Neuron Disease); Ankylosing Spondylitis; Antiphospholipid syndrome; Antisynthetase syndrome; Atopic allergy; Atopic dermatitis; Autoimmune aplastic anemia; Autoimmune arthritis; Autoimmune cardiomyopathy; Autoimmune enteropathy; Autoimmune granulocytopenia; Autoimmune hemolytic anemia; Autoimmune hepatitis; Autoimmune hypoparathyroidism; Autoimmune inner ear disease; Autoimmune lymphoproliferative syndrome; Autoimmune myocarditis; Autoimmune pancreatitis; Autoimmune peripheral neuropathy; Autoimmune ovarian failure; Autoimmune polyendocrine syndrome; Autoimmune progesterone dermatitis; Autoimmune thrombocytopenic purpura; Autoimmune thyroid disorders; Autoimmune urticarial; Autoimmune uveitis; Autoimmune vasculitis; Balo disease/Balo concentric sclerosis; Behçet's disease; Berger's disease; Bickerstaffs encephalitis; Blau syndrome; Bullous pemphigoid; Cancer; Castleman's disease; Celiac disease; Chagas disease; Chronic inflammatory demyelinating polyneuropathy; Chronic inflammatory demyelinating polyneuropathy; Chronic obstructive pulmonary disease; Chronic recurrent multifocal osteomyelitis; Churg-Strauss syndrome; Cicatricial pemphigoid; Cogan syndrome; Cold agglutinin disease; Complement component 2 deficiency; Contact dermatitis; Cranial arteritis; CREST syndrome; Crohn's disease; Cushing's Syndrome; Cutaneous leukocytoclastic angiitis; Dego's disease; Dercum's disease; Dermatitis herpetiformis; Dermatomyositis; Diabetes mellitus type 1; Diffuse cutaneous systemic sclerosis; Discoid lupus erythematosus; Dressler's syndrome; Drug-induced lupus; Eczema; Endometriosis; Enthesitis-related arthritis; Eosinophilic fasciitis; Eosinophilic gastroenteritis; Eosinophilic pneumonia; Epidermolysis bullosa acquisita; Erythema nodosum; Erythroblastosis fetalis; Essential mixed cryoglubulinemia; Evan's syndrome; Extrinsic and intrinsic reactive airways disease (asthma); Fibrodysplasia ossificans progressive; Fibrosing alveolitis (or Idiopathic pulmonary fibrosis); Gastritis; Gastrointestinal pemphigoid; Glomerulonephritis; Goodpasture's syndrome; Graves' disease; Guillain-Barre syndrome (GBS); Hashimoto's encephalopathy; Hashimoto's thyroiditis; Hemolytic anemia; Henoch-Schonlein purpura; Herpes gestationis (Gestational Pemphigoid); Hidradenitis suppurativa; Hughes-Stovin syndrome; Hypogammaglobulinemia; Idiopathic inflammatory demyelinating diseases; Idiopathic pulmonary fibrosis; Idiopathic thrombocytopenic purpura; IgA nephropathy; Immune glomerulonephritis; Immune nephritis; Immune pneumonitis; Inclusion body myositis; inflammatory bowel disease; Interstitial cystitis; Juvenile idiopathic arthritis aka Juvenile rheumatoid arthritis; Kawasaki's disease; Lambert-Eaton myasthenic syndrome; Leukocytoclastic vasculitis; Lichen planus; Lichen sclerosus; Linear IgA disease (LAD); Lupoid hepatitis aka Autoimmune hepatitis; Lupus erythematosus; Majeed syndrome; microscopic polyangiitis; Miller-Fisher syndrome; mixed connective tissue disease; Morphea; Mucha-Habermann disease aka *Pityriasis lichenoides* et *varioliformis acuta*; Multiple sclerosis; Myasthenia gravis; Myositis; Ménière's disease; Narcolepsy; Neuromyelitis optica (also Devic's disease); Neuromyotonia; Occular cicatricial pemphigoid; Opsoclonus myoclonus syndrome; Ord's thyroiditis; Palindromic rheumatism; PANDAS (pediatric autoimmune neuropsychiatric disorders associated with *streptococcus*); Paraneoplastic cerebellar degeneration; Paroxysmal nocturnal hemoglobinuria (PNH); Parry Romberg syndrome; Pars planitis; Parsonage-Turner syndrome; Pemphigus vulgaris; Perivenous encephalomyelitis; Pernicious anaemia; POEMS syndrome; *Polyarteritis nodosa*; Polymyalgia rheumatic; Polymyositis; Primary biliary cirrhosis; Primary sclerosing cholangitis; Progressive inflammatory neuropathy; Psoriasis; Psoriatic arthritis; pure red cell aplasia; Pyoderma gangrenosum; Rasmussen's encephalitis; Raynaud phenomenon; Reiter's syndrome; relapsing polychondritis; restless leg syndrome; retroperitoneal fibrosis; rheumatic fever; rheumatoid arthritis; Sarcoidosis; Schizophrenia; Schmidt syndrome; Schnitzler syndrome; Scleritis; Scleroderma; Sclerosing cholangitis; serum sickness; Sjögren's syndrome; Spondyloarthropathy; Stiff person syndrome; Still's disease; Subacute bacterial endocarditis (SBE); Susac's syndrome; Sweet's syndrome; Sydenham chorea; sympathetic ophthalmia; systemic lupus erythematosus; Takayasu's arteritis; temporal arteritis (also known as "giant cell arteritis"); thrombocytopenia; Tolosa-Hunt syndrome; transverse myelitis; ulcerative colitis; undifferentiated connective tissue disease; undifferentiated spondyloarthropathy; urticarial vasculitis; vasculitis; vitiligo; viral diseases such as Epstein Barr Virus (EBV), Hepatitis B, Hepatitis C, HIV, HTLV 1, Varicella-Zoster Virus (VZV) and Human Papilloma Virus (HPV); or Wegener's granulomatosis. In some embodiments, the autoimmune disease is an allergic condition, including those from asthma, food allergies, atopic dermatitis, chronic pain, and rhinitis.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

A compound or its pharmaceutically acceptable salt, isotopic variant, or prodrug as described herein can be used in an effective amount to treat a host, for example a human, with a skin disorder such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, the skin disorder is treated by topical administration of compounds known in the art in combination with the compounds disclosed herein. In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease 1 (PKD1) or 2 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome#arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysylhydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Weissenbacher-Zweymuller syndrome, Wolf-Hirschhorn syndrome, Wolff Periodic disease, Weissenbacher-Zweymuller syndrome and Xeroderma pigmentosum, among others.

IV. Combination Therapy

Any of the compounds described herein can be used in an effective amount alone or in combination to treat a host such as a human with a disorder as described herein.

The term "bioactive agent" is used to describe an agent, other than the compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI680 (AstraZeneca), PDR001 (Novartis), REGN2810 (Regeneron), SHR-12-1 (Jiangsu Hengrui Medicine Company and Incyte Corporation), TSR-042 (Tesaro), and the PD-Li/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors, include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In one embodiment, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In one embodiment, the bioactive agent is an HER-2 inhibitor. Examples of HER-2 inhibitors include trastuzumab, lapatinib, ado-trastuzumab emtansine, and pertuzumab.

In one embodiment, the bioactive agent is a CD20 inhibitor. Examples of CD20 inhibitors include obinutuzumab, rituximab, fatumumab, ibritumomab, tositumomab, and ocrelizumab.

In one embodiment, the bioactive agent is a JAK3 inhibitor. Examples of JAK3 inhibitors include tasocitinib.

In one embodiment, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(lH-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl] amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclaxmesylate, (2Z)-2-[(5Z)-5-[(3,5-dimethyl-lH-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl) phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In one embodiment, the bioactive agent is a kinase inhibitor. In one embodiment, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl] oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl) benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl) amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl) phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4] triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(lH-Indazol-4-yl)-6-[[4-(methylsulfonyl)-1-piperazinyl]methyl]-4-(4-morpholinyl)thieno[3,2-d] pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12, 15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl] phenyl}propanenitrile) (dactolisib), XL-765 (N-(3-(N-(3-(3, 5-dimethoxyphenylamino)quinoxalin-2-yl)sulfamoyl) phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis (prop-2-enyl)amino]methylidene]-5-hydroxy-9-(methoxymethyl)-9a,11a-dimethyl-1,4,7-trioxo-2,3,3a,9,10, 11-hexahydroindeno[4,5h]isochromen-10-yl] acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structure described in WO2014/071109.

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, for example, Cerdulatinib (4-(cyclopropylamino)-2-((4-(4-(ethylsulfonyl)piperazin-1-yl) phenyl)amino)pyrimidine-5-carboxamide), entospletinib (6-(1H-indazol-6-yl)-N-(4-morpholinophenyl)imidazo[1,2-a] pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl) amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R, 2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R, 2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl) amino)-2,2-dimethyl-2H-pyrido[3,2-b][1,4]oxazin-3(4H)-one), piceatannol (3-Hydroxyresveratol), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

In one embodiment, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-(2H-yl}phenyl) acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl) amino)-N-(2-hydroxyethoxy)-5-((3-oxo-1,2-oxazinan-2yl) methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3(trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the bioactive agent is an AKT inhibitor, including but not limited to, MK-2206, GSK690693, Perifosine, (KRX-0401), GDC-0068, Triciribine, AZD5363, Honokiol, PF-04691502, and Miltefosine, a FLT-3 inhibitor, including but not limited to, P406, Dovitinib, Quizartinib (AC220), Amuvatinib (MP-470), Tandutinib (MLN518), ENMD-2076, and KW-2449, or a combination thereof.

In one embodiment, the bioactive agent is an mTOR inhibitor. Examples of mTOR inhibitors include but are not limited to rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), RO5126766 (3-[[3-Fluoro-2-(methylsulfamoylamino)-4-pyridyl]methyl]-4-methyl-7-pyrimidin-2-yloxychromen-2-one), WX-554, RO4987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In one embodiment, the bioactive agent is a RAS inhibitor. Examples of RAS inhibitors include but are not limited to Reolysin and siG12D LODER.

In one embodiment, the bioactive agent is a HSP inhibitor. HSP inhibitors include but are not limited to Geldanamycin or 17-N-Allylamino-17-demethoxygeldanamycin (17AAG), and Radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, aFLT-3 inhibitor, a VEGFR inhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In one embodiment, the bioactive agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with a Degrader disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one embodiment, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-TL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

V. Pharmaceutical Compositions

Any of the compounds as disclosed herein can be administered as the neat chemical, but are more typically administered as a pharmaceutical composition, that includes an effective amount for a host, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In certain embodiments the pharmaceutical composition is in a dosage form that contains from about 0.1 mg to about 2000 mg, from about 10 mg to about 1000 mg, from about 50 mg to about 600 mg, or from about 100 mg to about 400 mg of the active compound. In another embodiment the pharmaceutical composition is in a dosage form that contains from about 0.1 mg to about 100 mg, from about 0.5 mg to about 100 mg, from about 1 mg to about 50 mg, or from about 2 mg to about 25 mg of the active compound. In another embodiment the pharmaceutical composition is in a dosage form that contains from about 0.1 mg to about 10 mg, from about 0.5 mg to about 8 mg, from about 0.5 mg to about 6 mg, or from about 0.5 mg to about 5 mg of the active compound. Examples are dosage forms with at least, or in some embodiments, not more than, 0.1, 1, 5, 10, 25, 50, 100, 200, 250, 300, 400, 500, 600, 700, or 750 mg of active compound, or its salt.

The pharmaceutical composition may also include a molar ratio of the active compound and an additional bioactive agent. For example the pharmaceutical composition may contain a molar ratio of about 0.5:1, about 1:1, about 2:1, about 3:1 or from about 1.5:1 to about 4:1 of an anti-inflammatory or immunosuppressing agent. Compounds disclosed herein may be administered orally, topically, parenterally, by inhalation or spray, sublingually, via implant, including ocular implant, transdermally, via buccal administration, rectally, as an ophthalmic solution, injection, including ocular injection, intraveneous, intra-aortal, intracranial, subdermal, intraperitioneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Pharmaceutically acceptable carriers are carriers that do not cause any severe adverse reactions in the human body when dosed in the amount that would be used in the corresponding pharmaceutical composition. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

Formulations suitable for rectal administration are typically presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Many methods and devices for drug delivery are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen O Y); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drug loading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

VI. Representative Compounds of the Present Invention

TABLE 1

| Cmp No. | Structure | Name |
|---|---|---|
| 1 | 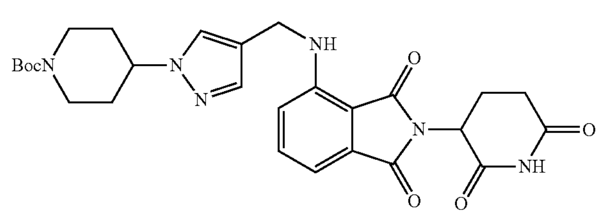 [SMILES: CC(C)(C)OC(=O)N1CCC(n2cc(CNc3cccc4c3C(=O)N(C3CCC(=O)NC3=O)C4=O)cn2)CC1] | Tert-butyl 4-(4-(((2-(2,6-dioxopiperidin-3-yl)-1,3-dioxoisoindolin-4-yl)amino)methyl)-1H-pyrazol-1-yl)piperidine-1-carboxylate |
| 2 | 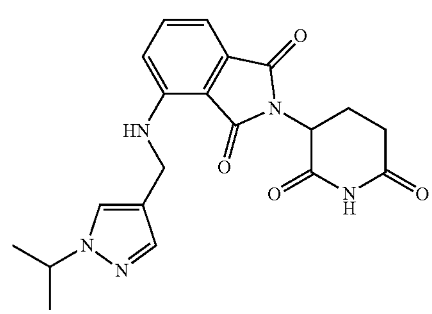 [SMILES: CC(C)n1cc(CNc2cccc3c2C(=O)N(C2CCC(=O)NC2=O)C3=O)cn1] | 2-(2,6-Dioxopiperidin-3-yl)-4-(((1-isopropyl-1H-pyrazol-4-yl)methyl)amino)isoindoline-1,3-dione |

TABLE 1-continued

| Cmp No. | Structure | Name |
|---|---|---|
| 3 | 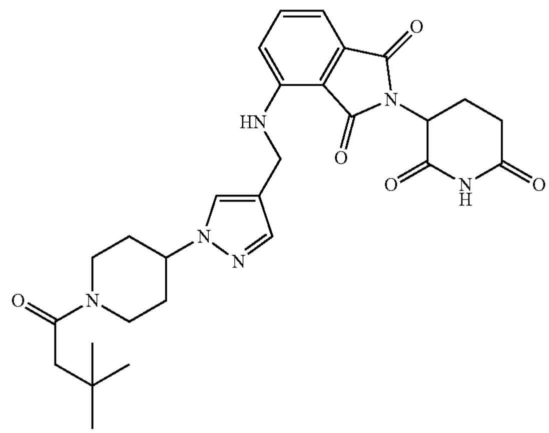 [SMILES: CC(C)(C)CC(=O)N1CCC(n2cc(CNc3cccc4c3C(=O)N(C3CCC(=O)NC3=O)C4=O)cn2)CC1] | 4-(((1-(1-(3,3-Dimethylbutanoyl)piperidin-4-yl)-1H-pyrazol-4-yl)methyl)amino)-2-(2,6-dioxopiperidin-3-yl)isoindoline-1,3-dione |
| 4 | 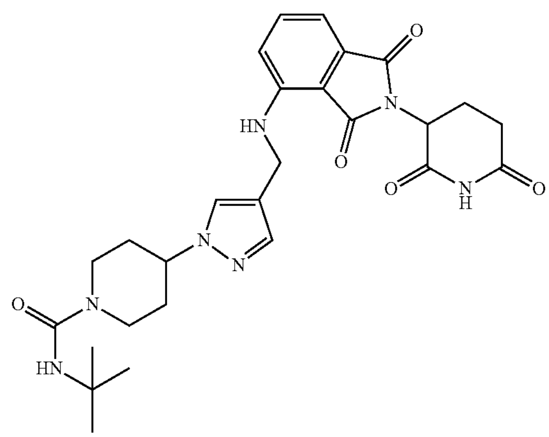 [SMILES: CC(C)(C)NC(=O)N1CCC(n2cc(CNc3cccc4c3C(=O)N(C3CCC(=O)NC3=O)C4=O)cn2)CC1] | N-(tert-butyl)-4-(4-(((2-(2,6-dioxopiperidin-3-yl)-1,3-dioxoisondolin-4-yl)amino)methyl)-1H-pyrazol-1-yl)piperidine-1-carboxamide |
| 5 | 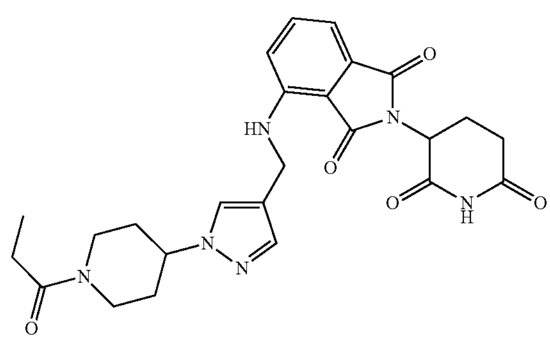 [SMILES: CCC(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-propionylpiperidin-4-yl)-1H-pyrazol-4-yl)methyl)amino)isoindoline-1,3-dione |
| 6 | 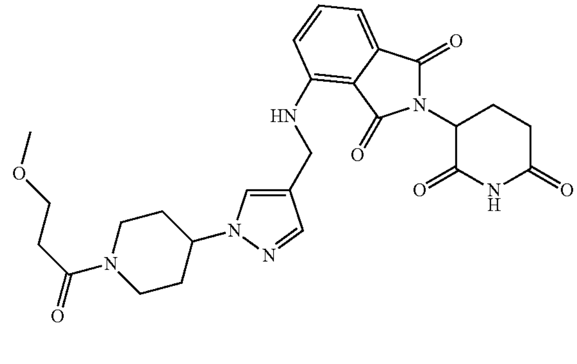 [SMILES: COCCC(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-(3-methoxypropanyl)piperidin-4-yl)-1H-pyrazol-4-yl)methyl)amino)isoindoline-1,3-dione |

TABLE 1-continued

| Cmp No. | Structure | Name |
|---|---|---|
| 7 | 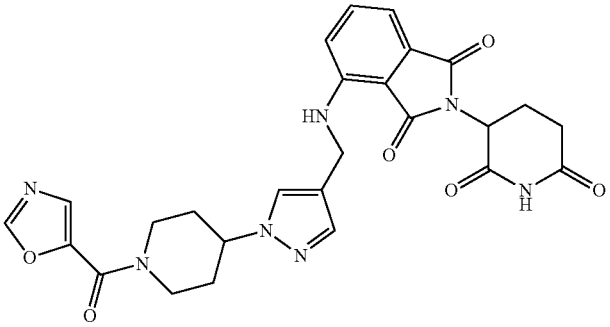 [SMILES: O=C1CCC(N2C(=O)c3cccc(NCc4cnn(C5CCN(C(=O)c6cnco6)CC5)c4)c3C2=O)C(=O)N1] | 2-(2,6-dioxopiperidin-3-yl)-4-(((1-(1-(oxazole-5-carbnonyl)piperidin-4-yl)-1H-pyrazol-4-yl)methyl)amino)isoindoline-1,3-dione |
| 8 | 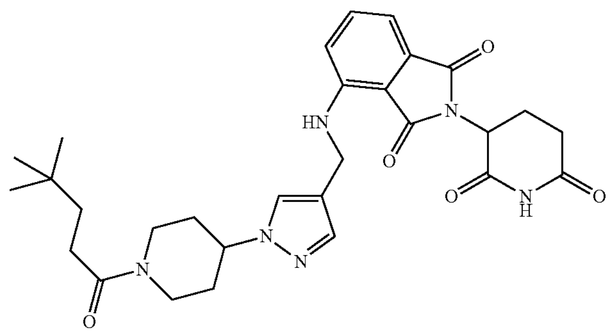 [SMILES: CC(C)(C)CCC(=O)N1CCC(n2cc(CNc3cccc4c3C(=O)N(C3CCC(=O)NC3=O)C4=O)cn2)CC1] | 4-(((1-(1-(4,4-dimethylpentanoyl)piperidin-4-yl)-1H-pyrazol-4-yl)methyl)amino)-2-(2,6-dioxopiperidin-3-yl)isoindoline-1,3-dione |
| 9 | 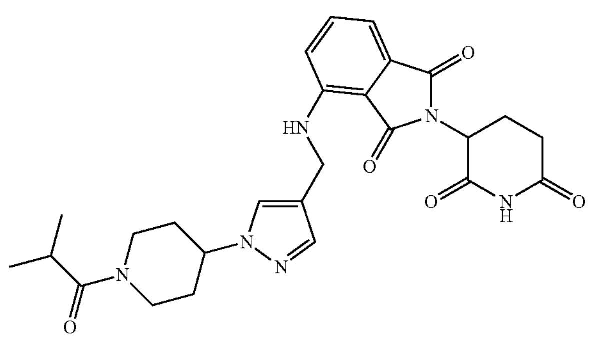 [SMILES: CC(C)C(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-isobutyrylpiperidin-4-yl)-1H-pyrazol-4-yl)methyl)amino)isoindoline-1,3-dione |
| 10 | 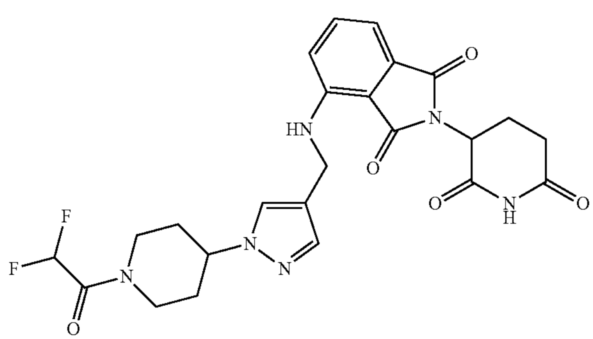 [SMILES: O=C1CCC(N2C(=O)c3cccc(NCc4cnn(C5CCN(C(=O)C(F)F)CC5)c4)c3C2=O)C(=O)N1] | 4-(((1-(1-(2,2-difluoroacetyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 11 | 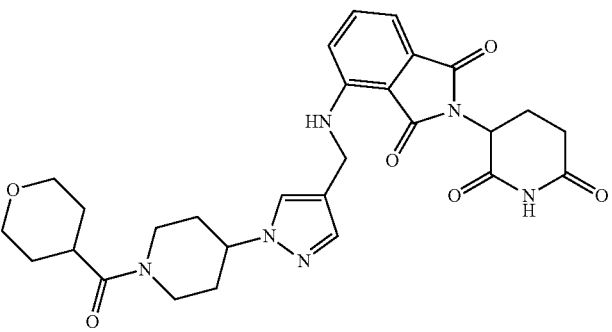 [SMILES: O=C1CCC(N2C(=O)c3cccc(NCc4cnn(C5CCN(C(=O)C6CCOCC6)CC5)c4)c3C2=O)C(=O)N1] | 2-(2,6-dioxopiperidin-3-yl)-4-(((1-(1-(tetrahydro-2H-pyran-4-carbonyl)piperidin-4-yl)-1H-pyrazol-4-yl)methyl)amino)isoindoline-1,3-dione |
| 12 | 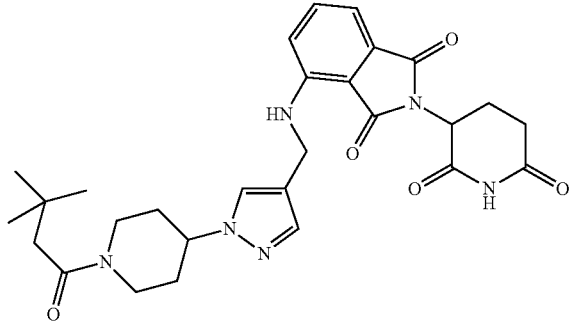 | 4-(((1-(1-(3,3-dimethylbutanoyl)piperidin-4-yl)-1H-pyrazol-4-yl)methyl)amino)-2-(2,6-dioxopiperidin-3-yl)isoindoline-1,3-dione |
| 13 | 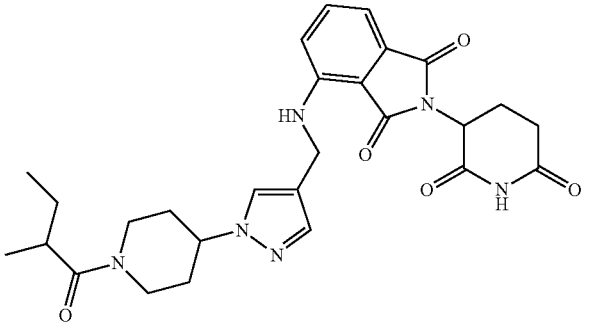 [SMILES: CCC(C)C(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-(2-methylbutanoyl)piperidin-4-yl)-1H-pyrazol-4-yl)methyl)amio)isoindoline-1,3-dione |
| 14 | 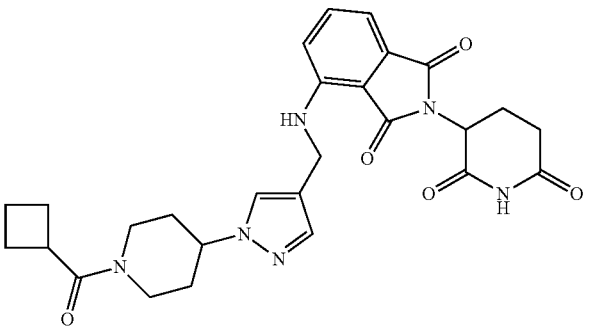 | 4-(((1-(1-(cyclobutanecarbonyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 15 | 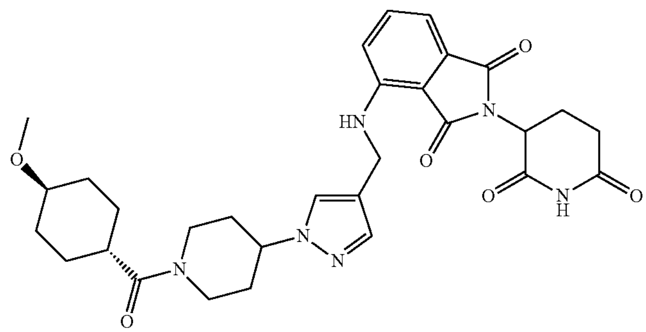 [SMILES: CO[C@H]1CC[C@H](C(=O)N2CCC(n3cc(CNc4cccc5c4C(=O)N(C4CCC(=O)NC4=O)C5=O)cn3)CC2)CC1] | 2-(2,6-dioxopiperidin-3-yl)-4-(((1-(1-((1r,4r)-4-methoxycyclohexane-1-carbonyl)piperidin-4-yl)-1H-pyrazol-4-yl)methyl)amino)isoindoline-1,3-dione |
| 16 | 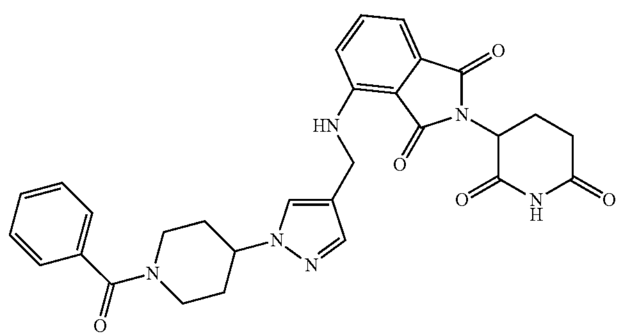 [SMILES: O=C1CCC(N2C(=O)c3cccc(NCc4cnn(C5CCN(C(=O)c6ccccc6)CC5)c4)c3C2=O)C(=O)N1] | 4-(((1-(1-benzoylpiperidin-4-yl)-1H-pyrazol-4-yl)methyl)amino)-2-(2,6-dioxopiperidin-3-yl)isoindoline-1,3-dione |
| 17 | 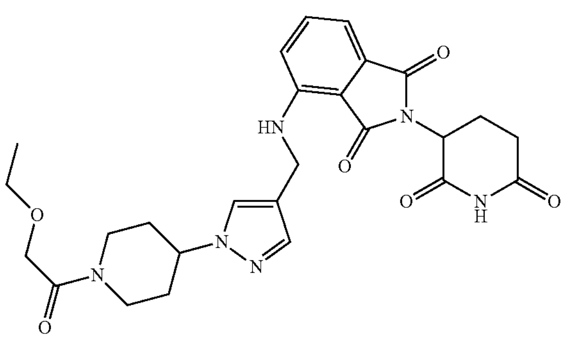 [SMILES: CCOCC(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-(2-ethoxyacetyl)piperidin-4-yl)-1H-pyrazol-4-yl)methyl)amino)isoindoline-1,3-dione |
| 18 | 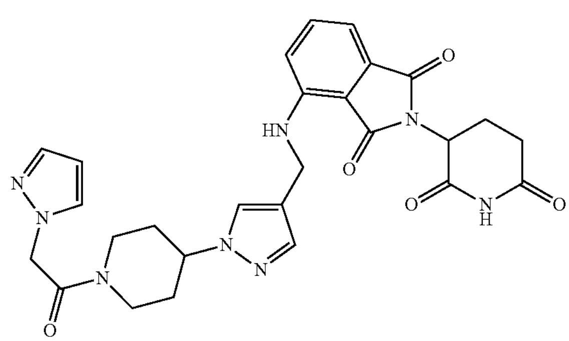 [SMILES: O=C1CCC(N2C(=O)c3cccc(NCc4cnn(C5CCN(C(=O)Cn6cccn6)CC5)c4)c3C2=O)C(=O)N1] | 4-(((1-(1-(2-(1H-pyrazol-1-yl)acetyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 19 | 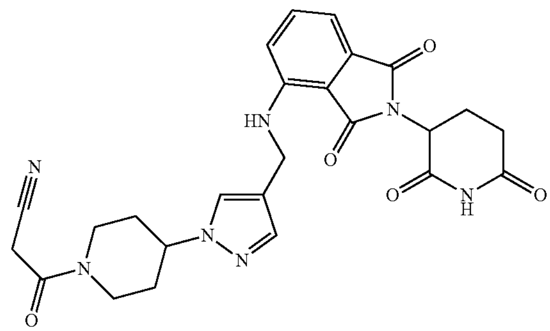 [SMILES: N#CCC(=O)N1CCC(n2cc(CNc3cccc4c3C(=O)N(C3CCC(=O)NC3=O)C4=O)cn2)CC1] | 3-(4-(4-(((2-(2,6-dioxopiperidin-3-yl)-1,3-dioxoisoindolin-4-yl)amino)methyl)-1H-pyrazol-1-yl)piperidin-1-yl)-3-oxopropanenitrile |
| 20 | 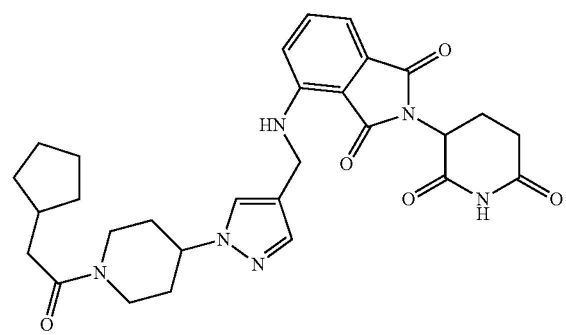 [SMILES: O=C1CCC(N2C(=O)c3cccc(NCc4cnn(C5CCN(C(=O)CC6CCCC6)CC5)c4)c3C2=O)C(=O)N1] | 4-(((1-(1-(2-cyclopentylacetyl)piperidin-4-yl)-1H-pyrazol-4-yl)methyl)amino)-2-(2,6-dioxopiperidin-3-yl)isoindoline-1,3-dione |
| 21 | 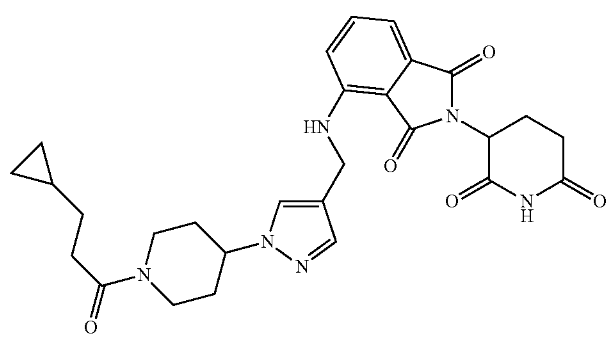 [SMILES: O=C1CCC(N2C(=O)c3cccc(NCc4cnn(C5CCN(C(=O)CCC6CC6)CC5)c4)c3C2=O)C(=O)N1] | 4-(((1-(1-(3-cyclopropylpropanoyl)piperidin-4-yl)-1H-pyrazol-4-yl)methyl)amino)-2-(2,6-dioxopiperidin-3-yl)isoindoline-1,3-dione |
| 22 | 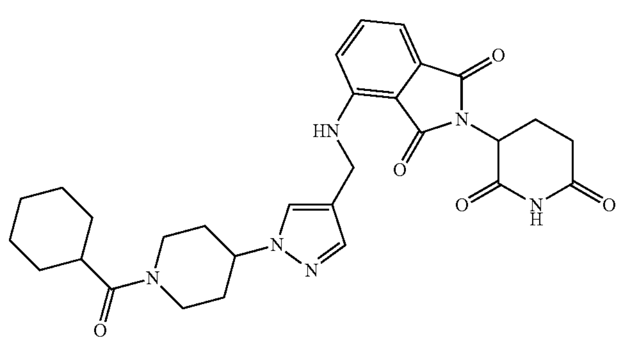 | 4-(((1-(1-(cyclohexanecarbonyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 23 | 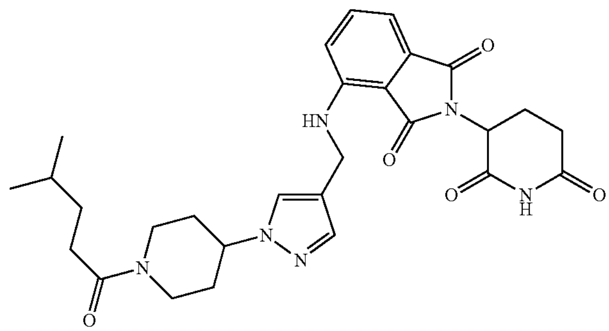 | 2-(2,6-dioxopiperidin-3-yl)-4-(((1-(1-(4-methylpentanoyl)piperidin-4-yl)-1H-pyrazol-4-yl)methyl)amino)isoindoline-1,3-dione |
| 24 | 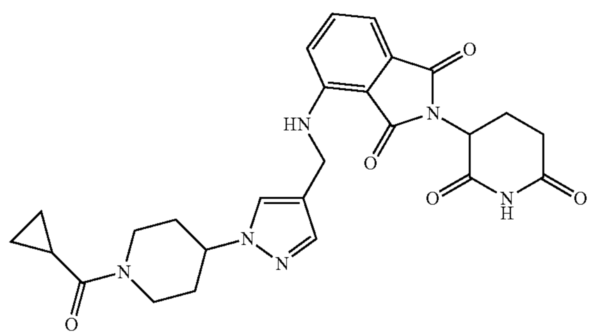 [SMILES: O=C1CCC(N2C(=O)c3cccc(NCc4cnn(C5CCN(C(=O)C6CC6)CC5)c4)c3C2=O)C(=O)N1] | 4-(((1-(1-(cyclopropanecarbonyl)piperidin-4-yl)-1H-pyrazol-4-yl)methyl)amino)-2-(2,6-dioxopiperidin-3-yl)isoindoline-1,3-dione |
| 25 | 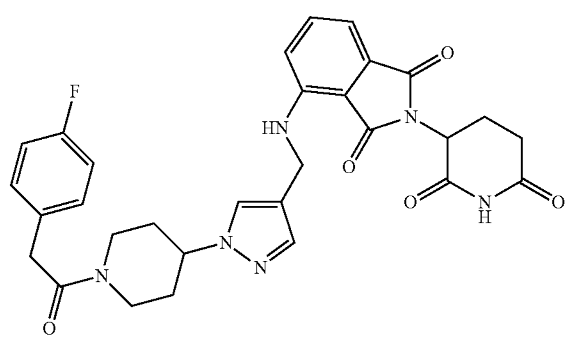 [SMILES: O=C1CCC(N2C(=O)c3cccc(NCc4cnn(C5CCN(C(=O)Cc6ccc(F)cc6)CC5)c4)c3C2=O)C(=O)N1] | 2-(2,6-dioxopiperidin-3-yl)-4-(((1-(1-(2-(4-fluorophenyl)acetyl)piperidin-4-yl)-1H-pyrazol-4-yl)methyl)amino)isoindoline-1,3-dione |
| 26 | 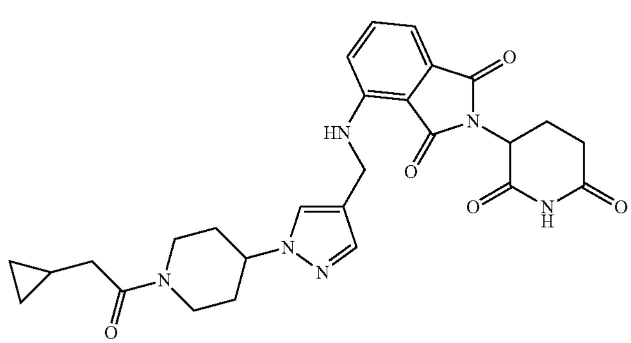 [SMILES: O=C1CCC(N2C(=O)c3cccc(NCc4cnn(C5CCN(C(=O)CC6CC6)CC5)c4)c3C2=O)C(=O)N1] | 4-(((1-(1-(2-cyclopropylacetyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 27 | 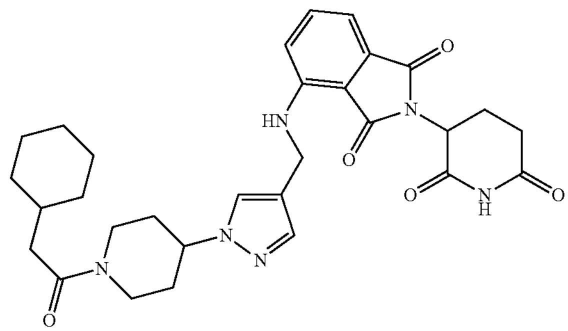 [SMILES: O=C1CCC(N2C(=O)c3cccc(NCc4cnn(C5CCN(C(=O)CC6CCCCC6)CC5)c4)c3C2=O)C(=O)N1] | 4-(((1-(1-(2-cyclohexylacetyl)piperidin-4-yl)-1H-pyrazol-4-yl)methyl)amino)-2-(2,6-dioxopiperidin-3-yl)isoindoline-1,3-dione |
| 28 | 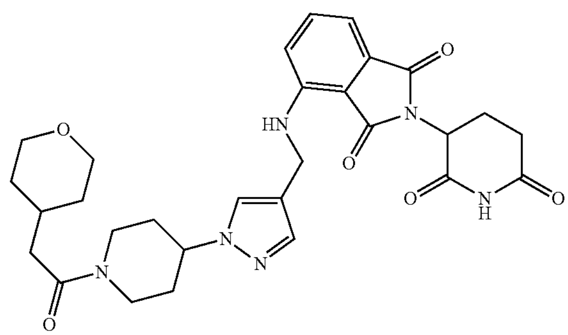 | 2-(2,6-dioxopiperidin-3-yl)-4-(((1-(1-(2-(tetrahydro-2H-pyrazin-4-yl)acetyl)piperidin-4-yl)-1H-pyrazol-4-yl)methyl)amino)isoindoline-1,3-dione |
| 29 | 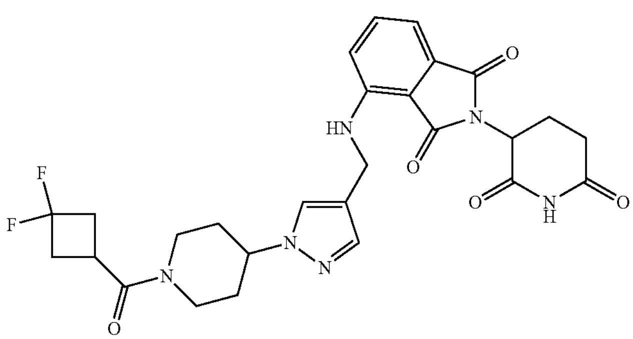 [SMILES: O=C1CCC(N2C(=O)c3cccc(NCc4cnn(C5CCN(C(=O)C6CC(F)(F)C6)CC5)c4)c3C2=O)C(=O)N1] | 4-(((1-(1-(3,3-difluorocyclobutane-1-carbonyl)piperidin-4-yl)-1H-pyrazol-4-yl)methyl)amino)-2-(2,6-dioxopiperidin-3-yl)isoindoline-1,3-dione |
| 30 | 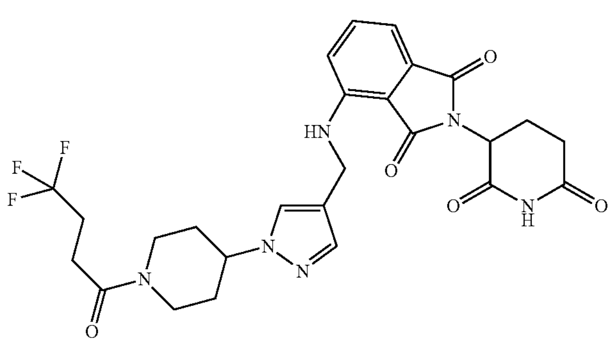 [SMILES: O=C1CCC(N2C(=O)c3cccc(NCc4cnn(C5CCN(C(=O)CCC(F)(F)F)CC5)c4)c3C2=O)C(=O)N1] | 2-(2,6-dioxopiperidin-3-yl)-4-(((1-(1-(4,4,4-trifluorobutanoyl)piperidin-4-yl)-1H-pyrazol-4-yl)methyl)amino)isoindoline-1,3-dione |

TABLE 1-continued

| Cmp No. | Structure | Name |
|---|---|---|
| 31 | 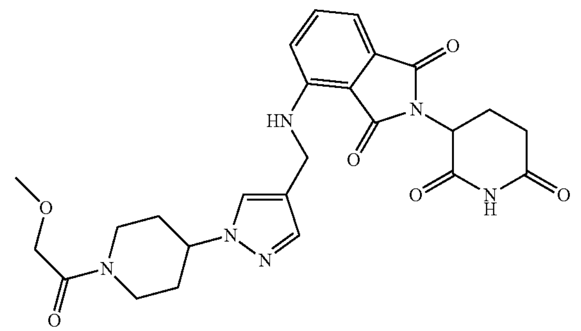 [SMILES: COCC(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-(2-methoxyacetyl)piperidin-4-yl)-1H-pyrazol-4-yl)methyl)amino)isoindoline-1,3-dione |
| 32 | 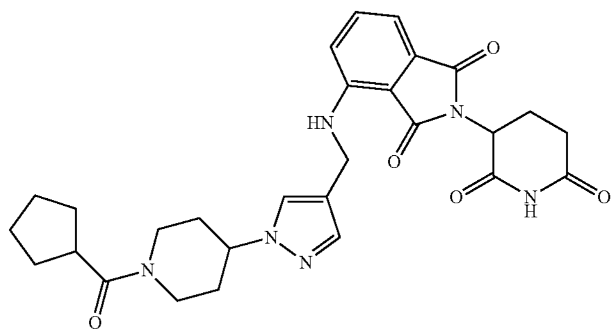 [SMILES: O=C1CCC(N2C(=O)c3cccc(NCc4cnn(C5CCN(C(=O)C6CCCC6)CC5)c4)c3C2=O)C(=O)N1] | 4-(((1-(1-(cyclopentanecarbonyl)piperidin-4-yl)-1H-pyrazol-4-yl)methyl)amino)-2-(2,6-dioxopiperidin-3-yl)isoindoline-1,3-dione |
| 33 | 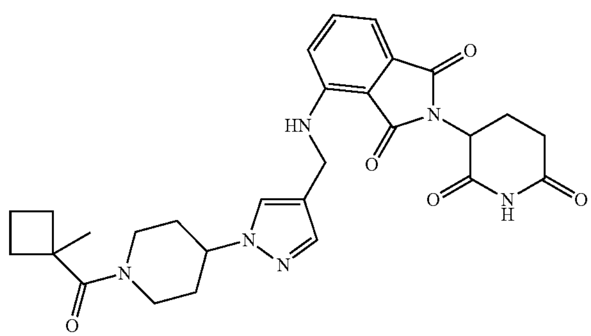 [SMILES: CC1(C(=O)N2CCC(n3cc(CNc4cccc5c4C(=O)N(C4CCC(=O)NC4=O)C5=O)cn3)CC2)CCC1] | 2-(2,6-dioxopiperidin-3-yl)-4-(((1-(1-(1-methylcyclobutane-1-carbonyl)piperidin-4-yl)-1H-pyrazol-4-yl)methyl)amino)isoindoline-1,3-dione |
| 34 | 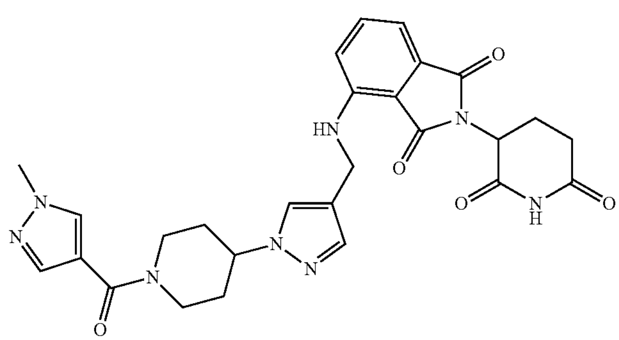 [SMILES: Cn1cc(C(=O)N2CCC(n3cc(CNc4cccc5c4C(=O)N(C4CCC(=O)NC4=O)C5=O)cn3)CC2)cn1] | 2-(2,6-dioxopiperidin-3-yl)-4-(((1-(1-(1-methyl-1H-pyrazole-4-carbonyl)piperidin-4-yl)-1H-pyrazol-4-yl)methyl)amino)isoindoline-1,3-dione |

TABLE 1-continued

| Cmp No. | Structure | Name |
|---|---|---|
| 35 | 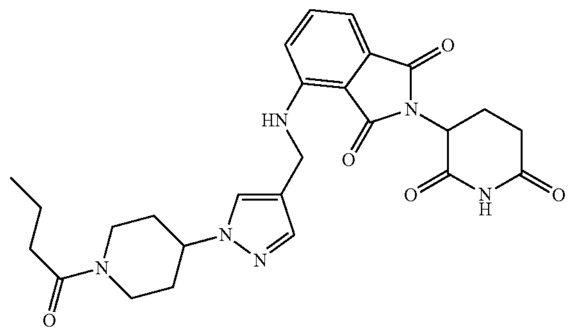 [SMILES: CCCC(=O)N1CCC(n2cc(CNc3cccc4c3C(=O)N(C3CCC(=O)NC3=O)C4=O)cn2)CC1] | 4-(((1-(1-butyrylpiperidin-4-yl)-1H-pyrazol-4-yl)methyl)amino)-2-(2,6-dioxopiperidin-3-yl)isoindoline-1,3-dione |
| 36 | 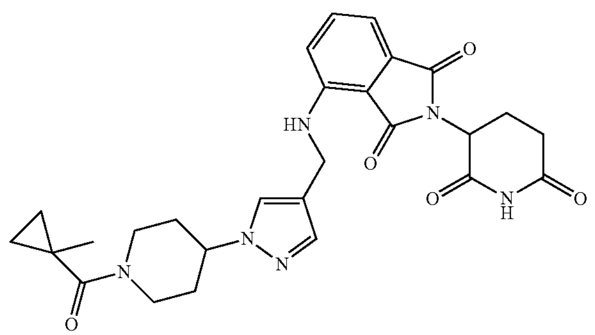 [SMILES: CC1(C(=O)N2CCC(n3cc(CNc4cccc5c4C(=O)N(C4CCC(=O)NC4=O)C5=O)cn3)CC2)CC1] | 2-(2,6-dioxopiperidin-3-yl)-4-(((1-(1-(1-methylcyclopropane-1-carbonyl)piperidin-4-yl)-1H-pyrazol-4-yl)methyl)amino)isoindoline-1,3-dione |
| 37 | 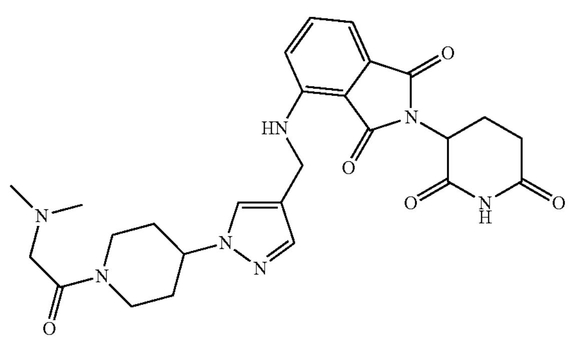 | 4-(((1-(1-(dimethylglycyl)piperidin-4-yl)-1H-pyrazol-4-yl)methyl)amino)-2-(2,6-dioxopiperidin-3-yl)isoindoline-1,3-dione |
| 38 | 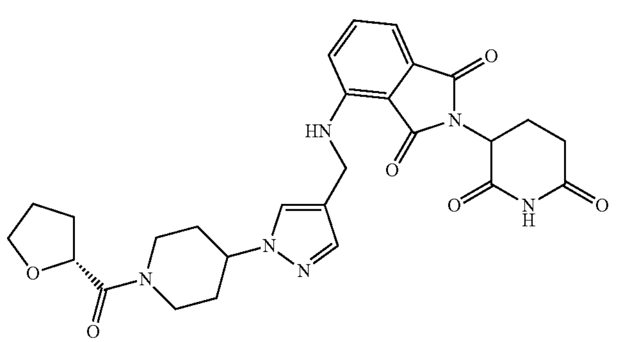 [SMILES: O=C1CCC(N2C(=O)c3cccc(NCc4cnn(C5CCN(C(=O)[C@H]6CCCO6)CC5)c4)c3C2=O)C(=O)N1] | 2-(2,6-dioxopiperidin-3-yl)-4-(((1-(1-((R)-tetrahydrofuran-2-carbonyl)piperidin-4-yl)-1H-pyrazol-4-yl)methyl)amino)isoindoline-1,3-dione |

TABLE 1-continued

| Cmp No. | Structure | Name |
|---|---|---|
| 39 | 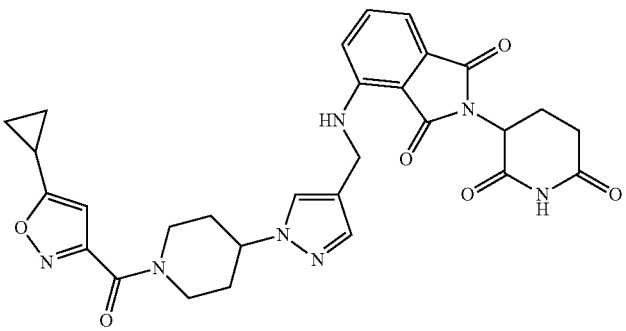 [SMILES: O=C1CCC(N2C(=O)c3cccc(NCc4cnn(C5CCN(C(=O)c6cc(C7CC7)on6)CC5)c4)c3C2=O)C(=O)N1] | 4-(((1-(1-(5-cyclopropylisoxazole-3-carbonyl)piperidin-4-yl)-1H-pyrazol-4-yl)methyl)amino)-2-(2,6-dioxopiperidin-3-yl)isoindoline-1,3-dione |
| 40 | 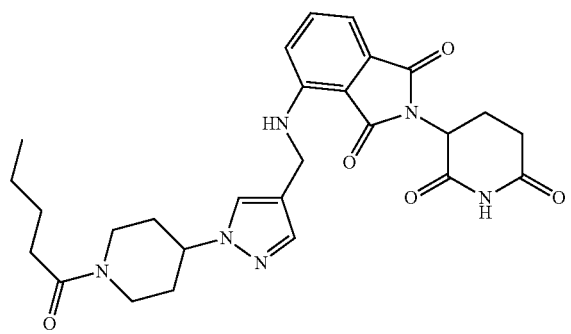 | 2-(2,6-dioxopiperidin-3-yl)-4-(((1-(1-pentanoylpiperidin-4-yl)-1H-pyrazol-4-yl)methyl)amino)isoindoline-1,3-dione |
| 41 | 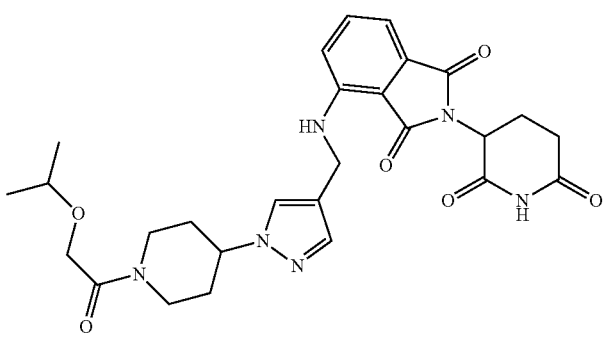 [SMILES: CC(C)OCC(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-(2-isopropoxyacetyl)piperidin-4-yl)-1H-pyrazol-4-yl)methyl)amino)-isoindoline-1,3-dione |
| 42 | 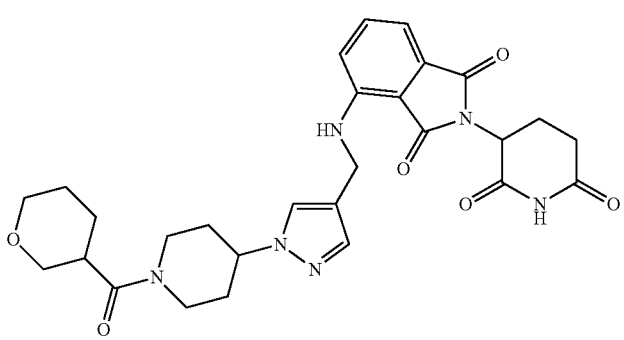 [SMILES: O=C1CCC(N2C(=O)c3cccc(NCc4cnn(C5CCN(C(=O)C6CCCOC6)CC5)c4)c3C2=O)C(=O)N1] | 2-(2,6-dioxopiperidin-3-yl)-4-(((1-(1-(tetrahydro-2H-pyran-3-carbonyl)piperidin-4-yl)-1H-pyrazol-4-yl)methyl)amino)isoindoline-1,3-dione |

TABLE 1-continued

| Cmp No. | Structure | Name |
|---|---|---|
| 43 | 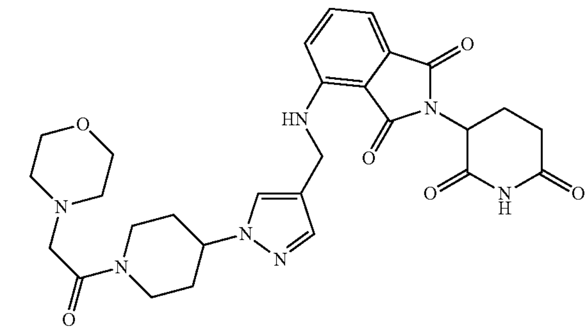 [SMILES: O=C1CCC(N2C(=O)c3cccc(NCc4cnn(C5CCN(C(=O)CN6CCOCC6)CC5)c4)c3C2=O)C(=O)N1] | 2-(2,6-dioxopiperidin-3-yl)-4-(((1-(1-(2-morpholinoacetyl)piperidin-4-yl)-1H-pyrazol-4-yl)methyl)amino)isoindoline-1,3-dione |
| 44 | 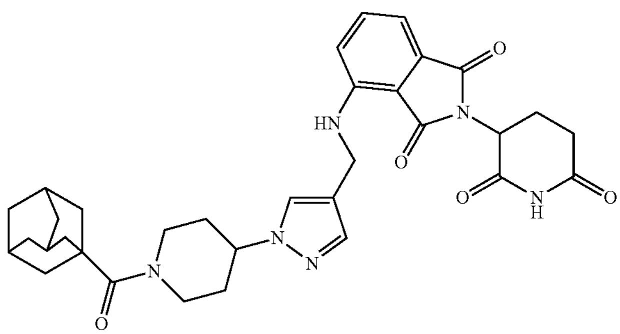 [SMILES: O=C1CCC(N2C(=O)c3cccc(NCc4cnn(C5CCN(C(=O)C67CC8CC(CC(C8)C6)C7)CC5)c4)c3C2=O)C(=O)N1] | 4-(((1-(1-(adamantane-1-carbonyl)piperidin-4-yl)-1H-pyrazol-4-yl)methyl)amino)-2-(2,6-dioxopiperidin-3-yl)isoindoline-1,3-dione |
| 45 | 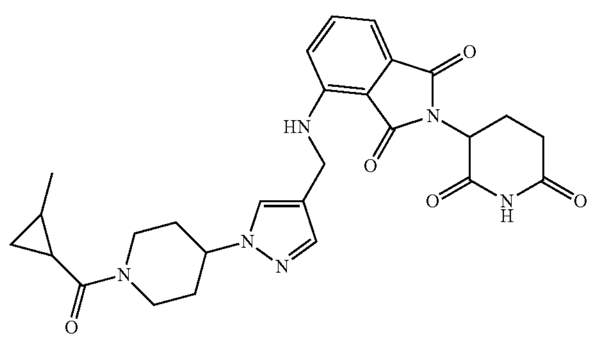 [SMILES: CC1CC1C(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-(2-methylcyclopropane-1-carbonyl)piperidin-4-yl)-1H-pyrazol-4-yl)methyl)amino)isondoline-1,3-dione |
| 46 | 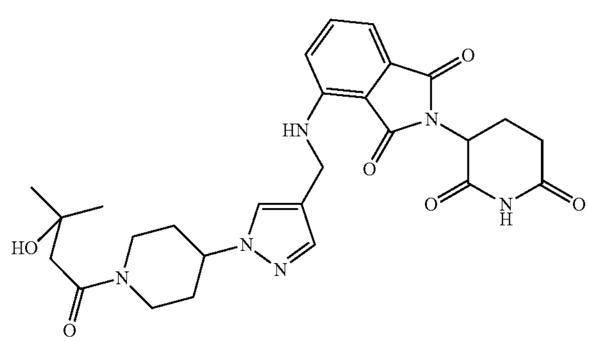 [SMILES: CC(C)(O)CC(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-(3-hydroxy-3-methylbutanoyl)piperidin-4-yl)-1H-pyrazol-4-yl)methyl)amino)isoindoline-1,3-dione |

TABLE 1-continued

| Cmp No. | Structure | Name |
|---|---|---|
| 47 | 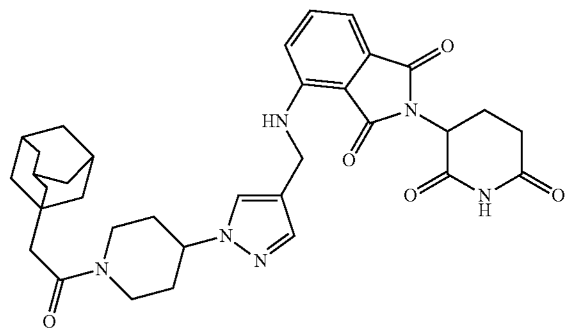 [SMILES: O=C1CCC(N2C(=O)c3cccc(NCc4cnn(C5CCN(C(=O)CC67CC8CC(CC(C8)C6)C7)CC5)c4)c3C2=O)C(=O)N1] | 4-(((1-(1-(2-(adamantan-1-yl)acetyl)piperidin-4-yl)-1H-pyrazol-4-yl)methyl)amino)-2-(2,6-dioxopiperidin-3-yl)isoindoline-1,3-dione |
| 48 | 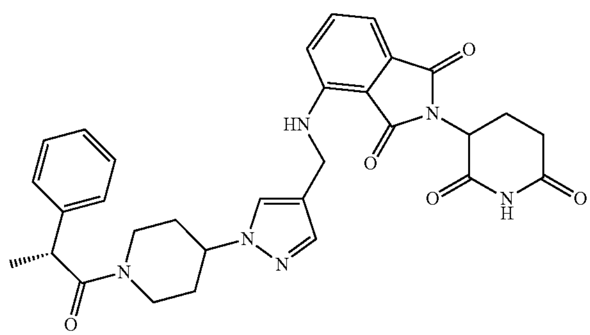 [SMILES: C[C@@H](C(=O)N1CCC(n2cc(CNc3cccc4c3C(=O)N(C3CCC(=O)NC3=O)C4=O)cn2)CC1)c1ccccc1] | 2-(2,6-dioxopiperidin-3-yl)-4-(((1-(1-((R)-2-phenylpropanoyl)piperidin-4-yl)-1H-pyrazol-4-yl)methyl)amino)isoindoline-1,3-dione |
| 49 | 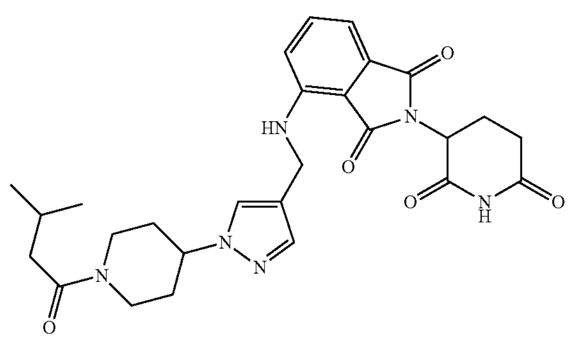 [SMILES: CC(C)CC(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-(3-methylbutanoyl)piperidin-4-yl)-1H-pyrazol-4-yl)methyl)amino)isoindoline-1,3-dione |
| 50 | 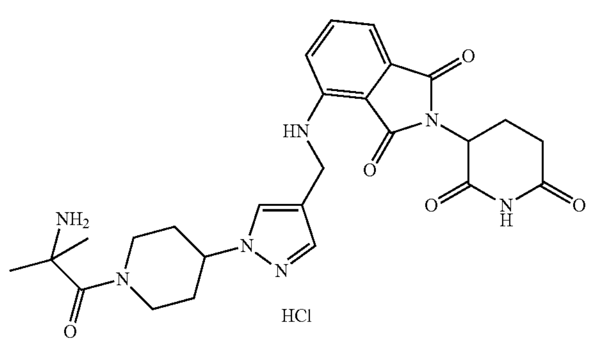 [SMILES: CC(C)(N)C(=O)N1CCC(n2cc(CNc3cccc4c3C(=O)N(C3CCC(=O)NC3=O)C4=O)cn2)CC1 ; Cl] | 4-(((1-(1-(2-amino-2-methylpropanoyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 51 | 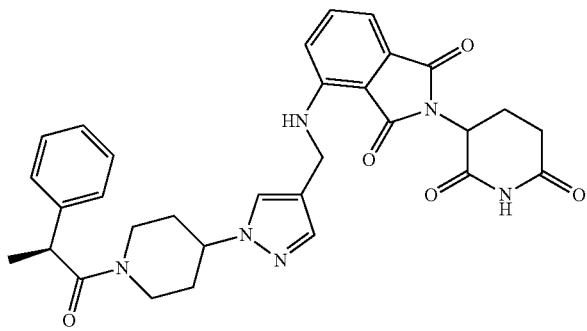 [SMILES: C[C@H](C(=O)N1CCC(n2cc(CNc3cccc4c3C(=O)N(C3CCC(=O)NC3=O)C4=O)cn2)CC1)c1ccccc1] | 2-(2,6-dioxopiperidin-3-yl)-4-(((1-(1-((S)-2-phenylpropanoyl)piperidin-4-yl)-1H-pyrazol-4-yl)methyl)amino)isoindoline-1,3-dione |
| 52 | 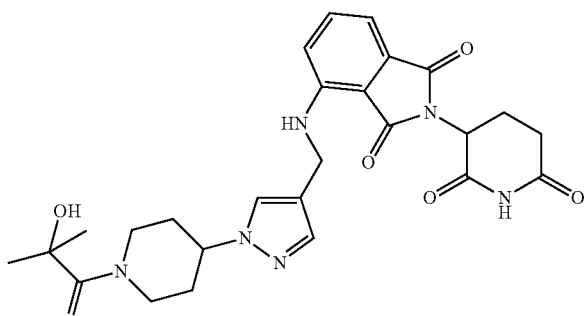 | 2-(2,6-dioxopiperidin-3-yl)-4-(((1-(1-(2-hydroxy-2-methylpropanoyl)piperidin-4-yl)-1H-pyrazol-4-yl)methyl)amino)isoindoline-1,3-dione |
| 53 | 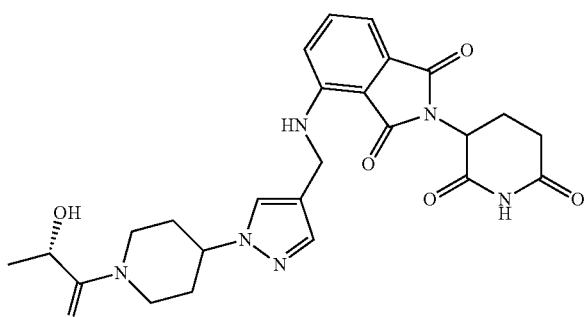 | 2-(2,6-dioxopiperidin-3-yl)-4-(((1-(1-((S)-2-hydroxypropanoyl)piperidin-4-yl)-1H-pyrazol-4-yl)methyl)amino)isoindoline-1,3-dione |
| 54 | 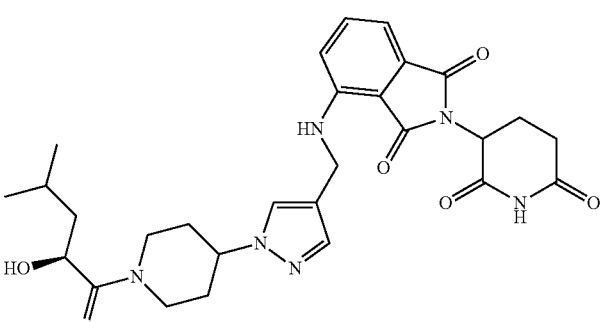 | 2-(2,6-dioxopiperidin-3-yl)-4-(((1-(1-((S)-2-hydroxy-4-methylpentanoyl)piperidin-4-yl)-1H-pyrazol-4-yl)methyl)amino)isoindoline-1,3-dione |

TABLE 1-continued

| Cmp No. | Structure | Name |
|---|---|---|
| 55 | 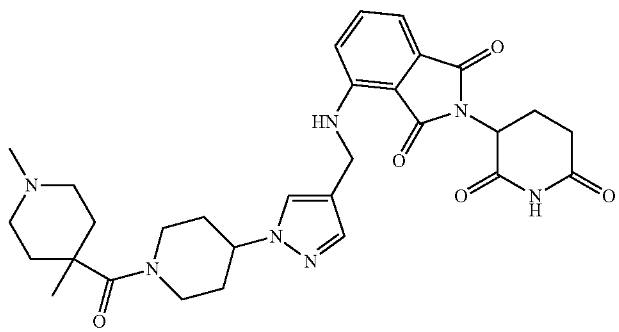 [SMILES: CN1CCC(C)(C(=O)N2CCC(n3cc(CNc4cccc5c4C(=O)N(C4CCC(=O)NC4=O)C5=O)cn3)CC2)CC1] | 4-(((1-(1-(1,4-dimethylpiperidine-4-carbonyl)piperidin-4-yl)-1H-pyrazol-4-yl)methyl)amino)-2-(2,6-dioxopiperidin-3-yl)isoindoline-1,3-dione |
| 56 | 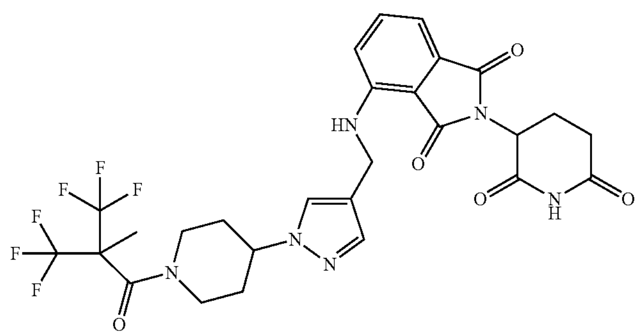 [SMILES: CC(C(=O)N1CCC(n2cc(CNc3cccc4c3C(=O)N(C3CCC(=O)NC3=O)C4=O)cn2)CC1)(C(F)(F)F)C(F)(F)F] | 2-(2,6-dioxopiperidin-3-yl)-4-(((1-(1-(3,3,3-trifluoro-2-methyl-2-(trifluoromethyl)propanoyl)piperidin-4-yl)-1H-pyrazol-4-yl)methyl)amino)isoindoline-1,3-dione |
| 57 | 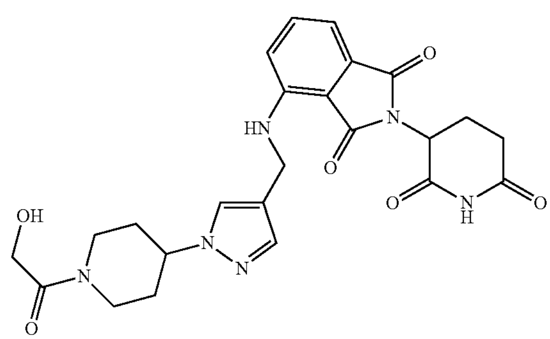 [SMILES: O=C1CCC(N2C(=O)c3cccc(NCc4cnn(C5CCN(C(=O)CO)CC5)c4)c3C2=O)C(=O)N1] | 2-(2,6-dioxopiperidin-3-yl)-4-(((1-(1-(2-hydroxyacetyl)piperidin-4-yl)-1H-pyrazol-4-yl)methyl)amino)isoindoline-1,3-dione |
| 58 | 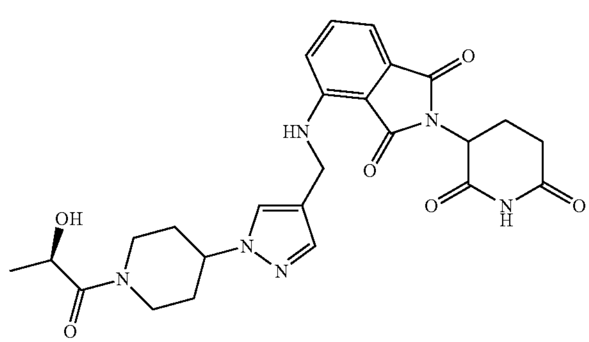 [SMILES: C[C@@H](O)C(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-((R)-2-hydroxypropanoyl)piperidin-4-yl)-1H-pyrazol-4-yl)methyl)amino)isoindoline-1,3-dione |

TABLE 1-continued

| Cmp No. | Structure | Name |
|---|---|---|
| 59 | 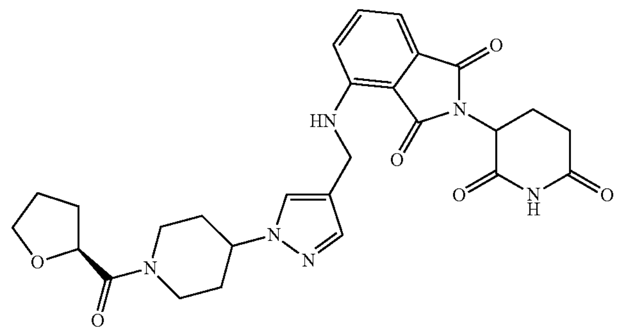 [SMILES: O=C1CCC(N2C(=O)c3cccc(NCc4cnn(C5CCN(C(=O)[C@@H]6CCCO6)CC5)c4)c3C2=O)C(=O)N1] | 2-(2,6-dioxopiperidin-3-yl)-4-(((1-(1-((S)-tetrahydrofuran-2-carbonyl)piperidin-4-yl)-1H-pyrazol-4-yl)methyl)amino)isoindoline-1,3-dione |
| 60 | 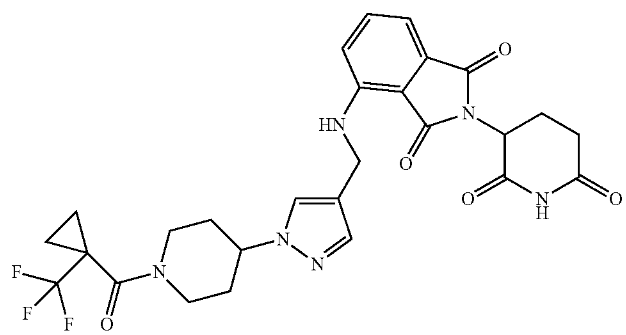 [SMILES: O=C1CCC(N2C(=O)c3cccc(NCc4cnn(C5CCN(C(=O)C6(C(F)(F)F)CC6)CC5)c4)c3C2=O)C(=O)N1] | 2-(2,6-dioxopiperidin-3-yl)-4-(((1-(1-(1-(trifluoromethyl)cyclopropane-1-carbonyl)piperidin-4-yl)-1H-pyrazol-4-yl)methyl)amino)isoindoline-1,3-dione |
| 61 | 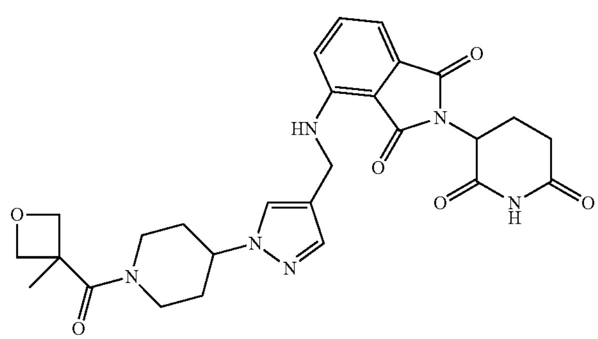 [SMILES: CC1(C(=O)N2CCC(n3cc(CNc4cccc5c4C(=O)N(C4CCC(=O)NC4=O)C5=O)cn3)CC2)COC1] | 2-(2,6-dioxopiperidin-3-yl)-4-(((1-(1-(3-methyloxetane-3-carbonyl)piperidin-4-yl)-1H-pyrazol-4-yl)methyl)amino)isoindoline-1,3-dione |
| 62 | 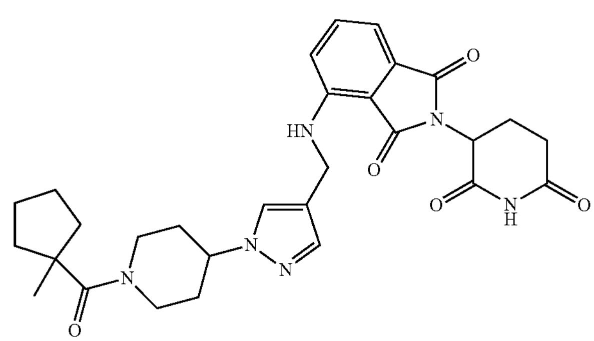 [SMILES: CC1(C(=O)N2CCC(n3cc(CNc4cccc5c4C(=O)N(C4CCC(=O)NC4=O)C5=O)cn3)CC2)CCCC1] | 2-(2,6-dioxopiperidin-3-yl)-4-(((1-(1-(1-methylcyclopentane-1-carbonyl)piperidin-4-yl)-1H-pyrazol-4-yl)methyl)amino)isoindoline-1,3-dione |

TABLE 1-continued

| Cmp No. | Structure | Name |
|---|---|---|
| 63 | 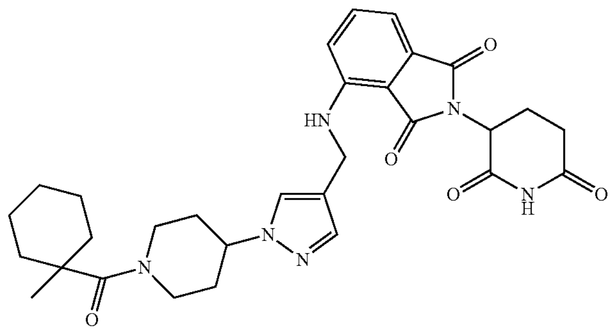 [SMILES: CC1(C(=O)N2CCC(n3cc(CNc4cccc5c4C(=O)N(C4CCC(=O)NC4=O)C5=O)cn3)CC2)CCCCC1] | 2-(2,6-dioxopiperidin-3-yl)-4-(((1-(1-(1-methylcyclohexane-1-carbonyl)piperidin-4-yl)-1H-pyrazol-4-yl)methyl)amino)isoindoline-1,3-dione |
| 64 | 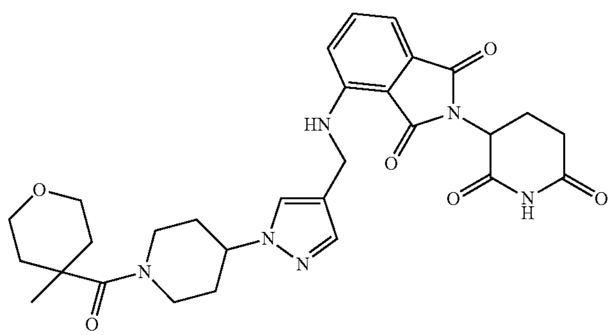 | 2-(2,6-dioxopiperidin-3-yl)-4-(((1-(1-(4-methyltetrahydro-2H-pyran-4-carbonyl)piperidin-4-yl)-1H-pyrazol-4-yl)methyl)amino)isoindoline-1,3-dione |
| 65 | 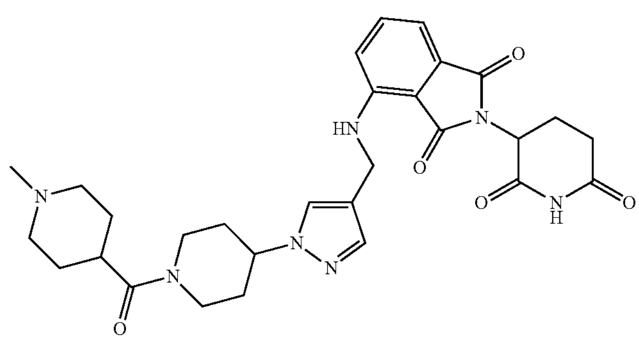 [SMILES: CN1CCC(C(=O)N2CCC(n3cc(CNc4cccc5c4C(=O)N(C4CCC(=O)NC4=O)C5=O)cn3)CC2)CC1] | 2-(2,6-dioxopiperidin-3-yl)-4-(((1-(1-(1-methylpiperidine-4-carbonyl)piperidin-4-yl)-1H-pyrazol-4-yl)methyl)amino)isoindoline-1,3-dione |
| 66 | 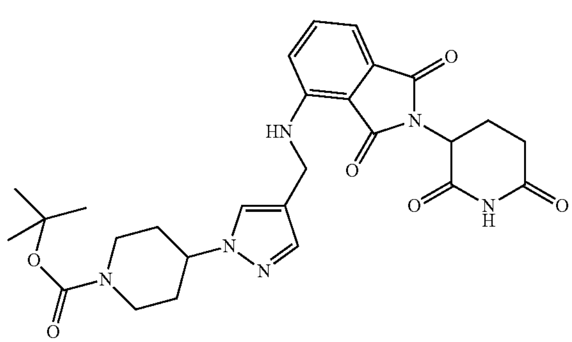 [SMILES: CC(C)(C)OC(=O)N1CCC(n2cc(CNc3cccc4c3C(=O)N(C3CCC(=O)NC3=O)C4=O)cn2)CC1] | tert-butyl 4-(4-(((2-(2,6-dioxopiperidin-3-yl)-1,3-dioxoisoindolin-4-yl)amino)methyl)-1H-pyrazol-1-yl)piperidine-1-carboxylate |

TABLE 1-continued

| Cmp No. | Structure | Name |
|---|---|---|
| 67 | 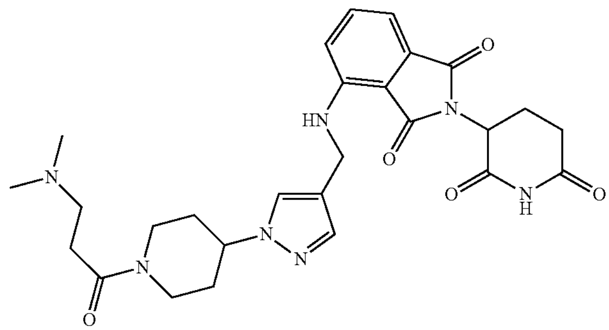 | 4-(((1-(1-(3-(dimethylamino)propanoyl)piperidin-4-yl)-1H-pyrazol-4-yl)methyl)amino)-2-(2,6-dioxopiperidin-3-yl)isoindoline-1,3-dione |
| 68 | 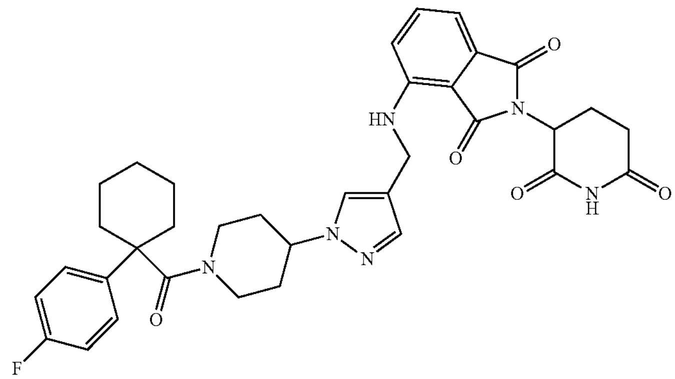 [SMILES: O=C1CCC(N2C(=O)c3cccc(NCc4cnn(C5CCN(C(=O)C6(c7ccc(F)cc7)CCCCC6)CC5)c4)c3C2=O)C(=O)N1] | 2-(2,6-dioxopiperidin-3-yl)-4-(((1-(1-(1-(4-fluorophenyl)cyclohexane-1-carbonyl)piperidin-4-yl)-1H-pyrazol-4-yl)methyl)amino)isoindoline-1,3-dione |
| 69 | 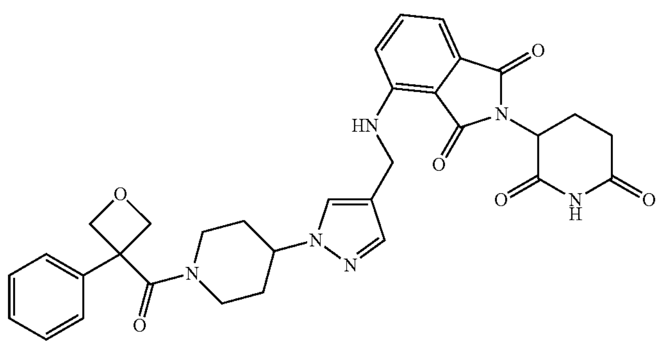 [SMILES: O=C1CCC(N2C(=O)c3cccc(NCc4cnn(C5CCN(C(=O)C6(c7ccccc7)COC6)CC5)c4)c3C2=O)C(=O)N1] | 2-(2,6-dioxopiperidin-3-yl)-4-(((1-(1-(3-phenyloxetane-3-carbonyl)piperidin-4-yl)-1H-pyrazol-4-yl)methyl)amino)isoindoline-1,3-dione |
| 70 | 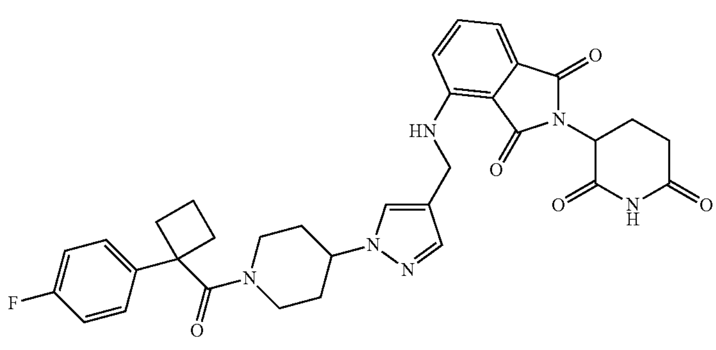 [SMILES: O=C1CCC(N2C(=O)c3cccc(NCc4cnn(C5CCN(C(=O)C6(c7ccc(F)cc7)CCC6)CC5)c4)c3C2=O)C(=O)N1] | 2-(2,6-dioxopiperiidn-3-yl)-4-(((1-(1-(1-(4-fluorophenyl)cyclobutane-1-carbonyl)piperidin-4-yl)-1H-pyrazol-4-yl)methyl)amino)isoindoline-1,3-dione |

TABLE 1-continued

| Cmp No. | Structure | Name |
|---|---|---|
| 71 | 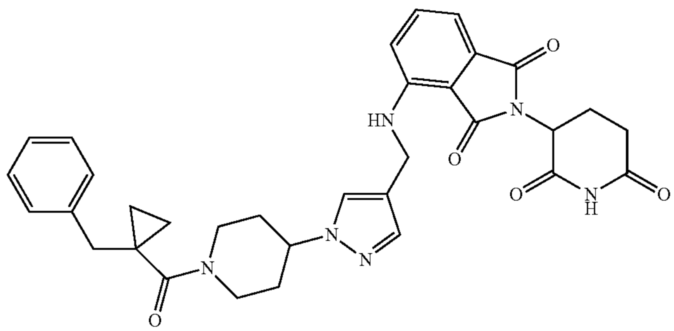 [SMILES: O=C1CCC(N2C(=O)c3cccc(NCc4cnn(C5CCN(C(=O)C6(Cc7ccccc7)CC6)CC5)c4)c3C2=O)C(=O)N1] | 4-(((1-(1-(1-benzylcyclopropane-1-carbonyl)piperidin-4-yl)-1H-pyrazol-4-yl)methyl)amino)-2-(2,6-dioxopiperidin-3-yl)isoindoline-1,3-dione |
| 72 | 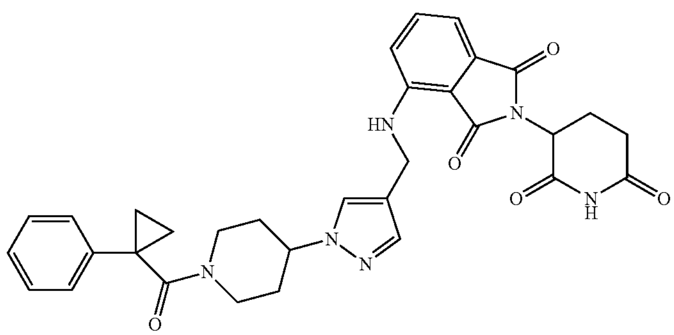 [SMILES: O=C1CCC(N2C(=O)c3cccc(NCc4cnn(C5CCN(C(=O)C6(c7ccccc7)CC6)CC5)c4)c3C2=O)C(=O)N1] | 2-(2,6-dioxopiperidin-3-yl)-4-(((1-(1-(1-phenylcyclopropane-1-carbonyl)piperidin-4-yl)-1H-pyrazol-4-yl)methyl)amino)isoindoline-1,3-dione |
| 73 | 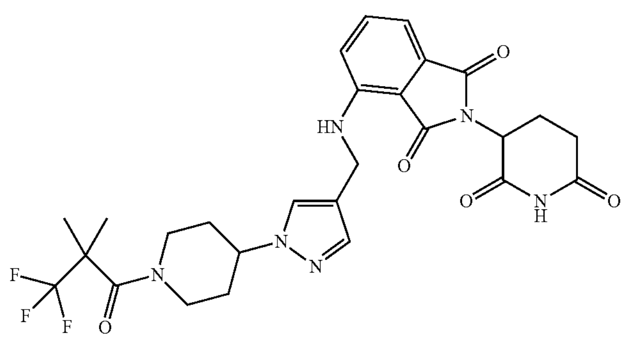 [SMILES: CC(C)(C(=O)N1CCC(n2cc(CNc3cccc4c3C(=O)N(C3CCC(=O)NC3=O)C4=O)cn2)CC1)C(F)(F)F] | 2-(2,6-dioxopiperidin-3-yl)-4-(((1-(1-(3,3,3-trifluoro-2,2-dimethylpropanoyl)piperidin-4-yl)-1H-pyrazol-4-yl)methyl)amino)isoindoline-1,3-dione |
| 74 | 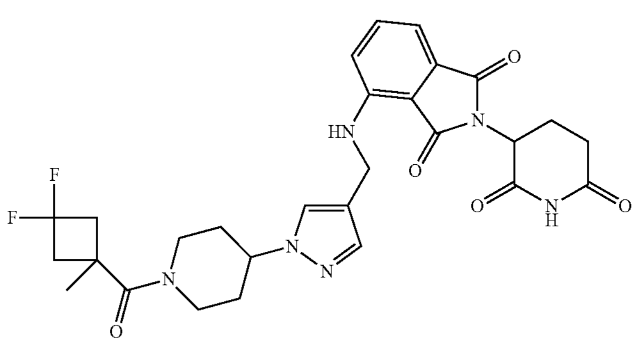 [SMILES: CC1(C(=O)N2CCC(n3cc(CNc4cccc5c4C(=O)N(C4CCC(=O)NC4=O)C5=O)cn3)CC2)CC(F)(F)C1] | 4-(((1-(1-(3,3-difluoro-1-methylcyclobutane-1-carbonyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 75 | 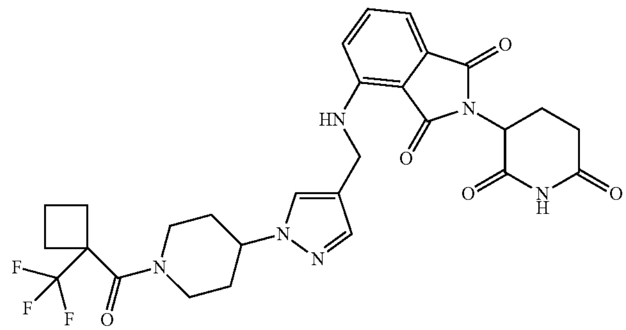 [SMILES: O=C1CCC(N2C(=O)c3cccc(NCc4cnn(C5CCN(C(=O)C6(C(F)(F)F)CCC6)CC5)c4)c3C2=O)C(=O)N1] | 2-(2,6-dioxopiperidin-3-yl)-4-(((1-(1-(1-(trifluoromethyl)cyclobutane-1-carbonyl)piperidin-4-yl)-1H-pyrazol-4-yl)methyl)amino)isoindoline-1,3-dione |
| 76 | 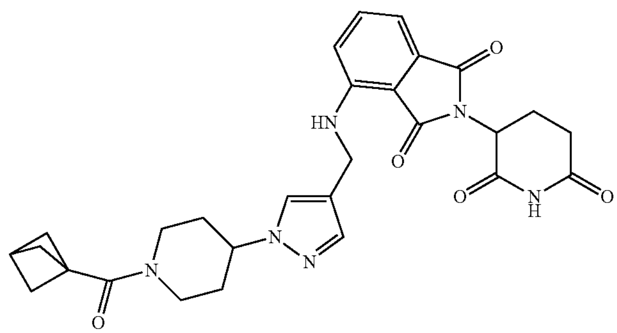 [SMILES: O=C1CCC(N2C(=O)c3cccc(NCc4cnn(C5CCN(C(=O)C67CC(C6)C7)CC5)c4)c3C2=O)C(=O)N1] | 2-(2,6-dioxopiperidin-3-yl)-4-(((1-(1-(1-(trifluoromethyl)cyclobutane-1-carbonyl)piperidin-4-yl)-1H-pyrazol-4-yl)methyl)amino)isoindoline-1,3-dione |
| 77 | 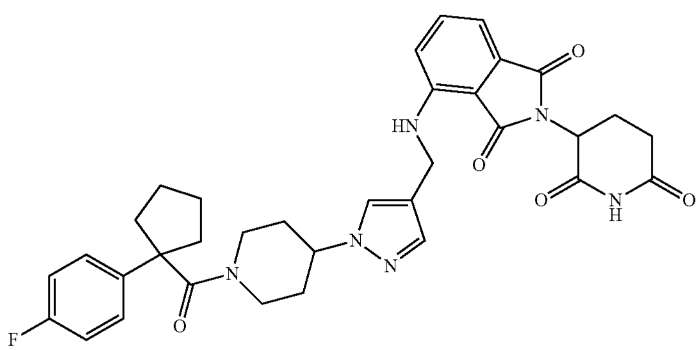 [SMILES: O=C1CCC(N2C(=O)c3cccc(NCc4cnn(C5CCN(C(=O)C6(c7ccc(F)cc7)CCCC6)CC5)c4)c3C2=O)C(=O)N1] | 2-(2,6-dioxopiperidin-3-yl)-4-(((1-(1-(1-(4-fluorophenyl)cyclopentane-1-carbonyl)piperidin-4-yl)-1H-pyrazol-4-yl)methyl)amino)isoindoline-1,3-dione |
| 78 | 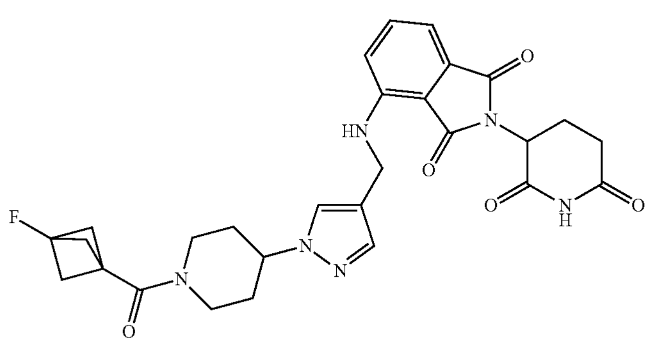 [SMILES: O=C1CCC(N2C(=O)c3cccc(NCc4cnn(C5CCN(C(=O)C67CC(F)(C6)C7)CC5)c4)c3C2=O)C(=O)N1] | 2-(2,6-dioxopiperidin-3-yl)-4-(((1-(1-(3-fluorobicyclo[1.1.1]pentane-1-carbonyl)piperidin-4-yl)-1H-pyrazol-4-yl)methyl)amino)isoindoline-1,3-dione |

TABLE 1-continued

| Cmp No. | Structure | Name |
|---|---|---|
| 79 | 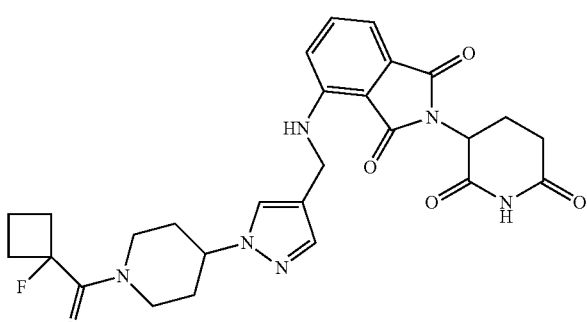 | 2-(2,6-dioxopiperidin-3-yl)-4-(((1-(1-(1-fluorocyclobutane-1-carbonyl)piperidin-4-yl)-1H-pyrazol-4-yl)methyl)amino)isoindoline-1,3-dione |
| 80 | 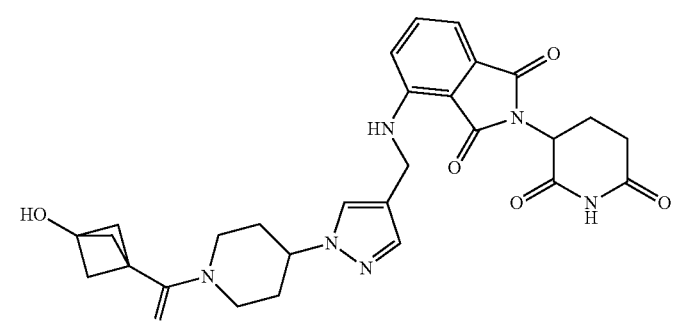 | 2-(2,6-dioxopiperidin-3-yl)-4-(((1-(1-(3-hydroxybicyclo[1.1.1]pentane-1-carbonyl)piperidin-4-yl)-1H-pyrazol-4-yl)methyl)amino)isoindoline-1,3-dione |
| 81 | 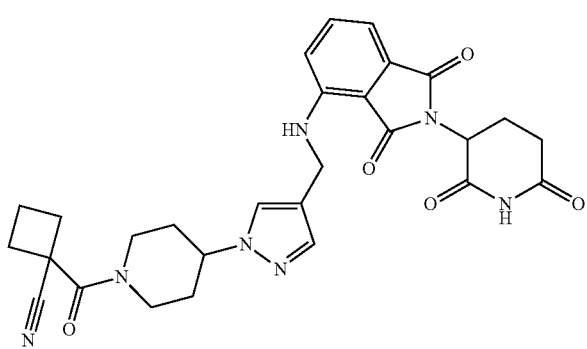 [SMILES: N#CC1(C(=O)N2CCC(n3cc(CNc4cccc5c4C(=O)N(C4CCC(=O)NC4=O)C5=O)cn3)CC2)CCC1] | 1-(4-(4-(((2-(2,6-dioxopiperidin-3-yl)-1,3-dioxoisoindolin-4-yl)amino)methyl)-1H-pyrazol-1-yl)piperidine-1-carbonyl)cyclobutane-1-carbonitrile |
| 82 | 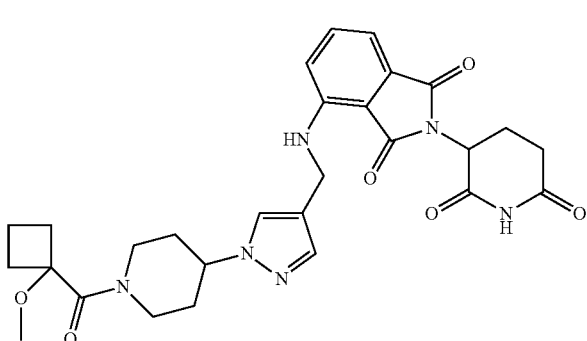 | 2-(2,6-dioxopiperidin-3-yl)-4-(((1-(1-(1-methoxycyclobutane-1-carbonyl)piperidin-4-yl)-1H-pyrazol-4-yl)methyl)amino)isoindoline-1,3-dione |

TABLE 1-continued

| Cmp No. | Structure | Name |
|---|---|---|
| 83 | 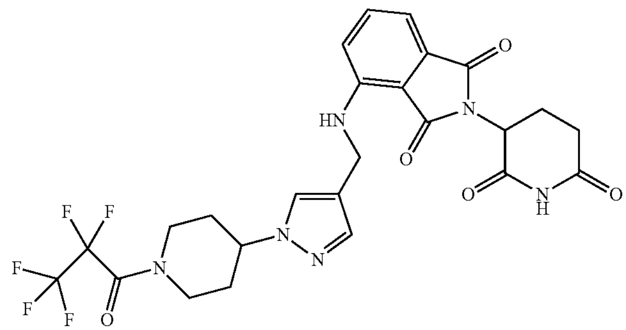 [SMILES: O=C1CCC(N2C(=O)c3cccc(NCc4cnn(C5CCN(C(=O)C(F)(F)C(F)(F)F)CC5)c4)c3C2=O)C(=O)N1] | 2-(2,6-dioxopiperidin-3-yl)-4-(((1-(1-(2,2,3,3,3-pentafluoropropanoyl)piperidin-4-yl)-1H-pyrazol-4-yl)methyl)amino)isoindoline-1,3-dione |
| 84 | 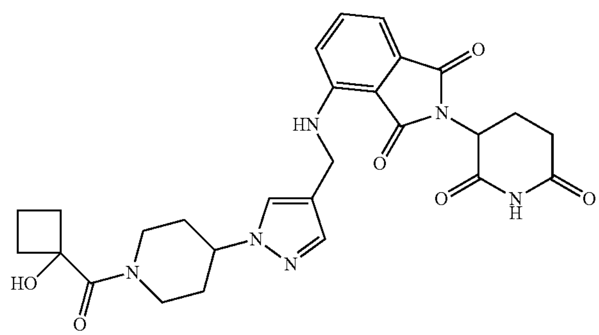 [SMILES: O=C1CCC(N2C(=O)c3cccc(NCc4cnn(C5CCN(C(=O)C6(O)CCC6)CC5)c4)c3C2=O)C(=O)N1] | 2-(2,6-dioxopiperidin-3-yl)-4-(((1-(1-(1-hydroxycyclobutane-1-carbonyl)piperidin-4-yl)-1H-pyrazol-4-yl)methyl)amino)isoindoline-1,3-dione |
| 85 | 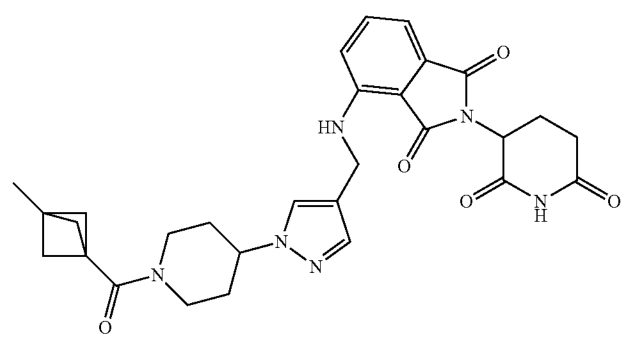 [SMILES: CC12CC(C(=O)N3CCC(n4cc(CNc5cccc6c5C(=O)N(C5CCC(=O)NC5=O)C6=O)cn4)CC3)(C1)C2] | 2-(2,6-dioxopiperidin-3-yl)-4-(((1-(1-(3-methylbicyclo[1.1.1]pentane-1-carbonyl)piperidin-4-yl)-1H-pyrazol-4-yl)methyl)amino)isoindoline-1,3-dione |
| 86 | 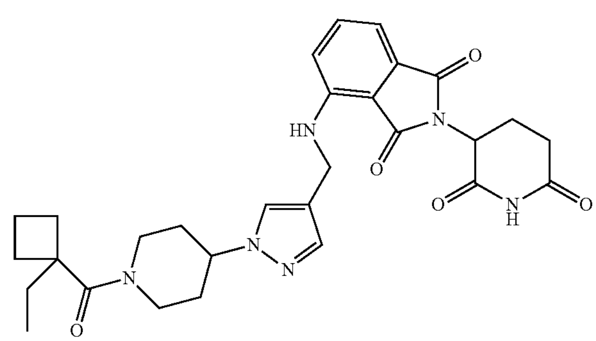 [SMILES: CCC1(C(=O)N2CCC(n3cc(CNc4cccc5c4C(=O)N(C4CCC(=O)NC4=O)C5=O)cn3)CC2)CCC1] | 2-(2,6-dioxopiperidin-3-yl)-4-(((1-(1-(1-ethylcyclobutane-1-carbonyl)piperidin-4-yl)-1H-pyrazol-4-yl)methyl)amino)isoindoline-1,3-dione |

TABLE 1-continued

| Cmp No. | Structure | Name |
|---|---|---|
| 87 | 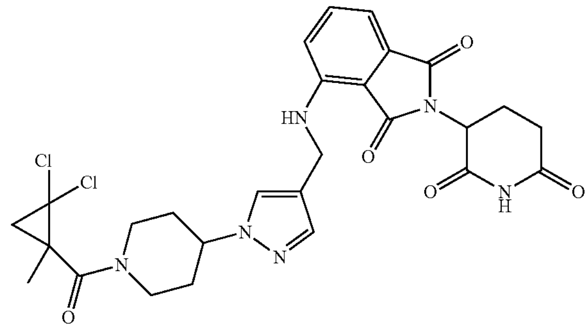 [SMILES: CC1(C(=O)N2CCC(n3cc(CNc4cccc5c4C(=O)N(C4CCC(=O)NC4=O)C5=O)cn3)CC2)CC1(Cl)Cl] | 4-(((1-(1-(2,2-dichloro-1-methylcyclopropane-1-carbonyl)piperidin-4-yl)-1H-pyrazol-4-yl)methyl)amino)-2-(2,6-dioxopiperidin-3-yl)isoindoline-1,3-dione |
| 88 | 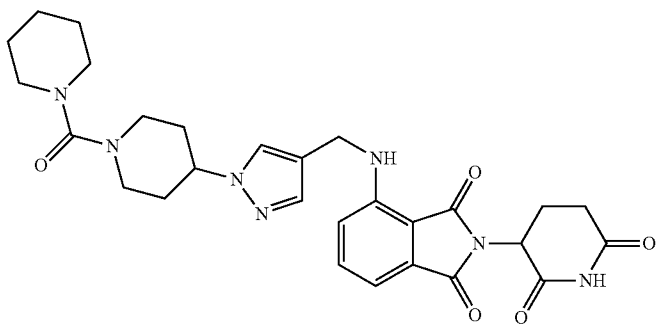 [SMILES: O=C1CCC(N2C(=O)c3cccc(NCc4cnn(C5CCN(C(=O)N6CCCCC6)CC5)c4)c3C2=O)C(=O)N1] | 2-(2,6-dioxopiperidin-3-yl)-4-(((1-(1-(piperidine-1-carbonyl)piperidin-4-yl)-1H-pyrazol-4-yl)methyl)amino)isoindoline-1,3-dione |
| 89 | 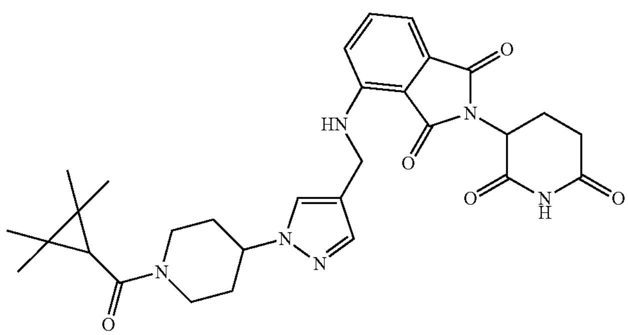 [SMILES: CC1(C)C(C(=O)N2CCC(n3cc(CNc4cccc5c4C(=O)N(C4CCC(=O)NC4=O)C5=O)cn3)CC2)C1(C)C] | 2-(2,6-dioxopiperidin-3-yl)-4-(((1-(1-(2,2,3,3,3-tetramethylcyclopropane-1-carbonyl)piperidin-4-yl)-1H-pyrazol-4-yl)methyl)amino)isoindoline-1,3-dione |
| 90 | 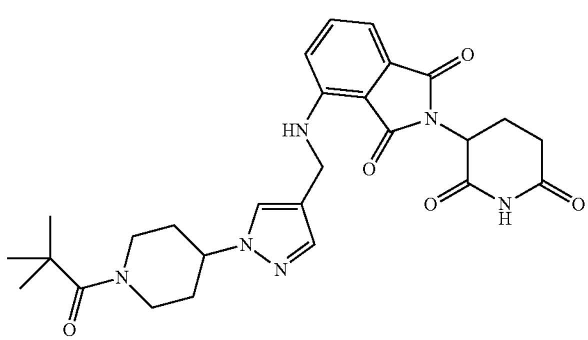 [SMILES: CC(C)(C)C(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-pivaloylpiperidin-4-yl)-1H-pyrazol-4-yl)methyl)amino)isoindoline-1,3-dione |

TABLE 1-continued

| Cmp No. | Structure | Name |
|---|---|---|
| 91 | 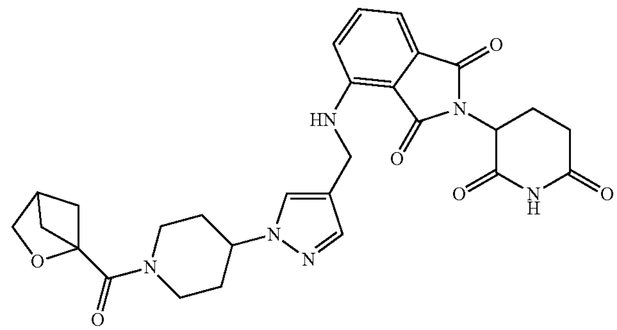 [SMILES: O=C1CCC(N2C(=O)c3cccc(NCc4cnn(C5CCN(C(=O)C67CC(CO6)C7)CC5)c4)c3C2=O)C(=O)N1] | 4-(((1-(1-(2-oxabicyclo[2.1.1]hexane-1-carbonyl)piperidin-4-yl)-1H-pyrazol-4-yl)methyl)amino)-2-(2,6-dioxopiperidin-3-yl)isoindoline-1,3-dione |
| 92 | 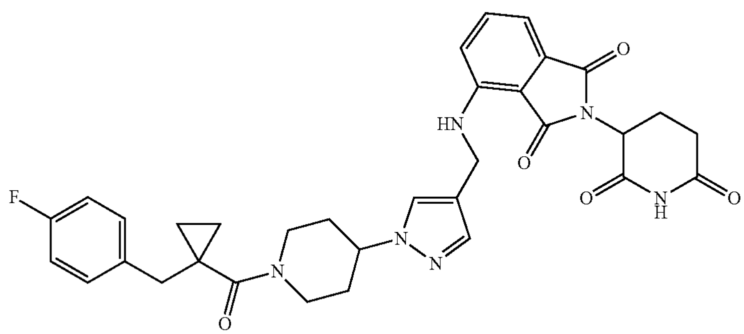 [SMILES: O=C1CCC(N2C(=O)c3cccc(NCc4cnn(C5CCN(C(=O)C6(Cc7ccc(F)cc7)CC6)CC5)c4)c3C2=O)C(=O)N1] | 2-(2,6-dioxopiperidin-3-yl)-4-(((1-(1-(1-(4-fluorobenzyl)cyclopropane-1-carbonyl)piperidin-4-yl)-1H-pyrazol-4-yl)methyl)amino)isoindoline-1,3-dione |
| 93 | 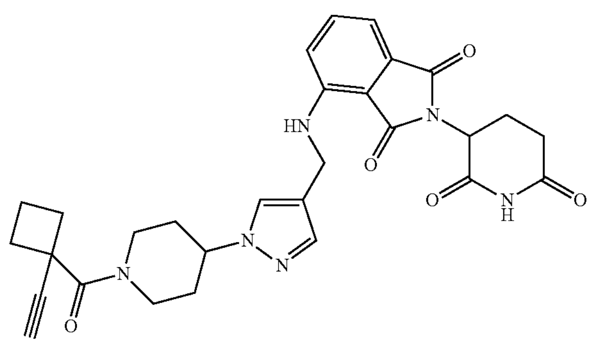 [SMILES: C#CC1(C(=O)N2CCC(n3cc(CNc4cccc5c4C(=O)N(C4CCC(=O)NC4=O)C5=O)cn3)CC2)CCC1] | 2-(2,6-dioxopiperidin-3-yl)-4-(((1-(1-(1-ethynylcyclobutane-1-carbonyl)piperidin-4-yl)-1H-pyrazol-4-yl)methyl)amino)isoindoline-1,3-dione |
| 94 | 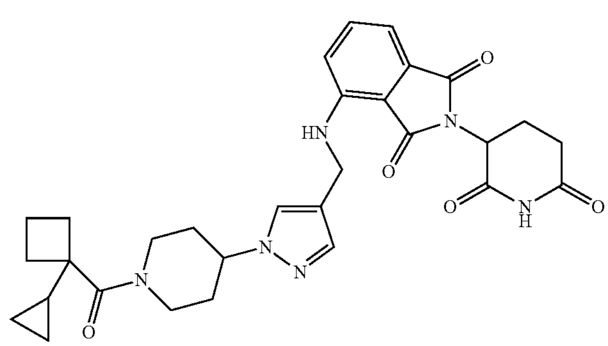 [SMILES: O=C1CCC(N2C(=O)c3cccc(NCc4cnn(C5CCN(C(=O)C6(C7CC7)CCC6)CC5)c4)c3C2=O)C(=O)N1] | 4-(((1-(1-(1-cyclopropylcyclobutane-1-carbonyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 95 | 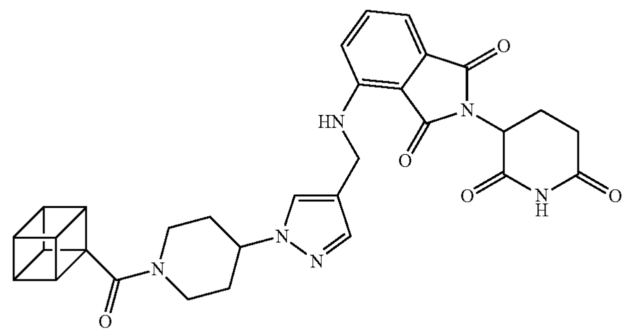 [SMILES: O=C1CCC(N2C(=O)c3cccc(NCc4cnn(C5CCN(C(=O)C67C8C9C%10C8C6C%10C97)CC5)c4)c3C2=O)C(=O)N1] | 4-(((1-(1-(((1s,4R,3R,4r,5r,6S,7S,8s)-cubane-1-carbonyl)piperidin-4-yl)-1H-pyrazol-4-yl)methyl)amino)-2-(2,6-dioxopiperidin-3-yl)isoindoline-1,3-dione |
| 96 | 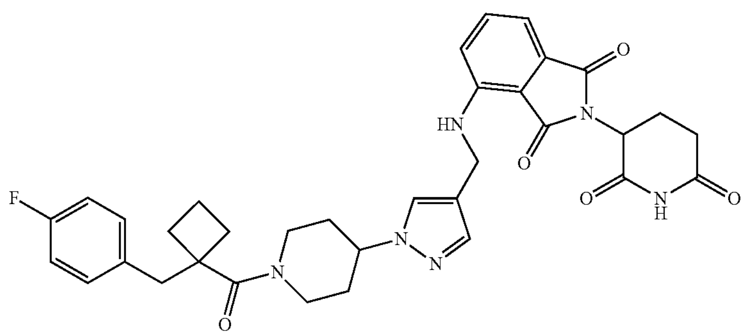 [SMILES: O=C1CCC(N2C(=O)c3cccc(NCc4cnn(C5CCN(C(=O)C6(Cc7ccc(F)cc7)CCC6)CC5)c4)c3C2=O)C(=O)N1] | 2-(2,6-dioxopiperidin-3-yl)-4-(((1-(1-(1-(4-fluorobenzyl)cyclobutane-1-carbonyl)piperidin-4-yl)-1H-pyrazol-4-yl)methyl)amino)isoindoline-1,3-dione |
| 97 | 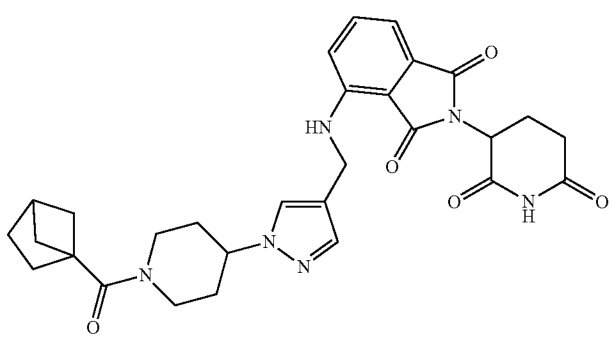 [SMILES: O=C1CCC(N2C(=O)c3cccc(NCc4cnn(C5CCN(C(=O)C67CCC(C6)C7)CC5)c4)c3C2=O)C(=O)N1] | 4-(((1-(1-(bicyclo[2.1.1]hexane-1-carbonyl)piperidin-4-yl)-1H-pyrazol-4-yl)methyl)amino)-2-(2,6-dioxopiperidin-3-yl)isoindoline-1,3-dione |
| 98 | 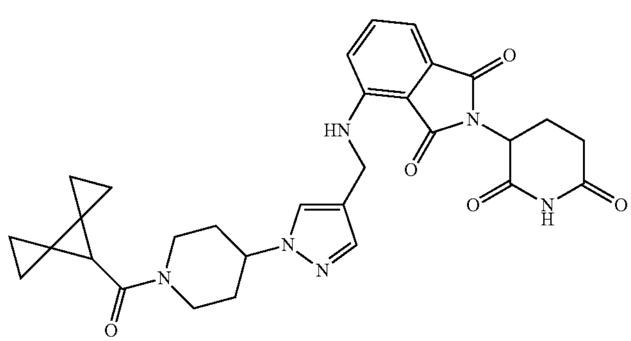 [SMILES: O=C1CCC(N2C(=O)c3cccc(NCc4cnn(C5CCN(C(=O)C6C7(CC7)C67CC7)CC5)c4)c3C2=O)C(=O)N1] | 2-(2,6-dioxopiperidin-3-yl)-4-(((1-(1-(dispiro[2.0.24.13]heptane-7-carbonyl)piperidin-4-yl)-1H-pyrazol-4-yl)methyl)amino)isoindoline-1,3-dione |

TABLE 1-continued

| Cmp No. | Structure | Name |
|---|---|---|
| 99 | 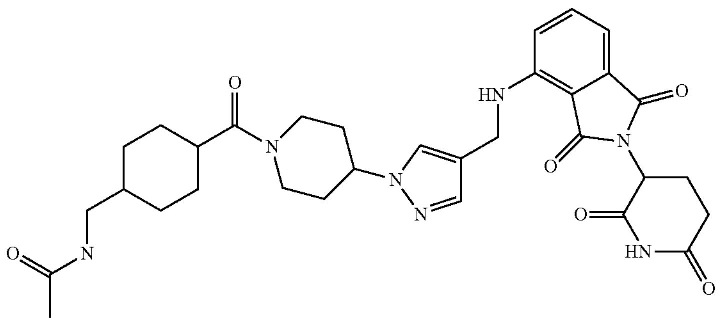 [SMILES: CC(=O)NCC1CCC(C(=O)N2CCC(n3cc(CNc4cccc5c4C(=O)N(C4CCC(=O)NC4=O)C5=O)cn3)CC2)CC1] | N-((4-(4-(4-(((2-(2,6-dioxopiperidin-3-yl)-1,3-dioxoisoindolin-4-yl)amino)methyl)-1H-pyrazol-1-yl)piperidine-1-carbonyl)cyclohexyl)methyl)acetamide |
| 100 | 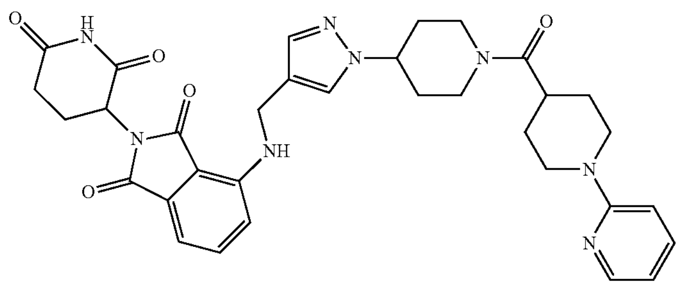 [SMILES: O=C1CCC(N2C(=O)c3cccc(NCc4cnn(C5CCN(C(=O)C6CCN(c7ccccn7)CC6)CC5)c4)c3C2=O)C(=O)N1] | 2-(2,6-dioxopiperidin-3-yl)-4-(((1-(1-(1-(pyridin-2-yl)piperidine-4-carbonyl)piperidin-4-yl)-1H-pyrazol-4-yl)methyl)amino)isoindoline-1,3-dione |
| 101 | 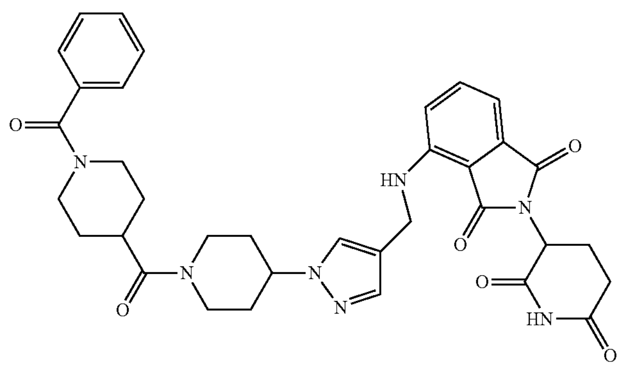 [SMILES: O=C1CCC(N2C(=O)c3cccc(NCc4cnn(C5CCN(C(=O)C6CCN(C(=O)c7ccccc7)CC6)CC5)c4)c3C2=O)C(=O)N1] | 4-(((1-(1-(1-benzoylpiperidine-4-carbonyl)piperidin-4-yl)-1H-pyrazol-4-yl)methyl)amino)-2-(2,6-dioxopiperidin-3-yl)isoindoline-1,3-dione |
| 102 | 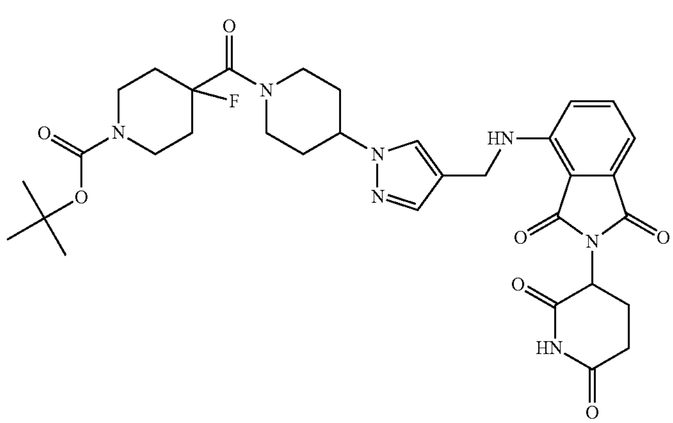 [SMILES: CC(C)(C)OC(=O)N1CCC(F)(C(=O)N2CCC(n3cc(CNc4cccc5c4C(=O)N(C4CCC(=O)NC4=O)C5=O)cn3)CC2)CC1] | tert-butyl 4-(4-(4-(((2-(2,6-dioxopiperidin-3-yl)-1,3-dioxoisoindolin-4-yl)amino)methyl)-1H-pyrazol-1-yl)piperidine-1-carbonyl)-4-fluoropiperidine-1-carboxylate |

TABLE 1-continued

| Cmp No. | Structure | Name |
|---|---|---|
| 103 | 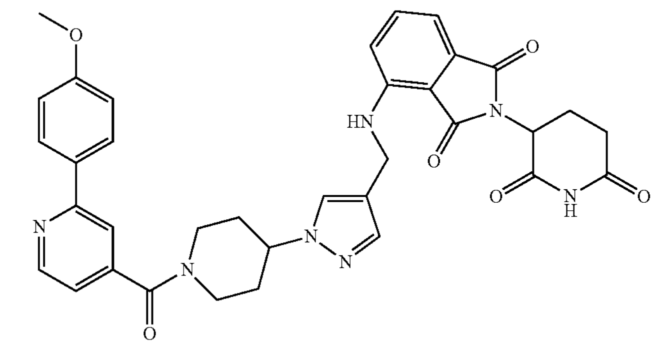 [SMILES: COc1ccc(-c2cc(C(=O)N3CCC(n4cc(CNc5cccc6c5C(=O)N(C5CCC(=O)NC5=O)C6=O)cn4)CC3)ccn2)cc1] | 2-(2,6-dioxopiperidin-3-yl)-4-(((1-(1-(2-(4-methoxyphenyl)isonicotinoyl)piperidin-4-yl)-1H-pyrazol-4-yl)methyl)amino)isoindoline-1,3-dione |
| 104 | 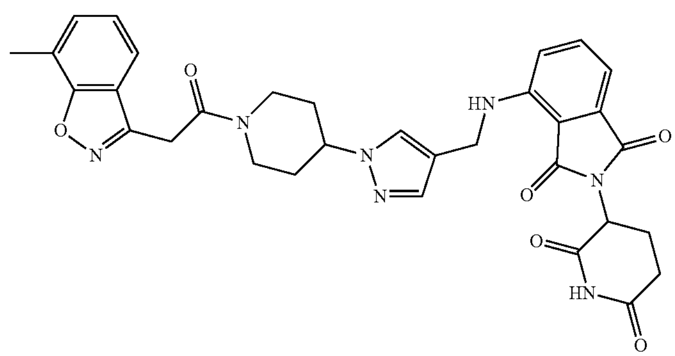 [SMILES: Cc1cccc2c(CC(=O)N3CCC(n4cc(CNc5cccc6c5C(=O)N(C5CCC(=O)NC5=O)C6=O)cn4)CC3)noc12] | 2-(2,6-dioxopiperidin-3-yl)-4-(((1-(1-(2-(7-methylbenzo[d]isoxazol-3-yl)acetyl)piperidin-4-yl)-1H-pyrazol-4-yl)methyl)amino)isoindoline-1,3-dione |
| 105 | 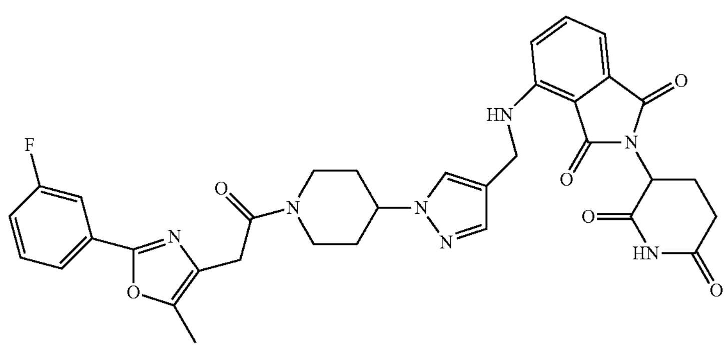 [SMILES: Cc1oc(-c2cccc(F)c2)nc1CC(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-(2-(2-(3-fluorophenyl)-5-methyloxazol-4-yl)acetyl)piperidin-4-yl)-1H-pyrazol-4-yl)methyl)amino)isoindoline-1,3-dione |
| 106 | 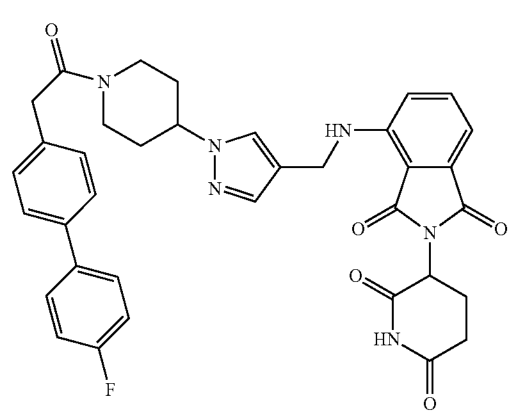 [SMILES: O=C1CCC(N2C(=O)c3cccc(NCc4cnn(C5CCN(C(=O)Cc6ccc(-c7ccc(F)cc7)cc6)CC5)c4)c3C2=O)C(=O)N1] | 2-(2,6-dioxopiperidin-3-yl)-4-(((1-(1-(2-(4'-fluoro-[1,1'-biphenyl]-4-yl)acetyl)piperidin-4-yl)-1H-pyrazol-4-yl)methyl)amino)isoindoline-1,3-dione |

TABLE 1-continued

| Cmp No. | Structure | Name |
|---|---|---|
| 107 | 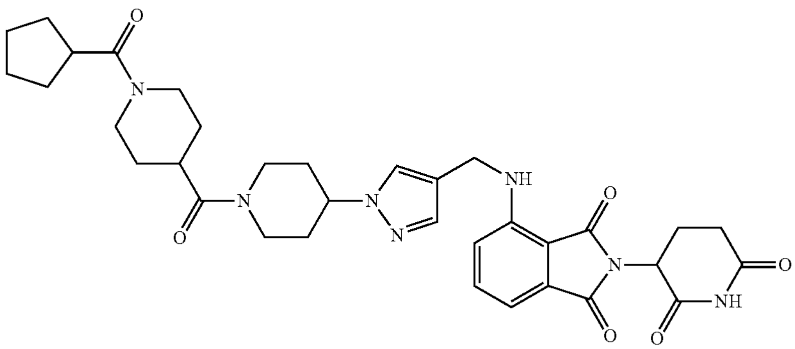 [SMILES: O=C1CCC(N2C(=O)c3cccc(NCc4cnn(C5CCN(C(=O)C6CCN(C(=O)C7CCCC7)CC6)CC5)c4)c3C2=O)C(=O)N1] | 4-(((1-(1-(1-(cyclopentanecarbonyl)piperidine-4-carbonyl)piperidin-4-yl)-1H-pyrazol-4-yl)methyl)amino)-2-(2,6-dioxopiperidin-3-yl)isoindoline-1,3-dione |
| 108 | 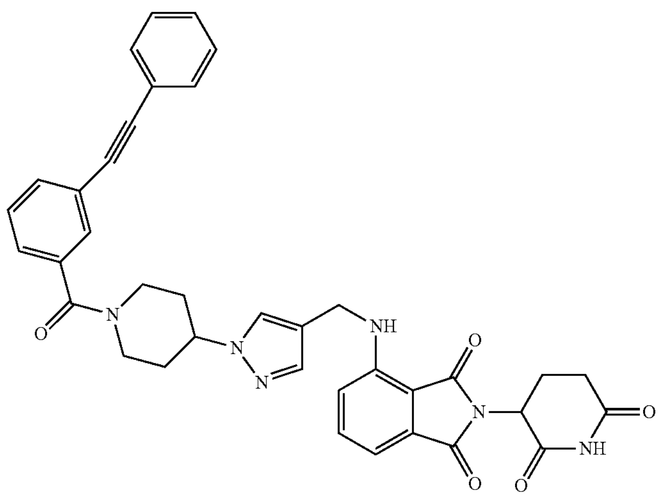 [SMILES: O=C1CCC(N2C(=O)c3cccc(NCc4cnn(C5CCN(C(=O)c6cccc(C#Cc7ccccc7)c6)CC5)c4)c3C2=O)C(=O)N1] | 2-(2,6-dioxopiperidin-3-yl)-4-(((1-(1-(3-(phenylethynyl)benzoyl)piperidin-4-yl)-1H-pyrazol-4-yl)methyl)amino)isoindoline-1,3-dione |
| 109 | 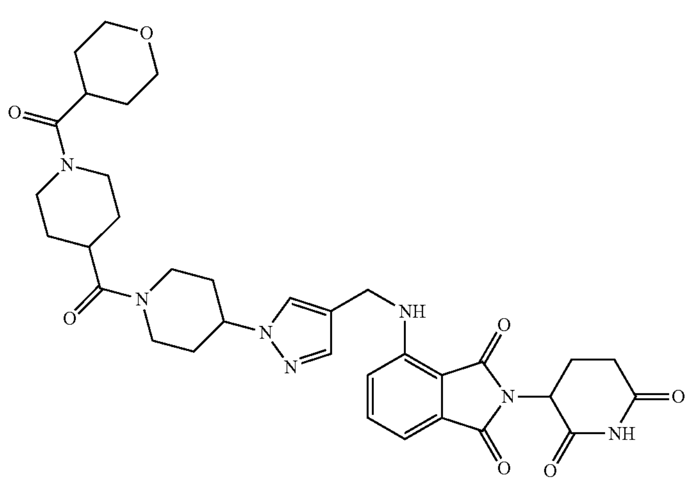 [SMILES: O=C1CCC(N2C(=O)c3cccc(NCc4cnn(C5CCN(C(=O)C6CCN(C(=O)C7CCOCC7)CC6)CC5)c4)c3C2=O)C(=O)N1] | 2-(2,6-dioxopiperidin-3-yl)-4-(((1-(1-(1-(tetrahydro-2H-pyran-4-carbonyl)piperidine-4-carbonyl)piperidin-4-yl)-1H-pyrazol-4-yl)methyl)amino)isoindoline-1,3-dione |

TABLE 1-continued

| Cmp No. | Structure | Name |
|---|---|---|
| 110 | 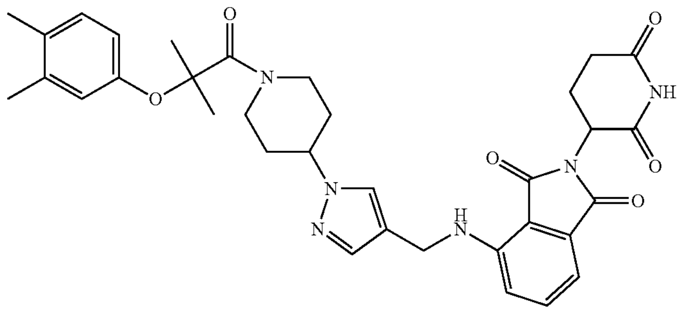 [SMILES: Cc1ccc(OC(C)(C)C(=O)N2CCC(n3cc(CNc4cccc5c4C(=O)N(C4CCC(=O)NC4=O)C5=O)cn3)CC2)cc1C] | 4-(((1-(1-(2-(3,4-dimethylphenoxy)-2-methylpropanoyl)piperidin-4-yl)-1H-pyrazol-4-yl)methyl)amino)-2-(2,6-dioxopiperidin-3-yl)isoindoline-1,3-dione |
| 111 | 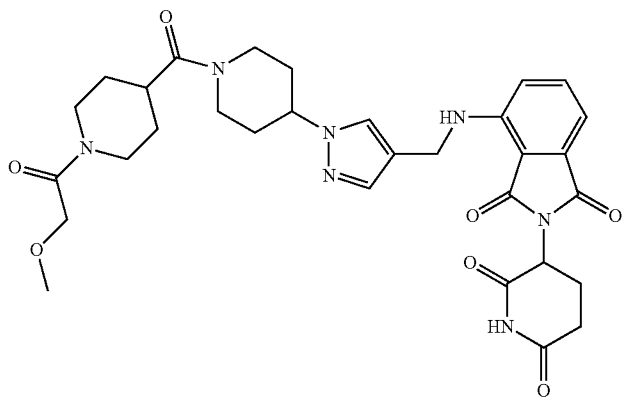 [SMILES: COCC(=O)N1CCC(C(=O)N2CCC(n3cc(CNc4cccc5c4C(=O)N(C4CCC(=O)NC4=O)C5=O)cn3)CC2)CC1] | 2-(2,6-dioxopiperidin-3-yl)-4-(((1-(1-(1-(2-methoxyacetyl)piperidine-4-carbonyl)piperidin-4-yl)-1H-pyrazol-4-yl)methyl)amino)isoindoline-1,3-dione |
| 112 | 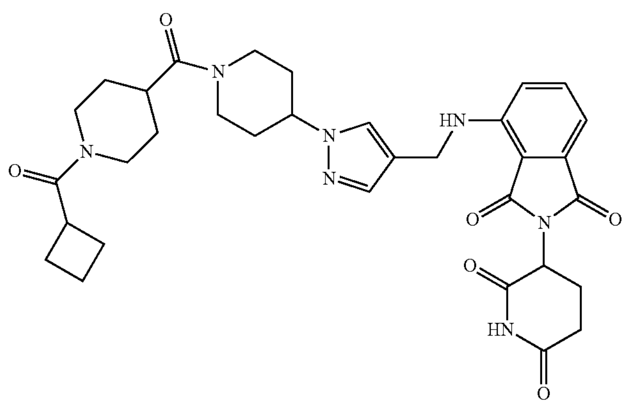 [SMILES: O=C1CCC(N2C(=O)c3cccc(NCc4cnn(C5CCN(C(=O)C6CCN(C(=O)C7CCC7)CC6)CC5)c4)c3C2=O)C(=O)N1] | 4-(((1-(1-(1-(cyclobutanecarbonyl)piperidine-4-carbonyl)piperidin-4-yl)-1H-pyrazol-4-yl)methyl)amino)-2-(2,6-dioxopiperidin-3-yl)isoindoline-1,3-dione |
| 113 | 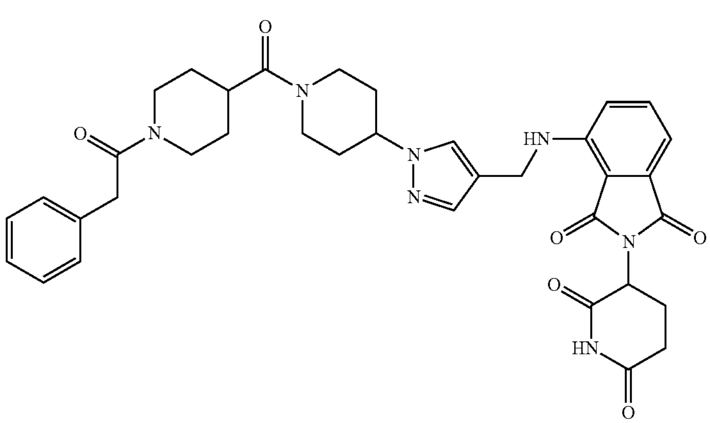 [SMILES: O=C1CCC(N2C(=O)c3cccc(NCc4cnn(C5CCN(C(=O)C6CCN(C(=O)Cc7ccccc7)CC6)CC5)c4)c3C2=O)C(=O)N1] | 2-(2,6-dioxopiperidin-3-yl)-4-(((1-(1-(1-(2-phenylacetyl)piperidine-4-carbonyl)piperidin-4-yl)-1H-pyrazol-4-yl)methyl)amino)isoindoline-1,3-dione |

TABLE 1-continued

| Cmp No. | Structure | Name |
|---|---|---|
| 114 | 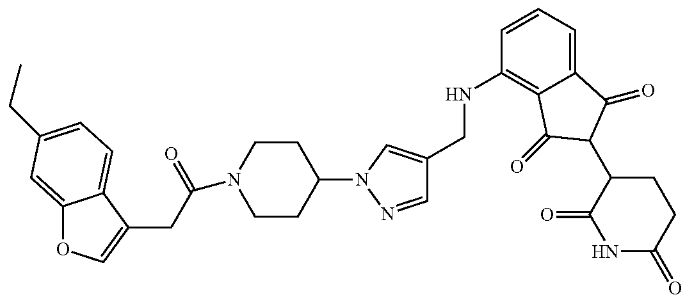 [SMILES: CCc1ccc2c(CC(=O)N3CCC(n4cc(CNc5cccc6c5C(=O)C(C5CCC(=O)NC5=O)C6=O)cn4)CC3)coc2c1] | 2-(2,6-dioxoopiperidin-3-yl)-4-(((1-(1-(2-(6-ethylbenzofuran-3-yl)acetyl)piperidin-4-yl)-1H-pyrazol-4-yl)methyl)amino)isoindoline-1,3-dione |
| 115 | 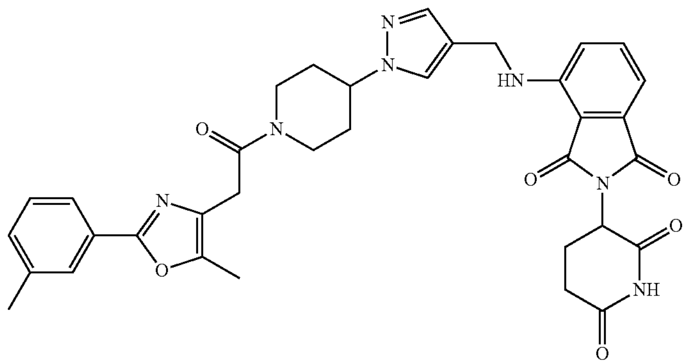 [SMILES: Cc1cccc(-c2nc(CC(=O)N3CCC(n4cc(CNc5cccc6c5C(=O)N(C5CCC(=O)NC5=O)C6=O)cn4)CC3)c(C)o2)c1] | 2-(2,6-dioxopiperidin-3-yl)-4-(((1-(1-(2-(5-methyl-2-(m-tolyl)oxazol-4-yl)acetyl)piperidin-4-yl)-1H-pyrazol-4-yl)methyl)amino)isoindoline-1,3-dione |
| 116 | 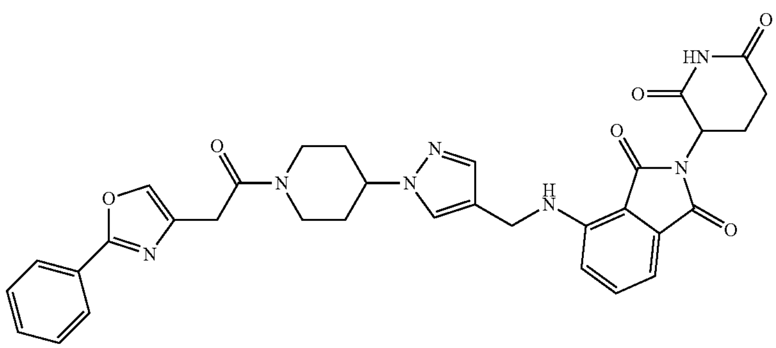 [SMILES: O=C1CCC(N2C(=O)c3cccc(NCc4cnn(C5CCN(C(=O)Cc6coc(-c7ccccc7)n6)CC5)c4)c3C2=O)C(=O)N1] | 2-(2,6-dioxopiperidin-3-yl)-4-(((1-(1-(2-(2-phenyloxazol-4-yl)acetyl)piperidin-4-yl)-1H-pyrazol-4-yl)methyl)amino)isoindoline-1,3-dione |
| 117 | 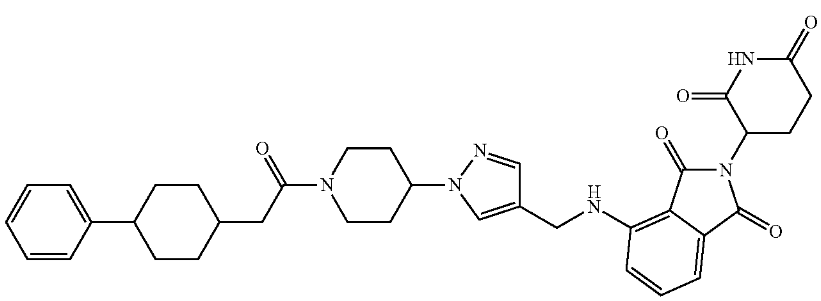 [SMILES: O=C1CCC(N2C(=O)c3cccc(NCc4cnn(C5CCN(C(=O)CC6CCC(c7ccccc7)CC6)CC5)c4)c3C2=O)C(=O)N1] | 2-(2,6-dioxopiperidin-3-yl)-4-(((1-(1-(2-(4-phenylcyclohexyl)acetyl)piperidin-4-yl)-1H-pyrazol-4-yl)methyl)amino)isoindoline-1,3-dione |
| 118 | 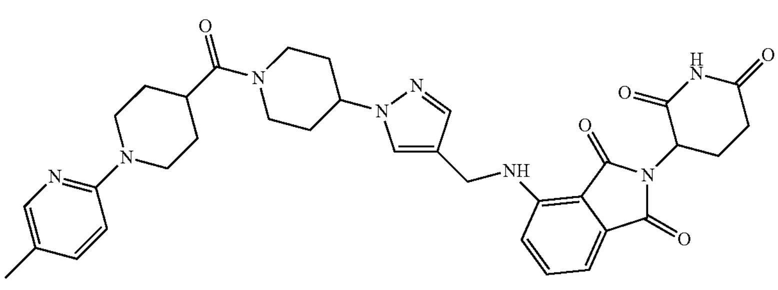 [SMILES: Cc1ccc(N2CCC(C(=O)N3CCC(n4cc(CNc5cccc6c5C(=O)N(C5CCC(=O)NC5=O)C6=O)cn4)CC3)CC2)nc1] | 2-(2,6-dioxopiperidin-3-yl)-4-(((1-(1-(5-methylpyridin-2-yl)piperidine-4-carbonyl)piperidin-4-yl)-1H-pyrazol-4-yl)methyl)amino)isoindoline-1,3-dione |

TABLE 1-continued

| Cmp No. | Structure | Name |
|---|---|---|
| 119 | 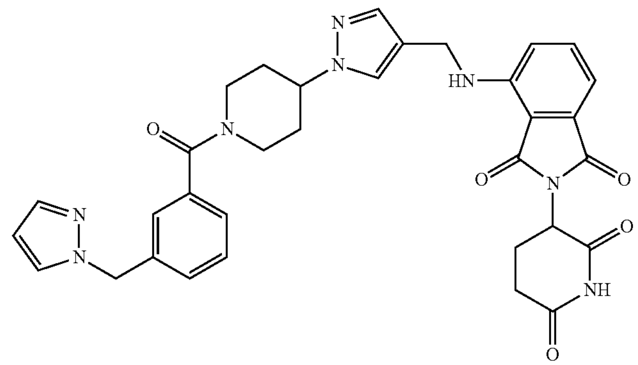 [SMILES: O=C1CCC(N2C(=O)c3cccc(NCc4cnn(C5CCN(C(=O)c6cccc(Cn7cccn7)c6)CC5)c4)c3C2=O)C(=O)N1] | 4-(((1-(1-(3-((1H-pyrazol-1-yl)methyl)benzoyl)piperidin-4-yl)-1H-pyrazol-4-yl)methyl)amino)-2-(2,6-dioxopiperidin-3-yl)isoindoline-1,3-dione |
| 120 | 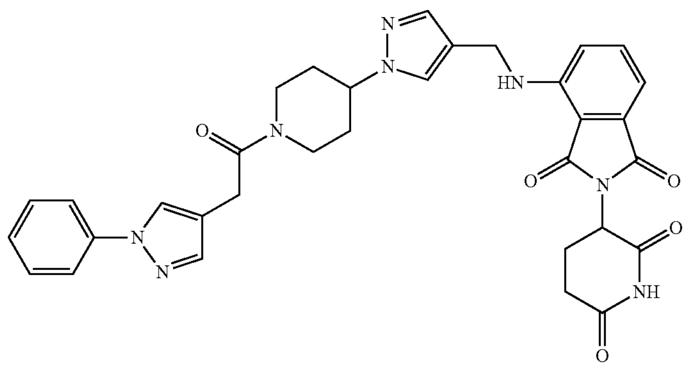 [SMILES: O=C1CCC(N2C(=O)c3cccc(NCc4cnn(C5CCN(C(=O)Cc6cnn(-c7ccccc7)c6)CC5)c4)c3C2=O)C(=O)N1] | 2-(2,6-dioxopiperidin-3-yl)-4-(((1-(1-(2-(1-phenyl-1H-pyrazol-4-yl)acetyl)piperidin-4-yl)-1H-pyrazol-4-yl)methyl)amino)isoindoline-1,3-dione |
| 121 | 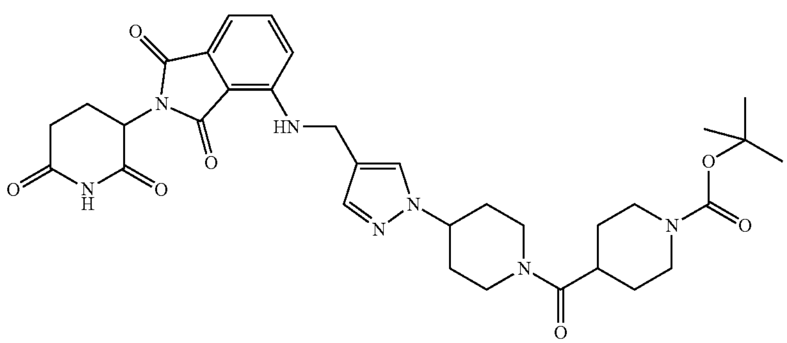 [SMILES: CC(C)(C)OC(=O)N1CCC(C(=O)N2CCC(n3cc(CNc4cccc5c4C(=O)N(C4CCC(=O)NC4=O)C5=O)cn3)CC2)CC1] | tert-butyl 4-(4-(4-(((2-(2,6-dioxopiperidin-3-yl)-1,3-dioxoisoindolin-4-yl)amino)methyl)-1H-pyrazol-1-yl)piperidine-1-carbonyl)piperidine-1-carboxylate |
| 122 | 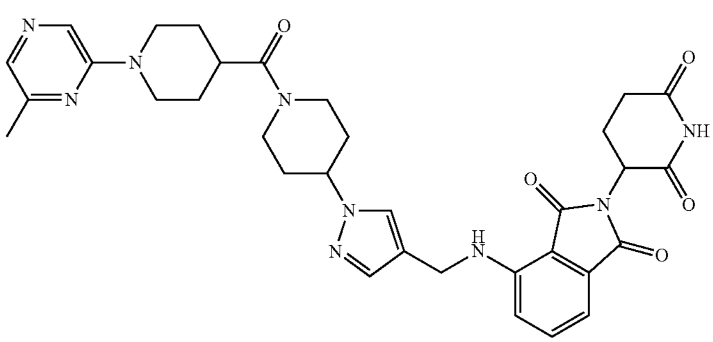 [SMILES: Cc1cncc(N2CCC(C(=O)N3CCC(n4cc(CNc5cccc6c5C(=O)N(C5CCC(=O)NC5=O)C6=O)cn4)CC3)CC2)n1] | 2-(2,6-dioxopiperidin-3-yl)-4-(((1-(1-(1-(6-methylpyrazin-2-yl)piperidine-4-carbonyl)piperidin-4-yl)-1H-pyrazol-4-yl)methyl)amino)isoindoline-1,3-dione |

TABLE 1-continued

| Cmp No. | Structure | Name |
|---|---|---|
| 123 | 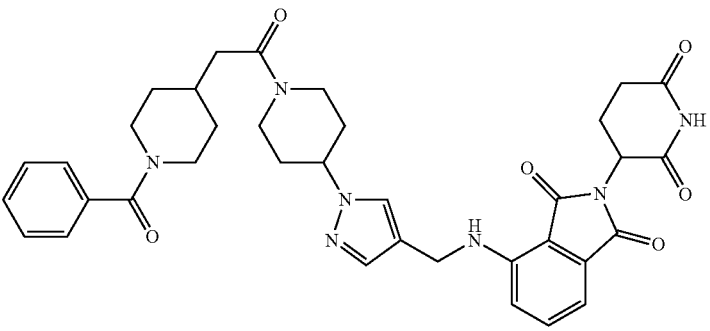 [SMILES: O=C1CCC(N2C(=O)c3cccc(NCc4cnn(C5CCN(C(=O)CC6CCN(C(=O)c7ccccc7)CC6)CC5)c4)c3C2=O)C(=O)N1] | 4-(((1-(1-(2-(1-benzoylpiperidin-4-yl)acetyl)piperidin-4-yl)-1H-pyrazol-4-yl)methyl)amino)-2-(2,6-dioxopiperidin-3-yl)isoindoline-1,3-dione |
| 124 | 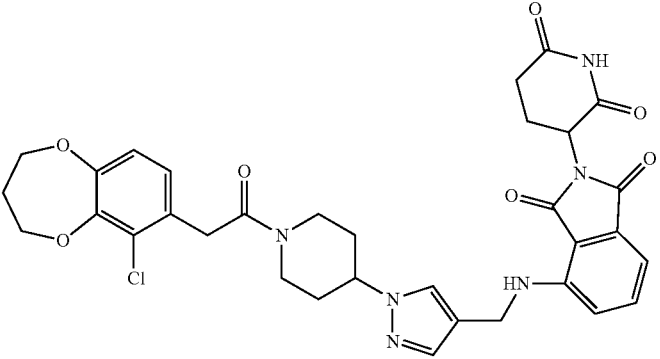 [SMILES: O=C1CCC(N2C(=O)c3cccc(NCc4cnn(C5CCN(C(=O)Cc6ccc7c(c6Cl)OCCCO7)CC5)c4)c3C2=O)C(=O)N1] | 4-(((1-(1-(2-(6-chloro-3,4-dihydro-2H-benzo[b][1,4]dioxepin-7-yl)acetyl)piperidin-4-yl)-1H-pyrazol-4-yl)methyl)amino)-2-(2,6-dioxopiperidin-3-yl)isoindoline-1,3-dione |
| 125 | 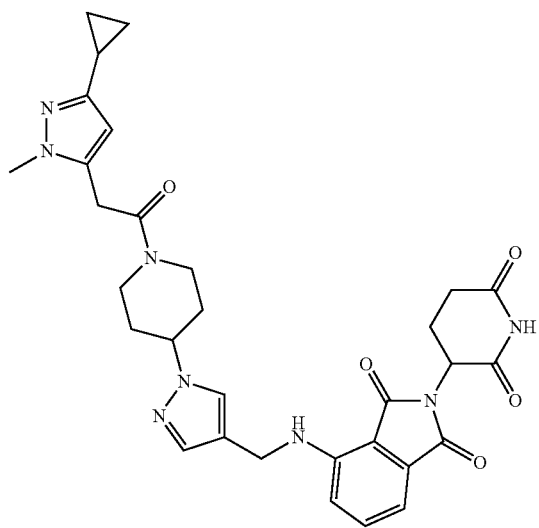 [SMILES: Cn1nc(C2CC2)cc1CC(=O)N1CCC(n2cc(CNc3cccc4c3C(=O)N(C3CCC(=O)NC3=O)C4=O)cn2)CC1] | 4-(((1-(1-(2-(3-cyclopropyl-1-methyl-1H-pyrazol-5-yl)acetyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 126 | 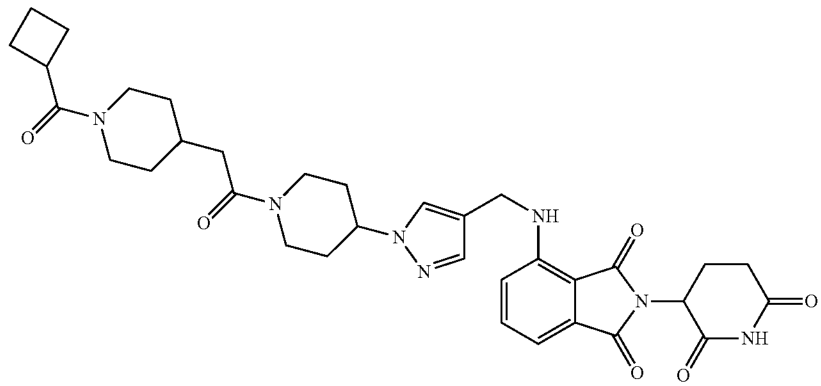 [SMILES: O=C1CCC(N2C(=O)c3cccc(NCc4cnn(C5CCN(C(=O)CC6CCN(C(=O)C7CCC7)CC6)CC5)c4)c3C2=O)C(=O)N1] | 4-(((1-(1-(2-(1-(cyclobutanecarbonyl)piperidin-4-yl)acetyl)piperidin-4-yl)-1H-pyrazol-4-yl)methyl)amino)-2-(2,6-dioxopiperidin-3-yl)isoindoline-1,3-dione |
| 127 | 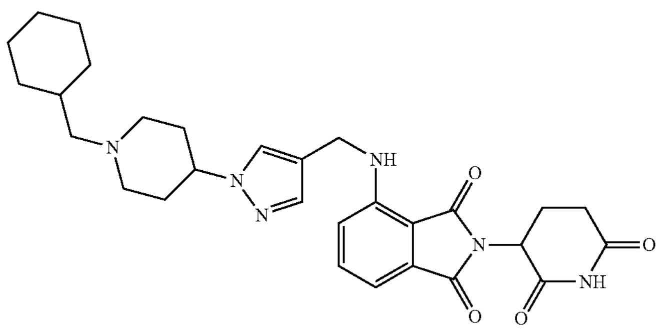 [SMILES: O=C1CCC(N2C(=O)c3cccc(NCc4cnn(C5CCN(CC6CCCCC6)CC5)c4)c3C2=O)C(=O)N1] | 4-(((1-(1-(cyclohexylmethyl)piperidin-4-yl)-1H-pyrazol-4-yl)methyl)amino)-2-(2,6-dioxopiperidin-3-yl)isoindoline-1,3-dione |
| 128 | 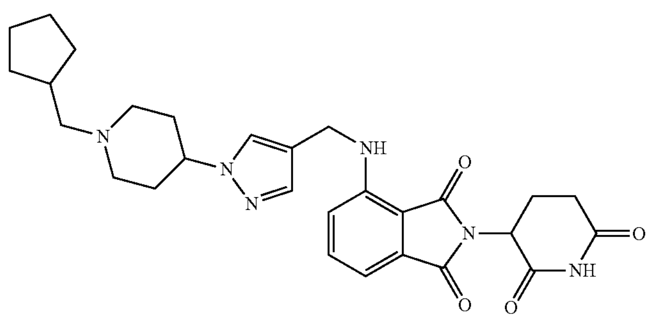 [SMILES: O=C1CCC(N2C(=O)c3cccc(NCc4cnn(C5CCN(CC6CCCC6)CC5)c4)c3C2=O)C(=O)N1] | 4-(((1-(1-(cyclopentylmethyl)piperidin-4-yl)-1H-pyrazol-4-yl)methyl)amino)-2-(2,6-dioxopiperidin-3-yl)isoindoline-1,3-dione |
| 129 | 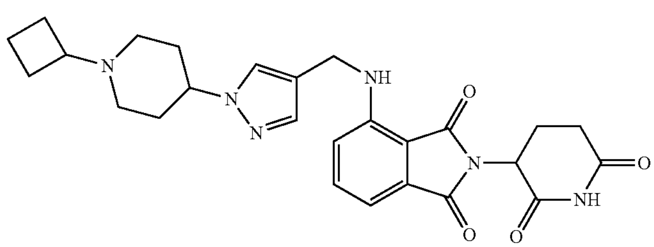 [SMILES: O=C1CCC(N2C(=O)c3cccc(NCc4cnn(C5CCN(C6CCC6)CC5)c4)c3C2=O)C(=O)N1] | 4-(((1-(1-cyclobutylpiperidin-4-yl)-1H-pyrazol-4-yl)methyl)amino)-2-(2,6-dioxopiperidine-3-yl)isoindoline-1,3-dione |
| 130 | 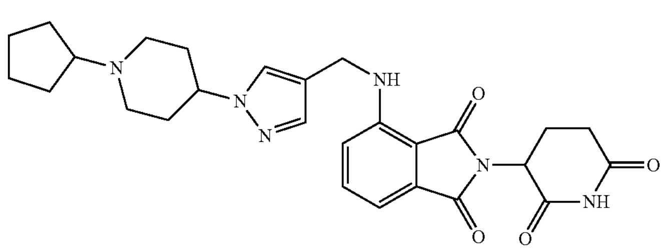 [SMILES: O=C1CCC(N2C(=O)c3cccc(NCc4cnn(C5CCN(C6CCCC6)CC5)c4)c3C2=O)C(=O)N1] | 4-(((1-(1-cyclopentylpiperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
| --- | --- | --- |
| 131 | 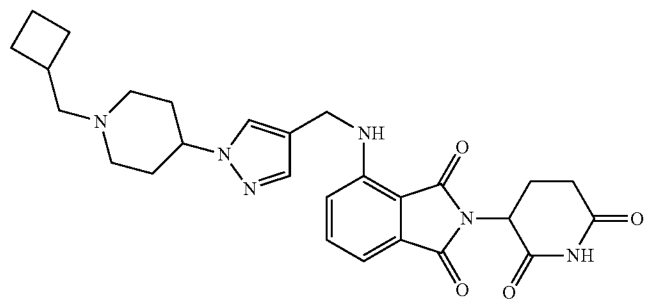 [SMILES: O=C1CCC(N2C(=O)c3cccc(NCc4cnn(C5CCN(CC6CCC6)CC5)c4)c3C2=O)C(=O)N1] | 4-(((1-(1-(cyclobutylmethyl)piperidin-4-yl)-1H-pyrazol-4-yl)methyl)amino)-2-(2,6-dioxopiperidin-3-yl)isoindoline-1,3-dione |
| 132 | 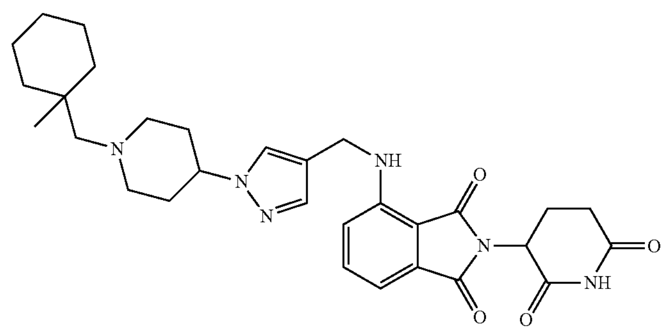 [SMILES: CC1(CN2CCC(n3cc(CNc4cccc5c4C(=O)N(C4CCC(=O)NC4=O)C5=O)cn3)CC2)CCCCC1] | 2-(2,6-dioxopiperidin-3-yl)-4-(((1-(1-((1-methylcyclohexyl)methyl)piperidin-4-yl)-1H-pyrazol-4-yl)methyl)amino)isoindoline-1,3-dione |
| 133 | 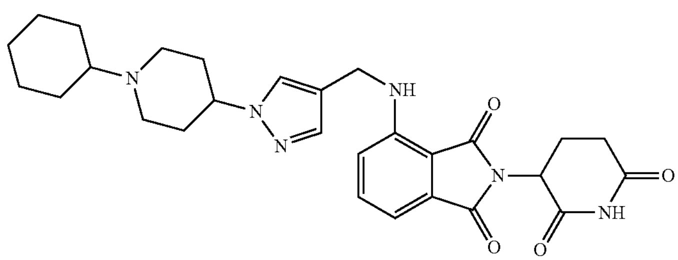 [SMILES: O=C1CCC(N2C(=O)c3cccc(NCc4cnn(C5CCN(C6CCCCC6)CC5)c4)c3C2=O)C(=O)N1] | 4-(((1-(1-cyclohexylpiperidin-4-yl)-1H-pyrazol-4-yl)methyl)amino)-2-(2,6-dioxopiperidin-3-yl)isoindoline-1,3-dione |
| 134 | 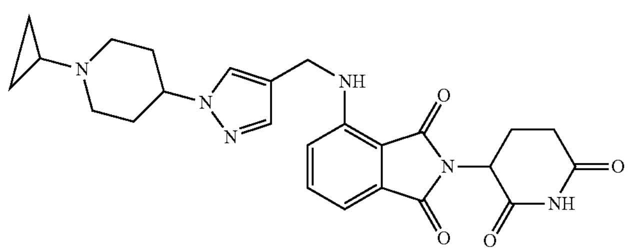 [SMILES: O=C1CCC(N2C(=O)c3cccc(NCc4cnn(C5CCN(C6CC6)CC5)c4)c3C2=O)C(=O)N1] | 4-(((1-(1-cyclopropylpiperidin-4-yl)-1H-pyrazol-4-yl)methyl)amino)-2-(2,6-dioxopiperidin-3-yl)isoindoline-1,3-dione |
| 135 | 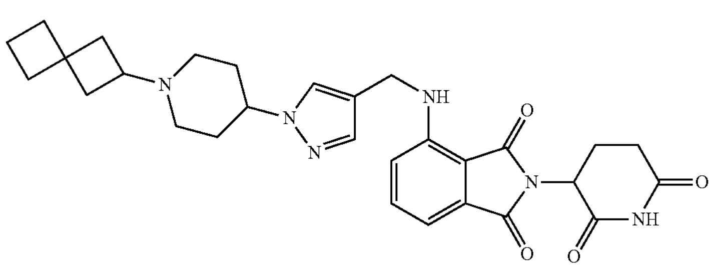 [SMILES: O=C1CCC(N2C(=O)c3cccc(NCc4cnn(C5CCN(C6CC7(CCC7)C6)CC5)c4)c3C2=O)C(=O)N1] | 2-(2,6-dioxopiperidin-3-yl)-4-(((1-(1-(spiro[3.3]heptan-2-yl)piperidin-4-yl)-1H-pyrazol-4-yl)methyl)amino)isoindoline-1,3-dione |

TABLE 1-continued

| Cmp No. | Structure | Name |
|---|---|---|
| 136 | 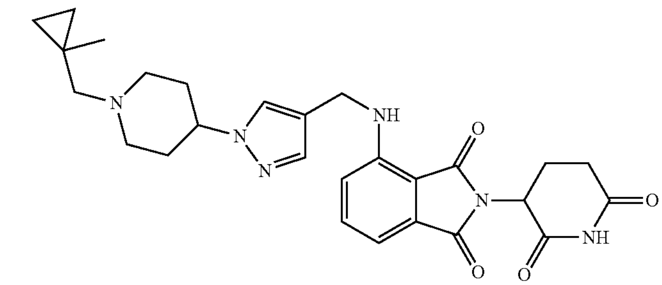 [SMILES: CC1(CN2CCC(n3cc(CNc4cccc5c4C(=O)N(C4CCC(=O)NC4=O)C5=O)cn3)CC2)CC1] | 2-(2,6-dioxopiperidin-3-yl)-4-(((1-(1-((1-methylcyclopropyl)methyl)piperidin-4-yl)-1H-pyrazol-4-yl)methyl)amino)isoindoline-1,3-dione |
| 137 | 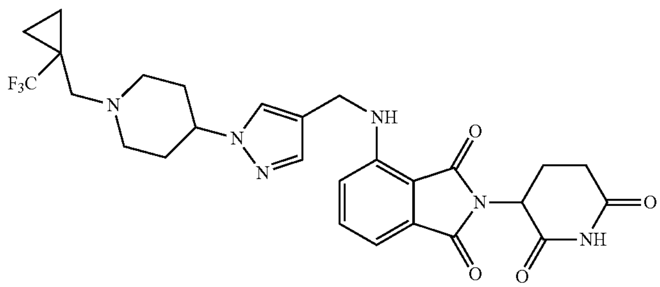 [SMILES: O=C1CCC(N2C(=O)c3cccc(NCc4cnn(C5CCN(CC6(C(F)(F)F)CC6)CC5)c4)c3C2=O)C(=O)N1] | 2-(2,6-dioxopiperidin-3-yl)-4-(((1-(1-((1-(trifluoromethyl)cyclopropyl)methyl)piperidin-4-yl)-1H-pyrazol-4-yl)methyl)amino)isoindoline-1,3-dione |
| 138 | 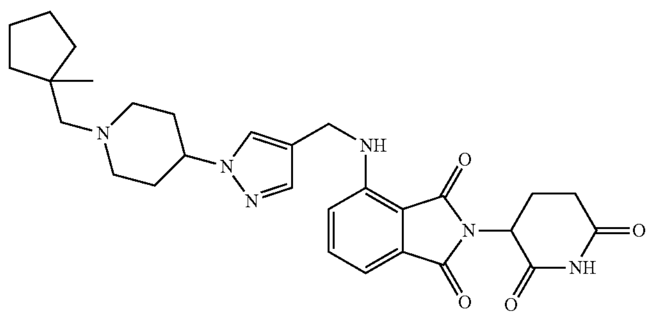 [SMILES: CC1(CN2CCC(n3cc(CNc4cccc5c4C(=O)N(C4CCC(=O)NC4=O)C5=O)cn3)CC2)CCCC1] | 2-(2,6-dioxopiperidin-3-yl)-4-(((1-(1-((1-methylcyclopentyl)methyl)piperidin-4-yl)-1H-pyrazol-4-yl)methyl)amino)isoindoline-1,3-dione |
| 139 | 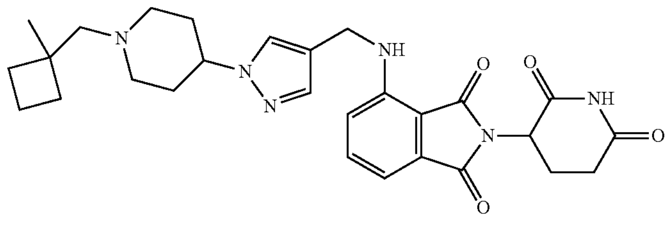 [SMILES: CC1(CN2CCC(n3cc(CNc4cccc5c4C(=O)N(C4CCC(=O)NC4=O)C5=O)cn3)CC2)CCC1] | 2-(2,6-dioxopiperidin-3-yl)-4-(((1-(1-((1-methylcyclobutyl)methyl)piperidin-4-yl)-1H-pyrazol-4-yl)methyl)amino)isoindoline-1,3-dione |
| 140 | 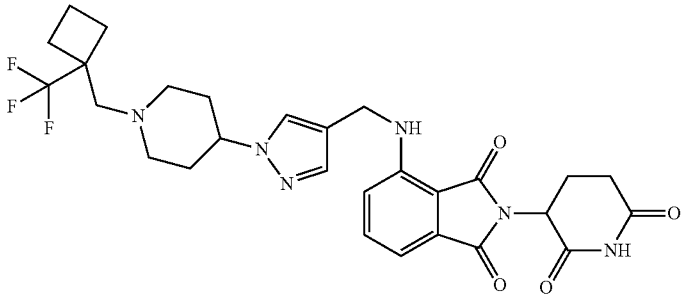 [SMILES: O=C1CCC(N2C(=O)c3cccc(NCc4cnn(C5CCN(CC6(C(F)(F)F)CCC6)CC5)c4)c3C2=O)C(=O)N1] | 2-(2,6-dioxopiperidin-3-yl)-4-(((1-(1-((1-(trifluoromethyl)cyclobutyl)methyl)piperidin-4-yl)-1H-pyrazol-4-yl)methyl)amino)isoindoline-1,3-dione |

TABLE 1-continued

| Cmp No. | Structure | Name |
|---|---|---|
| 141 | 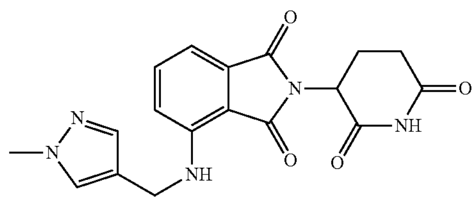 [SMILES: Cn1cc(CNc2cccc3c2C(=O)N(C2CCC(=O)NC2=O)C3=O)cn1] | 2-(2,6-dioxopiperidin-3-yl)-4-(((1-methyl-1H-pyrazol-4-yl)methyl)amino)isoindoline-1,3-dione |
| 142 | 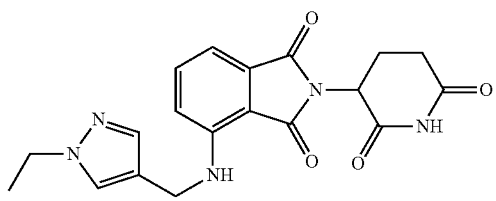 [SMILES: CCn1cc(CNc2cccc3c2C(=O)N(C2CCC(=O)NC2=O)C3=O)cn1] | 2-(2,6-dioxopiperidin-3-yl)-4-(((1-ethyl-1H-pyrazol-4-yl)methyl)amino)isoindoline-1,3-dione |
| 143 | 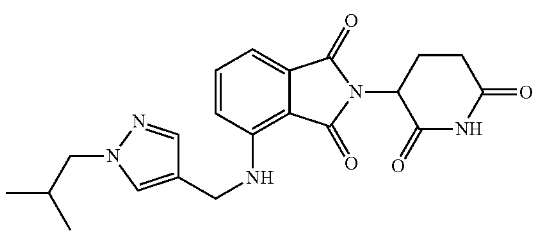 [SMILES: CC(C)Cn1cc(CNc2cccc3c2C(=O)N(C2CCC(=O)NC2=O)C3=O)cn1] | 2-(2,6-dioxopiperidin-3-yl)-4-(((1-isobutyl-1H-pyrazol-4-yl)methyl)amino)isoindoline-1,3-dione |
| 144 | 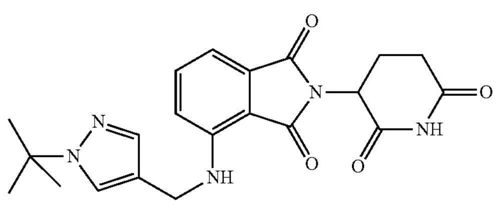 [SMILES: CC(C)(C)n1cc(CNc2cccc3c2C(=O)N(C2CCC(=O)NC2=O)C3=O)cn1] | 4-(((1-(tert-butyl)-1H-pyrazol-4-yl)methyl)amino)-2-(2,6-dioxopiperidin-3-yl)isoindoline-1,3-dione |
| 145 | 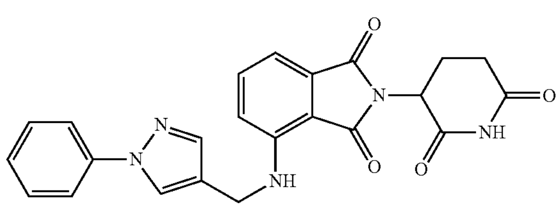 [SMILES: O=C1CCC(N2C(=O)c3cccc(NCc4cnn(-c5ccccc5)c4)c3C2=O)C(=O)N1] | 2-(2,6-dioxopiperidin-3-yl)-4-(((1-phenyl-1H-pyrazol-4-yl)methyl)amino)isoindoline-1,3-dione |
| 146 | 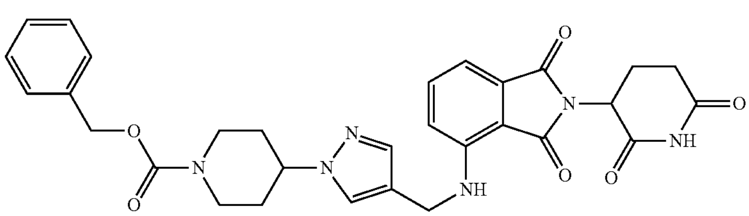 [SMILES: O=C1CCC(N2C(=O)c3cccc(NCc4cnn(C5CCN(C(=O)OCc6ccccc6)CC5)c4)c3C2=O)C(=O)N1] | benzyl 4-(4-(((2-(2,6-dioxopiperidin-3-yl)-1,3-dioxoisoindolin-4-yl)amino)methyl)-1H-pyrazol-1-yl)piperidine-1-carboxylate |
| 147 | 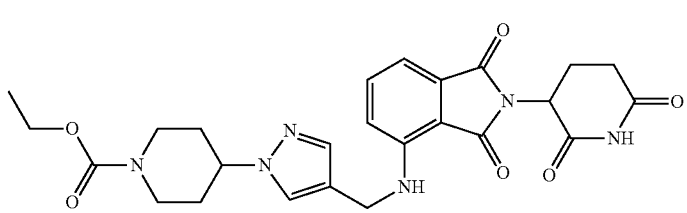 [SMILES: CCOC(=O)N1CCC(n2cc(CNc3cccc4c3C(=O)N(C3CCC(=O)NC3=O)C4=O)cn2)CC1] | ethyl 4-(4-(((2-(2,6-dioxopiperidin-3-yl)-1,3-dioxoisoindolin-4-yl)amino)methyl)-1H-pyrazol-1-yl)piperidine-1-carboxylate |

TABLE 1-continued

| Cmp No. | Structure | Name |
|---|---|---|
| 148 | 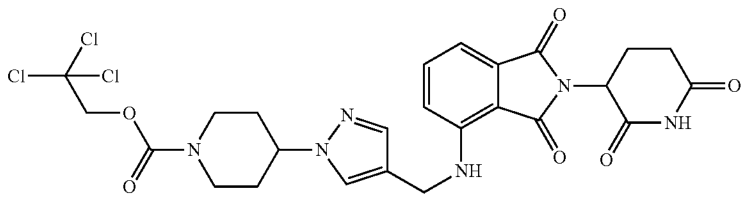 [SMILES: O=C1CCC(N2C(=O)c3cccc(NCc4cnn(C5CCN(C(=O)OCC(Cl)(Cl)Cl)CC5)c4)c3C2=O)C(=O)N1] | 2,2,2-trichloroethyl 4-(4-(((2-(2,6-dioxopiperidin-3-yl)-1,3-dioxoisoindolin-4-yl)amino)methyl)-1H-pyrazol-1-yl)piperidine-1-carboxylate |
| 149 | 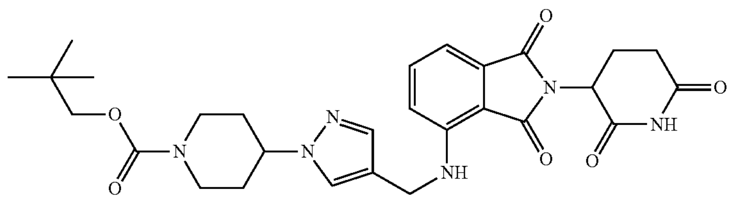 [SMILES: CC(C)(C)COC(=O)N1CCC(n2cc(CNc3cccc4c3C(=O)N(C3CCC(=O)NC3=O)C4=O)cn2)CC1] | neopentyl 4-(4-(((2-(2,6-dioxopiperidin-3-yl)-1,3-dioxoisoindolin-4-yl)amino)methyl)-1H-pyrazol-1-yl)piperidine-1-carboxylate |
| 150 | 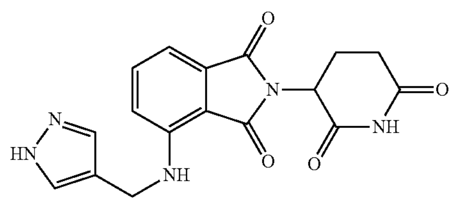 [SMILES: O=C1CCC(N2C(=O)c3cccc(NCc4cn[nH]c4)c3C2=O)C(=O)N1] | 4-(((1H-pyrazol-4-yl)methyl)amino)-2-(2,6-dioxopiperidin-3-yl)isoindoline-1,3-dione |
| 151 | 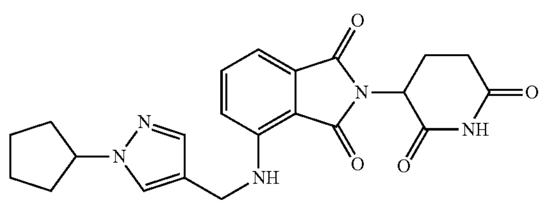 [SMILES: O=C1CCC(N2C(=O)c3cccc(NCc4cnn(C5CCCC5)c4)c3C2=O)C(=O)N1] | 4-(((1-cyclopentyl-1H-pyrazol-4-yl)methyl)amino)-2-(2,6-dioxopiperidin-3-yl)isoindoline-1,3-dione |
| 152 | 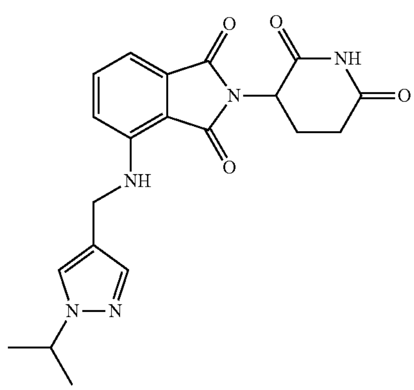 [SMILES: CC(C)n1cc(CNc2cccc3c2C(=O)N(C2CCC(=O)NC2=O)C3=O)cn1] | 2-(2,6-dioxopiperidin-3-yl)-4-(((1-isopropyl-1H-pyrazol-4-yl)methyl)amino)isoindoline-1,3-dione |
| 153 | 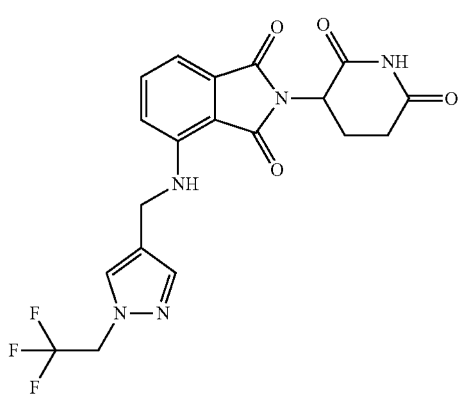 [SMILES: O=C1CCC(N2C(=O)c3cccc(NCc4cnn(CC(F)(F)F)c4)c3C2=O)C(=O)N1] | 2-(2,6-dioxopiperidin-3-yl)-4-(((1-(2,2,2-trifluoroethyl)-1H-pyrazol-4-yl)methyl)amino)isoindoline-1,3-dione |

TABLE 1-continued

| Cmp No. | Structure | Name |
|---|---|---|
| 154 | 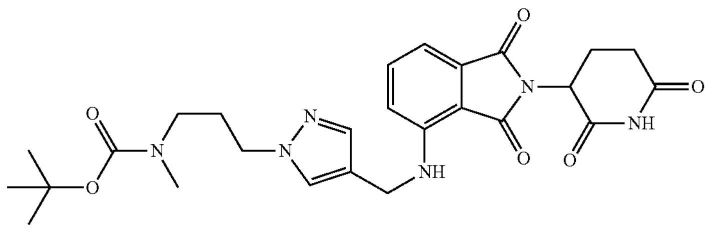 [SMILES: CN(CCCn1cc(CNc2cccc3c2C(=O)N(C2CCC(=O)NC2=O)C3=O)cn1)C(=O)OC(C)(C)C] | tert-butyl (3-(4-(((2-(2,6-dioxopiperidin-3-yl)-1,3-dioxoisoindolin-4-yl)amino)methyl)-1H-pyrazol-1-yl)propyl)(methyl)carbamate |
| 155 | 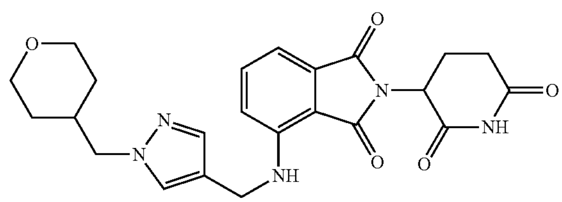 [SMILES: O=C1CCC(N2C(=O)c3cccc(NCc4cnn(CC5CCOCC5)c4)c3C2=O)C(=O)N1] | 2-(2,6-dioxopiperidin-3-yl)-4-(((1-((tetrahydro-2H-pyran-4-yl)methyl)-1H-pyrazol-4-yl)methyl)amino)isoindoline-1,3-dione |
| 156 | 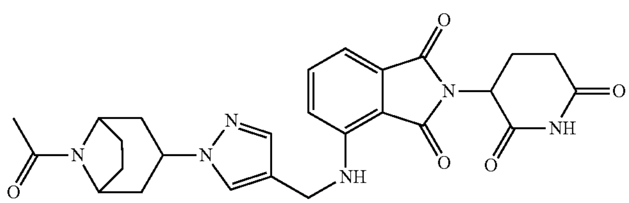 [SMILES: CC(=O)N1C2CCC1CC(n1cc(CNc3cccc4c3C(=O)N(C3CCC(=O)NC3=O)C4=O)cn1)C2] | 4-(((1-(8-acetyl-8-azabicyclo[3.2.1]octan-3-yl)-1H-pyrazol-4-yl)methyl)amino)-2-(2,6-dioxopiperidin-3-yl)isoindoline-1,3-dione |
| 157 | 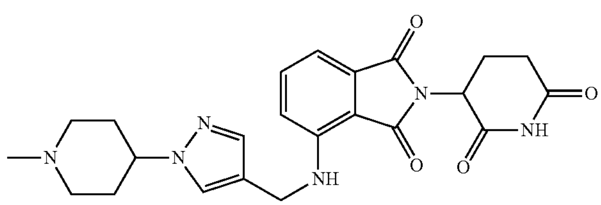 | 2-(2,6-dioxopiperidin-3-yl)-4-(((1-(1-methylpiperidin-4-yl)-1H-pyrazol-4-yl)methyl)amino)isoindoline-1,3-dione |
| 158 | 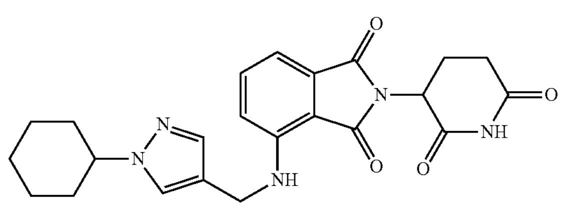 [SMILES: O=C1CCC(N2C(=O)c3cccc(NCc4cnn(C5CCCCC5)c4)c3C2=O)C(=O)N1] | 4-(((1-cyclohexyl-1H-pyrazol-4-yl)methyl)amino)-2-(2,6-dioxopiperidin-3-yl)isoindoline-1,3-dione |
| 159 | 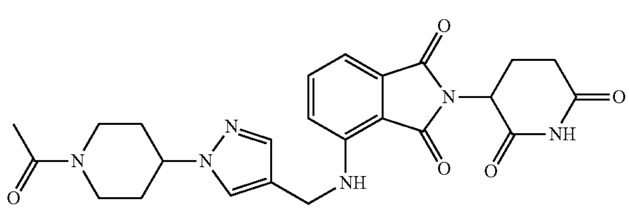 [SMILES: CC(=O)N1CCC(n2cc(CNc3cccc4c3C(=O)N(C3CCC(=O)NC3=O)C4=O)cn2)CC1] | 4-(((1-(1-acetylpiperidin-4-yl)-1H-pyrazol-4-yl)methyl)amino)-2-(2,6-dioxopiperidin-3-yl)isoindoline-1,3-dione |
| 160 | 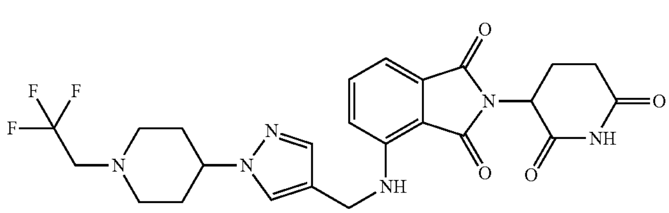 [SMILES: O=C1CCC(N2C(=O)c3cccc(NCc4cnn(C5CCN(CC(F)(F)F)CC5)c4)c3C2=O)C(=O)N1] | 2-(2,6-dioxopiperidin-3-yl)-4-(((1-(1-(2,2,2-trifluoroethyl)piperidin-4-yl)-1H-pyrazol-4-yl)methyl)amino)isoindoline-1,3-dione |

TABLE 1-continued

| Cmp No. | Structure | Name |
|---|---|---|
| 161 | 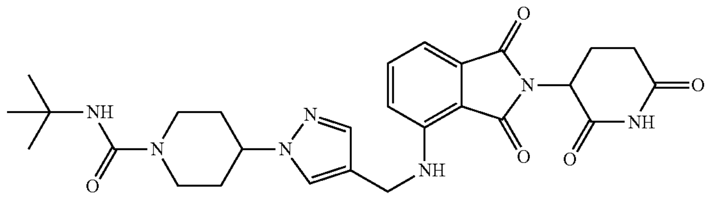 [SMILES: CC(C)(C)NC(=O)N1CCC(n2cc(CNc3cccc4c3C(=O)N(C3CCC(=O)NC3=O)C4=O)cn2)CC1] | N-(tert-butyl)-4-(4-(((2-(2,6-dioxopiperidin-3-yl)-1,3-dioxoisoindoline-4-yl)amino)methyl)-1H-pyrazol-1-yl)piperidine-1-carboxamide |
| 162 | 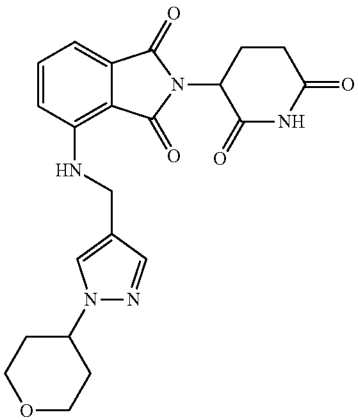 [SMILES: O=C1CCC(N2C(=O)c3cccc(NCc4cnn(C5CCOCC5)c4)c3C2=O)C(=O)N1] | 2-(2,6-dioxopiperidin-3-yl)-4-(((1-(tetrahydro-2H-pyran-4-yl)-1H-pyrazol-4-yl)methyl)amino)isoindoline-1,3-dione |
| 163 | 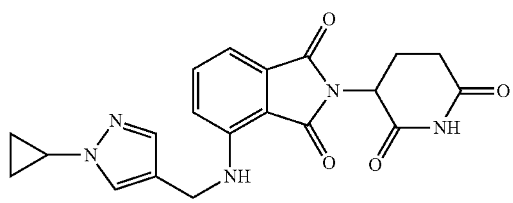 [SMILES: O=C1CCC(N2C(=O)c3cccc(NCc4cnn(C5CC5)c4)c3C2=O)C(=O)N1] | 4-(((1-cyclopropyl-1H-pyrazol-4-yl)methyl)amino)-2-(2,6-dioxopiperidin-3-yl)isoindoline-1,3-dione |
| 164 | 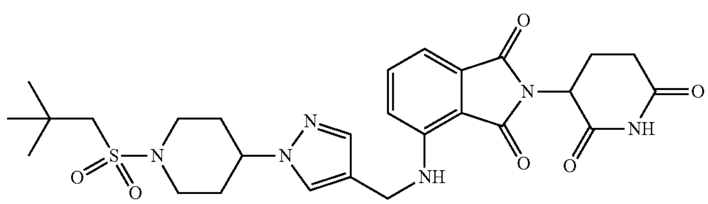 [SMILES: CC(C)(C)CS(=O)(=O)N1CCC(n2cc(CNc3cccc4c3C(=O)N(C3CCC(=O)NC3=O)C4=O)cn2)CC1] | 2-(2,6-dioxopiperidin-3-yl)-4-(((1-(1-(neopentylsulfonyl)piperidin-4-yl)-1H-pyrazol-4-y)methyl)amino)isoindoline-1,3-dione |
| 165 | 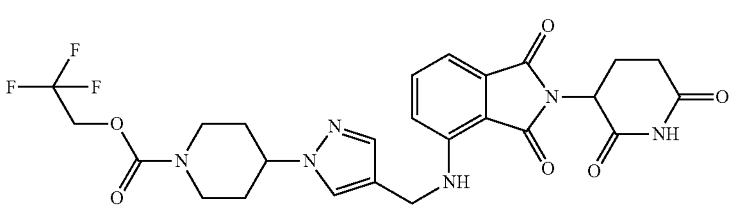 [SMILES: O=C1CCC(N2C(=O)c3cccc(NCc4cnn(C5CCN(C(=O)OCC(F)(F)F)CC5)c4)c3C2=O)C(=O)N1] | 2,2,2-trifluoroethyl 4-(4-(((2-(2,6-dioxopiperidin-3-yl)-1,3-dioxoisoindolin-4-yl)amino)methyl)-1H-pyrazol-1-yl)piperidine-1-carboxylate |
| 166 | 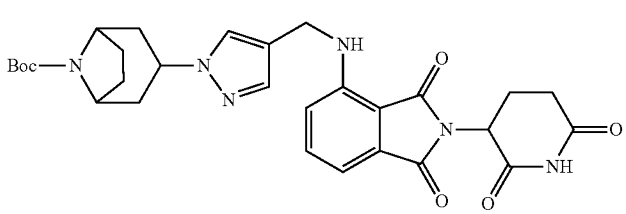 [SMILES: CC(C)(C)OC(=O)N1C2CCC1CC(n1cc(CNc3cccc4c3C(=O)N(C3CCC(=O)NC3=O)C4=O)cn1)C2] | tert-butyl 3-(4-(((2-(2,6-dioxopiperidin-3-yl)-1,3-dioxoisoindolin-4-yl)amino)methyl)-1H-pyrazol-1-yl)-8-azabicyclo[3.2.1]octane-8-carboxylate |

TABLE 1-continued

| Cmp No. | Structure | Name |
|---|---|---|
| 167 | 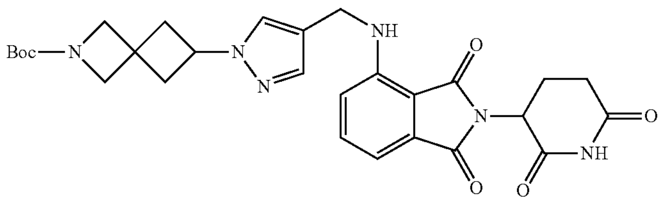 [SMILES: CC(C)(C)OC(=O)N1CC2(CC(n3cc(CNc4cccc5c4C(=O)N(C4CCC(=O)NC4=O)C5=O)cn3)C2)C1] | tert-butyl 6-(4-(((2-(2,6-dioxopiperidin-3-yl)-1,3-dioxoisoindolin-4-yl)amino)methyl)-1H-pyrazol-1-yl)-2-azaspiro[3.3]heptane-2-carboxylate |
| 168 | 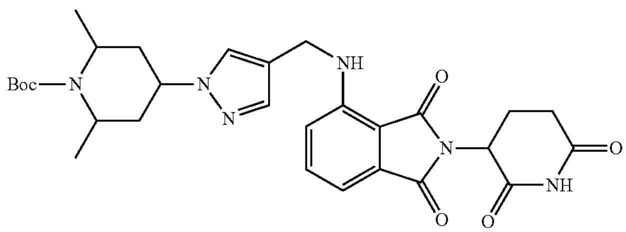 [SMILES: CC1CC(n2cc(CNc3cccc4c3C(=O)N(C3CCC(=O)NC3=O)C4=O)cn2)CC(C)N1C(=O)OC(C)(C)C] | tert-butyl 4-(4-(((2-(2,6-dioxopiperidin-3-yl)-1,3-dioxoisoindolin-4-yl)amino)methyl)-1H-pyrazol-1-yl)-2,6-dimethylpiperidine-1-carboxylate |
| 169 | 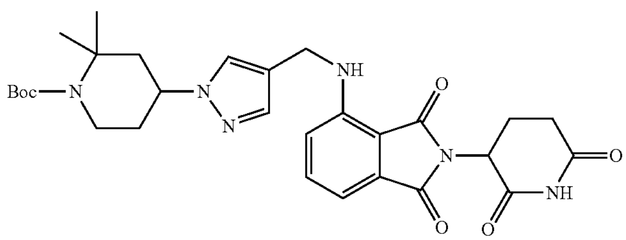 [SMILES: CC(C)(C)OC(=O)N1CCC(n2cc(CNc3cccc4c3C(=O)N(C3CCC(=O)NC3=O)C4=O)cn2)CC1(C)C] | tert-butyl 4-(4-(((2-(2,6-dioxopiperidin-3-yl)-1,3-dioxoisoindolin-4-yl)amino)methyl)-1H-pyrazol-1-yl)-2,2-dimethylpiperidine-1-carboxylate |
| 170 | 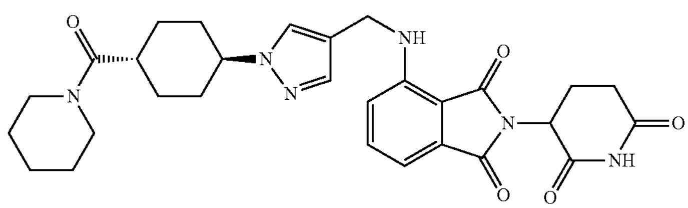 [SMILES: O=C1CCC(N2C(=O)c3cccc(NCc4cnn([C@H]5CC[C@H](C(=O)N6CCCCC6)CC5)c4)c3C2=O)C(=O)N1] | 2-(2,6-dioxopiperidin-3-yl)-4-(((1-((1r,4r)-4-(piperidine-1-carbonyl)cyclohexyl)-1H-pyrazol-4-yl)methyl)amino)isoindoline-1,3-dione |
| 171 | 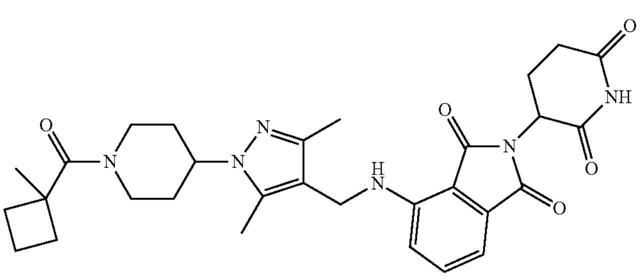 [SMILES: Cc1nn(C2CCN(C(=O)C3(C)CCC3)CC2)c(C)c1CNc1cccc2c1C(=O)N(C1CCC(=O)NC1=O)C2=O] | 4-(((3,5-dimethyl-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione |
| 172 | 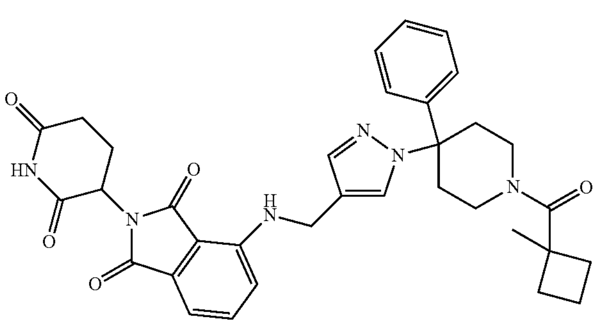 [SMILES: CC1(C(=O)N2CCC(c3ccccc3)(n3cc(CNc4cccc5c4C(=O)N(C4CCC(=O)NC4=O)C5=O)cn3)CC2)CCC1] | 2-(2,6-dioxopiperidin-3-yl)-4-(((1-(1-(1-methylcyclobutane-1-carbonyl)-4-phenylpiperidin-4-yl)-1H-pyrazol-4-yl)methyl)amino)isoindoline-1,3-dione |

TABLE 1-continued

| Cmp No. | Structure | Name |
|---|---|---|
| 173 | 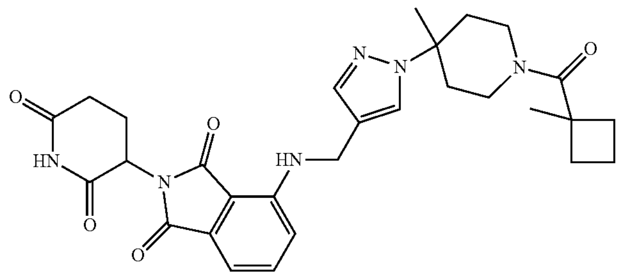 [SMILES: CC1(C(=O)N2CCC(C)(n3cc(CNc4cccc5c4C(=O)N(C4CCC(=O)NC4=O)C5=O)cn3)CC2)CCC1] | 2-(2,6-dioxopiperidin-3-yl)-4-(((1-(4-methyl-1-(1-methylcyclobutane-1-carbonyl)piperidin-4-yl)-1H-pyrazol-4-yl)methyl)amino)isoindoline-1,3-dione |
| 174 | 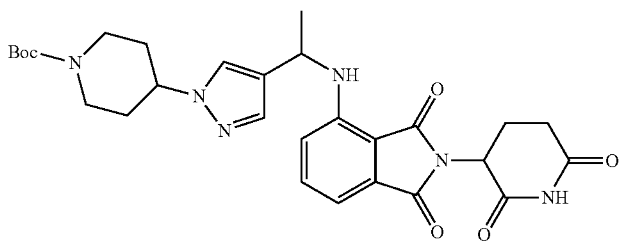 [SMILES: CC(Nc1cccc2c1C(=O)N(C1CCC(=O)NC1=O)C2=O)c1cnn(C2CCN(C(=O)OC(C)(C)C)CC2)c1] | tert-butyl 4-(4-(1-((2-(2,6-dioxopiperidin-3-yl)-1,3-dioxoisoindolin-4-yl)amino)ethyl)-1H-pyrazol-1-yl)piperidine-1-carboxylate |
| 175 | 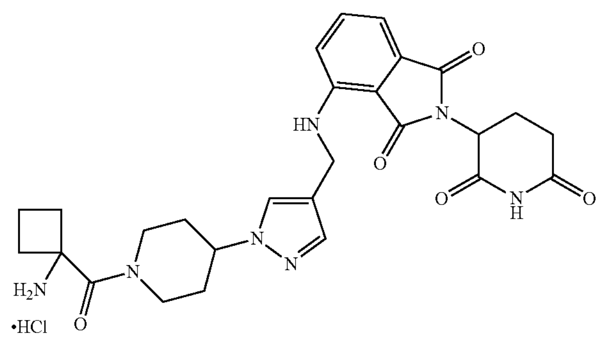 [SMILES: NC1(C(=O)N2CCC(n3cc(CNc4cccc5c4C(=O)N(C4CCC(=O)NC4=O)C5=O)cn3)CC2)CCC1 ; Cl] | 4-(((1-(1-(1-aminocyclobutane-1-carbonyl)piperidin-4-yl)-1H-pyrazol-4-yl)methyl)amino)-2-(2,6-dioxopiperidin-3-yl)isoindoline-1,3-dione |
| 176 | 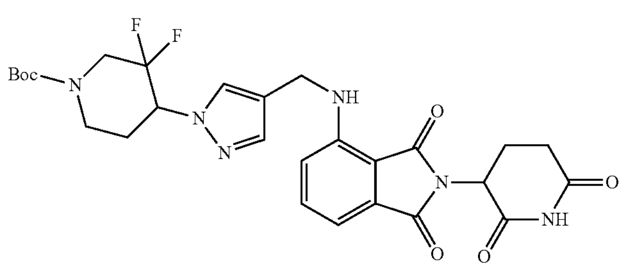 [SMILES: CC(C)(C)OC(=O)N1CCC(n2cc(CNc3cccc4c3C(=O)N(C3CCC(=O)NC3=O)C4=O)cn2)C(F)(F)C1] | tert-butyl 4-(4-(((2-(2,6-dioxopiperidin-3-yl)-1,3-dioxoisoindolin-4-yl)amino)methyl)-1H-pyrazol-1-yl)-3,3-difluoropiperidine-1-carboxylate |
| 177 | 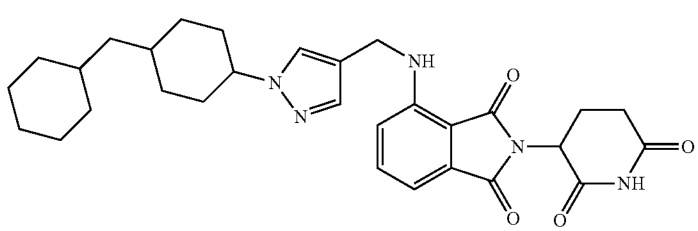 [SMILES: O=C1CCC(N2C(=O)c3cccc(NCc4cnn(C5CCC(CC6CCCCC6)CC5)c4)c3C2=O)C(=O)N1] | 4-(((1-(4-(cyclohexylmethyl)cyclohexyl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 178 | 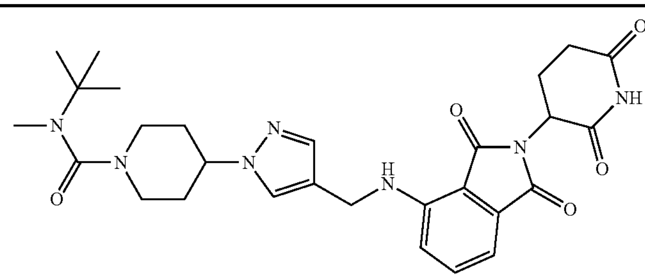 | N-(tert-butyl)-4-(4-(((2-(2,6-dioxopiperidin-3-yl)-1,3-dioxoisoindolin-4-yl)amino)methyl)-1H-pyrazol-1-yl)-N-methylpiperidine-1-carboxamide |
| 179 | 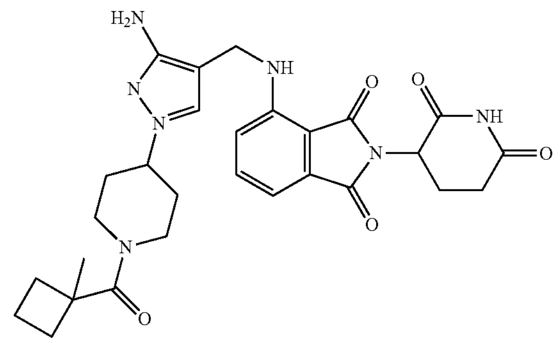 | 4-(((3-amino-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione |
| 180 | 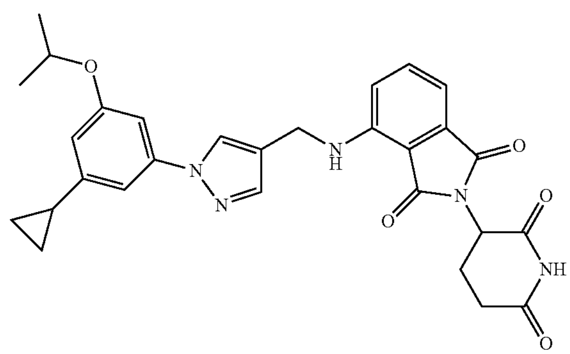 [SMILES: CC(C)Oc1cc(C2CC2)cc(-n2cc(CNc3cccc4c3C(=O)N(C3CCC(=O)NC3=O)C4=O)cn2)c1] | 4-(((1-(3-cyclopropyl-5-isopropoxyphenyl)-1H-pyrazol-4-yl)methyl)amino)-2-(2,6-dioxopiperidin-3-yl)isoindoline-1,3-dione |
| 181 | 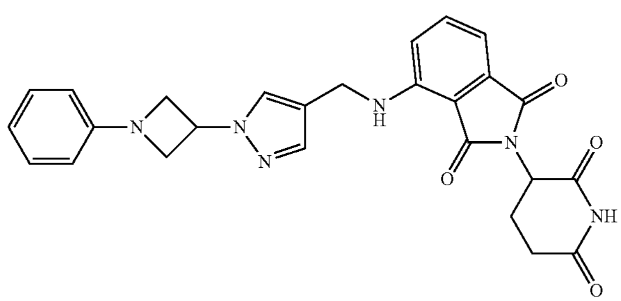 [SMILES: O=C1CCC(N2C(=O)c3cccc(NCc4cnn(C5CN(c6ccccc6)C5)c4)c3C2=O)C(=O)N1] | 2-(2,6-dioxopiperidin-3-yl)-4-(((1-(1-phenylazetidin-3-yl)-1H-pyrazol-4-yl)methyl)amino)isoindoline-1,3-dione |
| 182 | 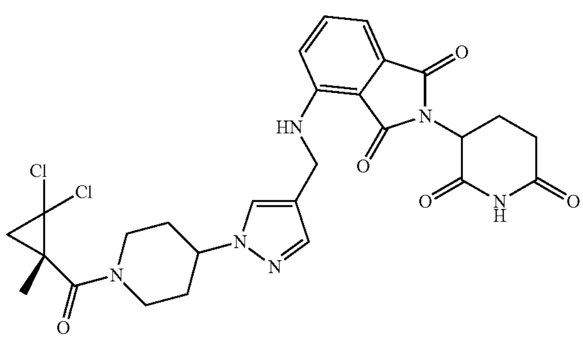 [SMILES: C[C@@]1(C(=O)N2CCC(n3cc(CNc4cccc5c4C(=O)N(C4CCC(=O)NC4=O)C5=O)cn3)CC2)CC1(Cl)Cl] | 4-(((1-(1-((S)-2,2-dichloro-1-methylcyclopropan-1-carbonyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 183 | 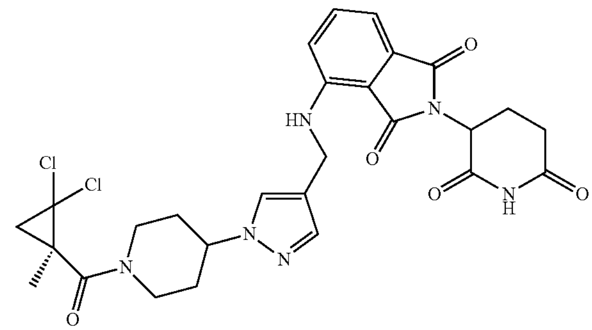 [SMILES: C[C@]1(C(=O)N2CCC(n3cc(CNc4cccc5c4C(=O)N(C4CCC(=O)NC4=O)C5=O)cn3)CC2)CC1(Cl)Cl] | 4-(((1-(1-((R)-2,2-dichloro-1-methylcyclopropane-1-carbonyl)piperidin-4-yl)-1H-pyrazol-4-yl)methyl)amino)-2-(2,6-dioxopiperidin-3-yl)isoindoline-1,3-dione |
| 184 | 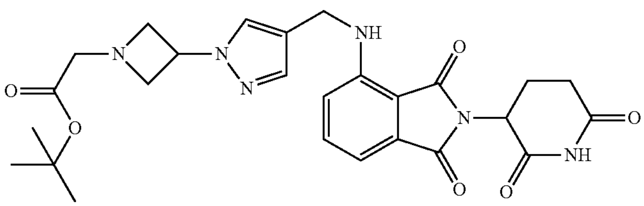 [SMILES: CC(C)(C)OC(=O)CN1CC(n2cc(CNc3cccc4c3C(=O)N(C3CCC(=O)NC3=O)C4=O)cn2)C1] | tert-butyl 2-(3-(4-(((2-(2,6-dioxopiperidin-3-yl)-1,3-dioxoisoindolin-4-yl)amino)methyl)-1H-pyrazol-1-yl)azetidin-1-yl)acetate |
| 185 | 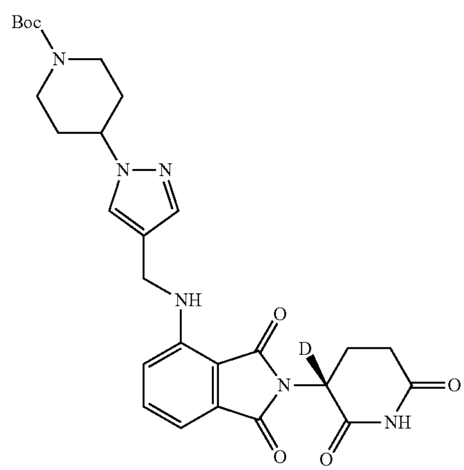 [SMILES: [2H][C@@]1(N2C(=O)c3cccc(NCc4cnn(C5CCN(C(=O)OC(C)(C)C)CC5)c4)c3C2=O)CCC(=O)NC1=O] | tert-butyl (R)-4-(4-(((2-(2,6-dioxopiperidin-3-yl)-3-d)-1,3-dioxoisoindolin-4-yl)amino)methyl)-1H-pyrazol-1-yl)piperidine-1-carboxylate |
| 186 | 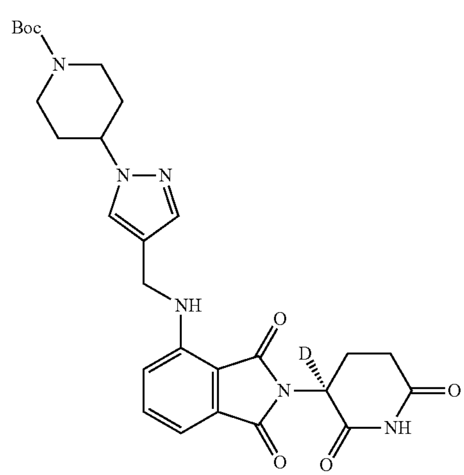 [SMILES: [2H][C@]1(N2C(=O)c3cccc(NCc4cnn(C5CCN(C(=O)OC(C)(C)C)CC5)c4)c3C2=O)CCC(=O)NC1=O] | tert-butyl (S)-4-(4-(((2-(2,6-dioxopiperidin-3-yl-3-d)-1,3-dioxoisoindolin-4-yl)amino)methyl)-1H-pyrazol-1-yl)piperidine-1-carboxylate |

TABLE 1-continued

| Cmp No. | Structure | Name |
| --- | --- | --- |
| 187 | 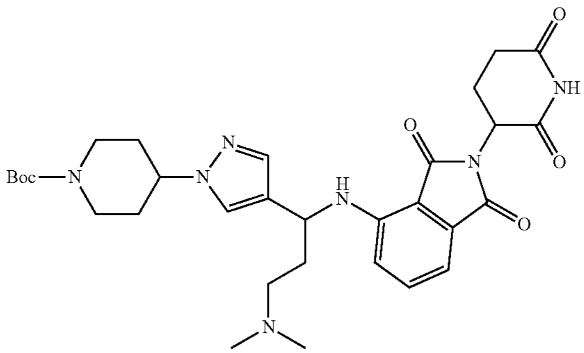 [SMILES: CN(C)CCC(Nc1cccc2c1C(=O)N(C1CCC(=O)NC1=O)C2=O)c1cnn(C2CCN(C(=O)OC(C)(C)C)CC2)c1] | tert-butyl 4-(4-(3-(dimethylamino)-1-((2-(2,6-dioxopiperidin-3-yl)-1,3-dioxoisoindolin-4-yl)amino)propyl)-1H-pyrazol-1-yl)piperidine-1-carboxylate |
| 188 | 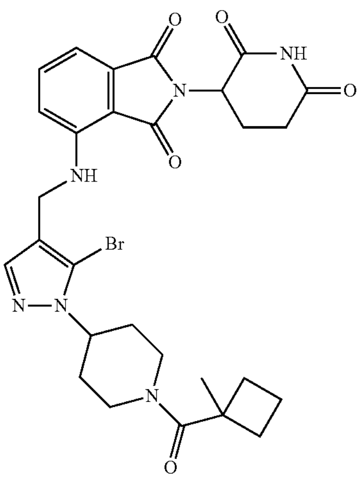 [SMILES: CC1(C(=O)N2CCC(n3ncc(CNc4cccc5c4C(=O)N(C4CCC(=O)NC4=O)C5=O)c3Br)CC2)CCC1] | 4-(((5-bromo-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione |
| 189 | 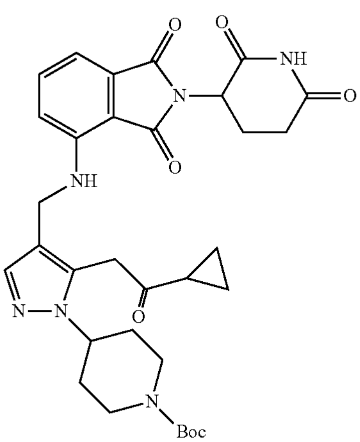 [SMILES: CC(C)(C)OC(=O)N1CCC(n2ncc(CNc3cccc4c3C(=O)N(C3CCC(=O)NC3=O)C4=O)c2CC(=O)C2CC2)CC1] | tert-butyl 4-(5-(2-cyclopropyl-2-oxoethyl)-4-(((2-(2,6-dixopiperidin-3-yl)-1,3-dioxoisoindolin-4-yl)amino)methyl)-1H-pyrazol-1-yl)piperidine-1-carboxylate |

TABLE 1-continued

| Cmp No. | Structure | Name |
|---|---|---|
| 190 | 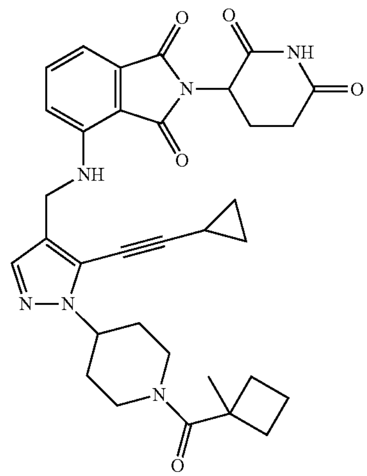 [SMILES: CC1(C(=O)N2CCC(n3ncc(CNc4cccc5c4C(=O)N(C4CCC(=O)NC4=O)C5=O)c3C#CC3CC3)CC2)CCC1] | 4-(((5-(Cyclopropylethynyl)-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione |
| 191 | 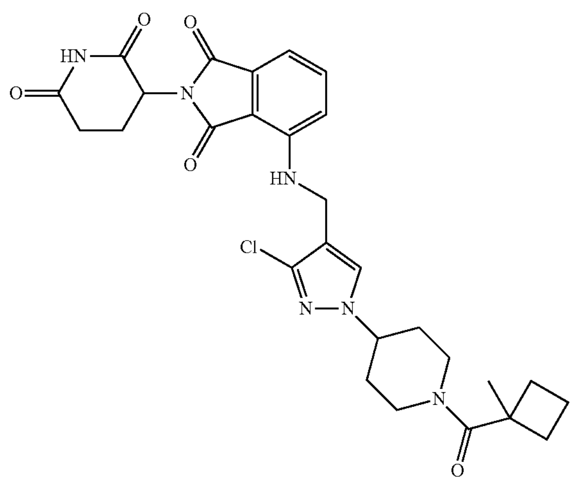 [SMILES: CC1(C(=O)N2CCC(n3cc(CNc4cccc5c4C(=O)N(C4CCC(=O)NC4=O)C5=O)c(Cl)n3)CC2)CCC1] | 3-(4-(((3-chloro-1-(1-(1-methylcyclobutane-1-carbonyl)piperidin-4-yl)-1H-pyrazol-4-yl)methyl)amino)-1,3-dioxo-2,3-dihydro-1H-inden-2-yl)piperidine-2,6-dione |
| 192 | 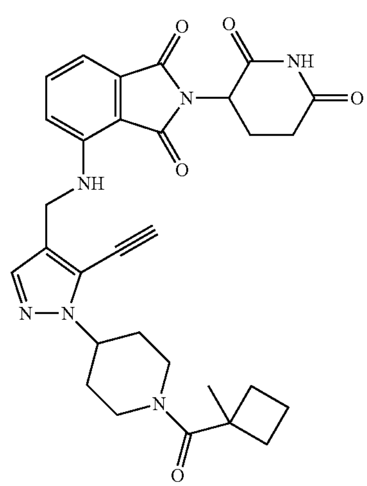 [SMILES: C#Cc1c(CNc2cccc3c2C(=O)N(C2CCC(=O)NC2=O)C3=O)cnn1C1CCN(C(=O)C2(C)CCC2)CC1] | 2-(2,6-dioxopiperidin-3-yl)-4-(((5-ethynyl-1-(1-(1-methylcyclobutane-1-carbonyl)piperidin-4-yl)-1H-pyrazol-4-yl)methyl)amino)isoindoline-1,3-dione |

TABLE 1-continued

| Cmp No. | Structure | Name |
|---|---|---|
| 193 | 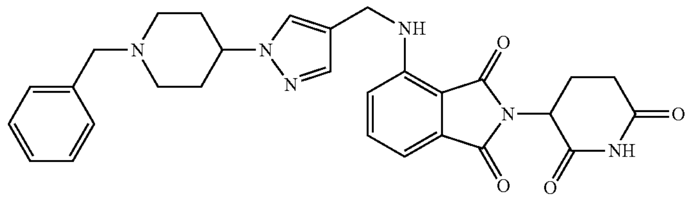 [SMILES: O=C1CCC(N2C(=O)c3cccc(NCc4cnn(C5CCN(Cc6ccccc6)CC5)c4)c3C2=O)C(=O)N1] | 4-(((1-(1-benzylpiperidin-4-yl)-1H-pyrazol-4-yl)methyl)amino)-2-(2,6-dioxopiperidin-3-yl)isoindoline-1,3-dione |
| 194 | 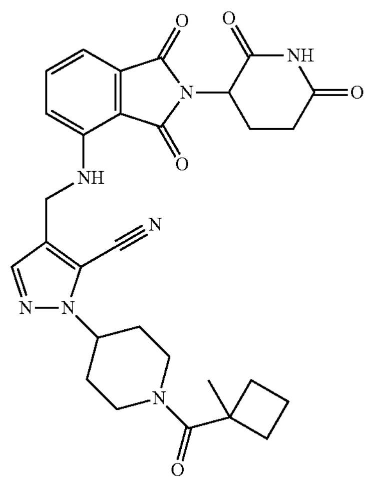 [SMILES: CC1(C(=O)N2CCC(n3ncc(CNc4cccc5c4C(=O)N(C4CCC(=O)NC4=O)C5=O)c3C#N)CC2)CCC1] | 4-(((2-(2,6-dioxopiperidin-3-yl)-1,3-dioxoisoindolin-4-yl)amino)methyl)-1-(1-(1-methylcyclobutane-1-carbonyl)piperidin-4-yl)-1H-pyrazole-5-carbonitrile |
| 195 | 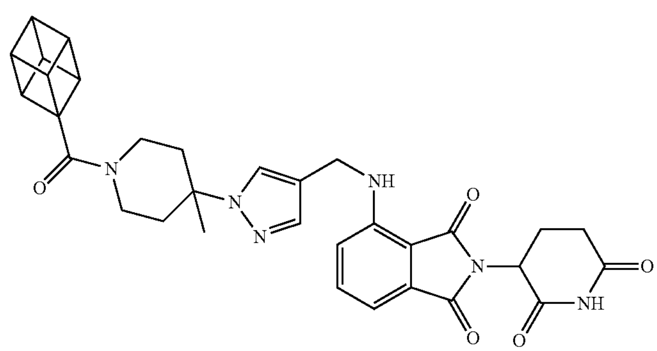 [SMILES: CC1(n2cc(CNc3cccc4c3C(=O)N(C3CCC(=O)NC3=O)C4=O)cn2)CCN(C(=O)C23C4C5C6C4C2C6C53)CC1] | 4-(((1-(1-(cubane-1-carbonyl)-4-methylpiperidin-4-yl)-1H-pyrazol-4-yl)methyl)amino)-2-(2,6-dioxopiperidin-3-yl)isoindoline-1,3-dione |
| 196 | 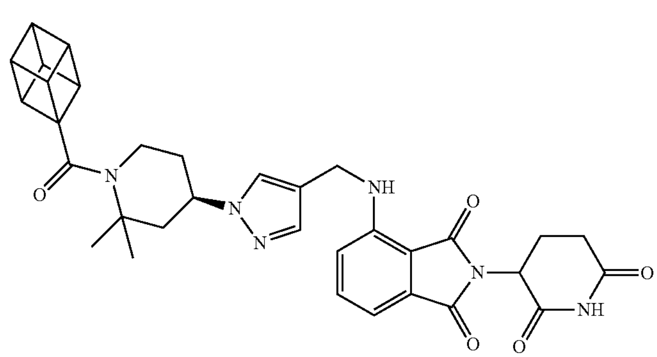 [SMILES: CC1(C)C[C@H](n2cc(CNc3cccc4c3C(=O)N(C3CCC(=O)NC3=O)C4=O)cn2)CCN1C(=O)C12C3C4C5C3C1C5C42] | 4-(((1-((R)-1-(cubane-1-carbonyl)-2,2-dimethylpiperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 197 | 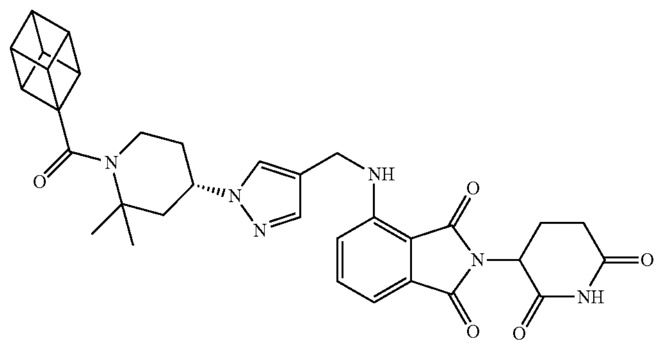 [SMILES: CC1(C)C[C@@H](n2cc(CNc3cccc4c3C(=O)N(C3CCC(=O)NC3=O)C4=O)cn2)CCN1C(=O)C12C3C4C5C3C1C5C42] | 4-(((1-((S)-1-(cubane-1-carbonyl)-2,2-dimethylpiperidin-4-yl)-1H-pyrazol-4-yl)methyl)amino)-2-(2,6-dioxopiperidin-3-yl)isoindoline-1,3-dione |
| 198 | 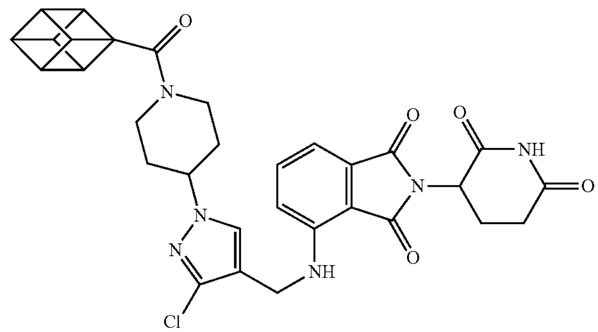 [SMILES: O=C1CCC(N2C(=O)c3cccc(NCc4cn(C5CCN(C(=O)C67C8C9C%10C8C6C%10C97)CC5)nc4Cl)c3C2=O)C(=O)N1] | 4-(((3-chloro-1-(1-(cubane-1-carbonyl)piperidin-4-yl)-1H-pyrazol-4-yl)methyl)amino)-2-(2,6-dioxopiperidin-3-yl)isoindoline-1,3-dione |
| 199 | 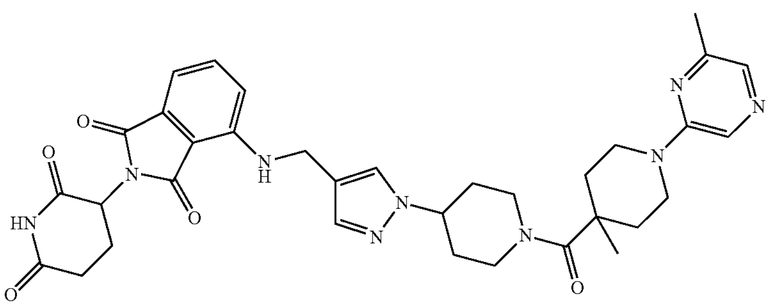 [SMILES: Cc1cncc(N2CCC(C)(C(=O)N3CCC(n4cc(CNc5cccc6c5C(=O)N(C5CCC(=O)NC5=O)C6=O)cn4)CC3)CC2)n1] | 2-(2,6-dioxopipeirdin-3-yl)-4-(((1-(1-(4-methyl-1-(6-methylpyrazin-2-yl)piperidine-4-carbonyl)piperidin-4-yl)-1H-pyrazol-4-yl)methyl)amino)isoindoline-1,3-dione |
| 200 | 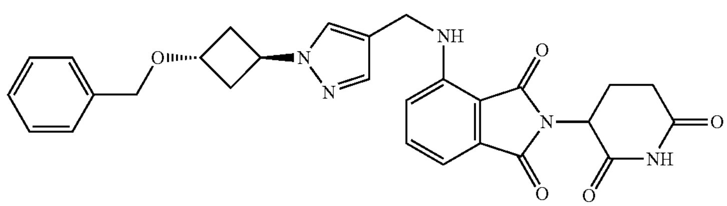 [SMILES: O=C1CCC(N2C(=O)c3cccc(NCc4cnn([C@H]5C[C@H](OCc6ccccc6)C5)c4)c3C2=O)C(=O)N1] | 4-(((1-((1r,3r)-3-(benzyloxy)cyclobutyl)-1H-pyrazol-4-yl)methyl)amino)-2-(2,6-dioxopiperidin-3-yl)isoindoline-1,3-dione |
| 201 | 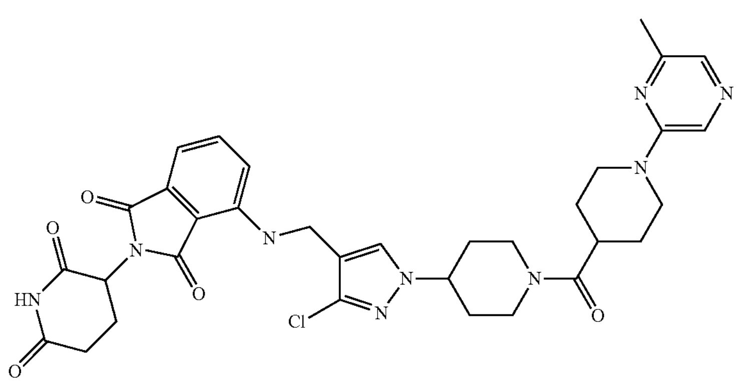 [SMILES: Cc1cncc(N2CCC(C(=O)N3CCC(n4cc(CNc5cccc6c5C(=O)N(C5CCC(=O)NC5=O)C6=O)c(Cl)n4)CC3)CC2)n1] | 4-(((3-chloro-1-(1-(1-(6-methylpyrazin-2-yl)piperidine-4-carbonyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 202 | 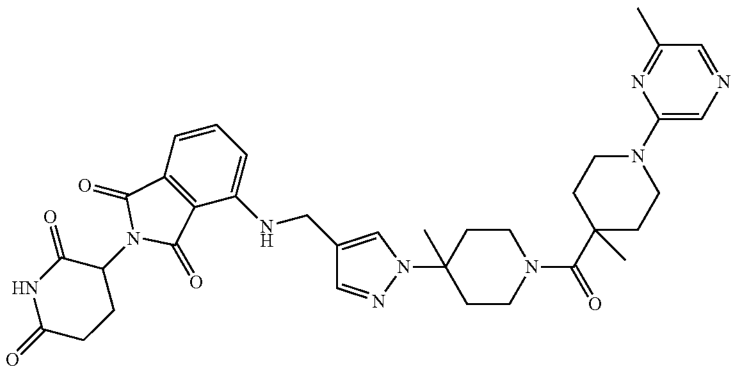 [SMILES: Cc1cncc(N2CCC(C)(C(=O)N3CCC(C)(n4cc(CNc5cccc6c5C(=O)N(C5CCC(=O)NC5=O)C6=O)cn4)CC3)CC2)n1] | 2-(2,6-dioxopiperidin-3-yl)-4-((((1-(4-methyl-1-(4-methyl-1-(6-methylpyrazin-2-yl)piperidine-4-carbonyl)piperidin-4-yl)-1H-pyrazol-4-yl)methyl)amino)isoindoline-1,3-dione |
| 203 | 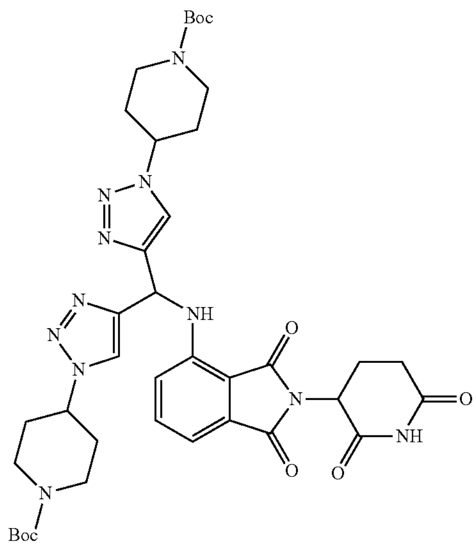 [SMILES: CC(C)(C)OC(=O)N1CCC(n2cc(C(Nc3cccc4c3C(=O)N(C3CCC(=O)NC3=O)C4=O)c3cn(C4CCN(C(=O)OC(C)(C)C)CC4)nn3)nn2)CC1] | di-tert-butyl 4,4'-(((((2-(2,6-dioxopiperidin-3-yl)-1,3-dioxoisoindolin-4-yl)amino)methylene)bis(1H-1,2,3-triazole-4,1-diyl))bis(piperidine-1-carboxylate |
| 204 | 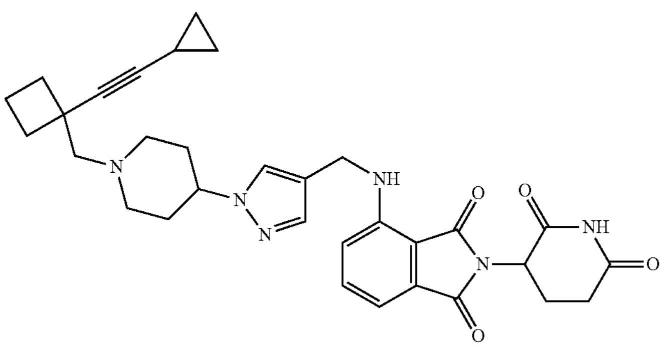 [SMILES: O=C1CCC(N2C(=O)c3cccc(NCc4cnn(C5CCN(CC6(C#CC7CC7)CCC6)CC5)c4)c3C2=O)C(=O)N1] | 4-(((1-(1-((1-(cyclopropylethynyl)cyclobutyl)methyl)piperidin-4-yl)-1H-pyrazol-4-yl)methyl)amino)-2-(2,6-dioxopiperidin-3-yl)isoindoline-1,3-dione |
| 206 | 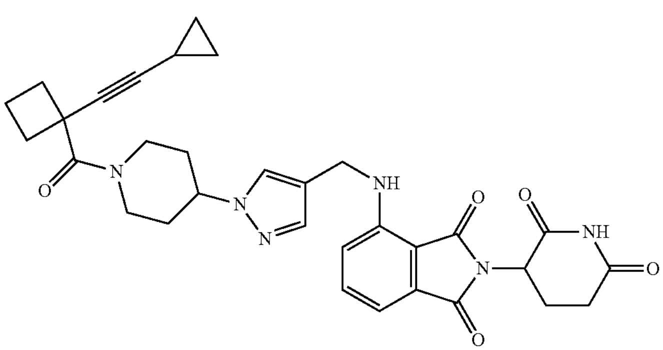 [SMILES: O=C1CCC(N2C(=O)c3cccc(NCc4cnn(C5CCN(C(=O)C6(C#CC7CC7)CCC6)CC5)c4)c3C2=O)C(=O)N1] | 4-(((1-(1-(1-(cyclopropylethynyl)cyclobutane-1-carbonyl)piperidin-4-yl)-1H-pyrazol-4-yl)methyl)amino)-2-(2,6-dioxopiperidin-3-yl)isoindoline-1,3-dione |

TABLE 1-continued

| Cmp No. | Structure | Name |
|---|---|---|
| 206 | 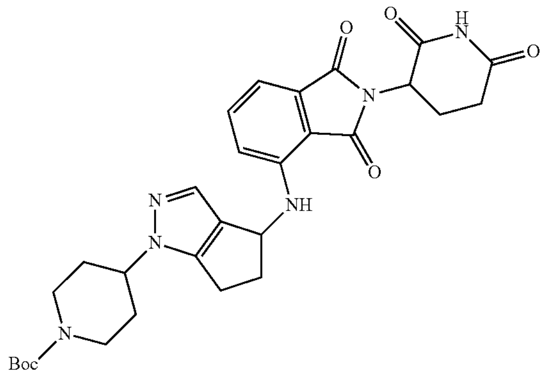 [SMILES: CC(C)(C)OC(=O)N1CCC(n2ncc3c2CCC3Nc2cccc3c2C(=O)N(C2CCC(=O)NC2=O)C3=O)CC1] | tert-butyl 4-(4-((2-(2,6-dioxopiperidin-3-yl)-1,3-dioxoisoindolin-4-yl)amino)-5,6-dihydrocyclopenta[c]pyrazol-1(4H)-yl)piperidine-1-carboxylate |
| 207 | 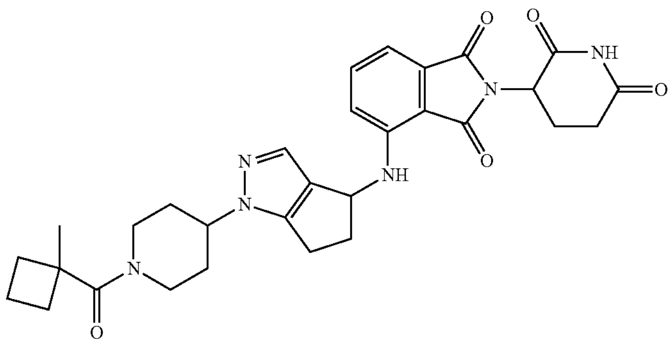 [SMILES: CC1(C(=O)N2CCC(n3ncc4c3CCC4Nc3cccc4c3C(=O)N(C3CCC(=O)NC3=O)C4=O)CC2)CCC1] | 2-(2,6-dioxopiperidin-3-yl)-4-((1-(1-(1-methylcyclobutane-1-carbonyl)piperidin-4-yl)-1,4,5,6-tetrahydrocyclopenta[c]pyrazol-4-yl)amino)isoindoline-1,3-dione |

VII. General Synthesis

The compounds described herein can be prepared by methods known by those skilled in the art. In one non-limiting example, the disclosed compounds can be made using the schemes below.

Compounds of the present invention with stereocenters may be drawn without stereochemistry for convenience. One skilled in the art will recognize that pure or enriched enantiomers and diastereomers can be prepared by methods known in the art. Examples of methods to obtain optically active materials include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the enantiomer is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step in the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e. chirality) in the product, which may be achieved by chiral catalysts or chiral auxiliaries;

vi) diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer;

vii) first- and second-order asymmetric transformations—a technique whereby diastereomers from the racemate quickly equilibrate to yield a preponderance in solution of the diastereomer from the desired enantiomer of where preferential crystallization of the diastereomer from the desired enantiomer perturbs the equilibrium such that eventually in principle all the material is converted to the crystalline diastereomer from the desired enantiomers. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including vial chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is place in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through;

xiv) simulated moving bed chromatography is used in one embodiment. A wide variety of chiral stationary phases are commercially available.

VIII. General Synthetic Methods to Prepare Compounds of the Present Invention

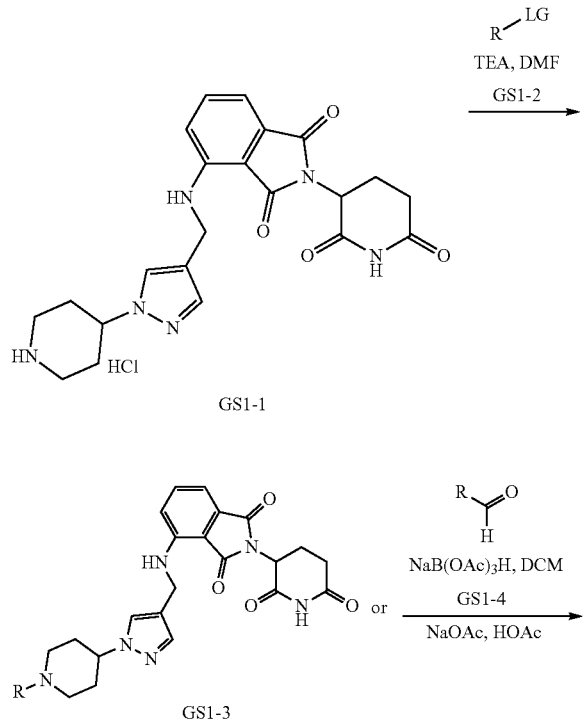

GS1-3

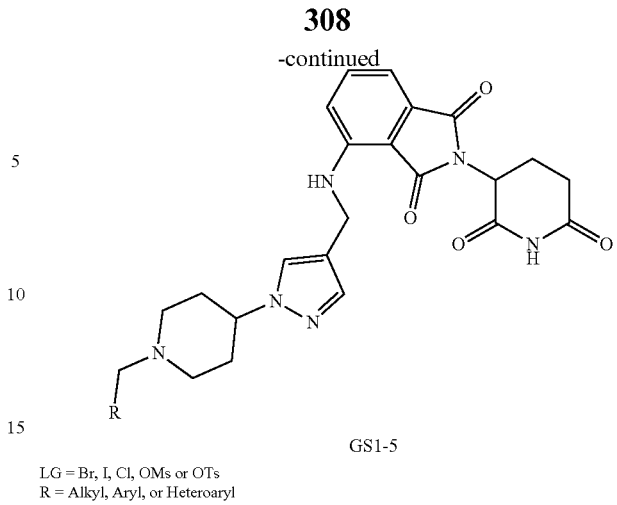

GS1-5

LG = Br, I, Cl, OMs or OTs
R = Alkyl, Aryl, or Heteroaryl

General Scheme 1: Preparation of Alkylated Piperidines
Step-1 Alkylation of Piperidine/Preparation of (GS1-3)

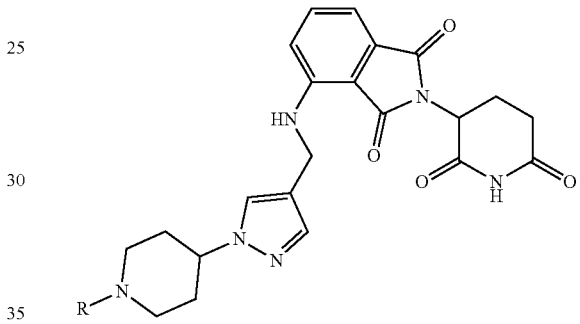

To the mixture of 2-(2,6-dioxopiperidin-3-yl)-4-((1-(piperidin-4-yl)-1H-pyrazol-4-yl)amino)isoindoline-1,3-dione (GS1-1) (100 mg) in DMF (3 ml) is added TEA (3 eq) and Electrophile (GS1-2) (1.1 eq) under ice cold condition. The reaction mixture is stirred at room temperature for 16 hours. At completion, the reaction mixture is diluted with ethyl acetate and washed with water and saturated NH$_4$Cl solution. The resulting organic phase is evaporated and submitted for prep-HPLC purification to afford product (GS1-3).

Step-1 Reductive Amination of Piperidine/Preparation of (GS1-5)

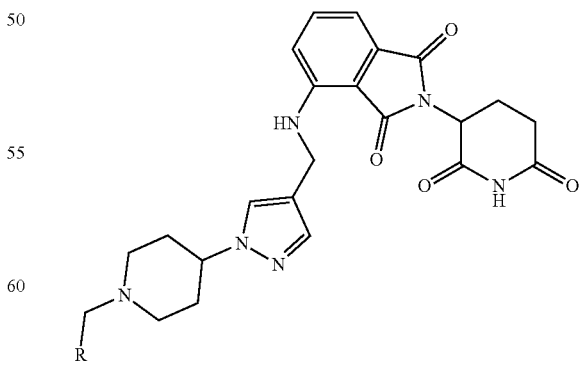

To the mixture of 2-(2,6-dioxopiperidin-3-yl)-4-((1-(piperidin-4-yl)-1H-pyrazol-4-yl)amino)isoindoline-1,3-dione (GS1-1) (100 mg) and aldehyde (GS1-4) (1 eq) in DCM (3 ml) is added NaOAc (2 eq) and Acetic acid (1 eq) at room temp. After stirring for 30 minutes, NaB(OAc)₃H (1.2 eq) is added under ice cold condition. The reaction mixture is then stirred at room temperature for 16 hours. At completion, the reaction mixture is diluted with DCM and washed with saturated NaHCO₃ solution and brine. The resulting organic phase is evaporated and purified by prep-HPLC purification to afford product (GS1-5).

dissolved in DMF. The crude material is purified by prep-HPLC purification to afford product (GS2-3).

IX. Representative Synthesis of Compounds of the Present Invention

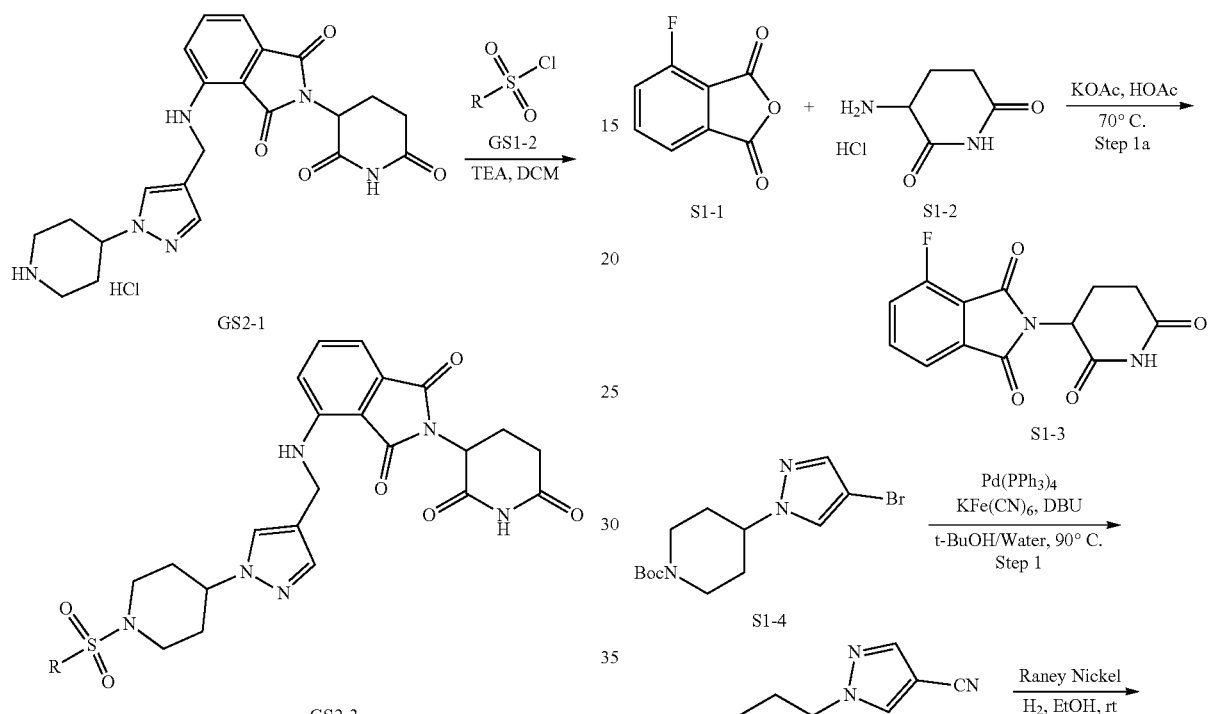

General Scheme 2: Preparation of Sulfonamide Containing Analogs

Step-1: Preparation of (GS2-3)

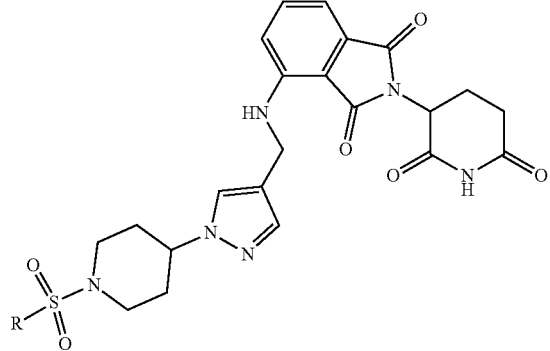

To 2-(2,6-dioxopiperidin-3-yl)-4-((1-(piperidin-4-yl)-1H-pyrazol-4-yl)amino)isoindoline-1,3-dione (GS2-1) (100 mg) in DCM (3 ml) is added TEA (3 eq) and sulfonyl chloride (GS2-2) (1.1 eq) under ice cold condition. The reaction mixture is stirred at room temperature for 16 hours. At completion, the reaction mixture the evaporated and

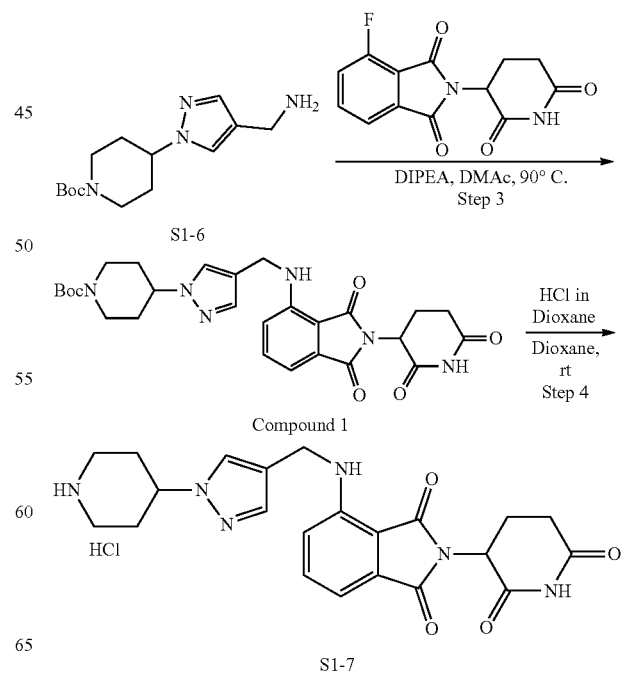

Step 1a: Synthesis of 2-(2,6-dioxo-3-piperidyl)-4-fluoro-isoindoline-1,3-dione (S1-3)

An oven dried round bottom flask was charged with a solution of 3-aminopiperidine-2,6-dione; hydrochloride S1-2 (9.91 g, 60.20 mmol) in Acetic acid (200 mL), 4-fluoroisobenzofuran-1,3-dione (10 g, 60.20 mmol) and Potassium Acetate (14.77 g, 150.51 mmol, 9.41 mL) were added. The reaction mixture was heated to 70° C. for 16 hours and the reaction mixture was then cooled to room temperature. The reaction mixture was concentrated under reduced pressure and the crude product was quenched with water (120 mL). The solid was filtered and dried under vacuum to yield 2-(2,6-dioxo-3-piperidyl)-4-fluoro-isoindoline-1,3-dione S1-3 as a violet solid (14 g, 43.43 mmol, 72.13% yield) 85.68% purity was observed in crude by LCMS.

LCMS: ES+277.0. $^1$H NMR (400 MHz, DMSO-$d_6$) δ 11.16 (s, 1H), 7.92-7.96 (m, 1H), 7.71-7.81 (m, 2H), 5.16 (dd, J=17.2, 7.2 Hz, 1H), 2.83-2.90 (m, 1H), 2.4-2.7 (m, 2H), 2.04-2.09 (m, 1H).

Step 1: Synthesis of tert-butyl 4-(4-cyanopyrazol-1-yl) piperidine-1-carboxylate (S1-5)

To a stirred solution of tert-butyl 4-(4-bromopyrazol-1-yl)piperidine-1-carboxylate S1-4 (1 g, 3.03 mmol) in tert-Butanol (7 mL) and water (7 mL) in a sealed tube was added Potassium ferrocyanide, trihydrate (511.65 mg, 1.21 mmol) and DBU (115.26 mg, 757.07 μmol) the reaction mixture was degassed with argon and then Palladium (0) tetrakis (triphenylphosphine) (174.97 mg, 151.41 μmol) was added and the sealed tube was closed tightly and the reaction was allowed to stir at 90° C. for 16 hours. The reaction mixture was filtered through a celite bed, washed with ethyl acetate and then concentrated. The crude residue was dissolved in ethyl acetate and washed with water, brine, dried over sodium sulphate and concentrated under reduced pressure. The crude product was then purified by column chromatography using (silica, gradient 25%-30% EtOAc/Hexane) to provide tert-butyl 4-(4-cyanopyrazol-1-yl) piperidine-1-carboxylate S1-5 (710 mg, 2.57 mmol, 84.85% yield). LCMS: ES+277.2. $^1$H NMR (400 MHz, DMSO-$d_6$) δ 8.64 (s, 1H), 8.07 (s, 1H), 4.42-4.48 (m, 1H), 4.00-4.05 (m, 2H), 2.90 (br, 2H), 2.00 (m, 2H), 1.71-1.80 (m, 2H), 1.41 (s, 9H).

Step 2: Synthesis of tert-butyl 4-[4-(aminomethyl) pyrazol-1-yl]piperidine-1-carboxylate (S1-6)

To a stirred solution of tert-butyl 4-(4-cyanopyrazol-1-yl) piperidine-1-carboxylate S1-5 (150 mg, 542.82 μmol) in ethanol (8 mL) was added Raney Nickel (slurry in $H_2O$, active catalyst, 46.51 mg, 542.82 μmol) and the reaction mixture was hydrogenated under balloon pressure, for 3 hours. TLC analysis confirmed the consumption of the starting material and the reaction mass was then filtered over a celite bed, washed with ethanol, and concentrated under reduced pressure to provide the crude tert-butyl 4-[4-(aminomethyl)pyrazol-1-yl]piperidine-1-carboxylate S1-6 (140 mg, 499.35 μmol, 91.99% yield) as a gummy liquid which was used in the next step without further purification. LCMS: ES+281.2.

Step 3: Synthesis of tert-butyl 4-[4-[[[2-(2,6-dioxo-3-piperidyl)-1,3-dioxo-isoindolin-4-yl]amino] methyl]pyrazol-1-yl]piperidine-1-carboxylate (Compound 1)

To a stirred solution of tert-butyl 4-[4-(aminomethyl) pyrazol-1-yl]piperidine-1-carboxylate S1-6 (120 mg, 428.01 μmol) in N,N dimethyl acetamide (2 mL) was added 2-(2,6-dioxo-3-piperidyl)-4-fluoro-isoindoline-1,3-dione (94.58 mg, 342.41 μmol) followed by N,N Diisopropyl ethylamine (110.64 mg, 856.03 μmol, 149.10 uL) in a sealed tube and the reaction mixture was heated at 90° C. and stirred for 2 hours. TLC analysis confirmed the formation of product and the reaction mixture was diluted with water and was extracted with ethyl acetate, the organic layer was washed with water and brine, dried over anhydrous sodium sulphate and concentrated under reduced pressure. The crude product thus obtained was purified by column chromatography over silica gel eluting with 2-3% of MeOH in DCM to afford tert-butyl 4-[4-[[[2-(2,6-dioxo-3-piperidyl)-1,3-dioxo-isoindolin-4-yl]amino]methyl]pyrazol-1-yl]piperidine-1-carboxylate Compound 1(30 mg, 55.91 μmol, 13.06% yield) as a yellow solid. LCMS: ES+537.2. $^1$H NMR (400 MHz, DMSO-$d_6$) δ 11.08 (s, 1H), 7.79 (s, 1H), 7.57 (t, J=7.8 Hz, 1H), 7.46 (s, 1H), 7.15 (d, J=8.5 Hz, 1H), 7.03 (d, J=7.6 Hz, 1H), 6.80 (m, 1H), 5.04 (dd, J=12.8, 5.4 Hz, 1H), 3.98-4.02 (m, 2H), 2.78-2.94 (m, 3H), 2.45-2.60 (m, 2H), 1.70-1.74 (m, 2H), 2.00-2.07 9 m, 1H), 1.90-2.00 (m, 2H), 1.40 (s, 9H).

Step 4: Synthesis of 2-(2,6-dioxo-3-piperidyl)-4-[[1-(4-piperidyl) pyrazol-4-yl]methylamino]isoindoline-1,3-dione (S1-7)

tert-butyl 4-[4-[[[2-(2,6-dioxo-3-piperidyl)-1,3-dioxo-isoindolin-4-yl]amino]methyl]pyrazol-1-yl]piperidine-1-carboxylate Compound 1 (20 mg, 37.27 μmol) was dissolved in Dioxane (1 mL) and HCl (13.93 mg, 111.82 μmol) was added and was allowed to stir for 2 hours at ambient temperature, TLC analysis confirmed the consumption of the starting material. The reaction mass was then concentrated under reduced pressure, triturated with diethyl ether, and the solid product obtained was lyophilized with water to afford 2-(2,6-dioxo-3-piperidyl)-4-[[1-(4-piperidyl) pyrazol-4-yl]methylamino]isoindoline-1,3-dione S1-7 (15 mg, 34.37 μmol, 92.20% yield) as yellow solid. LCMS: ES+ 437.2. $^1$H NMR (400 MHz, DMSO-$d_6$) δ 11.09 (s, 1H), 8.82 (s, 1H), 8.58 (s, 1H), 7.76 (s, 1H), 7.55-7.59 (m, 1H), 7.51 (s, 1H), 7.16 (d, J=8.8 Hz, 1H), 7.04 (d, J=7.1 Hz, 1H), 6.84 (br, 1H), 5.04 (dd, J=12.5, 5.2 Hz, 1H), 4.37-4.46 (m, 3H), 3.34-3.39 (m, 2H), 2.98-3.06 (m, 2H), 2.83-2.94 (m, 2H), 2.45-2.66 (m, 2H), 2.04-2.15 (m, 4H).

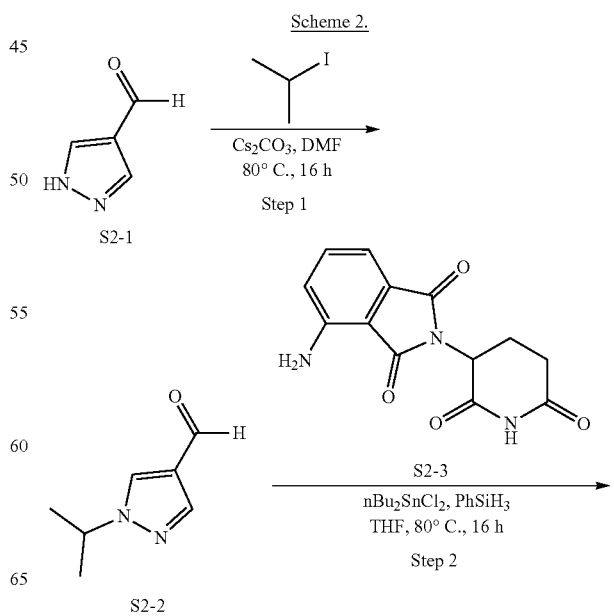

Scheme 2.

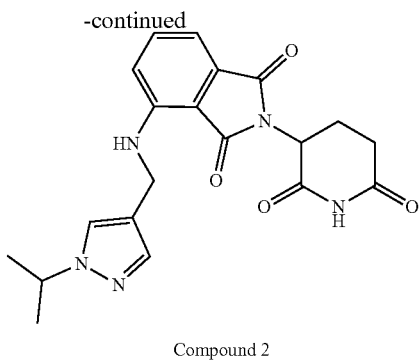

Compound 2

Step-1: Preparation of 1-Isopropyl-1H-pyrazole-4-carbaldehyde (S2-2)

To a stirred solution of 1H-pyrazole-4-carbaldehyde (S2-1) (200 mg, 2.08 mmol) in DMF (2 mL) was added 2-iodopropane (707.66 mg, 4.16 mmol, 416.27 uL) and Cesium carbonate (1.36 g, 4.16 mmol) at ambient temperature. The resulting mixture was heated at 80° C. for 16 hours. It was then cooled to room temperature, diluted with ice cold water and extracted with ethyl acetate. The combined extract was washed with brine, dried over sodium sulfate, and concentrated under reduced pressure. The reaction mixture was purified by flash chromatography (eluting with 30% ethyl acetate-hexane) to afford 1-isopropylpyrazole-4-carbaldehyde (S2-2) (200 mg, 1.45 mmol, 69.54% yield) as brown liquid. LCMS: ES+ 139.1.

Step-2: Preparation of 2-(2,6-Dioxo-piperidin-3-yl)-4-[(1-isopropyl-1H-pyrazol-4-ylmethyl)-amino]-isoindole-1,3-dione (Compound 2)

To a stirred solution of 4-amino-2-(2,6-dioxo-3-piperidyl) isoindoline-1,3-dione (3) (80 mg, 292.78 µmol) in THF (2 mL) in a sealed tube was added isopropylpyrazole-4-carbaldehyde (2) (48.54 mg, 351.33 µmol), Phenylsilane (31.68 mg, 292.78 µmol) and Dibutyltin dichloride (106.75 mg, 351.33 µmol, 78.49 uL) at ambient temperature. The resulting mixture was heated at 80° C. for 16 hours. Reaction mixture was them brought to room temperature and concentrated under reduced pressure. The crude was purified by flash chromatography (eluting with 3% MeOH-DCM) to afford 2-(2,6-dioxo-3-piperidyl)-4-[(1-isopropylpyrazol-4-yl)methylamino]isoindoline-1,3-dione (Compound 2) (52 mg, 131.51 µmol, 44.92% yield) as a yellow solid. $^1$H NMR (400 MHz, DMSO-d6) δ 11.08 (s, 1H), 7.74 (s, 1H), 7.57 (t, J=7.82 Hz, 1H), 7.43 (s, 1H), 7.15 (d, J=8.60 Hz, 1H), 7.03 (d, J=7.04 Hz, 1H), 6.80 (t, J=5.5 Hz, 1H), 5.05 (dd, J=12.68, 5.24 Hz, 1H), 4.45-4.42 (m, 1H), 4.36 (d, J=5.8 Hz, 2H), 2.91-2.84 (m, 1H), 2.65-2.50 (m, 2H), 2.03-2.00 (m, 1H), 1.36 (d, J=6.72 Hz, 6H); LC MS: ES+ 396.08.

Scheme 3.

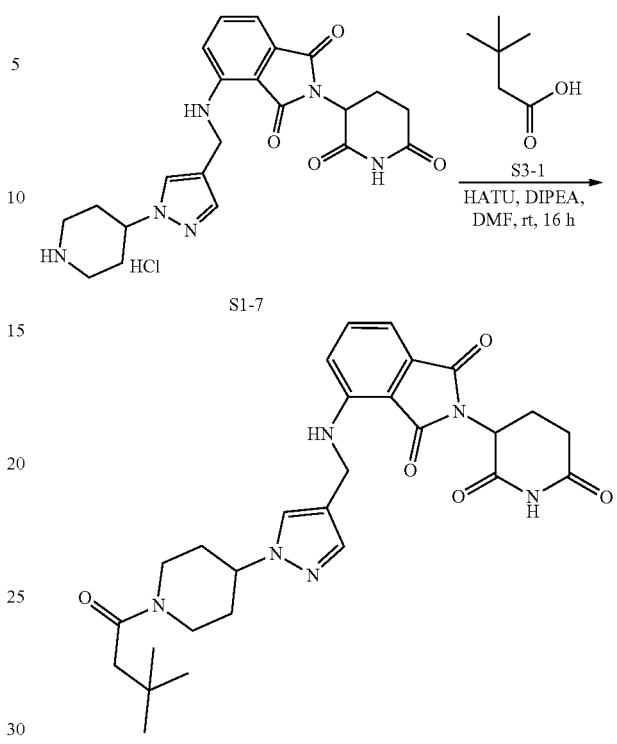

Compound 3

Step-1: Preparation of 4-({1-[1-(3,3-Dimethyl-butyryl)-piperidin-4-yl]-1H-pyrazol-4-ylmethyl}-amino)-2-(2,6-dioxo-piperidin-3-yl)-isoindole-1,3-dione (Compound 3)

To a stirred solution of 2-(2,6-dioxo-3-piperidyl)-4-[[1-(4-piperidyl) pyrazol-4-yl]methylamino]isoindoline-1,3-dione (S1-7) (50 mg, 105.73 µmol) in DMF (2 mL) was added 3,3-dimethylbutanoic acid (14.74 mg, 126.87 µmol, 16.16 uL) (S3-1) followed by HATU (60.30 mg, 158.59 µmol) and the reaction mixture was cooled to 0° C. and then DIPEA (68.32 mg, 528.63 µmol, 92.08 uL) was added. The reaction mixture was allowed to stir at room temperature overnight. The reaction mixture was then diluted with water and was extracted with ethyl acetate. Organic extract was washed with saturated aqueous NaHCO$_3$ solution, water, and brine, and then dried over sodium sulfate and concentrated under reduced pressure to obtain crude product. The crude product thus obtained was purified by preparative TLC plate (eluting with 3% of Methanol/DCM) to afford 4-({1-[1-(3,3-Dimethyl-butyryl)-piperidin-4-yl]-1H-pyrazol-4-ylmethyl}-amino)-2-(2,6-dioxo-piperidin-3-yl)-isoindole-1,3-dione (Compound 3) (25.0 mg, 46.76 µmol, 44% yield) as yellow solid. 1H NMR (400 MHz, DMSO-d6) δ 11.08 (s, 1H), 7.78 (s, 1H), 7.57 (t, J=7.82 Hz, 1H), 7.45 (s, 1H), 7.15 (d, J=8.52 Hz, 1H), 7.03 (d, J=7.04 Hz, 1H), 6.80 (t, J=5.5 Hz, 1H), 5.04 (dd, J=12.68, 5.24 Hz, 1H), 4.53-4.49 (m, 1H), 4.40-4.34 (m, 3H), 4.07-4.02 (m, 1H), 3.16-3.09 (m, 1H), 2.88-2.84 (m, 1H), 2.68-2.64 (m, 1H), 2.61-2.60 (m, 1H), 2.55-2.50 (m, 1H), 2.30-2.19 (m, 2H), 2.02-1.95 (m, 3H), 1.79-1.76 (m, 1H), 1.68-1.65 (m, 1H), 1.00 (s, 9H); LC MS: ES+ 535.2.

Scheme 4.

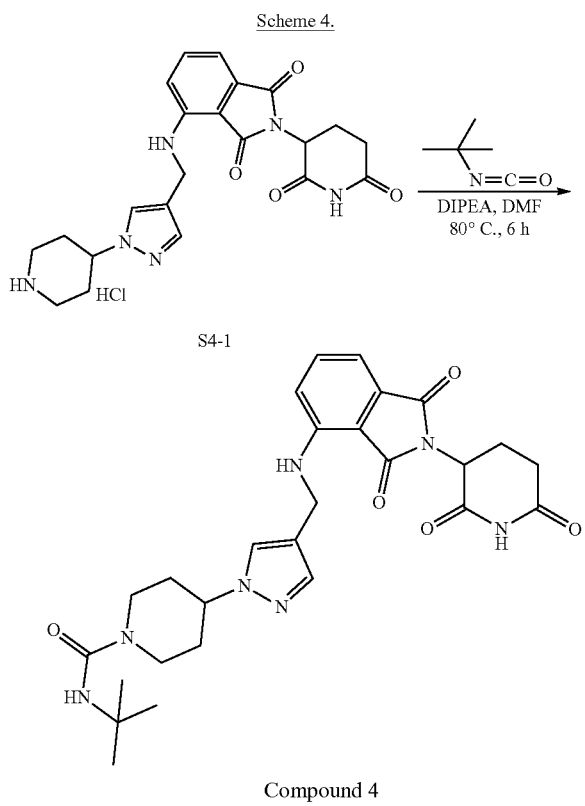

Compound 4

Step-1: Preparation of N-(tert-butyl)-4-(4-(((2-(2,6-dioxopiperidin-3-yl)-1,3-dioxoisoindolin-4-yl) amino)methyl)-1H-pyrazol-1-yl)piperidine-1-carboxamide (Compound 4)

To a stirred suspension of 2-(2,6-dioxo-3-piperidyl)-4-[[1-(4-piperidyl) pyrazol-4-yl]methylamino]isoindoline-1, 3-dione (S4-1) (40 mg, 84.58 μmol) in THF (3 mL) in a sealed tube at room temp, DIPEA (27.33 mg, 211.45 μmol, 36.83 uL) was added. The reaction mixture was cooled to 0° C., followed by dropwise addition of tert-butyl isocyanate (8.38 mg, 84.58 μmol, 9.66 uL). The resulting reaction mixture was then heated at 80° C. for 4 hours. LCMS showed desired product mass. TLC also showed a new spot at 0.3 Rf in 5% MeOH-DCM. The reaction mixture was then diluted with saturated NaHCO₃ solution and EtOAc, the layers were separated, organic layer were washed with water and brine and then dried over Na₂SO₄ and concentrated to provide a crude residue which was further purified by preparative TLC to afford N-tert-butyl-4-[4-[[[2-(2,6-dioxo-3-piperidyl)-1,3-dioxo-isoindolin-4-yl]amino]methyl]pyrazol-1-yl]piperidine-1-carboxamide Compound 4 (14 mg, 26.14 μmol, 30.90% yield, >99% purity) as a yellow solid. 1H NMR (400 MHz, DMSO-d6) δ 11.08 (s, 1H), 7.77 (s, 1H), 7.57 (t, J=7.82 Hz, 1H), 7.45 (s, 1H), 7.16 (d, J=8.56 Hz, 1H), 7.03 (d, J=7.04 Hz, 1H), 6.79 (t, J=5.60 Hz, 1H), 5.82 (s, 1H), 5.04 (dd, J=12.72, 5.28 Hz, 1H), 4.35 (d, J=5.8 Hz, 2H), 4.28-4.22 (m, 1H), 4.02-3.99 (m, 2H), 2.92-2.84 (m, 1H), 2.75-2.66 (m, 2H), 2.60-2.55 (m, 1H), 2.49-2.43 (m, 1H), 2.03-2.00 (m, 1H), 1.93-1.85 (m, 2H), 1.75-1.66 (m, 2H), 1.24 (s, 9H); LC MS: ES+ 536.5.

Example 1: Illustrative Preparation of Amide-Containing Compounds of the Present Invention

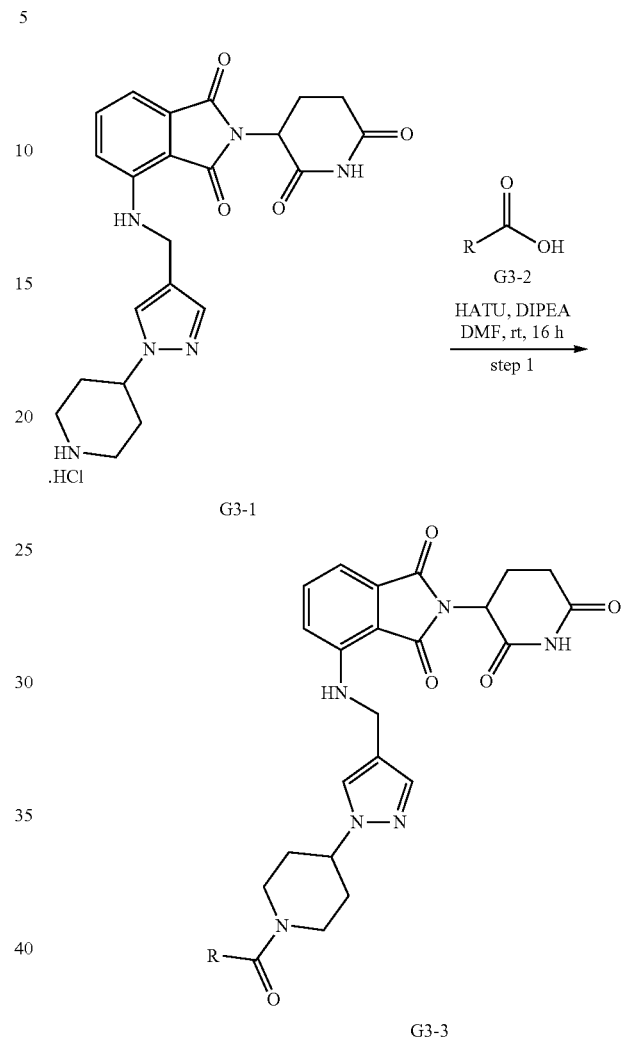

General Procedure A: (Reaction Done on 40 mg Scale to Synthesize Compounds 1-50)

HATU (1.5 mmol) and DIPEA (5.0 mmol) were added to a mixture of G3-1 (1 mmol) and G3-2 [1.2 mmol (0.9 mmol for free —OH acids)] in DMF (1 mL) at 0° C. The resulting solution was stirred at ambient temperature for 16 hours before the reaction mixture was diluted with water and extracted with ethyl acetate. The organic layer was washed with saturated aqueous NaHCO₃ solution, water, and brine, dried over sodium sulfate and concentrated under reduced pressure. The crude mass was purified by preparative TLC plate (eluting with 3% methanol in DCM) to afford G3-3.

General Procedure B (24 Amide Analogs):

To an equi-molar mixture of amine G3-1 and acid G3-2 in DMF (6 mL/mmol) were added HATU (1.5 equiv) and DIPEA (5.0 equiv) at 0° C. The resulting solution was stirred at ambient temperature for 16 hours. The reaction mixture was then diluted with ethyl acetate and washed with aqueous NaHCO₃ solution, water (×3) and brine. The organic layer was dried over anhydrous Na₂SO₄ and concentrated under reduced pressure. The crude mass was purified by Combi-Flash ISCO column eluting with 2% methanol in DCM to afford G3-3.

The following compounds were prepared according to general procedure A in example 1:

| Cmpd No. | Compound with Characterization Data |
| --- | --- |
| 5 | 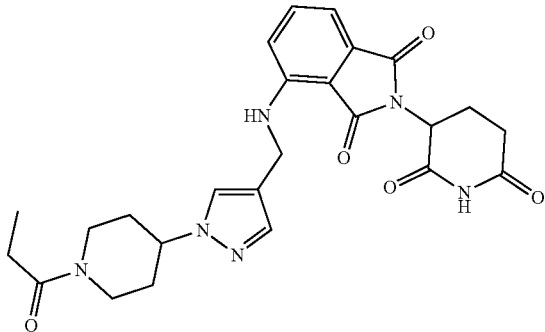 [SMILES: CCC(=O)N1CCC(n2cc(CNc3cccc4c3C(=O)N(C3CCC(=O)NC3=O)C4=O)cn2)CC1]<br>32.0 mg, 61.45% yield, yellow solid; $^1$H NMR (400 MHz, DMSO-d6) δ 11.08 (s, 1H), 7.78 (s, 1H), 7.57 (t, J = 7.84 Hz, 1H), 7.45 (s, 1H), 7.15 (d, J = 8.44 Hz, 1H), 7.03 (d, J = 6.96 Hz, 1H), 6.81-6.80 (m, 1H), 5.04 (dd, J = 12.8, 5.36 Hz, 1H), 4.47-4.34 (m, 4H), 3.94-3.89 (m, 1H), 3.16-3.12 (m, 1H), 2.90-2.82 (m, 1H), 2.68-2.55 (m, 2H), 2.50-2.44 (m, 1H), 2.33 (q, J = 14.88, 7.44 Hz, 2H), 2.02-1.92 (m, 3H), 1.82-1.75 (m, 1H), 0.98 (t, J = 7.34 Hz, 3H); LC MS: ES+ 493.1 |
| 6 | 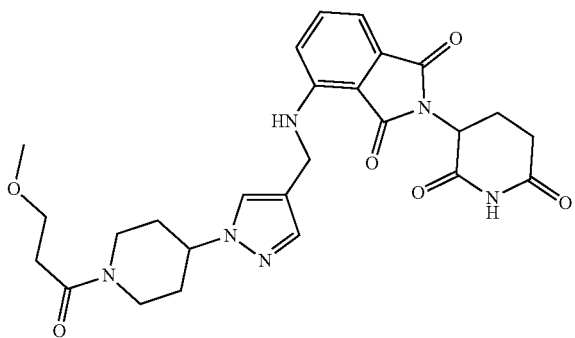 [SMILES: COCCC(=O)N1CCC(n2cc(CNc3cccc4c3C(=O)N(C3CCC(=O)NC3=O)C4=O)cn2)CC1]<br>15.0 mg, 27.15% yield, yellow solid; $^1$H NMR (400 MHz, DMSO-d6) δ 11.08 (s, 1H), 7.77 (s, 1H), 7.57 (t, J = 7.76 Hz, 1H), 7.45 (s, 1H), 7.15 (d, J = 8.44 Hz, 1H), 7.03 (d, J = 7.0 Hz, 1H), 6.81-6.79 (m, 1H), 5.04 (dd, J = 13.0, 5.72 Hz, 1H), 4.46-4.34 (m, 4H), 3.98-3.93 (m, 1H), 3.54 (t, J = 6.5 Hz, 2H), 3.22 (s, 3H), 3.15-3.09 (m, 1H), 2.91-2.84 (m, 1H), 2.72-2.64 (m, 1H), 2.59-2.55 (m, 3H), 2.45-2.42 (m, 1H), 2.05-1.93 (m, 3H), 1.82-1.78 (m, 1H), 1.68-1.64 (m, 1H); LC MS: ES+ 523.5. |
| 7 | 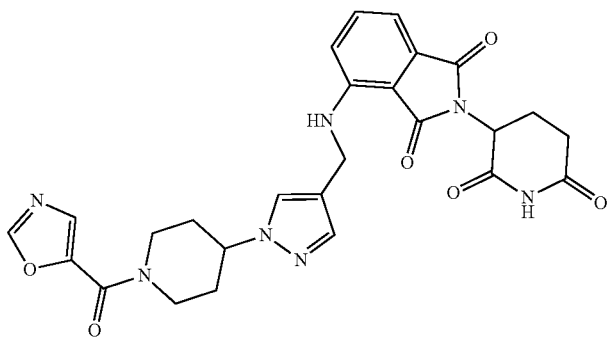 [SMILES: O=C1CCC(N2C(=O)c3cccc(NCc4cnn(C5CCN(C(=O)c6cnco6)CC5)c4)c3C2=O)C(=O)N1]<br>28.0 mg, 49.83% yield, yellow solid; $^1$H NMR (400 MHz, DMSO-d6) δ 11.08 (s, 1H), 8.54 (s, 1H), 7.80 (s, 1H), 7.71 (s, 1H), 7.57 (t, J = 7.82 Hz, 1H), 7.47 (s, 1H), 7.17-7.14 (m, 1H), 7.05-7.02 (m, 1H), 6.84-6.80 (m, 1H), 5.04 (dd, J = 12.8, 5.44 Hz, 1H), 4.52-4.18 (m, 5H), 2.89-2.84 (m, 1H), 2.60-2.55 (m, 2H), 2.51-2.50 (m, 2H), 2.08-2.00 (m, 3H), 1.98-1.85 (m, 2H); LC MS: ES+ 532.3. |

| Cmpd No. | Compound with Characterization Data |
| --- | --- |

8

18.0 mg, 31.03% yield, yellow solid; $^1$H NMR (400 MHz, DMSO-d6) δ 11.08 (s, 1H), 7.78 (s, 1H), 7.57 (t, J = 7.8 Hz, 1H), 7.45 (s, 1H), 7.15 (d, J = 8.6 Hz, 1H), 7.03 (d, J = 7.04 Hz, 1H), 6.81-6.80 (m, 1H), 5.04 (dd, J = 12.8, 5.48 Hz, 1H), 4.47-4.35 (m, 4H), 3.97-3.92 (m, 1H), 3.16-3.12 (m, 1H), 2.92-2.84 (m, 1H), 2.69-2.66 (m, 1H), 2.62-2.60 (m, 1H), 2.51-2.50 (m, 1H), 2.32-2.25 (m, 2H), 2.03-1.93 (m, 3H), 1.84-1.78 (m, 1H), 1.68-1.64 (m, 1H), 1.42-1.38 (m, 2H), 0.88 (s, 9H); LC MS: ES+ 549.25.

9

41.0 mg, 76.56% yield, yellow solid; $^1$H NMR (400 MHz, DMSO-d6) δ 11.08 (s, 1H), 7.79 (s, 1H), 7.57 (t, J = 7.82 Hz, 1H), 7.46 (s, 1H), 7.15 (d, J = 8.56 Hz, 1H), 7.03 (d, J = 7.0 Hz, 1H), 6.83-6.79 (m, 1H), 5.04 (dd, J = 12.8, 5.4 Hz, 1H), 4.60-4.34 (m, 4H), 4.10-3.95 (m, 1H), 3.16-3.14 (m, 1H), 2.92-2.84 (m, 2H), 2.66-2.55 (m, 2H), 2.51-2.50 (m, 1H), 2.03-1.95 (m, 3H), 1.90-1.75 (m, 1H), 1.76-1.55 (m, 1H), 1.01-0.99 (m, 6H); LC MS: ES+ 507.5.

10

31.0 mg 56.99% yield, yellow solid; $^1$H NMR (400 MHz, DMSO-d6) δ 11.08 (s, 1H), 7.78 (s, 1H), 7.57 (d, 7.8 Hz, 1H), 7.47 (s, 1H), 7.15 (d, J = 8.56 Hz, 1H), 7.03 (d, J = 7.04 Hz, 1H), 6.90-6.62 (m, 2H), 5.04 (dd, 12.84, 5.44 Hz, 1H), 4.49-4.32 (m, 4H), 3.97-3.92 (m, 1H), 3.25-3.22 (m, 1H), 2.93-2.84 (m, 2H), 2.60-2.50 (m, 2H), 2.08-1.99 (m, 3H), 1.90-1.85 (m, 1H), 1.78-1.72 (m, 1H); LC MS: ES+ 515.10.

| Cmpd No. | Compound with Characterization Data |
|---|---|
| 11 | 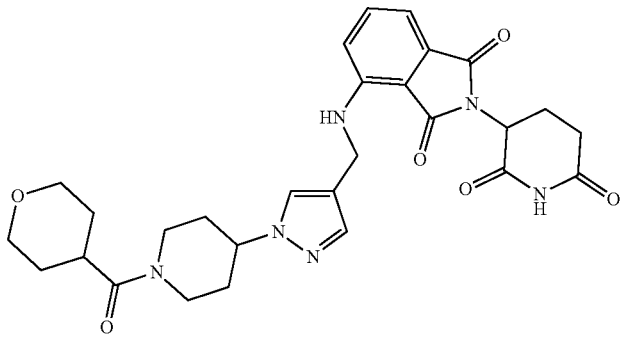

32.0 mg, 55.17% yield, yellow solid; $^1$H NMR (400 MHz, DMSO-d6) δ 11.08 (s, 1H), 7.78 (s, 1H), 7.57 (t, J = 7.84 Hz, 1H), 7.45 (s, 1H), 7.15 (d, J = 8.56 Hz, 1H), 7.03 (d, J = 7.04 Hz, 1H), 6.83-6.79 (m, 1H), 5.04 (dd, J = 12.8, 5.4 Hz, 1H), 4.48-4.34 (m, 4H), 4.09-4.04 (m, 1H), 3.85-3.82 (m, 2H), 3.40-3.34 (m, 2H), 3.20-3.11 (m, 1H), 2.91-2.83 (m, 2H), 2.68-2.50 (m, 2H), 2.04-1.95 (m, 3H), 1.85-1.75 (m, 1H), 1.68-1.48 (m, 5H), 1.26-1.24 (m, 1H); LC MS: ES+ 549.2. |
| 12 | 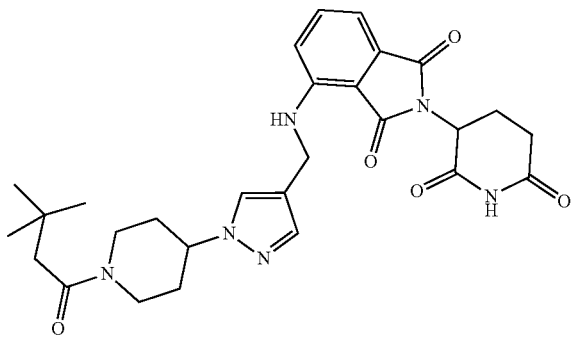 [SMILES: CC(C)(C)CC(=O)N1CCC(n2cc(CNc3cccc4c3C(=O)N(C3CCC(=O)NC3=O)C4=O)cn2)CC1]

25.0 mg, 44.23% yield, yellow solid; $^1$H NMR (400 MHz, DMSO-d6) δ 11.08 (s, 1H), 7.78 (s, 1H), 7.57 (t, J = Hz, 1H), 7.45 (s, 1H), 7.15 (d, J = 8.52 Hz, 1H), 7.03 (d, J = 7.04 Hz, 1H), 6.82-6.79 (m, 1H), 5.04 (dd, J = 12.68, 5.24 Hz, 1H), 4.53-4.49 (m, 1H), 4.40-4.32 (m, 3H), 4.07-4.02 (m, 1H), 3.17-3.09 (m, 1H), 2.92-2.82 (m, 1H), 2.68-2.64 (m, 1H), 2.62-2.60 (m, 1H), 2.55-2.50 (m, 1H), 2.31-2.19 (m, 2H), 2.02-1.95 (m, 3H), 1.79-1.75 (m, 1H), 1.69-1.63 (m, 1H), 1.01 (s, 9H); LC MS: ES+ 535.2. |
| 13 | 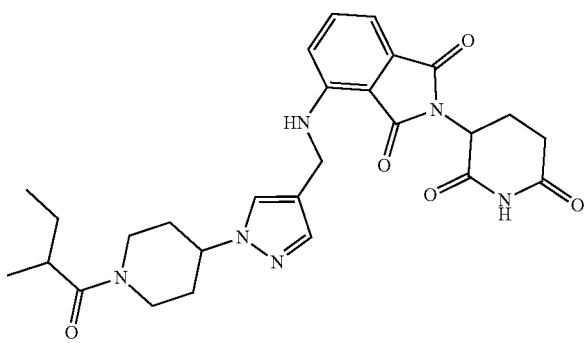 [SMILES: CCC(C)C(=O)N1CCC(n2cc(CNc3cccc4c3C(=O)N(C3CCC(=O)NC3=O)C4=O)cn2)CC1]

21.0 mg, 38.16% yield, yellow solid; $^1$H NMR (400 MHz, DMSO-d6) δ 11.08 (s, 1H), 7.79 (s, 1H), 7.57 (t, J = 7.78 Hz, 1H), 7.46 (s, 1H), 7.15 (dd, J = 8.6 Hz, 1H), 7.03 (d, J = 7.04 Hz, 1H), 6.81-6.79 (m, 1H), 5.05-5.02 (m, 1H), 4.60-4.32 (m, 4H), 4.15-3.98 (m, 1H), 3.23-3.08 (m, 1H), 2.92-2.88 (m, 1H), 2.75-2.70 (m, 1H), 2.67-2.65 (m, 1H), 2.51-2.50 (m, 2H), 2.03-1.99 (m, 3H), 1.90-1.20 (m, 4H), 1.00-0.96 (m, 3H), 0.84-0.80 (m, 3H); LC MS: ES+ 521.6. |

| Cmpd No. | Compound with Characterization Data |
|---|---|
| 14 | 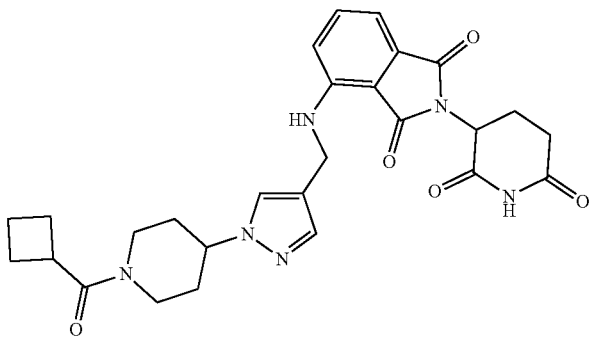 [SMILES: O=C1CCC(N2C(=O)c3cccc(NCc4cnn(C5CCN(C(=O)C6CCC6)CC5)c4)c3C2=O)C(=O)N1]

26.0 mg, 47.42% yield, yellow solid; $^1$H NMR (400 MHz, DMSO-d6) δ 11.08 (s, 1H), 7.77 (s, 1H), 7.57 (t, J = 7.86 Hz, 1H), 7.45 (s, 1H), 7.15 (d, J = 8.6 Hz, 1H), 7.03 (d, J = 7.04 Hz, 1H), 6.81-6.79 (m, 1H), 5.04 (dd, J = 12.84, 5.44 Hz, 1H), 4.45-4.34 (m, 4H), 3.80-3.70 (m, 1H), 3.37-3.33 (m, 1H), 3.31-3.29 (m, 1H), 3.10-3.00 (m, 1H), 2.92-2.50 (m, 3H), 2.19-1.55 (m, 11H); LC MS: ES+ 519.6. |
| 15 | 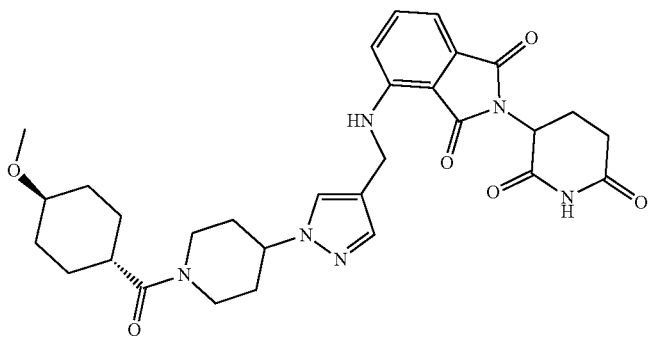 [SMILES: CO[C@H]1CC[C@H](C(=O)N2CCC(n3cc(CNc4cccc5c4C(=O)N(C4CCC(=O)NC4=O)C5=O)cn3)CC2)CC1]

20.0 mg, 32.81% yield, yellow solid; $^1$H NMR (400 MHz, DMSO-d6) δ 11.08 (s, 1H), 7.78 (s, 1H), 7.57 (t, J = 7.82 Hz, 1H), 7.45 (s, 1H), 7.15 (d, J = 8.56 Hz, 1H), 7.03 (d, J = 7.0 Hz, 1H), 6.83-6.79 (m, 1H), 5.04 (dd, J = 12.8, 5.48 Hz, 1H), 4.47-4.34 (m, 4H), 4.02-4.00 (m, 1H), 3.22 (s, 3H), 3.16-3.02 (m, 2H), 2.92-2.84 (m, 1H), 2.69-2.54 (m, 3H), 2.03-1.92 (m, 5H), 1.81-1.75 (m, 1H), 1.70-1.62 (m, 3H), 1.41-1.32 (m, 2H), 1.28-1.24 (m, 1H), 1.22-1.15 (m, 2H); LC MS: ES+ 577.7. |
| 16 | 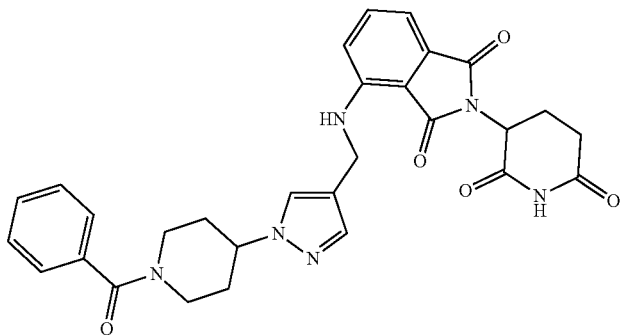 [SMILES: O=C1CCC(N2C(=O)c3cccc(NCc4cnn(C5CCN(C(=O)c6ccccc6)CC5)c4)c3C2=O)C(=O)N1]

13.0 mg, 22.75% yield, yellow solid; $^1$H NMR (400 MHz, DMSO-d6) δ 11.08 (s, 1H), 7.81 (s, 1H), 7.57 (d, J = 7.82 Hz, 1H), 7.47-7.40 (m, 6H), 7.15 (d, J = 8.64 Hz, 1H), 7.03 (d, J = 7.08 Hz, 1H), 6.83-6.80 (m, 1H), 5.07-5.02 (m, 1H), 4.60-4.35 (m, 4H), 3.66-3.58 (br, 1H), 3.22-3.15 (m, 1H), 2.92-2.85 (m, 2H), 2.60-2.50 (m, 2H), 2.03-2.00 (m, 3H), 1.87-1.83 (m, 2H); LC MS: ES+ 541.2. |

| Cmpd No. | Compound with Characterization Data |
|---|---|
| 17 | 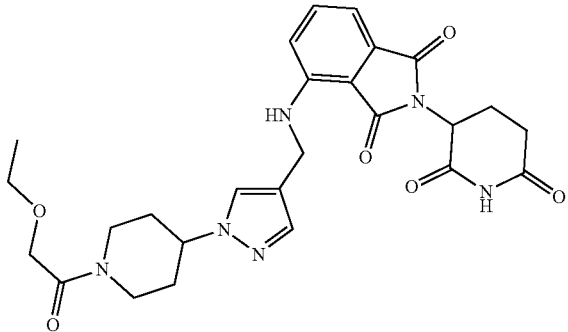 [SMILES: CCOCC(=O)N1CCC(n2cc(CNc3cccc4c3C(=O)N(C3CCC(=O)NC3=O)C4=O)cn2)CC1]

30.0 mg, 54.30% yield, yellow solid; $^1$H NMR (400 MHz, DMSO-d6) δ 11.08 (s, 1H), 7.77 (s, 1H), 7.57 (t, J = 7.84 Hz, 1H), 7.46 (s, 1H), 7.15 (d, J = 8.64 Hz, 1H). 7.03 (d, J = 7.04 HZ, 1H), 6.83-6.79 (m, 1H), 5.04 (dd, J = 12.76, 5.4 Hz, 1H), 4.41-4.35 (m, 4H), 4.14-4.09 (m, 2H), 3.92-3.86 (m, 1H), 3.50-3.44 (m, 2H), 3.12-3.10 (m, 1H), 2.90-2.84 (m, 1H), 2.73-2.65 (m, 1H), 2.60-2.50 (m, 2H), 2.04-1.95 (m, 3H), 1.85-1.81 (m, 1H), 1.72-1.69 (m, 1H), 1.12 (t, J = 6.98 Hz, 3H); LC MS: ES+ 523.5. |
| 18 | 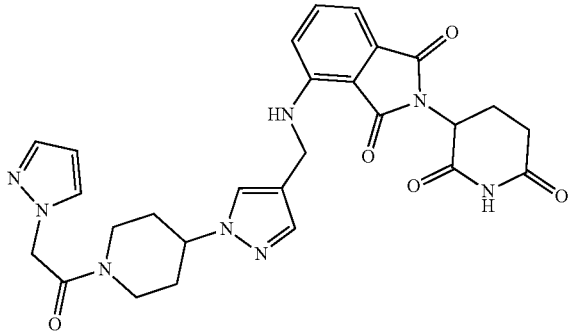 [SMILES: O=C1CCC(N2C(=O)c3cccc(NCc4cnn(C5CCN(C(=O)Cn6cccn6)CC5)c4)c3C2=O)C(=O)N1]

35.0 mg, 60.79% yield, yellow solid; $^1$H NMR (400 MHz, DMSO-d6) δ 11.09 (s, 1H), 7.77 (s, 1H), 7.65-7.64 (m, 1H), 7.57 (t, J = 7.8 Hz, 1H), 7.47 (s, 1H), 7.42-7.41 (m, 1H), 7.16 (d, J = 8.56 Hz, 1H), 7.04 (d, J = 7.0 Hz, 1H), 6.84-6.81 (m, 1H), 6.25-6.24 (m, 1H), 5.20-5.02 (m, 3H), 4.44-4.36 (m, 4H), 4.02-3.97 (m, 1H), 3.29-3.16 (m, 1H), 2.90-2.73 (m, 2H), 2.60-2.50 (m, 2H), 2.04-2.00 (m, 3H), 1.89-1.86 (m, 1H), 1.73-1.69 (m, 1H); LC MS: ES+ 545.5. |
| 19 | 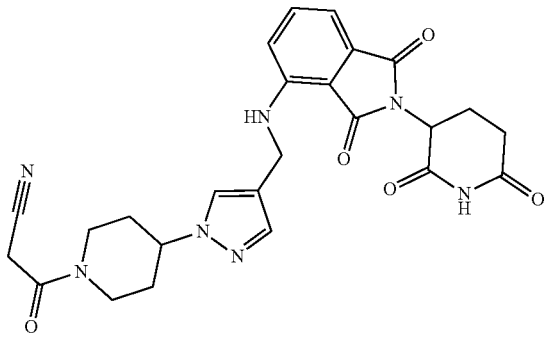 [SMILES: N#CCC(=O)N1CCC(n2cc(CNc3cccc4c3C(=O)N(C3CCC(=O)NC3=O)C4=O)cn2)CC1]

19.0 mg, 35.69% yield, yellow solid; $^1$H NMR (400 MHz, DMSO-d6) δ 11.08 (s, 1H), 7.76 (s, 1H), 7.57 (t, J = 7.82 Hz, 1H), 7.46 (s, 1H), 7.15 (d, J = 8.64 Hz, 1H), 7.03 (d, J = 7.04 Hz, 1H), 6.83-6.81 (m, 1H), 5.06-5.02 (m, 1H), 4.40-4.35 (m, 4H), 4.09-4.06 (m, 2H), 3.75-3.65 (m, 1H), 3.20-2.50 (m, 5H), 2.02-1.87 (m, 4H), 1.73-1.70 (m, 1H); LC MS: ES+ 504.3. |

| Cmpd No. | Compound with Characterization Data |
|---|---|
| 20 | 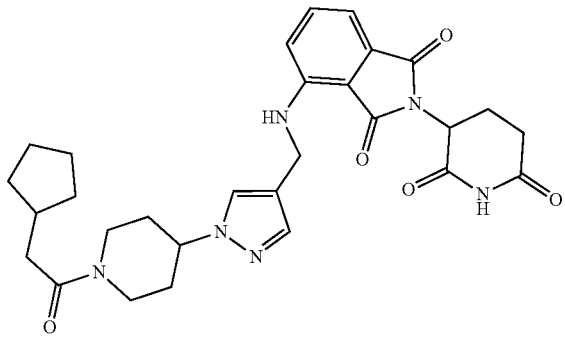 [SMILES: O=C1CCC(N2C(=O)c3cccc(NCc4cnn(C5CCN(C(=O)CC6CCCC6)CC5)c4)c3C2=O)C(=O)N1]

27.0 mg, 46.72% yield, yellow solid; ¹H NMR (400 MHz, DMSO-d6) δ 11.08 (s, 1H), 7.78 (s, 1H), 7.57 (t, J = 7.82 Hz, 1H), 7.45 (s, 1H), 7.15 (d, J = 8.56 Hz, 1H), 7.03 (d, J = 7.04 Hz, 1H), 6.82-6.79 (m, 1H), 5.04 (dd, J = 12.84, 5.44 Hz, 1H), 4.50-4.32 (m, 4H), 4.00-3.92 (m, 1H), 3.20-3.10 (m, 1H), 2.89-2.84 (m, 1H), 2.72-2.50 (m, 3H), 2.35-2.32 (m, 2H), 2.15-2.10 (m, 1H), 2.05-1.93 (m, 3H), 1.79-1.70 (m, 3H), 1.68-1.45 (m, 5H), 1.15-1.10 (m, 2H); LC MS: ES+ 547.22. |
| 21 | 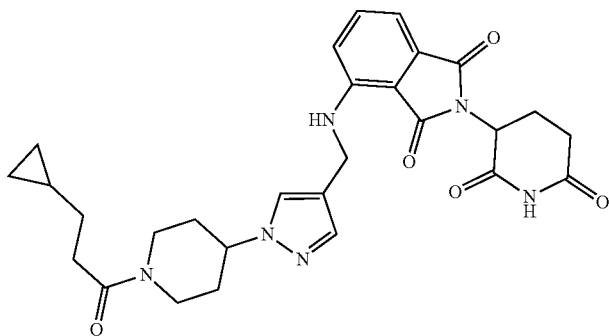 [SMILES: O=C1CCC(N2C(=O)c3cccc(NCc4cnn(C5CCN(C(=O)CCC6CC6)CC5)c4)c3C2=O)C(=O)N1]

15.0 mg, 26.64% yield, yellow solid; ¹H NMR (400 MHz, DMSO-d6) δ 11.08 (s, 1H), 7.78 (s, 1H), 7.57 (t, J = 7.84 Hz, 1H), 7.45 (s, 1H), 7.15 (d, J = 8.56 Hz, 1H), 7.03 (d, J = 7.04 Hz, 1H), 5.06-5.02 (m, 1H), 4.55-4.33 (m, 4H), 4.01-3.98 (m, 1H), 3.20-3.10 (m, 1H), 2.92-2.50 (m, 4H), 2.43-2.39 (m, 2H), 2.03-1.97 (m, 3H), 1.85-1.65 (m, 2H), 1.41-1.38 (m, 2H), 0.75-0.65 (m, 1H), 0.38-0.35 (m, 2H), 0.04-0.02 (m, 2H); LC MS: ES+ 533.6. |
| 22 | 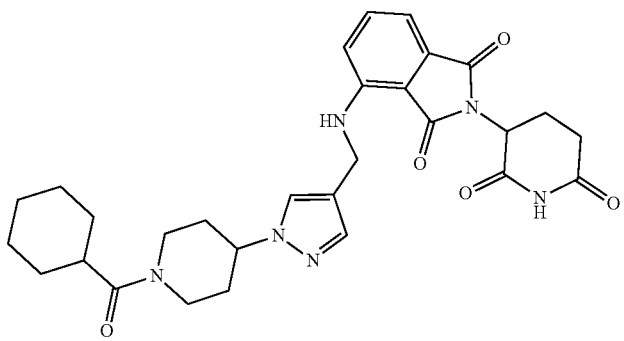 [SMILES: O=C1CCC(N2C(=O)c3cccc(NCc4cnn(C5CCN(C(=O)C6CCCCC6)CC5)c4)c3C2=O)C(=O)N1]

41.0 mg, 70.95% yield, yellow solid; ¹H NMR (400 MHz, DMSO-d6) δ 11.08 (s, 1H), 7.79 (s, 1H), 7.57 (t, J = 7.8 Hz, 1H), 7.45 (s, 1H), 7.15 (d, J = 8.56 Hz, 1H), 7.03 (d, J = Hz, 1H), 6.82-6.79 (m, 1H), 5.04 (dd, J=12.76, 5.36 Hz, 1H), 4.50-4.35 (m, 4H), 4.03-3.98 (m, 1H), 3.15-3.13 (m, 1H), 2.89-2.82 (m, 1H), 2.73-2.55 (m, 2H), 2.03-1.94 (m, 3H), 1.82-1.60 (m, 7H), 1.34-1.15 (m, 7H); LC MS: ES+ 547.21. |

| Cmpd No. | Compound with Characterization Data |
|---|---|

23

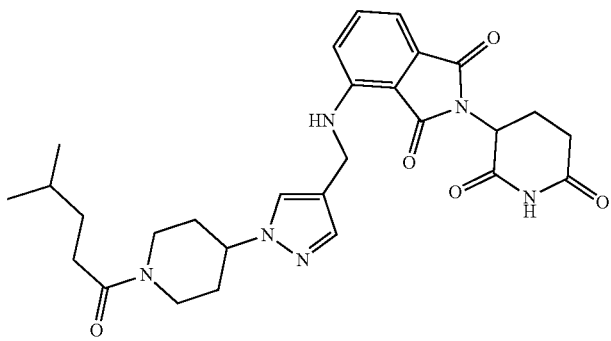 [SMILES: CC(C)CCC(=O)N1CCC(n2cc(CNc3cccc4c3C(=O)N(C3CCC(=O)NC3=O)C4=O)cn2)CC1]

31.0 mg, 54.85% yield, yellow solid; $^1$H NMR (400 MHz, DMSO-d6) δ 11.08 (s, 1H), 7.78 (s, 1H), 7.57 (t, J = 7.76 Hz, 1H), 7.45 (s, 1H), 7.15 (d, J = 8.56 Hz, 1H), 7.03 (d, J = 7.0 Hz, 1H), 6.83-6.79 (m, 1H), 5.04 (dd, J = 12.76, 5.36 Hz, 1H), 4.61-4.34 (m, 4H), 3.97-3.92 (m, 1H), 3.17-3.10 (m, 1H), 2.90-2.83 (m, 1H), 2.70-2.55 (m, 2H), 2.50-2.49 (m, 1H), 2.34-2.28 (m, 2H), 2.03-1.97 (m, 3H), 1.85-1.76 (m, 1H), 1.68-1.63 (m, 1H), 1.56-1.50 (m, 2H), 0.87-0.84 (m, 6H); LC MS: ES+ 535.24.

24

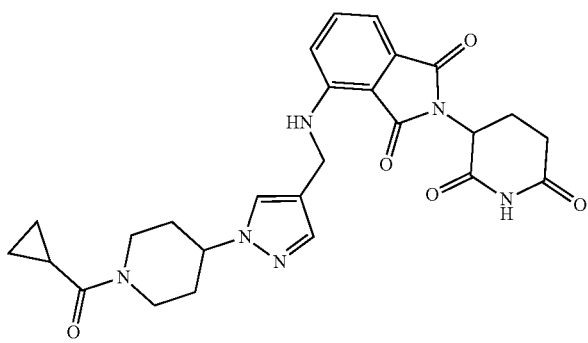 [SMILES: O=C1CCC(N2C(=O)c3cccc(NCc4cnn(C5CCN(C(=O)C6CC6)CC5)c4)c3C2=O)C(=O)N1]

27.0 mg, 50.62% yield, yellow solid; $^1$H NMR (400 MHz, DMSO-d6) δ 11.08 (s, 1H), 7.80 (s, 1H), 7.57 (t, J = 7.8 Hz, 1H), 7.46 (s, 1H), 7.15 (d, J = 8.6 Hz, 1H), 7.03 (d, J = 7.04 Hz, 1H), 6.83-6.79 (m, 1H), 5.04 (dd, J = 12.48, 5.16 Hz, 1H), 4.43-4.34 (m, 5H), 3.28-3.25 (m, 1H), 2.89-2.84 (m, 1H), 2.69-2.66 (m, 1H), 2.60-2.50 (m, 2H), 2.05-2.00 (m, 4H), 1.92-1.80 (m, 1H), 1.70-1.62 (m, 1H), 0.71-0.68 (m, 4H); LC MS: ES+ 505.5.

25

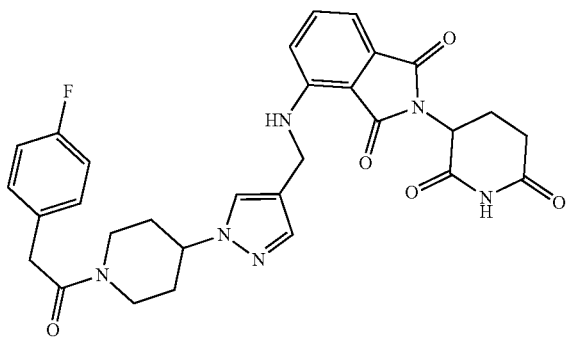 [SMILES: O=C1CCC(N2C(=O)c3cccc(NCc4cnn(C5CCN(C(=O)Cc6ccc(F)cc6)CC5)c4)c3C2=O)C(=O)N1]

18.0 mg, 29.73% yield, yellow solid; $^1$H NMR (400 MHz, DMSO-d6) δ 11.08 (s, 1H), 7.75 (s, 1H), 7.57 (t, J = 7.8 Hz, 1H), 7.45 (s, 1H), 7.28-7.24 (m, 2H), 7.17-7.09 (m, 3H), 7.05-7.02 (m, 1H), 6.83-6.79 (m, 1H), 5.04 (dd, J = 5.36, 12.72 Hz, 1H), 4.55-4.34 (m, 4H), 4.05-4.00 (m, 1H), 3.73 (s, 2H), 3.16-3.12 (m, 1H), 2.92-2.50 (4H), 1.97-1.93 (m, 3H), 1.70-1.65 (m, 2H); LC MS: ES+ 573.6.

| Cmpd No. | Compound with Characterization Data |
|---|---|

26

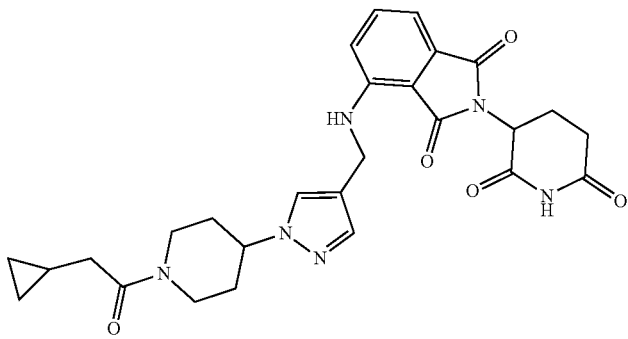 [SMILES: O=C1CCC(N2C(=O)c3cccc(NCc4cnn(C5CCN(C(=O)CC6CC6)CC5)c4)c3C2=O)C(=O)N1]

30.0 mg, 49.74% yield, yellow solid; $^1$H NMR (400 MHz, DMSO-d6) δ 11.08 (s, 1H), 7.78 (s, 1H), 7.57 (t, J = 7.86 Hz, 1H), 7.45 (s, 1H), 7.15 (d, J = 8.6 Hz, 1H), 7.03 (d, J = 7.08 Hz, 1H), 6.82-6.79 (m, 1H), 5.04 (dd, 12.96, 5.48 Hz, 1H), 4.48-4.34 (m, 4H), 3.93-3.88 (m, 1H), 3.16-3.09 (m, 1H), 2.92-2.82 (m, 1H), 2.70-2.55 (m, 3H), 2.28-2.26 (m, 2H), 2.02-1.96 (m, 3H), 1.82-1.77 (m, 1H), 1.68-1.66 (m, 1H), 0.96-0.93 (m, 1H), 0.45-0.43 (m, 2H), 0.12-0.10 (m, 2H); LC MS: ES+ 519.18.

27

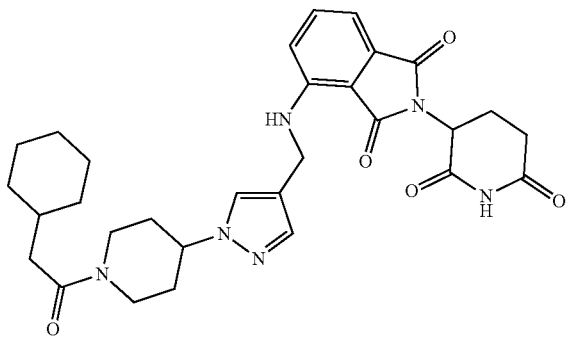 [SMILES: O=C1CCC(N2C(=O)c3cccc(NCc4cnn(C5CCN(C(=O)CC6CCOCC6)CC5)c4)c3C2=O)C(=O)N1]

18.0 mg, 30.37% yield, yellow solid; $^1$H NMR (400 MHz, DMSO-d6) δ 11.08 (s, 1H), 7.77 (s, 1H), 7.57 (t, J = 7.82 Hz, 1H), 7.45 (s, 1H), 7.15 (d, J = 8.56 Hz, 1H), 7.03 (d, J = 7.04 Hz, 1H), 6.82-6.78 (m, 1H), 5.04 (dd, J = 12.8, 5.44 Hz, 1H), 4.48-4.32 (m, 4H), 3.98-3.94 (m, 1H), 3.16-3.09 (m, 1H), 2.92-2.84 (m, 1H), 2.69-2.55 (m, 3H), 2.21-2.19 (m, 2H), 2.02-1.93 (m, 3H), 1.78-1.59 (m, 8H), 1.24-1.08 (m, 4H), 0.97-0.90 (m, 2H); LC MS: ES+ 561.29.

28

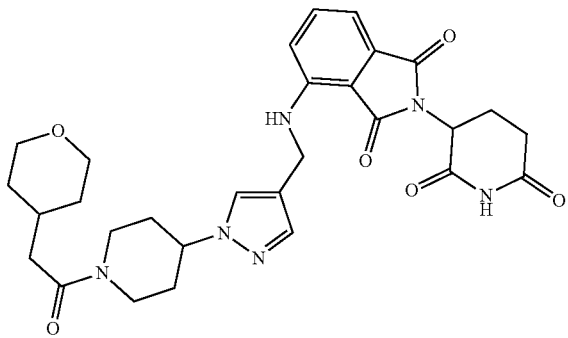

21.0 mg, 35.30% yield, yellow solid; $^1$H NMR (400 MHz, DMSO-d6) δ 11.09 (s, 1H), 7.78 (s, 1H), 7.57 (t, J = 7.96 Hz, 1H), 7.46 (s, 1H), 7.15 (d, J = 8.48 Hz, 1H), 7.03 (d, J = 6.92 Hz, 1H), 6.83-6.79 (m, 1H), 5.04 (dd, J = 12.96, 5.84 Hz, 1H), 4.47-4.35 (m, 4H), 4.01-3.94 (m, 1H), 3.83-3.79 (m, 2H), 3.16-3.09 (m, 1H), 2.92-2.84 (m, 1H), 2.67-2.55 (m, 3H), 2.52-2.50 (m, 1H), 2.28-2.26 (m, 2H), 2.00-1.90 (m, 4H), 1.79-1.76 (m, 1H), 1.67-1.64 (m, 1H), 1.60-1.55 (m, 2H), 1.23-1.16 (m, 3H); LC MS: ES+ 563.19.

| Cmpd No. | Compound with Characterization Data |
|---|---|
| 29 | 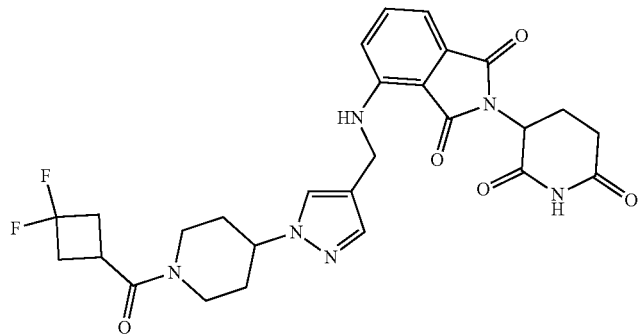 [SMILES: O=C1CCC(N2C(=O)c3cccc(NCc4cnn(C5CCN(C(=O)C6CC(F)(F)C6)CC5)c4)c3C2=O)C(=O)N1]<br>15.0 mg, 25.58% yield, yellow solid; ¹H NMR (400 MHz, DMSO-d6) δ 11.09 (s, 1H), 7.78 (s, 1H), 7.57 (t, J = 7.8 Hz, 1H), 7.45 (s, 1H), 7.15 (d, J = 8.56 Hz, 1H), 7.03 (d, J = 7.0 Hz, 1H), 6.82-6.79 (m, 1H), 5.04 (dd, J = 12.8, 5.52 Hz, 1H), 4.44-4.34 (m, 4H), 3.85-3.80 (m, 1H), 3.27-3.25 (m, 1H), 3.15-3.08 (m, 1H), 2.90-2.73 (m, 6H), 2.71-2.50 (m, 2H), 2.05-1.96 (m, 3H), 1.79-1.71 (m, 2H); LC MS: ES+ 555.3. |
| 30 | 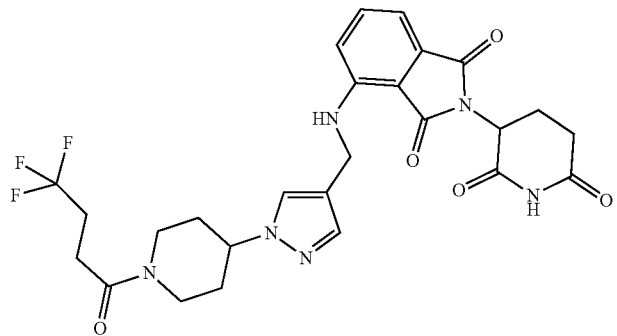 [SMILES: O=C1CCC(N2C(=O)c3cccc(NCc4cnn(C5CCN(C(=O)CCC(F)(F)F)CC5)c4)c3C2=O)C(=O)N1]<br>15.0 mg, 25.31% yield, yellow solid; ¹H NMR (400 MHz, DMSO-d6) δ 11.08 (s, 1H), 7.77 (s, 1H), 7.57 (t, J = 7.8 Hz, 1H), 7.46 (s, 1H), 7.15 (d, J = 8.6 Hz, 1H), 7.03 (d, J = 7.04 Hz, 1H), 6.83-6.79 (m, 1H), 5.04 (dd, J=12.8, 5.44 Hz, 1H), 4.46-4.34 (m, 4H), 3.96-3.92 (m, 1H), 3.17-3.10 (m, 1H), 2.92-2.84 (m, 1H), 2.75-2.50 (m, 7H), 2.02-1.98 (m, 3H), 1.85-1.82 (m, 1H), 1.71-1.67 (m, 1H); LC MS: ES+ 561.2. |
| 31 | 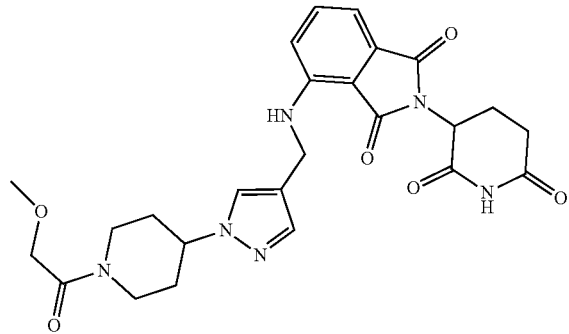<br>30.0 mg, 55.80% yield, yellow solid; ¹H NMR (400 MHz, DMSO-d6) δ 11.08 (s, 1H), 7.77 (s, 1H), 7.57 (t, J = 7.82 Hz, 1H), 7.46 (s, 1H), 7.15 (d, J = 8.56 Hz, 1H), 7.03 (d, J = 7.04 Hz, 1H), 6.82-6.79 (m, 1H), 5.04 (dd, J = 12.76, 5.48 Hz, 1H), 4.45-4.34 (m, 4H), 4.14-4.04 (m, 2H), 2.86-3.80 (m, 1H), 3.28 (s, 3H), 3.14-3.07 (m, 1H), 2.92-2.82 (m, 1H), 2.75-2.65 (m, 1H), 2.61-2.50 (m, 2H), 2.03-1.95 (m, 3H), 1.85-1.80 (m, 1H), 1.71-1.67 (m, 1H); LC MS: ES+ 509.3. |

| Cmpd No. | Compound with Characterization Data |
|---|---|
| 32 | 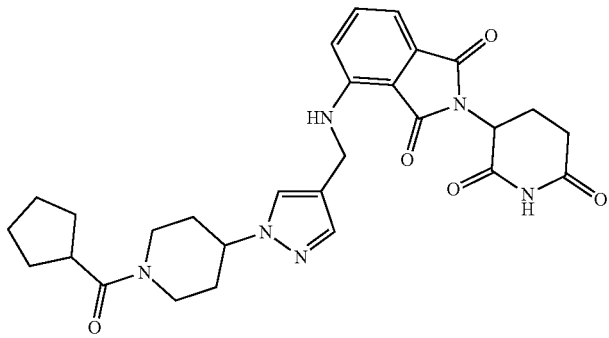 [SMILES: O=C1CCC(N2C(=O)c3cccc(NCc4cnn(C5CCN(C(=O)C6CCCC6)CC5)c4)c3C2=O)C(=O)N1]<br>30.0 mg, 53.28% yield, yellow solid; $^1$H NMR (400 MHz, DMSO-d6) δ 11.08 (s, 1H), 7.79 (s, 1H), 7.57 (t, J = 7.82 Hz, 1H), 7.45 (s, 1H), 7.15 (d, J = 8.56 Hz, 1H), 7.03 (d, J = 7.04 Hz, 1H), 6.82-6.79 (m, 1H), 5.04 (dd, J = 12.88, 5.48 Hz, 1H), 4.75-4.34 (m, 4H), 4.08-4.02 (m, 1H), 3.17-3.10 (m, 1H), 3.01-2.98 (m, 1H), 2.89-2.82 (m, 1H), 2.71-2.50 (m, 3H), 2.03-1.94 (m, 3H), 1.78-1.45 (m, 10 H); LC MS: ES+ 533.3. |
| 33 | 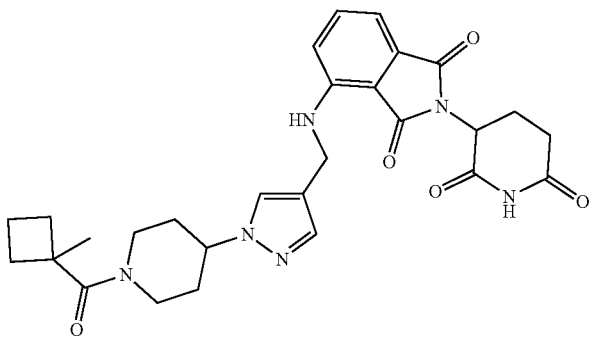 [SMILES: CC1(C(=O)N2CCC(n3cc(CNc4cccc5c4C(=O)N(C4CCC(=O)NC4=O)C5=O)cn3)CC2)CCC1]<br>40.0 mg, 71.04% yield, yellow solid; $^1$H NMR (400 MHz, DMSO-d6) δ 11.08 (s, 1H), 7.80 (s, 1H), 7.57 (t, J = 7.82 Hz, 1H), 7.45 (s, 1H), 7.15 (d, J = 8.56 Hz, 1H), 7.03 (d, J = 7.04 Hz, 1H), 6.83-6.79 (m, 1H), 5.04 (dd, J = 12.76, 5.44 Hz, 1H), 4.40-4.34 (m, 4H), 3.65-3.55 (m, 1H), 3.17-3.06 (m, 1H), 2.92-2.82 (m, 1H), 2.67-2.50 (m, 3H), 2.46-2.35 (m, 2H), 2.04-1.58 (m, 9H), 1.35 (s, 3H); LC MS: ES+ 533.3. |
| 34 | 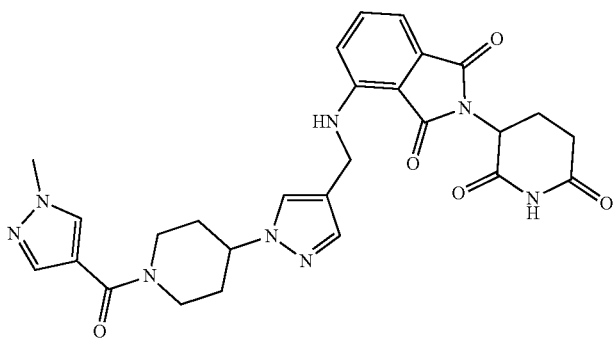 [SMILES: Cn1cc(C(=O)N2CCC(n3cc(CNc4cccc5c4C(=O)N(C4CCC(=O)NC4=O)C5=O)cn3)CC2)cn1]<br>27.0 mg, 46.90% yield, yellow solid; $^1$H NMR (400 MHz, DMSO-d6) δ 11.08 (S, 1H), 7.81 (s, 1H), 7.57 (t, J = 7.86 Hz, 1H), 7.48-7.45 (m, 2H), 7.15 (d, J = 8.56 Hz, 1H), 7.03 (d, J = 7.04 Hz, 1H), 6.84-6.79 (m, 1H), 6.49-6.46 (m, 1H), 5.04 (dd, J = 12.8, 5.36 Hz, 1H), 4.48-4.41 (m, 2H), 4.37-4.35 (m, 2H), 3.85-3.82 (m, 4H), 3.29-3.28 (m, 1H), 2.98-2.82 (m, 2H), 2.66-2.50 (m, 2H), 2.05-2.00 (m, 3H), 1.89-1.80 (m, 2H); LC MS: ES+ 545.3. |

| Cmpd No. | Compound with Characterization Data |
|---|---|
| 35 | 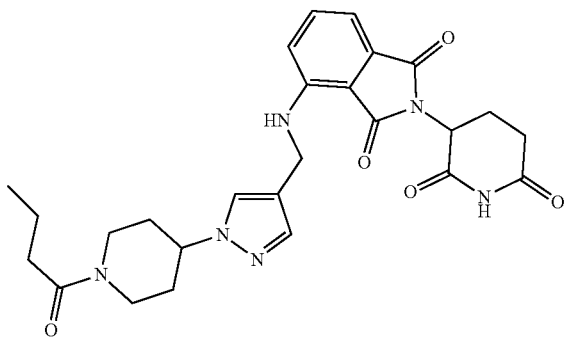

29.0 mg, 54.15% yield, yellow solid; ¹H NMR (400 MHz, DMSO-d6) δ 11.09 (s, 1H), 7.78 (s, 1H), 7.57 (t, J = 7.88 Hz, 1H), 7.45 (s, 1H), 7.15 (d, J = 8.6 Hz, 1H), 7.03 (d, J = 7.0 Hz, 1H), 6.83-6.79 (m, 1H), 5.04 (dd, J = 12.8, 5.32 Hz, 1H), 4.68-4.34 (m, 4H), 3.96-3.92 (m, 1H), 3.15-3.10 (m, 1H), 2.89-2.86 (m, 1H), 2.66-2.50 (3H), 2.30 (t, J = 7.38 Hz, 2H), 2.01-1.94 (m, 3H), 2.92-2.65 (m, 2H), 1.53-1.48 (m, 2H), 0.88 (t, J = 7.36 Hz, 3H); LC MS: ES+ 507.3. |
| 36 | 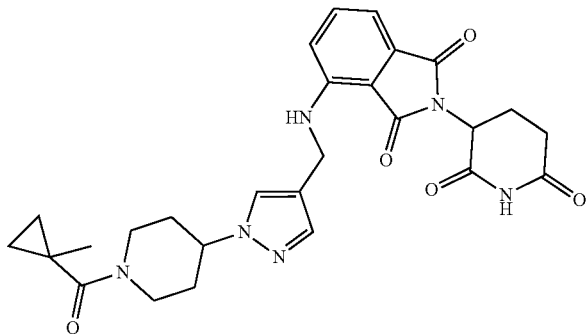 [SMILES: CC1(C(=O)N2CCC(n3cc(CNc4cccc5c4C(=O)N(C4CCC(=O)NC4=O)C5=O)cn3)CC2)CC1]

26.0 mg, 47.42% yield, yellow solid; ¹H NMR (400 MHz, DMSO-d6) δ 11.08 (s, 1H), 7.80 (s, 1H), 7.57 (t, J = 7.82 Hz, 1H), 7.46 (s, 1H), 7.15 (d, J = 8.6 Hz, 1H), 7.03 (d, J = 7.04 Hz, 1H), 6.83-6.79 (m, 1H), 5.04 (dd, J = 12.72, 5.4 Hz, 1H), 4.41-4.30 (m 5H), 2.93-2.83 (m, 3H), 2.60-2.50 (m, 2H), 2.02-1.99 (m, 3H), 1.79-1.73 (m, 2H), 1.22 (s, 3H), 0.81-0.78 (m, 2H), 0.54-0.53 (m, 2H); LC MS: ES+ 519.3. |
| 37 | 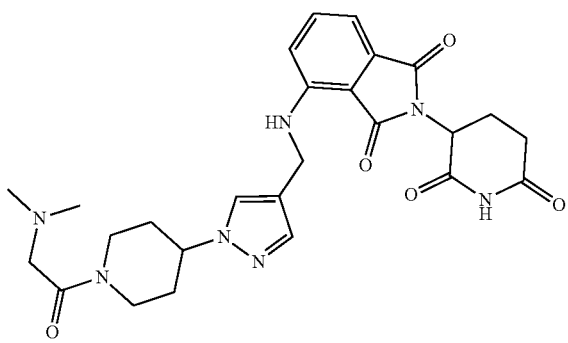 [SMILES: CN(C)CC(=O)N1CCC(n2cc(CNc3cccc4c3C(=O)N(C3CCC(=O)NC3=O)C4=O)cn2)CC1]

13.0 mg, 23.58% yield, yellow solid; ¹H NMR (400 MHz, DMSO-d6) δ 11.09 (s, 1H), 7.77 (s, 1H), 7.57 (t, J = 7.8 Hz, 1H), 7.46 (s, 1H), 7.15 (d, J = 8.52 Hz, 1H), 7.04 (d, J = 7.04 Hz, 1H), 6.83-6.79 (m, 1H), 5.04 (dd, J = 12.74, 5.36 Hz, 1H), 4.43-4.34 (m, 4H), 4.13-4.07 (m, 1H), 3.17-3.07 (m, 3H), 2.92-2.50 (m, 4H), 2.20 (s, 6H), 2.04-1.95 (m, 3H), 1.92-1.62 (m, 2H); LC MS: ES+ 522.3. |

| Cmpd No. | Compound with Characterization Data |
| --- | --- |
| 38 | 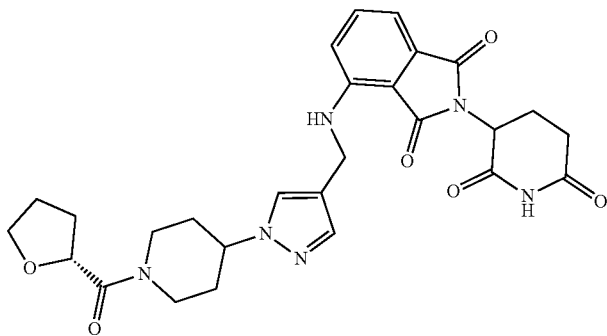 [SMILES: O=C1CCC(N2C(=O)c3cccc(NCc4cnn(C5CCN(C(=O)[C@H]6CCCO6)CC5)c4)c3C2=O)C(=O)N1]

36.0 mg, 63.70% yield, yellow solid; $^1$H NMR (400 MHz, DMSO-d6) δ 11.08 (s, 1H), 7.78 (s, 1H), 7.57 (t, J = 7.78 Hz, 1H), 7.45 (s, 1H), 7.15 (d, J = 8.56 Hz, 1H), 7.03 (d, J = 7.00 Hz, 1H), 6.83-6.79 (m, 1H), 5.04 (dd, J = 12.72, 5.32 Hz, 1H), 4.70-4.65 (m, 1H), 4.42-4.35 (m, 4H), 4.09-4.04 (m, 1H), 3.81-3.72 (m, 2H), 3.16-3.11 (m, 1H), 2.88-2.50 (m, 4H), 2.04-1.97 (m, 5H), 1.84-1.78 (m, 3H), 1.70-1.66 (m, 1H); LC MS: ES+ 535.3. |
| 39 | 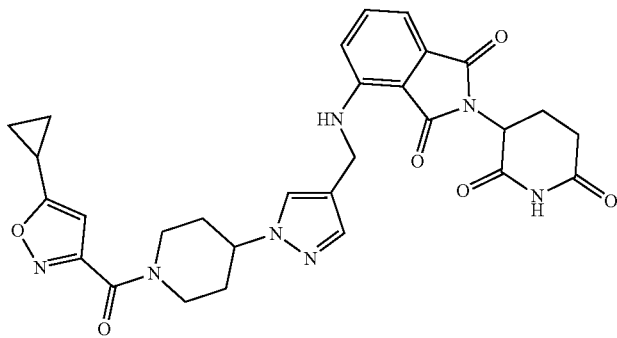 [SMILES: O=C1CCC(N2C(=O)c3cccc(NCc4cnn(C5CCN(C(=O)c6cc(C7CC7)on6)CC5)c4)c3C2=O)C(=O)N1]

12.0 mg, 19.86% yield, yellow solid; $^1$H NMR (400 MHz, DMSO-d6) δ 11.08 (s, 1H), 7.80 (s, 1H), 7.57 (t, J = 7.84 Hz, 1H), 7.46 (s, 1H), 7.15 (d, J = 8.56 Hz, 1H), 7.03 (d, J = 7.08 Hz, 1H), 6.83-6.79 (m, 1H), 6.43 (s, 1H), 5.04 (dd, J = 12.96, 5.52 Hz, 1H), 4.52-4.37 (m, 4H), 4.00-3.96 (m, 1H), 3.29-2.50 (m, 5H), 2.32-1.79 (m, 5H), 1.23-0.91 (m, 5H); LC MS: ES+ 572.2. |
| 40 | 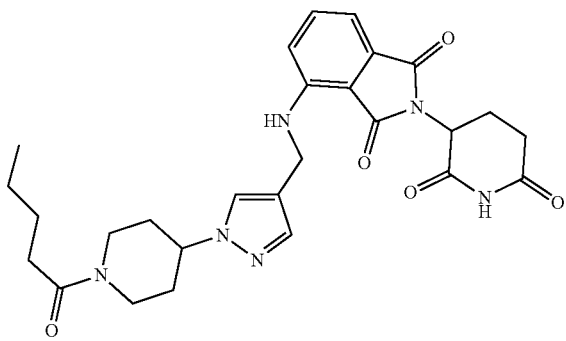 [SMILES: CCCCC(=O)N1CCC(n2cc(CNc3cccc4c3C(=O)N(C3CCC(=O)NC3=O)C4=O)cn2)CC1]

25.0 mg, 45.42% yield, yellow solid; $^1$H NMR (400 MHz, DMSO-d6) δ 11.08 (s, 1H), 7.78 (s, 1H), 7.57 (t, J = 7.84 Hz, 1H), 7.45 (s, 1H), 7.15 (d, J = 8.56 Hz, 1H), 7.03 (d, J = 7.08 Hz, 1H), 5.04 (m, 1H), 4.52-4.34 (m, 4H), 4.00-3.95 (m, 1H), 3.17-2.65 (m, 4H), 2.32 (t, J = 7.46 Hz, 2H), 2.05-1.27 (m, 10H), 0.87 (t, J = 7.32 Hz, 3H); LC MS: ES+ 521.3. |

| Cmpd No. | Compound with Characterization Data |
|---|---|
| 41 | 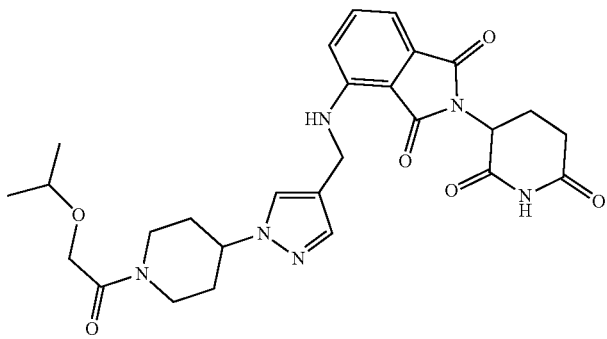 [SMILES: CC(C)OCC(=O)N1CCC(n2cc(CNc3cccc4c3C(=O)N(C3CCC(=O)NC3=O)C4=O)cn2)CC1]

4.0 mg, 7.05% yield, yellow solid; $^1$H NMR (400 MHz, DMSO-d6) δ 11.09 (s, 1H), 7.77 (s, 1H), 7.57 (t, J = 7.76 Hz, 1H), 7.46 (s, 1H), 7.15 (d, J = 8.56 Hz, 1H), 7.03 (d, J = 6.92 Hz, 1H), 6.83-6.79 (m, 1H), 5.06-5.02 (m, 1H), 4.38-4.35 (m, 4H), 4.10-4.08 (m, 2H), 4.00-3.95 (m, 1H), 3.61-3.57 (m, 1H), 3.12-2.50 (m, 5H), 2.02-1.58 (m, 5H), 1.11-1.09 (m, 6H) ); LC MS: ES+ 537.3. |
| 42 | 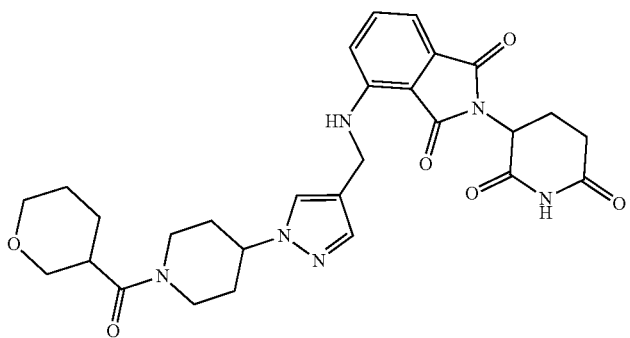 [SMILES: O=C1CCC(N2C(=O)c3cccc(NCc4cnn(C5CCN(C(=O)C6CCCOC6)CC5)c4)c3C2=O)C(=O)N1]

33.0 mg, 52.51% yield, yellow solid; $^1$H NMR (400 MHz, DMSO-d6) δ 11.08 (s, 1H), 7.78 (s, 1H), 7.57 (t, J = 7.82 Hz, 1H), 7.45 (s, 1H), 7.15 (d, J = 8.6 Hz, 1H), 7.03 (d, J = 7.08 Hz, 1H), 6.83-6.79 (m, 1H), 5.04 (dd, J = 12.8, 5.4 Hz, 1H), 4.45-4.35 (m, 4H), 4.05-4.01 (m, 1H), 3.81-3.79 (m, 2H), 3.34-2.50 (m, 8H), 2.03-1.56 (m, 9H); LC MS: ES+ 549.3. |
| 43 | 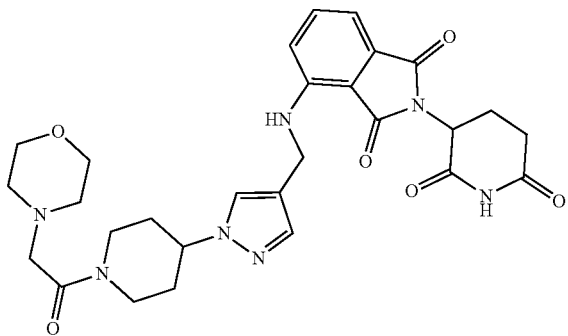 [SMILES: O=C1CCC(N2C(=O)c3cccc(NCc4cnn(C5CCN(C(=O)CN6CCOCC6)CC5)c4)c3C2=O)C(=O)N1]

6.0 mg, 10.07% yield, yellow solid; $^1$H NMR (400 MHz, DMSO-d6) δ 11.08 (s, 1H), 7.77 (s, 1H), 7.57 (t, J = 7.5 Hz, 1H), 7.46 (s, 1H), 7.15 (d, J = 8.4 Hz, 1H), 7.03 (d, J = 6.68 Hz, 1H), 6.83-6.79 (m, 1H), 5.04 (dd, J = 12.4, 5.4 Hz, 1H), 4.42-4.35 (m, 4H), 3.55 (br s, 4H), 3.16-3.01 (m, 2H), 2.88-2.83 (m, 1H), 2.71-2.50 (m, 4H), 2.39 (br s, 4H), 2.34-2.32 (m, 1H), 2.03-1.98 (m 2H), 1.88-1.84 (m, 1H), 1.67-1.65 (m, 1H); LC MS: ES+ 564.21. |

| Cmpd No. | Compound with Characterization Data |
|---|---|
| 44 | 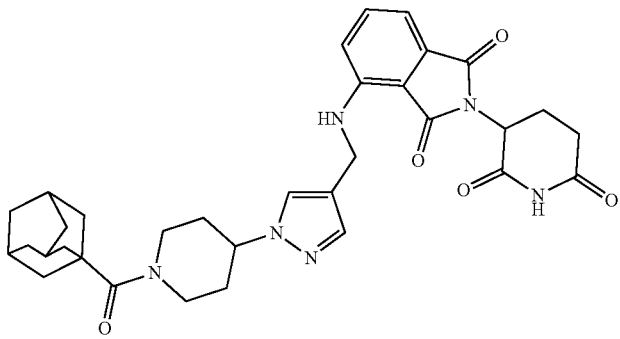 [SMILES: O=C1CCC(N2C(=O)c3cccc(NCc4cnn(C5CCN(C(=O)C67CC8CC(CC(C8)C6)C7)CC5)c4)c3C2=O)C(=O)N1]

37.0 mg, 58.45% yield, yellow solid; $^1$H NMR (400 MHz, DMSO-d6) δ 11.08 (s, 1H), 7.79 (s, 1H), 7.57 (t, J = 7.8 Hz, 1H), 7.45 (s, 1H), 7.15 (d, J = 8.6 Hz, 1H), 7.03 (d, J = 7.08 Hz, 1H), 6.82-6.78 (m, 1H), 5.04 (dd, J = 12.8, 5.36 Hz, 1H), 4.46-4.34 (m, 5H), 2.95-2.82 (m, 3H), 2.62-2.55 (m, 2H), 2.08-1.97 (m, 12H), 1.91-1.64 (m, 8H); LC MS: ES+ 599.4. |
| 45 | 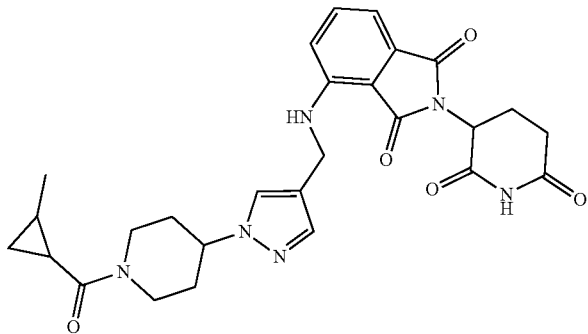 [SMILES: CC1CC1C(=O)N1CCC(n2cc(CNc3cccc4c3C(=O)N(C3CCC(=O)NC3=O)C4=O)cn2)CC1]

(16.0 mg, 29.18% yield, yellow solid; $^1$H NMR (400 MHz, DMSO-d6) δ 11.08 (s, 1H), 7.80 (s, 1H), 7.57 (t, J = 7.8 Hz, 1H), 7.46 (s, 1H), 7.15 (d, J = 8.56 Hz, 1H), 7.03 (d, J = 7.04 Hz, 1H), 6.81-6.79 (m, 1H), 5.04 (dd, J = 12.8, 5.4 Hz, 1H), 4.44-4.28 (m, 5H), 3.22-3.15 (m, 1H), 2.88-2.83 (m, 1H), 2.70-2.50 (m, 4H), 2.04-1.65 (m, 6H), 1.12-1.05 (m, 3H), 0.96-0.91 (m, 1H), 0.54-0.52 (m, 1H); LC MS: ES+ 519.18. |
| 46 | 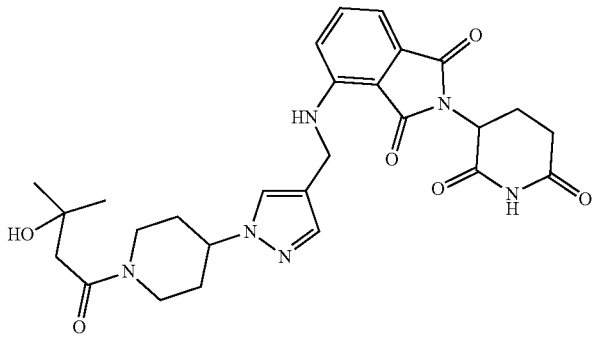 [SMILES: CC(C)(O)CC(=O)N1CCC(n2cc(CNc3cccc4c3C(=O)N(C3CCC(=O)NC3=O)C4=O)cn2)CC1]

6.0 mg, 10.58% yield, yellow solid; $^1$H NMR (400 MHz, DMSO-d6) δ 11.09 (s, 1H), 7.77 (s, 1H), 7.57 (t, J = 7.8 Hz, 1H), 7.46 (s, 1H), 7.15 (d, J = 8.56 Hz, 1H), 7.03 (d, J = 7.04 Hz, 1H), 6.83-6.79 (m, 1H), 5.04 (dd, J = 12.92, 5.36 Hz, 1H), 4.83 (s, 1H), 4.54-4.48 (m, 1H), 4.40-4.34 (m, 3H), 4.10-4.05 (m, 1H), 3.17-2.50 (m, 5H), 2.47-2.43 (m, 2H), 2.03-1.95 (m, 3H), 1.84-1.80 (m, 1H), 1.71-1.65 (m, 1H); LC MS: ES+ 537.2. |

| Cmpd No. | Compound with Characterization Data |
|---|---|
47
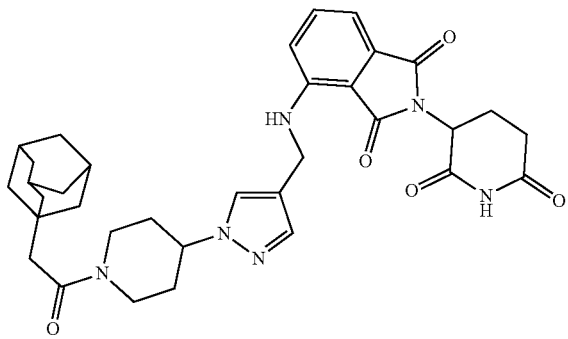 [SMILES: O=C1CCC(N2C(=O)c3cccc(NCc4cnn(C5CCN(C(=O)CC67CC8CC(CC(C8)C6)C7)CC5)c4)c3C2=O)C(=O)N1]
16.0 mg, 24.70% yield, yellow solid; $^1$H NMR (400 MHz, DMSO-d6) δ 11.08 (s, 1H), 7.78 (s, 1H), 7.57 (t, J = 7.8 Hz, 1H), 7.45 (s, 1H), 7.15 (d, J = 8.56 Hz, 1H), 7.03 (d, J = 7.04 Hz, 1H), 6.83-6.79 (m, 1H), 5.04 (dd, J = 12.76, 5.44 Hz, 1H), 4.54-4.49 (m, 1H), 4.37-4.32 (m, 3H), 4.08-4.03 (m, 1H), 3.17-3.10 (m, 1H), 2.89-2.82 (m, 1H), 2.69-2.50 (m, 4H), 2.22-2.17 (m, 1H), 2.08-1.90 (m, 7H), 1.79-1.71 (m, 1H), 1.66-1.55 (m, 12H); LC MS: ES+ 613.2.
48
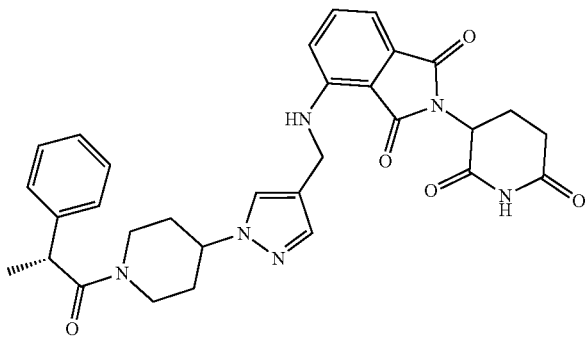 [SMILES: C[C@@H](C(=O)N1CCC(n2cc(CNc3cccc4c3C(=O)N(C3CCC(=O)NC3=O)C4=O)cn2)CC1)c1ccccc1]
15.0 mg, 24.95% yield, yellow solid; $^1$H NMR (400 MHz, DMSO-d6) δ 11.08 (s, 1H), 7.76-6.79 (m, 11H), 5.04 (dd, J = 12.72, 5.36 Hz, 1H), 4.52-3.92 (m, 6H), 3.13-2.92 (m, 1H), 2.92-2.50 (m, 4H), 2.04-1.84 (m, 3H), 1.81-1.60 (m, 1H), 1.55-1.45 (m, 1H), 1.30-1.26 (m, 3H), 0.81-0.71 (m, 1H); LC MS: ES+ 569.1.
49
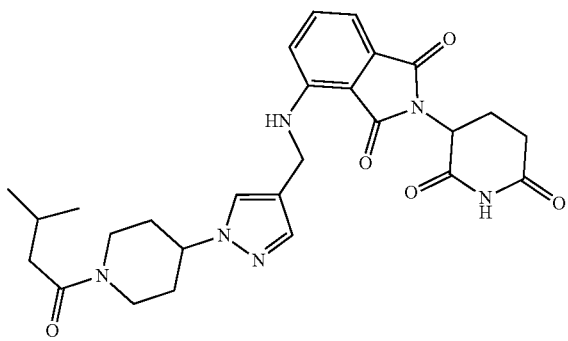 [SMILES: CC(C)CC(=O)N1CCC(n2cc(CNc3cccc4c3C(=O)N(C3CCC(=O)NC3=O)C4=O)cn2)CC1]
15.0 mg, 27.25% yield, yellow solid; $^1$H NMR (400 MHz, DMSO-d6) δ 11.08 (s, 1H), 7.78 (s, 1H), 7.57 (t, J = 7.82 Hz, 1H), 7.45 (s, 1H), 7.15 (d, J = 8.6 Hz, 1H), 7.03 (d, J = 7.08 Hz, 1H), 6.83-6.79 (m, 1H), 5.04 (dd, J = 12.76, 5.36 Hz, 1H), 4.52-4.34 (m, 4H), 3.98-3.94 (m, 1H), 3.16-2.51 (m, 5H), 2.21-2.20 (m, 2H), 2.04-1.93 (m, 4H), 1.78-1.74 (m, 1H), 1.66-1.63 (m, 1H), 0.90-0.89 (m, 6H); LC MS: ES+ 521.1.

| Cmpd No. | Compound with Characterization Data |
|---|---|
| 50 | 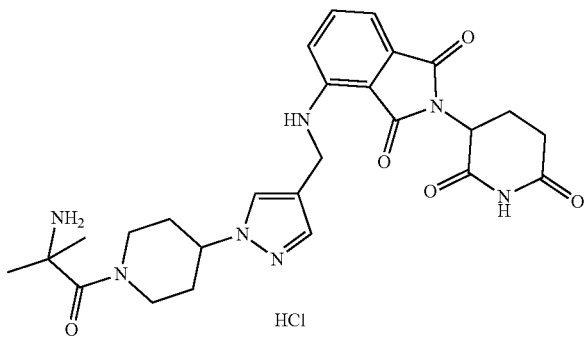 [SMILES: CC(C)(N)C(=O)N1CCC(n2cc(CNc3cccc4c3C(=O)N(C3CCC(=O)NC3=O)C4=O)cn2)CC1 ; Cl]<br>15.0 mg, 59.60% yield, yellow solid; ¹H NMR (400 MHz, DMSO-d6) δ 11.09 (s, 1H), 8.18-8.15 (m, 2H), 7.80 (s, 1H), 7.57 (t, J = 7.8 Hz, 1H), 7.48 (s, 1H), 7.15 (d, J = 8.6 Hz, 1H), 7.04 (d, J = 7.12 Hz, 1H), 6.83-6.79 (m, 1H), 5.04 (dd, J = 12.76, 5.48 Hz, 1H), 4.49-4.20 (m, 5H), 3.10-2.51 (m, 5H), 2.08-2.00 (m, 3H), 1.78-1.74 (m, 2H), 1.56 (s, 6H); LC MS: ES+ 522.2. |
| 51 | 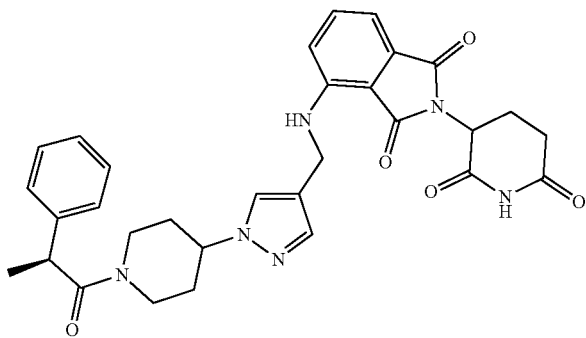 [SMILES: C[C@H](C(=O)N1CCC(n2cc(CNc3cccc4c3C(=O)N(C3CCC(=O)NC3=O)C4=O)cn2)CC1)c1ccccc1]<br>15.0 mg, 24.95% yield, yellow solid; ¹H NMR (400 MHz, DMSO-d6) δ 11.08 (s, 1H), 7.76-6.79 (m, 11H), 5.04 (dd, J = 12.72, 5.36 Hz, 1H), 4.53-3.90 (m, 6H), 3.13-2.55 (m, 4H), 2.04-1.47 (m, 5H), 1.30-1.23 (m, 3H), 0.77-0.75 (m, 1H); LC MS: ES+ 569.20. |
| 52 | 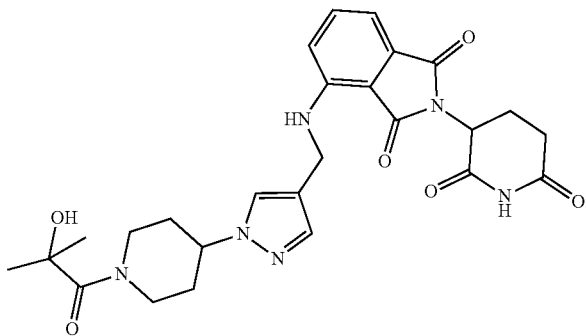 [SMILES: CC(C)(O)C(=O)N1CCC(n2cc(CNc3cccc4c3C(=O)N(C3CCC(=O)NC3=O)C4=O)cn2)CC1]<br>14.0 mg, 25.34% yield, yellow solid; ¹H NMR (400 MHz, DMSO-d6) δ 11.08 (s, 1H), 7.77 (s, 1H), 7.57 (t, J = 7.82 Hz, 1H), 7.46 (s, 1H), 7.15 (d, J = 8.56 Hz, 1H), 7.03 (d, J = 7.08 Hz, 1H), 6.83-6.79 (m, 1H), 5.41 (s, 1H), 5.04 (dd, J = 12.8, 5.4 Hz, 1H), 4.90-4.50 (br, 2H), 4.40-4.35 (m, 3H), 3.12-2.58 (m, 3H), 2.62-2.55 (m, 2H), 2.04-1.96 (m, 3H), 1.79-1.77 (br, 2H), 1.31 (s, 6H); LC MS: ES+ 523.5. |

| Cmpd No. | Compound with Characterization Data |
|---|---|
| 53 | 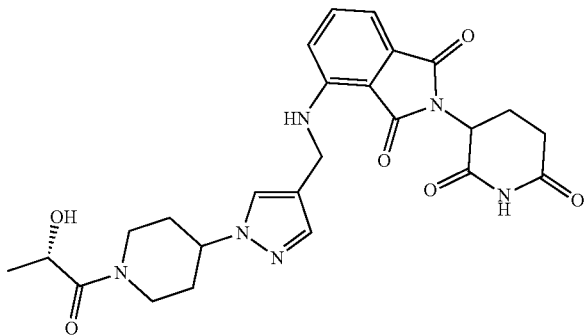 [SMILES: C[C@H](O)C(=O)N1CCC(n2cc(CNc3cccc4c3C(=O)N(C3CCC(=O)NC3=O)C4=O)cn2)CC1]<br>5.0 mg, 9.30% yield, yellow solid; $^1$H NMR (400 MHz, DMSO-d6) δ 11.08 (s, 1H), 7.77 (s, 1H), 7.57 (t, J = 7.8 Hz, 1H), 7.46 (s, 1H), 7.15 (d, J = 8.6 Hz, 1H), 7.03 (d, J = 7.04 Hz, 1H), 6.83-6.79 (m, 1H), 5.04 (dd, J = 12.8, 5.48 Hz, 1H), 4.91-4.86 (m, 1H), 4.45-4.34 (m, 4H), 4.09-4.06 (m, 1H), 3.12-2.50 (6H), 2.04-1.65 (m, 5H), 1.19-1.16 (m, 3H); LC MS: ES+ 509.09. |
| 54 | 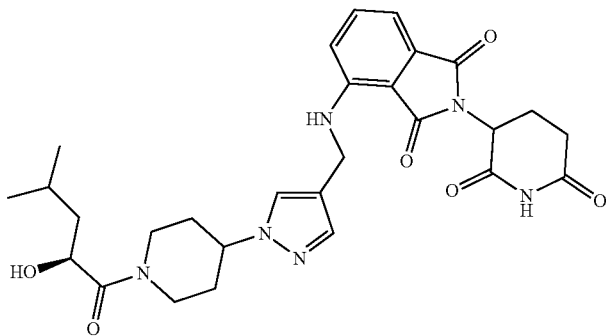<br>15.0 mg, 25.77% yield, yellow solid; $^1$H NMR (400 MHz, DMSO-d6) δ 11.08 (s, 1H), 7.78-7.77 (m, 1H), 7.57 (t, J = 7.82 Hz, 1H), 7.46 (s, 1H), 7.15 (d, J = 8.6 Hz, 1H), 7.03 (d, J = 7.04 Hz, 1H), 6.83-6.79 (m, 1H), 5.04 (dd, J = 12.64, 5.36 Hz, 1H), 4.82-4.76 (m, 1H), 4.42-4.35 (m, 5H), 4.06-4.02 (m, 1H), 3.16-2.55 (m, 4H), 2.49-2.47 (m, 1H), 2.04-1.98 (m, 3H), 1.84-1.30 (m, 5H), 0.91-0.90 (m, 6H); LC MS: ES+ 551.15. |
| 55 | 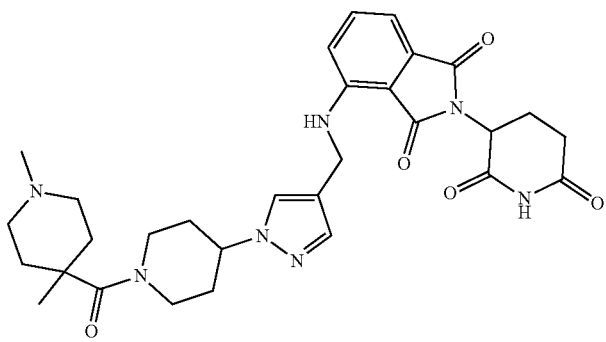 [SMILES: CN1CCC(C)(C(=O)N2CCC(n3cc(CNc4cccc5c4C(=O)N(C4CCC(=O)NC4=O)C5=O)cn3)CC2)CC1]<br>9 mg, 14.79% yield, yellow solid; $^1$H NMR (400 MHz, DMSO-d6) 11.08 (s, 1H), 7.76 (s, 1H), 7.54 (t, J = 7.64 Hz, 1H), 7.43 (s, 1H), 7.13 (d, J = 9 Hz, 1H), 7.01 (d, J = 7.08 Hz, 1H), 6.81 (t, J = 5.78 Hz, 1H), 5.04-5.00 (m, 1H), 4.34-4.30 (m, 4H), 2.92-2.88 (m, 3H), 2.62-2.52 (m, 2H), 2.41-2.35 (m, 1H), 2.25-2.20 (m, 2H), 2.12-2.07 (m, 2H), 2.01-1.91 (m, 4H), 1.72-1.67 (m, 2H), 1.47-1.41 (m, 2H), 1.15 (s, 3H); LC MS: ES+ 576.2. |

-continued

| Cmpd No. | Compound with Characterization Data |
|---|---|
| 56 | 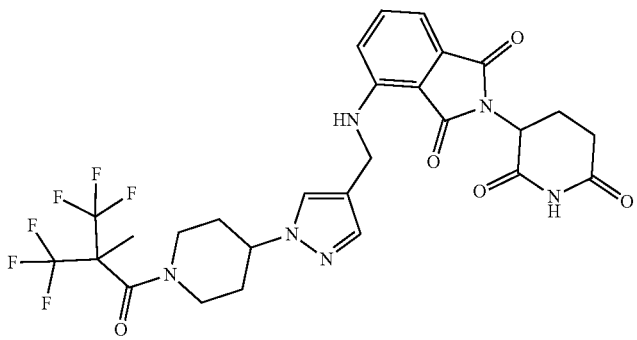 [SMILES: CC(C(=O)N1CCC(n2cc(CNc3cccc4c3C(=O)N(C3CCC(=O)NC3=O)C4=O)cn2)CC1)(C(F)(F)F)C(F)(F)F]<br>65 mg, 90.28% yield, yellow solid; ¹H NMR (400 MHz, DMSO-d6) 11.08 (s, 1H), 7.80 (s, 1H), 7.57 (t, j = 7.82 Hz, 1H), 7.47 (s, 1H), 7.15 (d, J = 8.6 Hz, 1H), 7.03 (d, J = 7.08 Hz, 1H), 6.81 (t, J = 5.78 Hz, 1H), 5.04 (dd, J = 12.64, 5.48 Hz, 1H), 4.48-4.44 (m, 1H), 4.37 (d, J = 5.8 Hz, 2H), 4.33-4.29 (m, 2H), 3.13-3.06 (m, 2H), 2.92-2.83 (m, 1H), 2.60-2.52 (m, 2H), 2.07-2.00 (m, 3H), 1.86 (s, 3H), 1.84-1.75 (m, 2H); LC MS: ES+ 629.16. |

Additional compounds prepared according to general Procedure A of example 1 include:

| No. | Compound with Characterization Data |
|---|---|
| 57 | 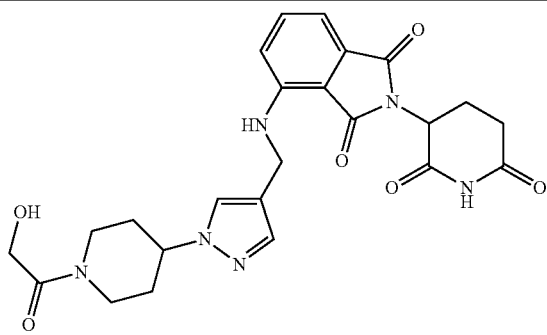<br>11.5 mg, 22.00% yield, yellow solid; ¹H NMR (400 MHz, DMSO-d6) δ 11.08 (s, 1H), 7.77 (s, 1H), 7.57 (t, J = 7.84 Hz, 1H), 7.45 (s, 1H), 7.15 (d, J = 8.56 Hz, 1H), 7.03 (d, J = 7.04 Hz, 1H), 6.82-6.79 (m, 1H), 5.06-5.02 (dd, J = 12.76, 5.24 Hz, 1H), 4.54-4.51 (m, 1H), 4.41-4.35 (m, 4H), 4.12-4.08 (m, 2H), 3.78-3.74 (m, 1H), 3.12-3.05 (m, 1H), 2.92-2.83 (m, 1H), 2.79-2.66 (m, 1H), 2.60-2.55 (m, 2H), 2.07-1.96 (m, 3H), 1.84-1.81 (m, 1H), 1.71-1.69 (m, 1H); LC MS: ES+ 495.5. |
| 58 | 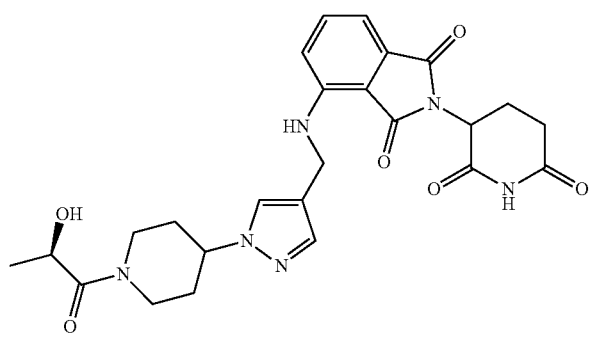 [SMILES: C[C@@H](O)C(=O)N1CCC(n2cc(CNc3cccc4c3C(=O)N(C3CCC(=O)NC3=O)C4=O)cn2)CC1]<br>11 mg, 20.46% yield, yellow solid; ¹H NMR (400 MHz, DMSO-d6) δ 11.08 (s, 1H), 7.78 (s, 1H), 7.57 (t, J = 7.86 Hz, 1H), 7.46 (s, 1H), 7.15 (d, J = 8.64 Hz, 1H), 7.03 (d, J = 7.00 Hz, 1H), 6.81-6.79 (m, 1H), 5.04 (dd, J = 12.88, 5.44 Hz, 1H), 4.88 (m, 1H), 4.44-4.35 (m, 5H), 4.12-4.08 (m, 1H), 3.14-3.10 (m, 1H), 2.9-2.83 (m, 1H), 2.78-2.72 (m, 1H), 2.62-2.55 (m, 2H), 2.60-2.53 (m, 2H), 2.01-1.98 (m, 3H), 1.84-1.81 (m, 1H), 1.75-1.68 (m, 1H); LC MS: ES+ 509.5. |

| No. | Compound with Characterization Data |
|---|---|
| 59 | 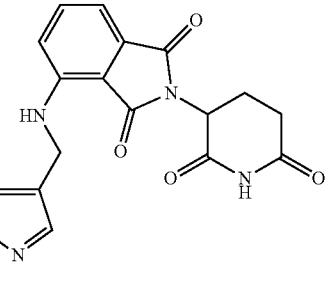 |

16 mg, 28.31% yield, yellow solid; $^1$H NMR (400 MHz, DMSO-d6) δ 11.09 (s, 1H), 7.78 (s, 1H), 7.57 (t, J = 7.84 Hz, 1H), 7.45 (s, 1H), 7.15 (d, J = 8.6 Hz, 1H), 7.03 (d, J = 7.04 Hz, 1H), 6.82-6.79 (m, 1H), 5.04 (dd, J = 12.84, 5.6 Hz, 1H), 4.69-4.66 (m, 1H), 4.41-4.35 (m, 3H), 4.08-4.05 (m, 1H), 3.79-3.74 (m, 2H), 3.15-3.12 (m, 1H), 2.91-2.84 (m, 1H), 2.72-2.66 (m, 1H), 2.60-2.55 (m, 2H), 2.02-1.98 (m, 4H), 1.83-1.79 (m, 2H), 1.69-1.68 (m, 1H), 1.22-1.18 (m, 2H), 0.88-0.82 (m, 1H); LC MS: ES+ 535.5.

| 60 | 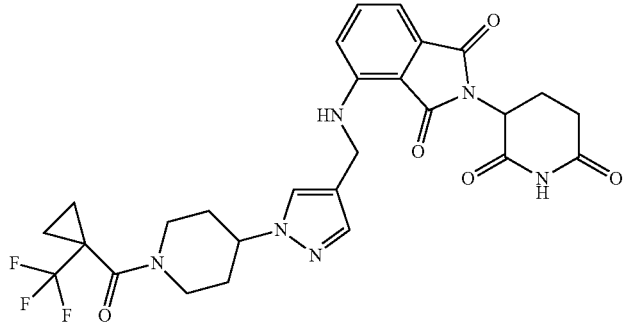 [SMILES: O=C1CCC(N2C(=O)c3cccc(NCc4cnn(C5CCN(C(=O)C6(C(F)(F)F)CC6)CC5)c4)c3C2=O)C(=O)N1] |
|---|---|

30 mg, 49.56% yield, yellow solid; $^1$H NMR (400 MHz, DMSO-d6) δ 11.08 (s, 1H), 7.79 (s, 1H), 7.57 (t, J = 7.84 Hz, 1H), 7.46 (s, 1H), 7.15 (d, J = 8.56 Hz, 1H), 7.03 (d, J = 7.04 Hz, 1H), 6.82-6.79 (m, 1H), 5.06-5.02 (dd, J = 12.72, 5.32 Hz, 1H), 4.44-4.32 (m, 5H), 2.91-2.84 (m, 2H), 2.66-2.55 (m, 2H), 2.07-2.01 (m, 3H), 1.79-1.76 (m, 2H), 1.33-1.28 (m, 2H), 1.23-1.20 (m, 3H); LC MS: ES+ 573.20.

| 61 | 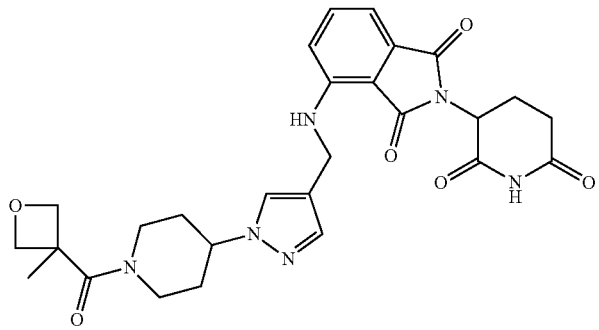 [SMILES: CC1(C(=O)N2CCC(n3cc(CNc4cccc5c4C(=O)N(C4CCC(=O)NC4=O)C5=O)cn3)CC2)COC1] |
|---|---|

27 mg, 44.09% yield, yellow solid; $^1$H NMR (400 MHz, DMSO-d6) δ 11.08 (s, 1H), 7.80 (s, 1H), 7.57 (t, J = 7.8 Hz, 1H), 7.46 (s, 1H), 7.15 (d, J = 8.52 Hz, 1H), 7.03 (d, J = 7.04 Hz, 1H), 6.80-6.79 (m, 1H), 5.06-5.02 (dd, J = 12.88, 5.32 Hz, 1H), 4.79-4.78 (m, 2H), 4.43-4.35 (m, 4H), 4.27-4.26 (m, 2H), 3.13-3.04 (m, 2H), 2.92-2.83 (m, 1H), 2.77-2.70 (m, 1H), 2.60-2.55 (m, 1H), 2.01-1.98 (m, 3H), 1.82-1.70 (m, 2H), 1.54 (s, 3H), 1.23-1.22 (m, 1H); LC MS: ES+ 535.2.

| No. | Compound with Characterization Data |
|---|---|
| 62 | 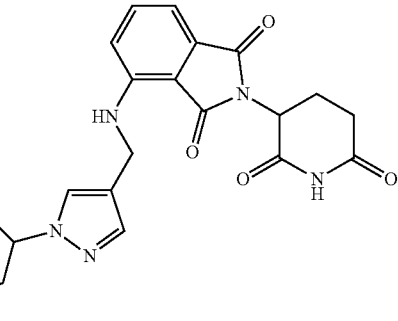<br>21 mg, 36.34% yield, yellow solid; $^1$H NMR (400 MHz, DMSO-d6) δ 11.08 (s, 1H), 7.80 (s, 1H), 7.57 (t, J = 7.84 Hz, 1H), 7.45 (s, 1H), 7.15 (d, J = 8.56 Hz, 1H), 7.03 (d, J = 7.04 Hz, 1H), 6.81-6.78 (m, 1H), 5.04 (dd, J = 12.88, 5.28 Hz, 1H), 4.38-4.27 (m, 5H), 2.92-2.84 (m, 3H), 2.66-2.55 (m, 2H), 2.09-1.98 (m, 5H), 1.74-1.71 (m, 2H), 1.57-1.50 (m, 6H), 1.21 (s, 3H); LC MS: ES+ 547.24. |
| 63 | <br>20 mg, 33.74% yield, yellow solid; $^1$H NMR (400 MHz, DMSO-d6) δ 11.08 (s, 1H), 7.79 (s, 1H), 7.57 (t, J = 7.82 Hz, 1H), 7.46 (s, 1H), 7.15 (d, J = 8.52 Hz, 1H), 7.03 (d, J = 7.08 Hz, 1H), 6.81-6.78 (m, 1H), 5.04 (dd, J = 12.8, 5.52 Hz, 1H), 4.41-4.35 (m, 5H), 2.94-2.84 (m, 3H), 2.66-2.55 (m, 2H), 2.01-1.93 (m, 5H), 1.74-1.69 (m, 2H), 1.46-1.37 (m, 5H), 1.33-1.23 (m, 3H), 1.5 (s, 3H); LC MS: ES+ 561.30. |
| 64 | 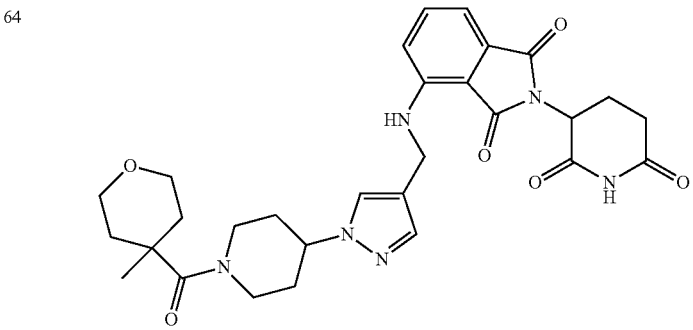<br>10 mg, 16.81% yield, yellow solid; $^1$H NMR (400 MHz, DMSO-d6) δ 11.08 (s, 1H), 7.79 (s, 1H), 7.57 (t, J = 7.88 Hz, 1H), 7.46 (s, 1H), 7.15 (d, J = 8.8 Hz, 1H), 7.03 (d, J = 7.0 Hz, 1H), 6.80-6.78 (m, 1H), 5.04 (dd, J = 12.64, 5.32 Hz, 1H), 4.43-4.33 (m, 4H), 3.62-3.61 (m, 2H), 3.49-3.44 (m, 2H), 2.96-2.84 (m, 4H), 2.60-2.50 (m, 1H), 2.5-2.32 (m, 2H), 2.0-1.98 (m, 4H), 1.73-1.67 (m, 2H), 1.45-1.33 (m, 2H), 1.23 (s, 3H); LC MS: ES+ 563.2. |

| No. | Compound with Characterization Data |
|---|---|
| 65 | 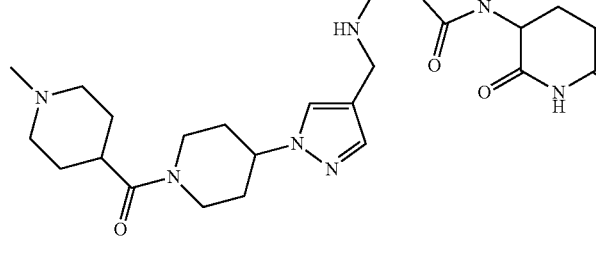<br>8 mg, 13.47% yield, yellow solid; ¹H NMR (400 MHz, DMSO-d6) δ 11.08 (s, 1H), 7.78 (s, 1H), 7.57 (t, J = 7.92 Hz, 1H), 7.45 (s, 1H), 7.15 (d, J = 8.8 Hz, 1H), 7.03 (d, J = 6.88 Hz, 1H), 6.82-6.79 (m, 1H), 5.06-5.03 (m, 1H), 4.46-4.44 (m, 2H), 4.36-4.35 (m, 3H), 4.02-3.99 (m, 2H), 3.15 (m, 2H), 2.87-2.76 (m, 2H), 2.66-2.60 (m, 1H), 2.12 (s, 3H), 2.03-2.00 (m, 3H), 1.88-1.78 (m, 3H), 1.74-1.56 (m, 4H), 1.23 (m, 2H); LC MS: ES+ 562.77. |
| 66 | 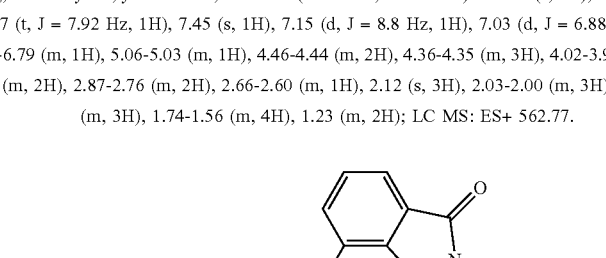<br>1.5 g, 76.39% yield, yellow solid; ¹H NMR (400 MHz, DMSO-d6) δ 11.08 (s, 1H), 7.78 (s, 1H), 7.57 (t, J = 7.78 Hz, 1H), 7.45 (s, 1H), 7.15 (d, J = 8.56 Hz, 1H), 7.03 (d, J = 7.04 Hz, 1H), 6.81-6.78 (m, 1H) 5.04 (dd, J = 12.88, 5.52 Hz, 1H), 4.36-4.29 (m, 3H), 4.01-3.98 (m, 2H), 2.93-2.84 (m, 3H), 2.66-2.55 (m, 2H), 2.02-1.95 (m, 3H), 1.75-1.69 (m, 2H), 1.38 (s, 9H); LC MS: ES+ 537.3. |
| 67 | 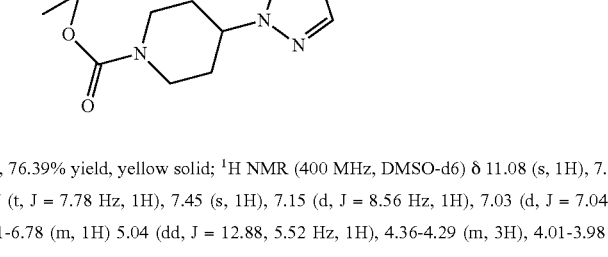<br>30 mg, 52.98% yield, yellow solid; ¹H NMR (400 MHz, DMSO-d6) δ 11.09 (s, 1H), 7.77 (s, 1H), 7.57 (t, J = 7.8 Hz, 1H), 7.46 (s, 1H), 7.15 (d, J = 8.56 Hz, 1H), 7.03 (d, J = 7.00 Hz, 1H), 6.82-6.81 (m, 1H), 5.04 (dd, J = 12.92, 5.28 Hz, 1H), 4.45-4.35 (m, 4H), 3.97-3.94 (m, 1H), 3.16-3.10 (m, 1H), 2.87-2.84 (m, 1H), 2.82-2.60 (m, 3H), 2.60-2.55 (m, 2H), 2.18 (s, 6H), 2.01-1.90 (m, 3H), 1.82-1.80 (m, 2H), 1.67-1.65 (m, 2H); LC MS: ES+ 536.2. |

| No. | Compound with Characterization Data |
|---|---|
| 68 | 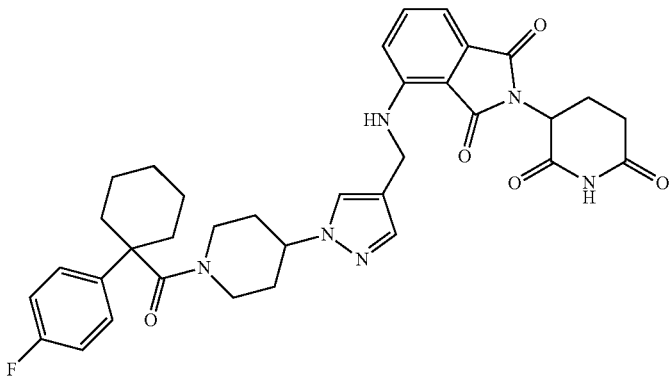 [SMILES: O=C1CCC(N2C(=O)c3cccc(NCc4cnn(C5CCN(C(=O)C6(c7ccc(F)cc7)CCCCC6)CC5)c4)c3C2=O)C(=O)N1]
20 mg, 29.53% yield, yellow solid; $^1$H NMR (400 MHz, DMSO-d6) δ 11.08 (s, 1H), 7.66 (s, 1H), 7.56 (t, J = 7.84 Hz, 1H), 7.41 (s, 1H), 7.29-7.25 (m, 2H), 7.19-7.12 (m, 3H), 7.03 (d, J = 6.96 Hz, 1H), 6.79 (m, 1H), 5.03 (dd, J = 13.04, 5.28 Hz, 1H), 4.34-4.32 (m, 2H), 4.21 (m, 1H), 2.95-2.82 (m, 2H), 2.69-2.55 (m, 4H), 2.32 (m, 2H), 2.18 (m, 2H), 1.75 (m, 2H), 1.59 (m, 6H), 1.4-1.25 (m, 2H) 1.23 (m, 2H); LC MS: ES+ 641.8. |
| 69 | 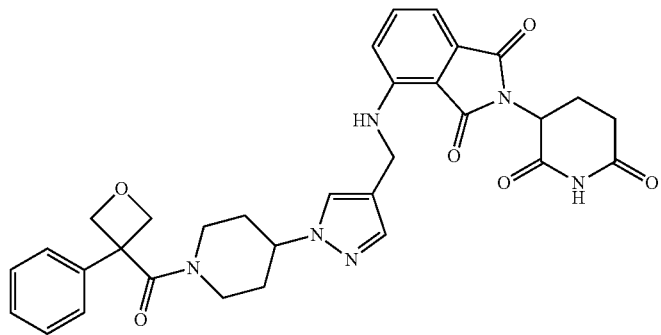 [SMILES: O=C1CCC(N2C(=O)c3cccc(NCc4cnn(C5CCN(C(=O)C6(c7ccccc7)COC6)CC5)c4)c3C2=O)C(=O)N1]
23 mg, 36.46% yield, yellow solid; $^1$H NMR (400 MHz, DMSO-d6) δ 11.08 (s, 1H), 7.69 (s, 1H), 7.56 (t, J = 7.8 Hz, 1H), 7.48-7.41 (m, 5H), 7.34-7.31 (m, 1H), 7.12 (d, J = 8.48 Hz, 1H), 7.03 (d, J = 7.16 Hz, 1H), 6.79-6.78 (m, 1H), 5.16-5.14 (m, 1H), 5.09-5.02 (m, 2H), 4.78-4.76 (m, 1H), 4.67-4.65 (m, 1H), 4.53-4.49 (m, 1H), 4.34-4.28 (m, 3H), 2.87-2.78 (m, 4H), 2.66-2.55 (m, 2H), 2.01-1.99 (m, 2H), 1.72-1.67 (m, 2H), 1.38-1.32 (m, 1H); LC MS: ES+ 597.7. |
| 70 | 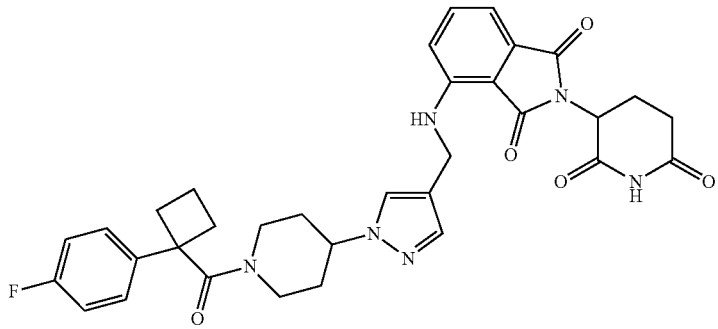 [SMILES: O=C1CCC(N2C(=O)c3cccc(NCc4cnn(C5CCN(C(=O)C6(c7ccc(F)cc7)CCC6)CC5)c4)c3C2=O)C(=O)N1]
30 mg, 46.32% yield, yellow solid; $^1$H NMR (400 MHz, DMSO-d6) δ 11.08 (s, 1H), 7.66 (s, 1H), 7.55 (t, J = 7.82 Hz, 1H), 7.40-7.38 (m, 3H), 7.21-7.17 (m, 2H), 7.13-7.11 (d, J = 8.6 Hz, 1H), 7.03 (d, J = 7.08 Hz, 1H), 6.80-6.77 (m, 1H), 5.04 (dd, J = 12.68, 5.28 Hz, 1H), 4.47 (m, 1H), 4.33-4.32 (m, 2H), 4.26-4.20 (m, 1H), 2.92-2.69 (m, 6H), 2.60-2.55 (m, 2H), 2.37-2.32 (m, 1H), 2.32-2.26 (m, 1H), 2.02-1.99 (m, 1H), 1.94-1.85 (m, 2H), 1.80-1.72 (m, 1H), 1.63-1.52 (m, 1H), 1.12-1.20 (m, 1H); LC MS: ES+ 613.27. |

| No. | Compound with Characterization Data |
|---|---|
| 71 | 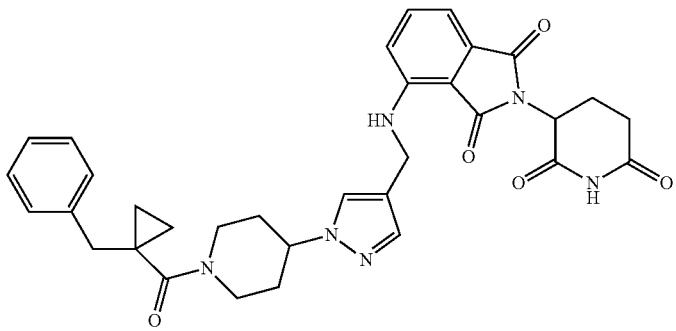 [SMILES: O=C1CCC(N2C(=O)c3cccc(NCc4cnn(C5CCN(C(=O)C6(Cc7ccccc7)CC6)CC5)c4)c3C2=O)C(=O)N1]

24 mg, 38.17% yield, yellow solid; $^1$H NMR (400 MHz, DMSO-d6) δ 11.08 (s, 1H), 7.76 (s, 1H), 7.57 (t, J = 7.8 Hz, 1H), 7.46 (s, 1H), 7.27-7.23 (m, 2H), 7.19-7.14 (m, 4H), 7.03 (d, J = 7.04 Hz, 1H), 6.83-6.80 (m, 1H), 5.04 (dd, J = 12.92, 5.4 Hz, 1H), 4.37-4.27 (m, 5H), 2.92-2.87 (m, 3H), 2.84-2.79 (m, 2H), 2.6-2.55 (m, 2H), 2.02-1.95 (m, 3H), 1.67-1.65 (m, 2H), 0.83-0.80 (m, 2H), 0.70-0.67 (m, 2H); LC MS: ES+ 595.25. |
| 72 | 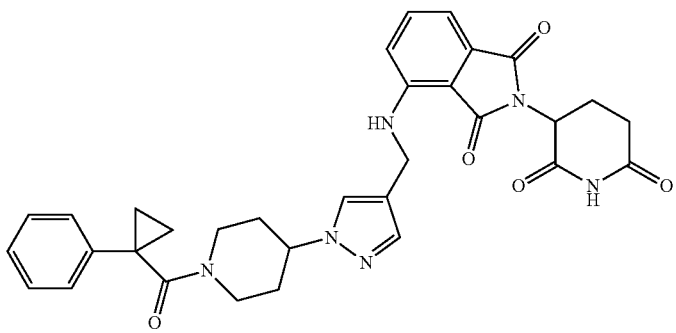 [SMILES: O=C1CCC(N2C(=O)c3cccc(NCc4cnn(C5CCN(C(=O)C6(c7ccccc7)CC6)CC5)c4)c3C2=O)C(=O)N1]

21 mg, 34.21% yield, yellow solid; $^1$H NMR (400 MHz, DMSO-d6) δ 11.08 (s, 1H), 7.70 (s, 1H), 7.56 (t, J = 7.8 Hz, 1H), 7.42 (s, 1H), 7.32-7.29 (m, 2H), 7.21-7.12 (m, 4H), 7.03 (d, J = 7.08 Hz, 1H), 6.81-6.78 (m, 1H), 5.04 (dd, J = 12.8, 5.52 Hz, 1H), 4.45-4.41 (m, 1H), 4.35-4.26 (m, 3H), 4.08-3.92 (m, 1H), 2.90-2.88 (m, 3H), 2.84-2.7 (m, 1H), 2.60-2.55 (m, 1H), 2.50-2.45 (m, 1H), 2.02-1.88 (m, 2H), 1.88-1.6 (m, 2H), 1.56-1.46 (m, 1H), 1.43-1.30 (m, 2H), 1.18-1.16 (m, 2H); LC MS: ES+ 581.27 |
| 73 | 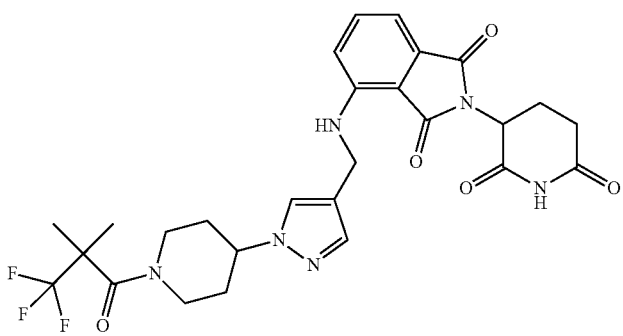 [SMILES: CC(C)(C(=O)N1CCC(n2cc(CNc3cccc4c3C(=O)N(C3CCC(=O)NC3=O)C4=O)cn2)CC1)C(F)(F)F]

15 mg, 24.69% yield, yellow solid; $^1$H NMR (400 MHz, DMSO-d6) δ 11.08 (s, 1H), 7.80 (s, 1H),7.57 (t, J = 7.82 Hz, 1H), 7.46 (s, 1H), 7.15 (d, J = 8.6 Hz, 1H), 7.03 (d, J = 7.2 Hz, 1H), 6.82-6.79 (m, 1H)5.04 (dd, J = 12.92, 5.64 Hz, 1H), 4.43-4.29 (m, 5H), 3.02-2.96 (m, 2H), 2.88-2.82 (m, 1H), 2.60-2.55 (m, 2H), 2.032.00 (m, 3H), 1.78-1.75 (m, 2H), 1.47 (s, 6H), LC MS: ES+ 575.3. |

| No. | Compound with Characterization Data |
|---|---|
| 74 | 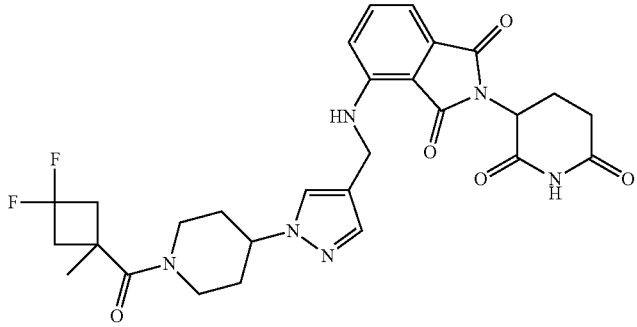 [SMILES: CC1(C(=O)N2CCC(n3cc(CNc4cccc5c4C(=O)N(C4CCC(=O)NC4=O)C5=O)cn3)CC2)CC(F)(F)C1]<br>10 mg, 16.64% yield, yellow solid; ¹H NMR (400 MHz, DMSO-d6) δ 11.07 (s, 1H), 7.80 (s, 1H), 7.57 (t, J = 15.52 Hz, 1H), 7.46 (s, 1H), 7.15 (d, J = 8.68 Hz, 1H), 7.03 (d, J = 7.0 Hz, 1H), 6.80-6.79 (m, 1H) 5.04 (dd, J = 12.4, 5.6 Hz, 1H), 4.41-4.35 (m, 4H), 3.55-3.62 (m, 1H), 3.18-3.15 (m, 1H), 3.1-2.95 (m, 3H), 2.9-2.84 (m, 1H), 2.78-2.73 (m, 1H), 2.6-2.55 (m, 2H), 2.05-1.95 (m, 3H), 1.83-1.73 (m, 3H), 1.40 (s, 3H); LC MS: ES+ 569.23. |
| 75 | 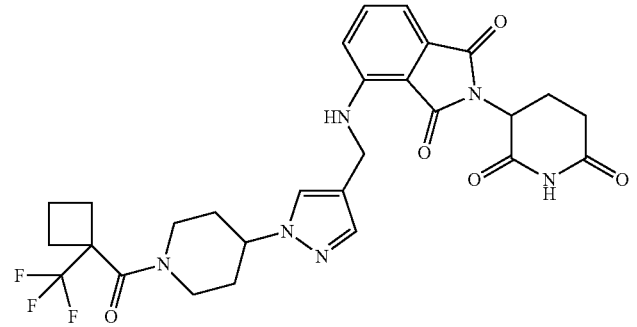 [SMILES: O=C1CCC(N2C(=O)c3cccc(NCc4cnn(C5CCN(C(=O)C6(C(F)(F)F)CCC6)CC5)c4)c3C2=O)C(=O)N1]<br>32 mg, 51.60% yield, yellow solid; ¹H NMR (400 MHz, DMSO-d6) δ 11.09 (s, 1H), 7.79 (s, 1H), 7.57 (t, J = 7.8 Hz, 1H), 7.46 (s, 1H), 7.15 (d, J = 8.6 Hz, 1H), 7.03 (d, J = 7.0 Hz, 1H), 6.83-6.80 (m, 1H), 5.04 (dd, J = 12.72, 5.28 Hz, 1H), 4.47-4.35 (m, 4H), 3.60-3.57 (m, 1H), 3.19-3.15 (m, 1H), 2.88-2.77 (m, 2H), 2.72-2.64 (m, 2H), 2.60-2.55 (m, 1H), 2.45-2.37 (m, 3H), 2.02-1.91 (m, 4H), 1.85-1.72 (m, 3H); LC MS: ES+ 587.25. |
| 76 | 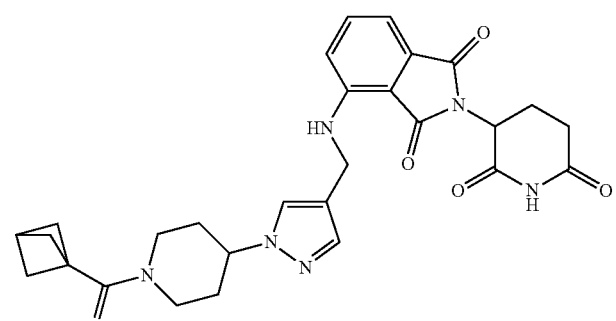<br>30 mg, 53.48% yield, yellow solid; ¹H NMR (400 MHz, DMSO-d6) δ 11.08 (s, 1H), 7.79 (s, 1H), 7.57 (t, J = 7.78 Hz, 1H), 7.45 (s, 1H), 7.15 (d, J = 8.56 Hz, 1H), 7.03 (d, J = 7.04 Hz, 1H), 6.81-6.79 (m, 1H), 5.04 (dd, J = 12.84, 5.4 Hz, 1H), 4.38-4.35 (m, 4H), 4.2-4.15 (m, 1H), 3.2-3.12 (m, 1H), 2.95-2.85 (m, 1H), 2.68-2.62 (m, 1H), 2.60-2.55 (m, 1H), 2.50-2.46 (m, 1H), 2.1-1.93 (m, 9H), 1.71-1.68 (m, 2H); LC MS: ES+ 531.3. |

| No. | Compound with Characterization Data |
|---|---|
| 77 | 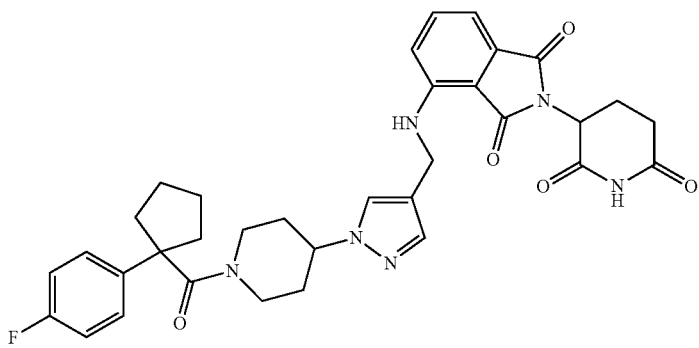 [SMILES: O=C1CCC(N2C(=O)c3cccc(NCc4cnn(C5CCN(C(=O)C6(c7ccc(F)cc7)CCCC6)CC5)c4)c3C2=O)C(=O)N1] |

26 mg, 39.24% yield, yellow solid; $^1$H NMR (400 MHz, DMSO-d6) δ 11.08 (s, 1H), 7.76 (s, 1H), 7.56 (t, J = 7.82 Hz, 1H), 7.41 (s, 1H), 7.24-7.21 (m, 2H), 7.17-7.12 (m, 3H), 7.03 (d, J = 7.0 Hz, 1H), 6.80-6.77 (m, 1H), 5.04 (dd, J = 12.68, 5.12 Hz, 1H), 4.45-4.5 (m, 1H), 4.34-4.32 (m, 2H), 4.25-4.19 (m, 1H), 3.42-3.52 (m, 1H), 2.92-2.84 (m, 1H), 2.73-2.66 (m, 2H), 2.60-2.55 (m, 2H), 2.35-2.25 (m, 2H), 2.07-1.96 (m, 1H), 1.95-1.85 (m, 3H), 1.52-1.6 (m, 6H), 1.25-1.15 (m, 1H); LC MS: ES+ 627.31.

| 78 | 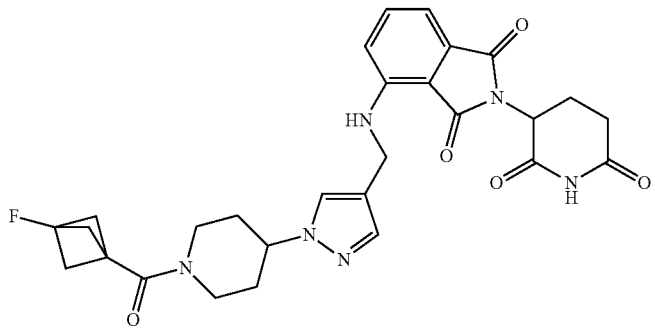 [SMILES: O=C1CCC(N2C(=O)c3cccc(NCc4cnn(C5CCN(C(=O)C67CC(F)(C6)C7)CC5)c4)c3C2=O)C(=O)N1] |

30 mg, 51.73% yield, yellow solid; $^1$H NMR (400 MHz, DMSO-d6) δ 11.08 (s, 1H), 7.78 (s, 1H), 7.57 (t, j = 7.78 Hz, 1H), 7.46 (s, 1H), 7.15 (d, J = 8.6, 1H), 7.03 (d, J = 7.0 Hz, 1H), 6.82-6.79 (m, 1H), 5.04 (dd, J = 12.64, 5.48 Hz, 1H), 4.40-4.35 (m, 4H), 4.04-4.00 (m, 1H), 3.20-3.14 (m, 1H), 2.88-2.84 (m, 1H) 2.76-2.71 (m, 1H), 2.60-2.52 (m, 2H), 2.41-2.32 (m, 6H), 2.02-1.95 (m, 3H), 1.74-1.67 (m, 2H); LC MS: ES+ 549.6

| 79 | 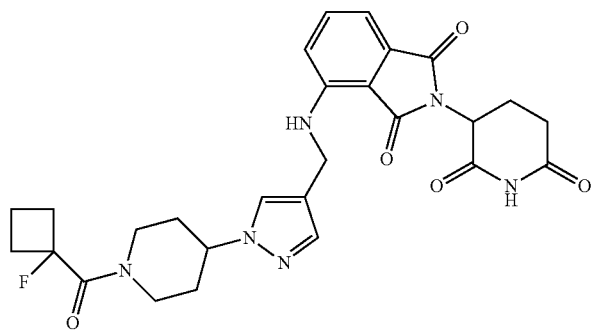 [SMILES: O=C1CCC(N2C(=O)c3cccc(NCc4cnn(C5CCN(C(=O)C6(F)CCC6)CC5)c4)c3C2=O)C(=O)N1] |

11 mg, 19.39% yield, yellow solid; $^1$H NMR (400 MHz, DMSO-d6) δ 11.08 (s, 1H), 7.80 (s, 1H), 7.57 (t, J = 7.7 Hz, 1H), 7.46 (s, 1H), 7.15 (d, J = 8.48 Hz, 1H), 7.03 (d, J = 7.04 Hz, 1H), 6.80-6.78 (m, 1H), 5.04 (dd, J = 12.24, 4.88 Hz, 1H), 4.41-4.35 (m, 4H), 3.86-3.82 (m, 1H), 3.18-3.1 (m, 1H), 2.87-2.84 (m, 2H), 2.72-2.60 (m, 2H), 2.60-2.55 (m, 1H), 2.40-2.32 (m, 1H), 2.03-2.00 (m, 3H), 1.86-1.73 (m, 3H), 1.52-1.46 (m, 1H), 1.25-1.15 (m, 2H); LC MS: ES+ 537.6.

| No. | Compound with Characterization Data |
|---|---|
| 80 | 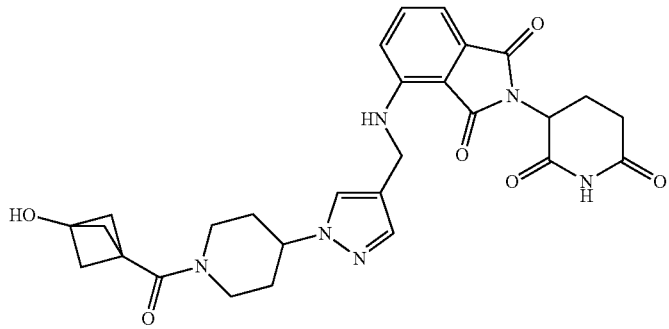 [SMILES: O=C1CCC(N2C(=O)c3cccc(NCc4cnn(C5CCN(C(=O)C67CC(O)(C6)C7)CC5)c4)c3C2=O)C(=O)N1]<br>10 mg, 17.31% yield, yellow solid; $^1$H NMR (400 MHz, DMSO-d6) δ 11.09 (s, 1H), 7.78 (s, 1H), 7.57 (t, j = 7.78 Hz, 1H), 7.45 (s, 1H), 7.15 (d, J = 8.6, 1H), 7.03 (d, J = 7.08 Hz, 1H), 6.83-6.78 (m, 1H), 6.35 (s, 1H), 5.07-5.02 (m, 1H), 4.40-4.35 (m, 4H), 4.08-4.05 (m, 1H), 3.16-3.10 (m, 1H), 2.89-2.84 (m, 1H) 2.71-2.64 (m, 1H), 2.60-2.52 (m, 2H), 2.08-1.89 (m, 9H), 1.73-1.65 (m, 2H); LC MS: ES+ 547.2. |
| 81 | 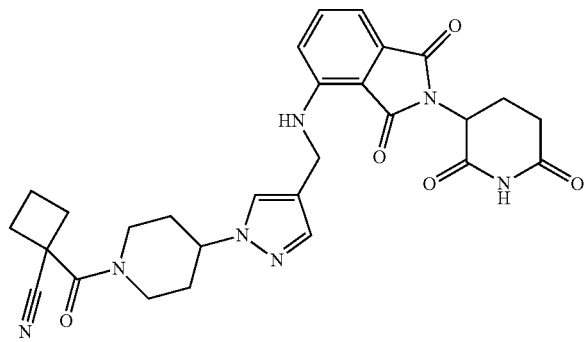 [SMILES: N#CC1(C(=O)N2CCC(n3cc(CNc4cccc5c4C(=O)N(C4CCC(=O)NC4=O)C5=O)cn3)CC2)CCC1]<br>23 mg, 40.02% yield, yellow solid; $^1$H NMR (400 MHz, DMSO-d6) δ 11.08 (s, 1H), 7.80 (s, 1H), 7.57 (t, J = 7.8 Hz, 1H), 7.47 (s, 1H), 7.15 (d, J = 8.56 Hz, 1H), 7.03 (d, J = 7.08 Hz, 1H), 6.83-6.80 (m, 1H), 5.04 (dd, J = 12.76, 5.48 Hz, 1H), 4.43-4.36 (m, 4H), 3.71-3.68 (m, 1H), 3.29-3.26 (m, 2H), 2.91-2.84 (m, 2H), 2.75-2.68 (m, 2H), 2.60-2.50 (m, 3H), 2.13-2.03 (m, 4H), 1.90-1.78 (m, 3H); LC MS: ES– 542.3. |
| 82 | 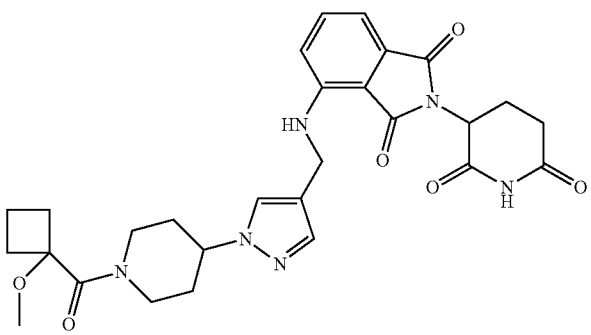<br>23 mg, 39.66% yield, yellow solid; $^1$H NMR (400 MHz, DMSO-d6) δ 11.08 (s, 1H), 7.79 (s, 1H), 7.57 (t, J = 7.8 Hz, 1H), 7.46 (s, 1H), 7.15 (d, J = 8.64 Hz, 1H), 7.03 (d, J = 7.08 Hz, 1H), 6.81-6.78 (m, 1H), 5.04 (dd, J = 12.8, 5.28 Hz, 1H), 4.47-4.35 (m, 4H), 4.09-4.05 (m, 1H), 3.11-3.08 (m, 1H), 3.04 (s, 3H), 2.87-2.75 (m, 2H), 2.60-2.55 (m, 3H), 2.46-2.44 (m, 1H), 2.13-2.00 (m, 5H), 1.78-1.78 (m, 3H), 1.55-1.50 (m, 1H); LC MS: ES+ 549.20. |

| No. | Compound with Characterization Data |
|---|---|
| 83 | 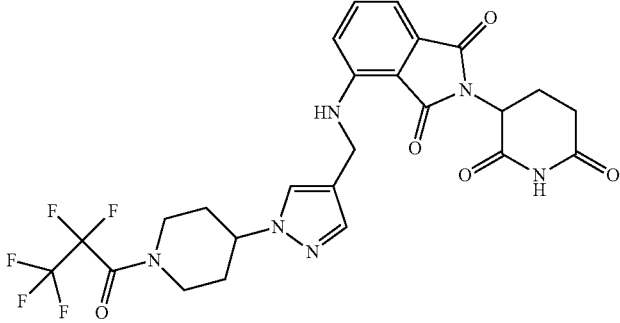

13 mg, 21.11% yield, yellow solid; $^1$H NMR (400 MHz, DMSO-d6) δ 11.08 (s, 1H), 7.82 (s, 1H), 7.57 (t, J = 7.78 Hz, 1H), 7.47 (s, 1H), 7.15 (d, J = 8.56 Hz, 1H), 7.03 (d, J = 7.0 Hz, 1H), 6.83-6.80 (m, 1H), 5.04 (dd, J = 12.8, 5.4 Hz, 1H), 4.53-4.47 (m, 1H), 4.37-4.34 (m, 3H), 4.06-4.03 (m, 1H), 3.46-3.40 (m, 1H) 3.09-3.03 (m, 1H), 2.92-2.83 (m, 1H), 2.60-2.55 (m, 2H), 2.14-2.08 (m, 2H), 2.03-2.00 (m, 1H), 1.88-1.83 (m, 2H); LC MS: ES+ 583.2. |
| 84 | 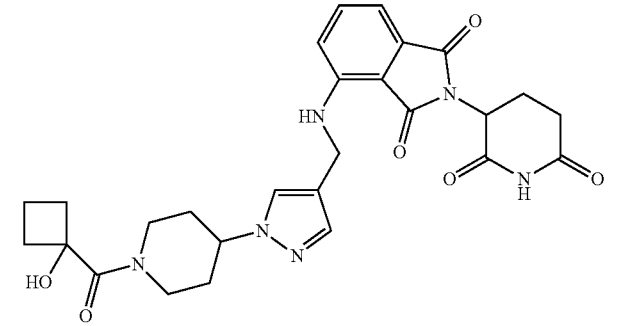 [SMILES: O=C1CCC(N2C(=O)c3cccc(NCc4cnn(C5CCN(C(=O)C6(O)CCC6)CC5)c4)c3C2=O)C(=O)N1]

13 mg, 23.00% yield, yellow solid; $^1$H NMR (400 MHz, DMSO-d6) δ 11.08 (s, 1H), 7.77 (s, 1H), 7.57 (t, J = 7.82 Hz, 1H), 7.45 (s, 1H), 7.15 (d, J = 8.6 Hz, 1H), 7.03 (d, J = 7.0 Hz, 1H), 6.81-6.79 (m, 1H), 5.92 (s, 1H) 5.04 (dd, J = 12.68, 5.16 Hz, 1H), 4.44-4.35 (m, 4H), 4.15-4.12 (m, 1H), 3.01-3.12 (m, 1H), 2.92-2.84 (m, 2H) 2.72-2.66 (m, 1H), 2.60-2.55 (m, 3H), 2.03-1.96 (m, 5H), 1.84-1.82 (m, 1H), 1.73-1.68 (m, 2H), 1.45-1.41 (m, 1H); LC MS: ES+ 535.22. |
| 85 | 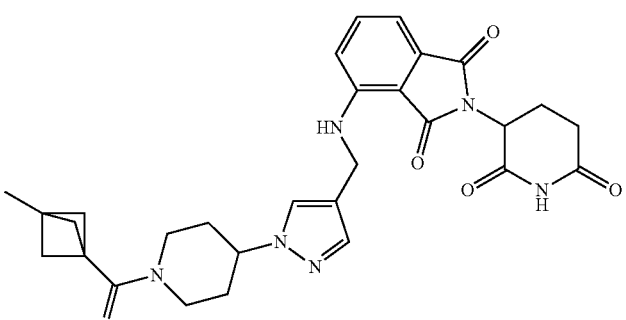

19 mg, 33.00% yield, yellow solid; $^1$H NMR (400 MHz, DMSO-d6) δ 11.08 (s, 1H), 7.78 (s, 1H), 7.57 (t, j = 7.78 Hz, 1H), 7.45 (s, 1H), 7.15 (d, J = 8.6, 1H), 7.03 (d, J = 7.08 Hz, 1H), 6.80 (t, J = 5.78 Hz, 1H), 5.05 (dd, J = 12.64, 5.48 Hz, 1H), 4.40-4.35 (m, 4H), 4.18-4.14 (m, 1H), 3.16-3.10 (m, 1H), 2.87-2.83 (m, 1H) 2.71-2.64 (m, 1H), 2.60-2.52 (m, 2H), 2.04-2.01 (m, 2H), 1.99-1.90 (m, 7H), 1.75-1.65 (m, 2H), 1.14 (s, 3H); LC MS: ES+ 545.6. |

| No. | Compound with Characterization Data |
|---|---|
| 86 | 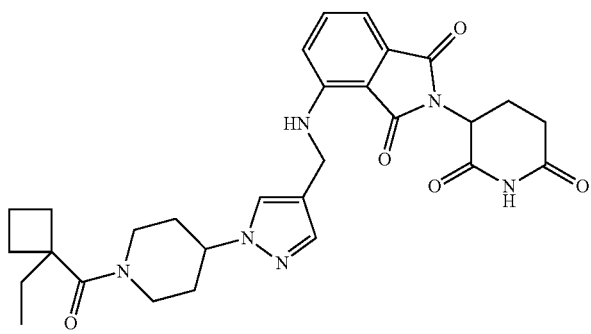 [SMILES: CCC1(C(=O)N2CCC(n3cc(CNc4cccc5c4C(=O)N(C4CCC(=O)NC4=O)C5=O)cn3)CC2)CCC1] |

24 mg, 41.53% yield, yellow solid; ¹H NMR (400 MHz, DMSO-d6) δ 11.08 (s, 1H), 7.79 (s, 1H), 7.57 (t, J = 7.8 Hz, 1H), 7.46 (s, 1H), 7.15 (d, J = 8.64 Hz, 1H), 7.03 (d, J = 7.08 Hz, 1H), 6.81-6.78 (m, 1H), 5.04 (dd, J = 12.8, 5.4 Hz, 1H), 4.41-4.35 (m, 4H), 3.65-3.55 (m, 1H), 3.1-3.0 (m, 1H) 2.92-2.84 (m, 1H), 2.73-2.55 (m, 4H), 2.45-2.3 (m, 2H), 2.09-1.96 (m, 3H), 1.84-1.64 (m, 7H), 0.76 (t, J = 7.36 Hz 3H); LC MS: ES+ 547.2.

| 87 | 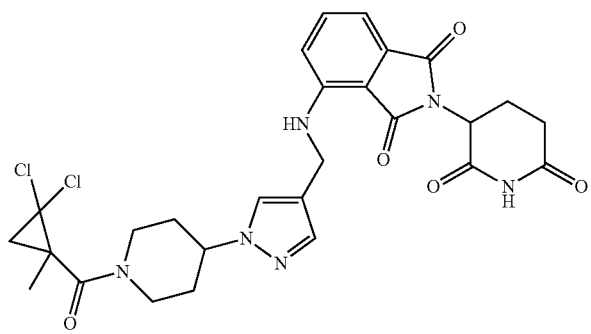 [SMILES: CC1(C(=O)N2CCC(n3cc(CNc4cccc5c4C(=O)N(C4CCC(=O)NC4=O)C5=O)cn3)CC2)CC1(Cl)Cl] |

30.0 mg, 48.30% yield, yellow solid;

The following compounds were made according the general procedure B of example 1:

| No. | Compound with Characterization Data |
|---|---|
| 8 | 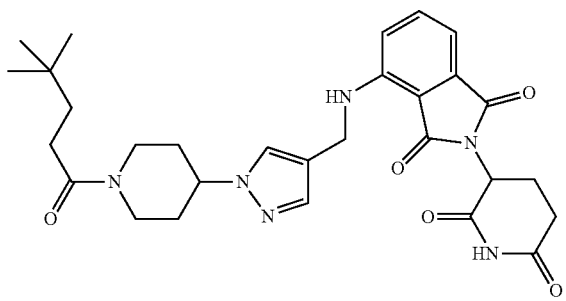 [SMILES: CC(C)(C)CCC(=O)N1CCC(n2cc(CNc3cccc4c3C(=O)N(C3CCC(=O)NC3=O)C4=O)cn2)CC1] |

140 mg, 48.27% yield, yellow solid; 1H NMR (400 MHz, DMSO-d6) δ 11.07 (s, 1H), 7.78 (s, 1H), 7.59 (t, J = 7.72 Hz, 1H), 7.46 (s, 1H), 7.15 (d, J = 8.52 Hz, 1H), 7.03 (d, J = 7.16 Hz, 1H), 6.80 (t, J = 5.5 Hz, 1H), 5.04 (dd, J = 12.72, 5.48 Hz, 1H), 4.46-4.35 (m, 4H), 3.95-3.92 (m, 1H), 3.17-3.11 (m, 1H), 2.92-2.83 (m, 1H) 2.69-2.52 (m, 3H), 2.29-2.25 (m, 2H), 2.07-1.90 (m, 3H), 1.82-1.80 (m, 1H), 1.70-1.65 (m, 1H) 1.42-1.38 (m, 2H) 0.87 (s, 9H); LC MS: ES+ 549.7.

| No. | Compound with Characterization Data |
|---|---|
| 20 | 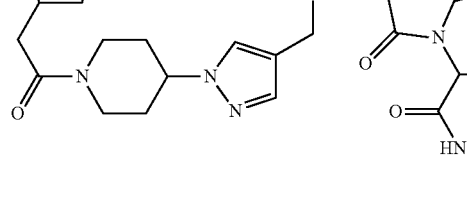<br>135 mg, 46.72% yield, yellow solid; 1H NMR (400 MHz, DMSO-d6) δ 11.08 (s, 1H), 7.78 (s, 1H), 7.57 (t, J = 7.8 Hz, 1H), 7.45 (s, 1H), 7.15 (d, J = 8.52 Hz, 1H), 7.03 (d, J = 7.2 Hz, 1H), 6.80 (m, 1H), 5.05 (dd, J = 12.76, 4.76 Hz, 1H), 4.47-4.35 (m, 4H), 3.97-3.94 (m, 1H), 3.15-3.09 (m, 1H), 2.87-2.83 (m, 1H) 2.69-2.64 (m, 2H), 2.60-2.52 (m, 1H), 2.35-2.33 (m, 2H), 2.14-2.10 (m, 1H), 2.00-1.94 (m, 3H), 1.75-1.64 (m, 4H), 1.57-1.48 (m, 4H) 1.08-1.15 (m, 2H); LC MS: ES+ 547.7. |
| 23 | 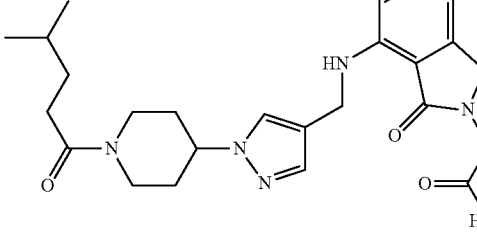<br>150 mg, 53.08% yield, yellow solid; 1H NMR (400 MHz, DMSO-d6) δ 11.07 (s, 1H), 7.78 (s, 1H), 7.57 (t, J = 7.82 Hz, 1H), 7.45 (s, 1H), 7.15 (d, J = 8.56 Hz, 1H), 7.03 (d, J = 7.04 Hz, 1H), 6.80 (t, J = 5.62 Hz, 1H), 5.05 (dd, J = 12.72, 5.28 Hz, 1H), 4.46-4.35 (m, 4H), 3.95-3.92 (m, 1H), 3.16-3.10 (m, 1H), 2.88-2.84 (m, 1H) 2.66-2.64 (m, 2H), 2.33-2.29 (m, 2H), 2.01-1.94 (m, 3H), 1.92-1.63 (m, 2H), 1.55-1.53 (m, 1H), 1.41-1.35 (m, 2H) 1.24-1.22 (m, 1H) 0.87 (d, J = 6.56, 6H); LC MS: ES+ 535.7. |
| 25 | 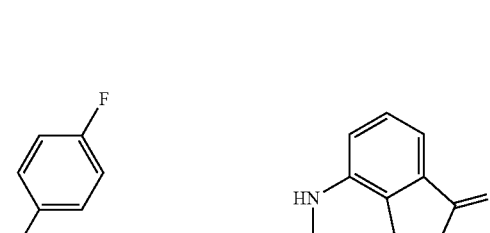<br>165 mg, 54.51% yield, yellow solid; 1H NMR (400 MHz, DMSO-d6) δ 11.08 (s, 1H), 7.75 (s, 1H), 7.56 (t, J = 7.78 Hz, 1H), 7.45 (s, 1H), 7.27-7.24 (m, 2H), 7.16-7.09 (m, 3H), 7.03 (d, J = 7.00 Hz, 1H), 6.80 (m, 1H), 5.05 (dd, J = 12.76, 5.20 Hz, 1H), 4.45-4.35 (m, 4H), 4.04-4.01 (m, 1H), 3.73 (s, 2H), 3.17-3.10 (m, 1H), 2.87-2.84 (m, 1H), 2.74-2.68 (m, 1H), 2.60-2.52 (m, 2H), 2.03-1.95 (m, 3H), 1.72-1.66 (m, 2H); LC MS: ES+ 573.7. |

| No. | Compound with Characterization Data |
|---|---|
| 27 | 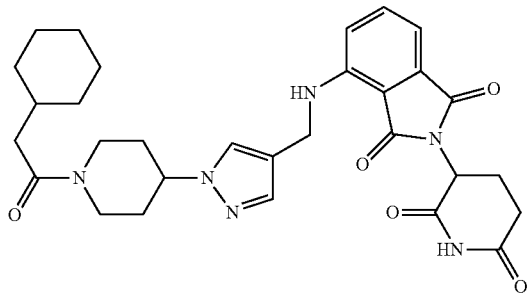 [SMILES: O=C1CCC(N2C(=O)c3cccc(NCc4cnn(C5CCN(C(=O)CC6CCCCC6)CC5)c4)c3C2=O)C(=O)N1] |

180 mg, 60.73% yield, yellow solid; 1H NMR (400 MHz, DMSO-d6) δ 11.08 (s, 1H), 7.77 (s, 1H), 7.57 (t, J = 7.76 Hz, 1H), 7.45 (s, 1H), 7.15 (d, J = 8.56 Hz, 1H), 7.03 (d, J = 7.04 Hz, 1H), 6.80 (m, 1H), 5.05 (dd, J = 12.68, 5.28 Hz, 1H), 4.47-4.44 (m, 1H), 4.36-4.35 (m, 3H), 3.97-3.94 (m, 1H), 3.15-3.09 (m, 1H), 2.92-2.84 (m, 1H) 2.69-2.55 (m, 2H), 2.21-2.19 (m, 2H), 2.07-1.90 (m, 3H), 1.80-1.58 (m, 8H), 1.23-1.06 (m, 4H), 0.93-0.83 (m, 2H); LC MS: ES+ 561.7.

| | |
|---|---|
| 32 | 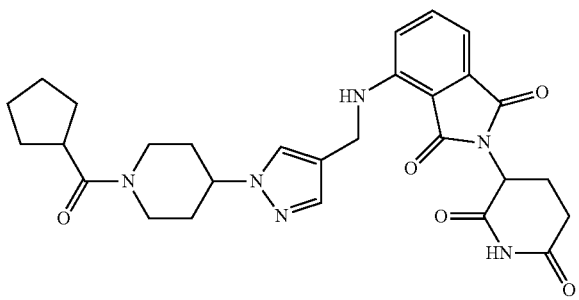 [SMILES: O=C1CCC(N2C(=O)c3cccc(NCc4cnn(C5CCN(C(=O)C6CCCC6)CC5)c4)c3C2=O)C(=O)N1] |

170 mg, 60.38% yield, yellow solid; 1H NMR (400 MHz, DMSO-d6) δ 11.07 (s, 1H), 7.79 (s, 1H), 7.57 (t, J = 7.68 Hz, 1H), 7.45 (s, 1H), 7.15 (d, J = 8.64 Hz, 1H), 7.03 (d, J = 7.00 Hz, 1H), 6.79 (m, 1H), 5.05 (dd, J = 12.36, 5.00 Hz, 1H), 4.47-4.44 (m, 1H), 4.40-4.35 (m, 3H), 4.06-4.03 (m, 1H), 3.16-3.10 (m, 1H), 3.01-2.98 (m, 1H) 2.92-2.84 (m, 1H), 2.70-2.55 (m, 3H), 2.07-1.95 (m, 3H), 1.75-1.51 (m, 10H); LC MS: ES+ 533.7.

| | |
|---|---|
| 44 | 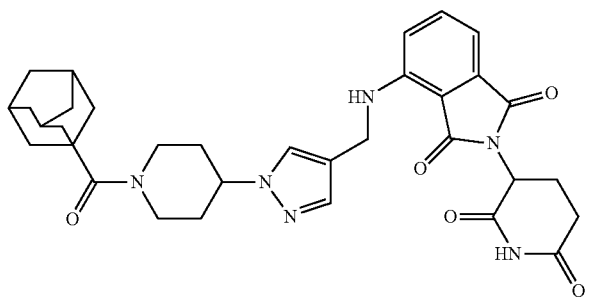 [SMILES: O=C1CCC(N2C(=O)c3cccc(NCc4cnn(C5CCN(C(=O)C67CC8CC(CC(C8)C6)C7)CC5)c4)c3C2=O)C(=O)N1] |

145 mg, 45.82% yield, yellow solid; 1H NMR (400 MHz, DMSO-d6) δ 11.07 (s, 1H), 7.79 (s, 1H), 7.57 (t, J = 7.82 Hz, 1H), 7.45 (s, 1H), 7.15 (d, J = 8.6 Hz, 1H), 7.03 (d, J = 6.96 Hz, 1H), 6.79 (t, J = 5.78 Hz, 1H), 5.05 (dd, J = 12.72, 5.32 Hz, 1H), 4.44-4.35 (m, 5H), 2.94-2.84 (m, 3H), 2.6-2.55 (m, 2H), 2.07-1.90 (m, 12H) 1.74-1.68 (m, 8H); LC MS: ES+ 599.8.

| No. | Compound with Characterization Data |
|---|---|
| 47 | 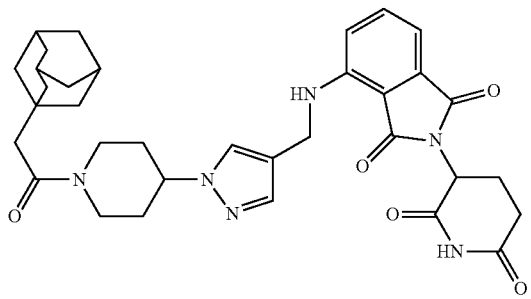 [SMILES: O=C1CCC(N2C(=O)c3cccc(NCc4cnn(C5CCN(C(=O)CC67CC8CC(CC(C8)C6)C7)CC5)c4)c3C2=O)C(=O)N1]<br>170 mg, 52.49% yield, yellow solid; 1H NMR (400 MHz, DMSO-d6) δ 11.08 (s, 1H), 7.78 (s, 1H), 7.57 (t, J = 7.80 Hz, 1H), 7.45 (s, 1H), 7.15 (d, J = 8.56 Hz, 1H), 7.03 (d, J = 7.08 Hz, 1H), 6.80 (m, 1H), 5.05 (dd, J = 12.88, 5.4 Hz, 1H), 4.53-4.49 (m, 1H), 4.36-4.35 (m, 3H), 4.07-4.03 (m, 1H), 3.16-3.10 (m, 1H) 2.92-2.84 (m, 1H), 2.68-2.55 (m, 2H), 2.20-2.17 (m, 1H), 2.09-1.84 (m, 8H), 1.84-1.75 (m, 1H), 1.71-1.57 (m, 13H); LC MS: ES+ 613.8. |
| 60 | 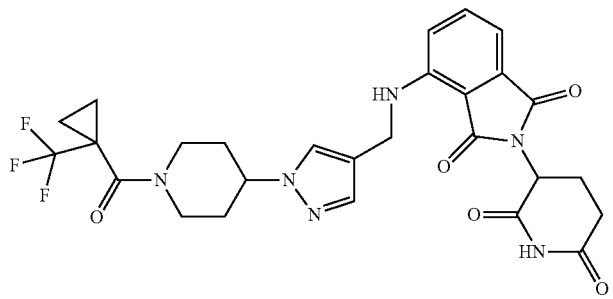 [SMILES: O=C1CCC(N2C(=O)c3cccc(NCc4cnn(C5CCN(C(=O)C6(C(F)(F)F)CC6)CC5)c4)c3C2=O)C(=O)N1]<br>150 mg, 49.56% yield, yellow solid; 1H NMR (400 MHz, DMSO-d6) δ 11.08 (s, 1H), 7.79 (s, 1H), 7.57 (t, J = 7.78 Hz, 1H), 7.46 (s, 1H), 7.15 (d, J = 8.56 Hz, 1H), 7.03 (d, J = 6.96 Hz, 1H), 6.80 (m, 1H), 5.05 (dd, J = 12.88, 5.48 Hz, 1H), 4.44-4.32 (m, 5H), 3.1-3.02 (m, 1H), 2.92-2.84 (m, 1H), 2.67-2.55 (m, 1H) 2.07-1.98 (m, 4H), 1.79-1.77 (m, 2H), 1.29-1.15 (m, 5H); LC MS: ES+ 573.4. |
| 62 | 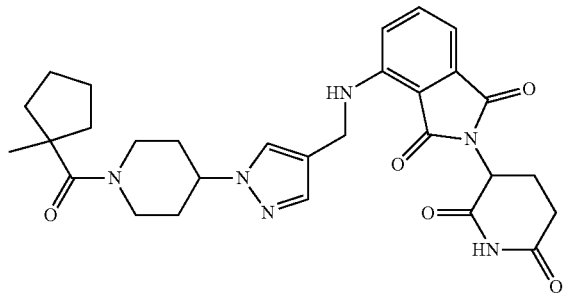 [SMILES: CC1(C(=O)N2CCC(n3cc(CNc4cccc5c4C(=O)N(C4CCC(=O)NC4=O)C5=O)cn3)CC2)CCCC1]<br>150 mg, 51.91% yield, yellow solid; 1H NMR (400 MHz, DMSO-d6) δ 11.08 (s, 1H), 7.79 (s, 1H), 7.57 (t, J = 7.78 Hz, 1H), 7.45 (s, 1H), 7.15 (d, J = 8.6 Hz, 1H), 7.03 (d, J = 7.04 Hz, 1H), 6.80 (m, 1H), 5.05 (dd, J = 12.64, 5.36 Hz, 1H), 4.44-4.27 (m, 5H), 2.92-2.84 (m, 3H), 2.67-2.55 (m, 2H) 2.08-1.98 (m, 5H), 1.77-1.68 (m, 2H), 1.57-1.50 (m, 6H), 1.15 (s, 3H); LC MS: ES+ 547.4. |

| No. | Compound with Characterization Data |
|---|---|
| 63 | 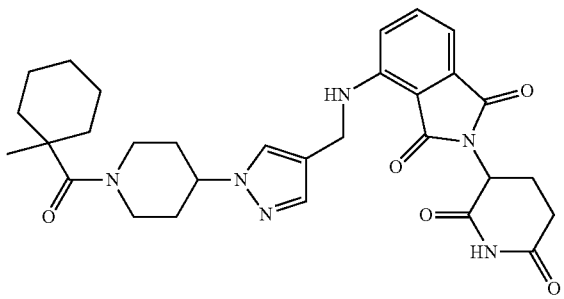 [SMILES: CC1(C(=O)N2CCC(n3cc(CNc4cccc5c4C(=O)N(C4CCC(=O)NC4=O)C5=O)cn3)CC2)CCCCC1]<br>130 mg, 43.86% yield, yellow solid; 1H NMR (400 MHz, DMSO-d6) δ 11.08 (s, 1H), 7.79 (s, 1H), 7.57 (t, J = 7.8 Hz, 1H), 7.46 (s, 1H), 7.15 (d, J = 8.56 Hz, 1H), 7.03 (d, J = 7.0 Hz, 1H), 6.80 (t, J = 5.72 Hz, 1H), 5.05 (dd, J = 12.72, 5.4 Hz, 1H), 4.44-4.35 (m, 5H), 2.94-2.83 (m, 3H), 2.60-2.55 (m, 2H), 2.02-1.93 (m, 5H) 1.74-1.65 (m, 2H), 1.45-1.37 (m, 5H), 1.31-1.23 (m, 3H), 1.17 (s, 3H); LC MS: ES+ 561.4. |
| 70 | 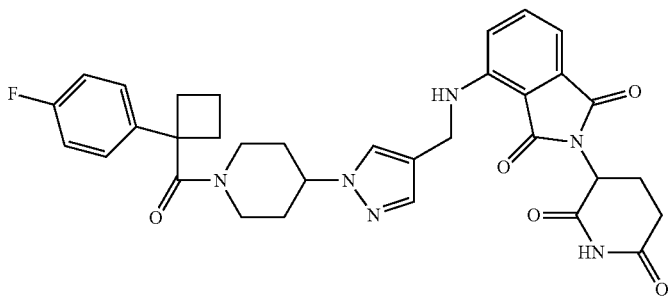 [SMILES: O=C1CCC(N2C(=O)c3cccc(NCc4cnn(C5CCN(C(=O)C6(c7ccc(F)cc7)CCC6)CC5)c4)c3C2=O)C(=O)N1]<br>130 mg, 40.14% yield, yellow solid; 1H NMR (400 MHz, DMSO-d6) δ 11.08 (s, 1H), 7.66 (s, 1H), 7.55 (t, J = 7.84 Hz, 1H), 7.40-7.38 (m, 3H), 7.19 (t, J = 8.62 Hz, 2H), 7.12 (d, J = 8.56 Hz, 1H), 7.03 (d, J = 6.96 Hz, 1H), 6.78 (m, 1H), 5.05 (dd, J = 12.72, 5.32 Hz, 1H), 4.47-4.45 (m, 1H), 4.33-4.32 (m, 2H), 4.26-4.23 (m, 2H), 2.92-2.67 (m, 6H), 2.60-2.55 (m, 1H), 2.38-2.32 (m, 1H) 2.30-2.25 (m, 1H), 2.02-1.85 (m, 3H), 1.78-1.75 (m, 1H), 1.63-1.52 (m, 2H), 1.2-1.16 (m, 1H); LC MS: ES+ 613.2. |
| 72 | 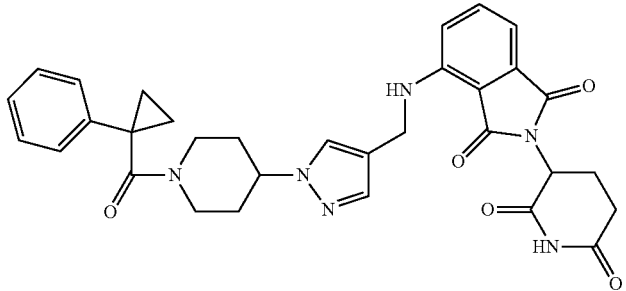 [SMILES: O=C1CCC(N2C(=O)c3cccc(NCc4cnn(C5CCN(C(=O)C6(c7ccccc7)CC6)CC5)c4)c3C2=O)C(=O)N1]<br>150 mg, 48.87% yield, yellow solid; 1H NMR (400 MHz, DMSO-d6) δ 11.08 (s, 1H), 7.70 (s, 1H), 7.56 (t, J = 7.78 Hz, 1H), 7.42 (s, 1H), 7.31 (t, J = 7.52 Hz, 2H), 7.21-7.12 (m, 4H), 7.03 (d, J = 6.96 Hz, 1H), 6.79 (m, 1H), 5.05 (dd, J = 12.76, 5.44 Hz, 1H), 4.44-4.29 (m, 4H), 4.03-4.01 (m, 1H), 2.91-2.84 (m, 3H), 2.60-2.55 (m, 1H), 2.07-1.98 (m, 2H) 1.90-1.54 (m, 2H), 1.43-1.30 (m, 1H), 1.23-1.06 (m, 6H); LC MS: ES+ 581.4. |

| No. | Compound with Characterization Data |
|---|---|
| 73 | 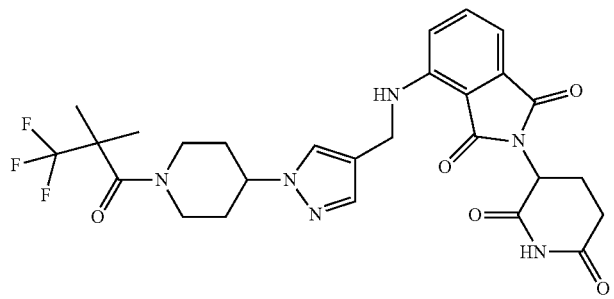 [SMILES: CC(C)(C(=O)N1CCC(n2cc(CNc3cccc4c3C(=O)N(C3CCC(=O)NC3=O)C4=O)cn2)CC1)C(F)(F)F]
160 mg, 52.68% yield, yellow solid; 1H NMR (d6-DMSO, 400 MHz) δ d 11.08 (s, 1H), 7.80 (s, 1H), 7.57 (t, J = 7.78 Hz, 1H), 7.46 (s, 1H), 7.15 (d, J = 8.54 Hz, 1H), 7.03 (d, J = 8.54 Hz, 1H), 6.80 (t, J = 5.6 Hz, 1H), 5.04 (dd, J = 12.76, 5.28 Hz, 1H), 4.44-4.29 (m, 5H), 3.02-2.96 (m, 2H), 2.92-2.84 (m, 1H), 2.60-2.49 (m, 2H), 2.07-1.90 (m, 3H), 1.80-1.72 (m, 2H), 1.47 (s, 6H); LC MS: ES+ 575.7. |
| 75 | 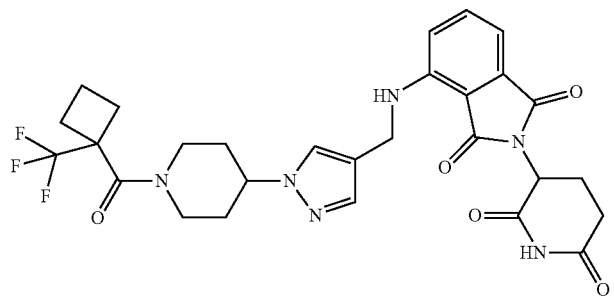 [SMILES: O=C1CCC(N2C(=O)c3cccc(NCc4cnn(C5CCN(C(=O)C6(C(F)(F)F)CCC6)CC5)c4)c3C2=O)C(=O)N1]
155 mg, 49.99% yield, yellow solid; 1H NMR (d6-DMSO, 400 MHz) δ 11.07 (s, 1H), 7.79 (s, 1H), 7.57 (t, J = 6.98 Hz, 1H), 7.46 (s, 1H), 7.15 (d, J = 8.12 Hz, 1H), 7.03 (d, J = 8.12 Hz, 1H), 6.80 (brs, 1H), 5.06-5.03 (m, 1H), 4.47-.4.35 (m, 4H), 3.59-3.55 (m, 1H), 3.17-3.13 (m, 1H), 2.90-2.84 (m, 2H), 2.72-2.64 (m, 2H), 2.60-2.35 (m, 4H), 2.06-1.90 (m, 4H), 1.81-1.75 (m, 3H); LC MS: ES+ 587.7. |
| 74 | 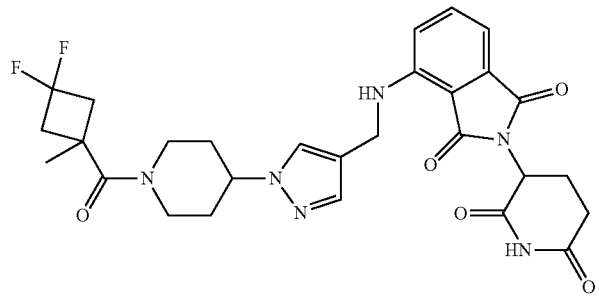 [SMILES: CC1(C(=O)N2CCC(n3cc(CNc4cccc5c4C(=O)N(C4CCC(=O)NC4=O)C5=O)cn3)CC2)CC(F)(F)C1]
140 mg, 46.58% yield, yellow solid; 1H NMR (d6-DMSO, 400 MHz) δ 11.08 (s, 1H), 7.80 (s, 1H), 7.57 (t, J = 6.98 Hz, 1H), 7.46 (s, 1H), 7.15 (d, J = 8.12 Hz, 1H), 7.03 (d, J = 8.12 Hz, 1H), 6.81 (t, J = 5.64 Hz, 1H), 5.04 (dd J = 12.88, 5.56 Hz, 1H), 4.41-4.35 (m, 4H), 3.61-3.59 (m, 1H), 3.21-3.19 (m, 1H), 3.04-3.01 (m, 2H), 2.87-2.84 (m, 1H), 2.75-2.73 (m, 1H), 2.60-2.49 (m, 4H), 2.01-1.97 (m, 3H), 1.91-1.77 (m, 2H), 1.40 (s, 3H); LC MS: ES+ 569.3 |

| No. | Compound with Characterization Data |
|---|---|
| 76 | 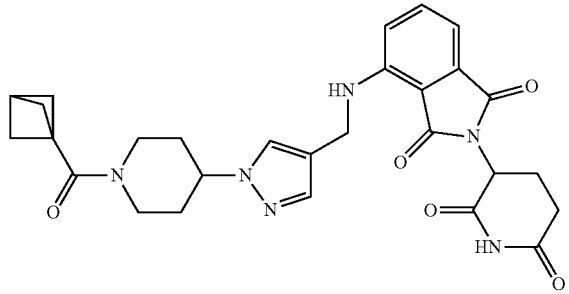 [SMILES: O=C1CCC(N2C(=O)c3cccc(NCc4cnn(C5CCN(C(=O)C67CC(C6)C7)CC5)c4)c3C2=O)C(=O)N1]
160 mg, 57.05% yield, yellow solid; 1H NMR (d6-DMSO, 400 MHZ) δ 11.09 (s, 1H), 7.78 (s, 1H), 7.57 (t, J = 7.8 Hz, 1H), 7.45 (s, 1H), 7.15 (d, J = 8.64 Hz, 1H), 7.03 (d, J = 8.64 Hz, 1H), 6.80 (brs, 1H), 5.05-5.01 (m, 1H), 4.38-4.34 (m, 4H), 4.20-4.16 (m, 1H), 3.17-3.13 (m, 1H), 2.98-2.83 (m, 1H), 2.69-2.66 (m, 1H), 2.55-2.49 (m, 2H), 2.10-1.95 (m, 10H), 1.79-1.62 (m, 2H); LC MS: ES+ 531.3 |
| 81 | 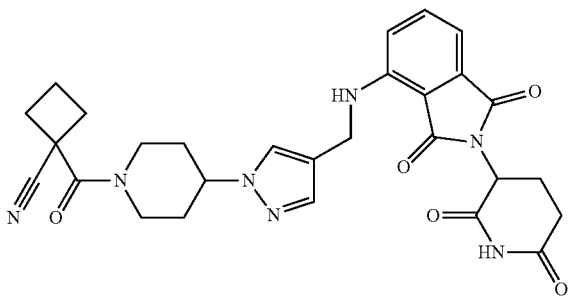 [SMILES: N#CC1(C(=O)N2CCC(n3cc(CNc4cccc5c4C(=O)N(C4CCC(=O)NC4=O)C5=O)cn3)CC2)CCC1]
150 mg, 52.20% yield, yellow solid; 1H NMR (d6-DMSO, 400 MHZ) δ 11.07 (s, 1H), 7.79 (s, 1H), 7.57 (t, J = 7.68 Hz, 1H), 7.47 (s, 1H), 7.15 (d, J = 8.52 Hz, 1H), 7.03 (d, J = 8.52 Hz, 1H), 6.81 (brs, 1H), 5.04 (dd, J = 11.52, 4.48 Hz, 1H), 4.43-4.36 (m, 4H), 3.71-3.68 (m, 1H), 3.30-3.24 (m, 1H), 2.91-2.84 (m, 2H), 2.75-2.68 (m, 2H), 2.60-2.49 (m, 4H), 2.13-2.03 (m, 4H), 1.89-1.75 (m, 3H); LC MS: ES+ 544.7. |
| 79 | 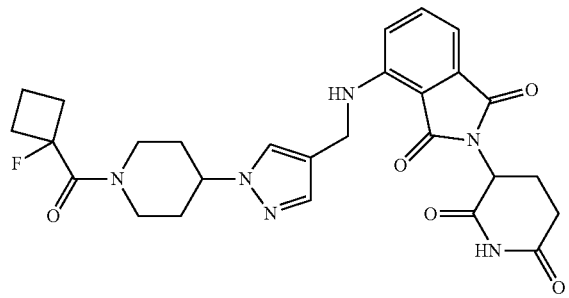 [SMILES: O=C1CCC(N2C(=O)c3cccc(NCc4cnn(C5CCN(C(=O)C6(F)CCC6)CC5)c4)c3C2=O)C(=O)N1]
130 mg, 45.83% yield, yellow solid; 1H NMR (d6-DMSO, 400 MHZ) δ 11.08 (s, 1H), 7.80 (s, 1H), 7.57 (t, J = 7.68 Hz, 1H), 7.46 (s, 1H), 7.15 (d, J = 8.48 Hz, 1H), 7.03 (d, J = 8.48 Hz, 1H), 6.80 (brs, 1H), 5.04 (dd, J = 12.76, 5.2 Hz, 1H), 4.41-4.35 (m, 4H), 3.86-3.82 (m, 1H), 3.21-3.15 (m, 1H), 2.92-2.84 (m, 2H), 2.68-2.33 (m, 6H), 2.05-1.98 (m, 3H), 1.83-1.73 (m, 3H), 1.52-1.45 (m, 1H); LC MS: ES+ 537.4 |

| No. | Compound with Characterization Data |
|---|---|
| 77 | 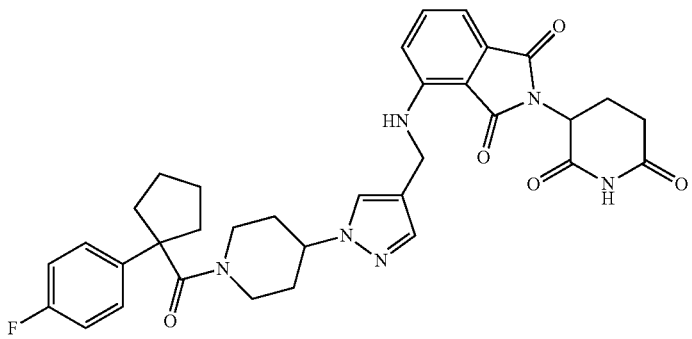 [SMILES: O=C1CCC(N2C(=O)c3cccc(NCc4cnn(C5CCN(C(=O)C6(c7ccc(F)cc7)CCCC6)CC5)c4)c3C2=O)C(=O)N1]
170 mg, 51.32% yield, yellow solid; 1H NMR (d6-DMSO, 400 MHZ) δ 11.08 (s, 1H), 7.67 (s, 1H), 7.55 (t, J = 7.82 Hz, 1H), 7.41 (s, 1H), 7.24-7.21 (m, 2H), 7.17-7.11 (m, 3H), 7.02 (d, J = 7.04 Hz, 1H), 6.79 (t, J = 5.74 Hz, 1H), 5.03 (dd, J = 12.88, 5.48 Hz, 1H), 4.50-4.41 (brs, 1H), 4.33 (d, J = 5.72 Hz, 2H), 4.25-4.19 (m, 1H), 3.49-3.39 (brs, 1H), 2.87-2.84 (m, 1H), 2.73-2.67 (m, 2H), 2.59-2.49 (m, 2H), 2.35-2.28 (m, 2H), 2.02-1.99 (m, 1H), 1.92-1.88 (m, 2H0, 1.62 (brs, 5H); LC MS: ES+ 625.36 |
| 86 | 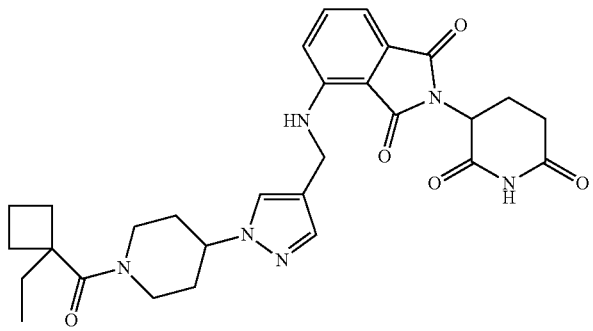 [SMILES: CCC1(C(=O)N2CCC(n3cc(CNc4cccc5c4C(=O)N(C4CCC(=O)NC4=O)C5=O)cn3)CC2)CCC1]
155 mg, 53.64% yield, yellow solid; 1H NMR (d6-DMSO, 400 MHZ) δ 11.08 (s, 1H), 7.79 (s, 1H), 7.57 (t, J = 7.78 Hz, 1H), 7.46 (s, 1H), 7.15 (d, J = 8.56 Hz, 1H), 7.03 (d, J = 8.56 Hz, 1H), 6.80 (t, J = 5.22 Hz, 1H), 5.04 (dd, J = 12.8, 5.2 Hz, 1H), 4.45-4.35 (m, 4H), 3.63-3.59 (m, 1H), 3.09-3.05 9M, 1H), 2.92-2.84 (m, 1H), 2.67-2.49 (m, 3H), 2.39-2.35 (m, 2H), 2.03-1.96 (m, 3H), 1.86-1.82 (m, 3H), 1.75-1.63 (m, 5H), 0.76 (t J = 7.26 Hz, 3H); LC MS: ES+ 547.5 |
| 78 | 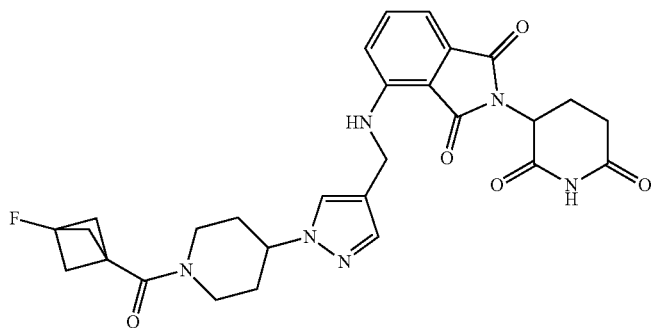 [SMILES: O=C1CCC(N2C(=O)c3cccc(NCc4cnn(C5CCN(C(=O)C67CC(F)(C6)C7)CC5)c4)c3C2=O)C(=O)N1]
170 mg, 58.62% yield, yellow solid; 1H NMR (d6-DMSO, 400 MHZ) δ 11.08 (s, 1H), 7.78 (s, 1H), 7.57 (t, J = 7.78 Hz, 1H), 7.46 (s, 1H), 7.15 (d, J = 8.56 Hz, 1H), 7.03 (d, J = 8.56 Hz, 1H), 6.80 (t, J = 5.42 Hz, 1H), 5.04 (dd, J = 12.76, 5.4 Hz, 1H), 4.42-4.35 (m, 4H), 4.04-4.00 (m, 1H), 3.20-3.14 (m, 1H), 2.92-2.83 (m, 1H), 2.77-2.71 (m, 1H), 2.60-2.49 (m, 2H), 2.50 (s, 6H), 2.07-1.95 (m, 3H), 1.77-1.68 (m, 2H); LC MS: ES+ 549.2 |

| No. | Compound with Characterization Data |
|---|---|
| 85 | 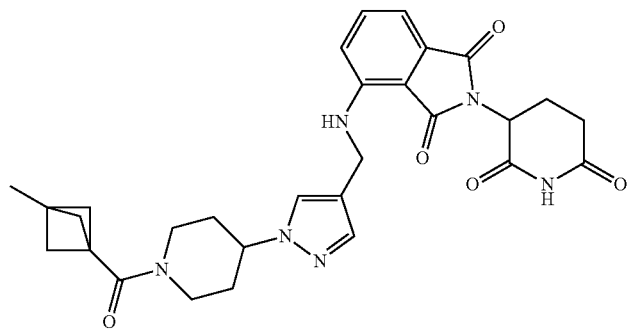 [SMILES: CC12CC(C(=O)N3CCC(n4cc(CNc5cccc6c5C(=O)N(C5CCC(=O)NC5=O)C6=O)cn4)CC3)(C1)C2]<br>140 mg, 48.63% yield, yellow solid; 1H NMR (d6-DMSO, 400 MHZ) δ 11.08 (s, 1H), 7.78 (s, 1H), 7.57 (t, J = 7.78 Hz, 1H), 7.45 (s, 1H), 7.15 (d, J = 8.48 Hz, 1H), 7.03 (d, J = 8.48 Hz, 1H), 6.80 (brs, 1H), 5.04 (dd, J = 12.72, 5.48 Hz, 1H), 4.38-4.33 (m, 4H), 4.17-4.14 (m, 1H), 3.17-3.10 (m, 1H), 2.92-2.83 (m, 1H), 2.70-2.64 (m, 1H), 2.60-2.49 (m, 2H), 2.03-1.92 (m, 9H), 1.73-1.65 (m, 2H), 1.46 (s, 3H); LC MS: ES+ 545.3 |
| 88 | 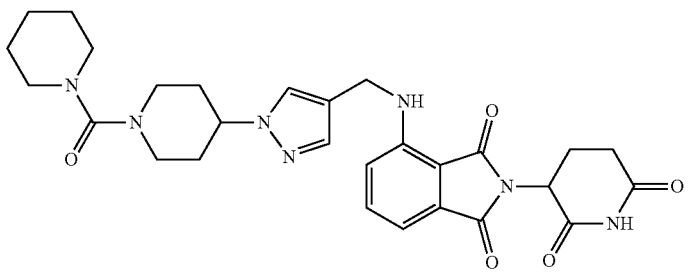 [SMILES: O=C1CCC(N2C(=O)c3cccc(NCc4cnn(C5CCN(C(=O)N6CCCCC6)CC5)c4)c3C2=O)C(=O)N1]<br>190 mg, 97.69% yield, yellow solid; 1H NMR (d6-DMSO, 400 MHZ) δ 11.08 (s, 1H), 7.78 (s, 1H), 7.57 (t, J = 7.74 Hz, 1H), 7.45 (s, 1H), 7.15 (d, J = 8.6 Hz, 1H), 7.03 (d, J = 8.6 Hz, 1H), 6.80 (brs, 1H), 5.04 (dd, J = 12.8, 5.36 Hz, 1H), 4.36 (d, J = 5.64 Hz, 2H), 4.30-4.24 (m, 1H), 3.63-3.56 (m, 2H), 3.11 (brs, 4H), 2.87-2.81 (m, 3H), 2.60-2.49 (m, 2H), 2.03-1.80 (m, 5H), 1.51-1.46 (m, 6H); LC MS: ES+ 548.4 |
| 71 | 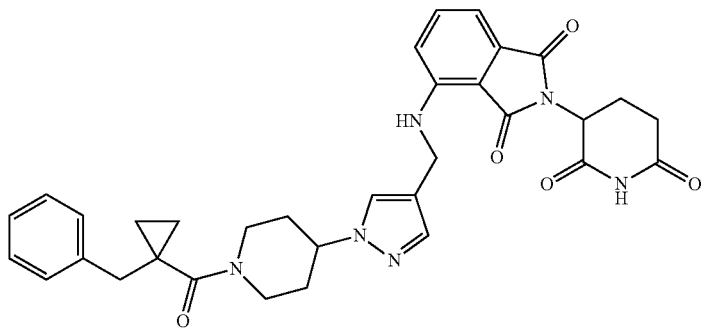 [SMILES: O=C1CCC(N2C(=O)c3cccc(NCc4cnn(C5CCN(C(=O)C6(Cc7ccccc7)CC6)CC5)c4)c3C2=O)C(=O)N1]<br>120 mg, 47.72% yield, yellow solid; 1H NMR (400 MHz, DMSO-d6) 11.09 (s, 1H), 7.76 (s, 1H), 7.57 (t, J = 7.84 Hz, 1H), 7.46 (s, 1H), 7.27-7.23 (m, 2H), 7.19-7.14 (m, 4H), 7.03 (d, J = 7.04 Hz, 1H), 6.82 (brs, 1H), 5.04 (dd, J = 12.64, 4.88 Hz, 1H), 4.36 (d, J = 5.72 Hz, 1H), 4.30-4.27 (m, 2H), 2.92-2.84 (m, 3H), 2.79 (s, 2H), 2.60-2.49 (m, 2H), 2.03-1.95 (m, 3H), 1.69-1.63 (m, 2H), 0.81 (s, 2H), 0.69 (s, 2H); LC MS: ES+ 595.4 |

| No. | Compound with Characterization Data |
|---|---|
| 89 | 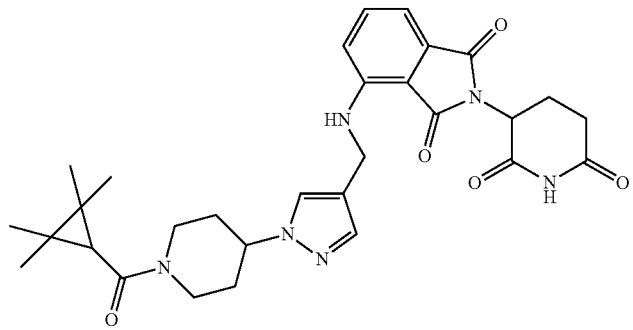 [SMILES: CC1(C)C(C(=O)N2CCC(n3cc(CNc4cccc5c4C(=O)N(C4CCC(=O)NC4=O)C5=O)cn3)CC2)C1(C)C] |

128 mg, 43.19% yield, yellow solid; 1H NMR (400 MHz, DMSO-d6) 11.09 (s, 1H), 7.78 (s, 1H), 7.57 (t, J = 7.74 Hz, 1H), 7.46 (s, 1H), 7.16 (d, J = 8.48 Hz, 1H), 7.03 (d, J = 7 Hz, 1H), 6.81 (brs, 1H), 5.04 (dd, J = 12.72, 5.24 Hz, 1H), 4.43-4.35 (m, 4H), 4.02-3.98 (m, 1H), 3.18-3.12 (m, 1H), 2.88-2.84 (m, 1H), 2.66-2.49 (m, 3H), 2.02-1.94 (m, 3H), 1.80-1.78 (m, 1H), 1.65-1.62 (m, 1H), 1.13 (s, 6H), 1.06 (s, 6H); LC MS: ES+ 561.4

| 90 | 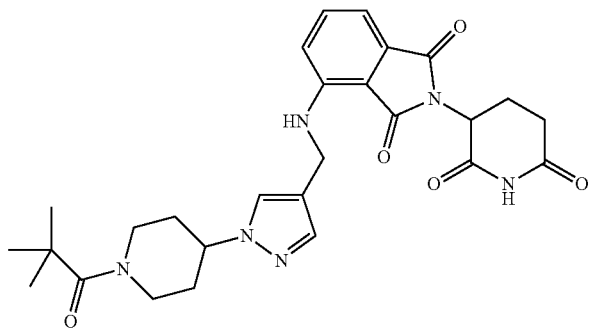 [SMILES: CC(C)(C)C(=O)N1CCC(n2cc(CNc3cccc4c3C(=O)N(C3CCC(=O)NC3=O)C4=O)cn2)CC1] |
|---|---|

106 mg, 48.15% yield, yellow solid; 1H NMR (400 MHz, DMSO-d6) 11.09 (s, 1H), 7.79 (s, 1H), 7.57 (t, J = 7.84 Hz, 1H), 7.45 (s, 1H), 7.15 (d, J = 8.6 Hz, 1H), 7.03 (d, J = 7.04 Hz, 1H), 6.80 (t, J = 5.72, 1H), 5.04 (dd, J = 12.72, 5.4 Hz, 1H), 4.41-4.32 (m, 5H), 2.95-2.84 (m, 3H), 2.60-2.49 (m, 2H), 2.01-1.98 (m, 3H), 1.76-1.70 (m, 2H), 1.20 (s, 0H); LC MS: ES+ 521.4

| 91 | 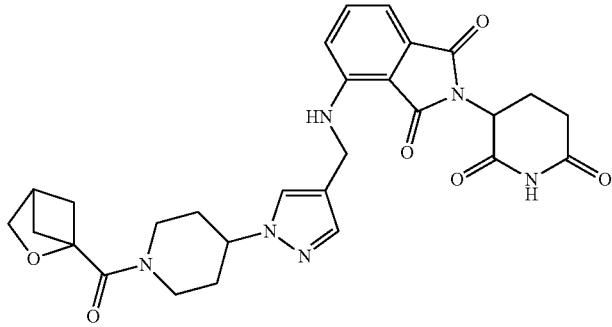 [SMILES: O=C1CCC(N2C(=O)c3cccc(NCc4cnn(C5CCN(C(=O)C67CC(CO6)C7)CC5)c4)c3C2=O)C(=O)N1] |
|---|---|

125 mg, 72.10% yield, yellow solid; 1H NMR (400 MHz, DMSO-d6) 11.09 (s, 1H), 7.79 (s, 1H), 7.57 (t, J = 7.78 Hz, 1H), 7.45 (s, 1H), 7.15 (d, J = 8.56 Hz, 1H), 7.03 (d, J = 7 Hz, 1H), 6.80 (brs, 1H), 5.04 (dd, J = 12.76, 5.32 Hz, 1H), 4.42-4.35 (m, 4H), 4.27-4.24 (m, 1H), 3.77 (s, 2H), 3.16-3.10 (m, 1H), 2.92-2.84 (m, 2H), 2.78-2.72 (m, 1H), 2.60-2.49 (m, 2H), 2.07-1.99 (m, 5H), 1.80-1.61 (m, 4H); LC MS: ES+ 547.2

| No. | Compound with Characterization Data |
|---|---|
| 92 | 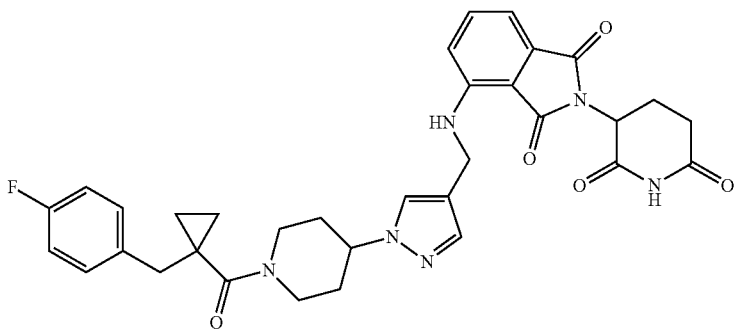 [SMILES: O=C1CCC(N2C(=O)c3cccc(NCc4cnn(C5CCN(C(=O)C6(Cc7ccc(F)cc7)CC6)CC5)c4)c3C2=O)C(=O)N1]
110 mg, 42.46% yield, yellow solid; 1H NMR (400 MHz, DMSO-d6) 11.09 (s, 1H), 7.78 (s, 1H), 7.57 (t, J = 7.84 Hz, 1H), 7.46 (s, 1H), 7.23-7.20 (m, 2H), 7.15 (d, J = 8.4 Hz, 1H), 7.10-7.02 (m, 3H), 6.81 (brs, 1H), 5.06-5.03 (m, 1H), 4.36 (d, J = 5.6 Hz, 2H), 4.30-4.27 (m, 2H), 2.93-2.84 (m, 3H), 2.78 (s, 2H), 2.60-2.49 (m, 2H), 2.04-1.97 (m, 3H), 1.73-1.66 (m, 2H), 0.82 (s, 2H), 0.70 (s, 2H); LC MS: ES+ 613.4 |
| 93 | 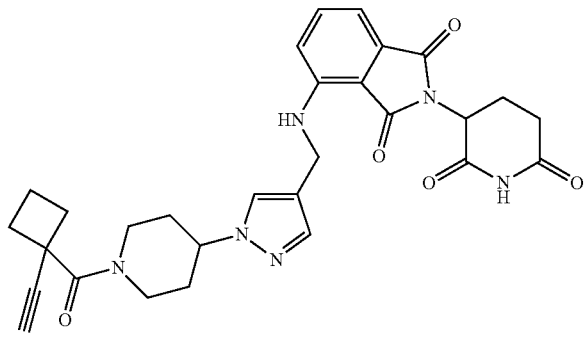 [SMILES: C#CC1(C(=O)N2CCC(n3cc(CNc4cccc5c4C(=O)N(C4CCC(=O)NC4=O)C5=O)cn3)CC2)CCC1]
120 mg, 69.73% yield, yellow solid; 1H NMR (400 MHz, DMSO-d6) 11.09 (s, 1H), 7.79 (s, 1H), 7.57 (t, J = 7.8 Hz, 1H), 7.46 (s, 1H), 7.15 (d, J = 8.6 Hz, 1H), 7.03 (d, J = 6.96 Hz, 1H), 6.81 (brs, 1H), 5.05-5.02 (m, 1H), 4.40-4.35 (m, 4H), 3.87-3.84 (m, 1H), 3.47 (s, 1H), 3.16-3.12 (m, 1H), 2.89-2.77 (m, 2H), 2.66-2.49 (m, 4H), 2.25-2.22 (m, 2H), 2.07-1.97 (m, 4H), 1.89-1.85 (m, 1H), 1.76-1.70 (m, 2H; LC MS: ES+ 543.4 |
| 94 | 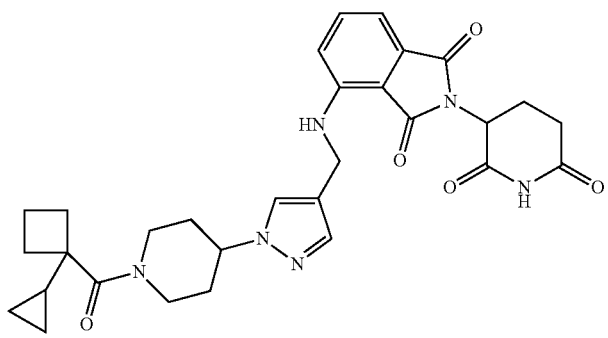 [SMILES: O=C1CCC(N2C(=O)c3cccc(NCc4cnn(C5CCN(C(=O)C6(C7CC7)CCC6)CC5)c4)c3C2=O)C(=O)N1]
110 mg, 62.08% yield, yellow solid; 1H NMR (400 MHz, DMSO-d6) 11.09 (s, 1H), 7.80 (s, 1H), 7.57 (t, J = 7.82 Hz, 1H), 7.46 (s, 1H), 7.16 (d, J = 8.6 Hz, 1H), 7.03 (d, J = 7.0 Hz, 1H), 6.81 (brs, 1H), 5.04 (dd, J = 12.76, 5.2 Hz, 1H), 4.40-4.35 (m, 4H), 3.72-3.68 (m, 1H), 3.10-3.08 (m, 1H), 2.91-2.84 (m, 1H), 6.69-2.65 (m, 1H), 2.60-2.49 (m, 2H), 2.34-2.30 (m, 2H), 2.00-1.97 (m, 3H), 1.73-1.68 (m, 5H), 1.59-1.57 (m, 1H), 0.86-0.84 (m, 1H), 0.45 (d, J = 8.08 Hz, 2H), 0.31 (s, 2H); LC MS: ES+ 559.3 |

| No. | Compound with Characterization Data |
|---|---|

95

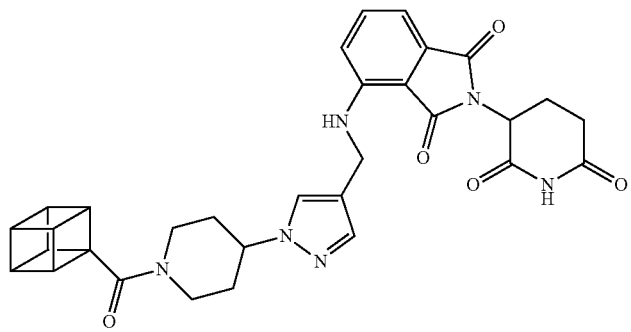 [SMILES: O=C1CCC(N2C(=O)c3cccc(NCc4cnn(C5CCN(C(=O)C67C8C9C%10C8C6C%10C97)CC5)c4)c3C2=O)C(=O)N1]

115 mg, 63.99% yield, yellow solid; 1H NMR (400 MHz, DMSO-d6) 11.08 (s, 1H), 7.80 (s, 1H), 7.57 (t, J = 7.82 Hz, 1H), 7.46 (s, 1H), 7.15 (d, J = 8.52 Hz, 1H), 7.03 (d, J = 6.96 Hz, 1H), 6.80 (brs, 1H), 5.04 (dd, J = 12.8, 5.4 Hz, 1H), 4.42-4.35 (m, 4H), 4.19 (s, 3H), 3.99 (s, 4H), 3.39-3.33 (m, 1H), 3.23-3.20 (m, 1H), 2.87-2.84 (m, 1H), 2.76-2.70 (m, 1H), 2.60-2.49 (m, 2H), 2.03-1.97 (m, 3H), 1.86-1.84 (m, 1H), 1.69-1.67 (m, 1H); LC MS: ES+ 567.4

96

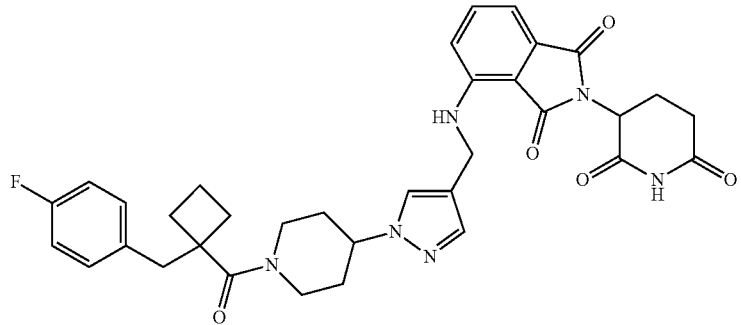 [SMILES: O=C1CCC(N2C(=O)c3cccc(NCc4cnn(C5CCN(C(=O)C6(Cc7ccc(F)cc7)CCC6)CC5)c4)c3C2=O)C(=O)N1]

95 mg, 35.85% yield, yellow solid; 1H NMR (400 MHz, DMSO-d6) 11.08 (s, 1H), 7.78 (s, 1H), 7.57 (t, J = 7.78 Hz, 1H), 7.46 (s, 1H), 7.20-7.14 (m, 3H), 7.10-7.02 (m, 3H), 6.80 (t, J = 11.28 Hz, 1H), 5.04 (dd, J = 12.76, 5.36 Hz, 1H), 4.39-4.35 (m, 4H), 3.60-3.55 (m, 1H), 3.08-2.98 (m, 3H), 2.89-2.85 (m, 1H), 2.68-2.66 (m, 1H), 2.60-2.49 (m, 2H), 2.35-2.33 (m, 2H)<2.02-1.98 (m, 5H), 1.78-1.71 (m, 3H), 1.61-1.59 (m, 1H); LC MS: ES+ 627.0

60

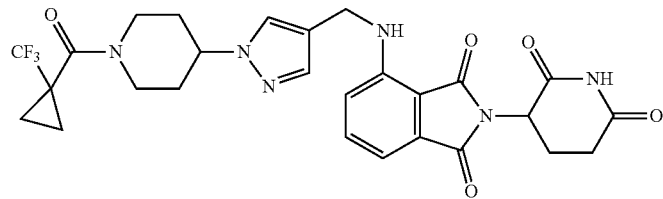 [SMILES: O=C1CCC(N2C(=O)c3cccc(NCc4cnn(C5CCN(C(=O)C6(C(F)(F)F)CC6)CC5)c4)c3C2=O)C(=O)N1]

110 mg, 36.34% yield, yellow solid; 1H NMR (400 MHz, DMSO-d6) 11.09 (s, 1H), 7.79 (s, 1H), 7.57 (t, J = 7.82 Hz, 1H), 7.46 (s, 1H), 7.15 (d, J = 8.52 Hz, 1H), 7.03 (d, J = 7.04 Hz, 1H), 6.82 (t, J = 5.68 Hz, 1H), 5.04 (dd, J = 12.76, 5.36 Hz, 1H), 4.44-4.31 (m, 5H), 3.18-2.81 (m, 3H), 2.60-2.49 (m, 2H), 2.07-2.01 (m, 3H), 1.79-1.76 (m, 2H), 1.31-1.20 (m, 4H); LC MS: ES+ 573.6

62

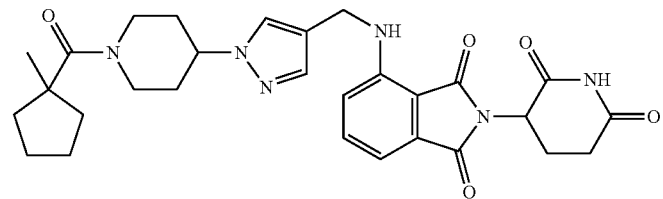 [SMILES: CC1(C(=O)N2CCC(n3cc(CNc4cccc5c4C(=O)N(C4CCC(=O)NC4=O)C5=O)cn3)CC2)CCCC1]

220 mg, 19.03% yield, yellow solid; 1H NMR (400 MHz, DMSO-d6) 11.08 (s, 1H), 7.80 (s, 1H), 7.57 (t, J = 7.78 Hz, 1H), 7.45 (s, 1H), 7.15 (d, J = 8.6 Hz, 1H), 7.03 (d, J = 7.04 Hz, 1H), 6.82 (t, J = 5.32 Hz, 1H), 5.04 (dd, J = 12.76, 5.36 Hz, 1H), 4.41-4.26 (m, 5H), 2.92-2.84 (m, 3H), 2.60-2.49 (m, 2H), 2.08-1.98 (m, 5H), 1.77-1.69 (m, 2H), 1.57-1.50 (m, 6H), 1.21 (s, 3H); LC MS: ES+ 547.3

| No. | Compound with Characterization Data |
|---|---|
| 97 | 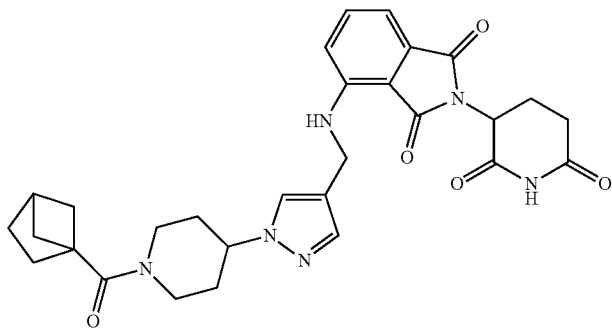 [SMILES: O=C1CCC(N2C(=O)c3cccc(NCc4cnn(C5CCN(C(=O)C67CCC(C6)C7)CC5)c4)c3C2=O)C(=O)N1]
115 mg, 49.93% yield, yellow solid; 1H NMR (400 MHz, DMSO-d6) 11.09 (s, 1H), 7.79 (s, 1H), 7.57 (t, J = 7.74 Hz, 1H), 7.45 (s, 1H), 7.15 (d, J = 8.68 Hz, 1H), 7.03 (d, J = 6.84 Hz, 1H), 6.81 (brs, 1H), 5.04 (dd, J = 12.8, 5.56 Hz, 1H), 4.40-4.35 (m, 4H), 3.75-3.73 (m, 1H), 3.43-3.09 (m, 1H), 2.91-2.84 (m, 1H), 2.68-2.66 (m, 1H), 2.60-2.49 (m, 2H), 2.31-2.29 (m, 1H), 2.01-1.98 (m, 3H), 1.72-1.68 (m, 7H), 1.33 (s, 2H); LC MS: ES+ 545.4 |
| 75 | 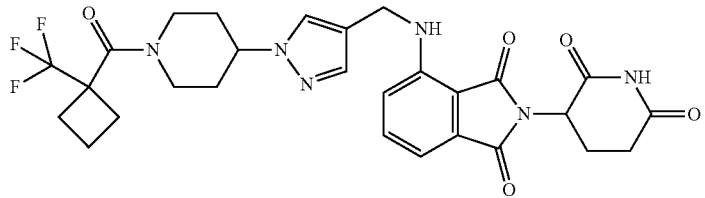 [SMILES: O=C1CCC(N2C(=O)c3cccc(NCc4cnn(C5CCN(C(=O)C6(C(F)(F)F)CCC6)CC5)c4)c3C2=O)C(=O)N1]
400 mg, 43.00% yield, yellow solid; 1H NMR (400 MHz, DMSO-d6) 11.09 (s, 1H), 7.79 (s, 1H), 7.57 (t, J = 7.76 Hz, 1H), 7.46 (s, 1H), 7.15 (d, J = 8.56 Hz, 1H), 7.03 (d, J = 7.04 Hz, 1H), 6.81 (brs, 1H), 5.04 (dd, J = 12.8, 5.4 Hz, 1H), 4.47-4.35 (m, 4H), 3.60-3.57 (m, 1H), 3.18-3.12 (m, 1H), 2.92-2.81 (m, 2H), 2.72-2.64 (m, 3H), 2.60-2.49 (m, 3H), 2.07-1.90 (m, 4H), 1.78-1.75 (m, 3H); LC MS: ES− 585.6 |
| 98 | 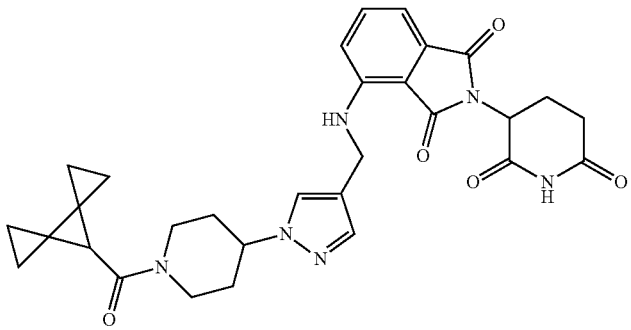 [SMILES: O=C1CCC(N2C(=O)c3cccc(NCc4cnn(C5CCN(C(=O)C6C7(CC7)C67CC7)CC5)c4)c3C2=O)C(=O)N1]
24 mg, 50.98% yield, yellow solid; 1H NMR (400 MHz, DMSO-d6) 11.08 (s, 1H), 7.77 (s, 1H), 7.57 (t, J = 7.82 Hz, 1H), 7.45 (s, 1H), 7.15 (d, J = 8.56 Hz, 1H), 7.03 (d, J = 7.04 Hz, 1H), 6.80 (t, J = 5.8 Hz, 1H), 5.04 (dd, J = 12.72, 5.48 Hz, 1H), 4.36-4.32 (m, 4H), 3.94-3.91 (m, 1H), 3.11-3.07 (m, 1H), 2.87-2.84 (m, 1H), 2.66-2.49 (m, 3H), 2.021.96 (m, 3H), 1.68-1.66 (m, 2H), 0.96-0.91 (m, 4H), 0.71-0.68 (m, 4H); LC MS: ES+ 557.3 |

| No. | Compound with Characterization Data |
|---|---|
| 99 | 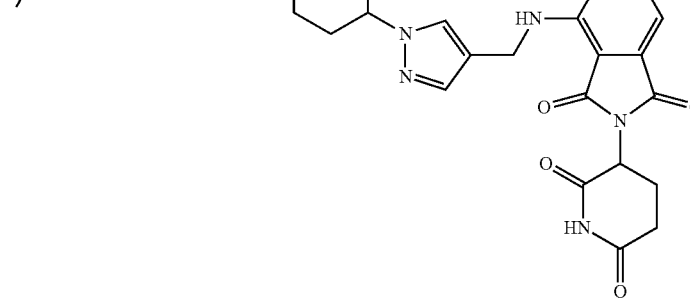 |

17 mg, 22.82% yield, yellow solid; 1H NMR (400 MHz, DMSO-d6) 11.08 (s, 1H), 7.78 (s, 1H), 7.57 (t, J = 7.4 Hz, 1H), 7.45 (s, 1H), 7.15 (d, J = 9.32 Hz, 1H), 7.03 (d, J = 6.96 Hz, 1H), 6.80 (brs, 1H), 5.05-5.03 (m, 1H), 4.45-4.42 (m, 1H), 4.36 (d, J = 6.04 Hz, 2H), 3.15-3.13 (m, 1H), 2.89-2.85 (m, 2H), 2.60-2.49 (m, 2H), 2.02-1.96 (m, 3H), 1.81 (s, 3H), 1.78-1.65 (m, 5H), 1.33-1.29 (m, 4H), 0.96-0.93 (m, 2H); LC MS: ES+ 618.5

| 100 | 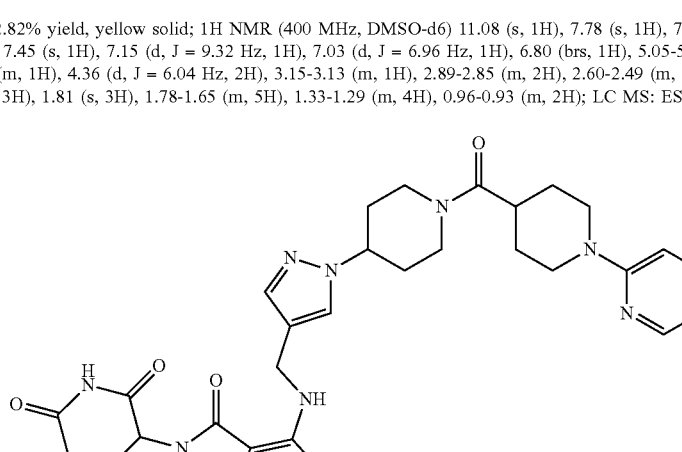 |

32 mg, 48.45% yield, yellow solid; 1H NMR (400 MHz, DMSO-d6) 11.08 (s, 1H), 8.09 (d, J = 3.72 Hz, 1H), 7.79 (s, 1H), 7.57 (t, J = 7.78 Hz, 1H), 7.51-7.46 (m, 2H), 7.16 (d, J = 8.6 Hz, 1H), 7.03 (d, J = 7.08 Hz, 1H), 6.82-6.80 (m, 2H), 6.60-6.57 (m, 1H), 5.04 (dd, J = 12.8, 5.36 Hz, 1H), 4.47-4.36 (m, 4H), 4.30-4.27 (m, 2H), 4.13-4.10 (m, 1H), 3.19-3.17 (m, 1H), 2.93-2.84 (m, 4H), 2.70-2.56 (m, 3H), 2.03-1.96 (m, 3H), 1.82-1.80 (m, 1H), 1.68-1.65 (m, 3H), 1.56-1.49 (m, 2H); LC MS: ES+ 625.5

| 101 | 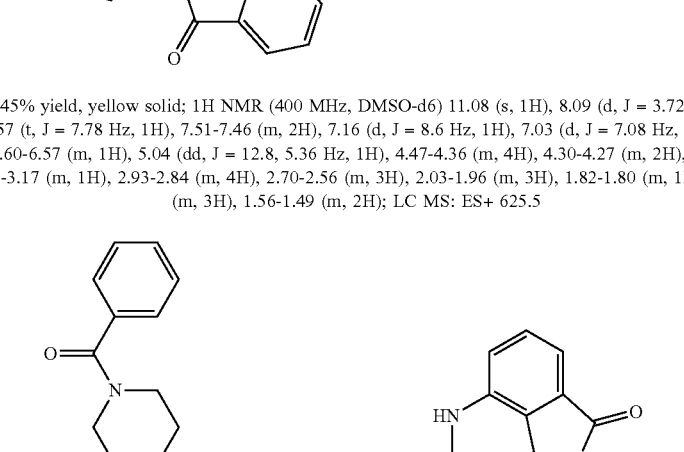 |

25 mg, 36.0% yield, yellow solid; 1H NMR (400 MHz, DMSO-d6) 11.08 (s, 1H), 7.78 (s, 1H), 7.56 (t, J = 7.76 Hz, 1H), 7.45-7.36 (m, 5H), 7.15 (d, J = 8.52 Hz, 7.03 (d, J = 7.0 Hz, 1H), 6.80 (brs, 1H), 5.04 (dd, J = 12.68, 5.4 Hz, 1H), 4.47-4.35 (m, 5H), 4.11-4.09 (m, 1H), 3.55-3.53 (m, 1H), 3.19-3.12 (m, 2H), 2.99-2.97 (m, 1H), 2.87-2.84 (m, 2H), 2.68-2.66 (m, 1H), 2.60-2.49 (m, 2H), 2.04-1.99 (m, 3H), 1.82-1.45 (m, 6H); LC MS: ES+ 652.8

| No. | Compound with Characterization Data |
|---|---|
| 102 | 30 mg, 42.08% yield, yellow solid; 1H NMR (400 MHz, DMSO-d6) 11.08 (s, 1H), 7.79 (s, 1H), 7.58-5.56 (m, 1H), 7.46 (s, 1H), 7.15 (d, J = 8.88 Hz, 1H), 7.03 (d, J = 7.2 Hz, 1H), 6.80 (brs, 1H), 5.05-5.03 (m, 1H), 4.43-4.35 (m, 4H), 3.81-3.78 (m, 2H), 3.09-3.00 (m, 2H), 2.91-2.85 (m, 2H), 2.60-2.49 (m, 2H), 2.07-1.91 (m, 6H), 1.81-1.76 (m, 2H), 1.40 (s, 9H); LC MS: ES+ 667.0 |
| 103 | 28 mg, 40.44% yield, yellow solid; 1H NMR (400 MHz, DMSO-d6) 11.07 (s, 1H), 8.68 (d, J = 4.96 Hz, 1H), 8.09 (d, J = 8.8 Hz, 2H), 7.89 (s, 1H), 7.81 (s, 1H), 7.57 (t, J = 7.78 Hz, 1H), 7.47 (s, 1H), 7.28 (d, J = 4.44 Hz, 1H), 7.15 (d, J = 8.56 Hz, 1H), 7.05-7.02 (m, 3H), 6.81 (brs, 1H), 5.04 (dd, J = 12.72, 5.56 Hz, 1H), 4.58-4.54 (m, 1H), 4.44-4.41 (m, 1H), 4.37 (d, J = 5.8 Hz, 2H), 3.82 (s, 3H), 3.58-3.55 (m, 1H), 3.23-3.21 (m, 1H), 2.95-2.84 (m, 2H), 2.60-2.49 (m, 2H), 2.32-1.85 (m, 5H); LC MS: ES+ 648.3 |
| 104 | 25 mg, 34.01% yield, yellow solid; 1H NMR (400 MHz, DMSO-d6) 11.09 (s, 1H), 7.77 (s, 1H), 7.59-7.55 (m, 2H), 7.47 (s, 1H), 7.43 (d, J = 7.0 Hz, 1H), 7.26 (t, J = 7.52 Hz, 1H), 7.16 (d, J = 8.64 Hz, 1H), 7.04 (d, J = 7.0 Hz, 1H), 6.82 (t, J = 5.74 Hz, 1H), 5.04 (dd, J = 12.84, 5.4 Hz, 1H), 4.43-4.36 (m, 4H), 4.23 (s, 3H), 4.13-4.10 (m, 1H), 3.25-3.23 (m, 1H), 2.88-2.75 (m, 2H), 2.60-2.49 (m, 5H), 2.07-1.98 (m, 3H), 1.91-1.88 (m, 1H), 1.74-1.70 (m, 1H); LC MS: ES+ 610.4 |

| No. | Compound with Characterization Data |
|---|---|
| 105 | 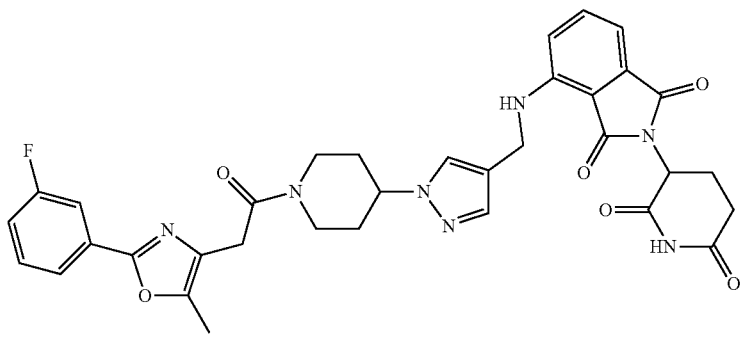 [SMILES: Cc1oc(-c2cccc(F)c2)nc1CC(=O)N1CCC(n2cc(CNc3cccc4c3C(=O)N(C3CCC(=O)NC3=O)C4=O)cn2)CC1] |

18 mg, 42.62% yield, yellow solid; 1H NMR (400 MHz, DMSO-d6) 11.09 (s, 1H), 7.76-7.73 (m, 2H), 7.63 (d, J = 9.64 Hz, 1H), 7.58-7.52 (m, 2H), 7.46 (s, 1H), 7.32 (t, J = 8.76 Hz, 1H), 7.15 (d, J = 8.64 Hz, 1H), 7.03 (d, J = 7.12 Hz, 1H), 6.80 (t, J = 5.5 Hz, 1H), 5.04 (dd, J = 12.96, 5.68 Hz, 1H), 4.45-4.35 (m, 4H), 4.15-4.12 (m, 1H), 3.67-3.62 (m, 2H), 3.26-3.20 (m, 1H), 2.87-2.84 (m, 1H), 2.77-2.71 (m, 1H), 2.60-2.49 (m, 2H), 2.34 (s, 3H), 2.07-1.89 (m, 4H), 1.72-1.70 (m, 1H); LC MS: ES+ 654.8

| 106 | 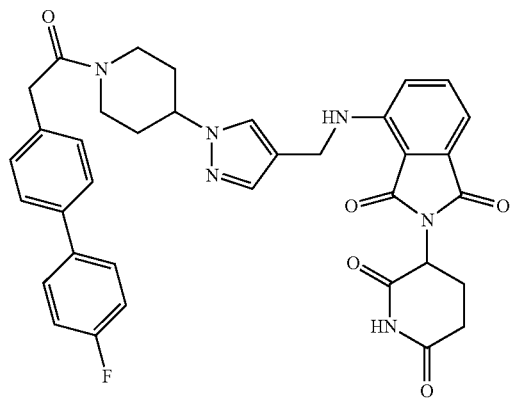 [SMILES: O=C1CCC(N2C(=O)c3cccc(NCc4cnn(C5CCN(C(=O)Cc6ccc(-c7ccc(F)cc7)cc6)CC5)c4)c3C2=O)C(=O)N1] |

35 mg, 49.14% yield, yellow solid; 1H NMR (400 MHz, DMSO-d6) 11.08 (s, 1H), 7.75 (s, 1H), 7.70-7.67 (m, 2H), 7.60-7.54 (m, 3H), 7.45 (s, 1H), 7.32 (d, J = 8.12 Hz, 2H), 7.27 (t, J = 8.82 Hz, 2H), 7.14 (d, J = 8.56 Hz, 1H), 7.03 (d, 7.04 Hz, 1H), 6.80 (t, J = 5.62 Hz, 1H), 5.04 (dd, J = 12.72, 5.44 Hz, 1H), 4.48-4.44 (m, 1H), 4.39-4.35 (m, 3H), 4.08-4.05 (m, 1H), 3.83-3.73 (m, 2H), 3.18-3.12 (m, 1H), 2.92-2.83 (m, 1H), 2.76-2.70 (m, 1H), 2.60-2.49 (m, 2H), 2.02-1.96 (m, 3H), 1.73-1.69 (m, 2H); LC MS: ES+ 649.7

| 107 | 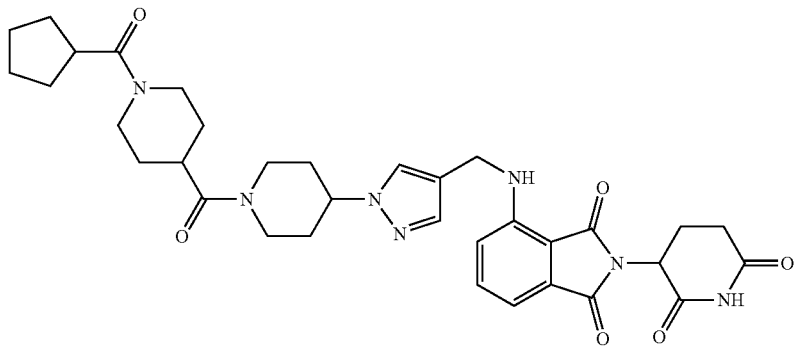 [SMILES: O=C1CCC(N2C(=O)c3cccc(NCc4cnn(C5CCN(C(=O)C6CCN(C(=O)C7CCCC7)CC6)CC5)c4)c3C2=O)C(=O)N1] |

38 mg, 52.82% yield, Yellow Solid; 1H NMR (400 MHz, DMSO-d6): δ 11.08 (s, 1H), 7.78 (s, 1H), 7.59-7.55 (m, 1H), 7.46 (s, 1H), 7.16 (d, J = 8 Hz, 1H), 7.04 (d, J = 8 Hz, 1H), 6.81 (t, J = 4 Hz, 1H), 5.05-5.02 (m, 1H), 4.46-4.35 (m, 5H), 4.10-4.07 (m, 2H), 3.98-3.95 (m, 2H), 3.25-3.17 (m, 1H), 3.10-3.06 (m, 1H), 3.03-2.86 (m, 2H), 2.84-2.67 (m, 1H), 2.66-2.55 (m, 2H), 2.01-1.96 (m, 3H), 1.81-1.51 (m, 13H), 1.31-1.23 (m, 2H). LCMS (ES+) = 644.1 [M + H]+

| No. | Compound with Characterization Data |
|---|---|
| 108 | 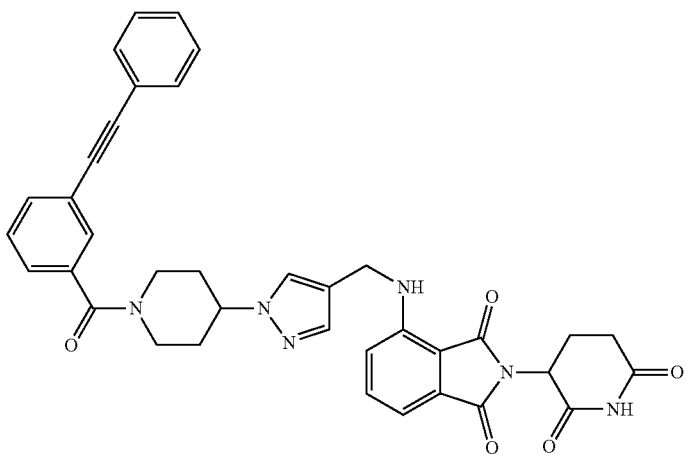 [SMILES: O=C1CCC(N2C(=O)c3cccc(NCc4cnn(C5CCN(C(=O)c6cccc(C#Cc7ccccc7)c6)CC5)c4)c3C2=O)C(=O)N1]<br>20 mg, 28.84% yield, Yellow Solid; 1H NMR (400 MHz, DMSO-d6): δ 11.08 (s, 1H), 7.82 (s, 1H), 7.64 (d, J = 8 Hz, 1H), 7.58-7.55 (m, 4H), 7.52 (t, J = 8 Hz, 1H), 7.46-7.43 (m, 4H), 7.1 4 (d, J = 8 Hz, 1H), 7.04 (d, J = 8 Hz, 1H), 6.83 (t, J = 4 Hz, 1H), 5.06-5.02 (m, 1H), 4.44-4.43 (m, 2H), 4.37-4.36 (d, J = 4 Hz, 2H), 3.60 (bs, 1H), 3.20 (bs, 1H), 2.88-2.84 (m, 2H), 2.59-2.55 (m, 1H), 2.02-1.86 (m, 6H). LCMS (ES+) = 641.1 [M + H]+. |
| 109 | 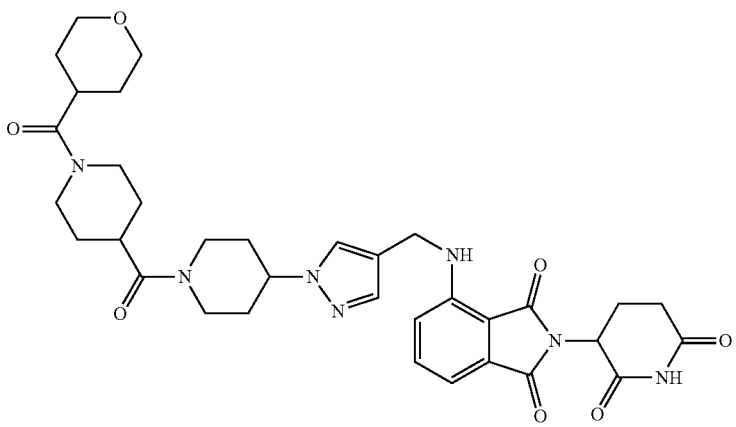 [SMILES: O=C1CCC(N2C(=O)c3cccc(NCc4cnn(C5CCN(C(=O)C6CCN(C(=O)C7CCOCC7)CC6)CC5)c4)c3C2=O)C(=O)N1]<br>25 mg, 35.37% yield, Yellow Solid; 1H NMR (400 MHz, DMSO-d6): δ 11.08 (s, 1H), 7.78 (s, 1H), 7.59 (t, J = 8 Hz, 1H), 7.46 (s, 1H), 7.16 (d, J = 8 Hz, 1H), 7.04 (d, J = 8 Hz, 1H), 6.82 (m, 1H), 5.06-5.02 (m, 1H), 4.46-4.42 (m, 1H), 4.37-4.35 (m, 4H), 4.10-4.07 (m, 1H), 4.00-3.96 (m, 1H), 3.84-3.81 (m, 2H), 3.40-3.37 (m, 2H), 3.30-3.16 (m, 1H), 3.13-3.05 (m, 1H), 2.94-2.83 (m, 3H), 2.66-2.55 (m, 4H), 2.01-1.98 (m, 3H), 1.95-1.81 (m, 1H), 1.78-1.56 (m, 8H), 1.13-1.12 (m, 1H). LCMS (ES+) = 660.2 [M + H]+. |
| 110 | 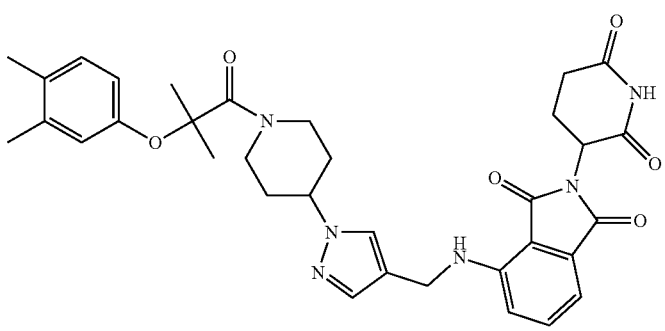 [SMILES: Cc1ccc(OC(C)(C)C(=O)N2CCC(n3cc(CNc4cccc5c4C(=O)N(C4CCC(=O)NC4=O)C5=O)cn3)CC2)cc1C]<br>30 mg, 41.07% yield, Yellow Solid; 1H NMR (400 MHz, DMSO-d6): δ 11.08 (s, 1H), 7.58-7.54 (s, 2H), 7.41 (s, 1H), 7.13-7.11 (m, 1H), 7.04-6.98 (m, 2H), 6.78 (s, 1H), 6.62 (s, 1H), 6.51-6.49 (d, 1H), 5.06-5.02 (m, 1H), 4.65-4.62 (m, 1H), 4.54-4.53 (m, 1H), 4.34-4.27 (m, 3H), 3.12-3.06 (m, 1H), 2.87-2.84 (m, 1H), 2.69 (m, 1H), 2.60-2.55 (m, 1H), 2.12-2.10 (m, 6H), 2.02-1.99 (m, 2H), 1.84-1.82 (m, 1H), 1.64-1.61 (m, 1H), 1.51 (m, 6H), 1.40 (m, 1H). LCMS (ES+) = 627.1 [M + H]+ |

| No. | Compound with Characterization Data |
|---|---|
| 111 | 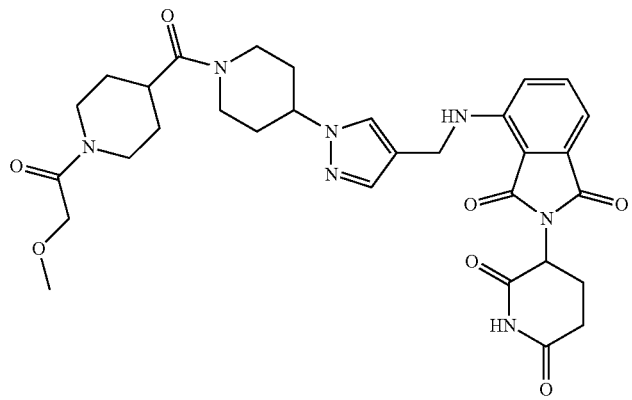 [SMILES: COCC(=O)N1CCC(C(=O)N2CCC(n3cc(CNc4cccc5c4C(=O)N(C4CCC(=O)NC4=O)C5=O)cn3)CC2)CC1]
(7 mg, 10.15% yield, 95% purity, yellow solid); 1H NMR (400 MHz, DMSO-d6) δ 11.08 (s, 1H), 7.79 (s, 1H), 7.57 (t, J = 7.8 Hz, 1H), 7.46 (s, 1H), 7.15 (d, J = 8.56 Hz, 1H), 7.03 (d, J = 7.08 Hz, 1H), 6.81 (brs, J = 5.76 Hz, 1H), 5.04 (dd, J = 12.8, 5.4 Hz, 1H), 4.46-4.33 (m, 5H), 4.11-4.02 (m, 3H), 3.77-3.76 (m, 1H), 3.27 (s, 3H), 3.19-3.17 (m, 1H), 3.06-3.00 (m, 1H), 2.95-2.84 (m, 3H), 2.61-2.49 (m, 3H), 2.05-1.97 (m, 3H), 1.81-1.78 (m, 1H), 1.65-1.57 (m, 3H), 1.52-1.49 (m, 1H), 1.39-1.36 (m, 1H); LC MS: ES+ 620.5 |
| 112 | 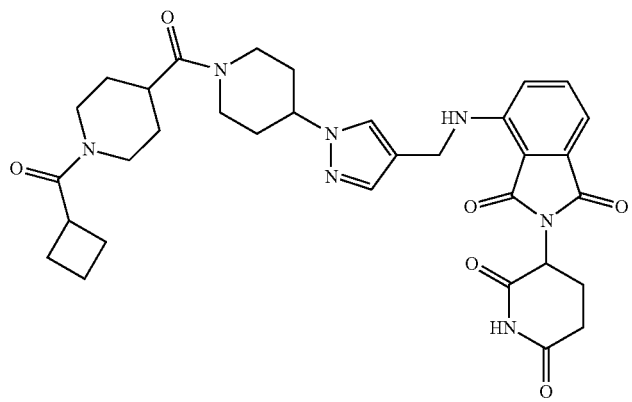 [SMILES: O=C1CCC(N2C(=O)c3cccc(NCc4cnn(C5CCN(C(=O)C6CCN(C(=O)C7CCC7)CC6)CC5)c4)c3C2=O)C(=O)N1]
(20 mg, 29.31% yield, 97.55% purity, yellow solid); 1H NMR (400 MHz, CDCl3) δ 8.01 (brs, 1H), 7.51-7.47 (m, 2H), 7.38 (s, 1H), 7.13 (d, J = 7.12 Hz, 1H), 6.92 (d, J = 8.24 Hz, 1H), 6.40 (brs, 1H), 4.89 (dd, J = 11.88, 5.36 Hz, 1H), 4.73-4.69 (m, 1H), 4.58-4.54 (m, 1H), 4.35 (d, J = 5.36 Hz, 2H), 4.33-4.30 (m, 1H), 4.02-3.98 (m, 1H), 3.78-3.74 (m, 1H), 3.26-3.21 (m, 2H), 3.00-2.94 (m, 1H), 2.91-2.84 (m, 1H), 2.80-2.64 (m, 5H), 2.38-2.29 (m, 2H), 2.22-2.09 (m, 5H), 1.97-1.82 (m, 4H), 1.74-1.66 (m, 3H); LC MS: ES+ 630.5 |
| 113 | 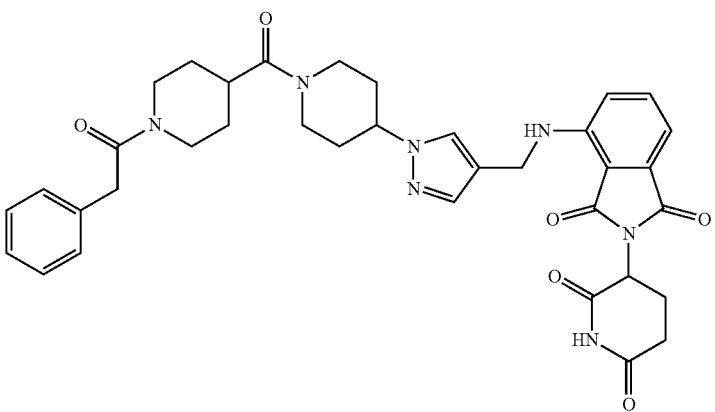 [SMILES: O=C1CCC(N2C(=O)c3cccc(NCc4cnn(C5CCN(C(=O)C6CCN(C(=O)Cc7ccccc7)CC6)CC5)c4)c3C2=O)C(=O)N1]
(18.0 mg, 23.18% yield, 98.23% purity, yellow solid); 1H NMR (400 MHz, DMSO-d6) δ 11.09 (s, 1H), 7.78 (s, 1H), 7.57 (t, J = 7.8 Hz, 1H), 7.45 (s, 1H), 7.32-7.28 (m, 2H), 7.23-7.21 (m, 3H), 7.15 (d, J = 8.56 Hz, 1H), 7.03 (d, J = 7 Hz, 1H), 6.81-6.79 (m, 1H), 5.04 (dd, J = 12.8, 5.4 Hz, 1H), 4.47-4.35 (m, 5H), 4.07-4.04 (m, 1H), 3.95-3.92 (m, 1H), 3.70 (s, 2H), 3.18-3.11 (m, 1H), 3.07-3.01 (m, 1H), 3.92-2.83 (m, 2H), 2.99-2.49 (m, 4H), 2.03-1.93 (m, 3H), 1.82-1.79 (m, 1H), 1.65-1.53 (m, 3H), 1.38-1.25 (m, 2H); LC MS: ES+ 665.5 |

| No. | Compound with Characterization Data |
|---|---|
| 114 | 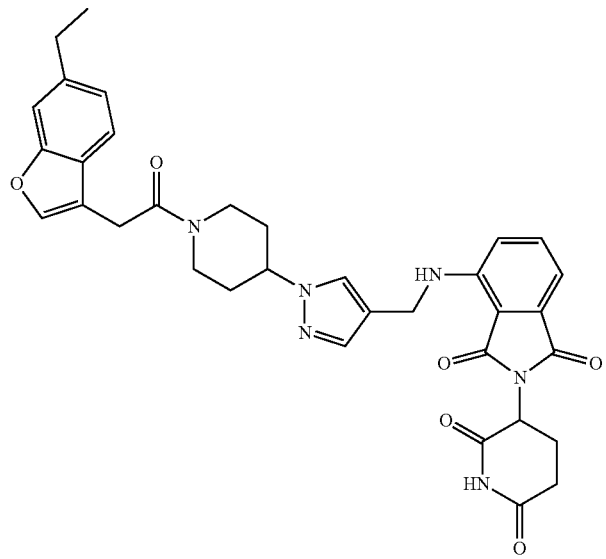 [SMILES: CCc1ccc2c(CC(=O)N3CCC(n4cc(CNc5cccc6c5C(=O)N(C5CCC(=O)NC5=O)C6=O)cn4)CC3)coc2c1] (25.0 mg, 33.57% yield, 95.77% purity, yellow solid); 1H NMR (400 MHz, DMSO-d6) δ 11.09 (s, 1H), 7.79 (s, 1H), 7.73 (s, 1H), 7.56 (t, J = 7.8 Hz, 1H), 7.50 (s, J = 7.92 Hz, 1H), 7.44 (s, 1H), 7.37 (s, 1H), 7.14 (d, J = 8.56 Hz, 1H), 7.10 (d, J = 8.12 Hz, 1H), 7.03 (d, J = 7 Hz, 1H), 6.80 (t, J = 5.44 Hz, 1H), 5.04 (dd, J = 12.8, 5.4 Hz, 1H), 4.47-4.43 (m, 1H), 4.37-4.34 (m, 3H), 4.12-4.08 (m, 1H), 3.79 (s, 2H), 3.21-3.15 (m, 1H), 2.92-2.83 (m, 1H), 2.76-2.67 (m, 3H), 2.55-2.49 (m, 2H), 2.03-1.95 (m, 3H), 1.77-1.66 (m, 2H), 1.21 (t, J = 7.6 Hz, 3H); LC MS: ES+ 623.4 |
| 115 | 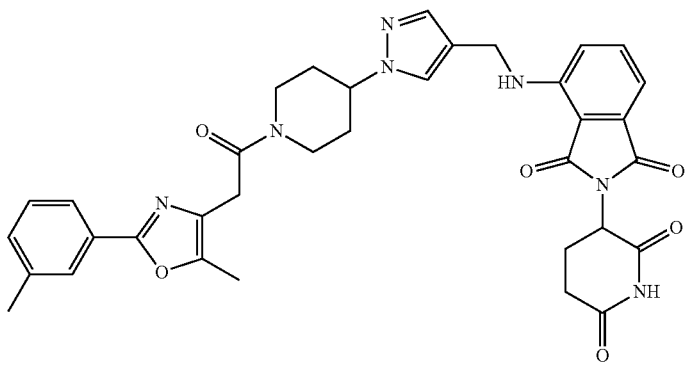 [SMILES: Cc1cccc(-c2nc(CC(=O)N3CCC(n4cc(CNc5cccc6c5C(=O)N(C5CCC(=O)NC5=O)C6=O)cn4)CC3)c(C)o2)c1] (35.0 mg, 50.95% yield, 100% purity, yellow solid); 1H NMR (400 MHz, DMSO-d6) δ 11.09 (s, 1H), 7.78 (s, 1H), 7.72 (s, 1H), 7.69 (d, J = 7.76 Hz, 1H), 7.56 (t, J = 7.82 Hz, 1H), 7.46 (s, 1H), 7.37 (t, J = 7.6 Hz, 1H), 7.28 (d, J = 7.64 Hz, 1H), 7.14 (d, J = 8.56 Hz, 1H), 7.03 (d, J = 7 Hz, 1H), 6.82-6.80 (m, 1H), 5.04 (dd, J = 12.8, 5.4 Hz, 1H), 4.45-4.39 (m, 2H), 4.35 (d, J = 5.68 Hz, 2H), 4.16-4.12 (m, 1H), 3.65-.364 (m, 2H), 3.25-3.19 (m, 1H), 2.88-2.84 (m, 1H), 2.76-2.72 (m, 1H), 2.55-2.49 (m, 2H), 2.35 (s, 3H), 2.33 (s, 3H), 2.08-1.96 (m, 3H), 1.89-1.87 (m, 1H), 1.71-1.69 (m, 1H); LC MS: ES+ 650.4 |

| No. | Compound with Characterization Data |
|---|---|
| 116 | 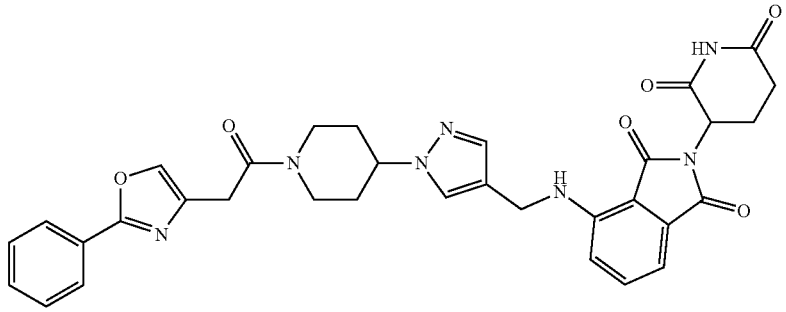 [SMILES: O=C1CCC(N2C(=O)c3cccc(NCc4cnn(C5CCN(C(=O)Cc6coc(-c7ccccc7)n6)CC5)c4)c3C2=O)C(=O)N1]<br>(30.0 mg, 41.39% yield, 90.67% purity, yellow solid); 1H NMR (400 MHz, DMSO-d6) δ 11.09 (s, 1H), 8.04 (s, 1H), 7.96-7.94 (m, 2H), 7.77 (s, 1H), 7.58-7.51 (m, 4H), 7.46 (s, 1H), 7.15 (d, J = 8.56 Hz, 1H), 7.03 (d, J = 7.04 Hz, 1H), 6.81 (t, J = 5.54 Hz, 1H), 5.04 (dd, J = 12.8, 5.4 Hz, 1H), 4.47-4.39 (m, 2H), 4.35 (d, J = 5.68 Hz, 2H), 4.14-4.11 (m, 1H), 3.74 (s, 2H), 3.26-3.20 (m, 1H), 2.88-2.83 (m, 1H), 2.78-2.72 (m, 1H), 2.55-2.49 (m, 2H), 2.07-1.88 (m, 4H), 1.74-1.70 (m, 1H); LC MS: ES+ 622.2 |
| 117 | 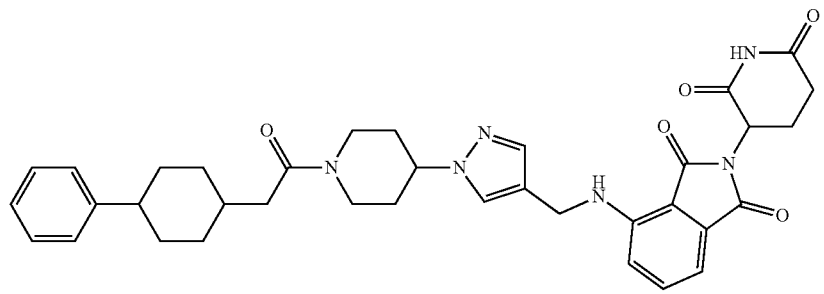 [SMILES: O=C1CCC(N2C(=O)c3cccc(NCc4cnn(C5CCN(C(=O)CC6CCC(c7ccccc7)CC6)CC5)c4)c3C2=O)C(=O)N1]<br>(28.0 mg, 36.47% yield, 95% purity, yellow solid); 1H NMR (400 MHz, DMSO-d6) δ 11.09 (s, 1H), 7.78 (s, 1H), 7.56 (t, J = 7.78 Hz, 1H), 7.46 (s, 1H), 7.27-7.20 (m, 4H), 7.16-7.14 (m, 2H), 7.03 (d, J = 7.04 Hz, 1H), 6.81 (t, J = 5.58 Hz, 1H), 5.04 (dd, J = 12.8, 5.4 Hz, 1H), 4.49-4.46 (m, 1H), 4.40-4.35 (m, 3H), 4.09-3.97 (m, 1H), 3.18-3.12 (m, 1H), 2.92-2.83 (m, 1H), 2.72-2.68 (m, 1H), 2.60-2.49 (m, 3H), 2.27-2.26 (m, 1H), 2.21-2.19 (m, 1H), 2.06-1.96 (m, 3H), 1.83-1.56 (m, 9H), 1.49-1.40 (m, 1H), 1.12-1.08 (m, 1H); LC MS: ES+ 637.2 |
| 118 | 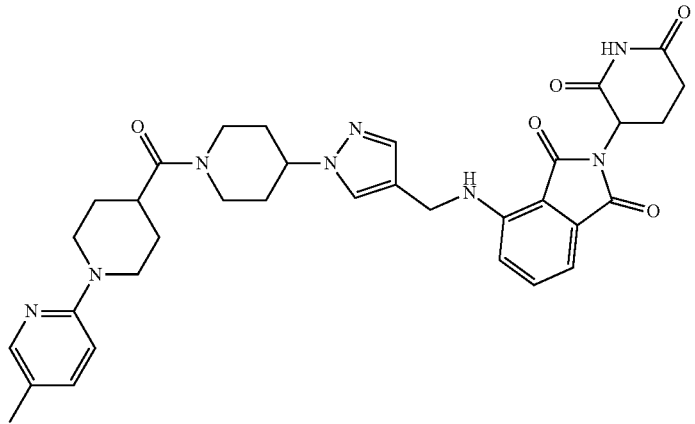 [SMILES: Cc1ccc(N2CCC(C(=O)N3CCC(n4cc(CNc5cccc6c5C(=O)N(C5CCC(=O)NC5=O)C6=O)cn4)CC3)CC2)nc1]<br>(18.0 mg, 23.37% yield, 95% purity, yellow solid); 1H NMR (400 MHz, DMSO-d6) δ 11.09 (s, 1H), 7.92 (s, 1H), 7.79 (s, 1H), 7.57 (t, J = 7.8 Hz, 1H), 7.46 (s, 1H), 7.35 (d, J = 8.32 Hz), 7.15 (d, J = 8.56 Hz, 1H), 7.03 (d, J = 7.08 Hz, 1H), 6.81 (t, J = 5.76 Hz, 1H), 6.76 (d, J = 8.52 Hz, 1H), 5.04 (dd, J = 12.8, 5.4 Hz, 1H), 4.46-4.35 (m, 4H), 4.22-4.19 (m, 2H), 4.12-4.08 (m, 1H), 3.20-3.16 (m, 1H), 2.90-2.79 (m, 4H), 2.68-2.66 (m, 1H), 2.55-2.49 (m, 2H), 2.12 (s, 3H), 2.07-1.92 (m, 3H), 1.83-1.81 (m, 1H), 1.68-1.60 (m, 3H), 1.56-1.50 (m, 2H); LC MS: ES+ 639.0 |

| No. | Compound with Characterization Data |
|---|---|
| 119 | 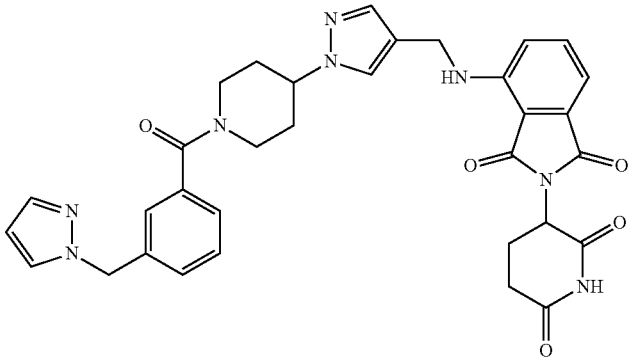 [SMILES: O=C1CCC(N2C(=O)c3cccc(NCc4cnn(C5CCN(C(=O)c6cccc(Cn7cccn7)c6)CC5)c4)c3C2=O)C(=O)N1]<br>(18 mg, 27.43% yield, 100% purity, yellow solid); 1H NMR (400 MHz, DMSO-d6) δ 11.08 (s, 1H), 7.84 (s, 1H), 7.80 (s, 1H), 7.56 (t, J = 7.82 Hz, 1H), 7.47-7.45 (m, 2H), 7.40-7.38 (m, 1H), 7.32 (d, J = 7.8 Hz, 1H), 7.26 (d, J = 7.8 Hz, 1H), 7.21 (s, 1H), 7.15 (d, J = 8.56 Hz, 1H), 7.03 (d, J = 7 Hz, 1H), 6.84-6.80 (m, 1H), 6.26 (s, 1H), 5.38 (s, 2H), 5.04 (dd, J = 12.8, 5.4 Hz, 1H), 4.47-4.35 (m, 4H), 3.62-3.58 (m, 1H), 3.15-3.13 (m, 1H), 2.93-2.84 (m, 2H), 2.60-5.49 (m, 2H), 2.03-1.82 (m, 5H); LC MS: ES+ 621.3 |
| 120 | 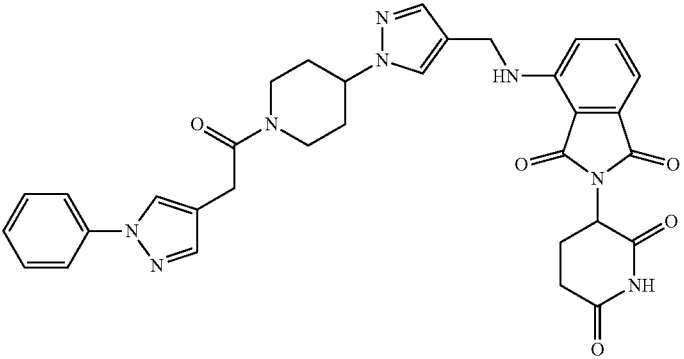 [SMILES: O=C1CCC(N2C(=O)c3cccc(NCc4cnn(C5CCN(C(=O)Cc6cnn(-c7ccccc7)c6)CC5)c4)c3C2=O)C(=O)N1]<br>(34 mg, 51.45% yield, 99.3% purity, yellow solid); 1H NMR (400 MHz, DMSO-d6) δ 11.08 (s, 1H), 8.32 (s, 1H), 7.80-7.76 (m, 3H), 7.61 (s, 1H), 7.56 (t, J = 7.82 Hz, 1H), 7.49-7.45 (m, 3H), 7.27 (t, J = 7.5 Hz, 1H), 7.14 (d, J = 8.56 Hz, 1H), 7.03 (d, J = 7 Hz, 1H), 6.81-6.79 (m, 1H), 5.04 (dd, J = 12.8, 5.4 Hz, 1H), 4.47-4.35 (m, 4H), 4.09-4.05 (m, 1H), 3.66-3.64 (m, 2H), 3.24-3.17 (m, 1H), 2.87-2.84 (m, 1H), 2.75-2.72 (m, 1H), 2.55-2.49 (m, 2H), 2.08-1.96 (m, 3H), 1.80-1.76 (m, 2H); LC MS: ES+ 621.3 |
| 121 | 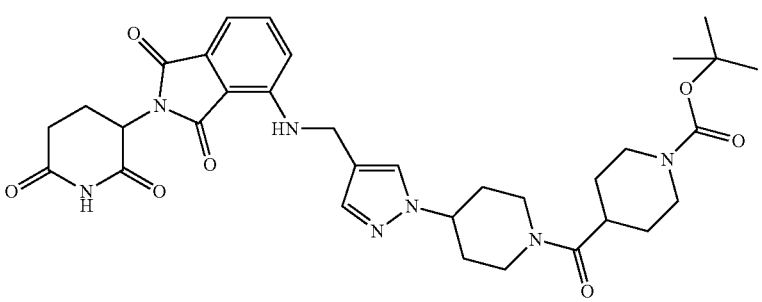 [SMILES: CC(C)(C)OC(=O)N1CCC(C(=O)N2CCC(n3cc(CNc4cccc5c4C(=O)N(C4CCC(=O)NC4=O)C5=O)cn3)CC2)CC1]<br>(55.0 mg, 63.58% yield, 95% purity, yellow solid); 1H NMR (400 MHz, DMSO-d6) δ 11.08 (s, 1H), 7.78 (s, 1H), 7.57 (t, J = 7.8 Hz, 1H), 7.46 (s, 1H), 7.15 (d, J = 8.56 Hz, 1H), 7.03 (d, J = 7.08 Hz, 1H), 6.80 (t, J = 5.76 Hz, 1H), 5.04 (dd, J = 12.8, 5.4 Hz, 1H), 4.46-4.35 (m, 4H), 4.08-4.04 (m, 1H), 3.93-3.91 (m, 2H), 3.17-3.15 (m, 1H), 2.89-2.80 (m, 4H), 2.70-2.64 (m, 1H), 2.55-2.49 (m, 2H), 2.02-1.95 (m, 3H), 1.81-1.77 (m, 1H), 1.66-1.58 (m, 3H), 1.40-1.31 (m, 11H); LC MS: ES+ 648.8 |

| No. | Compound with Characterization Data |
|---|---|
| 122 | 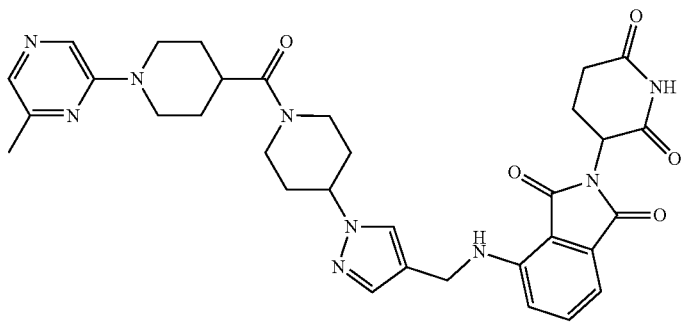 [SMILES: Cc1cncc(N2CCC(C(=O)N3CCC(n4cc(CNc5cccc6c5C(=O)N(C5CCC(=O)NC5=O)C6=O)cn4)CC3)CC2)n1]<br>4.47 mg, 9.32% yield, Yellow Solid; 1H NMR (400 MHz, DMSO-d6): δ 11.08 (s, 1H), 8.09 (s, 1H), 7.79 (s, 1H), 7.69 (s, 1H), 7.57 (t, 1H), 7.46 (s, 1H), 7.16-7.14 (d, 1H), 7.04-7.03 (d, 1H), 6.81 (t, 1H), 5.06-5.02 (m, 1H), 4.47-4.31 (m, 5H), 4.13-4.10 (m, 1H), 3.22-3.15 (m, 1H), 2.96-2.83 (m, 4H), 2.66 (s, 1H), 2.60-2.50 (m, 1H), 2.32-2.28 (s, 3H), 2.03-2.00 (m, 3H), 1.83-1.80 (m, 1H), 1.70-1.68 (m, 3H), 1.62 (m, 2H), 1.53-1.50 (s, 3H). LCMS: ES+ 640.5. |
| 123 | 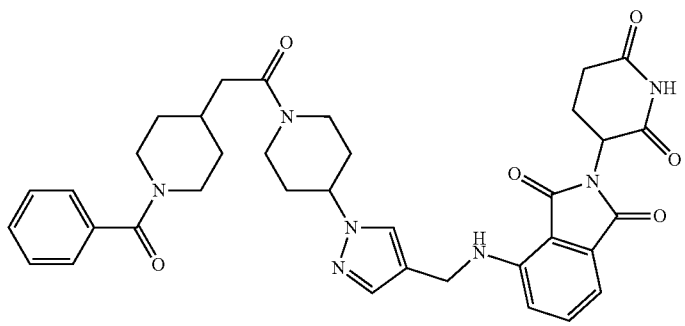 [SMILES: O=C1CCC(N2C(=O)c3cccc(NCc4cnn(C5CCN(C(=O)CC6CCN(C(=O)c7ccccc7)CC6)CC5)c4)c3C2=O)C(=O)N1]<br>29.62 mg, 13.04% yield, Yellow Solid; 1H NMR (400 MHz, DMSO-d6): δ 11.08 (s, 1H), 7.77 (s, 1H), 7.57 (t, 1H), 7.45-7.42 (m, 4H), 7.35-7.34 (m, 2H), 7.16-7.14 (d, 1H), 7.04-7.02 (m, 1H), 6.81-6.80 (m, 1H), 5.06-5.02 (m, 1H), 4.47-4.44 (m, 2H), 4.39-4.35 (m, 3H), 3.99-3.95 (d, 1H), 3.52-3.50 (m, 1H), 3.16-3.10 (m, 1H), 3.03 (m, 1H), 2.96-2.91 (m, 2H), 2.76 (m, 1H), 2.64-2.60 (m, 1H), 2.55-2.46 (m, 1H), 2.32-2.30 (m, 2H), 2.01-1.95 (m, 4H), 1.79-1.77 (m, 2H), 1.52 (m, 2H), 1.14 (brs, 2H). LCMS: ES+ 666.6. |
| 124 | 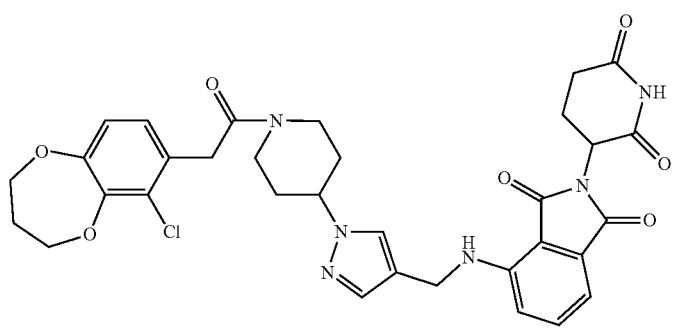 [SMILES: O=C1CCC(N2C(=O)c3cccc(NCc4cnn(C5CCN(C(=O)Cc6ccc7c(c6Cl)OCCCO7)CC5)c4)c3C2=O)C(=O)N1]<br>4.87 mg, 8.58% yield, Yellow Solid; 1H NMR (400 MHz, DMSO-d6): δ 11.08 (s, 1H), 7.75 (s, 1H), 7.57 (t, 1H), 7.45 (s, 1H), 7.16-7.14 (d, 1H), 7.04-7.02 (d, 1H), 7.00-6.99 (d, 1H), 6.81-6.79 (m, 2H), 5.06-5.02 (m, 1H), 4.44-4.35 (m, 4H), 4.17-4.12 (m, 4H), 4.03-3.99 (d, 1H), 3.69-3.59 (m, 2H), 3.50 (s, 1H), 3.13 (t, 1H), 2.91-2.83 (m, 1H), 2.71-2.66 (m, 1H), 2.60-2.55 (m, 1H), 2.13-2.10 (m, 2H), 2.03-1.94 (m, 3H), 1.77-1.66 (m, 2H). LCMS: ES+ 661.2. |

| No. | Compound with Characterization Data |
|---|---|
| 125 | 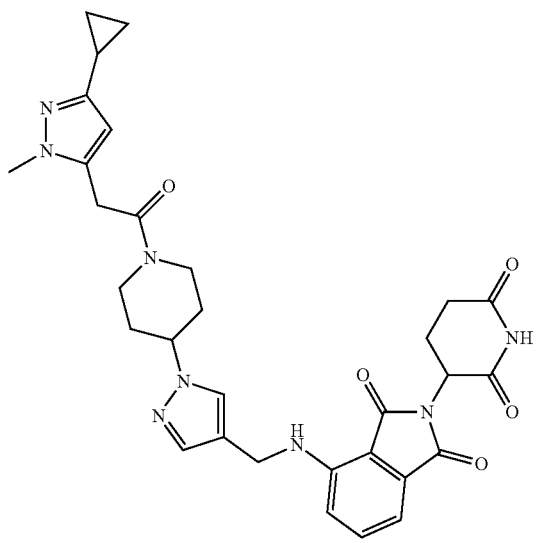 [SMILES: Cn1nc(C2CC2)cc1CC(=O)N1CCC(n2cc(CNc3cccc4c3C(=O)N(C3CCC(=O)NC3=O)C4=O)cn2)CC1] |

34.97 mg, 51.59% yield, Yellow Solid; 1H NMR (400 MHz, DMSO-d6): δ 11.07 (brs, 1H), 7.77 (s, 1H), 7.57 (t, 1H), 7.46 (s, 1H), 7.16-7.14 (d, 1H), 7.04-7.03 (d, 1H), 6.82-6.81 (m, 1H), 5.74 (s, 1H), 5.06-5.02 (m, 1H), 4.37-4.36 (m, 4H), 4.00-3.96 (m, 1H), 3.76 (s, 2H), 3.58 (s, 3H), 3.20-3.14 (m, 1H), 2.90-2.87 (m, 1H), 2.77-2.74 (m, 1H), 2.55-2.50 (m, 2H), 1.96 (m, 3H), 1.77-1.69 (m, 3H), 1.23 (s, 1H), 0.78-0.77 (m, 2H), 0.55-0.54 (m, 2H). LCMS: ES+ 599.2.

| | |
|---|---|
| 126 | 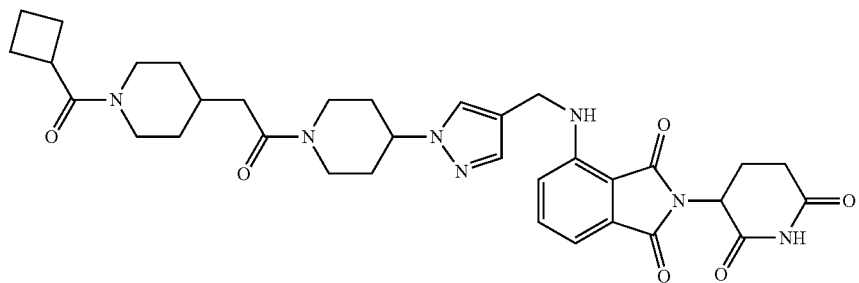 [SMILES: O=C1CCC(N2C(=O)c3cccc(NCc4cnn(C5CCN(C(=O)CC6CCN(C(=O)C7CCC7)CC6)CC5)c4)c3C2=O)C(=O)N1] |

24 mg, 35% yield, yellow solid; 1H NMR (400 MHz, DMSO-d6): δ 11.08 (s, 1H), 7.77 (s, 1H), 7.59-7.55 (t, J = 8 Hz, 1H), 7.45 (s, 1H), 7.16 (d, J = 8 Hz, 1H), 7.04 (d, J = 8 Hz, 1H), 6.81-6.78 (m, 1H), 5.06-5.02 (m, 1H), 4.47 (bd, J = 12 Hz, 1H), 4.39-4.28 (m, 4H), 3.97 (bd, J = 12 Hz, 1H), 3.65 (bd, J = 12 Hz, 1H), 3.29-3.25 (m, 1H), 3.15 (m, 1H), 2.92-2.84 (m, 2H), 2.70-2.64 (m, 1H), 2.55 (bs, 1H), 2.27-2.25 (d, J = 8 Hz, 2H), 2.16-1.95 (m, 8H), 1.90-1.78 (m, 3H), 1.75-1.67 (m, 4H), 1.10-0.95 (m, 2H). LCMS: ES+ 644.2.

Example 2: Illustrative Preparation of Compounds of the Present Invention Synthesized by Reductive Amination

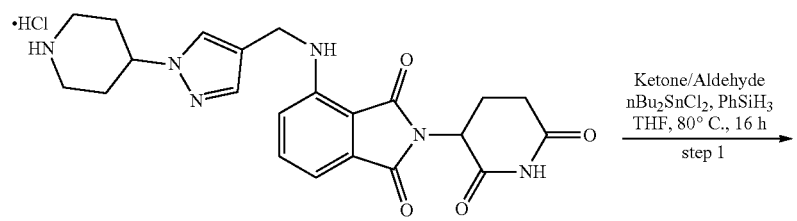

G4-1

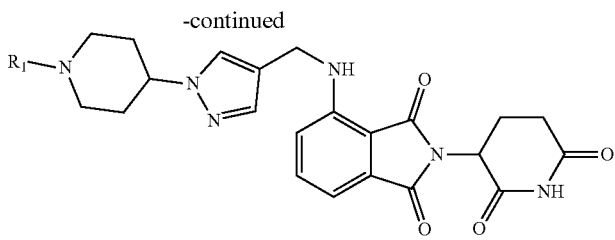

G4-2

To a mixture of G4-1 (1 mmol) and the aldehyde/ketone (1 mmol) in THF (3 mL) were added phenylsilane (1 mmol) and dibutyltin(II)trichloride (1.2 mmol). The resulting solution was heated in a sealed tube at 80° C. for 16 hours. The reaction mixture was cooled to room temperature and concentrated under reduced pressure. The crude mass was then purified by CombiFlash ISCO column eluting with 2% methanol in DCM to afford G4-2.

The following compounds were made according the general procedure of example 2:

| No. | Compound with Characterization Data |
|---|---|
| 127 | 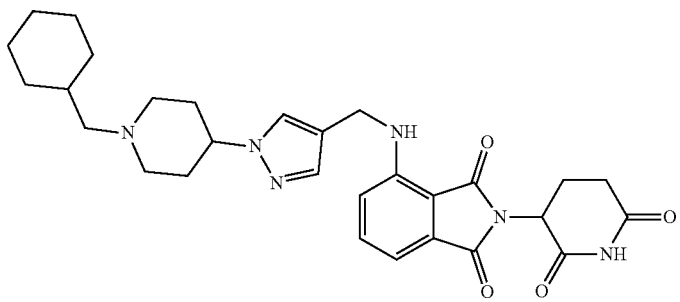 [SMILES: O=C1CCC(N2C(=O)c3cccc(NCc4cnn(C5CCN(CC6CCCCC6)CC5)c4)c3C2=O)C(=O)N1]

90 mg, 49.94% yield, yellow solid; 1H NMR (400 MHz, DMSO-d6) 11.09 (s, 1H), 7.77 (s, 1H), 7.57 (t, j = 7.84 Hz, 1H), 7.44 (s, 1H), 7.15 (d, J = 8.56 Hz, 1H), 7.03 (d, J = 8.56 Hz, 1H), 6.79 (brs, 1H), 5.05 (dd, J = 12.72, 5.24 Hz, 1H), 4.35 (d, J = 5.72 Hz, 2H), 4.07-4.03 (m, 1H), 2.87-2.84 (m, 3H), 2.60-2.54 (m, 1H), 2.06 (d, J = 6.76 Hz, 2H), 2.03-1.84 (m, 7H), 1.73-1.63 (m, 5H), 1.48-1.43 (m, 1H), 1.23-1.15 (m, 4H), 0.86-0.80 (m, 2H); LC MS: ES+ 533.3 |
| 128 | 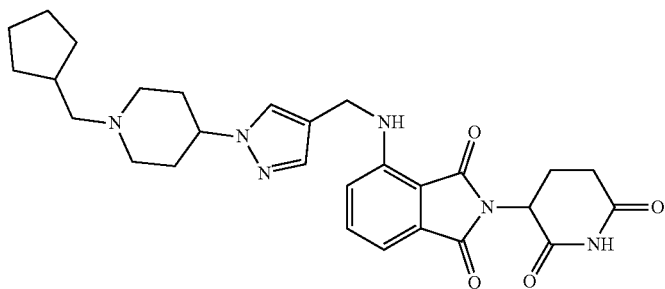 [SMILES: O=C1CCC(N2C(=O)c3cccc(NCc4cnn(C5CCN(CC6CCCC6)CC5)c4)c3C2=O)C(=O)N1]

85 mg, 48.45% yield, yellow solid; 1H NMR (400 MHz, DMSO-d6) 11.09 (s, 1H), 7.77 (s, 1H), 7.57 (t, j = 7.84 Hz, 1H), 7.44 (s, 1H), 7.15 (d, J = 8.56 Hz, 1H), 7.03 (d, J = 8.56 Hz, 1H), 6.80 (brs, 1H), 5.05 (dd, J = 12.72, 5.24 Hz, 1H), 4.35 (d, J = 5.72 Hz, 2H), 4.07-4.03 (m, 1H), 2.94-2.88 (m, 3H), 2.60-2.49 (m, 2H), 2.18-2.16 (m, 2H), 2.06-1.84 (m, 8H), 1.68-1.65 (m, 2H), 1.54-1.47 (m, 4H), 1.18-1.14 (m, 2H); LC MS: ES+ 519.3 |

| No. | Compound with Characterization Data |
|---|---|
| 129 | 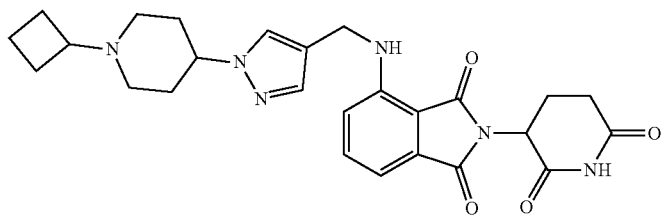 [SMILES: O=C1CCC(N2C(=O)c3cccc(NCc4cnn(C5CCN(C6CCC6)CC5)c4)c3C2=O)C(=O)N1] |

60 mg, 36.15% yield, yellow solid; 1H NMR (400 MHz, DMSO-d6) 11.09 (s, 1H), 7.76 (s, 1H), 7.57 (t, j = 7.84 Hz, 1H), 7.44 (s, 1H), 7.15 (d, J = 8.56 Hz, 1H), 7.03 (d, J = 8.56 Hz, 1H), 6.80 (brs, 1H), 5.05 (dd, J = 12.72, 5.24 Hz, 1H), 4.35 (d, J = 5.72 Hz, 2H), 4.07-4.03 (m, 1H), 2.89-2.83 (m, 3H), 2.69-2.67 (m, 1H), 2.60-2.49 (m, 2H), 2.02-1.92 (m, 5H), 1.88-1.72 (m, 6H), 1.62-1.58 (m, 2H); LC MS: ES+ 491.3

| 130 | 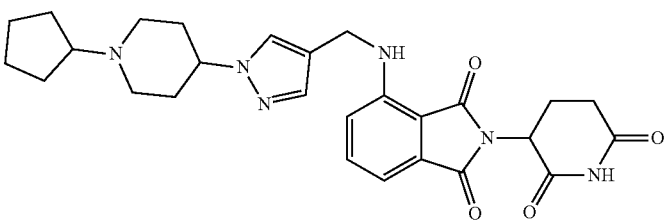 |
|---|---|

65 mg, 40.61% yield, yellow solid; 1H NMR (400 MHz, DMSO-d6) 11.09 (s, 1H), 7.76 (s, 1H), 7.57 (t, j = 7.84 Hz, 1H), 7.43 (s, 1H), 7.15 (d, J = 8.56 Hz, 1H), 7.03 (d, J = 8.56 Hz, 1H), 6.79 (brs, 1H), 5.05 (dd, J = 12.72, 5.24 Hz, 1H), 4.35 (d, J = 5.72 Hz, 2H), 4.07-4.03 (m, 1H), 2.99-2.96 (m, 2H), 2.68-2.64 (m, 1H), 2.60-2.49 (m, 3H), 2.03-1.77 (m, 9H), 1.60-1.55 (m, 2H), 1.52-1.46 (m, 2H), 1.35-1.30 (m, 2H); LC MS: ES+ 505.3

| 131 | 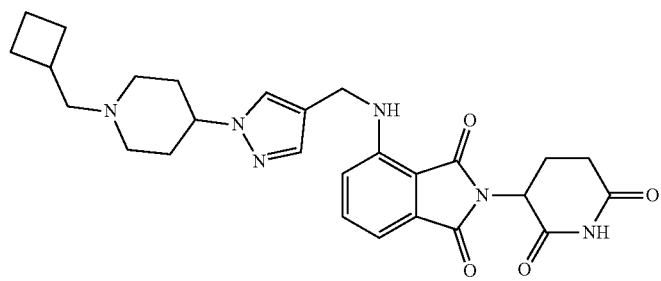 |
|---|---|

65 mg, 39.46% yield, yellow solid; 1H NMR (400 MHz, DMSO-d6) 11.09 (s, 1H), 7.76 (s, 1H), 7.57 (t, j = 7.66 Hz, 1H), 7.43 (s, 1H), 7.15 (d, J = 8.64 Hz, 1H), 7.03 (d, J = 8.64 Hz, 1H), 6.78 (brs, 1H), 5.04 (dd, J = 12.4, 4.76 Hz, 1H), 4.34 (d, J = 5.48 Hz, 2H), 4.04-4.02 (m, 1H), 2.88-2.81 (m, 3H), 2.60-2.49 (m, 3H), 2.33 (d, J = 6.8 Hz, 2H), 2.02-1.94 (m, 5H), 1.88-1.72 (m, 6H), 1.66-1.59 (m, 2H); LC MS: ES+ 505.3

| 132 | 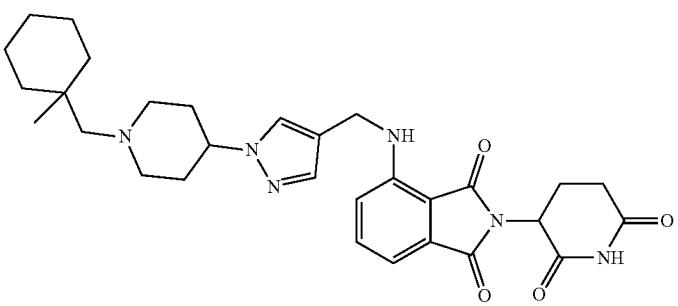 |
|---|---|

62 mg, 26.82% yield, yellow solid; 1H NMR (400 MHz, DMSO-d6) 11.08 (s, 1H), 7.77 (s, 1H), 7.57 (t, j = 7.74 Hz, 1H), 7.44 (s, 1H), 7.15 (d, J = 8.64 Hz, 1H), 7.03 (d, J = 8.64 Hz, 1H), 6.78 (t, J = 5.68 Hz, 1H), 5.04 (dd, J = 12.4, 4.76 Hz, 1H), 4.35 (d, J = 5.48 Hz, 2H), 4.05-4.02 (m, 1H), 2.87-2.84 (m, 1H), 2.80-2.77 (m, 2H), 2.60-2.49 (m, 2H), 2.37-2.32 (m, 2H), 2.10 (s, 2H), 2.01-1.98 (m, 1H), 1.91-1.86 (m, 4H), 1.43-1.27 (m, 4H), 1.23-1.16 (m, 6H), 0.84 (s, 3H); LC MS: ES+ 547.0

| No. | Compound with Characterization Data |
| --- | --- |
| 133 | 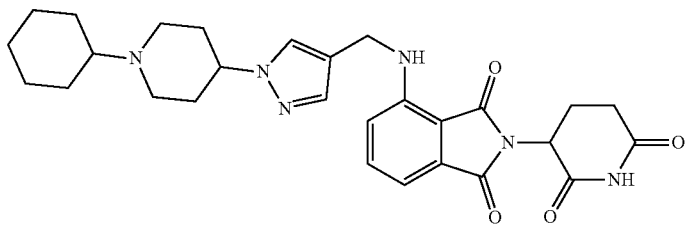

65 mg, 39.52% yield, yellow solid; 1H NMR (400 MHz, DMSO-d6) 11.09 (s, 1H), 7.76 (s, 1H), 7.57 (t, J = 7.76 Hz, 1H), 7.43 (s, 1H), 7.15 (d, J = 8.52 Hz, 1H), 7.03 (d, J = 6.96 Hz, 1H), 6.79 (brs, 1H), 5.04 (dd, J = 12.92, 5.48 Hz, 1H), 4.35 (d, J = 5.44 Hz, 2H), 4.05-4.02 (m, 1H), 2.90-2.84 (m, 3H), 2.60-2.49 (m, 2H), 2.32-2.30 (m, 2H), 2.01-1.93 (m, 3H), 1.83-1.73 (m, 5H), 1.58-1.55 (m, 1H), 1.23-1.19 (m, 4H), 1.08-1.06 (m, 1H); LC MS: ES+ 519.4 |
| 134 | 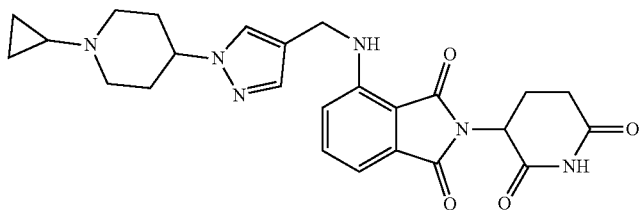

90 mg, 22.33% yield, yellow solid; 1H NMR (400 MHz, DMSO-d6) 11.09 (s, 1H), 7.76 (s, 1H), 7.56 (t, J = 7.8 Hz, 1H), 7.43 (s, 1H), 7.15 (d, J = 8.56 Hz, 1H), 7.03 (d, J = 7.04 Hz, 1H), 6.78 (t, J = 5.52 Hz 1H), 5.04 (dd, J = 12.84, 5.36 Hz, 1H), 4.35 (d, J = 5.6 Hz, 2H), 4.12-4.06 (m, 1H), 3.38-3.32 (m, 2H), 2.99-2.90 (m, 1H), 2.60-2.49 (m, 2H), 2.30-2.25 (m, 2H), 2.02-2.00 (m, 1H), 1.92-1.90 (m, 2H), 1.83-1.77 (m, 2H), 1.59-1.53 (m, 1H), 1.44-1.38 (m, 2H), 1.29-1.23 (m, 2H); LC MS: ES+ 477.0 |
| 135 | 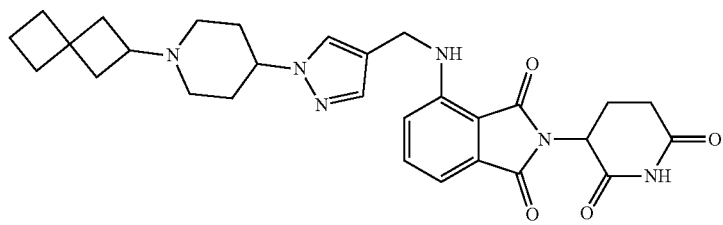 [SMILES: O=C1CCC(N2C(=O)c3cccc(NCc4cnn(C5CCN(C6CC7(CCC7)C6)CC5)c4)c3C2=O)C(=O)N1]

90 mg, 38.91% yield, yellow solid; 1H NMR (400 MHz, DMSO-d6) 11.09 (s, 1H), 7.76 (s, 1H), 7.57 (t, J = 7.82 Hz, 1H), 7.44 (s, 1H), 7.15 (d, J = 8.56 Hz, 1H), 7.03 (d, J = 7.0 Hz, 1H), 6.79 (brs, 1H), 5.04 (dd, J = 12.84, 5.4 Hz, 1H), 4.35 (d, J = 5.36 Hz, 2H), 4.05-4.03 (m, 1H), 2.92-2.80 (m, 3H), 2.60-2.49 (m, 3H), 2.02-1.69 (m, 17H); LC MS: ES+ 531.1 |
| 136 | 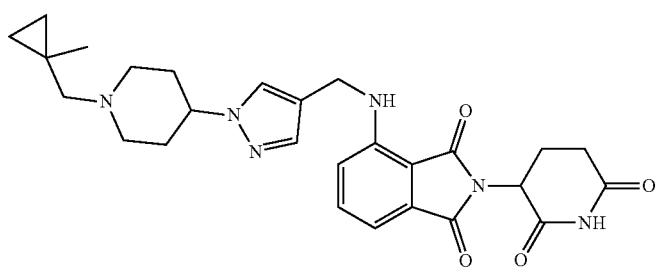 [SMILES: CC1(CN2CCC(n3cc(CNc4cccc5c4C(=O)N(C4CCC(=O)NC4=O)C5=O)cn3)CC2)CC1]

53 mg, 24.10% yield, yellow solid; 1H NMR (400 MHz, DMSO-d6) 11.08 (s, 1H), 7.78 (s, 1H), 7.57 (t, J = 7.62 Hz, 1H), 7.44 (s, 1H), 7.16 (d, J = 8.56 Hz, 1H), 7.03 (d, J = 8.56 Hz, 1H), 6.79 (brs, 1H), 5.06-5.03 (m, 1H), 4.35 (d, J = 4.88 Hz, 2H), 4.07-4.05 (m, 1H), 3.01-2.99 (m, 2H), 2.91-2.84 (m, 1H), 2.60-2.49 (m, 2H), 2.11 (s, 2H), 2.08-1.87 (m, 7H), 1.02 (s, 3H), 0.27 (s, 2H), 0.23 (s, 2H); LC MS: ES+ 505.5 |

| No. | Compound with Characterization Data |
|---|---|

137

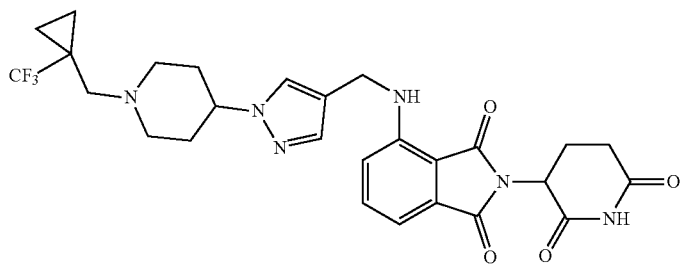 [SMILES: O=C1CCC(N2C(=O)c3cccc(NCc4cnn(C5CCN(CC6(C(F)(F)F)CC6)CC5)c4)c3C2=O)C(=O)N1]

70 mg, 29.63% yield, yellow solid; 1H NMR (400 MHz, DMSO-d6) 11.09 (s, 1H), 7.78 (s, 1H), 7.57 (t, J = 7.8 Hz, 1H), 7.44 (s, 1H), 7.15 (d, J = 8.64 Hz, 1H), 7.03 (d, J = 6.88 Hz, 1H), 6.79 (brs, 1H), 5.04 (dd, J = 12.64, 5.04 Hz, 1H), 4.35 (d, J = 5.28 Hz, 2H), 4.08-4.06 (m, 1H), 2.98-2.95 (m, 2H), 2.89-2.85 (m, 1), 2.60-2.49 (m, 3H), 2.08-2.00 (m, 2H), 1.94-1.85 (m, 3H), 0.95 (s, 2H), 0.72 (s, 2H); LC MS: ES+ 559.4

138

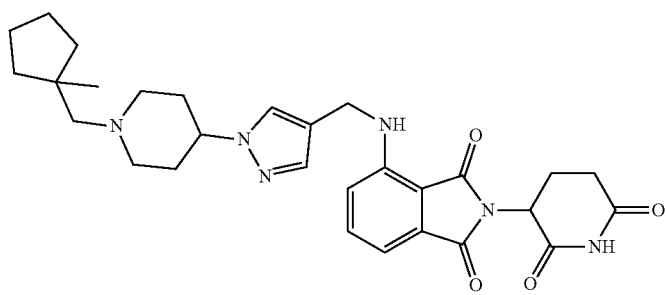 [SMILES: CC1(CN2CCC(n3cc(CNc4cccc5c4C(=O)N(C4CCC(=O)NC4=O)C5=O)cn3)CC2)CCCC1]

30 mg, 12.92% yield, yellow solid; 1H NMR (400 MHz, DMSO-d6) 11.08 (s, 1H), 7.77 (s, 1H), 7.57 (t, J = 7.8 Hz, 1H), 7.43 (s, 1H), 7.15 (d, J = 8.52 Hz, 1H), 7.03 (d, J = 7 Hz, 1H), 6.79 (t, J = 5.88 Hz, 1H), 5.04 (dd, J = 12.8, 5.4 Hz, 1H), 4.35 (d, J = 5.84 Hz, 2H), 4.05-4.03 (m, 1H), 2.86-2.83 (m, 3H), 2.60-2.49 (m, 2H), 2.32-2.22 (m, 2H), 2.19 (s, 2H), 2.02-1.98 (m, 1H), 1.92-1.86 (m, 4H), 1.58-1.50 (m, 4H), 1.44-1.40 (m, 2H), 1.28-1.18 (m, 2H), 0.93 (s, 3H); LC MS: ES+ 533.2

139

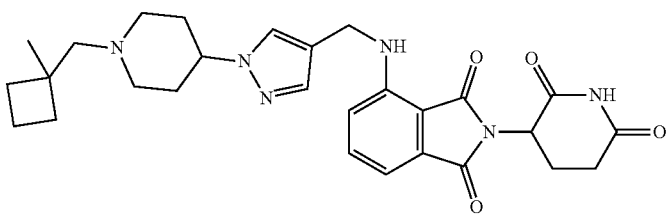

650 mg, 45.60% yield, yellow solid; 1H NMR (400 MHz, DMSO-d6) 11.10 (s, 1H), 7.77 (s, 1H), 7.57 (t, j = 7.80 Hz, 1H), 7.43 (s, 1H), 7.15 (d, J = 8.52 Hz, 1H), 7.03 (d, J = 8.52 Hz, 1H), 6.78 (m, 1H), 5.05 (dd, J = 12.8, 5.4 Hz, 1H), 4.35 (d, J = 5.64 Hz, 2H), 4.06-4.02 (m, 1H), 2.92-2.84 (m, 1H), 2.77-2.75 (m, 2H), 2.60-2.49 (m, 2H), 2.24 (s, 2H), 2.05-1.96 (m, 3H), 1.94-1.81 (m, 7H), 1.78-1.70 (m, 1H), 1.61-1.57 (m, 2H), 1.14 (s, 3H); LC MS: ES+ 519.4

| No. | Compound with Characterization Data |
|---|---|
| 140 | 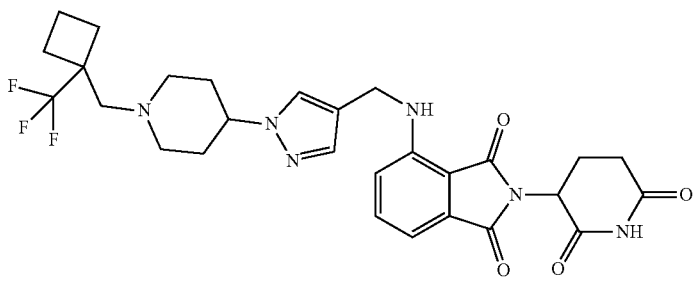 [SMILES: O=C1CCC(N2C(=O)c3cccc(NCc4cnn(C5CCN(CC6(C(F)(F)F)CCC6)CC5)c4)c3C2=O)C(=O)N1]<br><br>15 mg, 14.29% yield, yellow solid; 1H NMR (400 MHz, DMSO-d6) 11.08 (s, 1H), 7.78 (s, 1H), 7.57 (t, J = 7.74 Hz, 1H), 7.44 (s, 1H), 7.16 (d, J = 8.56 Hz, 1H), 7.03 (d, J = 7.04 Hz, 1H), 6.78 (brs, 1H), 5.04 (dd, J = 13.0, 5.52 Hz, 1H), 4.35 (d, J = 5.76 Hz, 2H), 4.10-4.08 (m, 1H), 2.89-2.84 (m, 3H), 2.60-2.49 (m, 4H), 2.31-2.25 (m, 2H), 2.17-2.12 (m, 2H), 2.07-2.00 (m, 3H), 1.94-1.80 (m, 6H); LC MS: ES+ 573.4 |

Example 3: Illustrative Synthesis of Compounds of the Present Invention by Nucleophilic Aromatic Substitution

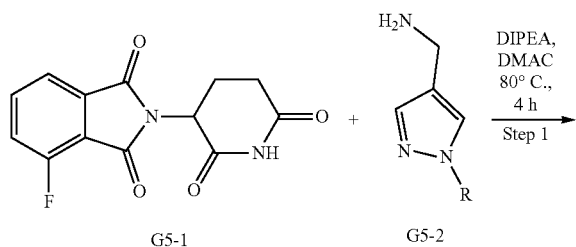

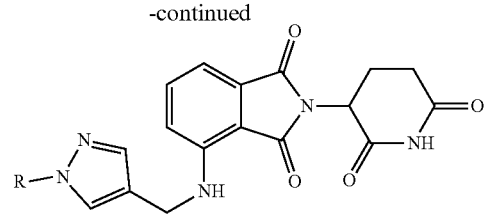

G5-3

To the stirred solution of 2-(2,6-di oxo-3-piperidyl)-4-fluoro-isoindoline-1,3-di one G5-1 (1 mmol) in DMAC (1 mL) in a sealed tube was added DIPEA (2.2 mmol) followed by G5-2 (1.2 mmol). The reaction was heated at 80° C. for 4 hours and then quenched with ice cold water, extracted with ethyl acetate, washed with brine, dried over sodium sulfate, and concentrated under reduced pressure. The crude mixture was purified by preparative TLC (1% methanol in dichloromethane) to afford G5-3 as a yellow solid.

The following compounds were prepared using the procedure of Example 3:

| No. | Compound with Characterization Data |
|---|---|
| 141 | 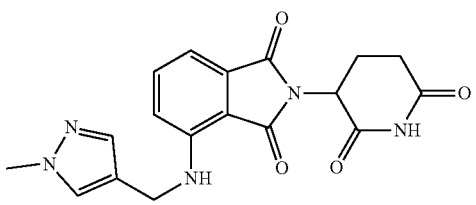 [SMILES: Cn1cc(CNc2cccc3c2C(=O)N(C2CCC(=O)NC2=O)C3=O)cn1]<br><br>Yellow solid, 16 mg, 12.03%; 1H NMR (400 MHz, DMSO-d6) δ11.08 (s, 1H), 7.65 (s, 1H), 7.59-7.54 (m, 1H), 7.41 (s, 1H), 7.13 (d, J = 8.6 Hz, 1H), 7.03 (d, J = 7.00 Hz, 1H), 6.83 (t, J = 5.72 Hz, 1H), 5.04 (dd, J = 12.72, 5.28 Hz, 1H), 4.35 (d, J = 5.76 Hz, 2H), 3.77 (s, 3H), 2.94-2.83 (m, 1H), 2.64-2.51 (m, 2H), 2.03-2.00 (m, 1H); LC MS: ES+ 368.06. |

| No. | Compound with Characterization Data |
|---|---|
| 142 | 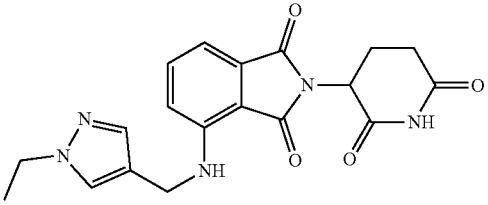 [SMILES: CCn1cc(CNc2cccc3c2C(=O)N(C2CCC(=O)NC2=O)C3=O)cn1]
Yellow solid, 12 mg, 8.69%; 1H NMR (400 MHz, DMSO-d6) δ 11.09 (s, 1H), 7.70 (s, 1H), 7.59-7.55 (m, 1H), 7.42 (s, 1H), 7.14 (d, J = 8.52 Hz, 1H), 7.03 (d, J = 7.04 Hz, 1H), 6.81 (t, J = 5.68 Hz, 1H), 5.04 (dd, J = 13.00, 5.48 Hz, 1H), 4.35 (d, J = 5.16 Hz, 2H), 4.06 (q, J = 14.48, 7.2 Hz, 2H), 2.91-2.84 (m, 1H), 2.65-2.49 (m, 2H), 2.03-2.00 (m, 1H), 1.32 (t, J = 7.26 Hz, 3H); LC MS: ES+ 382.00. |
| 143 | 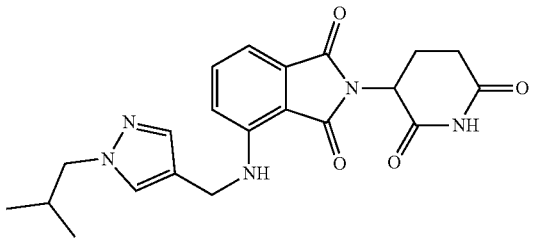 [SMILES: CC(C)Cn1cc(CNc2cccc3c2C(=O)N(C2CCC(=O)NC2=O)C3=O)cn1]
Yellow solid, 12 mg, 8.10%; 1H NMR (400 MHz, DMSO-d6) δ 11.08 (s, 1H), 7.67 (s, 1H), 7.58-7.53 (m, 1H), 7.43 (s, 1H), 7.12 (d, J = 8.56 Hz, 1H), 7.03 (d, J = 6.96 Hz, 1H), 6.82 (t, J = 5.24 Hz, 1H), 5.04 (dd, J = 12.68, 4.84 Hz, 1H), 4.36 (d, J = 5.72 Hz, 2H), 3.84 (d, J = 7.12 Hz, 2H), 2.88-2.83 (m, 2H), 2.66-2.50 (m, 2H), 2.05-2.00 (m, 2H), 0.79 (d, J = 6.60 Hz, 6H); LC MS: ES+ 410.4. |
| 144 | 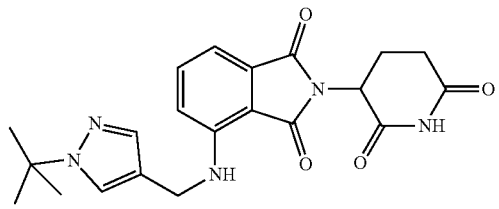 [SMILES: CC(C)(C)n1cc(CNc2cccc3c2C(=O)N(C2CCC(=O)NC2=O)C3=O)cn1]
Yellow solid, 7 mg, 4.72%; 1H NMR (400 MHz, DMSO-d6) δ 11.08 (s, 1H), 7.82 (s, 1H), 7.60-7.55 (m, 1H), 7.45 (s, 1H), 7.18 (d, J = 8.56 Hz, 1H), 7.03 (d, J=7.04 Hz, 1H), 6.81-6.74 (m, 1H), 5.04 (dd, J = 12.88, 5.32 Hz, 1H), 4.35 (d, J = 5.76 Hz, 2H), 2.91-2.83 (m, 1H), 2.66-2.49 (m, 2H), 2.05-2.00 (m, 1H), 1.46 (s, 9H); LC MS: ES+ 410.4. |
| 145 | 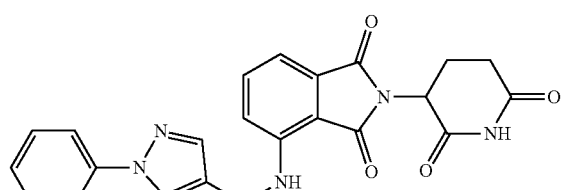
Yellow solid, 17 mg, 10.93%; 1H NMR (400 MHz, DMSO-d6) δ 11.09 (s, 1H), 8.49 (s, 1H), 7.79-7.75 (m, 3H), 7.59-7.56 (m, 1H), 7.50-7.45 (m, 2H), 7.30-7.26 (m, 1H), 7.29 (d, J = 8.60 Hz, 1H), 7.04 (d, J = 7.12 Hz, 1H), 6.97 (t, J = 5.82 Hz, 1H), 5.05 (dd, J = 12.76, 5.20 Hz, 1H), 4.47 (d, J = 5.88 Hz, 2H), 2.89-2.84 (m, 1H), 2.65-2.49 (m, 2H), 2.05-2.00 (m, 1H); LC MS: ES+ 430.4. |

Example 4: Illustrative Preparation of Carbamate-Containing Compounds of the Present Invention

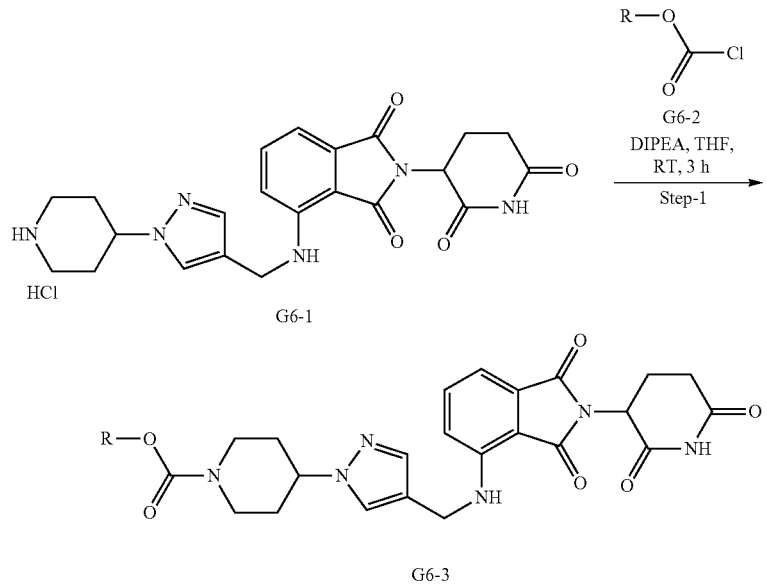

To the stirred solution of 2-(2,6-dioxo-3-piperidyl)-4-[[1-(1-BLAH-4-piperidyl)pyrazol-4-yl]methylamino]isoindoline-1,3-dione G6-1 (1 mmol) in THF (1 mL) was added DIPEA (2.5 mmol) followed by G6-2 (1 mmol). The reaction was stirred at room temperature for 2-4 hours before being quenched with ice cold water, extracted with ethyl acetate, washed with saturated aqueous sodium bicarbonate solution and brine, dried over sodium sulfate and concentrated under reduced pressure. The crude mixture was purified by preparative TLC (2-5% methanol in dichloromethane) to afford G6-3 as a yellow solid.

The following compounds were prepared according to the procedure of example 4:

| No. | Compound with Characterization Data |
|---|---|
| 146 | [structure] Yellow solid, 10 mg, 27.63%; 1H NMR (400 MHz, DMSO-d6) δ 11.08 (s, 1H), 7.78 (s, 1H), 7.59-7.55 (m, 1H), 7.45 (s, 1H), 7.37-7.31 (m, 4H), 7.16-7.14 (d, J = 8.48 Hz, 1H), 7.04-7.02 (d, J = 7.08 Hz, 1H), 6.81-6.78 (t, J = 5.62Hz, 1H), 6.54 (s, 1H), 5.08-5.02 (m, 3H), 4.36-4.33 (m, 2H), 4.09-4.06 (m, 2H), 3.00-2.83 (m, 4H), 2.67-2.50 (m, 2H), 2.02-1.95 (m, 3H), 1.80-1.74 (m, 2H), LC MS: ES+ 571.5. |
| 147 | [structure] Yellow solid, 12 mg, 37.20%; 1H NMR (400 MHz, DMSO-d6) δ 11.09 (s, 1H), 7.78 (s, 1H), 7.59-7.55 (m, 1H), 7.45 (s, 1H), 7.16-7.14 (d, J = 8.60 Hz, 1H), 7.04-7.02 (d, J = 7.00 Hz, 1H), 6.81-6.78 (m, 1H), 5.04 (dd, J = 12.88, 5.6 1H), 4.36-4.29 (m, 3H), 4.04 (q, J = 12.00, 7.00 Hz, 3H), 3.00-2.83 (m, 4H), 2.67-2.44 (m, 2H), 1.79-1.69 (m, 2H), 1.23-1.18 (m, 3H), LC MS: ES+ 509.1. |

| No. | Compound with Characterization Data |
|---|---|
| 148 | 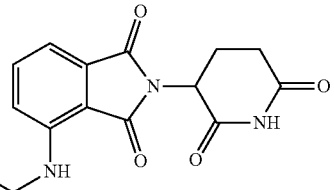

Yellow solid, 25 mg, 64.41%; 1H NMR (400 MHz, DMSO-d6) δ 11.08 (s, 1H), 7.79 (s, 1H), 7.59-7.55 (m, 1H), 7.46 (s, 1H), 7.16-7.14 (d, J = 8.60 Hz, 1H), 7.04-7.02 (d, J = 7.04 Hz, 1H), 6.55-6.53 (m, 1H), 5.04 (dd, J = 12.84, 5.32 Hz 1H), 4.86 (s, 2H), 4.38-4.35 (m,2H)4.10 (br, 2H), 3.17-2.50 (m, 5H), 2.03-2.00 (m, 3H), 1.84-1.78 (m, 2H), LC MS: ES+ 611.4. |
| 149 | 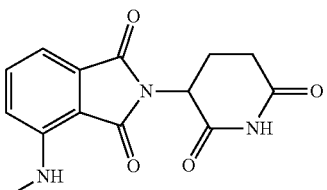

Yellow solid, 16 mg, 34.36%; 1H NMR (400 MHz, DMSO-d6) δ 11.09 (s, 1H), 7.79 (s, 1H), 7.59-7.55 (m, 1H), 7.45 (s, 1H), 7.16-7.14 (d, J = 8.68 Hz, 1H), 7.04-7.02 (d, J = 7.08 Hz, 1H), 6.82-6.79 (m, 1H), 5.04 (dd, J = 12.44, 5.24 1H), 4.36-4.31 (m, 2H), 4.07-4.04 (m, 2H), 3.17 (s, 2H)2.97-2.83 (m, 4H), 2.67-2.45 (m, 2H), 2.03-1.95 (m, 3H), 1.76-1.74 (m, 2H), 0.90(s, 9H), LC MS: ES+ 551.2. |

Example 5: Synthesis of 2-(2,6-Dioxo-piperidin-3-yl)-4-[(1H-pyrazol-4-ylmethyl)-amino]-isoindole-1,3-dione (Compound 150)

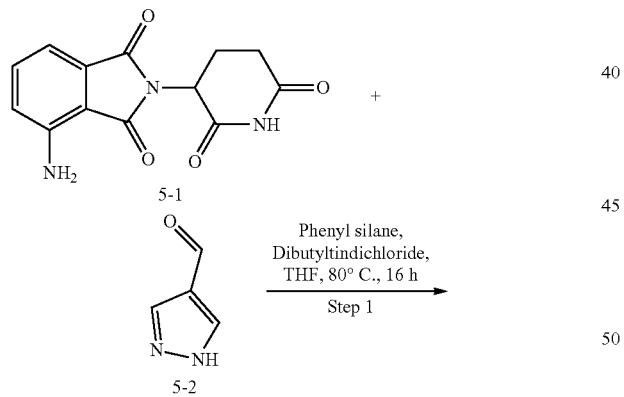

To the stirred solution of 4-amino-2-(2,6-dioxo-3-piperidyl)isoindoline-1,3-dione 5-1 (100.00 mg, 365.97 umol) and 1H-pyrazole-4-carbaldehyde 5-2 (35.17 mg, 365.97 umol) in THF (3 mL) in a sealed tube were added phenylsilane (39.60 mg, 365.97 umol, 45.10 uL) and dibutyltin dichloride (133.44 mg, 439.17 umol, 98.12 uL). The reaction was heated at 80° C. for 16 hours and diluted with water and extracted with ethyl acetate. The organic layer was washed with brine, dried over sodium sulfate and concentrated under reduced pressure. The crude material was purified by preparative TLC (2% methanol in dichloromethane) to afford 2-(2,6-dioxo-3-piperidyl)-4-(1H-pyrazol-4-ylmethylamino)isoindoline-1,3-dione (Compound 150) (51 mg, 144.34 umol, 39.44% yield) as a yellow solid. 1H NMR (400 MHz, DMSO-d6) δ 12.75 (br, 1H), 11.08 (s, 1H), 7.70-7.60 (br, 1H), 7.58-7.54 (m, 2H), 7.15 (d, J=8.56 Hz, 1H), 7.03 (d, J=7.08 Hz, 1H), 6.79 (t, J=5.84 Hz, 1H), 5.04 (dd, J=12.76, 5.32 Hz, 1H), 4.38 (d, J=5.60 Hz, 2H), 2.91-2.84 (m, 1H), 2.60-2.49 (m, 2H), 2.03-2.00 (m, 1H), LC MS: ES+ 354.05.

Example 6: Synthesis of 4-[(1-Cyclopentyl-H-pyrazol-4-ylmethyl)-amino]-2-(2,6-dioxo-piperidin-3-yl)-isoindole-1,3-dione Compound 151

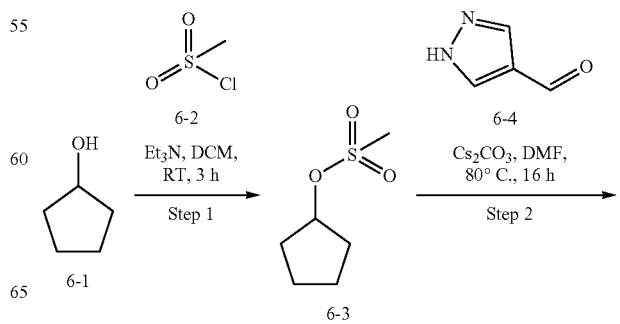

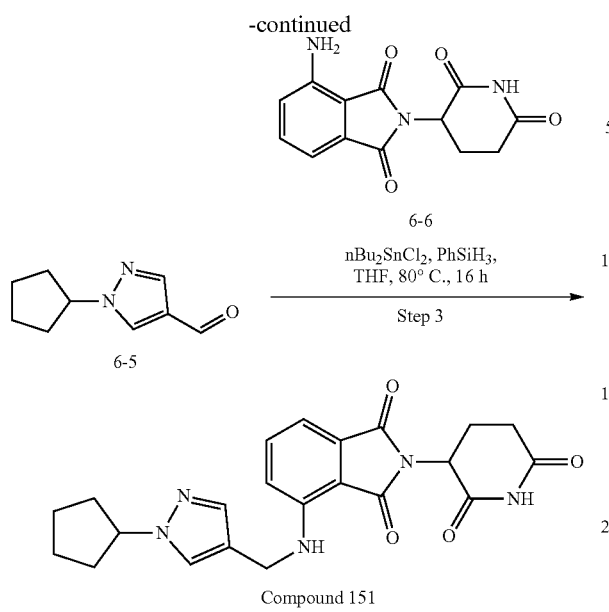

Step-1: Preparation of Methanesulfonic Acid Cyclopentyl Ester

To the stirred solution of cyclopentanol 6-1 (200 mg, 2.32 mmol, 210.53 uL) in DCM (5 mL) was added triethyl amine (587.41 mg, 5.81 mmol, 809.11 uL) followed bt methanesulfonyl chloride 6-2 (292.59 mg, 2.55 mmol, 197.69 uL) at 0° C. The reaction was stirred at room temperature for 3 hours. The reaction was diluted with DCM, washed with aq. NaHCO$_3$ solution and brine, dried over sodium sulfate and concentrated under reduced pressure to afford cyclopentyl methanesulfonate 6-3 (310 mg, 1.89 mmol, 81.30% yield) as a brown liquid. The crude material was directly forwarded onto the next step.

Step-2: Preparation of 1-Cyclopentyl-1H-pyrazole-4-carbaldehyde

To the stirred solution of cyclopentyl methanesulfonate 6-3 (380 mg, 2.31 mmol) in DMF (2 mL) was added 1H-pyrazole-4-carbaldehyde 6-4 (266.81 mg, 2.78 mmol) and cesium carbonate (1.51 g, 4.63 mmol) at 0° C. The reaction was heated at 80° C. for 16 hours and then diluted with ice cold water, extracted with ethyl acetate, washed with brine, dried over sodium sulfate, and concentrated under reduced pressure. The crude material was purified by flash chromatography using 0%-30% ethyl acetate/hexane to afford 1-cyclopentylpyrazole-4-carbaldehyde 5 (280 mg, 1.71 mmol, 73.69% yield) as a brown liquid. 1H NMR (400 MHz, DMSO-d6) δ 9.77 (s, 1H), 8.50 (s, 1H), 7.98 (s, 1H), 4.80-4.73 (m, 1H), 2.13-2.05 (m, 2H), 1.98-1.87 (m, 2H), 1.83-1.77 (m, 2H), 1.69-1.67 (m, 2H).

Step-3: Preparation of 4-[(1-Cyclopentyl-1H-pyrazol-4-ylmethyl)-amino]-2-(2,6-dioxo-piperidin-3-yl)-isoindole-1,3-dione To the stirred solution of 4-amino-2-(2,6-dioxo-3-piperidyl)isoindoline-1,3-dione 6-6 (100 mg, 365.97 umol) and 1-cyclopentylpyrazole-4-carbaldehyde 6-5 (60.09 mg, 365.97 umol) in THF (4 mL) in a sealed tube was added phenylsilane (39.60 mg, 365.97 umol, 45.10 uL) and dibutyltin dichloride (133.44 mg, 439.17 umol, 98.12 uL). The reaction was heated at 80° C. for 16 hours. The reaction mixture was diluted with ethyl acetate, washed with water, brine, dried over sodium sulfate and concentrated under reduced pressure. The crude material was purified by preparative TLC (1% methanol in dichloromethane) to afford 4-[(1-cyclopentylpyrazol-4-yl)methylamino]-2-(2,6-dioxo-3-piperidyl)isoindoline-1,3-dione (Compound 151) (25.0 mg, 59.32 umol, 16.21% yield) as yellow solid. 1H NMR (400 MHz, DMSO-d6) δ 11.08 (s, 1H), 7.74 (s, 1H), 7.59-7.55 (m, 1H), 7.43 (s, 1H), 7.15 (d, J=8.6 Hz, 1H), 7.03 (d, J=7.08 Hz, 1H), 6.82-6.79 (m, 1H), 5.06-5.03 (m, 1H), 4.64-4.61 (m, 1H), 4.35 (d, J=5.72 Hz, 2H), 2.94-2.84 (m, 1H), 2.62-2.50 (m, 1H), 2.05-1.98 (m, 3H), 1.87-1.82 (m, 2H), 1.76-1.61 (m, 2H), 1.60-1.59 (m, 2H); LC MS: ES+ 422.06.

Example 7: Synthesis of 2-(2,6-Dioxo-piperidin-3-yl)-4-[(1-isopropyl-1H-pyrazol-4-ylmethyl)-amino]-isoindole-1,3-dione (Compound 152)

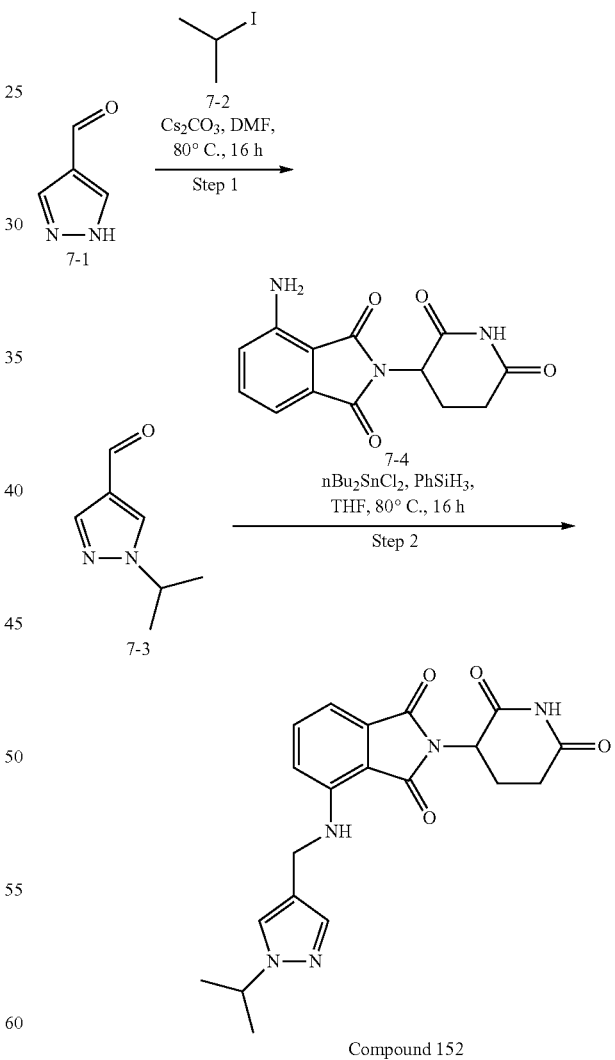

Step-1: Preparation of 1-Isopropyl-1H-pyrazole-4-carbaldehyde

To the stirred solution of 1H-pyrazole-4-carbaldehyde 7-1 (200 mg, 2.08 mmol) in DMF (2 mL) were added 2-iodopropane 7-2 (707.66 mg, 4.16 mmol, 416.27 uL) and cesium carbonate (1.36 g, 4.16 mmol) at 0° C. The reaction was heated at 80° C. for 16 hours and then diluted with ice cold water, extracted with ethyl acetate, washed with brine, dried over sodium sulfate, and concentrated under reduced pressure. The Crude material was purified by flash chromatography using 0%-30% ethyl acetate/hexane to afford 1-isopropylpyrazole-4-carbaldehyde 7-3 (200 mg, 1.45 mmol, 69.54% yield) as brown liquid. LCMS: ES+ 139.1.

Step-2: Preparation of 2-(2,6-Dioxo-piperidin-3-yl)-4-[(1-isopropyl-1H-pyrazol-4-ylmethyl)-amino]-isoindole-1,3-dione To the stirred solution of 4-amino-2-(2,6-dioxo-3-piperidyl)isoindoline-1,3-dione 7-4 (80 mg, 292.78 umol) in THF (2 mL) in a sealed tube was added isopropylpyrazole-4-carbaldehyde 7-3 (48.54 mg, 351.33 umol), phenylsilane (31.68 mg, 292.78 umol) and dibutyltin dichloride (106.75 mg, 351.33 umol, 78.49 uL) at room temperature. The reaction was heated at 80° C. for 16 hours and then concentrated under reduced pressure. Crude material was purified by flash chromatography using 0-5% MeOH-DCM to afford 2-(2,6-dioxo-3-piperidyl)-4-[(1-isopropylpyrazol-4-yl)methylamino]isoindoline-1,3-dione (Compound 152) (52 mg, 131.51 umol, 44.92% yield) as a yellow solid. 1H NMR (400 MHz, DMSO-d6) δ11.08 (s, 1H), 7.74 (s, 1H), 7.59-7.55 (m, 1H), 7.43 (s, 1H), 7.16 (d, J=8.6 Hz, 1H), 7.03 (d, J=7.04 Hz, 1H), 6.78 (t, J=5.84 Hz, 1H), 5.04 (dd, J=12.76, 5.48 Hz, 1H), 4.46-4.42 (m, 1H), 4.35 (d, J=5.8 Hz, 2H), 2.91-2.84 (m, 1H), 2.66-2.49 (m, 2H), 2.03-1.98 (m, 1H), 1.35 (d, J=7.32 Hz, 6H); LC MS: ES+ 369.08.

Example 8: Synthesis of 2-(2,6-Dioxo-piperidin-3-yl)-4-{[1-(2,2,2-trifluoro-ethyl)-1H-pyrazol-4-ylmethyl]-amino}-isoindole-1,3-dione (Compound 153)

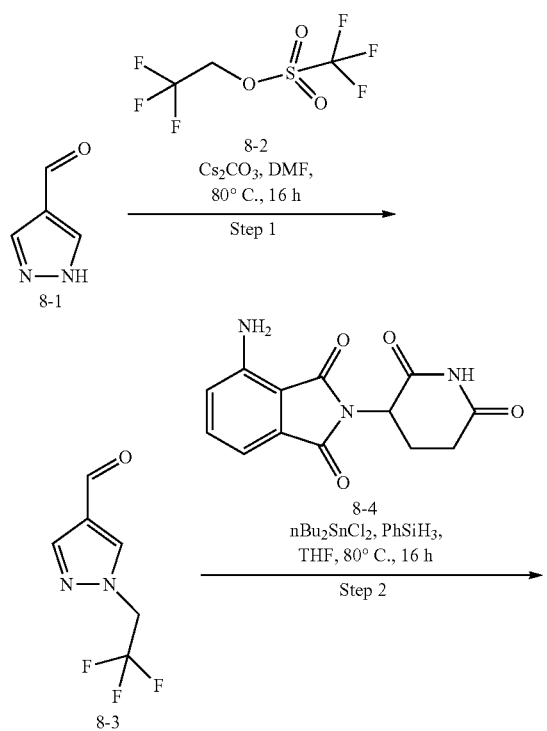

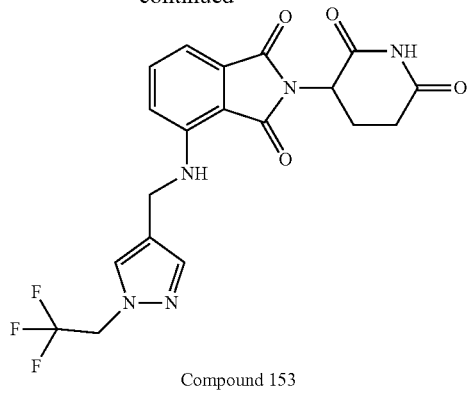

Compound 153

Step-1: Preparation of 1-(2,2,2-Trifluoro-ethyl)-1H-pyrazole-4-carbaldehyde

To the stirred solution of 1H-pyrazole-4-carbaldehyde 8-1 (200 mg, 2.08 mmol) in DMF (5 mL) was added cesium carbonate (1.70 g, 5.20 mmol) and 2,2,2-trifluoroethyl trifluoromethanesulfonate 8-2 (579.73 mg, 2.50 mmol, 360.08 uL). The reaction was heated at 60° C. for 16 hours and then quenched with cold water. The organic layer was extracted with ethyl acetate, washed with saturated aqueous solution of NaHCO$_3$, dried over Na$_2$SO$_4$ and concentrated under reduced pressure to afford crude material that was purified by column chromatography to afford 1-(2,2,2-trifluoroethyl)pyrazole-4-carbaldehyde 3 (60 mg, 336.87 umol, 16.18% yield) as a gummy liquid. 1H NMR (400 MHz, DMSO-d6) δ 9.85 (s, 1H), 8.60 (s, 1H), 8.10 (s, 1H), 5.27 (q, J=18.12, 9.00 Hz, 2H).

Step-2: Preparation of 2-(2,6-Dioxo-piperidin-3-yl)-4-{[1-(2,2,2-trifluoro-ethyl)-1H-pyrazol-4-ylmethyl]-amino}-isoindole-1,3-dione To the stirred solution of 4-amino-2-(2,6-dioxo-3-piperidyl)isoindoline-1,3-dione 8-4 (80 mg, 292.78 umol) and 1-(2,2,2-trifluoroethyl)pyrazole-4-carbaldehyde 8-3 (52.15 mg, 292.78 umol) in THF (4 mL) in a sealed tube was added phenylsilane (31.68 mg, 292.78 umol, 36.08 uL) and dibutyltin dichloride (106.75 mg, 351.33 umol, 78.49 uL). The reaction was heated at 80° C. for 16 hours. The reaction mixture was diluted with ethyl acetate and water. Layers were separated and organic layer was washed with brine, dried over Na$_2$SO$_4$, concentrated under reduced pressure to afford crude mass that was purified by preparative TLC plate (eluting with 2% Methanol/DCM) to afford 2-(2,6-dioxo-3-piperidyl)-4-[[1-(2,2,2-trifluoroethyl)pyrazol-4-yl]methylamino]isoindoline-1,3-dione (Compound 153) (38 mg, 87.28 umol, 29.81% yield) as yellow solid. 1H NMR (400 MHz, DMSO-d6) δ11.08 (s, 1H), 7.81 (s, 1H), 7.58 (s, 1H), 7.57-7.54 (m, 1H), 7.13 (d, J=8.56 Hz, 1H), 7.03 (d, J=7.00 Hz, 1H), 6.94 (t, J=6.06 Hz, 1H), 5.10-5.02 (m, 3H), 4.41 (d, J=6.00 Hz, 2H), 2.92-2.83 (m, 1H), 2.61-2.49 (m, 2H), 2.07-2.00 (m, 1H); LC MS. ES+ 436.3.

Example 9. Synthesis of [3-(4-Formyl-pyrazol-1-yl)-propyl]-methyl-carbamic acid tert-butyl ester (Compound 154)

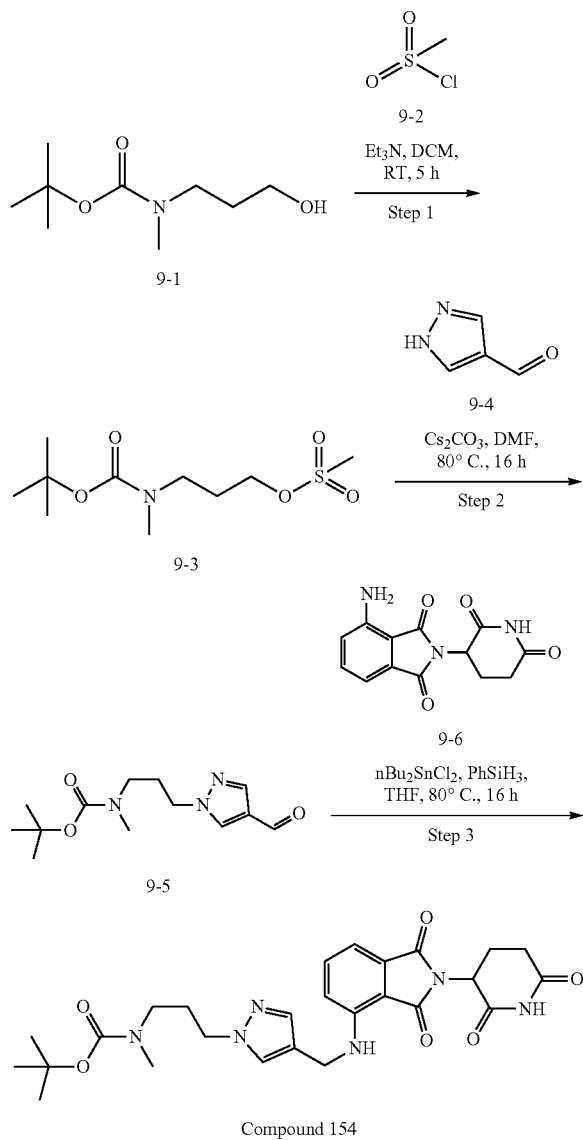

Compound 154

Step-1: Preparation of Methanesulfonic acid 3-(tert-butoxycarbonyl-methyl-amino)-propyl ester To the stirred solution of tert-butyl N-(3-hydroxypropyl)-N-methyl-carbamate 9-1 (200 mg, 1.06 mmol) in DCM (5 mL) was added TEA (106.94 mg, 1.06 mmol, 147.30 uL) and methanesulfonyl chloride 9-2 (121.06 mg, 1.06 mmol, 81.80 uL). The reaction was stirred at room temperature for 5 hours and then diluted with ethyl acetate and washed with saturated aqueous sodium bicarbonate solution, water and brine. The organic later was dried over sodium sulfate and concentrated under reduced pressure to afford 3-[tert-butoxycarbonyl(methyl)amino]propyl methanesulfonate 9-3 (150 mg, 561.08 umol, 53.09% yield) as gum. 1H NMR (400 MHz, DMSO-d6) δ 4.17 (t, J=6.20 Hz, 2H), 3.24 (t, J=6.96 Hz, 2H), 3.16 (s, 3H), 2.78-2.72 (m, 3H), 1.89-1.84 (m, 2H), 1.39 (s, 9H).

Step-2: Preparation of [3-(4-Formyl-pyrazol-1-yl)-propyl]-methyl-carbamic acid tert-butyl ester To the stirred solution of 3-[tert-butoxycarbonyl(methyl)amino]propyl methanesulfonate 9-3 (333.87 mg, 1.25 mmol) in DMF (3 mL) was added cesium carbonate (847.72 mg, 2.60 mmol) and 1H-pyrazole-4-carbaldehyde 9-4 (100 mg, 1.04 mmol). The reaction mixture was heated at 60° C. for 16 hours. The reaction mixture was quenched with cold water and organic layer was extracted with ethyl acetate. The organic layer was washed with saturated solution of NaHCO3, dried over Na2SO4 and concentrated under reduced pressure to afford crude material that was purified by column chromatography (1% methanol in dichloromethane) to afford tert-butyl N-[3-(4-formylpyrazol-1-yl)propyl]-N-methyl-carbamate 9-5 (130 mg, 486.30 umol, 46.73% yield) as a gummy liquid. LCMS: ES+ 268.1.

Step-3: Preparation of [3-(4-{[2-(2,6-Dioxo-piperidin-3-yl)-1,3-dioxo-2,3-dihydro-1H-isoindol-4-ylamino]-methyl}-pyrazol-1-yl)-propyl]-methyl-carbamic acid tert-butyl ester To a stirred solution of 4-amino-2-(2,6-dioxo-3-piperidyl)isoindoline-1,3-dione 9-6 (80 mg, 292.78 umol) and tert-butyl N-[3-(4-formylpyrazol-1-yl)propyl]-N-methyl-carbamate 9-5 (78.27 mg, 292.78 umol) in THF (4 mL) in a sealed tube was added phenylsilane (31.68 mg, 292.78 umol) and dibutyltin dichloride (106.75 mg, 351.33 umol, 78.49 uL). The reaction was heated at 80° C. for 16 hours. The reaction mixture was diluted with ethyl acetate, washed with waster, brine, dried over Na2SO4 and concentrated under reduced pressure to afford crude mass which was purified by Preparative TLC Plate (eluting with 2.5% Methanol/DCM) to afford tert-butyl N-[3-[4-[[[2-(2,6-dioxo-3-piperidyl)-1,3-dioxo-isoindolin-4-yl]amino]methyl]pyrazol-1-yl]propyl]-N-methyl-carbamate (Compound 154) (22 mg, 41.81 umol, 14.28% yield, 99.7% purity) as a yellow solid. 1H NMR (400 MHz, DMSO-d6) δ11.08 (s, 1H), 7.72 (s, 1H), 7.58-7.54 (m, 1H), 7.44 (s, 1H), 7.13 (d, J=8.60 Hz, 1H), 7.03 (d, J=7.04 Hz, 1H), 6.82 (t, J=6.32 Hz, 1H), 5.04 (dd, J=12.64, 5.32 Hz, 1H), 4.36 (d, J=5.64 Hz, 2H), 4.02 (t, J=6.92 Hz, 2H), 3.11 (t, J=7.02 Hz, 2H), 2.92-2.83 (m, 1H), 2.72 (s, 3H), 2.60-2.49 (m, 2H), 2.03-2.00 (m, 1H), 1.93-1.90 (m, 2H), 1.32 (s, 9H); LC MS. ES+ 525.3.

Example 10. Synthesis of 2-(2,6-Dioxo-piperidin-3-yl)-4-{[1-(tetrahydro-pyran-4-ylmethyl)-1H-pyrazol-4-ylmethyl]-amino}-isoindole-1,3-dione (Compound 155)

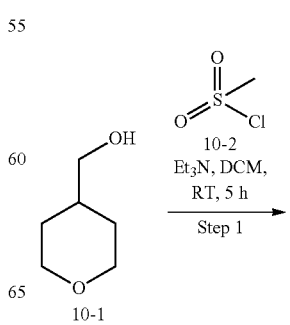

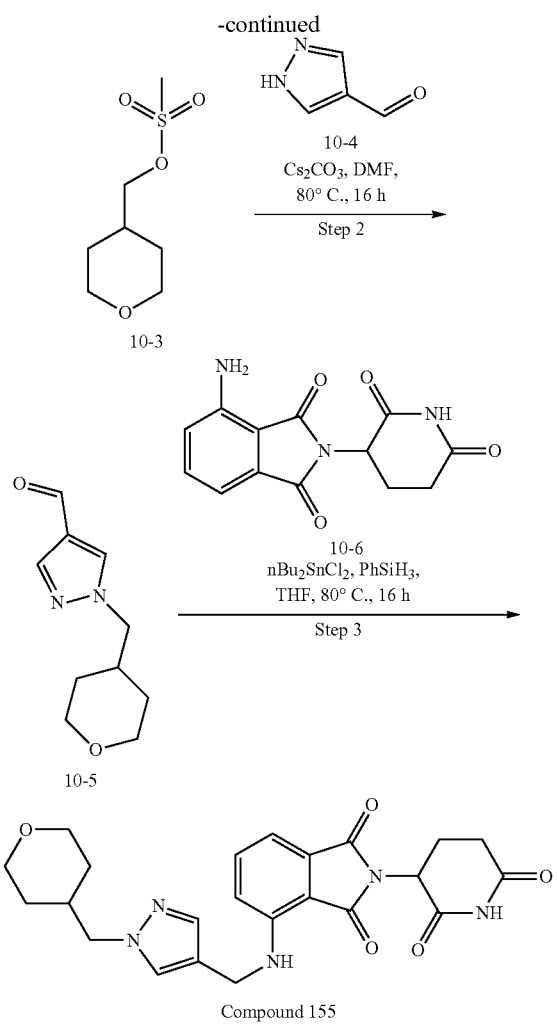

98.07% yield) as gum. 1H NMR (400 MHz, DMSO-d6) δ 4.1-4.0 (m, 2H), 3.85 (dd, J=11.28, 3.96 Hz, 2H), 3.34-3.26 (m, 2H), 3.17 (s, 3H), 1.98-1.88 (m, 1H), 1.60-1.55 (m, 2H), 1.31-1.20 (m, 2H).

Step-2: Preparation of 1-(Tetrahydro-pyran-4-ylmethyl)-1H-pyrazole-4-carbaldehyde To the stirred solution of 1H-pyrazole-4-carbaldehyde 10-4 (133.97 mg, 1.39 mmol) and tetrahydropyran-4-ylmethyl methanesulfonate 10-3 (325 mg, 1.67 mmol) in DMF (10 mL) was added $Cs_2CO_3$ (2.34 g, 2.79 mmol). The reaction was heated at 80° C. for 16 hours and then cooled to room temperature, diluted with ethyl acetate, washed with water, brine, dried over sodium sulfate and concentrated under reduced pressure to afford 1-(tetrahydropyran-4-ylmethyl)pyrazole-4-carbaldehyde 10-5 (130 mg, 669.31 umol, 48.00% yield) as gum. 1H NMR (400 MHz, DMSO-d6) δ9.87 (s, 1H), 8.45 (s, 1H), 7.99 (s, 1H), 4.08 (d, J=7.16, 2H), 3.82 (dd, J=14.16, 2.92 Hz, 2H), 3.27-3.21 (m, 2H), 2.10-2.04 (m, 1H), 1.39-1.34 (m, 2H), 1.27-1.17 (m, 2H).

Step-3: Preparation of 2-(2,6-Dioxo-piperidin-3-yl)-4-{[1-(tetrahydro-pyran-4-ylmethyl)-1H-pyrazol-4-ylmethyl]-amino}-isoindole-1,3-dione To stirred solution of 4-amino-2-(2,6-dioxo-3-piperidyl)isoindoline-1,3-dione 10-6 (80 mg, 292.78 umol) and 1-(tetrahydropyran-4-ylmethyl)pyrazole-4-carbaldehyde 10-5 (56.87 mg, 292.78 umol) in THF (4 mL) in a sealed tube was added phenylsilane (31.68 mg, 292.78 umol, 36.08 uL) and dibutyltin dichloride (106.75 mg, 351.33 umol, 78.49 uL). The reaction mixture was heated at 80° C. for 16 hours and then diluted with ethyl acetate and water. The layers were separated and the organic layer was washed with brine, dried over $Na_2SO_4$ and concentrated under reduced pressure to afford crude mass which was purified by Preparative TLC Plate (eluting with 2% Methanol/DCM) to afford 2-(2,6-dioxo-3-piperidyl)-4-[[1-(tetrahydropyran-4-ylmethyl)pyrazol-4-yl]methylamino]isoindoline-1,3-dione (Compound 155) (51 mg, 111.83 umol, 38.20% yield, 99% purity) as Yellow solid. 1H NMR (400 MHz, DMSO-d6) δ11.08 (s, 1H), 7.68 (s, 1H), 7.57-7.53 (m, 1H), 7.43 (s, 1H), 7.12 (d, J=8.60 Hz, 1H), 7.03 (d, J=7.04 Hz, 1H), 6.83 (t, J=5.94 Hz, 1H), 5.04 (dd, J=12.84, 5.36 Hz, 1H), 4.36 (d, J=5.68 Hz, 2H), 3.93 (d, J=7.16 Hz, 2H), 3.79 (dd, J=11.16, 2.92 Hz, 2H), 3.25-3.18 (m, 2H), 2.89-2.84 (m, 1H), 2.60-2.50 (m, 2H), 2.03-1.96 (m, 2H), 1.34-1.31 (m, 2H), 1.23-1.15 (m, 2H); LC MS: ES+ 452.1.

Example 11. Synthesis of 4-{[1-(8-Acetyl-8-azabicyclo[3.2.1]oct-3-yl)-1H-pyrazol-4-ylmethyl]-amino}-2-(2,6-dioxo-piperidin-3-yl)-isoindole-1,3-dione (Compound 156)

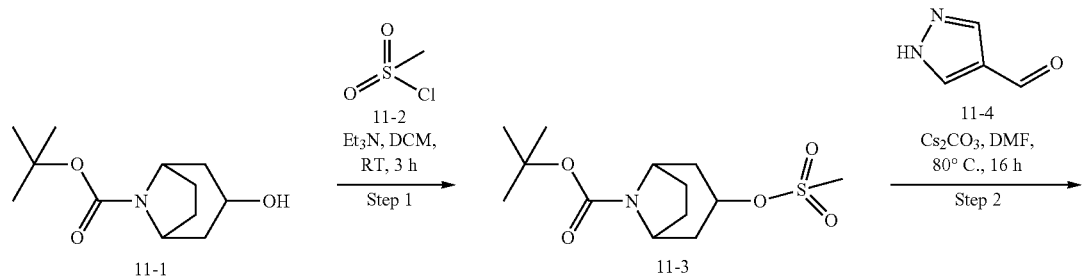

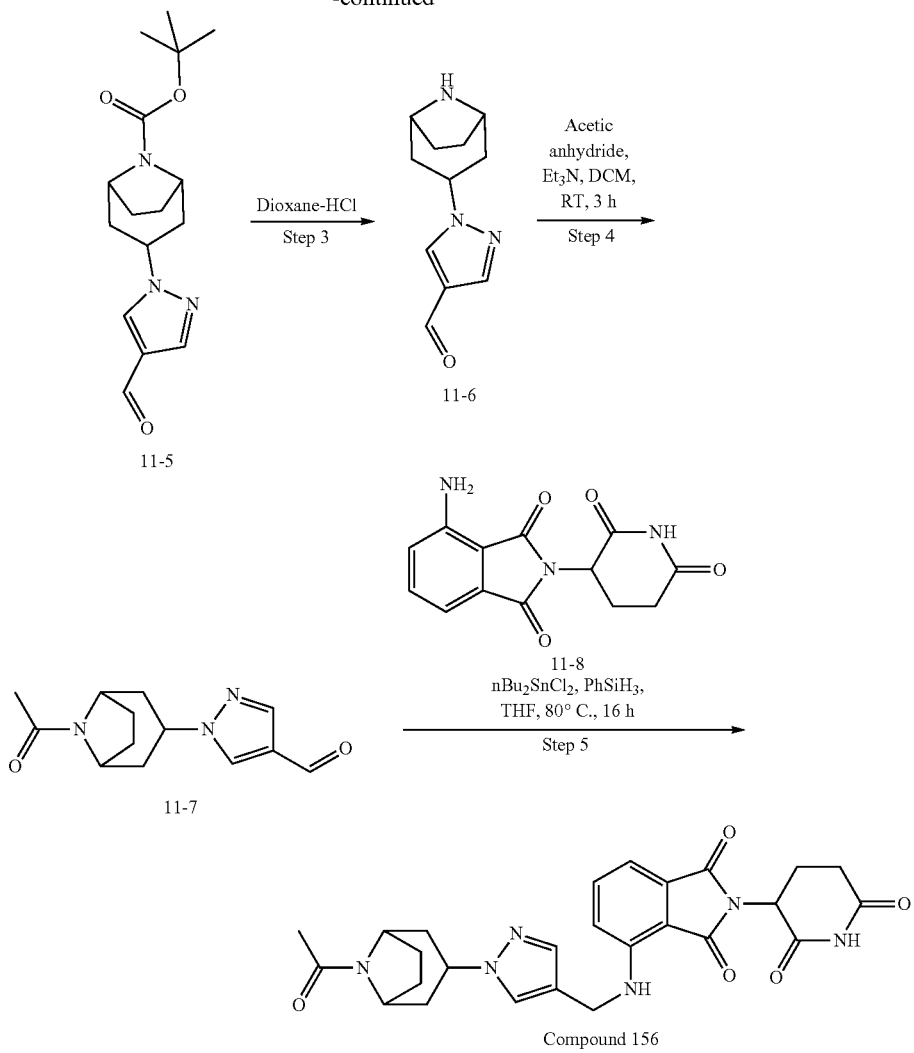

Compound 156

Step-1: Preparation of 3-Methanesulfonyloxy-8-aza-bicyclo[3.2.1]octane-8-carboxylic acid tert-butyl ester To the stirred solution of tert-butyl 3-hydroxy-8-azabicyclo[3.2.1]octane-8-carboxylate 11-1 (200 mg, 879.90 umol, 210.52 uL) in DCM (5 mL) was added TEA (222.59 mg, 2.20 mmol, 306.60 uL) and methanesulfonyl chloride 11-2 (110.87 mg, 967.89 umol, 74.91 uL) at 0° C. The reaction was stirred at room temperature for 3 hours and diluted with DCM, washed with saturated aqueous $NaHCO_3$ solution and brine, dried over sodium sulfate, and concentrated under reduced pressure to afford tert-butyl 3-methylsulfonyl-8-azabicyclo[3.2.1]octane-8-carboxylate 11-3 (250 mg, 863.89 umol, 98.18% yield) as a brown liquid. The crude material was used in next step.

Step-2: Preparation of 3-(4-Formyl-pyrazol-1-yl)-8-aza-bicyclo[3.2.1]octane-8-carboxylic acid tert-butyl ester To the stirred solution of 1H-pyrazole-4-carbaldehyde 11-4 (220 mg, 2.29 mmol) in DMF (5 mL) was added tert-butyl 3-methylsulfonyl-8-azabicyclo[3.2.1]octane-8-carboxylate 11-3 (662.58 mg, 2.29 mmol) and cesium carbonate (1.86 g, 5.72 mmol) at 0° C. The reaction was heated at 80° C. for 16 hours and diluted with ice cold water and extracted with ethyl acetate. The organic layer was washed with brine, dried over sodium sulfate, and concentrated under reduced pressure. The crude material was purified by flash chromatography using 0%-30% Ethyl acetate/Hexane to afford tert-butyl 3-(4-formylpyrazol-1-yl)-8-azabicyclo[3.2.1]octane-8-carboxylate 11-5 (150 mg, 491.21 umol, 21.45% yield) as a brown liquid. LCMS: ES+ 306.3.

Step-3: Preparation of 1-(8-Aza-bicyclo[3.2.1]oct-3-yl)-1H-pyrazole-4-carbaldehyde To a stirred solution of tert-butyl 3-(4-formylpyrazol-1-yl)-8-azabicyclo[3.2.1]octane-8-carboxylate 11-5 (150 mg, 491.21 umol) was added dioxane.HCl (1 mL) at 0° C. The reaction mixture was stirred at room temperature for 4 hours and then evaporated under reduced pressure. The crude material was washed with pentane to afford 1-(8-azabicyclo[3.2.1]octan-3-yl)pyrazole-4-carbaldehyde 11-6 (100 mg, 487.20 umol, 99.18% yield) as a off-white solid. 1H NMR (400 MHz, DMSO-d6) δ 9.80 (s, 1H), 9.20 (br, 1H), 9.08 (br, 1H), 8.48 (s, 1H), 8.04 (s, 1H), 4.87-4.79 (m, 1H), 4.10 (brs, 2H), 2.37-2.31 (m, 2H), 2.24-2.10 (m, 2H), 2.02 (s, 4H);

Step-4: Preparation of 1-(8-Acetyl-8-aza-bicyclo[3.2.1]oct-3-yl)-1H-pyrazole-4-carbaldehyde To a stirred solution of 1-(8-azabicyclo[3.2.1]octan-3-yl)pyrazole-4-carbaldehyde 11-6 (100 mg, 487.20 umol) in DCM (2 mL) was added TEA (123.25 mg, 1.22 mmol, 169.76 uL) and acetic anhydride (59.68 mg, 584.64 umol, 55.26 uL) at 0° C. The reaction was stirred for 3 hours and diluted with DCM, washed with water and brine, dried over sodium sulfate, and concentrated under reduced pressure to afford 1-(8-acetyl-8-azabicyclo[3.2.1]octan-3-yl)pyrazole-4-carbaldehyde 11-7 (100 mg, 404.38 umol, 83.00% yield) as a brown liquid. The crude material was used to next step LCMS: ES+ 248.1.

Step-5: Preparation of 4-{[1-(8-Acetyl-8-aza-bicyclo[3.2.1]oct-3-yl)-1H-pyrazol-4-ylmethyl]-amino}-2-(2,6-dioxo-piperidin-3-yl)-isoindole-1,3-dione To the stirred solution of 4-amino-2-(2,6-dioxo-3-piperidyl)isoindoline-1,3-dione 11-8 (100 mg, 365.97 umol) and 1-(8-acetyl-8-azabicyclo[3.2.1]octan-3-yl)pyrazole-4-carbaldehyde 11-7 (108.60 mg, 439.17 umol) in THF (2 mL) (in a sealed tube) was added phenylsilane (39.60 mg, 365.97 umol, 45.10 uL) and dibutyltin dichloride (133.44 mg, 439.17 umol, 98.12 uL). The reaction mixture was heated at 80° C. for 16 hours and then concentrated under reduced pressure. The crude was purified by column chromatography using 0-2% MeOH-DCM to afford 4-[[1-(8-acetyl-8-azabicyclo[3.2.1]octan-3-yl)pyrazol-4-yl]methylamino]-2-(2,6-dioxo-3-piperidyl)isoindoline-1,3-dione (Compound 156) (50 mg, 99.10 umol, 27.08% yield) as a yellow solid. 1H NMR (400 MHz, DMSO-d6) δ11.09 (s, 1H), 7.75 (s, 1H), 7.58-7.54 (m, 1H), 7.43 (s, 1H), 7.13 (d, J=8.60 Hz, 1H), 7.03 (d, J=7.04 Hz, 1H), 6.83 (m, 1H), 5.04 (dd, J=12.80, 5.40 Hz, 1H), 4.79-4.70 (m, 1H), 4.51 (br, 1H), 4.36-4.33 (m, 2H), 4.28-4.26 (m, 1H), 2.89-2.84 (m, 1H), 2.60-2.45 (m, 2H), 2.02-1.79 (m, 9H); LC MS: ES+ 505.1.

Example 12: Synthesis of 2-(2,6-Dioxo-piperidin-3-yl)-4-{[1-(1-methyl-piperidin-4-yl)-1H-pyrazol-4-ylmethyl]-amino}-isoindole-1,3-dione (Compound 157)

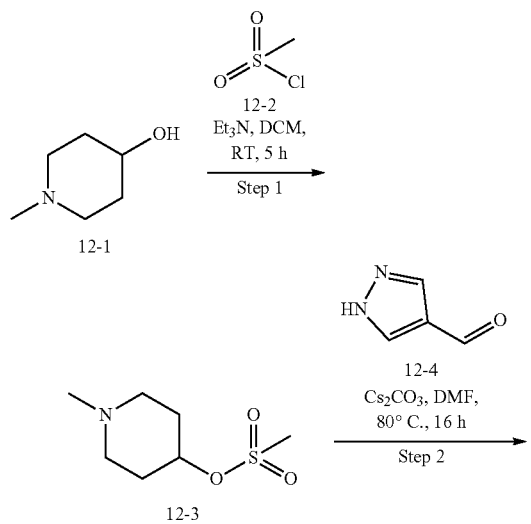

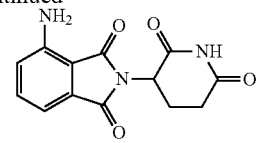

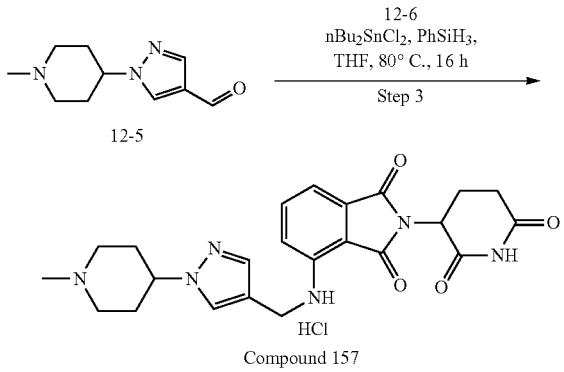

Step-1: Preparation of Methanesulfonic acid 1-methyl-piperidin-4-yl ester

To a stirred solution of 1-methylpiperidin-4-ol 12-1 (200 mg, 1.74 mmol, 210.52 uL) in DCM (5 mL) was added TEA (439.29 mg, 4.34 mmol, 605.09 uL) and methanesulfonyl chloride 12-2 (218.81 mg, 1.91 mmol, 147.84 uL) at 0° C. The reaction mixture was stirred at room temperature for 3 hours and then diluted with DCM, washed with saturated aqueous NaHCO3 solution, brine, dried over sodium sulfate, and concentrated under reduced pressure to afford 1-methyl-4-piperidyl) methanesulfonate 12-3 (290 mg, 1.50 mmol, 86.41% yield) as a brown liquid. The crude was used into next step.

Step-2: Preparation of 1-(1-Methyl-piperidin-4-yl)-1H-pyrazole-4-carbaldehyde

To a stirred solution of 1H-pyrazole-4-carbaldehyde 12-4 (300 mg, 3.12 mmol) in DMF (5 mL) was added (1-methyl-4-piperidyl) methanesulfonate 12-3 (724.08 mg, 3.75 mmol) and cesium carbonate (2.54 g, 7.81 mmol) at 0° C. The reaction mixture was then heated at 80° C. for 16 hours and then diluted with ice cold water, extracted with ethyl acetate, washed with brine, dried over sodium sulfate, and concentrated under reduced pressure. The crude was purified by flash chromatography using 0%-10% MeOH-DCM to afford (1-methyl-4-piperidyl)pyrazole-4-carbaldehyde 12-5 (190 mg, 983.21 umol, 31.49% yield) as a brown liquid. LCMS: ES+ 194.1.

Step-3: Preparation of 2-(2,6-Dioxo-piperidin-3-yl)-4-{[1-(1-methyl-piperidin-4-yl)-1H-pyrazol-4-ylmethyl]-amino}-isoindole-1,3-dione To a stirred solution of 4-amino-2-(2,6-dioxo-3-piperidyl)isoindoline-1,3-dione 12-6 (80 mg, 292.78 umol) and 1-(1-methyl-4-piperidyl)pyrazole-4-carbaldehyde 12-5 (67.89 mg, 351.33 umol) in THF (3 mL) (in a sealed tube) was added phenylsilane (31.68 mg, 292.78 umol) and dibutyltin dichloride (106.75 mg, 351.33 umol, 78.49 uL). The reaction mixture was heated at 80° C. for 16 hours and then concentrated under reduced pressure. The crude was purified by column chromatography using 0%-10% MeOH-DCM to afford 2-(2,6-dioxo-3-piperidyl)-4-[[1-(1-methyl-4-piperidyl)pyrazol-4-yl]methylamino]isoindoline-1,3-dione (Compound 157) (30.0 mg, 66.59 umol, 22.75% yield) as a yellow solid. 1H NMR (400 MHz, DMSO-d6) δ11.09 (s, 1H), 10.1 (br, 1H), 7.77 (s, 1H), 7.59-7.55 (m, 1H), 7.51 (s, 1H), 7.16 (d, J=8.56 Hz, 1H), 7.04 (d, J=7.04 Hz, 1H), 6.84 (m, 1H), 5.04 (dd, J=12.90, 5.64 Hz, 1H), 4.39-4.36 (m, 2H), 3.52-3.47 (m, 2H), 3.12-3.01 (m, 2H), 2.91-2.81 (m, 1H), 2.76 (s, 3H), 2.60-2.50 (m, 2H), 2.22-2.12 (m, 4H), 2.03-2.018 (m, 1H); LC MS: ES+ 451.2.

Example 13: Synthesis of 4-[(1-Cyclohexyl-1H-pyrazol-4-ylmethyl)-amino]-2-(2,6-dioxo-piperidin-3-yl)-isoindole-1,3-dione (Compound 158)

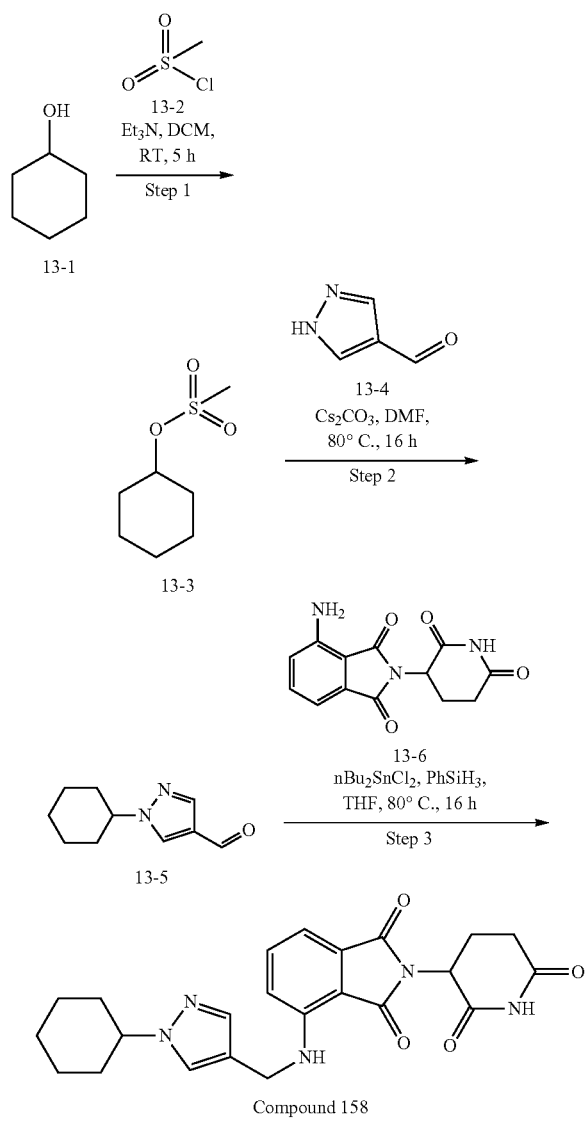

Step-1: Preparation of Methanesulfonic acid cyclohexyl ester

To a stirred solution of cyclohexanol 13-1 (300 mg, 3.00 mmol, 315.46 uL) in DCM (5 mL) was added triethylamine (757.72 mg, 7.49 mmol, 1.04 mL). The reaction was cooled to 0° C. followed by the dropwise addition of methanesulfonyl chloride 13-2 (411.73 mg, 3.59 mmol, 278.19 uL). The reaction mixture was stirred at room temperature for 4 hours and then diluted with a saturated aqueous solution of NaHCO$_3$. The layers were separated and the organic layer was washed with water and brine and dried over Na$_2$SO$_4$ to afford cyclohexyl methanesulfonate 13-3 (500 mg, 2.81 mmol, 93.65% yield) as gummy yellow solid. 1H NMR (400 MHz, DMSO-d6) δ 4.64-4.58 (m, 1H), 3.34 (s, 3H), 1.92-1.87 (m, 2H), 1.68-1.65 (m, 2H), 1.56-1.44 (m, 3H), 1.40-1.29 (m, 2H), 1.27-1.17 (m, 1H).

Step-2: Preparation of 1-Cyclohexyl-1H-pyrazole-4-carbaldehyde

To a stirred solution of 1H-pyrazole-4-carbaldehyde 13-4 (220 mg, 2.29 mmol) in DMF (5 mL) was added cesium carbonate (1.86 g, 5.72 mmol) and cyclohexyl methanesulfonate 13-3 (489.74 mg, 2.75 mmol). The reaction mixture was heated at 60° C. for 16 hours. The reaction mixture was quenched with cold water and extracted with ethyl acetate. The organic layer was washed with a saturated aqueous solution of NaHCO$_3$, dried over Na$_2$SO$_4$ and concentrated under reduced pressure to afford crude which was purified by column chromatography to afford 1-cyclohexylpyrazole-4-carbaldehyde 13-5 (220 mg, 1.23 mmol, 53.91% yield) as gummy liquid. LC MS: ES+ 179.

Step-3: Preparation of 4-[(1-Cyclohexyl-1H-pyrazol-4-ylmethyl)-amino]-2-(2,6-dioxo-piperidin-3-yl)-isoindole-1,3-dione To stirred solution of 4-amino-2-(2,6-dioxo-3-piperidyl) isoindoline-1,3-dione 13-6 (80 mg, 292.78 umol) and 1-cyclohexylpyrazole-4-carbaldehyde 13-5 (52.18 mg, 292.78 umol) in THF (4 mL) (in a sealed tube) was added phenylsilane (31.68 mg, 292.78 umol, 36.08 uL) and dibutyltin dichloride (106.75 mg, 351.33 umol, 78.49 uL). The reaction mixture was heated at 80° C. for 16 hours and was diluted with ethyl acetate and water. The layers were separated and the organic layer was washed with brine, dried over Na$_2$SO$_4$ and concentrated under reduced pressure to afford crude mass which was purified by Preparative TLC Plate (eluting with 3% Methanol/DCM) to afford 4-[(1-cyclohexylpyrazol-4-yl)methylamino]-2-(2,6-dioxo-3-piperidyl)isoindoline-1,3-dione (Compound 158) (22 mg, 50.52 umol, 17.26% yield) as Yellow solid. 1H NMR (400 MHz, DMSO-d6) δ 11.08 (s, 1H), 7.73 (s, 1H), 7.57 (t, J=7.8 Hz, 1H), 7.42 (s, 1H), 7.15 (d, J=8.6 Hz, 1H), 7.03 (d, J=7.04 Hz, 1H), 6.80-6.77 (m, 1H), 5.04 (dd, J=12.84, 5.44 Hz, 1H), 4.36-4.34 (m, 2H), 4.09-4.03 (m, 1H), 2.88-2.84 (m, 1H), 2.60-2.50 (m, 2H), 2.04-1.93 (m, 3H), 1.79-1.75 (m, 2H), 1.69-1.58 (m, 3H), 1.41-1.30 (m, 2H), 1.23-1.16 (m, 1H) LC MS: ES+ 436.2.

Example 14. Synthesis of 4-{[1-(1-Acetyl-piperidin-4-yl)-1H-pyrazol-4-ylmethyl]-amino}-2-(2,6-dioxo-piperidin-3-yl)-isoindole-1,3-dione (Compound 159)

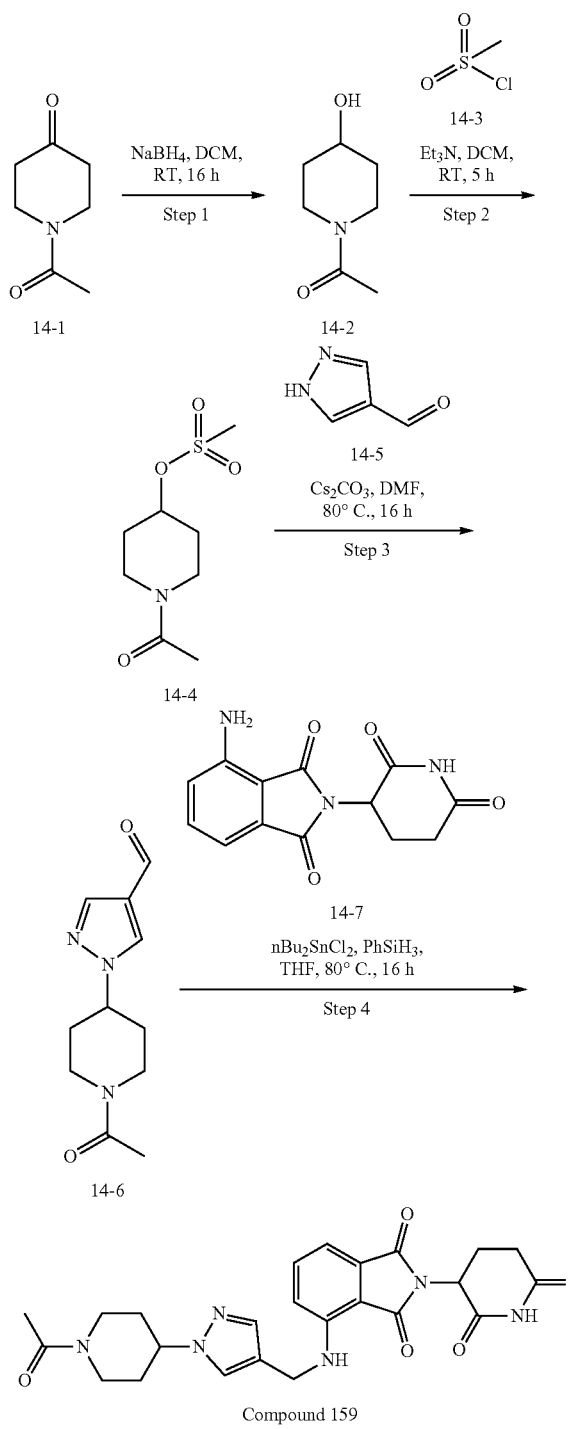

Step-1: Preparation of 1-(4-Hydroxy-piperidin-1-yl)-ethanone

To the stirred solution of 1-acetylpiperidin-4-one 14-1 (1500 mg, 10.63 mmol) in DCM (25 mL) was added NaBH$_4$ (803.94 mg, 21.25 mmol, 751.34 uL) at 0° C. The reaction mixture was stirred at room temperature for 16 hours and then was quenched with saturated aqueous ammonium chloride solution and extracted with DCM. The organic layer was dried over sodium sulfate and concentrated under reduced pressure. Crude mass was purified by column chromatography eluting at 1% methanol in dichloromethane to afford 1-(4-hydroxy-1-piperidyl)ethanone 14-2 (1.3 g, 9.08 mmol, 85.45% yield) as gum. 1H NMR (400 MHz, DMSO-d6) δ 4.72-4.71 (m, 1H), 3.89-3.85 (m, 1H), 3.68-3.60 (m, 2H), 3.15-3.09 (m, 1H), 2.98-2.91 (m, 1H), 1.97 (s, 3H), 1.74-1.63 (m, 2H), 1.35-1.16 (m, 2H).

Step-2: Preparation of Methanesulfonic acid 1-acetyl-piperidin-4-yl ester

To the stirred solution of 1-(4-hydroxy-1-piperidyl)ethanone (310 mg, 2.17 mmol) in DCM (10 mL) was added TEA (438.16 mg, 4.33 mmol, 603.53 uL) and methanesulfonyl chloride 14-3 (297.61 mg, 2.60 mmol, 201.09 uL). The reaction mixture was stirred at room temperature for 5 hours and then diluted with ethyl acetate, washed with saturated sodium bicarbonate solution, water and brine. The crude material was dried over sodium sulfate and concentrated under reduced pressure to afford (1-acetyl-4-piperidyl)methanesulfonate 14-4 (410 mg, 1.85 mmol, 85.58% yield) as a gum. The product used in the next step was a mixture of 14-4 and its chloro-variant.

Step-3: Preparation of 1-(1-Acetyl-piperidin-4-yl)-1H-pyrazole-4-carbaldehyde To a stirred solution of 1H-pyrazole-4-carbaldehyde 14-5 (120 mg, 1.25 mmol) in DMF (4 mL) was added cesium carbonate (1.02 g, 3.12 mmol) and (1-acetyl-4-piperidyl)methanesulfonate 14-4 (331.61 mg, 1.50 mmol). The reaction mixture was heated at 60° C. for 16 hours and then quenched with cold water and extracted with ethyl acetate. The organic layer was washed with a saturated aqueous solution of NaHCO$_3$, dried over Na$_2$SO$_4$ and concentrated under vacuum to afford crude which was purified by column chromatography to afford 1-(1-acetyl-4-piperidyl)pyrazole-4-carbaldehyde 14-6 (80 mg, 361.57 umol, 28.95% yield) as a gummy liquid. LC MS: ES+222.2.

Step-4: Preparation of 4-{[1-(1-Acetyl-piperidin-4-yl)-1H-pyrazol-4-ylmethyl]-amino}-2-(2,6-dioxo-piperidin-3-yl)-isoindole-1,3-dione To stirred solution of 4-amino-2-(2,6-dioxo-3-piperidyl)isoindoline-1,3-dione 14-7 (80 mg, 292.78 umol) and 1-(1-acetyl-4-piperidyl)pyrazole-4-carbaldehyde 14-6 (64.78 mg, 292.78 umol) in THF (4 mL) (in a sealed tube) was added phenylsilane (31.68 mg, 292.78 umol, 36.08 uL) and dibutyltin dichloride (106.75 mg, 351.33 umol, 78.49 uL). The reaction mixture was heated at 80° C. for 16 hours and then diluted with ethyl acetate and water. The layers were separated and the organic layer was washed with brine, dried over Na$_2$SO$_4$ and concentrated under reduced pressure to afford crude mass which was purified by Preparative TLC Plate (eluting with 3% Methanol/DCM) to afford 4-[[1-(1-acetyl-4-piperidyl)pyrazol-4-yl]methylamino]-2-(2,6-dioxo-3-piperidyl)isoindoline-1,3-dione (Compound 159) (22 mg, 45.98 umol, 15.70% yield) as yellow solid. 1H NMR (400 MHz, DMSO-d6) δ 11.08 (s, 1H), 7.77 (s, 1H), 7.59-7.55 (m, 1H), 7.45 (s, 1H), 7.16-7.14 (d, J=8.56 Hz, 1H), 7.04-7.02 (d, J=7.04 Hz, 1H), 6.81-6.78 (M, 1H), 5.04

(dd, J=12.84, 5.48 Hz, 1H), 4.44-4.33 (m, 4H), 3.89-3.84 (m, 2H), 3.18-3.12 (t, J=11.82 Hz, 1H), 2.88-2.83 (m, 1H), 2.69-2.49 (m, 4H), 2.01-1.93 (m, 5H), 1.84-1.81 (m, 1H), 1.68-1.64 (m, 1H), LC MS: ES+ 479.5.

Example 15. Preparation of 2-(2,6-Dioxo-piperidin-3-yl)-4-({1-[1-(2,2,2-trifluoro-ethyl)-piperidin-4-yl]-1H-pyrazol-4-ylmethyl}-amino)-isoindole-1,3-dione (Compound 160)

separated, washed with brine, dried over sodium sulfate, and concentrated under reduced pressure. Crude material was purified by preparative TLC Plate (eluting with 3% methanol in dichloromethane) to afford 2-(2,6-dioxo-3-piperidyl)-4-[[1-[1-(2,2,2-trifluoroethyl)-4-piperidyl]pyrazol-4-yl]methylamino]isoindoline-1,3-dione (Compound 160) (15.0 mg, 28.93 umol, 45.61% yield) as yellow solid. 1H NMR (400 MHz, DMSO-d6) δ 11.08 (s, 1H), 7.78 (s, 1H), 7.59-7.55 (m, 1H), 7.44 (s, 1H), 7.16-7.14 (d, J=8.56 Hz, 1H), 7.04-7.02 (d, J=7.04 Hz, 1H), 6.81-6.78 (m, 1H), 5.04

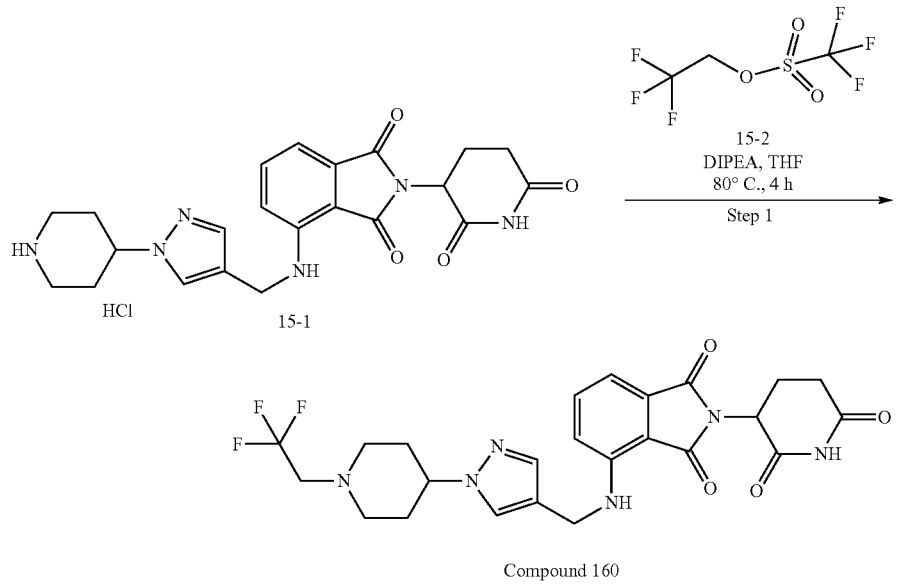

To a stirred solution of 2-(2,6-dioxo-3-piperidyl)-4-[[1-(1-BLAH-4-piperidyl)pyrazol-4-yl]methylamino]isoindoline-1,3-dione 15-1 (30 mg, 63.44 umol) in THF (1 mL) was added DIPEA (20.50 mg, 158.59 umol, 27.62 uL) followed by 2,2,2-trifluoroethyl trifluoromethanesulfonate 15-2 (14.72 mg, 63.44 umol, 9.14 uL). The reaction mixture was heated at 80° C. for 4 hours and then quenched with ice cold water and extracted with ethyl acetate. The organic layer was (dd, J=12.84, 5.48 Hz, 1H), 4.36-4.35 (d, J=5.84 Hz, 2H), 4.18-4.16 (m, 1H), 3.29-3.16 (m, 2H), 2.98-2.95 (m, 2H), 2.88-2.46 (m, 3H), 1.92-1.87 (m, 5H), LC MS: ES+ 519.5.

Example 16. Preparation of 4-(4-{[2-(2,6-Dioxo-piperidin-3-yl)-1,3-dioxo-2,3-dihydro-1H-isoindol-4-ylamino]-methyl}-pyrazol-1-yl)-piperidine-1-carboxylic acid tert-butylamide (Compound 161)

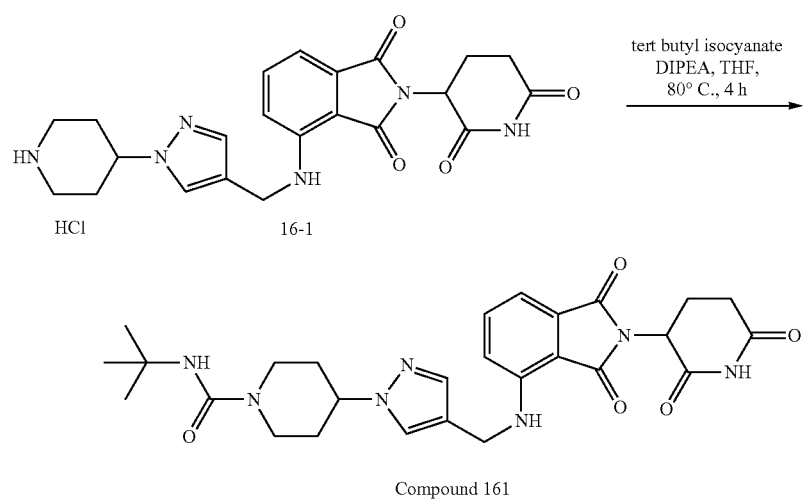

To a stirred suspension of 2-(2,6-dioxo-3-piperidyl)-4-[[1-(1-BLAH-4-piperidyl)pyrazol-4-yl]methylamino]isoindoline-1,3-dione 16-1 (40 mg, 84.58 umol) in THF (3 mL) in a sealed tube was added DIPEA (27.33 mg, 211.45 umol, 36.83 uL). The reaction was cooled to 0° C. and tert-butyl isocyanate (8.38 mg, 84.58 umol, 9.66 uL) was added dropwise. The reaction was heated at 80° C. for 4 hours and then diluted with saturated aqueous NaHCO$_3$ solution and ethyl acetate. The layers were separated, organic layer was washed with water, brine, dried over Na$_2$SO$_4$ and concentrated under reduced pressure to afford crude mass, which was purified by Preparative TLC Plate (eluting with 3% Methanol/DCM) to afford N-tert-butyl-4-[4-[[[2-(2,6-dioxo-3-piperidyl)-1,3-dioxo-isoindolin-4-yl]amino]methyl]pyrazol-1-yl]piperidine-1-carboxamide (Compound 161) (14 mg, 26.14 umol, 30.90% yield) as yellow solid.

1H NMR (400 MHz, DMSO-d6) δ 11.08 (s, 1H), 7.77 (s, 1H), 7.59-7.55 (m, 1H), 7.45 (s, 1H), 7.17-7.15 (d, J=8.56 Hz, 1H), 7.04-7.02 (d, J=7.04 Hz, 1H), 6.81-6.78 (M, 1H), 5.82 (s, 1H), 5.04 (dd, J=12.72, 5.28 Hz, 1H), 4.36-4.35 (d, J=5.8 Hz, 2H), 43.28-4.22 (m, 1H), 4.02-3.99 (m, 2H), 2.92-2.84 (m, 1H), 2.75-2.66 (m, 2H), 2.60-2.50 (m, 2H), 2.03-2.00 (m, 1H), 1.91-1.83 (m, 2H), 1.75-1.66 (m, 2H), 1.24 (s, 9H), LC MS: ES+ 536.5.

Example 17. Synthesis of 2-(2,6-Dioxo-piperidin-3-yl)-4-{[1-(tetrahydro-pyran-4-yl)-1H-pyrazol-4-ylmethyl]-amino}-isoindole-1,3-dione (Compound 162)

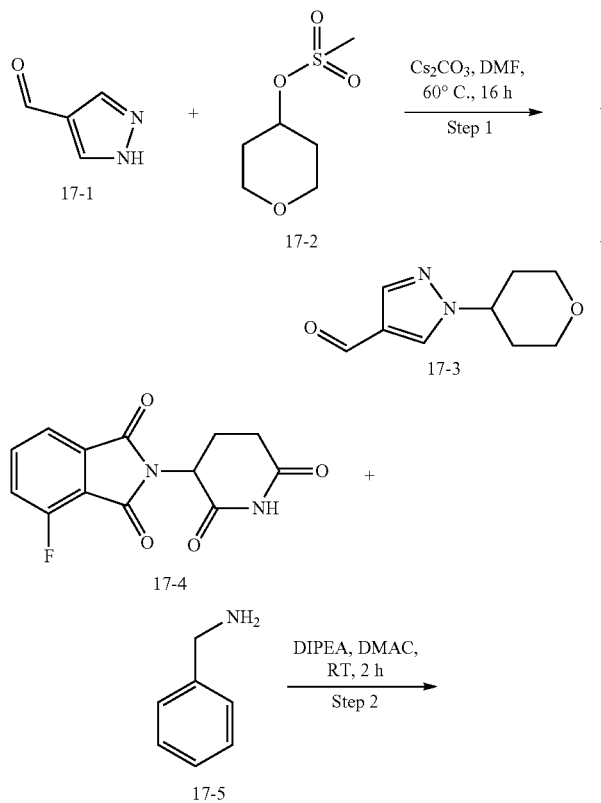

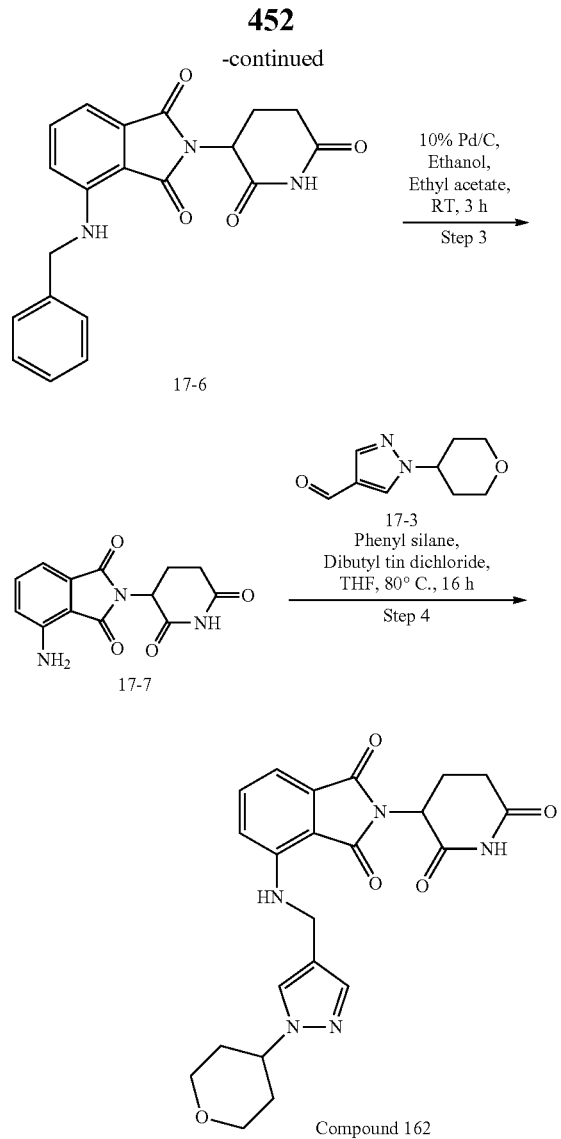

Step-1: Preparation of 1-(Tetrahydro-2H-pyran-4-yl)-1H-pyrazole-4-carbaldehyde

To the stirred solution of tetrahydropyran-4-yl methanesulfonate 17-2 (675.22 mg, 3.75 mmol) in DMF (5 mL) were added cesium carbonate (3.05 g, 9.37 mmol) and 1H-pyrazole-4-carbaldehyde 17-1 (300 mg, 3.12 mmol). The reaction mixture was heated at 60° C. for 16 hours and was then quenched with cold water. The organic layer was extracted with ethyl acetate, washed with saturated solution of sodium bicarbonate, dried over sodium sulfate and concentrated under reduced pressure to afford crude which was purified by column chromatography to afford 1-tetrahydropyran-4-ylpyrazole-4-carbaldehyde 17-3 (210 mg, 1.17 mmol, 37.33% yield) as gummy solid. LC MS: ES+ 181.1.

Step-2: Preparation of 4-Benzylamino-2-(2,6-dioxo-piperidin-3-yl)-isoindole-1,3-dione To a stirred solution of phenylmethanamine 17-5 (387.93 mg, 3.62 mmol) in DMAC (10 mL) was added DIPEA (935.78 mg, 7.24 mmol, 1.26 mL) and the reaction mixture was stirred for 15 minutes. Then to the reaction mixture was added 2-(2,6-dioxo-3-piperidyl)-4-fluoro-isoindoline-1,3-dione 17-4 (1 g, 3.62 mmol) and the reaction was stirred at room temperature for 2 hours. The reaction mixture was quenched with cold water and the organic layer was extracted with ethyl acetate, washed with saturated solution of NaHCO₃, dried over Na₂SO₄ and concentrated under vacuum pump to afford crude which was purified by column chromatography to afford 4-(benzylamino)-2-(2,6-dioxo-3-piperidyl)isoindoline-1,3-dione 17-6 (700 mg, 1.93 mmol, 53.21% yield) as yellow solid. LC MS: ES+ 364.2.

Step-3: Preparation of 4-Amino-2-(2,6-dioxo-piperidin-3-yl)-isoindole-1,3-dione

The stirred solution of 4-(benzylamino)-2-(2,6-dioxo-3-piperidyl)isoindoline-1,3-dione 17-6 (700 mg, 1.93 mmol) in ethanol (5 mL) was degassed for 15 minutes under argon. To the reaction mixture was added Pd/C (233.97 mg, 1.93 mmol) and the reaction mixture was subjected to hydrogenation under hydrogen balloon for 3 hours. The reaction mixture was filtered through a celite bed and the filtrate was concentrated under vacuum pump to afford crude which was purified by column chromatography to afford product 4-amino-2-(2,6-dioxo-3-piperidyl)isoindoline-1,3-dione 17-7 (80 mg, 292.78 umol, 15.20% yield) as yellow solid. LC MS: ES+ 274.3.

Step-4: Preparation of 2-(2,6-Dioxo-piperidin-3-yl)-4-{[1-(tetrahydro-pyran-4-yl)-1H-pyrazol-4-ylmethyl]-amino}-isoindole-1,3-dione To the stirred solution of 4-amino-2-(2,6-dioxo-3-piperidyl)isoindoline-1,3-dione 17-7 (80 mg, 292.78 umol) and 1-tetrahydropyran-4-ylpyrazole-4-carbaldehyde (52.76 mg, 292.78 umol) in THF (4 mL) (in a sealed tube) was added phenyl silane (31.68 mg, 292.78 umol, 36.08 uL) and dibutyltin dichloride (106.75 mg, 351.33 umol, 78.49 uL). The reaction mixture was heated at 80° C. for 16 hours at which point LCMS showed product mass response. The reaction mixture was diluted with ethyl acetate and water and the layers were separated. The organic layer was washed with brine, dried over Na₂SO₄ and concentrated under reduced pressure to afford crude mass which was purified by Preparative TLC (eluting with 2.5% MeOH/DCM) to afford 2-(2,6-dioxo-3-piperidyl)-4-[(1-tetrahydropyran-4-ylpyrazol-4-yl)methylamino]isoindoline-1,3-dione (Compound 162) (55 mg, 125.73 umol, 42.94% yield) as white off solid. 1H NMR (400 MHz, DMSO-d6) δ 11.08 (s, 1H), 7.78 (s, 1H), 7.57 (t, J=7.82 Hz, 1H), 7.46 (s, 1H), 7.16 (d, J=8.56 Hz, 1H), 7.03 (d, J=7.0 Hz, 1H), 6.80 (t, J=5.74 Hz, 1H), 5.04 (dd, J=12.76, 5.36 Hz, 1H), 4.37-4.31 (m, 3H), 3.93-3.91 (m, 2H), 3.45-3.39 (m, 2H), 2.89-2.83 (m, 1H), 2.60-2.50 (m, 2H), 2.04-2.01 (m, 1H), 2.00-1.90 (m, 4H); LC MS: ES+ 438.3.

Example 18. Preparation of 2-(2,6-Dioxo-piperidin-3-yl)-4-({1-[1-(1-methyl-cyclobutylmethyl)-piperidin-4-yl]-1H-pyrazol-4-ylmethyl}-amino)-isoindole-1,3-dione (Compound 139)

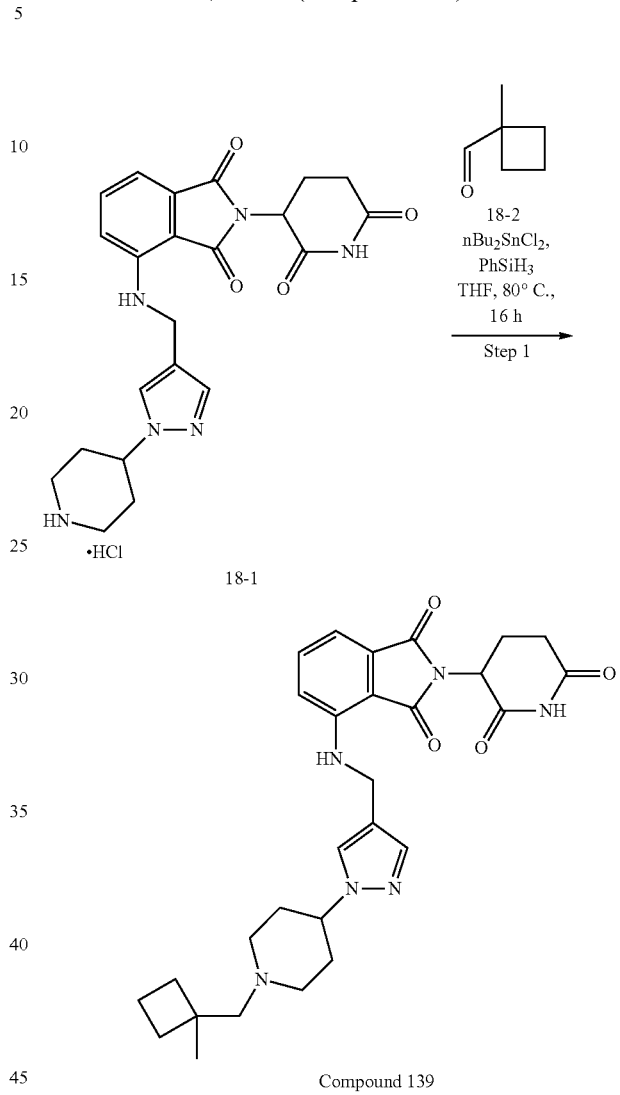

Compound 139

To a stirred solution of 2-(2,6-dioxo-3-piperidyl)-4-[[1-(1-BLAH-4-piperidyl)pyrazol-4-yl]methylamino]isoindoline-1,3-dione 18-1 (50.0 mg, 107.09 umol) in THF (2.0 mL) in a sealed tube was added 1-methylcyclobutanecarbaldehyde 18-2 (10.51 mg, 107.09 umol, 10.41 uL) followed by the addition of phenylsilane (11.59 mg, 107.09 umol, 13.20 uL) and dibutyltin dichloride (39.05 mg, 128.51 umol, 28.71 uL) and the reaction was heated at 80° C. for 16 hours. The reaction mixture was filtered and washed with 10% MeOH-DCM and then evaporated under reduced pressure to obtain the crude compound which was purified by flash chromatography (using 0-5% MeOH-DCM) and then by Preparative TLC Plate (eluting with 4% Methanol/DCM) to afford 2-(2,6-dioxo-3-piperidyl)-4-[[1-[1-[(1-methylcyclobutyl)methyl]-4-piperidyl]pyrazol-4-yl]methylamino]isoindoline-1,3-dione (Compound 139) (7.0 mg, 13.50 umol, 12.60% yield) as yellow solid. ¹H NMR (400 MHz, DMSO-d6) δ 11.07 (s, 1H), 7.77 (s, 1H), 7.57 (t, J=7.72 Hz, 1H), 7.44 (s, 1H), 7.15 (d, J=8.6 Hz, 1H) 7.03 (d, J=6.92 Hz, 1H), 6.80-6.78 (m, 1H), 5.04 (dd, J=12.52, 5.08 Hz, 1H), 4.35 (d, J=5.52 Hz, 2H), 4.05 (brs, 1H), 2.87-2.84 (m, 1H), 2.78-2.75 (m, 2H), 2.60-2.50 (m, 2H), 2.25-2.24 (m, 2H), 2.06-1.79 (m, 10H), 1.73-1.71 (m, 1H), 1.60 (m, 2H), 1.14 (s, 3H); LC MS: ES+ 519.6.

Example 19. Synthesis of 4-[(1-Cyclopropyl-1H-pyrazol-4-ylmethyl)-amino]-2-(2,6-dioxo-piperidin-3-yl)-isoindole-1,3-dione (Compound 163)

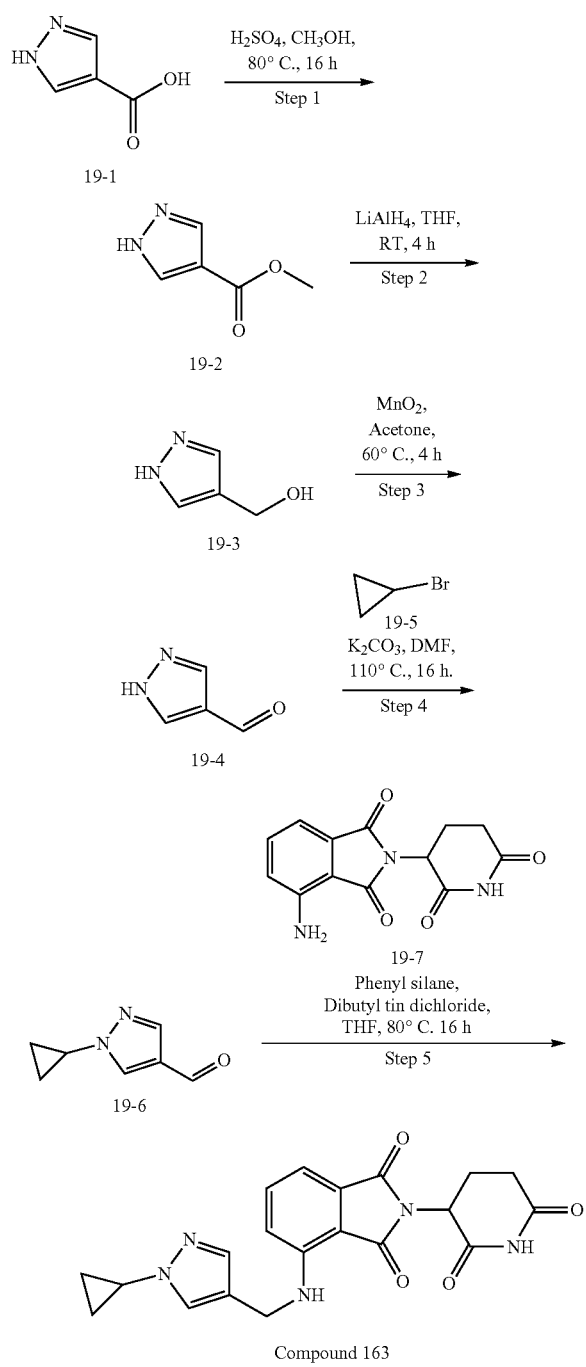

Compound 163

Step-1: Preparation of 1H-Pyrazole-4-carboxylic acid methyl ester

To the stirred solution of 1H-pyrazole-4-carboxylic acid 19-1 (20 g, 178.43 mmol) in methanol (100 mL) was added $H_2SO_4$ (17.50 g, 178.43 mmol, 9.51 mL) at 0° C. and the reaction mixture was refluxed for 16 hours at 80° C. Solvent was evaporated and the crude material was neutralized by saturated sodium bicarbonate solution. The aqueous layer was extracted with ethyl acetate and washed with brine. After separation, the organic layer was dried over sodium sulfate and evaporated to obtain methyl 1H-pyrazole-4-carboxylate 19-2 (21 g, 166.52 mmol, 93.32% yield) as white solid. LC MS: ES+ 127.0.

Step-2: Preparation of (1H-Pyrazol-4-yl)-methanol

To the stirred solution of methyl 1H-pyrazole-4-carboxylate 19-2 (19 g, 150.66 mmol) in THF (500 mL) was added lithium aluminium hydride (8.58 g, 225.99 mmol) portionwise at 0° C. The reaction mixture was stirred at room temperature for 4 hours and then cooled to room temperature and quenched by Fieser workup. The organic later was filtered through celite and concentrated under reduced pressure to afford 1H-pyrazol-4-ylmethanol 19-3 (11.2 g, 114.17 mmol, 75.78% yield) as white solid. LC MS: ES+ 99.0

Step-3: Preparation of 1H-Pyrazole-4-carbaldehyde

To a stirred solution of 1H-pyrazol-4-ylmethanol 19-3 (4000 mg, 40.77 mmol) in acetone (10 mL) was added manganese dioxide (35.45 g, 407.73 mmol). The reaction mixture was heated at 60° C. for 4 hours and then filtered through celite and concentrated under reduced pressure. The crude material was purified by column chromatography at 2% methanol in dichloromethane to afford 1H-pyrazole-4-carbaldehyde 19-4 (2.05 g, 21.33 mmol, 52.33% yield) as light yellow solid. $^1$H NMR (400 MHz, DMSO-d6) δ 13.55 (br s, 1H), 9.84 (s, 1H), 8.49 (br s, 1H), 8.00 (br s, 1H);

Step-4: Preparation of 1-Cyclopropyl-1H-pyrazole-4-carbaldehyde

To the stirred solution of 1H-pyrazole-4-carbaldehyde 19-4 (200 mg, 2.08 mmol) in DMF (2 mL) in a sealed tube were added potassium carbonate (719.19 mg, 5.20 mmol, 314.06 uL) and bromocyclopropane 19-5 (251.80 mg, 2.08 mmol, 166.76 uL). The reaction mixture was heated at 110° C. for 16 hours and then cooled to room temperature, diluted with ethyl acetate, washed with water, brine, dried over sodium sulfate and concentrated under reduced pressure. The crude material was purified by column chromatography to afford 1-cyclopropylpyrazole-4-carbaldehyde 19-6 (25 mg, 183.62 umol, 8.82% yield) as gum. $^1$H NMR (400 MHz, DMSO-d6) δ 9.75 (s, 1H), 8.53 (s, 1H), 7.95 (s, 1H), 3.86-3.82 (m, 1H), 1.10-1.08 (m, 2H), 1.03-0.98 (m, 2H).

Step-5: Preparation of 4-[(1-Cyclopropyl-1H-pyrazol-4-ylmethyl)-amino]-2-(2,6-dioxo-piperidin-3-yl)-isoindole-1,3-dione To the stirred solution of 4-amino-2-(2,6-dioxo-3-piperidyl)isoindoline-1,3-dione 19-7 (50 mg, 182.99 umol) and 1-cyclopropylpyrazole-4-carbaldehyde 19-6 (24.91 mg, 182.99 umol) in THF (3 mL) (in a sealed tube) was added phenyl silane (19.80 mg, 182.99 umol, 22.55 uL) and dibutyltin dichloride (66.72 mg, 219.58 umol, 49.06 uL). The reaction mixture was heated at 80° C. for 16 hours at which point LCMS showed product mass response. The reaction mixture was diluted with ethyl acetate and water. The layers were separated and the organic layer was washed with brine, dried over sodium sulfate and concentrated under reduced pressure to afford crude mass which was purified by Preparative TLC Plate (eluting with 3% methanol in dichloromethane) to afford 4-[(1-cyclopropylpyrazol-4-yl)methylamino]-2-(2,6-dioxo-3-piperidyl)isoindoline-1,3-dione (Compound 163) (10 mg, 25.23 umol, 13.79% yield, 99.25% purity) as yellow solid. $^1$H NMR (400 MHz, DMSO-d6) δ 11.08 (s, 1H), 7.76 (s, 1H), 7.57 (t, J=7.8 Hz, 1H), 7.41 (s, 1H), 7.14 (d, J=8.56 Hz, 1H), 7.03 (d, J=7.0 Hz, 1H), 6.81 (t, J=5.68 Hz, 1H), 5.04 (dd, J=12.92, 5.32 Hz, 1H), 4.34 (d, J=5.92 Hz, 2H), 3.67-3.65 (m, 1H), 2.90-2.86 (m, 1H), 2.60-2.55 (m, 2H), 2.04-2.00 (m, 1H), 0.97-0.95 (m, 2H), 0.92-0.89 (m, 2H); LC MS: ES+ 394.3.

Example 20: Preparation of 4-({1-[1-(2,2-Dimethyl-propane-1-sulfonyl)-piperidin-4-yl]-1H-pyrazol-4-ylmethyl}-amino)-2-(2,6-dioxo-piperidin-3-yl)-isoindole-1,3-dione (Compound 164)

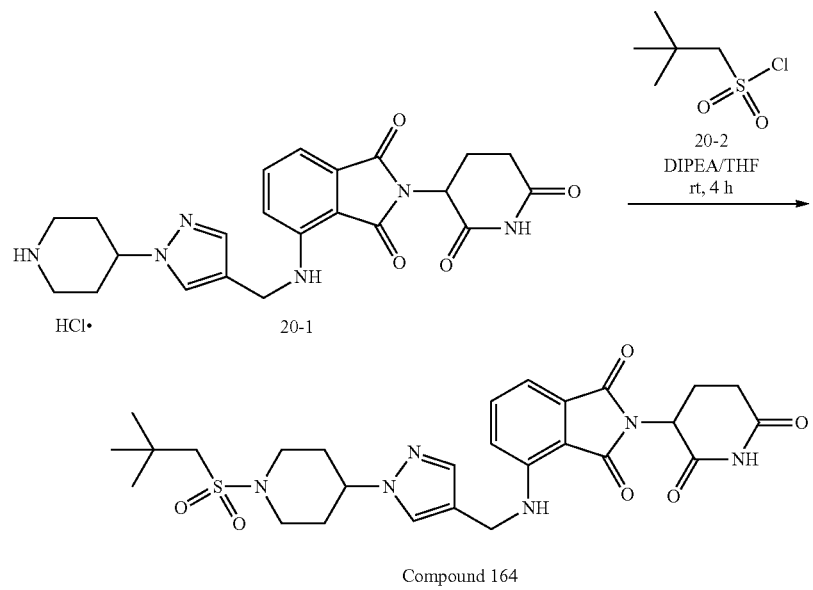

To stirred a suspension of 2-(2,6-dioxo-3-piperidyl)-4-[[1-(1-BLAH-4-piperidyl)pyrazol-4-yl]methylamino]isoindoline-1,3-dione 20-1 (100 mg, 211.45 umol) in THF (3 mL) was added DIPEA (68.32 mg, 528.63 umol, 92.08 uL) and the reaction mixture was cooled to 0° C. followed by the dropwise addition of 2,2-dimethylpropane-1-sulfonyl chloride 20-2 (36.09 mg, 211.45 umol). The reaction mixture was stirred at room temperature for 4 hours and then diluted with saturated NaHCO$_3$ solution and ethyl acetate. The layers were separated and the organic layer was washed with water, brine, dried over Na$_2$SO$_4$ and concentrated under reduced pressure to afford crude which was purified by Preparative TLC Plate (eluting with 3% MeOH/DCM) to afford 4-[[1-[1-(2,2-dimethylpropylsulfonyl)-4-piperidyl]pyrazol-4-yl]methylamino]-2-(2,6-dioxo-3-piperidyl)isoindoline-1,3-dione (Compound 164) (7 mg, 11.92 umol, 5.64% yield, 97.14% purity) as yellow solid. $^1$H NMR (400 MHz, DMSO-d6) δ 11.09 (s, 1H), 7.81 (s, 1H), 7.57 (t, J=7.8 Hz, 1H), 7.47 (s, 1H), 7.15 (d, J=8.56 Hz, 1H), 7.03 (d, J=7.0 Hz, 1H), 6.81 (t, J=5.68 Hz, 1H), 5.04 (dd, J=12.92, 5.32 Hz, 1H), 4.36 (d, J=5.88 Hz, 2H), 4.25-4.19 (m, 1H), 3.67-3.62 (m, 2H), 2.93 (s, 2H), 2.90-2.88 (m, 3H), 2.55-2.50 (m, 2H), 2.09-2.02 (m, 3H), 1.91-1.88 (m, 2H), 1.09 (s, 9H). LC MS: ES+ 571.6.

Example 21. Preparation of 4-(4-{[2-(2,6-Dioxo-piperidin-3-yl)-1,3-dioxo-2,3-dihydro-1H-isoindol-4-ylamino]-methyl}-pyrazol-1-yl)-piperidine-1-carboxylic acid 2,2,2-trifluoro-ethyl ester (Compound 165)

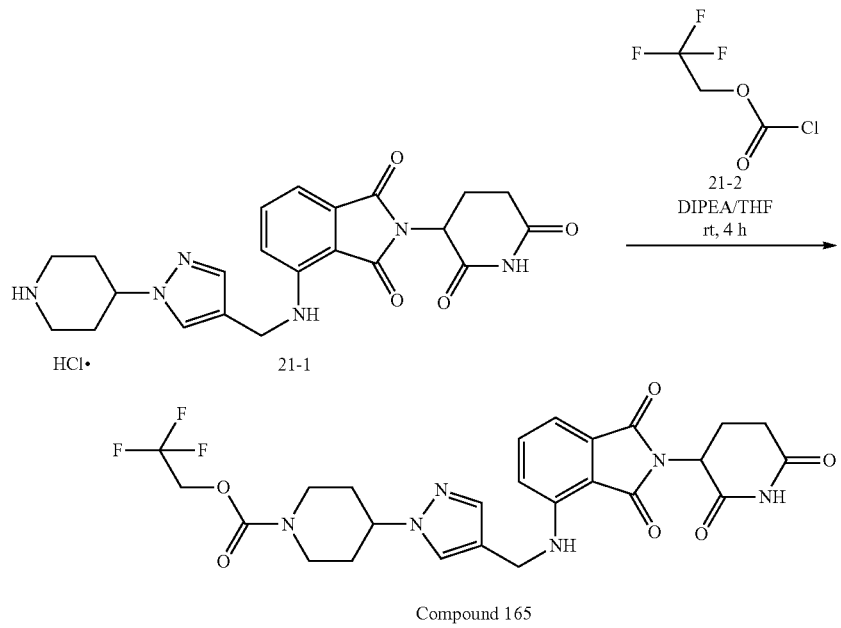

Compound 165

To the stirred solution of 2-(2,6-dioxo-3-piperidyl)-4-[[1-(1-BLAH-4-piperidyl)pyrazol-4-yl]methylamino]isoindoline-1,3-dione 21-1 (40 mg, 84.58 umol) in THF (1 mL) was added DIPEA (27.33 mg, 211.45 umol, 36.83 uL) followed by 2,2,2-trifluoroethoxycarbonyl chloride 21-2 (13.74 mg, 84.58 umol). The reaction mixture was stirred at room temperature for 4 hours and then quenched with ice cold water, extracted with ethyl acetate, washed with saturated sodium bicarbonate solution, brine, dried over sodium sulfate, and concentrated under reduced pressure. The crude material was purified by preparative TLC Plate (eluting with 3% methanol in dichloromethane) to afford 2,2,2-trifluoro-ethyl 4-[4-[[[2-(2,6-dioxo-3-piperidyl)-1,3-dioxo-isoindolin-4-yl]amino]methyl]pyrazol-1-yl]piperidine-1-carboxylate (Compound 165) (21 mg, 37.33 umol, 44.14% yield) as yellow solid. $^1$H NMR (400 MHz, DMSO-d6) δ 11.09 (s, 1H), 7.79 (s, 1H), 7.57 (t, J=7.8 Hz, 1H), 7.46 (s, 1H), 7.15 (d, J=8.56 Hz, 1H), 7.03 (d, J=7.0 Hz, 1H), 6.81 (t, J=5.68 Hz, 1H), 5.04 (dd, J=12.92, 5.32 Hz, 1H), 4.72-4.69 (m, 2H), 4.36-4.33 (m, 3H), 4.05-4.01 (m, 2H), 3.19-2.95 (m, 2H), 2.87-2.84 (m, 1H), 2.55-2.49 (m, 2H), 2.01-1.98 (m, 3H), 1.82-1.76 (m, 2H); LC MS: ES+ 563.1.

Example 22. Synthesis of Preparation of tert-Butyl 3-(4-(((2-(2,6-dioxopiperidin-3-yl)-1,3-dioxoisoindolin-4-yl)amino)methyl)-1H-pyrazol-1-yl)-8-azabicyclo[3.2.1]octane-8-carboxylate (Compound 166)

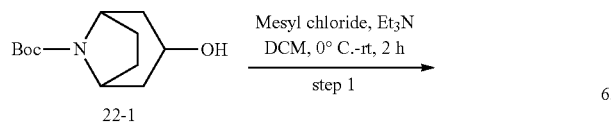

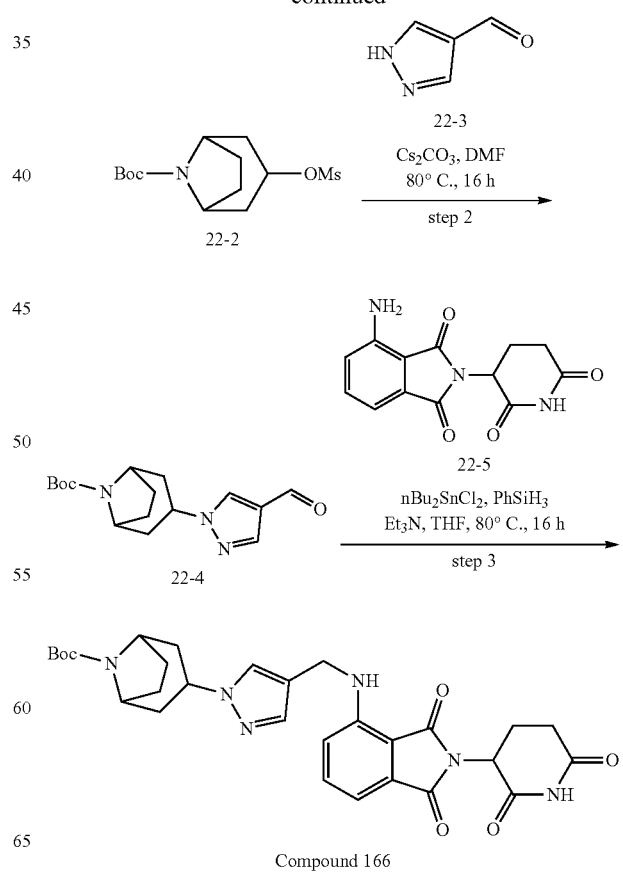

Compound 166

Step-1: Preparation of tert-Butyl 3-((methylsulfonyl)oxy)-8-azabicyclo[3.2.1]octane-8-carboxylate To a stirred solution of tert-butyl 3-hydroxy-8-azabicyclo[3.2.1]octane-8-carboxylate 22-1 (500 mg, 2.20 mmol) in DCM (10 mL) cooled to 0° C. was added triethylamine (445.18 mg, 4.40 mmol, 613.20 uL) followed by mesyl chloride (327.58 mg, 2.86 mmol, 221.34 uL) and the reaction mixture was allowed to stir at room temperature for 16 hours. The reaction mass was diluted with DCM and washed with water and brine solution, dried over anhydrous sodium sulphate and evaporated under reduced pressure to afford tert-butyl 3-methylsulfonyloxy-8-azabicyclo[3.2.1]octane-8-carboxylate 22-2 (600 mg, 1.96 mmol, 89.32% yield) as off-white solid that was used as such for next step without further purification. $^1$H NMR (d6-DMSO, 400 MHZ) δ 5.00-4.92 (m, 1H), 4.11-4.10 (m, 2H), 3.20 (s, 3H), 2.06 (br s, 2H), 1.87-1.85 (m, 2H), 1.74-1.70 (m, 2H), 1.63-1.60 (m, 2H), 1.39 (s, 9H).

Step-2: Preparation of tert-Butyl 3-(4-formyl-1H-pyrazol-1-yl)-8-azabicyclo[3.2.1]octane-8-carboxylate To a stirred solution of tert-butyl 3-methylsulfonyloxy-8-azabicyclo[3.2.1]octane-8-carboxylate 22-2 (650 mg, 2.13 mmol) and 1H-pyrazole-4-carbaldehyde 22-3 (204.51 mg, 2.13 mmol) in DMF (10 mL) was added cesium carbonate (1.39 g, 4.26 mmol) and the reaction mixture was stirred at 80° C. for 16 hours. The reaction mixture was diluted with water and extracted with ethyl acetate. The organic layer was washed with water and dried over anhydrous sodium sulphate to afford the crude product. The crude thus obtained was purified by column chromatography (eluting with 30-35% of ethyl acetate in hexane) to afford tert-butyl 3-(4-formyl-H-pyrazol-1-yl)-8-azabicyclo[3.2.1]octane-8-carboxylate 22-4 (250 mg, 736.81 umol, 34.62% yield, 90% purity) as gummy liquid that was carried forward.

Step-3: Preparation of tert-Butyl 3-(4-(((2-(2,6-dioxopiperidin-3-yl)-1,3-dioxoisoindolin-4-yl)amino)methyl)-1H-pyrazol-1-yl)-8-azabicyclo[3.2.1]octane-8-carboxylate (Compound 166)

Compound 166 was synthesized following the general reductive amination procedure of Example 19 to afford tert-butyl 3-[4-[[[2-(2,6-dioxo-3-piperidyl)-1,3-dioxo-isoindolin-4-yl]amino]methyl]pyrazol-1-yl]-8-azabicyclo[3.2.1]octane-8-carboxylate (50 mg, 88.87 umol, 13.57% yield) as a yellow solid. $^1$H NMR (d6-DMSO, 400 MHZ) δ 11.09 (s, 1H), 7.99 (s, 1H), 7.55 (t, J=7.7 Hz, 1H), 7.48 (s, 1H), 7.14 (d, J=8.72 Hz, 1H), 7.03 (d, J=7.0 Hz, 1H), 6.82 (m, 1H), 5.04 (dd, J=12.48, 5.12 Hz, 1H), 4.39-4.32 (m, 3H), 4.06 (br s, 2H), 2.88-2.84 (m, 1H), 2.67-2.55 (m, 2H), 2.54-2.50 (m, 4H), 2.32-2.22 (m, 2H), 2.03-2.00 (m, 2H), 1.68-1.66 (m, 2H), 1.41 (s, 9H); LC MS: ES+ 563.6.

Example 23. Synthesis of tert-Butyl 6-(4-(((2-(2,6-dioxopiperidin-3-yl)-1,3-dioxoisoindolin-4-yl)amino)methyl)-1H-pyrazol-1-yl)-2-azaspiro[3.3]heptane-2-carboxylate (Compound 167)

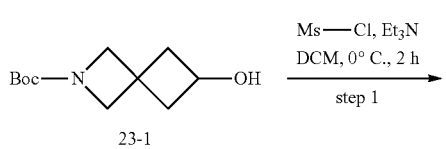

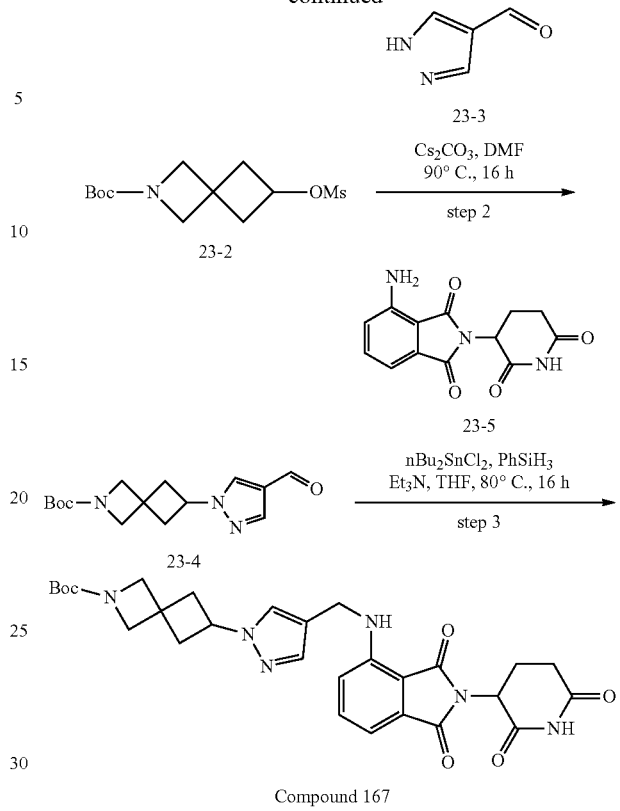

Compound 167

Step-1: Preparation of tert-Butyl 6-((methylsulfonyl)oxy)-2-azaspiro[3.3]heptane-2-carboxylate To a stirred solution of tert-butyl 6-hydroxy-2-azaspiro[3.3]heptane-2-carboxylate 23-1 (500 mg, 2.34 mmol) in dichloromethane (10 mL) at 0° C. was added triethylamine (474.46 mg, 4.69 mmol, 653.53 uL) followed by mesyl chloride (402.83 mg, 3.52 mmol, 272.18 uL) drop wise. The reaction mixture was allowed to stir at ambient temperature for 1 hour. The reaction mass was then diluted with DCM and washed with water, a saturated solution of NaHCO$_3$ and brine. The organic layer was dried over anhydrous sodium sulphate and evaporated under reduced pressure to afford crude product that was triturated with diethyl ether to afford tert-butyl 6-methylsulfonyloxy-2-azaspiro[3.3]heptane-2-carboxylate 23-2 (500 mg, 1.72 mmol, 73.20% yield) as white semisolid. $^1$H NMR (d6-DMSO, 400 MHZ) δ 4.89-4.85 (m, 1H), 3.85-3.81 (m, 4H), 3.13 (s, 3H), 2.63-2.60 (m, 2H), 2.37-2.34 (m, 2H), 1.35 (s, 9H);

Step-2: Preparation of tert-Butyl 6-(4-formyl-1H-pyrazol-1-yl)-2-azaspiro[3.3]heptane-2-carboxylate To a stirred solution of tert-butyl 6-methylsulfonyloxy-2-azaspiro[3.3]heptane-2-carboxylate 23-2 (500 mg, 1.72 mmol) and 1H-pyrazole-4-carbaldehyde 23-3 (164.89 mg, 1.72 mmol) in DMF (10 mL) was added cesium carbonate (1.12 g, 3.43 mmol) and the reaction mixture was stirred at 80° C. for 16 hours. The reaction mixture was diluted with cold water and EtOAc, and the layers were separated. The organic layer was washed with water, brine, dried over Na$_2$SO$_4$ and concentrated under reduced pressure to afford crude which was purified by column chromatography to afford tert-butyl 6-(3-formylpyrazol-1-yl)-2-azaspiro[3.3]heptane-2-carboxylate 23-4 (420 mg, 1.44 mmol, 84.01% yield) as gummy solid. LC MS: ES+ 292.2.

Step-3: Preparation of tert-Butyl 6-(4-(((2-(2,6-dioxopiperidin-3-yl)-1,3-dioxoisoindolin-4-yl)amino)methyl)-1H-pyrazol-1-yl)-2-azaspiro[3.3]heptane-2-carboxylate (Compound 167)

Compound 167 was synthesized following general reductive amination procedure of Example 19 to afford tert-butyl 6-[4-[[[2-(2,6-dioxo-3-piperidyl)-1,3-dioxo-isoindolin-4-yl]amino]methyl]pyrazol-1-yl]-2-azaspiro[3.3]heptane-2-carboxylate (80 mg, 145.83 umol, 23.37% yield) as yellow solid. $^1$H NMR (d6-DMSO, 400 MHZ) δ 11.08 (s, 1H), 7.74 (s, 1H), 7.56 (t, J=7.8 Hz, 1H), 7.47 (s, 1H), 7.13 (d, J=8.56 Hz, 1H), 7.03 (d, J=7.0 Hz, 1H), 6.82 (t, J=5.7 Hz, 1H), 5.04 (dd, J=12.76, 5.36 Hz, 1H), 4.72-4.67 (m, 1H), 4.35 (d, J=5.72 Hz, 2H), 3.92 (br s, 2H), 3.82 (br s, 2H), 2.89-2.84 (m, 1H), 2.69-2.55 (m, 6H), 2.04-2.00 (m, 1H), 1.36 (s, 9H); LC MS: ES+ 549.4.

Example 24. Synthesis of tert-Butyl 4-(4-(((2-(2,6-dioxopiperidin-3-yl)-1,3-dioxoisoindolin-4-yl)amino)methyl)-1H-pyrazol-1-yl)-2,6-dimethylpiperidine-1-carboxylate (Compound 168)

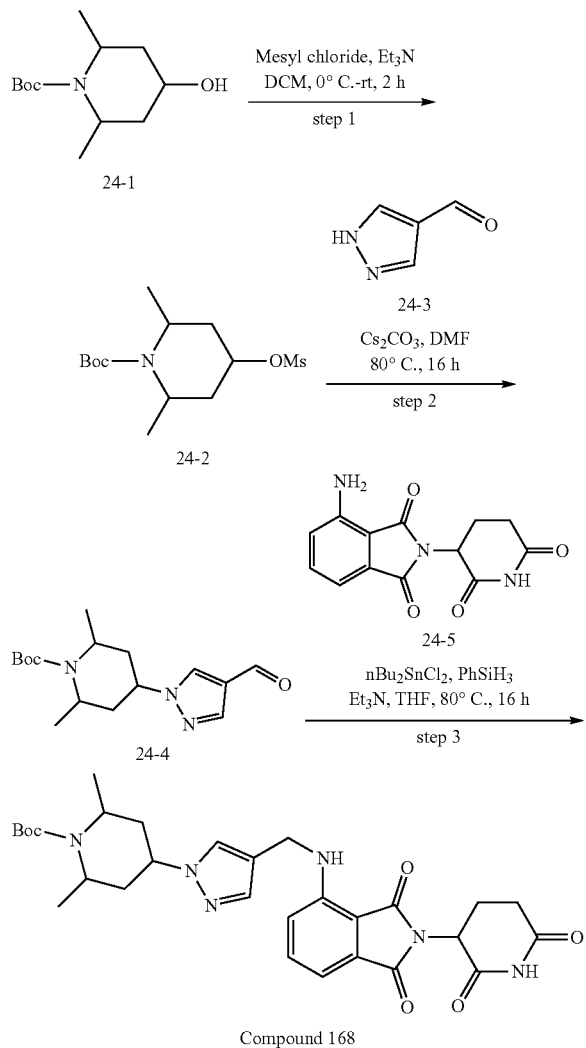

Compound 168

Step-1: Preparation of tert-Butyl 2,6-dimethyl-4-((methylsulfonyl)oxy)piperidine-1-carboxylate To the stirred solution of tert-butyl 4-hydroxy-2,6-dimethyl-piperidine-1-carboxylate 24-1 (300.0 mg, 1.31 mmol) in DCM (4 mL) was added triethylamine (264.76 mg, 2.62 mmol, 364.69 uL) at 0° C. followed by methanesulfonyl chloride (224.79 mg, 1.96 mmol, 151.89 uL) at 0° C. After 10 minutes, the reaction mixture was allowed to warm to room temperature and stir for 1 hour. The reaction mixture was diluted with ethyl acetate and washed with sodium bicarbonate solution, water and brine solution. The organic fraction was separated, dried over anhydrous sodium sulphate and evaporated under reduced pressure to obtain tert-butyl 2,6-dimethyl-4-methylsulfonyloxy-piperidine-1-carboxylate 24-2 (400.0 mg, 1.30 mmol, 99.46% yield) as the crude compound that was used directly in the next step without purification. LC MS: ES+ 308.4.

Step-2: Preparation of tert-Butyl 4-(4-formyl-1H-pyrazol-1-yl)-2,6-dimethylpiperidine-1-carboxylate To the stirred solution of tert-butyl 2,6-dimethyl-4-methylsulfonyloxy-piperidine-1-carboxylate 24-2 (400.0 mg, 1.30 mmol) in DMF (3.5 mL) was added cesium carbonate (847.92 mg, 2.60 mmol) and 1H-pyrazole-4-carbaldehyde 3 (125.03 mg, 1.30 mmol). The reaction mixture was heated at 70° C. for 16 hours. The reaction mixture was diluted with ethyl acetate, water and brine solution. The organic fraction was separated, dried over anhydrous sodium sulphate and evaporated under reduced pressure to obtain the crude compound purified by flash chromatography using (0-30% ethyl acetate-hexane) to afford tert-butyl 4-(4-formylpyrazol-1-yl)-2,6-dimethyl-piperidine-1-carboxylate 24-4 (200.0 mg, 650.65 umol, 50.00% yield) as off white solid. LC MS: ES+ 308.3.

Step-3: Preparation of tert-Butyl 4-(4-(((2-(2,6-dioxopiperidin-3-yl)-1,3-dioxoisoindolin-4-yl)amino)methyl)-1H-pyrazol-1-yl)-2,6-dimethylpiperidine-1-carboxylate (Compound 168)

Compound 168 was synthesized following general reductive amination procedure of Example 19 to afford tert-butyl 4-[4-[[[2-(2,6-dioxo-3-piperidyl)-1,3-dioxo-isoindolin-4-yl]amino]methyl]pyrazol-1-yl]-2,6-dimethyl-piperidine-1-carboxylate as a mixture of cis-trans isomers (200.0 mg, 354.21 umol, 59.88% yield) as yellow solid. $^1$H NMR (d6-DMSO, 400 MHZ) δ 11.09 (s, 1H), 7.79 (d, J=10.08 Hz, 1H), 7.57 (t, J=7.62 Hz, 1H), 7.47-7.46 (m, 1H), 7.15 (d, J=8.48 Hz, 1H), 7.03 (d, J=7.08 Hz, 1H), 6.83-6.81 (m, 1H), 5.04 (dd, J=12.64, 5.44 Hz, 1H), 4.73-4.62 (m, 1H), 4.36-4.25 (m, 3H), 3.71-3.43 (m, 1H), 2.92-2.84 (m, 1H), 2.66-2.50 (m, 2H), 2.22-2.14 (m, 1H), 2.03-1.78 (m, 4H), 1.40 (s, 9H), 1.32-1.12 (m, 6H); LC MS: ES+ 565.2.

Example 25. Synthesis of tert-Butyl 4-(4-(((2-(2,6-dioxopiperidin-3-yl)-1,3-dioxoisoindolin-4-yl)amino)methyl)-1H-pyrazol-1-yl)-2,2-dimethylpiperidine-1-carboxylate (Compound 169)

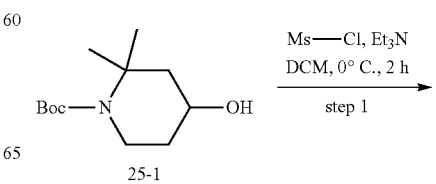

25-1

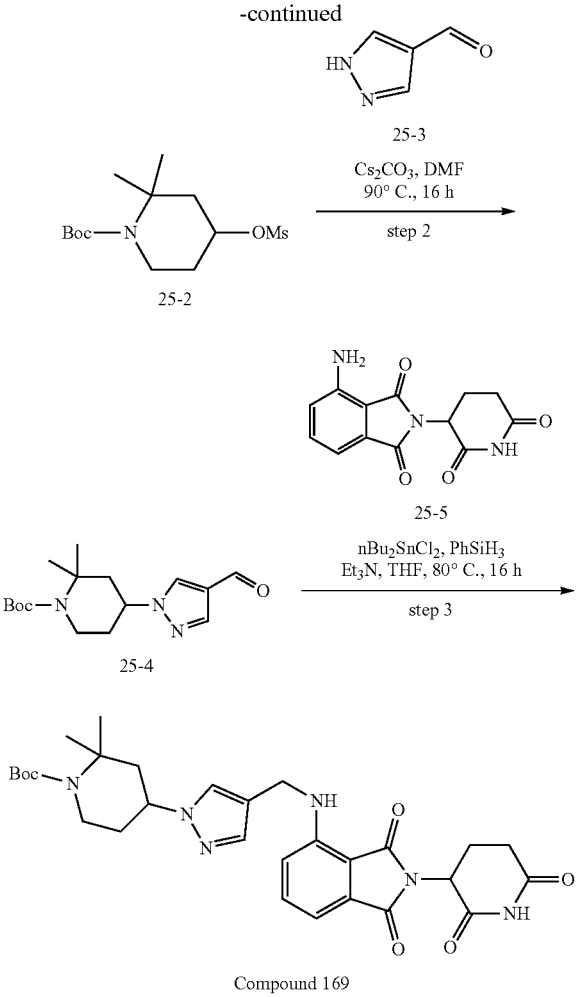

Step-1: Preparation of tert-Butyl 2,2-dimethyl-4-((methylsulfonyl)oxy)piperidine-1-carboxylate To a stirred solution of tert-butyl 4-hydroxy-2,2-dimethyl-piperidine-1-carboxylate 25-1 (500 mg, 2.18 mmol) in dichloromethane (10 mL) at 0° C. was added triethylamine (441.27 mg, 4.36 mmol, 607.81 uL) followed by mesyl chloride (374.65 mg, 3.27 mmol, 253.14 uL) dropwise. The reaction mixture was allowed to stir at ambient temperature for 1 hour and then was diluted with DCM and washed with water, a saturated solution of NaHCO₃ and brine. The organic layer was dried over anhydrous sodium sulphate and evaporated under reduced pressure to afford crude product that was purified by column chromatography to afford tert-butyl 2,2-dimethyl-4-methylsulfonyloxy-piperidine-1-carboxylate 25-2 (500 mg, 1.63 mmol, 74.60% yield) as colorless oil which was used directly in the next step without purification.

Step-2: Preparation of tert-Butyl (S)-4-(4-formyl-1H-pyrazol-1-yl)-2,2-dimethylpiperidine-1-carboxylate To a stirred solution of tert-butyl 2,2-dimethyl-4-methyl-sulfonyloxy-piperidine-1-carboxylate 25-2 (650 mg, 2.11 mmol) and 1H-pyrazole-4-carbaldehyde 3 (203.17 mg, 2.11 mmol) in DMF (10 mL) was added cesium carbonate (1.38 g, 4.23 mmol) and the reaction mixture was stirred at 80° C. for 16 hours. The reaction mixture was diluted with cold water and EtOAc and the layers were separated. The organic layer was washed with water, brine, dried over Na₂SO₄ and concentrated under reduced pressure to afford crude which was purified by column chromatography to afford tert-butyl 4-(4-formylpyrazol-1-yl)-2,2-dimethyl-piperidine-1-carboxylate 25-4 (310 mg, 1.01 mmol, 47.70% yield) as gummy solid. LC MS: ES+ 308.3.

Step-3: Preparation of tert-Butyl 4-(4-(((2-(2,6-dioxopiperidin-3-yl)-1,3-dioxoisoindolin-4-yl)amino)methyl)-1H-pyrazol-1-yl)-2,2-dimethylpiperidine-1-carboxylate (Compound 169)

Compound 169 was synthesized following general reductive amination procedure of Example 19 to afford tert-butyl 4-[4-[[[2-(2,6-dioxo-3-piperidyl)-1,3-dioxo-isoindolin-4-yl]amino]methyl]pyrazol-1-yl]-2,2-dimethyl-piperidine-1-carboxylate (130 mg, 230.24 umol, 38.92% yield) as yellow solid. ¹H NMR (d6-DMSO, 400 MHZ) δ 11.09 (s, 1H), 7.78 (s, 1H), 7.57 (t, J=7.82 Hz, 1H), 7.46 (s, 1H), 7.15 (d, J=8.52 Hz, 1H), 7.03 (d, J=7.04 Hz, 1H), 6.81 (m, 1H), 5.04 (dd, J=12.72, 5.24 Hz, 1H), 4.48-4.43 (m, 1H), 4.36 (d, J=5.64 Hz, 2H), 3.83-3.78 (m, 1H), 3.25-3.18 (m, 1H), 2.92-2.84 (m, 1H), 2.67-2.55 (m, 2H), 2.07-1.95 (m, 3H), 1.82-1.78 (m, 2H), 1.46 (s, 3H), 1.40 (s, 9H), 1.31 (s, 3H); LC MS: ES+ 565.4.

Example 26. Synthesis of 1-((1r,4r)-4-(Piperidine-1-carbonyl)cyclohexyl)-1H-pyrazole-4-carbaldehyde (Compound 170)

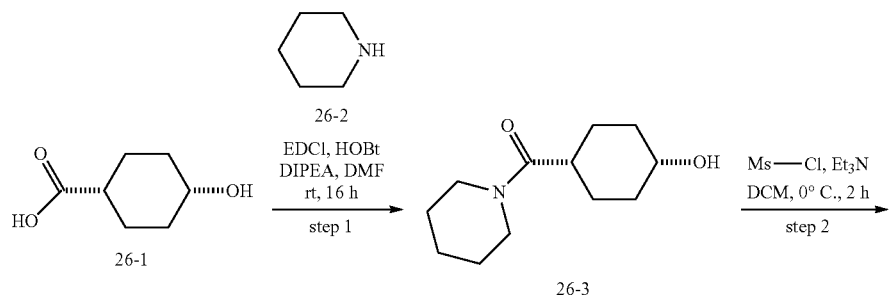

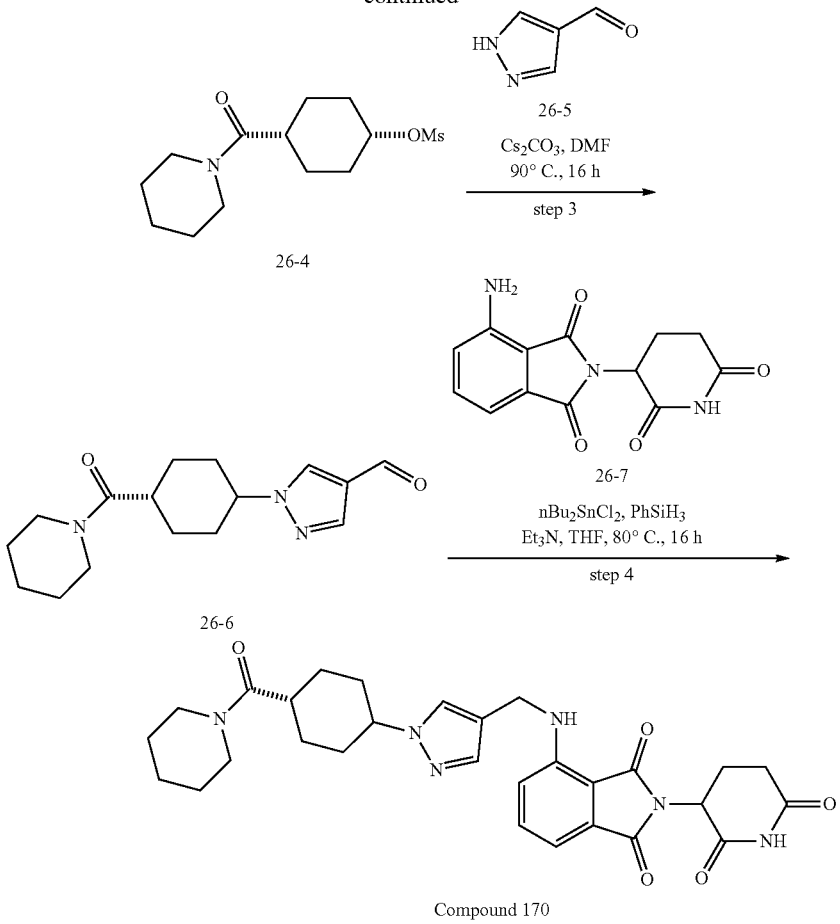

Compound 170

Step-1: Preparation of ((1s,4s)-4-Hydroxycyclohexyl)(piperidin-1-yl)methanone To the stirred solution of 4-hydroxycyclohexanecarboxylic acid 26-1 (600.0 mg, 4.16 mmol) in DMF (6 mL) was added piperidine 26-2 (354.37 mg, 4.16 mmol, 411.10 uL) and N,N-diisopropylethylamine (1.61 g, 12.49 mmol, 2.17 mL) at 0° C. followed by 1-ethyl-3-(3-dimethylaminopropyl)carbodiimide Hydrochloride (1.60 g, 8.32 mmol) and hydroxybenzotriazole (1.12 g, 8.32 mmol). The reaction mixture was stirred at room temperature for 16 hours. The reaction mixture was diluted with water and extracted with 20% isopropanol-DCM. The organic fraction was washed with sodium bicarbonate solution and water and separated. The mixture was then dried over anhydrous sodium sulphate and evaporated under reduced pressure to obtain the crude compound which was purified by column chromatography using (0-5% MeOH-DCM) to afford (4-hydroxycyclohexyl)-(1-piperidyl)methanone 26-3 (715 mg, 3.38 mmol, 81.31% yield) as white solid. LC MS: ES+ 212.1

Step-2: Preparation of (1s,4s)-4-(Piperidine-1-carbonyl)cyclohexyl methanesulfonate To the stirred solution of (4-hydroxycyclohexyl)-(1-piperidyl)methanone 26-3 (500.0 mg, 2.37 mmol) in DCM (6.0 mL) was added triethylamine (478.89 mg, 4.73 mmol, 659.63 uL) at 0° C. followed by methanesulphonylchloride (677.66 mg, 5.92 mmol, 457.88 uL). The reaction was allowed to warm to room temperature and stir for 1 hour. The reaction mixture was diluted with DCM and washed with sodium bicarbonate solution, water and brine solution. The organic fraction was separated, dried over anhydrous sodium sulphate and evaporated under reduced pressure to obtain [4-(piperidine-1-carbonyl)cyclohexyl] methanesulfonate 26-4 (642.0 mg, 2.22 mmol, 93.75% yield) as crude compound which was used directly in the next step without purification. LC MS: ES+ 290.1.

Step-3: Preparation of 1-((1r,4r)-4-(Piperidine-1-carbonyl)cyclohexyl)-1H-pyrazole-4-carbaldehyde To the stirred solution of [4-(piperidine-1-carbonyl)cyclohexyl] methanesulfonate 26-4 (642.0 mg, 2.22 mmol) in DMF (5 mL) was added cesium carbonate (1.45 g, 4.44 mmol) followed by 1H-pyrazole-4-carbaldehyde 26-5 (213.17 mg, 2.22 mmol). The reaction mixture was heated at 70° C. for 16 hours and diluted with ethyl acetate, washed with water and brine solution, and the organic fraction was separated. The organic layer was dried over anhydrous sodium sulphate and evaporated under reduced pressure to obtain the crude which was purified by flash chromatography using (0-20% ethyl acetate-hexane) to afford 1-[4-(piperidine-1-carbonyl)cyclohexyl]pyrazole-4-carbaldehyde (150.0 mg, 518.36 umol, 23.37% yield) as white solid. LC MS: ES+ 290.2.

Step-4: Preparation of 2-(2,6-Dioxopiperidin-3-yl)-4-(((1-((1r,4r)-4-(piperidine-1-carbonyl)cyclohexyl)-1H-pyrazol-4-yl)methyl)amino)isoindoline-1,3-dione Compound 170 was synthesized following general reductive amination procedure of Example 19 to afford 2-(2,6-dioxo-3-piperidyl)-4-[[(1S)-1-[4-(piperidine-1-carbonyl)cyclohexyl]pyrazol-4-yl]methylamino]isoindoline-1,3-dione (140.0 mg, 256.12 umol, 60.39% yield) as yellow solid. $^1$H NMR (d6-DMSO, 400 MHZ) δ 11.06 (s, 1H), 7.68 (s, 1H), 7.54 (t, J=7.82 Hz, 1H), 7.40 (s, 1H), 7.12 (d, J=8.56 Hz, 1H), 7.01 (d, J=7.04 Hz, 1H), 6.78 (m, 1H), 5.02 (dd, J=12.8, 5.36 Hz, 1H), 4.33 (d, J=5.6 Hz, 2H), 4.10-4.04 (m, 1H), 3.40-3.38 (m, 4H), 2.88-2.82 (m, 1H), 2.64-2.53 (m, 2H), 2.52-2.50 (m, 1H), 1.98-1.95 (m, 3H), 1.80-1.69 (m, 4H), 1.54-1.19 (m, 8H); LC MS: ES+ 547.3.

Example 27: Synthesis of 4-(((3,5-Dimethyl-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione (Compound 171)

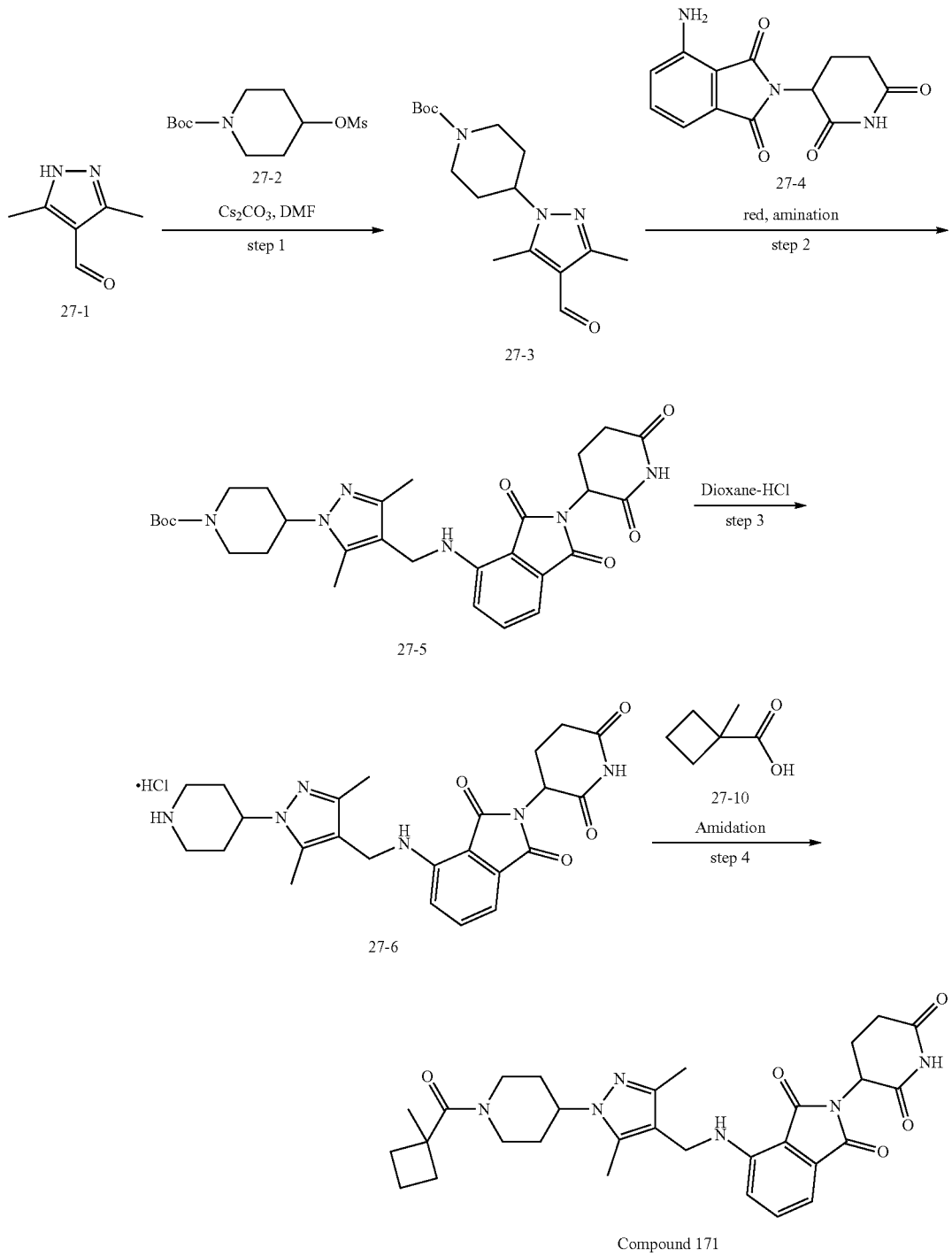

Compound 171

Step-1: Preparation of tert-Butyl 4-(4-formyl-3,5-dimethyl-1H-pyrazol-1-yl)piperidine-1-carboxylate To the stirred solution of 3,5-dimethyl-1H-pyrazole-4-carbaldehyde 27-1 (250 mg mg, 2.01 mmol) in DMF (8 mL) cesium carbonate (1.31 g, 4.03 mmol) was added and the reaction was heated at 60° C. for 20 minutes followed by the addition of tert-butyl 4-methylsulfonylpiperidine-1-carboxylate 27-2 (689.46 mg, 2.62 mmol). The reaction stirred at 60° C. for 3 hours. Ice cooled water was added and the organics were extracted with ethyl acetate. The organic portion was separated, dried over sodium sulfate and concentrated. The crude residue was purified by column chromatography to afford tert-butyl 4-(4-formyl-3,5-dimethyl-pyrazol-1-yl)piperidine-1-carboxylate 27-3 (550 mg, 1.79 mmol, 88.85% yield) as off white solid. LC MS: ES+ 308.3.

Step-2: Preparation of tert-Butyl 4-(4-(((2-(2,6-dioxopiperidin-3-yl)-1,3-dioxoisoindolin-4-yl)amino) methyl)-3,5-dimethyl-1H-pyrazol-1-yl)piperidine-1-carboxylate To the stirred solution 4-amino-2-(2,6-dioxo-3-piperidyl) isoindoline-1,3-dione 27-4 (250 mg, 914.93 umol) and tert-butyl 4-(4-formyl-3,5-dimethyl-pyrazol-1-yl)piperidine-1-carboxylate 27-3 (281.24 mg, 914.93 umol) in THE (3 mL) dibutyltin trichloride (278.00 mg, 914.93 umol, 204.41 uL) was added followed by phenylsilane (99.01 mg, 914.93 umol) at room temperature. The reaction mixture was heated at 80° C. for 12 hours and then concentrated. The crude residue was purified by column chromatography to afford tert-butyl 4-[4-[[[2-(2,6-dioxo-3-piperidyl)-1,3-dioxo-isoindolin-4-yl]amino]methyl]-3,5-dimethyl-pyrazol-1-yl]piperidine-1-carboxylate 27-5 (350 mg, 619.87 umol, 67.75% yield) as yellow solid. LC MS: ES+ 565.4.

Step-3: Preparation of 4-(((3,5-Dimethyl-1-(piperidin-4-yl)-1H-pyrazol-4-yl)methyl)amino)-2-(2,6-dioxopiperidin-3-yl)isoindoline-1,3-dione hydrochloride To solid tert-butyl 4-[4-[[[2-(2,6-dioxo-3-piperidyl)-1,3-dioxo-isoindolin-4-yl]amino]methyl]-3,5-dimethyl-pyrazol-1-yl]piperidine-1-carboxylate 27-5 (300 mg, 531.32 umol) 4M dioxane-HCl (4 mL) was added and the reaction stirred for 2 hours. The volatiles were removed to obtain 4-[[3,5-dimethyl-1-(4-piperidyl)pyrazol-4-yl]methylamino]-2-(2,6-dioxo-3-piperidyl)isoindoline-1,3-dione; hydrochloride 27-6 (250 mg, 499.02 umol, 93.92% yield). LC MS: ES+ 465.4.

Step-4: Preparation of 4-(((3,5-Dimethyl-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione Compound 171 was synthesized following the general amidation procedure using HATU/DIPEA of Example 1 to afford 4-[[3,5-dimethyl-1-[1-(1-methylcyclobutanecarbonyl)-4-piperidyl]pyrazol-4-yl]methylamino]-2-(2,6-dioxo-3-piperidyl)isoindoline-1,3-dione (175 mg, 312.14 umol, 72.50% yield) as yellow solid. 1H NMR (d6-DMSO, 400 MHZ) δ 11.08 (s, 1H), 7.62 (t, J=7.76 Hz, 1H), 7.17 (d, J=8.52 Hz, 1H), 7.06 (d, J=7.08 Hz, 1H), 6.22 (m, 1H), 5.03 (dd, J=12.84, 5.36 Hz, 1H), 4.46-4.44 (m, 1H), 4.30-4.28 (m, 1H), 4.25-4.23 (m, 2H), 3.61 (br, 1H), 3.12 (br, 1H), 2.90-2.54 (m, 3H), 2.44-2.39 (m, 2H), 2.26 (s, 3H), 2.11 (s, 3H), 2.02-1.61 (m, 8H), 1.36 (s, 3H), 1.28-1.26 (m, 2H); LC MS: ES+ 561.3.

Example 28. Synthesis of 2-(2,6-Dioxopiperidin-3-yl)-4-(((1-(1-(1-methylcyclobutane-1-carbonyl)-4-phenylpiperidin-4-yl)-1H-pyrazol-4-yl)methyl)amino)isoindoline-1,3-dione (Compound 172)

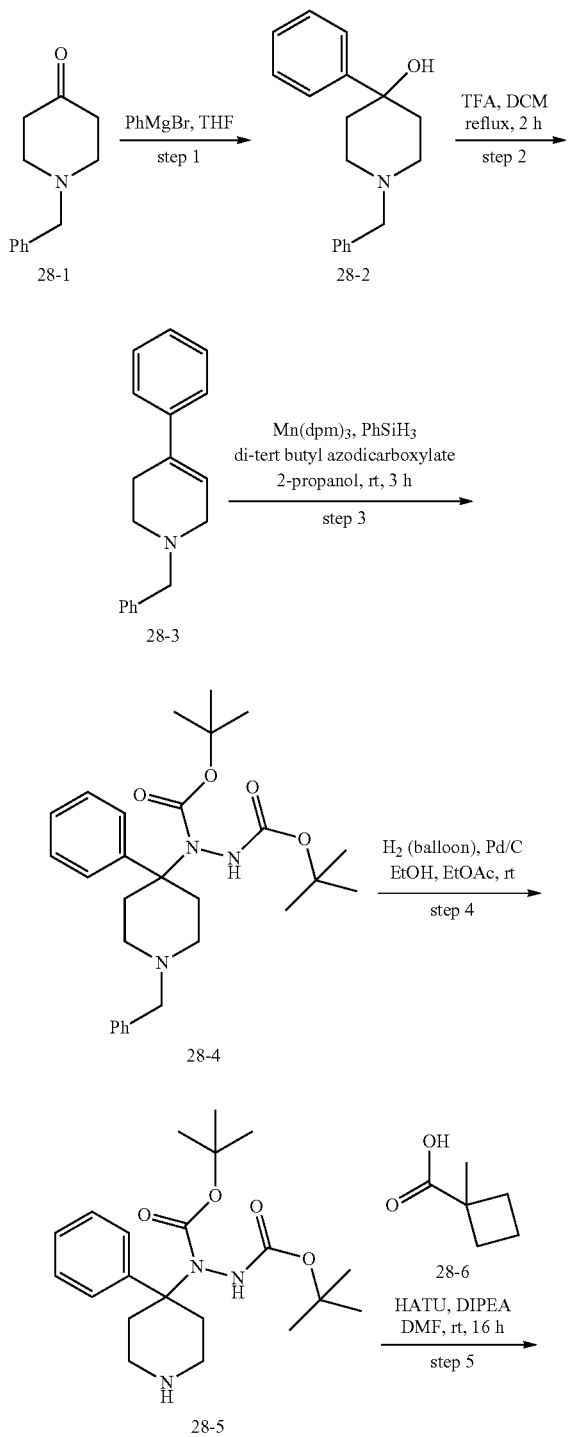

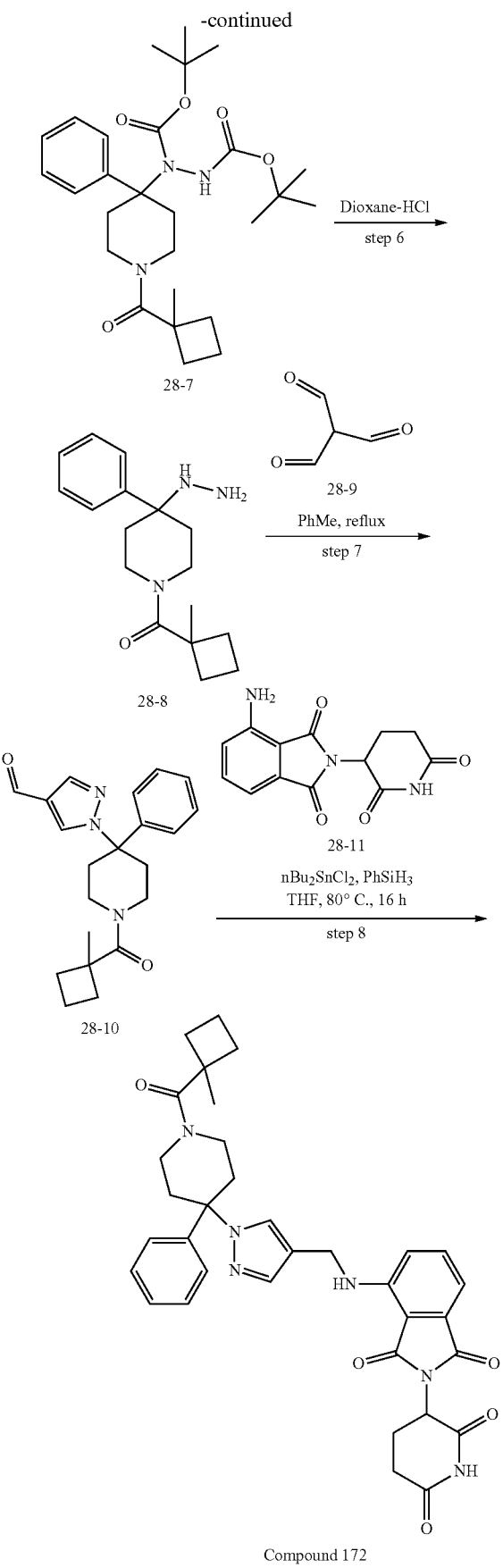

Step-1: Preparation of 1-Benzyl-4-phenylpiperidin-4-ol

To the stirred solution of 1-benzylpiperidin-4-one 28-1 (5 g, 26.42 mmol, 4.72 mL) in THF (10 mL), bromo(phenyl) magnesium (11.98 g, 66.05 mmol) was added at −78° C. and the reaction was stirred for 12 hours at room temperature under $N_2$ atmosphere. The reaction mixture was quenched with saturated sodium chloride solution and extracted with ethyl acetate (25 ml). The organic layers was separated, dried over sodium sulfate and concentrated under vacuum to afford 1-benzyl-4-phenyl-piperidin-4-ol 28-2 (6 g, 17.95 mmol, 67.95% yield, 80% purity) as light yellow solid. LC MS: ES+ 206.2.

Step-2: Preparation of 1-Benzyl-4-phenyl-1,2,3,6-tetrahydropyridine

A solution of 1-benzyl-4-phenyl-piperidin-4-ol 28-2 (1 g, 3.74 mmol) in TFA (10 mL) was heated at 50° C. for 3 hours. The reaction mixture was cooled at room temperature and poured into ice cooled water. The aqueous portion was neutralized with aqueous $NH_3$ solution (pH-10) and extracted with ethyl acetate. The organic portion was evaporated and the crude residue was purified by column chromatography to afford 1-benzyl-4-phenyl-3,6-dihydro-2H-pyridine 28-3 (800 mg, 2.57 mmol, 68.62% yield, 80% purity) as brown sticky solid was forwarded to the next step.

Step-3: Preparation of di-tert-Butyl 1-(1-benzyl-4-phenylpiperidin-4-yl)hydrazine-1,2-dicarboxylate To the stirred solution of 1-benzyl-4-phenyl-3,6-dihydro-2H-pyridine 28-3 (480.73 mg, 1.93 mmol) in 2-propanol (10 mL), phenylsilane (208.63 mg, 1.93 mmol) and [(Z)-1-tert-butyl-3-hydroxy-4,4-dimethyl-pent-2-enylidene]oxonium; manganese (1.18 g, 1.93 mmol) were added at 0° C. followed by tert-butyl (NE)-N-tert-butoxycarbonyliminocarbamate (665.90 mg, 2.89 mmol). After complete addition, the reaction mixture was stirred at room temperature for 6 hours. The reaction mass was evaporated to afford crude tert-butyl N-(1-benzyl-4-phenyl-4-piperidyl)-N-(tert-butoxycarbonylamino)carbamate 28-4 (500 mg, 1.04 mmol, 53.85% yield) as brown gum. LC MS: ES+ 482.7.

Step-4: Preparation of di-tert-Butyl 1-(4-phenylpiperidin-4-yl)hydrazine-1,2-dicarboxylate To a stirred solution of tert-butyl N-(1-benzyl-4-phenyl-4-piperidyl)-N-(tert-butoxycarbonylamino)carbamate 28-4 (500 mg, 1.04 mmol) in EtOH (4 mL) and ethyl acetate (4 mL) palladium (110.48 mg, 1.04 mmol) was added and the reaction was hydrogenated at room temperature under balloon pressure for 12 hours. The reaction mixture was filtered through celite bed and the filtrate was collected and concentrated under vacuum to afford crude tert-butyl N-(tert-butoxycarbonylamino)-N-(4-phenyl-4-piperidyl)carbamate 28-5 (350 mg, 625.79 umol, 60.28% yield, 70% purity) as yellow sticky solid.

Step-5: Preparation of di-tert-Butyl 1-(1-(1-methylcyclobutane-1-carbonyl)-4-phenylpiperidin-4-yl)hydrazine-1,2-dicarboxylate To the stirred solution of 1-methylcyclobutanecarboxylic acid 6 (85 mg, 744.69 umol) in DMF (4 mL), HATU (311.47 mg, 819.16 umol) was added followed by DIPEA (192.49 mg, 1.49 mmol, 259.42 uL) and tert-butyl N-(tert-butoxy-carbonylamino)-N-(4-phenyl-4-piperidyl)carbamate 28-5 (291.55 mg, 744.69 umol) under argon atmosphere. The reaction mixture was stirred for 6 hours at room temperature. Ice cooled water was added to reaction mixture and extracted with ethyl acetate. The organic portion was separated, dried over sodium sulfate and concentrated to afford crude tert-butyl N-(tert-butoxycarbonylamino)-N-[1-(1-methylcyclobutanecarbonyl)-4-phenyl-4-piperidyl]carbamate 28-7 (300 mg, 615.22 umol, 82.61% yield) as brown sticky solid. This crude was carried forward in next step. LC MS: ES+ 488.2.

Step-6: Preparation of (4-Hydrazinyl-4-phenylpiperidin-1-yl)(1-methylcyclobutyl)methanone To the tert-butyl N-(tert-butoxycarbonylamino)-N-[1-(1-methylcyclobutanecarbonyl)-4-phenyl-4-piperidyl]carbamate 28-7 (600 mg, 1.23 mmol) 4M dioxane-HCl (4 mL) was added and the reaction was stirred for 2 hours. Volatiles were removed under vacuum to afford crude material which was treated with amberlyst-21 resin to afford crude (4-hydrazino-4-phenyl-1-piperidyl)-(1-methylcyclobutyl)methanone 28-8 (350 mg, 864.57 umol, 70.27% yield, 80% purity) as brown sticky solid that was carried forward in next step.

Step-7: Preparation of 1-(1-(1-Methylcyclobutane-1-carbonyl)-4-phenylpiperidin-4-yl)-1H-pyrazole-4-carbaldehyde A solution of methanetricarbaldehyde 28-9 (100 mg, 999.27 umol) and (4-hydrazino-4-phenyl-1-piperidyl)-(1-methylcyclobutyl)methanone 28-8 (124.76 mg, 434.12 umol) in toluene (2.50 mL) was refluxed at 110° C. for 12 hours. Solvent was evaporated and the crude material was purified by Preparative TLC Plate to afford 1-[1-(1-methylcyclobutanecarbonyl)-4-phenyl-4-piperidyl]pyrazole-4-carbaldehyde 28-10 (25 mg, 69.71 umol, 16.06% yield, 98% purity) LC MS: ES+ 352.5.

Step-8: Preparation of 2-(2,6-Dioxopiperidin-3-yl)-4-(((1-(1-(1-methylcyclobutane-1-carbonyl)-4-phenylpiperidin-4-yl)-1H-pyrazol-4-yl)methyl)amino)isoindoline-1,3-dione Compound 172 was synthesized following general reductive amination the procedure of Example 19 to afford 2-(2,6-dioxo-3-piperidyl)-4-[[1-[1-(1-methylcyclobutanecarbonyl)-4-phenyl-4-piperidyl]pyrazol-4-yl]methylamino]isoindoline-1,3-dione (18 mg, 27.71 umol, 7.57% yield, 93.71% purity) as yellow solid. $^1$H NMR (d6-DMSO, 400 MHZ) δ 11.09 (s, 1H), 8.04 (s, 1H), 7.59 (s, 1H), 7.55 (t, J=7.84 Hz, 1H), 7.25-7.19 (m, 3H), 7.13 (d, J=8.52 Hz, 1H), 7.04 (d, J=6.92 Hz, 1H), 6.92-6.88 (m, 3H), 5.05 (dd, J=12.52, 4.92 Hz, 1H), 4.42 (d, J=5.44 Hz, 1H), 4.24-4.22 (m, 1H), 4.52-4.50 (m, 1H), 2.95-2.55 (m, 6H), 2.45-2.20 (m, 5H), 2.02-2.01 (m, 1H), 1.99-1.90 (m, 1H), 1.78-1.76 (m, 2H), 1.61-1.59 (m, 1H), 1.33 (s, 3H); LC MS: ES+ 609.4.

Example 29: Synthesis of 2-(2,6-Dioxopiperidin-3-yl)-4-(((1-(4-methyl-1-(1-methylcyclobutane-1-carbonyl)piperidin-4-yl)-1H-pyrazol-4-yl)methyl)amino)isoindoline-1,3-dione (Compound 173)

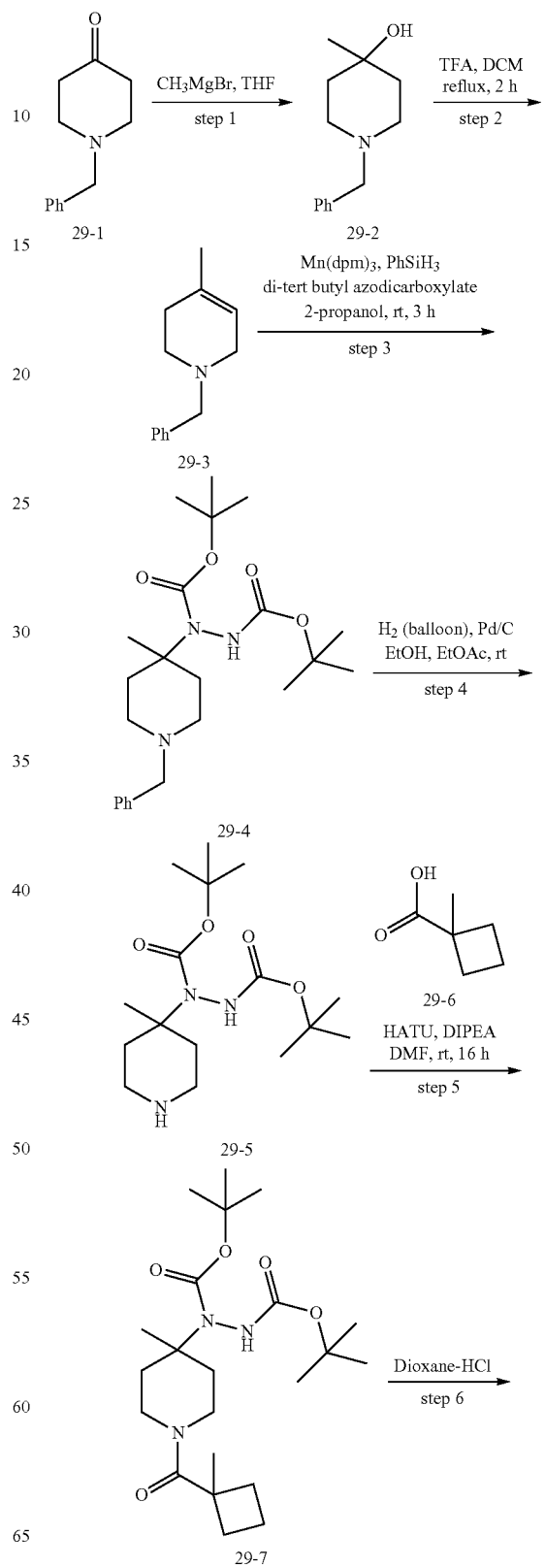

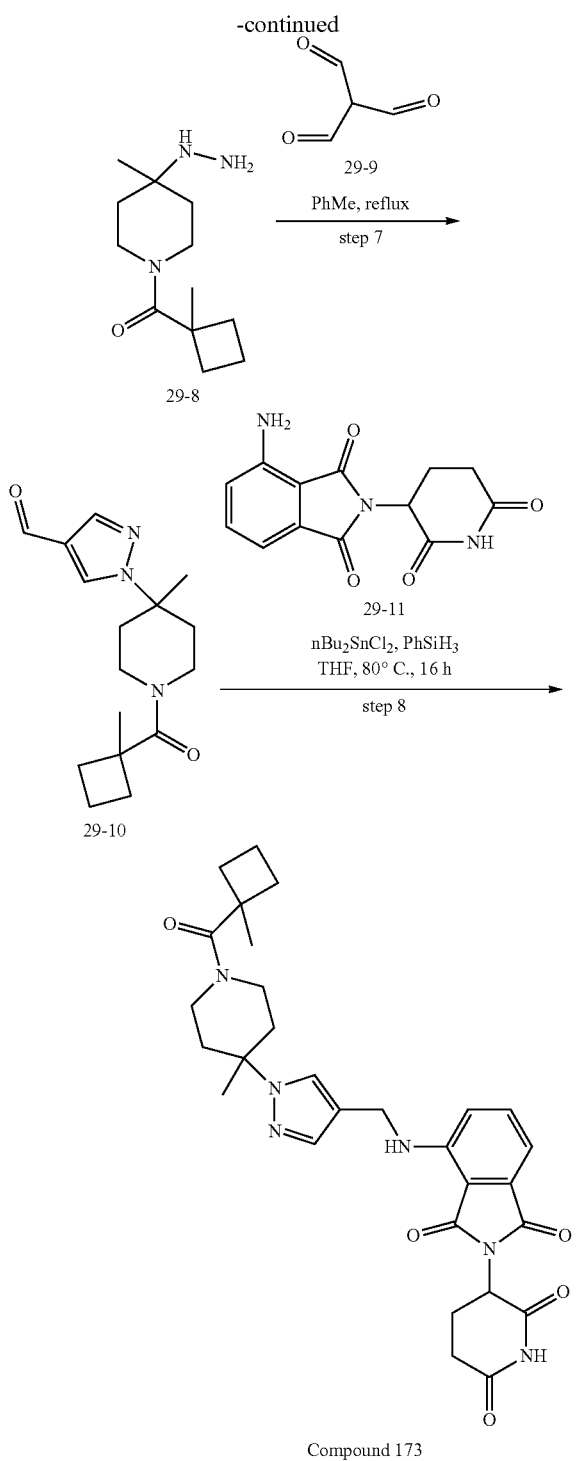

sodium sulfate and concentrated under vacuum to afford 1-benzyl-4-methyl-piperidin-4-ol 29-2 (850 mg, 4.14 mmol, 78.36% yield) as brown gum. LC MS: ES+ 269.4.

Step-2: Preparation of 1-Benzyl-4-methyl-1,2,3,6-tetrahydropyridine

A solution of 1-benzyl-4-methyl-piperidin-4-ol 29-2 (2 g, 9.74 mmol) in TFA (10 mL) was heated at 50° C. for 3 hours. The reaction mixture was cooled at room temperature and poured into ice cold water. The aqueous part was neutralized with aq NH₃ solution (pH-10) and extracted with ethyl acetate. The organic portion was evaporated and the crude residue was purified by column chromatography to afford 1-benzyl-4-methyl-1,2,3,6-tetrahydropyridine 29-3 (1.6 g, 5.13 mmol, 52.62% yield, 60% purity) as light yellow gum. LC MS: ES+ 188.3.

Step-3: Preparation of di-tert-Butyl 1-(1-benzyl-4-methylpiperidin-4-yl)hydrazine-1,2-dicarboxylate To the stirred solution of 1-benzyl-4-methyl-3,6-dihydro-2H-pyridine 29-3 (800 mg, 4.27 mmol) in 2-propanol (10 mL) phenylsilane (462.24 mg, 4.27 mmol) and [(Z)-1-tert-butyl-3-hydroxy-4,4-dimethyl-pent-2-enylidene]oxonium manganese (2.61 g, 4.27 mmol) were added at 0° C. followed by tert-butyl (NE)-N-tert-butoxycarbonyliminocarbamate (1.48 g, 6.41 mmol). The reaction mixture was stirred at same temperature for 6 hours. The reaction mass was evaporated and the crude residue was purified by column chromatography to afford tert-butyl N-(1-benzyl-4-methyl-4-piperidyl)-N-(tert-butoxycarbonylamino)carbamate 29-4 (600 mg, 1.37 mmol, 32.14% yield, 96% purity) as brown gum. LC MS: ES+ 420.0.

Step-4: Preparation of di-tert-Butyl 1-(4-methylpiperidin-4-yl)hydrazine-1,2-dicarboxylate To the stirred solution of tert-butyl N-(1-benzyl-4-methyl-4-piperidyl)-N-(tert-butoxycarbonylamino)carbamate 29-4 (400 mg, 953.39 umol) in EtOH (5 mL) and ethyl acetate (5 mL) palladium (101.46 mg, 953.39 umol) was added and the reaction was hydrogenated at room temperature under balloon pressure for 12 hours. The reaction mixture was filtered through celite bed and the filtrate was collected and concentrated under vacuum to afford crude di-tert-butyl 1-(4-methylpiperidin-4-yl)hydrazine-1,2-dicarboxylate 29-5 (290 mg, 528.18 umol, 55.40% yield, 60% purity) as brown gum that was directly used in the next step.

Step-5L Preparation of di-tert-Butyl 1-(4-methyl-1-(1-methylcyclobutane-1-carbonyl)piperidin-4-yl)hydrazine-1,2-dicarboxylate To the stirred solution of 1-methylcyclobutanecarboxylic acid 29-6 (200 mg, 1.75 mmol) in DMF (4 mL) HATU (732.86 mg, 1.93 mmol) was added followed by DIPEA (452.91 mg, 3.50 mmol, 610.39 uL) and tert-butyl N-(tert-butoxycarbonylamino)-N-(4-methyl-4-piperidyl) carbamate 29-5 (577.24 mg, 1.75 mmol) under inert atmosphere. The reaction mixture was stirred for 6 hours before ice cold water was added to reaction mixture and the organic layer was extracted with ethyl acetate. The organic portion was separated, dried over sodium sulfate and concentrated to afford crude tert-butyl N-(tert-butoxycarbonylamino)-N-[4-methyl-1-(1-methylcyclobutanecarbonyl)-4-piperidyl]carbamate 29-7 (250 mg, 587.46 umol, 33.53% yield) as sticky solid that was carried forward in next step.

Step-6: Preparation of (4-Hydrazinyl-4-methylpiperidin-1-yl)(1-methylcyclobutyl)methanone To a solution of tert-butyl N-(tert-butoxycarbonylamino)-N-[4-methyl-1-(1-methylcyclobutanecarbonyl)-4-piperidyl]carbamate 29-7 (250 mg, 587.46 umol) 4M Dioxane-HCl (4 mL) was added and the reaction was stirred for 8 hours at room temperature. Volatiles were removed under vacuum to afford crude material which was treated with amberlyst-21 resin to afford (4-hydrazino-4-methyl-1-piperidyl)-(1-methylcyclobutyl)methanone 29-8 (130 mg, 496.58 umol, 84.53% yield) as brown gum. LC MS: ES+ 226.3.

Step-7: Preparation of 1-(4-Methyl-1-(1-methylcyclobutane-1-carbonyl)piperidin-4-yl)-1H-pyrazole-4-carbaldehyde A mixture solution of methanetricarbaldehyde 29-9 (100 mg, 999.27 umol) and (4-hydrazino-4-methyl-1-piperidyl)-(1-methylcyclobutyl)methanone 29-8 (97.82 mg, 434.12 umol) in toluene (5 mL) was refluxed at 110° C. for 12 hours. Solvent was evaporated and crude material was purified by Preparative TLC plate to afford 1-[4-methyl-1-(1-methylcyclobutanecarbonyl)-4-piperidyl]pyrazole-4-carbaldehyde 29-10 (35 mg, 120.95 umol, 27.86% yield). LC MS: ES+ 290.2.

Step-8: Preparation of 2-(2,6-Dioxopiperidin-3-yl)-4-(((1-(4-methyl-1-(1-methylcyclobutane-1-carbonyl)piperidin-4-yl)-1H-pyrazol-4-yl)methyl)amino)isoindoline-1,3-dione Compound 173 was synthesized following general reductive amination procedure of Example 19 to afford 2-(2,6-dioxo-3-piperidyl)-4-[[1-[4-methyl-1-(1-methylcyclobutanecarbonyl)-4-piperidyl]pyrazol-4-yl]methylamino]isoindoline-1,3-dione (7.5 mg, 13.36 umol, 11.06% yield, 97.39% purity) as yellow solid. $^1$H NMR (d6-DMSO, 400 MHZ) δ 11.08 (s, 1H), 7.92 (s, 1H), 7.57 (t, J=7.58 Hz, 1H), 7.49 (s, 1H), 7.16 (d, J=8.84 Hz, 1H), 7.04 (d, J=6.92 Hz, 1H), 6.78 (m, 1H), 5.06-5.02 (m, 1H), 4.37 (d, J=5.76 Hz, 2H), 3.69-3.65 (m, 1H), 3.09-3.08 (m, 2H), 2.89-2.86 (m, 1H), 2.59-2.55 (m, 2H), 2.42-2.32 (m, 4H), 2.03-1.88 (m 2H), 1.77-1.75 (m, 4H), 1.61-1.60 (m, 2H), 1.38 (s, 3H), 1.32 (s, 3H); LC MS: ES+ 547.4.

Example 30. Synthesis of tert-Butyl 4-(4-(1-((2-(2,6-dioxopiperidin-3-yl)-1,3-dioxoisoindolin-4-yl)amino)ethyl)-1H-pyrazol-1-yl)piperidine-1-carboxylate (Compound 174)

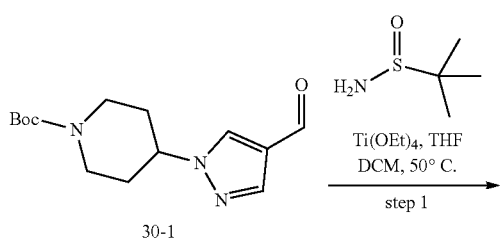

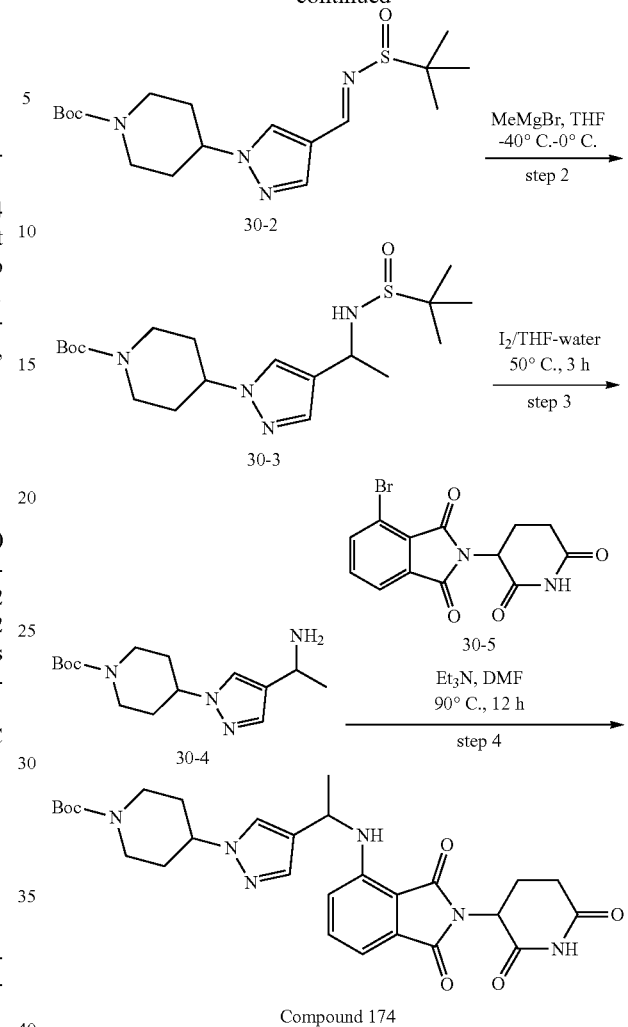

Compound 174

Step-1: Preparation of tert-Butyl (E)-4-(4-(((tert-butylsulfinyl)imino)methyl)-1H-pyrazol-1-yl)piperidine-1-carboxylate A mixture of tert-butyl 4-(4-formylpyrazol-1-yl)piperidine-1-carboxylate 30-1 (2 g, 7.16 mmol) 2-methylpropane-2-sulfinamide (954.56 mg, 7.88 mmol) and ethanolate titanium (4+) (1.80 g, 7.88 mmol, 1.65 mL) in THF (10 mL) was stirred at 50° C. for 12 hours. The reaction was quenched with water (5 mL) and the resulting suspension was filtered through a short pad of Silica gel (200-300 mesh). The solid cake was washed with ethyl acetate, and the separated organic layer was washed with brine. The organic layer was dried over anhydrous Na$_2$SO$_4$, filtered, and concentrated under reduced pressure. The residue was purified by flash column chromatography eluting with petroleum ether/EtOAc (5:1) to afford tert-butyl 4-[4-[(Z)-tert-butylsulfinyliminomethyl]pyrazol-1-yl]piperidine-1-carboxylate 30-2 (2.2 g, 5.23 mmol, 73.02% yield) LC MS: ES+ 383.2.

Step-2: Preparation of tert-Butyl 4-(4-(1-((tert-butylsulfinyl)amino)ethyl)-1H-pyrazol-1-yl)piperidine-1-carboxylate To the stirred solution of tert-butyl 4-[4-[(Z)-tert-butylsulfinyliminomethyl]pyrazol-1-yl]piperidine-1-carboxylate 30-2 (800 mg, 2.09 mmol) in THF (10 mL) methyl-magnesium bromide (364.59 mg, 3.14 mmol, 353.97 uL) was added and the reaction was stirred for 16 hours at room temperature. Ice cold water was added to the reaction mixture and extracted with ethyl acetate. The organic portion was separated, dried over sodium sulfate and concentrated under vacuum to afford crude tert-butyl 4-[4-[1-(tert-butylsulfinylamino)ethyl]pyrazol-1-yl]piperidine-1-carboxylate 30-3 (630 mg, 1.58 mmol, 75.58% yield) that was used in the next step.

Step-3: Preparation of tert-Butyl 4-(4-(1-aminoethyl)-1H-pyrazol-1-yl)piperidine-1-carboxylate To the stirred solution of tert-butyl 4-[4-[1-(tert-butylsulfinylamino)ethyl]pyrazol-1-yl]piperidine-1-carboxylate 30-3 (600 mg, 1.51 mmol) in THF (5 mL) and water (1 mL) molecular iodine (38.21 mg, 150.54 umol) was added portion-wise and the reaction mixture was heated at 50° C. for 3 hours. The reaction mixture was diluted with ethyl acetate (20 mL) and quenched with water. The organic portion was separated and concentrated under vacuum to afford tert-butyl 4-[4-(1-aminoethyl)pyrazol-1-yl]piperidine-1-carboxylate 30-4 (400 mg, 1.36 mmol, 90.26% yield) which was used in the next step without additional purification. LC MS: ES+ 295.4.

Step-4: Preparation of tert-Butyl 4-(4-(1-((2-(2,6-dioxopiperidin-3-yl)-1,3-dioxoisoindolin-4-yl)amino)ethyl)-1H-pyrazol-1-yl)piperidine-1-carboxylate To the solution of 4-bromo-2-(2,6-dioxo-3-piperidyl)isoindoline-1,3-dione 30-5 (350 mg, 1.04 mmol) and tert-butyl 4-[4-(1-aminoethyl)pyrazol-1-yl]piperidine-1-carboxylate 30-4 (305.64 mg, 1.04 mmol) in DMF (3 mL) N,N-diethylethanamine (105.05 mg, 1.04 mmol, 144.70 uL) was added and the reaction was heated to 90° C. and stirred for 12 hours. Ice cold water was added to reaction mixture and extracted with ethyl acetate (20 mL). The organic portion was separated and concentrated under vacuum. The crude residue was purified by column chromatography to afford tert-butyl 4-[4-[1-[[2-(2,6-dioxo-3-piperidyl)-1,3-dioxo-isoindolin-4-yl]amino]ethyl]pyrazol-1-yl]piperidine-1-carboxylate (Compound 174) (100 mg, 181.62 umol, 17.49% yield) as yellow solid. $^1$H NMR (d6-DMSO, 400 MHZ) δ 11.10 (s, 1H), 7.81 (s, 1H), 7.61-7.55 (m, 1H), 7.46 (s, 1H), 7.17-7.14 (m, 1H), 7.05 (d, J=7.0 Hz, 1H), 6.42-6.40 (m, 1H), 5.04 (dd, J=12.76, 5.96 Hz, 1H), 4.88-4.85 (m, 1H), 4.30-4.28 (m, 1H), 4.02-3.99 (m, 2H), 2.90-2.80 (m, 3H), 2.67-2.55 (m, 2H), 2.07-1.93 (m, 3H), 1.76-1.68 (m, 2H), 1.51 (d, J=6.4 Hz, 3H), 1.40 (s, 9H); LC MS: ES+ 551.3.

Example 31. Synthesis of tert-Butyl 4-(4-(1-((2-(2,6-dioxopiperidin-3-yl)-1,3-dioxoisoindolin-4-yl)amino)ethyl)-1H-pyrazol-1-yl)piperidine-1-carboxylate (Compound 175)

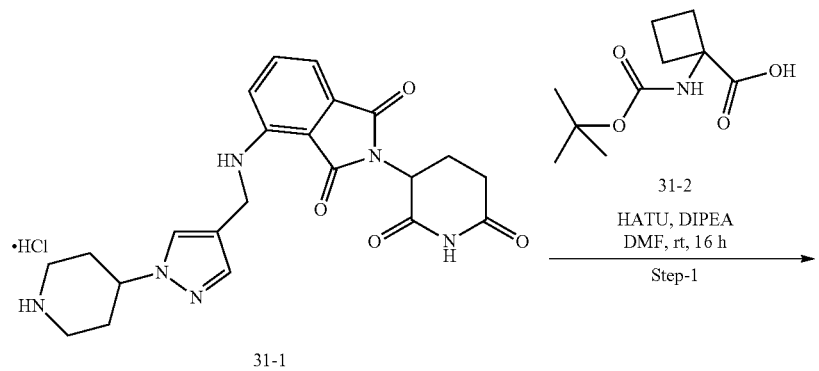

31-1

31-2
HATU, DIPEA
DMF, rt, 16 h
Step-1

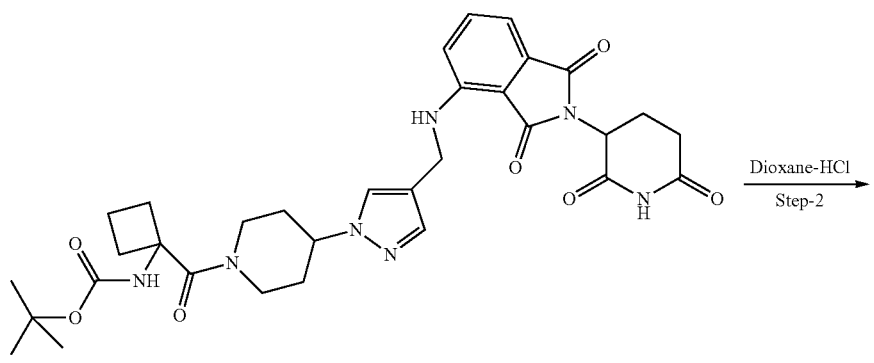

Dioxane-HCl
Step-2

31-3

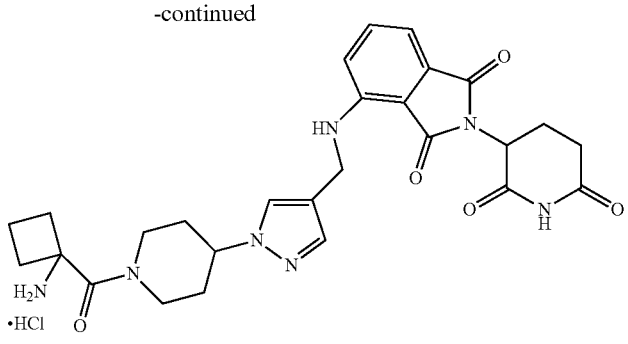

Compound 175

Step-1: Preparation of {1-[4-(4-{[2-(2,6-Dioxo-piperidin-3-yl)-1,3-dioxo-2,3-dihydro-1H-isoindol-4-ylamino]-methyl}-pyrazol-1-yl)-piperidine-1-carbonyl]-cyclobutyl}-carbamic acid tert-butyl ester To a stirred solution of 4-[[1-(1-chloropiperidin-1-ium-4-yl)pyrazol-4-yl]methylamino]-2-(2,6-dioxo-3-piperidyl)isoindoline-1,3-dione 31-1 (250 mg, 528.63 umol) in DMF (2 mL) was added 1-tert-butoxycarbonylamino-cyclobutanecarboxylic acid 31-2 (634.35 umol) followed by HATU (301.50 mg, 792.94 umol) and the reaction mixture was cooled to 0° C. DIPEA (341.60 mg, 2.64 mmol, 460.38 uL) was added and the reaction mixture was allowed to stirred at room temperature overnight. The reaction mixture was diluted with water and extracted with ethyl acetate. The organic layer was washed with saturated sodium bicarbonate solution, water and brine, dried over sodium sulphate and concentrated under reduced pressure to afford the crude product. The crude product thus obtained was purified by preparative TLC Plate (eluting with 3% of MeOH in DCM) to afford {1-[4-(4-{[2-(2,6-Dioxo-piperidin-3-yl)-1,3-dioxo-2,3-dihydro-1H-isoindol-4-ylamino]-methyl}-pyrazol-1-yl)-piperidine-1-carbonyl]-cyclobutyl}-carbamic acid tert-butyl ester 31-3 (170 mg, 268.27 umol, 50.75% yield) as yellow solid. LC MS: ES+ 634.4.

Step-2: Preparation of 4-({1-[1-(1-Amino-cyclobutanecarbonyl)-piperidin-4-yl]-1H-pyrazol-4-ylmethyl}-amino)-2-(2,6-dioxo-piperidin-3-yl)-isoindole-1,3-dione hydrochloride To the stirred solution of tert-butyl N-[1-[4-[4-[[[2-(2,6-dioxo-3-piperidyl)-1,3-dioxo-isoindolin-4-yl]amino]methyl]pyrazol-1-yl]piperidine-1-carbonyl]cyclobutyl]carbamate 31-3 (160 mg, 252.49 umol) in dioxane (2 mL) was added 4M dioxane-HCl (252.49 umol, 2 mL) at 0° C. The reaction mixture was stirred at room temperature for 2 hours and then concentrated under reduced pressure to afford 4-[[1-[1-(1-aminocyclobutanecarbonyl)-4-piperidyl]pyrazol-4-yl]methylamino]-2-(2,6-dioxo-3-piperidyl)isoindoline-1,3-dione hydrochloride (Compound 175) (115 mg, 215.53 umol, 85.36% yield) as yellow solid. $^1$H NMR (d6-DMSO, 400 MHZ) δ 11.09 (s, 1H), 8.89-8.83 (br s, 2H), 7.78 (s, 1H), 7.57 (t, J=7.76 Hz, 1H), 7.47 (s, 1H), 7.15 (d, J=8.64 Hz, 1H), 7.04 (d, J=7.08 Hz, 1H), 6.82 (br, 1H), 5.04 (dd, J=12.68, 5.24 Hz, 1H), 4.38-4.37 (m, 2H), 4.12-3.92 (m, 2H), 3.03-3.02 (m, 2H), 2.92-2.84 (m, 1H), 2.74-2.67 (m, 2H), 2.60-2.55 (m, 2H), 2.33-2.32 (m, 2H), 2.20-2.15 (m, 1H), 2.03-2.01 (m, 3H), 1.88-1.79 (m, 3H); LC MS. ES+ 534.3.

Example 32. Synthesis of tert-Butyl 4-(4-(((2-(2,6-dioxopiperidin-3-yl)-1,3-dioxoisoindolin-4-yl)amino)methyl)-1H-pyrazol-1-yl)-3,3-difluoropiperidine-1-carboxylate (Compound 176)

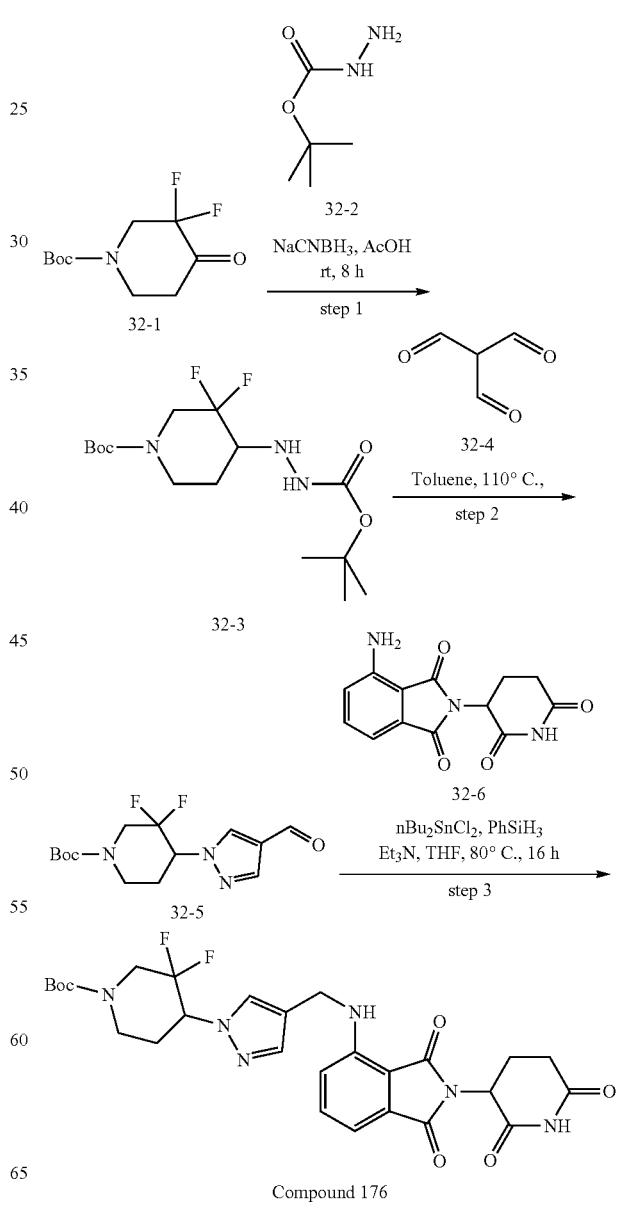

Compound 176

Step-1: Preparation of tert-Butyl (S)-3,3-difluoro-4-(4-formyl-1H-pyrazol-1-yl)piperidine-1-carboxylate The solution of tert-butyl 3,3-difluoro-4-oxo-piperidine-1-carboxylate 32-1 (200 mg, 850.24 umol) and tert-butyl N-aminocarbamate 32-2 (449.48 mg, 3.40 mmol, 165.29 uL) in acetic acid (3 mL) was stirred at room temperature for 10 minutes followed by the addition of sodium cyanoboranuide (349.64 mg, 850.24 umol). The reaction was stirred for 8 hours and then was diluted with DCM (20 mL) and quenched with saturated sodium bicarbonate solution. The organic portion was separated and washed with water and brine. After separation, the organic phase was dried over sodium sulfate and concentrated to obtain crude tert-butyl 4-(2-tert-butoxycarbonylhydrazino)-3,3-difluoro-piperidine-1-carboxylate 32-3 (250 mg, 711.46 umol, 83.68% yield) used as crude for the next step.

Step-2: Preparation of tert-Butyl(S)-3,3-difluoro-4-(4-formyl-1H-pyrazol-1-yl)piperidine-1-carboxylate A solution of tert-butyl 4-(2-tert-butoxycarbonylhydrazino)-3,3-difluoro-piperidine-1-carboxylate 32-3 (120 mg, 341.50 umol) and methanetricarbaldehyde (34.18 mg, 341.50 umol) in toluene was refluxed at 110° C. for 12 hours. Solvent was evaporated to afford tert-butyl (S)-3,3-difluoro-4-(4-formyl-1H-pyrazol-1-yl)piperidine-1-carboxylate (60.00 mg, 190.29 umol) as crude that was directly used in the next step without any purification.

Step-3: Preparation of tert-Butyl 4-(4-(((2-(2,6-dioxopiperidin-3-yl)-1,3-dioxoisoindolin-4-yl)amino)methyl)-1H-pyrazol-1-yl)-3,3-difluoropiperidine-1-carboxylate Compound 176 was synthesized following general reductive amination procedure of Example 19 to afford tert-butyl 4-[4-[[[2-(2,6-dioxo-3-piperidyl)-1,3-dioxo-isoindolin-4-yl]amino]methyl]pyrazol-1-yl]-3,3-difluoro-piperidine-1-carboxylate (18.0 mg, 31.44 umol, 16.52% yield) as yellow solid. 1H NMR (d6-DMSO, 400 MHZ) δ 11.09 (s, 1H), 7.82 (s, 1H), 7.58-7.53 (m, 2H), 7.16 (d, J=8.44 Hz, 1H), 7.03 (d, J=7.08 Hz, 1H), 6.88-6.86 (m, 1H), 5.04-5.02 (m, 2H), 4.40-4.38 (m, 2H), 4.22-4.00 (m, 2H), 3.04-3.00 (m, 2H), 2.92-2.82 (m, 1H), 2.62-2.55 (m, 2H), 2.32-2.12 (m, 1H), 2.03-2.01 (m, 2H), 1.41 (s, 9H); LC MS. ES– 571.4.

Example 33. Synthesis of 4-(((1-(4-(Cyclohexylmethyl)cyclohexyl)-1H-pyrazol-4-yl)methyl)amino)-2-(2,6-dioxopiperidin-3-yl)isoindoline-1,3-dione (Compound 177)

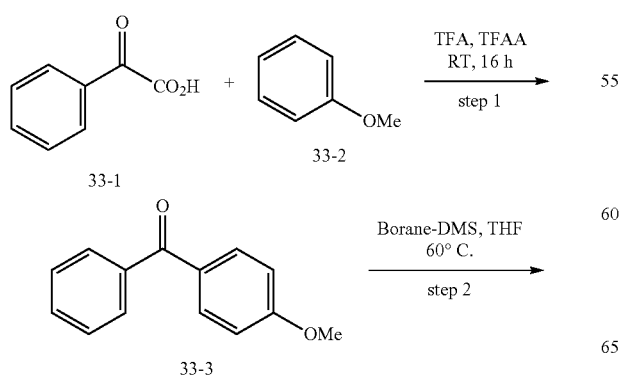

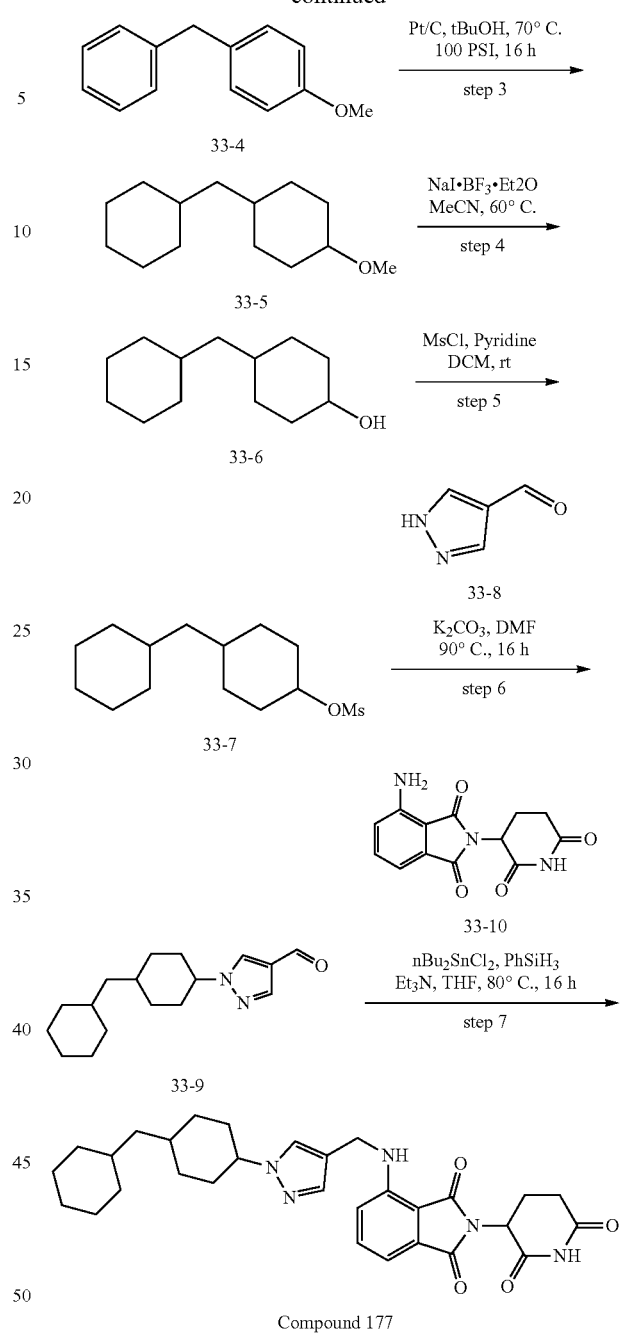

Step-1: Preparation of (4-Methoxyphenyl)(phenyl)methanone

A mixture of benzoic acid 1 (1 g, 8.19 mmol, 757.58 uL) and anisole 2 (885.50 mg, 8.19 mmol, 890.84 uL) in 2,2,2-trifluoroacetic acid (14.80 g, 129.80 mmol, 10 mL) was stirred in the presence of (2,2,2-trifluoroacetyl) 2,2,2-trifluoroacetate (171.99 mg, 818.86 umol, 115.43 uL) for 12 hours. Volatiles were removed under reduced pressure to afford (4-methoxyphenyl)-phenyl-methanone 33-3 (1.3 g, 6.13 mmol, 74.80% yield). LC MS: ES+ 213.2.

Step-2: Preparation of 1-Benzyl-4-methoxybenzene

To the solution of (4-methoxyphenyl)-phenyl-methanone 33-3 (1 g, 4.71 mmol) in THF (12 mL) borane; methylsulfanylmethane (357.93 mg, 4.71 mmol, 446.86 uL) was added at 0° C. and the reaction was heated to 60° C. and stirred for 12 hours. The reaction mixture was cooled to room temperature, quenched with methanol, and was again heated at 60° C. for 30 minutes. The reaction mass was then concentrated under vacuum and re-dissolved in diethyl ether (20 mL). The organic portion was washed with water/brine, separated, and concentrated to afford 1-benzyl-4-methoxybenzene 33-4 (900 mg, 4.54 mmol, 96.35% yield). 1H NMR (d6-DMSO, 400 MHZ) δ 7.30-7.25 (m, 2H), 7.20-7.15 (m, 3H), 7.12-7.09 (m, 2H), 6.84-6.81 (m, 2H), 3.92 (s, 2H), 3.77 (s, 3H).

Step-3: Preparation of 1-(Cyclohexylmethyl)-4-methoxycyclohexane

A stirred solution of 1-benzyl-4-methoxy-benzene 33-4 (850 mg, 4.29 mmol) in EtOH (20 mL) was hydrogenated in the presence of platinum on carbon 5% (500 mg) in an autoclave at 80° C. under 50 atm pressure for 12 hours. After completion, the reaction mixture was filtered through celite bed and the filtrate was collected and concentrated under vacuum to afford 1-(cyclohexylmethyl)-4-methoxy-cyclohexane 33-5 (700 mg, 3.33 mmol, 77.62% yield).

Step-4: Preparation of 4-(Cyclohexylmethyl)cyclohexan-1-ol

To a stirred solution of 1-(cyclohexylmethyl)-4-methoxy-cyclohexane 33-5 (200 mg, 950.77 umol) in acetonitrile (2 mL), iodosodium (285.03 mg, 1.90 mmol, 77.66 uL) and diethyloxonio(trifluoro)boranuide (269.88 mg, 1.90 mmol) were added at room temperature. After complete addition, the reaction mixture was heated at 70° C. for 5 hours and then diluted with diethyl ether (15 mL) and washed with saturated sodium bicarbonate solution. The ether layer was separated and washed with sodium thiosulfate solution. After separation, the organic portion was concentrated under vacuum to afford 4-(cyclohexylmethyl)cyclohexan-1-ol 33-6 (200 mg, 1.02 mmol) that was carried forward in next step.

Step-5: Preparation of 4-(Cyclohexylmethyl)cyclohexyl methanesulfonate

To the stirred solution of 4-(cyclohexylmethyl)cyclohexanol 33-6 (200 mg, 1.02 mmol) in DCM (5 mL) 4-methylbenzenesulfonyl chloride (291.32 mg, 1.53 mmol) was added followed by triethyl amine (206.17 mg, 2.04 mmol, 283.97 uL). The reaction was stirred for 6 hours at room temperature and then quenched with saturated sodium bicarbonate solution. The organic portion was separated, dried over sodium sulfate and concentrated under vacuum to afford crude [4-(cyclohexylmethyl)cyclohexyl] 4-methylbenzenesulfonate 33-7 (250 mg, 713.24 umol, 70.01% yield) which was directly used in next step.

Step-6: Preparation of 1-(4-(Cyclohexylmethyl)cyclohexyl)-1H-pyrazole-4-carbaldehyde To the stirred solution of 1H-pyrazole-4-carbaldehyde 33-8 (50 mg, 520.36 umol) in DMF (2 mL), potassium carbonate, anhydrous, 99% (143.83 mg, 1.04 mmol, 62.81 uL) was added and the reaction was heated at 60° C. for 10 minutes followed by the addition of [4-(cyclohexylmethyl)cyclohexyl] 4-methylbenzenesulfonate 33-7 (182.39 mg, 520.36 umol). The reaction mixture was stirred for 12 hours at the same temperature and then cooled to room temperature before ice cold water was added. The aqueous portion was extracted with ethyl acetate, separated and concentrated to afford crude 1-[4-(cyclohexylmethyl)cyclohexyl]pyrazole-4-carbaldehyde 33-9 (80 mg, 291.55 umol, 56.03% yield) that was directly used in the next step.

Step-7: Preparation of 4-(((1-(4-(Cyclohexylmethyl)cyclohexyl)-1H-pyrazol-4-yl)methyl)amino)-2-(2,6-dioxopiperidin-3-yl)isoindoline-1,3-dione Compound 177 was synthesized following the general reductive amination procedure of Example 19 to afford 4-[[1-[4-(cyclohexylmethyl)cyclohexyl]pyrazol-4-yl]methylamino]-2-(2,6-dioxo-3-piperidyl)isoindoline-1,3-dione (15 mg, 28.21 umol, 9.68% yield) as yellow solid. 1H NMR (d6-DMSO, 400 MHZ) δ 11.08 (s, 1H), 7.72 (s, 1H), 7.57 (t, J=7.8 Hz, 1H), 7.41 (s, 1H), 7.15 (d, J=8.6 Hz, 1H), 7.03 (d, J=7.04 Hz, 1H), 6.79-6.77 (m, 1H), 5.06-5.03 (m, 1H), 4.36-4.34 (m, 2H), 4.04-4.02 (m, 1H), 2.95-2.85 (m, 1H), 2.60-2.55 (m, 2H), 2.02-1.95 (m, 4H), 1.82-1.45 (m, 8H), 1.40-0.75 (m, 10H); LC MS. ES+ 532.3.

Example 34: Synthesis of N-(tert-Butyl)-4-(4-(((2-(2,6-dioxopiperidin-3-yl)-1,3-dioxoisoindolin-4-yl)amino)methyl)-1H-pyrazol-1-yl)-N-methylpiperidine-1-carboxamide (Compound 178)

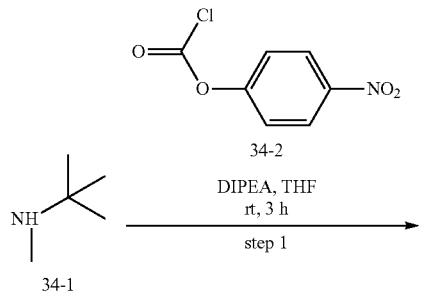

489                                                                                                              490

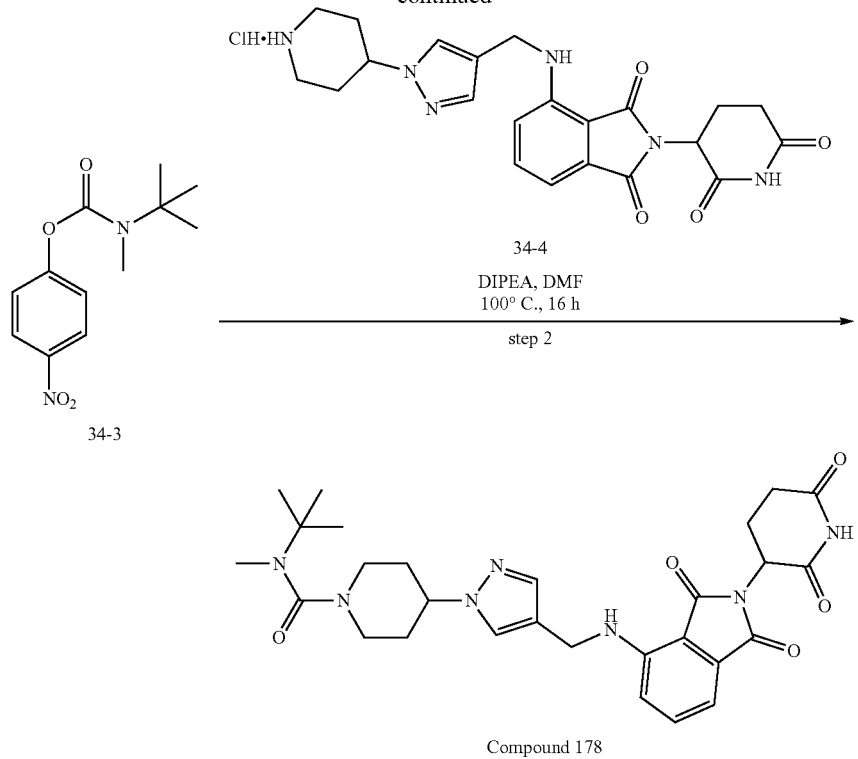

Compound 178

Step-1: Preparation of 4-Nitrophenyl tert-butyl(methyl)carbamate

To the stirred solution of N,2-dimethylpropan-2-amine 34-1 (200.0 mg, 2.29 mmol, 275.10 uL) and (4-nitrophenyl) carbonochloridate 34-2 (508.75 mg, 2.52 mmol) in THF (4 mL) was added N,N-Diisopropylethylamine (444.83 mg, 3.44 mmol, 599.50 uL) under cold conditions and the reaction was continued to stir at room temperature for 2 hours. The reaction mixture was diluted with ethyl acetate and washed with water and brine solution. The organic fraction was separated, dried over anhydrous sodium sulphate and evaporated under reduced pressure to obtain the crude which was purified by flash chromatography using (0-30% ethyl acetate-hexane) to afford (4-nitrophenyl) N-tert-butyl-N-methyl-carbamate 34-3 (460.0 mg, 1.82 mmol, 79.47% yield) as an off-white solid. LC MS: ES+ 253.3.

Step-2: Preparation of N-(tert-Butyl)-4-(4-(((2-(2,6-dioxopiperidin-3-yl)-1,3-dioxoisoindolin-4-yl)amino)methyl)-1H-pyrazol-1-yl)-N-methylpiperidine-1-carboxamide To the stirred solution of 4-[[1-(1-chloro-4-piperidyl)pyrazol-4-yl]methylamino]-2-(2,6-dioxo-3-piperidyl)isoindoline-1,3-dione 34-3 (149.98 mg, 317.13 umol) and (4-nitrophenyl) N-tert-butyl-N-methyl-carbamate (80.0 mg, 317.13 umol) in DMF (1.5 mL) was added N,N-diisopropylamine (96.27 mg, 951.38 umol, 134.08 uL) and the reaction mixture was heated at 100° C. for 16 hours. The reaction mixture was diluted with ethyl acetate, washed with sodium bicarbonate solution and water and the organic fraction was separated. The organics were dried over anhydrous sodium sulphate and evaporated under reduced pressure to obtain the crude which was purified by preparative TLC plate method to afford N-tert-butyl-4-[4-[[[2-(2,6-dioxo-3-piperidyl)-1,3-dioxo-isoindolin-4-yl]amino]methyl]pyrazol-1-yl]-N-methyl-piperidine-1-carboxamide (Compound 178) (20.0 mg, 34.93 umol, 11.02% yield, 96% purity, 000) as yellow solid. 1H NMR (d6-DMSO, 400 MHZ) δ; 11.09 (s, 1H), 7.78 (s, 1H), 7.57 (t, J=7.72 Hz, 1H), 7.45 (s, 1H), 7.16 (d, J=8.52 Hz, 1H), 7.03 (d, J=7.08 Hz, 1H), 6.82-6.81 (m 1H), 5.04 (dd, J=12.2, 5.24 Hz, 1H), 4.36 (d, J=5.44 Hz, 2H), 4.28-4.25 (m, 1H), 3.73-3.69 (m, 2H), 2.91-2.78 (m, 3H), 2.70 (s, 3H), 2.67-2.55 (m, 2H), 2.01-2.00 (m, 1H), 1.94-1.92 (m, 2H), 1.81-1.73 (m, 2H), 1.24 (s, 9H); LC MS: ES+ 550.4.

Example 35: Synthesis of 4-(((3-Amino-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione (Compound 179)

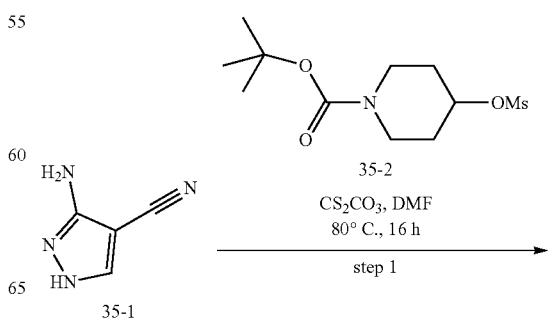

491

-continued

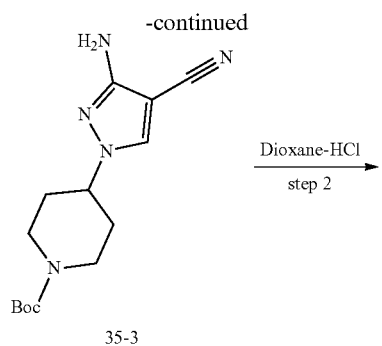

35-3

Dioxane-HCl
step 2

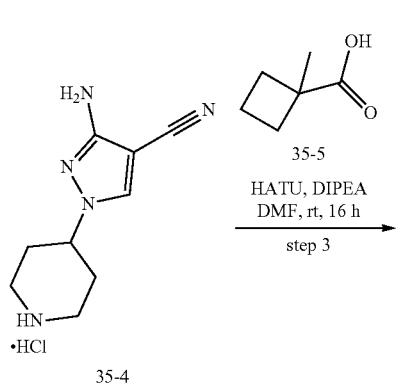

35-4

HATU, DIPEA
DMF, rt, 16 h
step 3

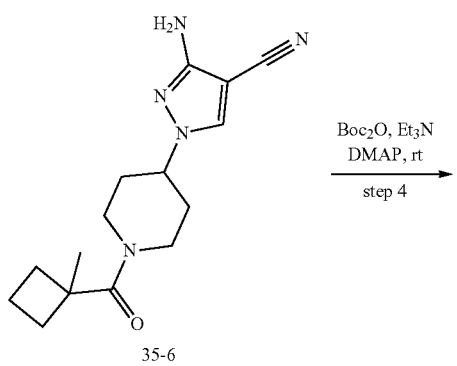

35-6

Boc₂O, Et₃N
DMAP, rt
step 4

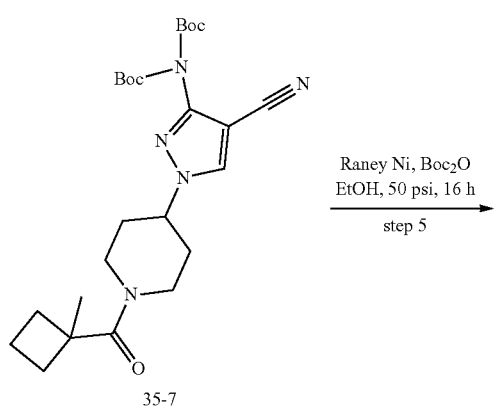

35-7

Raney Ni, Boc₂O
EtOH, 50 psi, 16 h
step 5

492

-continued

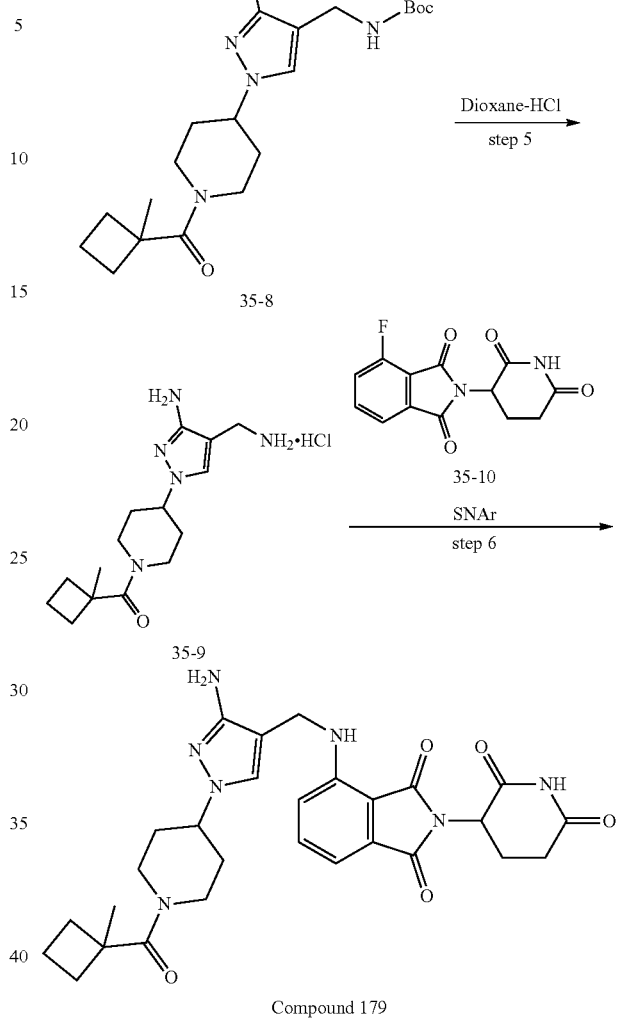

Compound 179

Step-1: Preparation of tert-Butyl 4-(3-amino-4-cyano-1H-pyrazol-1-yl)piperidine-1-carboxylate To a stirred solution of 3-amino-1H-pyrazole-4-carbonitrile 35-1 (3 g, 27.75 mmol) and tert-butyl 4-methylsulfonyloxypiperidine-1-carboxylate 35-2 (9.30 g, 33.30 mmol) in DMF (25 mL) was added cesium carbonate (27.13 g, 83.26 mmol). The reaction was heated at 80° C. for 16 hours and then diluted with ethyl acetate and washed with water and brine. The organic layer was dried over sodium sulphate and evaporated under reduced pressure to obtain the crude product which was purified by flash chromatography over silica gel eluting with (3% EtOAc/DCM) to afford tert-butyl 4-(3-amino-4-cyano-pyrazol-1-yl)piperidine-1-carboxylate 35-3 (1.7 g, 5.83 mmol, 21.03% yield) as white solid. LC MS: ES+ 292.2.

Step-2: Preparation of 3-Amino-1-(piperidin-4-yl)-1H-pyrazole-4-carbonitrile hydrochloride To a stirred suspension of tert-butyl 4-(3-amino-4-cyano-pyrazol-1-yl)piperidine-1-carboxylate 35-3 (1 g, 3.43 mmol)

in dioxane (2.0 mL), 4M dioaxne-HCl (3 mL) was added at 0° C. and the reaction mixture was stirred for 3 hours at room temperature. Volatiles are removed under vacuum, and washed with diethyl ether to afford 3-amino-1-(piperidin-4-yl)-1H-pyrazole-4-carbonitrile hydrochloride 35-4 (500 mg, 1.87 mmol, 54.38% yield, 85% purity). 1H NMR (d6-DMSO, 400 MHZ) δ 9.15-9.14 (m, 1H), 8.97-8.96 (m, 1H), 8.16 (s, 1H), 4.27-4.22 (m, 1H), 3.35-3.31 (m, 2H), 3.01-2.97 (m, 2H), 2.09-2.00 (m, 4H);

Step-3: Preparation of 3-Amino-1-(1-(1-methylcyclobutane-1-carbonyl)piperidin-4-yl)-1H-pyrazole-4-carbonitrile To the stirred solution of 1-methylcyclobutanecarboxylic acid 35-5 (481.25 mg, 4.22 mmol) and 3-amino-1-(4-piperidyl)pyrazole-4-carbonitrile hydrochloride 35-4 (800.0 mg, 3.51 mmol) in DMF (3 mL) was added DIPEA (2.27 g, 17.57 mmol, 3.06 mL) at 0° C. The reaction mixture was stirred at 0° C. for 10 minutes and HATU (2.00 g, 5.27 mmol) was added. The reaction was stirred at room temperature for 16 hours and then diluted with ethyl acetate and washed with saturated sodium bicarbonate solution, water and brine. The organic layer was dried over sodium sulfate, concentrated under reduced pressure, and purified by combiflash eluting at (0%-2% methanol in dichloromethane) to afford 3-amino-1-(1-(1-methylcyclobutane-1-carbonyl)piperidin-4-yl)-1H-pyrazole-4-carbonitrile 35-6 (600 mg, 1.98 mmol, 56.46% yield, 95% purity, 000) as sticky liquid. LC MS: ES+ 288.2.

Step-4: Preparation of tert-Butyl N-tert-butoxycarbonyl-N-[4-cyano-1-[1-(1-methylcyclobutanecarbonyl)-4-piperidyl]pyrazol-3-yl]carbamate To the stirred solution of 3-amino-1-[1-(1-methylcyclobutanecarbonyl)-4-piperidyl]pyrazole-4-carbonitrile 35-6 (400.0 mg, 1.39 mmol) in THF (5 mL) was added triethylamine (281.71 mg, 2.78 mmol, 388.03 uL) under cold conditions followed by the addition of boc-anhydride (911.40 mg, 4.18 mmol, 958.36 uL) and DMAP (34.01 mg, 278.40 umol). The reaction was stirred at room temperature for 16 hours and then diluted with ethyl acetate and washed with water and brine solution. The organic fraction was separated, dried over anhydrous sodium sulphate and evaporated under reduced pressure to obtain the crude compound which was purified by flash chromatography using (0%-30% ethyl acetate—DCM) to afford tert-butyl N-tert-butoxycarbonyl-N-[4-cyano-1-[1-(1-methylcyclobutanecarbonyl)-4-piperidyl]pyrazol-3-yl]carbamate 35-7 (210.0 mg, 430.69 umol, 30.94% yield) as colorless gum. LC MS: ES+ 488.4.

Step-5: Preparation of tert-Butyl (tert-butoxycarbonyl)(4-(((tert-butoxycarbonyl)amino)methyl)-1-(1-(1-methylcyclobutane-1-carbonyl)piperidin-4-yl)-1H-pyrazol-3-yl)carbamate The stirred solution of tert-butyl N-tert-butoxycarbonyl-N-[4-cyano-1-[1-(1-methylcyclobutanecarbonyl)-4-piperidyl]pyrazol-3-yl]carbamate 35-7 (210.0 mg, 430.69 umol) and di-tert-butyl dicarbonate (188.00 mg, 861.38 umol, 197.68 uL) in ethanol (5.0 mL) was degassed for 15 minutes under argon atmosphere followed by the addition of Raney Ni (36.90 mg, 430.69 umol). The reaction was stirred for 16 hours at 50 psi in parr shaker and was then filtered over a celite bed. The filtrate was evaporated under reduced pressure to obtain the crude which was purified by column chromatography using (0-2% MeOH-DCM) to afford tert-butyl (tert-butoxycarbonyl)(4-(((tert-butoxycarbonyl)amino)methyl)-1-(1-(1-methylcyclobutane-1-carbonyl)piperidin-4-yl)-1H-pyrazol-3-yl)carbamate 35-8 (150.0 mg, 253.49 umol, 58.86% yield) as colorless gum. LC MS: ES+ 592.6.

Step-6: Preparation of (4-(3-Amino-4-(aminomethyl)-1H-pyrazol-1-yl)piperidin-1-yl)(1-methylcyclobutyl)methanone hydrochloride To the stirred solution of tert-butyl N-tert-butoxycarbonyl-N-[4-[(tert-butoxycarbonylamino)methyl]-1-[1-(1-methylcyclobutanecarbonyl)-4-piperidyl]pyrazol-3-yl]carbamate 35-8 (150.0 mg, 253.49 umol) in dioxane (1 mL) was added hydrochloric acid in dioxane (253.49 umol, 4 mL) and the reaction was stirred at room temperature for 2 hours. The solvent was evaporated under reduced pressure and the solid obtained was washed with ether and pentane to afford (4-(3-amino-4-(aminomethyl)-1H-pyrazol-1-yl)piperidin-1-yl)(1-methylcyclobutyl)methanone hydrochloride 35-9 (120.0 mg, 329.39 umol, 129.94% yield) as yellow solid. LC MS: ES+ 292.2.

Step-7: Preparation of 4-(((3-Amino-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione To the stirred solution of [4-[3-(chloroamino)-4-[(chloroamino)methyl]pyrazol-1-yl]-1-piperidyl]-(1-methylcyclobutyl)methanone 35-9 (130.0 mg, 356.84 umol), 2-(2,6-dioxo-3-piperidyl)-4-fluoro-isoindoline-1,3-dione 10 (98.57 mg, 356.84 umol) in NMP (1.5 mL) was added N,N-diisopropylethylamine (138.36 mg, 1.07 mmol, 186.46 uL) and the reaction mixture was heated at 80° C. for 16 hours. The reaction mixture was diluted with ethyl acetate, washed with sodium bicarbonate solution, water and brine and the organic fraction was separated. The organic layer was then dried over anhydrous sodium sulphate and evaporated under reduced pressure to obtain the crude compound which was purified by preparative TLC plate method developing the plate in 2% MeOH-ethyl acetate to afford 4-[[3-amino-1-[1-(1-methylcyclobutanecarbonyl)-4-piperidyl]pyrazol-4-yl]methylamino]-2-(2,6-dioxo-3-piperidyl)isoindoline-1,3-dione (Compound 179) (12.0 mg, 20.82 umol, 5.83% yield, 95% purity, 000) as yellow solid. ¹H NMR (d6-DMSO, 400 MHZ) δ 11.08 (s, 1H), 7.56 (t, J=7.78 Hz, 1H), 7.47 (s, 1H), 7.16 (d, J=8.4 Hz, 1H), 7.01 (d, J=7.04 Hz, 1H), 6.79-6.77 (m, 1H), 5.03 (dd, J=12.96, 5.92 Hz, 1H), 4.73 (s, 2H), 4.37-4.35 (m, 1H), 4.18 (d, J=5.24 Hz, 2H), 4.04-4.01 (m, 1H), 3.57-3.56 (m, 1H), 3.05-3.03 (m, 1H), 2.87-2.84 (m, 1H), 2.66-2.56 (m, 2H), 2.42-2.32 (m, 3H), 2.02-1.98 (m, 1H), 1.89-1.87 (m, 3H), 1.80-1.78 (m, 2H), 1.61-1.58 (m, 3H), 1.33 (s, 3H); LC MS. ES+ 549.5.

Example 36. Synthesis of 4-{[1-(3-Cyclopropyl-5-isopropoxy-phenyl)-1H-pyrazol-4-ylmethyl]-amino}-2-(2,6-dioxo-piperidin-3-yl)-isoindole-1,3-dione (Compound 180)

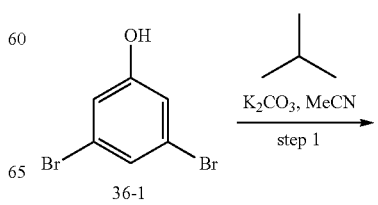

36-1

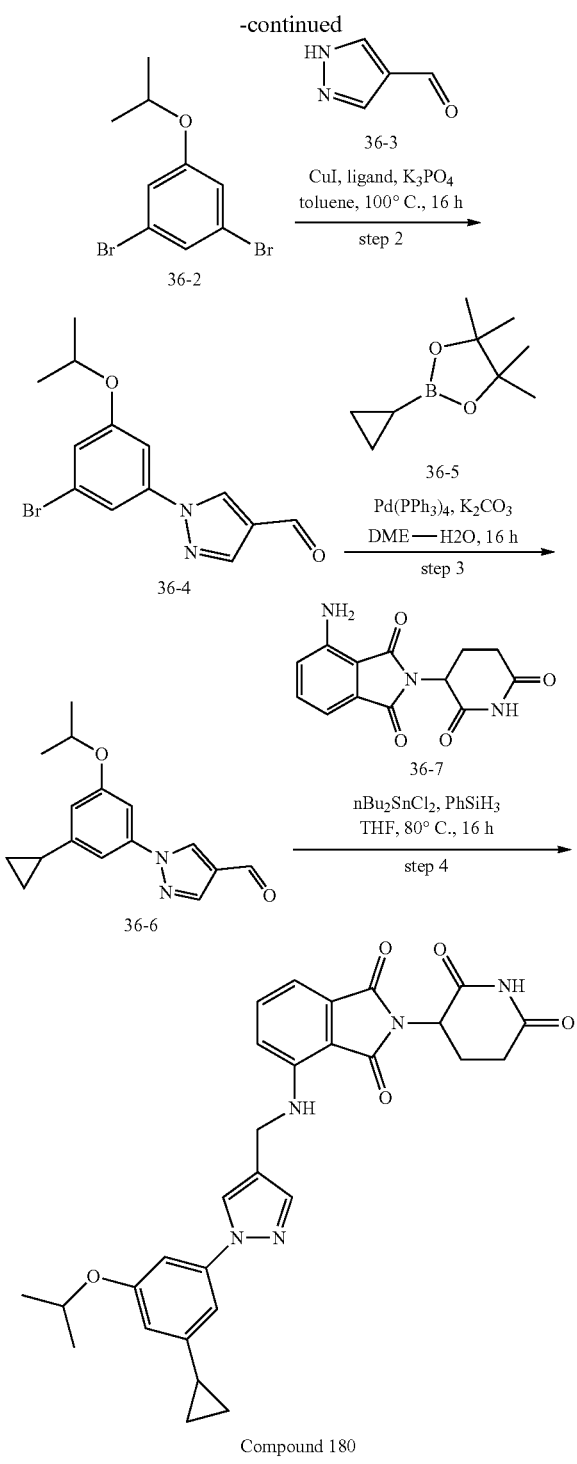

Compound 180

(1:9)) confirmed that the starting material was consumed after 5 hours and which point the reaction was quenched with an ice-water slurry and the organics were extracted by ethyl acetate (50 mL×3). The combined organic layers were dried over anhydrous sodium sulfate and concentrated under reduced pressure to obtain crude reaction mass that was subjected to column chromatography using combi-flash (eluted in 2-3% ethyl acetate in hexane to afford 1,3-dibromo-5-isopropoxy-benzene (3.2 g, 10.88 mmol, 91.40% yield) as clear liquid. m/z=293.

Step-1: Preparation of 1,3-Dibromo-5-isopropoxy-benzene

To a stirred solution of 3, 5-dibromophenol (3 g, 11.91 mmol) in DMF (15 mL) was added potassium carbonate (3.29 g, 23.82 mmol, 1.44 mL) at room temperature and the reaction was stirred for 30 minutes. To this reaction mixture, 2-iodopropane (2.43 g, 14.29 mmol, 1.43 mL) was added dropwise and the resulting reaction mixture was stirred at 80-90° C. TLC (mobile phase of ethyl acetate: n-hexane Step-2: Preparation of 1-(3-Bromo-5-isopropoxy-phenyl)-1H-pyrazole-4-carbaldehyde To a stirred solution of 1,3-dibromo-5-isopropoxy-benzene (500 mg, 1.70 mmol) in toluene (15 mL) were added 1H-pyrazole-4-carbaldehyde (179.77 mg, 1.87 mmol) and potassium phosphate tribasic anhydrous (722.05 mg, 3.40 mmol) and the reaction was degassed with $N_2$ for 10 minutes. Copper (I) iodide (64.78 mg, 340.16 umol, 11.53 uL) and N,N'-dimethylcyclohexane-1,2-diamine (48.38 mg, 340.16 umol) were added to the reaction and the reaction was again degassed for 10 minutes. The reaction was heated to 130° C. for 16 hours in a sealed tube at which point TLC confirmed the formation of product. The reaction was cooled and diluted with water and EtOAc. The organics was separated and aqueous part was extracted with EtOAc. The combined organics was washed with water and brine, dried over $Na_2SO_4$, and concentrated to afford crude compound that was purified by combi-flash using 20-50% EtOAc in hexane to afford 1-(3-bromo-5-isopropoxy-phenyl)-1H-pyrazole-4-carbaldehyde (190 mg, 583.84 umol, 34.33% yield, 95% purity, 000) as brown solid. m/z=309.

Step-3: Preparation of 1-(3-Cyclopropyl-5-isopropoxy-phenyl)-1H-pyrazole-4-carbaldehyde A mixture of 1-(3-bromo-5-isopropoxy-phenyl)pyrazole-4-carbaldehyde (420 mg, 1.36 mmol), 2-cyclopropyl-4,4,5,5-tetramethyl-1,3,2-dioxaborolane (273.95 mg, 1.63 mmol, 297.12 uL), and potassium carbonate (2 M, 4.79 mL) in DME (15 mL) was degassed followed by the addition of palladium(0) tetrakis(triphenylphosphine) (78.49 mg, 67.93 umol). The reaction was heated to 95° C. for 16 hours under argon. The reaction mixture was diluted with EtOAc and washed with water. The aqueous layer was extracted with ethyl acetate (2×30 ml). The combined organics were dried over $Na_2SO_4$ and concentrated to afford the crude product that was purified using 20-50% EtOAc in hexane by combi-flash to afford 1-(3-cyclopropyl-5-isopropoxy-phenyl)-1H-pyrazole-4-carbaldehyde (210 mg, 543.79 umol, 40.03% yield, 70% purity, 000) as sticky gel. m/z=270.

Step-4: Preparation of 4-{[1-(3-Cyclopropyl-5-isopropoxy-phenyl)-1H-pyrazol-4-ylmethyl]-amino}-2-(2,6-dioxo-piperidin-3-yl)-isoindole-1,3-dione To a stirred solution of 1-(3-cyclopropyl-5-isopropoxy-phenyl)pyrazole-4-carbaldehyde (80 mg, 295.94 umol) and 4-amino-2-(2,6-dioxo-3-piperidyl)isoindoline-1,3-dione (80.86 mg, 295.94 umol) in THF (2 ml) was added dibutyltindichloride (107.90 mg, 355.13 umol, 79.34 uL) followed by the addition of phenylsilane (32.02 mg, 295.94 umol, 36.47 uL). The reaction was heated at reflux temperature for 16 hours at which point TLC and LCMS confirmed the formation of product. The reaction was cooled, quenched with water, and extracted with EtOAc. The combined organics was washed with water and brine and dried over sodium sulphate. Crude was purified by combi-flash using 30-80% EtOAc in hexane and re-purified by preparative HPLC to afford 4-[[1-(3-cyclopropyl-5-isopropoxy-phenyl)pyrazol-4-yl]methylamino]-2-(2,6-dioxo-3-piperidyl)isoindoline-1,3-dione (27 mg, 50.34 umol, 17.01% yield, 98.37% purity, 000) (Compound 180) as yellow solid. 1H NMR (400 MHz, DMSO-d6): δ 11.1 (bs, 1H), 8.52 (s, 1H), 7.71 (s, 1H), 7.59 (t, J=8 Hz, 1H), 7.18 (d, J=8 Hz, 1H), 7.09 (s, 1H), 7.05-7.03 (m, 2H), 6.97 (t, J=8 Hz, 1H), 6.53 (s, 1H), 5.08-5.03 (m, 1H), 4.68-4.65 (m, 1H), 4.46 (d, J=8 Hz, 2H), 2.88-2.85 (m, 1H), 2.60-2.50 (m, 2H), 2.03-2.01 (m, 1H), 1.95-1.91 (m, 1H), 1.28 (d, J=8 Hz, 6H), 0.97-0.92 (m, 2H), 0.75-0.72 (m, 2H). LCMS (ES+)=528.2 [M+H]$^+$.

Example 37. Synthesis of 2-(2, 6-Dioxo-piperidin-3-yl)-4-{[1-(1-phenyl-azetidin-3-yl)-1H-pyrazol-4-ylmethyl]-amino}-isoindole-1, 3-Dione (Compound 181)

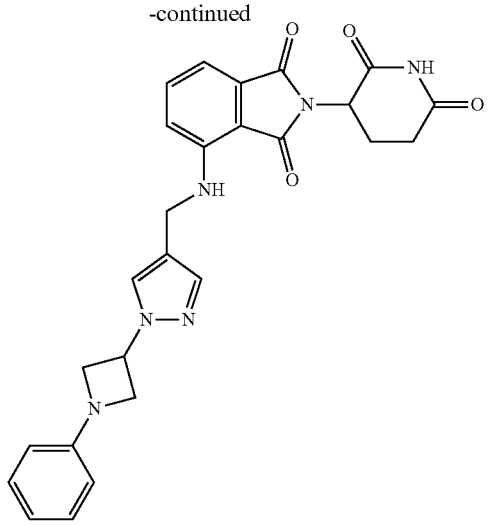

Compound 181

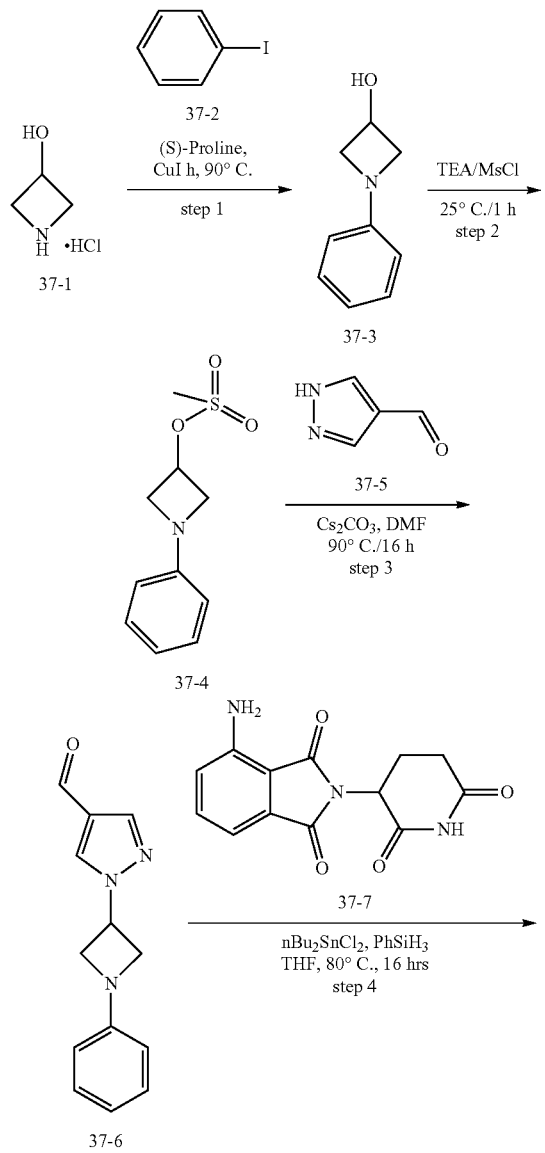

Step-1: Preparation of 1-Phenyl-azetidin-3-ol

In a sealed tube, a solution of iodobenzene (1 g, 4.90 mmol, 546.45 uL), azetidin-3-ol as hydrochloride salt (1.07 g, 14.71 mmol, 021) and proline (112.87 mg, 980.35 umol) were mixed with DMSO (10 mL). Potassium carbonate (3.39 g, 24.51 mmol, 1.48 mL) and copper (I) iodide (93.35 mg, 490.18 umol, 16.61 uL) were added and the tube was sealed with a teflon-lined cap. The reaction mixture was heated to 90° C. for 16 hours. After consumption of starting material, the reaction mixture was diluted with water and extracted with ethyl acetate, dried over sodium sulphate, filtered and concentrated under reduced pressure to afford crude material that was purified by combi-flash column chromatography (using 30% ethyl acetate in n-hexane) to afford 1-phenyl-azetidin-3-ol (650 mg, 4.14 mmol, 84.44% yield, 95% purity, 000) as colorless sticky liquid. LCMS (ES+)=150.0 [M+H]+.

Step-2: Preparation of Methanesulfonic acid 1-phenyl-azetidin-3-yl ester

To a stirred solution of 1-phenylazetidin-3-ol (600 mg, 4.02 mmol) in DCM (10 mL) was added triethylamine (813.92 mg, 8.04 mmol, 1.12 mL) and the reaction mixture was heated to 25° C. for 1 hour. After consumption of starting material, the reaction mass was diluted with water, extracted with DCM, washed with brine, dried over anhydrous sodium sulphate and concentrated to afford crude methanesulfonic acid 1-phenyl-azetidin-3-yl ester (900 mg, 3.92 mmol, 97.48% yield, 99% purity, 000) as colorless liquid that was used in the next step without further purification. LCMS (ES+)=228.0 [M+H]+.

Step-3: Preparation of 1-(1-Phenyl-azetidin-3-yl)-1H-pyrazole-4-carbaldehyde

To a stirred solution of (1-phenylazetidin-3-yl) methanesulfonate (500 mg, 2.20 mmol) and 1H-pyrazole-4-carbaldehyde (317.08 mg, 3.30 mmol) in DMF (10 mL) was added cesium carbonate (1.43 g, 4.40 mmol) and the reaction mixture was heated to 80° C. for 16 hours. After consumption of starting material, the reaction mass was diluted with water, extracted with ethyl acetate, washed with brine, dried over anhydrous sodium sulphate and evaporated under reduced pressure. The crude was purified by combi-flash column chromatography (using 30% ethyl acetate in n-hexane) to afford 1-(1-phenyl-azetidin-3-yl)-1H-pyrazole-4-carbaldehyde (300 mg, 1.23 mmol, 55.80% yield, 93% purity, 000) as light yellow solid. LCMS (ES+)=227.8 [M+H]+

Step-4: Preparation of 2-(2, 6-Dioxo-piperidin-3-yl)-4-{[1-(1-phenyl-azetidin-3-yl)-1H-pyrazol-4-ylmethyl]-amino}-isoindole-1, 3-Dione In a sealed tube, to a stirring solution of 1-(1-phenylazetidin-3-yl)pyrazole-4-carbaldehyde (200 mg, 880.04 umol) and 4-amino-2-(2,6-dioxo-3-piperidyl)isoindoline-1,3-dione (240.47 mg, 880.04 umol) in THF (10 mL) was added phenylsilane (95.23 mg, 880.04 umol, 108.59 uL) and dibutyltindichloride (320.88 mg, 1.06 mmol, 235.94 uL). The reaction mixture was heated to 70° C. for 16 hours. After consumption of starting material, excess solvent was evaporated under reduced pressure and the reaction mass was dissolved in ethyl acetate and washed with water. The organic layer dried over sodium sulphate, filtered and concentrated in vacuo to afford the crude product. This crude was purified by prep-HPLC to afford 2-(2, 6-dioxo-piperidin-3-yl)-4-{[1-(1-phenyl-azetidin-3-yl)-1H-pyrazol-4-ylmethyl]-amino}-isoindole-1, 3-Dione (Compound 181) (28 mg, 56.06 umol, 6.37% yield, 97.01% purity, 000) as yellow solid. LCMS (ES+)=485.5 [M+H]+. 1H NMR (400 MHz, DMSO-d6): δ 11.08 (brs, 1H), 7.90 (s, 1H), 7.58-7.55 (m, 2H), 7.21-7.14 (m, 3H), 7.04-7.02 (d, 1H), 6.89 (m, 1H), 6.72 (t, 1H), 6.50-6.48 (d, 2H), 5.34 (t, 1H), 5.06-5.02 (m, 1H), 4.39-4.37 (d, 2H), 4.26 (t, 2H), 4.02 (t, 2H), 2.87 (m, 1H), 2.60-2.55 (m, 2H), 2.03-2.01 (m, 1H).

Example 38. Synthesis of 4-(((1-(1-((R)-2,2-Dichloro-1-methylcyclopropane-1-carbonyl)piperidin-4-yl)-1H-pyrazol-4-yl)methyl)amino)-2-(2,6-dioxopiperidin-3-yl)isoindoline-1,3-dione (Compound 182) and 4-(((1-(1-((S)-2,2-Dichloro-1-methylcyclopropane-1-carbonyl)piperidin-4-yl)-1H-pyrazol-4-yl)methyl)amino)-2-(2,6-dioxopiperidin-3-yl)isoindoline-1,3-dione (Compound 183)

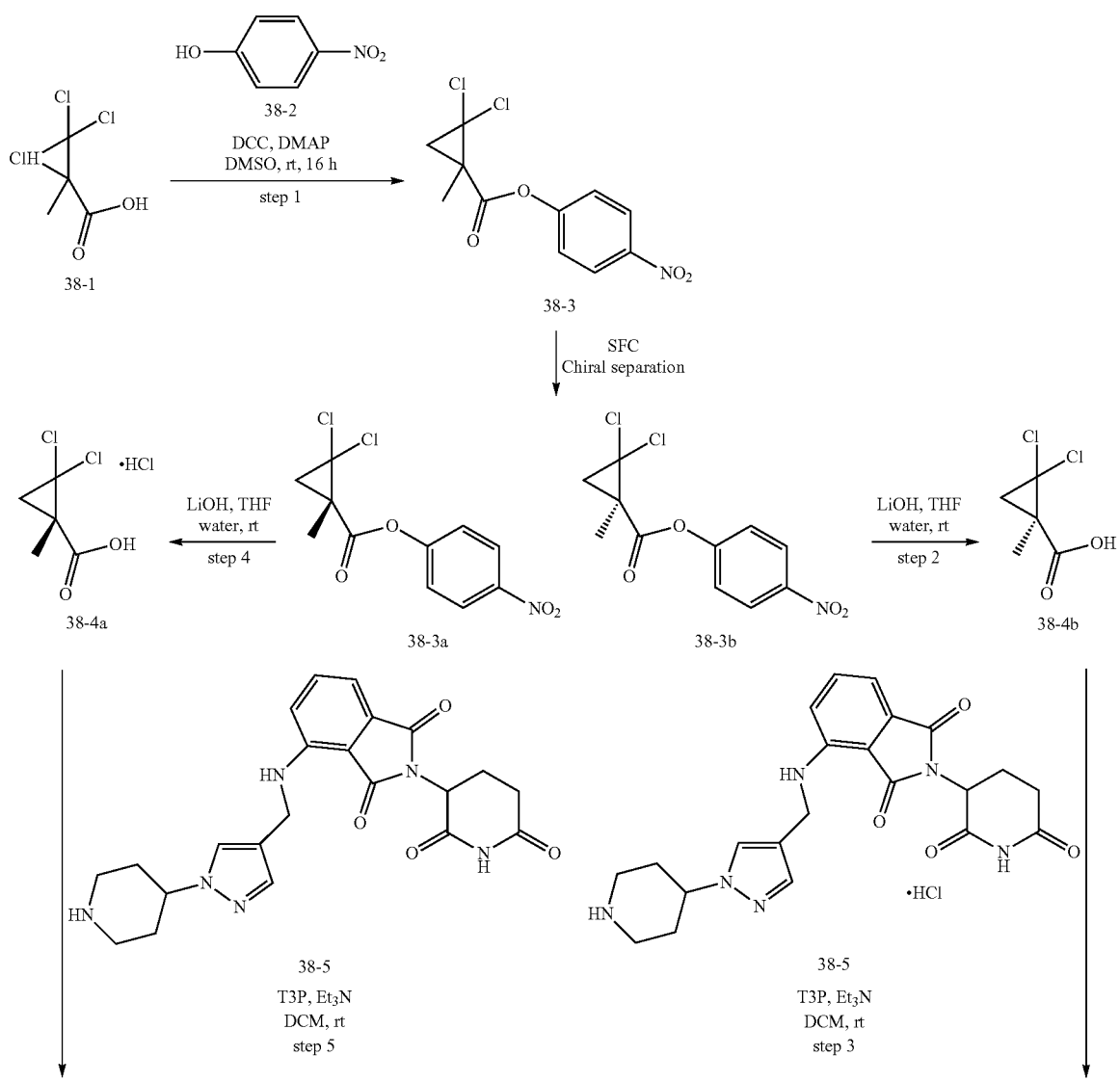

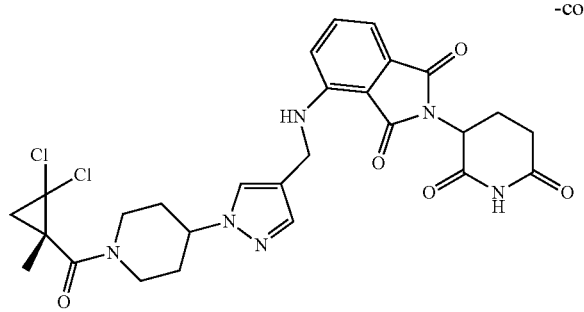

Compound 182

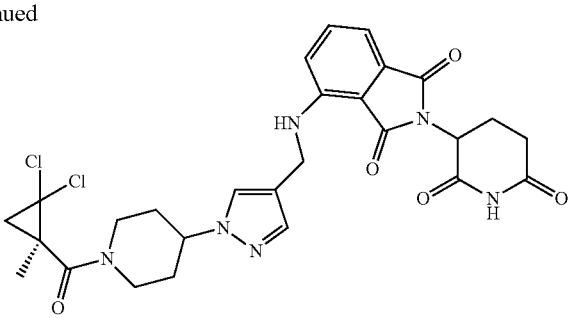

Compound 183

Step-1: Preparation of 4-Nitrophenyl 2,2-dichloro-1-methylcyclopropane-1-carboxylate To a stirred solution of 2,2-dichloro-1-methyl-cyclopropanecarboxylic acid 38-1 (1 g, 5.92 mmol) in DMSO (20.0 mL) were added 4-nitrophenol 38-2 (987.72 mg, 7.10 mmol), DMAP (722.86 mg, 5.92 mmol) and DCC (1.46 g, 7.10 mmol) and the reaction mixture was stirred at room temperature for 16 hours. The reaction was then diluted with ether and organic part was washed with water and brine, dried over sodium sulfate, and concentrated under reduced pressure to afford crude material. Crude was then purified by column chromatography using (0%-10% ethyl acetate/hexane) to afford 4-nitrophenyl 2,2-dichloro-1-methylcyclopropane-1-carboxylate 38-3 (1.2 g, 4.14 mmol, 69.91%). Compound 38-3 was then dissolved in MeOH and was separated via SFC Chiral separation using a Chiralpak IG (4.6×250 mm), 5 with a mobile phase of hexane/ethanol/IP amine (80:20:0.1) and a flow rate of 1.0 mL/min to afford 4-nitrophenyl (R)-2,2-dichloro-1-methylcyclopropane-1-carboxylate 38-3b (250 mg, ee-100%) and 4-nitrophenyl (S)-2,2-dichloro-1-methylcyclopropane-1-carboxylate 38-3a (250 mg, ee-98.32%).

38-3b: $^1$H NMR (d6-DMSO, 400 MHZ) δ 8.33 (d, J=9.04 Hz, 2H), 7.49 (d, J=9.04 Hz, 2H), 2.37 (d, J=8.12 Hz, 1H), 1.99 (d, J=8.04 Hz, 1H), 1.70 (s, 3H).

38-3a: $^1$H NMR (d6-DMSO, 400 MHZ) δ 8.33 (d, J=9.04 Hz, 2H), 7.49 (d, J=9.04 Hz, 2H), 2.37 (d, J=8.12 Hz, 1H), 1.99 (d, J=8.04 Hz, 1H), 1.70 (s, 3H).

Step-2: Preparation of (R)-2,2-Dichloro-1-methylcyclopropane-1-carboxylic acid A stirred solution of (4-nitrophenyl) (1R)-2,2-dichloro-1-methyl-cyclopropanecarboxylate 38-3b (250.00 mg, 861.77 umol) in THF (8 mL) was cooled to 0° C. and lithium hydroxide monohydrate, 98% (43.40 mg, 1.03 mmol, 28.74 uL) dissolved in water (2 mL) was added. The reaction mixture was allowed to stir at room temperature for 3 hours. The reaction mixture was evaporated under reduced pressure, diluted with water, and extracted with ethyl acetate. The aqueous solution was acidified with 1N HCl to a pH-4 and was extracted with ethyl acetate. The organic layer was dried over sodium sulphate and evaporated under reduced pressure to afford (1R)-2,2-dichloro-1-methyl-cyclopropanecarboxylic acid 38-4b (140 mg, 828.37 umol, 96.12% yield) which was used for next step without further purification.

Step-3: Preparation of 4-(((1-(1-((R)-2,2-Dichloro-1-methylcyclopropane-1-carbonyl)piperidin-4-yl)-1H-pyrazol-4-yl)methyl)amino)-2-(2,6-dioxopiperidin-3-yl)isoindoline-1,3-dione To a stirred solution of 4-[[1-(1-chloropiperidin-1-ium-4-yl)pyrazol-4-yl]methylamino]-2-(2,6-dioxo-3-piperidyl)isoindoline-1,3-dione 38-5 (200 mg, 422.90 umol) in DCM (10 mL) was added (1R)-2,2-dichloro-1-methyl-cyclopropanecarboxylic acid 38-4b (85.77 mg, 507.48 umol) followed by triethylamine (171.17 mg, 1.69 mmol, 235.78 uL) at 0° C. and the reaction mixture was allowed to stir at room temperature for 16 hours. The reaction mixture was diluted with DCM and washed with saturated sodium bicarbonate solution followed by water and brine, dried over sodium sulphate and concentrated under reduced pressure to afford the crude product. The crude product thus obtained was purified by column chromatography over silica gel eluting with 2.5% of MeOH in DCM to afford 4-[[1-[1-[(1R)-2,2-dichloro-1-methyl-cyclopropanecarbonyl]-4-piperidyl]pyrazol-4-yl]methylamino]-2-(2,6-dioxo-3-piperidyl)isoindoline-1,3-dione (Compound 182) (105 mg, 178.74 umol, 42.26% yield) as yellow solid. $^1$H NMR (d6-DMSO, 400 MHZ) δ 11.08 (s, 1H), 7.82 (d, J=3.76 Hz, 1H), 7.59-7.55 (m, 1H), 7.48 (d, J=4.96 Hz, 1H), 7.16 (d, J=8.56 Hz, 1H), 7.04 (d, J=6.88 Hz, 1H), 6.84-6.79 (m, 1H), 5.04 (dd, J=13.04, 5.32 Hz, 1H), 4.46-4.34 (m, 4H), 3.92-3.75 (m, 1H), 3.47-3.31 (m, 1H), 2.92-2.82 (m, 2H), 2.62-2.55 (m, 2H), 2.20-2.16 (m, 1H), 2.07-1.85 (m, 4H), 1.67-1.63 (m, 2H), 1.48 (d, J=12.84 Hz, 3H); LC MS: ES+ 587.2.

Step-4: Preparation of (S)-2,2-Dichloro-1-methylcyclopropane-1-carboxylic acid A stirred solution of (4-nitrophenyl) (1S)-2,2-dichloro-1-methyl-cyclopropanecarboxylate 38-3a (250.00 mg, 861.77 umol) in THF (8 mL) was cooled to 0° C. and lithium hydroxide monohydrate, 98% (43.40 mg, 1.03 mmol, 28.74 uL) dissolved in water (2 mL) was added. The reaction mixture was allowed to stir at room temperature for 3 hours. The reaction mixture was evaporated under reduced pressure, diluted with water, and extracted with ethyl acetate. The aqueous solution was acidified with 1N HCl to a pH-4 and was extracted with ethyl acetate. The organic layer was dried over sodium sulphate and evaporated under reduced pressure to afford (1S)-2,2-dichloro-1-methyl-cyclopropanecarboxylic acid 38-4a (140 mg, 828.37 umol, 96.12% yield) which was used for next step without further purification.

Step-5: Preparation of 4-(((1-(1-((S)-2,2-Dichloro-1-methylcyclopropane-1-carbonyl)piperidin-4-yl)-1H-pyrazol-4-yl)methyl)amino)-2-(2,6-dioxopiperidin-3-yl)isoindoline-1,3-dione To a stirred solution of 4-[[1-(1-chloropiperidin-1-ium-4-yl)pyrazol-4-yl]methylamino]-2-(2,6-dioxo-3-piperidyl)isoindoline-1,3-dione 38-5 (200 mg, 422.90 umol) in DCM (2 mL) was added (1S)-2,2-dichloro-1-methyl-cyclopropanecarboxylic acid 38-4a (85.77 mg, 507.48 umol) followed by triethylamine (171.17 mg, 1.69 mmol, 235.78 uL) at 0° C. and the reaction mixture was allowed to stir at room temperature for 16 hours. The reaction mixture was diluted with DCM, washed with saturated sodium bicarbonate solution, water and brine, dried over sodium sulphate and concentrated under reduced pressure to afford the crude product. The crude product thus obtained was purified by column chromatography over silica gel eluting with 2.5% of MeOH in DCM to afford 4-[[1-[1-[(1S)-2,2-dichloro-1-methyl-cyclopropanecarbonyl]-4-piperidyl]pyrazol-4-yl]methylamino]-2-(2,6-dioxo-3-piperidyl)isoindoline-1,3-dione (Compound 183) (105 mg, 178.74 umol, 42.26% yield) as yellow solid. $^1$H NMR (d6-DMSO, 400 MHZ) δ 11.08 (s, 1H), 7.82 (d, J=3.76 Hz, 1H), 7.59-7.55 (m, 1H), 7.48 (d, J=4.96 Hz, 1H), 7.16 (d, J=8.64 Hz, 1H), 7.04 (d, J=6.96 Hz, 1H), 6.84-6.79 (m, 1H), 5.04 (dd, J=12.76, 5.0 Hz, 1H), 4.46-4.34 (m, 4H), 3.92-3.75 (m, 1H), 3.47-3.31 (m, 1H), 2.92-2.82 (m, 2H), 2.62-2.55 (m, 2H), 2.20-2.16 (m, 1H), 2.07-1.85 (m, 4H), 1.67-1.63 (m, 2H), 1.48 (d, J=12.84 Hz, 3H); LC MS: ES+ 587.2.

Example 39. Synthesis of tert-butyl 2-(3-(4-(((2-(2,6-Dioxopiperidin-3-yl)-1,3-dioxoisoindolin-4-yl)amino)methyl)-1H-pyrazol-1-yl)azetidin-1-yl)acetate (Compound 184)

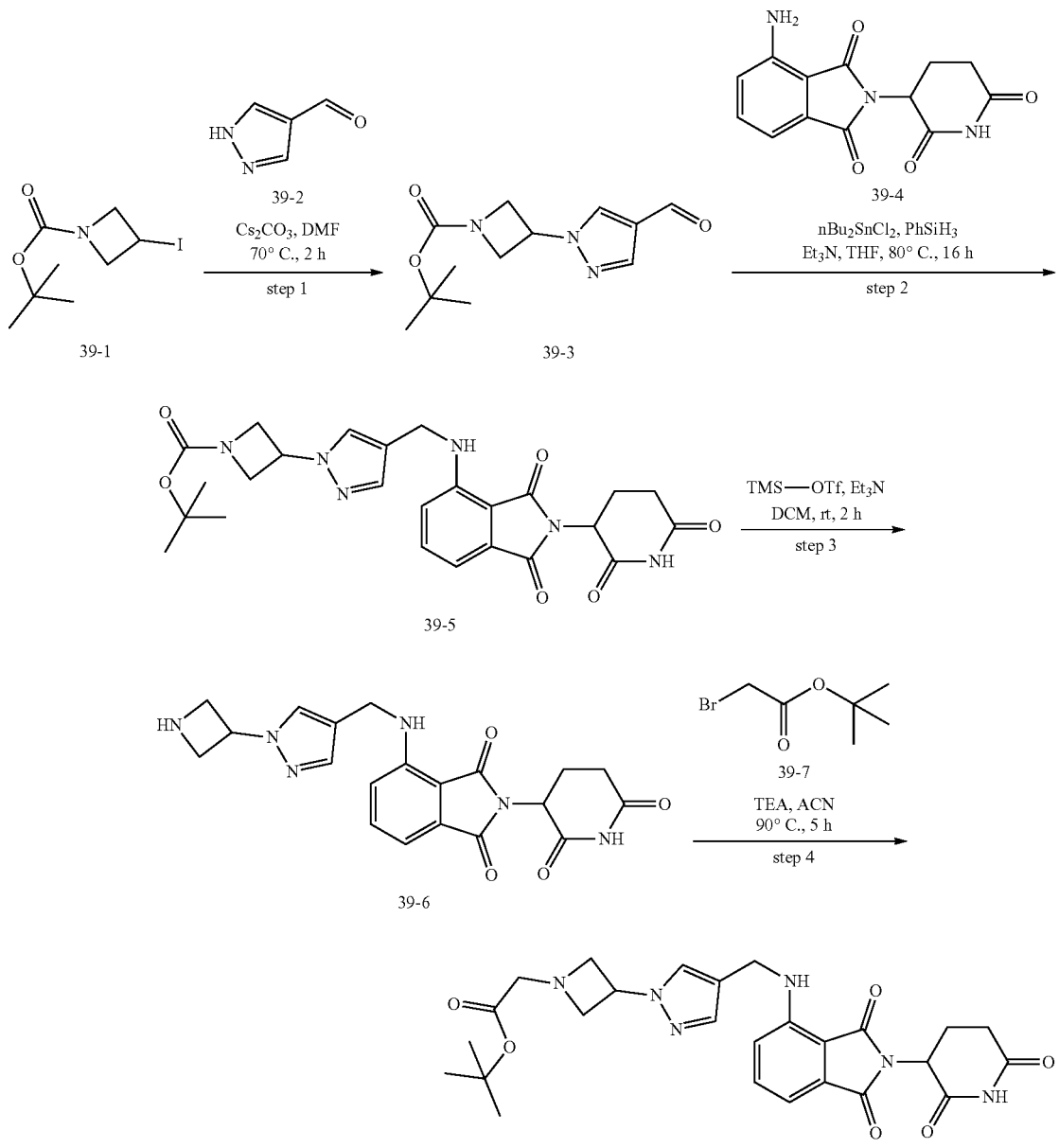

Compound 184

Step-1: Preparation of tert-Butyl 3-(4-formyl-1H-pyrazol-1-yl)azetidine-1-carboxylate To a stirred solution of 1H-pyrazole-4-carbaldehyde 39-2 (1 g, 10.41 mmol) in DMF (10 mL) was added tert-butyl 3-iodoazetidine-1-carboxylate 39-1 (2.95 g, 10.41 mmol) and cesium carbonate (5.09 g, 15.61 mmol) and the reaction mixture was heated at 90° C. for 16 hours. Volatiles were removed and the residue was diluted with water and ethyl acetate. The layers were separated and the organic part was dried over $Na_2SO_4$ and evaporated under reduced pressure to afford crude that was purify by column chromatography to afford tert-butyl 3-(4-formyl-H-pyrazol-1-yl)azetidine-1-carboxylate 39-3 (2 g, 7.88 mmol, 75.71% yield, 99% purity, 000) as off-white solid. LC MS: ES+ 252.0.

Step-2: Preparation of tert-Butyl 3-(4-(((2-(2,6-dioxopiperidin-3-yl)-1,3-dioxoisoindolin-4-yl)amino)methyl)-1H-pyrazol-1-yl)azetidine-1-carboxylate To a stirred solution 4-amino-2-(2,6-dioxo-3-piperidyl)isoindoline-1,3-dione 39-4 (500 mg, 1.83 mmol) and tert-butyl 3-(4-formylpyrazol-1-yl)azetidine-1-carboxylate 39-3 (459.81 mg, 1.83 mmol) in THE (3 mL) butyltinpentachloride (516.36 mg, 1.83 mmol, 305.54 uL) was added followed by phenylsilane (198.01 mg, 1.83 mmol) at room temperature. After complete addition, the reaction mixture was heated at 80° C. for 12 hours. Volatiles were removed under reduced pressure to afford crude which was purify by column chromatography by eluting (50% EtOAC:Hexane) to afford tert-butyl 3-(4-(((2-(2,6-dioxopiperidin-3-yl)-1,3-dioxoisoindolin-4-yl)amino)methyl)-1H-pyrazol-1-yl)azetidine-1-carboxylate 39-5 (500 mg, 747.26 umol, 40.84% yield, 76% purity, 000) as yellow solid. LC MS: ES+ 509.4.

Step-3: Preparation of 4-(((1-(Azetidin-3-yl)-1H-pyrazol-4-yl)methyl)amino)-2-(2,6-dioxopiperidin-3-yl)isoindoline-1,3-dione To a stirred solution of tert-butyl 3-[4-[[[2-(2,6-dioxo-3-piperidyl)-1,3-dioxo-isoindolin-4-yl]amino]methyl]pyrazol-1-yl]azetidine-1-carboxylate 39-5 (400 mg, 786.59 umol) in DCM (8 mL) was added trimethylsilyl trifluoromethanesulfonate (262.24 mg, 1.18 mmol, 228.03 uL) and TEA (119.39 mg, 1.18 mmol, 164.45 uL) at 0° C. The reaction was stirred for 2 hours at room temperature and was then quenched with water, extracted with 10% MeOH in DCM, dried over $Na_2SO_4$, and evaporated under reduced pressure to afford crude 4-(((1-(azetidin-3-yl)-1H-pyrazol-4-yl)methyl)amino)-2-(2,6-dioxopiperidin-3-yl)isoindoline-1,3-dione 39-6 (320 mg, 783.53 umol, 99.61% yield, purity, 000) as yellow solid. LC MS: ES+ 409.2.

Step-4: Preparation of tert-butyl 2-(3-(4-(((2-(2,6-Dioxopiperidin-3-yl)-1,3-dioxoisoindolin-4-yl)amino)methyl)-1H-pyrazol-1-yl)azetidin-1-yl)acetate To a stirred solution of 4-[[1-(azetidin-3-yl)pyrazol-4-yl]methylamino]-2-(2,6-dioxo-3-piperidyl)isoindoline-1,3-dione 39-6 (320 mg, 783.53 umol) in ACN (7 mL) was added tert-butyl 2-bromoacetate 39-7 (168.11 mg, 861.88 umol, 126.40 uL) and TEA (79.29 mg, 783.53 umol, 109.21 uL). The reaction mixture was stirred at 90° C. for 5 hours. Volatiles were removed and the residue was diluted with water and ethyl acetate. The layers were separated and the organic part was dried over $Na_2SO_4$ and concentrated under reduced pressure to afford crude which was purify by prep-TLC to afford tert-butyl 2-(3-(4-(((2-(2,6-dioxopiperidin-3-yl)-1,3-dioxoisoindolin-4-yl)amino)methyl)-1H-pyrazol-1-yl)azetidin-1-yl)acetate (Compound 184) (18 mg, 32.77 umol, 4.18% yield, 95.14% purity, 000) as yellow solid. $^1$H NMR (d6-DMSO, 400 MHZ) δ 11.09 (s, 1H), 7.86 (s, 1H), 7.56 (t, J=7.84 Hz, 1H), 7.51 (s, 1H), 7.14 (d, J=8.64 Hz, 1H), 7.03 (d, J=7.04 Hz, 1H), 6.88-6.85 (m, 1H), 5.04 (dd, J=12.8, 5.28 Hz, 1H), 4.99-4.95 (m, 1H), 4.39-4.36 (m, 2H), 3.80-3.75 (m, 2H), 3.45-3.43 (m, 2H), 3.26-3.23 (m, 2H), 2.91-2.83 (m, 1H), 2.66-2.55 (m, 2H), 2.03-2.00 (m, 1H), 1.39 (s, 9H); LC MS: ES+ 523.3.

Example 40. Synthesis of tert-butyl 4-[4-[[[2-[(3R)-3-deuterio-2,6-dioxo-3-piperidyl]-1,3-dioxo-isoindolin-4-yl]amino]methyl]pyrazol-1-yl]piperidine-1-carboxylate (Compound 185) and tert-butyl 4-[4-[[[2-[(3S)-3-deuterio-2,6-dioxo-3-piperidyl]-1,3-dioxo-isoindolin-4-yl]amino]methyl]pyrazol-1-yl]piperidine-1-carboxylate (Compound 186)

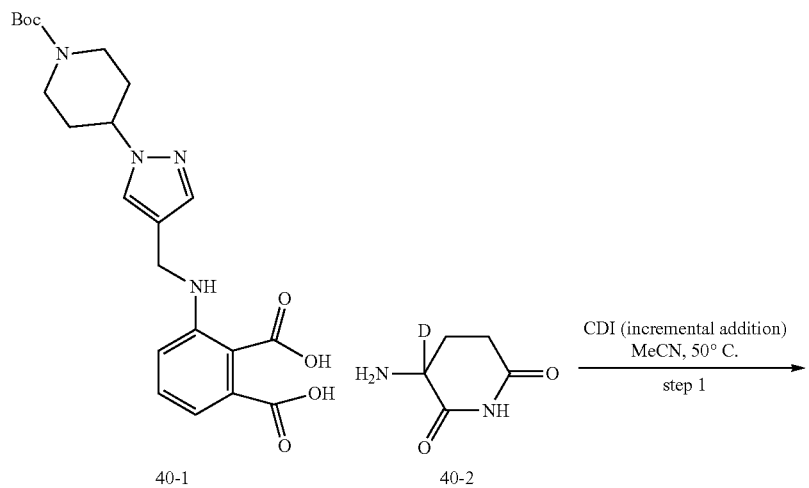

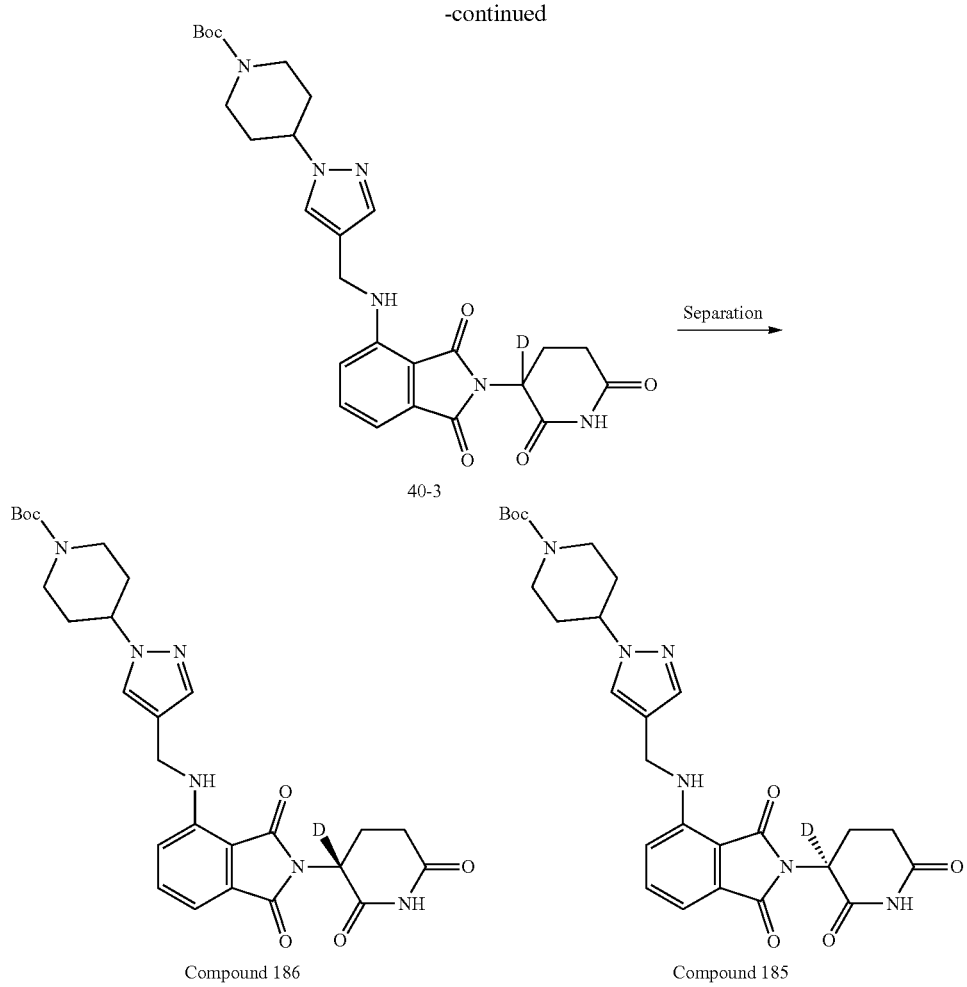

Step-1: Preparation of tert-Butyl 4-(4-(((2-(2,6-dioxopiperidin-3-yl-3-d)-1,3-dioxoisoindolin-4-yl)amino)methyl)-1H-pyrazol-1-yl)piperidine-1-carboxylate To the stirred solution of 3-[[1-(1-tert-butoxycarbonyl-4-piperidyl)pyrazol-4-yl]methylamino]phthalic acid 40-1 (150.0 mg, 337.47 umol) in ACN (3 mL) was added carbonyldiimidazole (71.14 mg, 438.72 umol) at 45° C. and the heating was continued for 20 minutes. Then the reaction mixture was cooled to room temperature and carbonyldiimidazole (71.14 mg, 438.72 umol) was added followed by 3-(amino)-3-deuterio-piperidine-2,6-dione 40-2 (83.83 mg, 506.21 umol). The reaction mixture was stirred at room temperature for 2 hours. TLC and LCMS confirmed formation of product. To the reaction mixture was further added carbonyldiimidazole (82.08 mg, 506.21 umol) and the reaction was stirred for 2 hours at room temperature and then for 1 hour at 50° C. The reaction mixture was diluted with ethyl acetate, washed with water and the organic fraction was separated. The organic layer was then dried over anhydrous sodium sulphate and evaporated under reduced pressure to obtain the crude which was purified by flash chromatography using (0-1% MeOH-DCM) to afford the tert-butyl 4-(4-(((2-(2,6-dioxopiperidin-3-yl-3-d)-1,3-dioxoisoindolin-4-yl)amino)methyl)-1H-pyrazol-1-yl)piperidine-1-carboxylate 40-3 (130 mg) as a mixture of two isomers. Compound 40-3 was dissolved in MeOH and the two isomers were separated by chiral preparative HPLC using a Chiralpak IC (4.6×250 mm), 5 column (mobile phase: ACN: 100; flow rate: 1.0 ml/min) to afford tert-butyl 4-[4-[[[2-[(3R)-3-deuterio-2,6-dioxo-3-piperidyl]-1,3-dioxo-isoindolin-4-yl]amino]methyl]pyrazol-1-yl]piperidine-1-carboxylate (Compound 185) (50.0 mg, 93.01 umol, 27.56% yield) as (60% D-incorporation, peak-1, eluted first, % ee-99.74) $^1$H NMR (d6-DMSO, 400 MHZ) δ 11.08 (s, 1H), 7.78 (s, 1H), 7.57 (t, J=7.8 Hz, 1H), 7.45 (s, 1H), 7.15 (d, J=8.52 Hz, 1H), 7.03 (d, J=7.04 Hz, 1H), 6.79 (t, J=5.54 Hz, 1H), 5.06-5.03 (m, 0.4H), 4.36-4.26 (m, 3H), 4.02-3.98 (m, 2H), 2.92-2.83 (m, 3H), 2.66-2.53 (m, 2H), 2.03-1.92 (m, 3H), 1.76-1.67 (m, 2H), 1.40 (s, 9H); LC MS: ES+ 538.4 and tert-butyl 4-[4-[[[2-[(3S)-3-deuterio-2,6-dioxo-3-piperidyl]-1,3-dioxo-isoindolin-4-yl]amino]methyl]pyrazol-1-yl]piperidine-1-carboxylate (Compound 186) (45.0 mg, 83.71 umol, 24.80% yield) as (60% D-incorporation, peak 2, eluted second, % ee-93.08) both as yellow solid. $^1$H NMR (d6-DMSO, 400 MHZ) 11.08 (s, 1H), 7.78 (s, 1H), 7.57 (t, J=7.8 Hz, 1H), 7.45 (s, 1H), 7.15 (d, J=8.52 Hz, 1H), 7.03 (d, J=7.04 Hz, 1H), 6.79 (t, J=5.54 Hz, 1H), 5.06-5.03 (m, 0.4H), 4.36-4.26 (m, 3H), 4.02-3.98 (m, 2H), 2.92-2.83 (m, 3H), 2.66-2.53 (m, 2H), 2.03-1.92 (m, 3H), 1.76-1.67 (m, 2H), 1.40 (s, 9H); LC MS: ES+ 538.4.

509

Example 41. Synthesis of tert-Butyl 4-(4-(3-(dimethylamino)-1-((2-(2,6-dioxopiperidin-3-yl)-1,3-dioxoisoindolin-4-yl)amino)propyl)-1H-pyrazol-1-yl)piperidine-1-carboxylate (Compound 187)

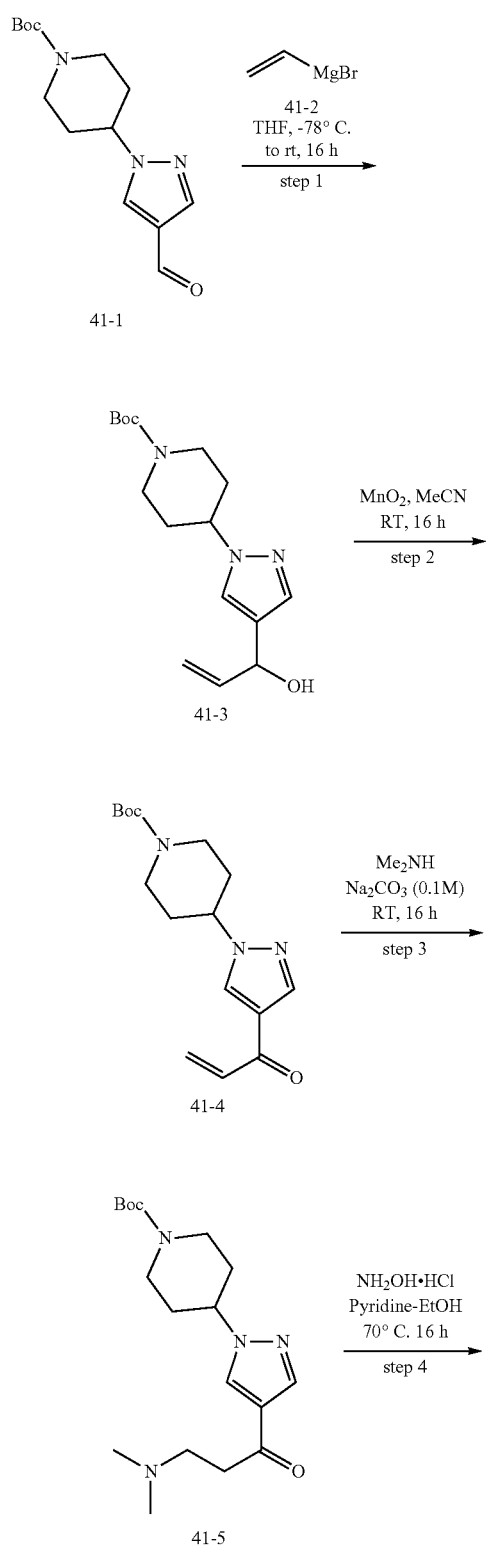

510

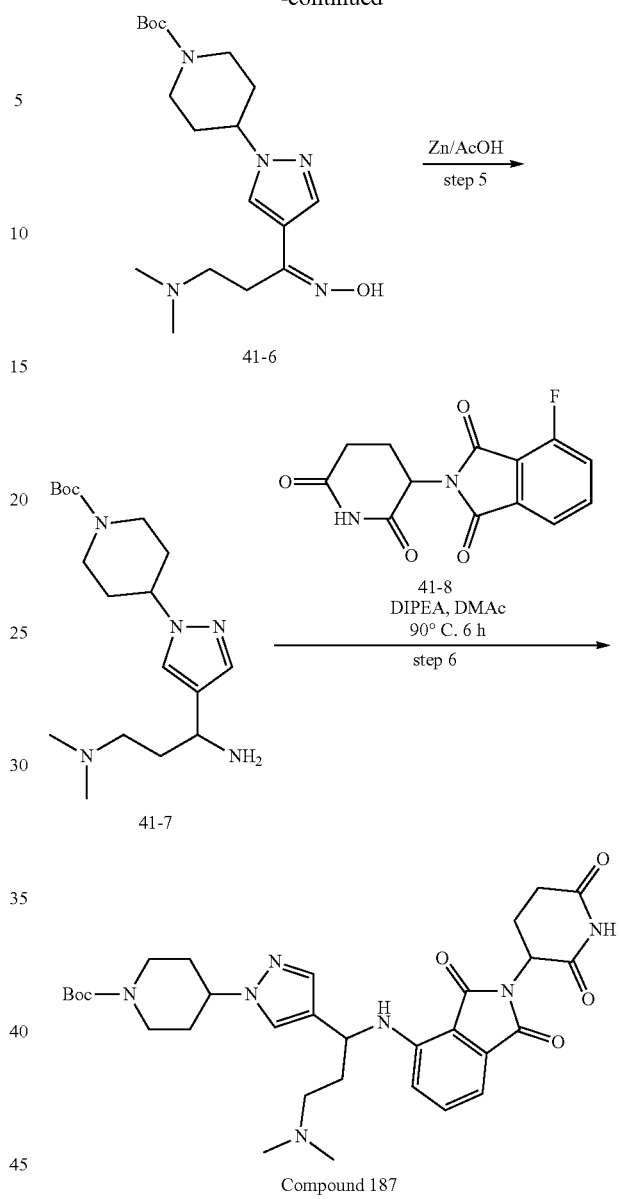

Step-1: Preparation of tert-Butyl 4-(4-(1-hydroxyallyl)-1H-pyrazol-1-yl)piperidine-1-carboxylate To a stirred solution of tert-butyl 4-(4-formylpyrazol-1-yl)piperidine-1-carboxylate 41-1 (2 g, 7.16 mmol) in THF (50 mL) was added vinyl magnesium bromide 41-2 (1 M, 10.74 mL) at −78° C. and the reaction was stirred at room temperature for 16 hours. Reaction mixture was quenched with saturated NH₄Cl solution and extracted with ethyl acetate. Crude material was purified by column chromatography (100-200 silica; 30% ethyl acetate in hexane to afford tert-butyl 4-[4-(1-hydroxyallyl)pyrazol-1-yl]piperidine-1-carboxylate 41-3 (1.7 g, 5.53 mmol, 77.24% yield). $^1$H NMR (d6-DMSO, 400 MHZ) δ 7.60 (s, 1H), 7.30 (s, 1H), 6.04-5.95 (m, 1H), 5.22-5.17 (m, 2H), 5.04-4.99 (m, 2H), 4.31-4.25 (m, 1H), 4.05-4.00 (m, 2H), 2.90-2.85 (m, 2H), 1.95-1.92 (m, 2H), 1.77-1.69 (m, 2H), 1.40 (s, 9H).

Step-2: Preparation of tert-Butyl 4-(4-acryloyl-1H-pyrazol-1-yl)piperidine-1-carboxylate To a stirred solution of tert-butyl 4-[4-(1-hydroxyallyl)pyrazol-1-yl]piperidine-1-carboxylate 41-3 (1.6 g, 5.21 mmol) in acetonitrile (25 mL) was added manganese oxide (2.58 g, 36.44 mmol) and the reaction mixture was stirred at room temperature for 16 hours. The reaction mixture was filtered through a celite bed and washed with ethyl acetate. Filtrate was then washed with water and saturated aqueous sodium bicarbonate solution, brine, dried over sodium sulfate and concentrated. Crude material was purified by combiflash column in 30-40% EtOAc in hexane to afford tert-butyl 4-(4-prop-2-enoylpyrazol-1-yl)piperidine-1-carboxylate 41-4 (900 mg, 2.95 mmol, 56.62% yield) as white solid. LC MS: ES+ 306.2.

Step-3: Preparation of tert-Butyl 4-(4-(3-(dimethylamino)propanoyl)-1H-pyrazol-1-yl)piperidine-1-carboxylate To a stirred solution of tert-butyl 4-(4-prop-2-enoylpyrazol-1-yl)piperidine-1-carboxylate 41-4 (900 mg, 2.95 mmol) in water (10 mL) was added N-methylmethanamine (2 M, 1.23 mL) and (0.1 M) sodium carbonate (2.46 mmol, 2.73 mL) and the reaction mixture was stirred at room temperature for 16 hours. Reaction mixture was diluted with ethyl acetate and washed with saturated aqueous sodium bicarbonate solution. The layers were separated and organic part was dried over sodium sulfate. The organic portion was concentrated to afford tert-butyl 4-[4-[3-(dimethylamino)propanoyl]pyrazol-1-yl]piperidine-1-carboxylate 41-5 (600 mg, 1.71 mmol, 69.71% yield) as crude. LC MS: ES+ 351.4.

Step-4: Preparation of tert-Butyl (Z)-4-(4-(3-(dimethylamino)-1-(hydroxyimino)propyl)-1H-pyrazol-1-yl)piperidine-1-carboxylate To the stirred solution of tert-butyl 4-[4-[3-(dimethylamino)propanoyl]pyrazol-1-yl]piperidine-1-carboxylate 41-5 (200.0 mg, 570.69 umol) in ethanol (4 mL) was added hydroxylamine hydrochloride (79.32 mg, 1.14 mmol, 47.49 uL) and pyridine (1 mL). The reaction mixture was heated at 80° C. for 16 hours. Solvent in the reaction mixture was evaporated under reduced pressure and washed with ether and pentane to afford tert-butyl 4-[4-[(E)-C-[2-(dimethylamino)ethyl]-N-hydroxy-carbonimidoyl]pyrazol-1-yl]piperidine-1-carboxylate 41-6 (200.0 mg, 547.24 umol, 95.89% yield) as off white solid. LC MS: ES+ 366.4.

Step-5: Preparation of tert-Butyl 4-(4-(1-amino-3-(dimethylamino)propyl)-1H-pyrazol-1-yl)piperidine-1-carboxylate To the stirred solution of tert-butyl 4-[4-[(E)-C-[2-(dimethylamino)ethyl]-N-hydroxy-carbonimidoyl]pyrazol-1-yl]piperidine-1-carboxylate 41-6 (350.0 mg, 957.67 umol) in acetic acid (5 mL) was added zinc (313.11 mg, 4.79 mmol, 43.85 uL) and the reaction mixture was heated at 60° C. for 24 hours. The reaction mixture was filtered over celite bed and the filtrate was evaporated under reduced pressure and washed with pentane to afford the crude compound that was purified by reverse phase preparative HPLC using a LYMC: YMC-Actus Triart C-18 (250×20 mm, 5) HOT-WATER column with a flow rate of 5 mL/min and a run time of 20 minutes (Solvent A: ACN; Solvent B: NaHCO$_3$) to isolate tert-butyl 4-(4-(1-amino-3-(dimethylamino)propyl)-1H-pyrazol-1-yl)piperidine-1-carboxylate 41-7 (52.0 mg, 147.94 umol, 15.45% yield) as colorless gum. LC MS: ES+ 352.4.

Step-6: Preparation of tert-Butyl 4-(4-(3-(dimethylamino)-1-((2-(2,6-dioxopiperidin-3-yl)-1,3-dioxoisoindolin-4-yl)amino)propyl)-1H-pyrazol-1-yl)piperidine-1-carboxylate To the stirred solution of tert-butyl 4-[4-[1-amino-3-(dimethylamino)propyl]pyrazol-1-yl]piperidine-1-carboxylate 41-7 (40.0 mg, 113.80 umol) in NMP (1.0 mL) was added N,N-diisopropylethylamine (36.77 mg, 284.51 umol, 49.56 uL) followed by 2-(2,6-dioxo-3-piperidyl)-4-fluoro-isoindoline-1,3-dione 41-8 (34.58 mg, 125.18 umol). The reaction was heated at 90° C. for 16 hours and was then diluted with ethyl acetate and washed with sodium bicarbonate solution, water. The organic fraction was separated and dried over anhydrous sodium sulphate and evaporated under reduced pressure to obtain the crude compound which was purified by preparative TLC plate (eluting with 4% MeOH-DCM) to afford tert-butyl 4-[4-[3-(dimethylamino)-1-[[2-(2,6-dioxo-3-piperidyl)-1,3-dioxo-isoindolin-4-yl]amino]propyl]pyrazol-1-yl]piperidine-1-carboxylate (Compound 187) (4 mg, 6.31 umol, 5.55% yield, 95.89% purity, 000) as yellow solid. $^1$H NMR (d6-DMSO, 400 MHZ) δ 11.08 (s, 1H), 7.76 (s, 1H), 7.52 (t, J=7.86 Hz, 1H), 7.43 (s, 1H), 7.19 (br s, 1H), 7.06-7.00 (m, 2H), 5.05 (dd, J=12.76, 5.24 Hz, 1H), 4.81-4.80 (m, 1H), 4.31-4.25 (m, 1H), 4.01-3.97 (m, 2H), 2.89-2.84 (m, 4H), 2.60-2.56 (m, 2H), 2.17 (s, 6H), 2.04-1.98 (m, 2H), 1.95-1.90 (m, 2H), 1.73-1.68 (m, 2H), 1.39 (s, 9H); LC MS: ES+608.5.

Example 42. Synthesis of 4-(((5-Bromo-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione (Compound 188)

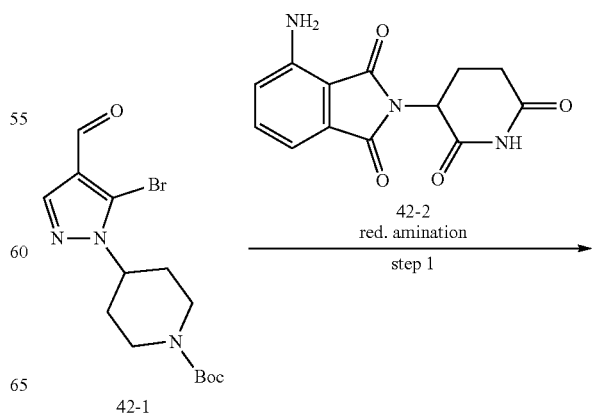

42-1

42-2
red. amination
step 1

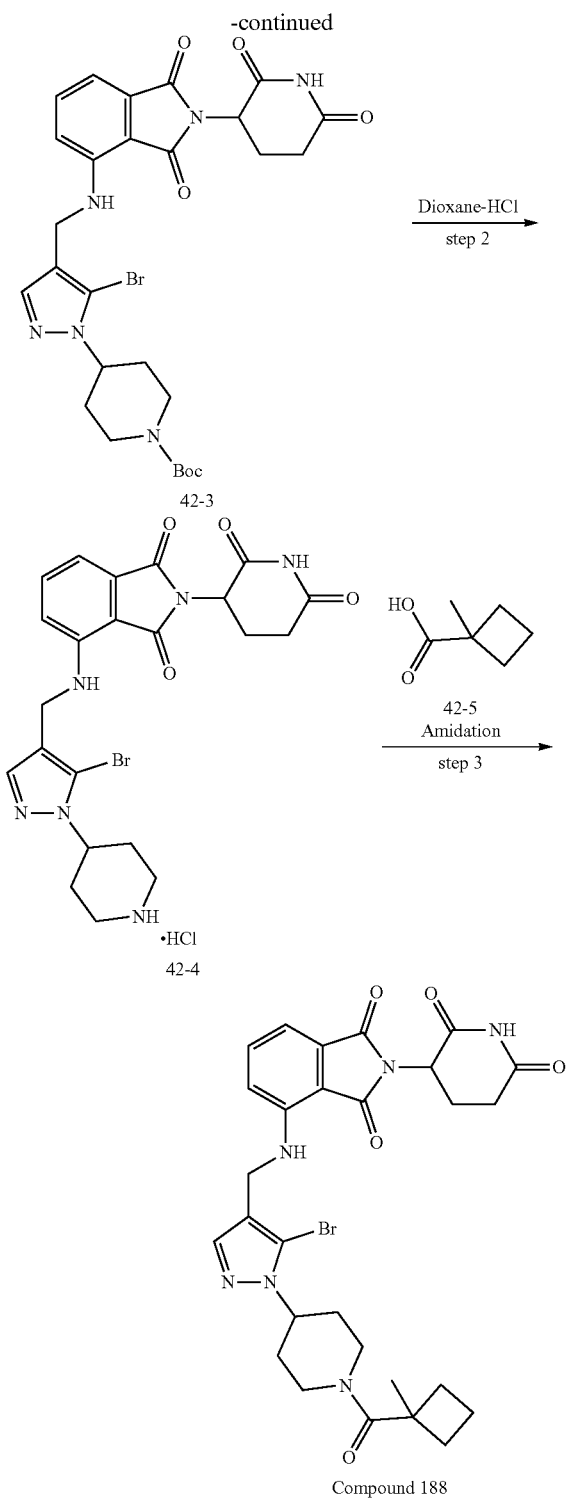

bromo-4-formyl-pyrazol-1-yl)piperidine-1-carboxylate 42-1 (131.10 mg, 365.97 umol) followed dibutyltin dichloride (133.44 mg, 439.17 umol, 98.12 uL) and phenylsilane (39.60 mg, 365.97 umol, 45.16 uL). Reaction mixture was heated at 80° C. for 16 hours and then concentrated to afford crude mass which was purified by column chromatography using (0%-20% EtOAc-DCM) to afford tert-butyl 4-[5-bromo-4-[[[2-(2,6-dioxo-3-piperidyl)-1,3-dioxo-isoindolin-4-yl]amino]methyl]pyrazol-1-yl]piperidine-1-carboxylate 42-3 (80 mg, 129.98 umol, 35.52% yield) as yellow solid. LC MS: ES+ 615.2, 617.5 (Bromo pattern).

Step-2: Preparation of 4-(((5-Bromo-1-(piperidin-4-yl)-1H-pyrazol-4-yl)methyl)amino)-2-(2,6-dioxopiperidin-3-yl)isoindoline-1,3-dione hydrochloride To a stirred solution of tert-butyl 4-[5-bromo-4-[[[2-(2,6-dioxo-3-piperidyl)-1,3-dioxo-isoindolin-4-yl]amino]methyl]pyrazol-1-yl]piperidine-1-carboxylate 42-3 (100 mg, 162.48 umol) in dioxane (2 mL), 4M Dioxane HCl (5 mL) was added dropwise at 0° C. Reaction mixture was then stirred at room temperature for 3 hours and then concentrated under reduced pressure, washed with ether and dried to afford 4-[[5-bromo-1-(4-piperidyl)pyrazol-4-yl]methylamino]-2-(2,6-dioxo-3-piperidyl)isoindoline-1,3-dione hydrochloride 42-4 (89 mg, 161.28 umol, 99.27% yield) as yellow solid. LC MS: ES+ 515.3, 515.3 (Bromo pattern).

Step-3: Preparation of 4-(((5-Bromo-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione To a stirred solution of 4-[[5-bromo-1-(4-piperidyl)pyrazol-4-yl]methylamino]-2-(2,6-dioxo-3-piperidyl)isoindoline-1,3-dione; hydrochloride 42-4 (100 mg, 181.22 umol) in DMF (2 mL) was added 1-methylcyclobutanecarboxylic acid 42-5 (20.68 mg, 181.22 umol, 18.47 uL) and the reaction mixture was cooled to 0° C. followed HATU (103.36 mg, 271.83 umol) and DIPEA (93.68 mg, 724.87 umol, 126.26 uL). Reaction mixture was allowed to stir at room temperature for 16 hours and was then diluted with water and extracted with ethyl acetate. Organic layer was washed with saturated sodium bicarbonate solution, water and brine, dried over sodium sulphate and concentrated under reduced pressure to afford the crude product. Crude product thus obtained was purified by column chromatography over silica gel eluting with 2.5-3% of MeOH in DCM to afford 4-[[5-bromo-1-[1-(1-methylcyclobutanecarbonyl)-4-piperidyl]pyrazol-4-yl]methylamino]-2-(2,6-dioxo-3 piperidyl)isoindoline-1,3-dione (Compound 188) (50 mg, 81.77 umol, 45.12% yield, 100% purity, 000) as yellow solid. $^1$H NMR (d6-DMSO, 400 MHZ) δ 11.09 (s, 1H), 7.64 (s, 1H), 7.59 (t, J=7.8 Hz, 1H), 7.13 (d, J=8.6 Hz, 1H), 7.06 (d, J=7.04 Hz, 1H), 6.80 (t, J=5.56 Hz, 1H), 5.04 (dd, J=12.8, 5.56 Hz, 1H), 4.57-4.50 (m, 1H), 4.45-4.41 (m, 1H), 4.34-4.33 (m, 2H), 3.64-3.62 (m, 1H), 3.18-3.16 (m, 1H), 2.92-2.83 (m, 1H), 2.74-2.72 (m, 1H), 2.60-2.55 (m, 2H), 2.43-2.32 (m, 2H), 2.07-1.99 (m, 1H), 1.96-1.66 (m, 8H), 1.65-0.9 (m, 1H), 1.35 (s, 3H); LC MS: ES+ 611.3, 613.3 (Bromo pattern).

Step-1: Preparation of tert-Butyl 4-(5-bromo-4-(((2-(2,6-dioxopiperidin-3-yl)-1,3-dioxoisoindolin-4-yl)amino)methyl)-1H-pyrazol-1-yl)piperidine-1-carboxylate To the stirred solution of 4-amino-2-(2,6-dioxo-3-piperidyl)isoindoline-1,3-dione 42-2 (100 mg, 365.97 umol) in THF (4 mL) in a sealed tube was added tert-butyl 4-(5-

Example 43. Final report of tert-Butyl 4-[5-(2-cyclopropyl-2-oxo-ethyl)-4-[[[2-(2,6-dioxo-3-piperidyl)-1,3-dioxo-isoindolin-4-yl]amino]methyl]pyrazol-1-yl]piperidine-1-carboxylate (Compound 189) and 4-(((5-(Cyclopropylethynyl)-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione (Compound 190)
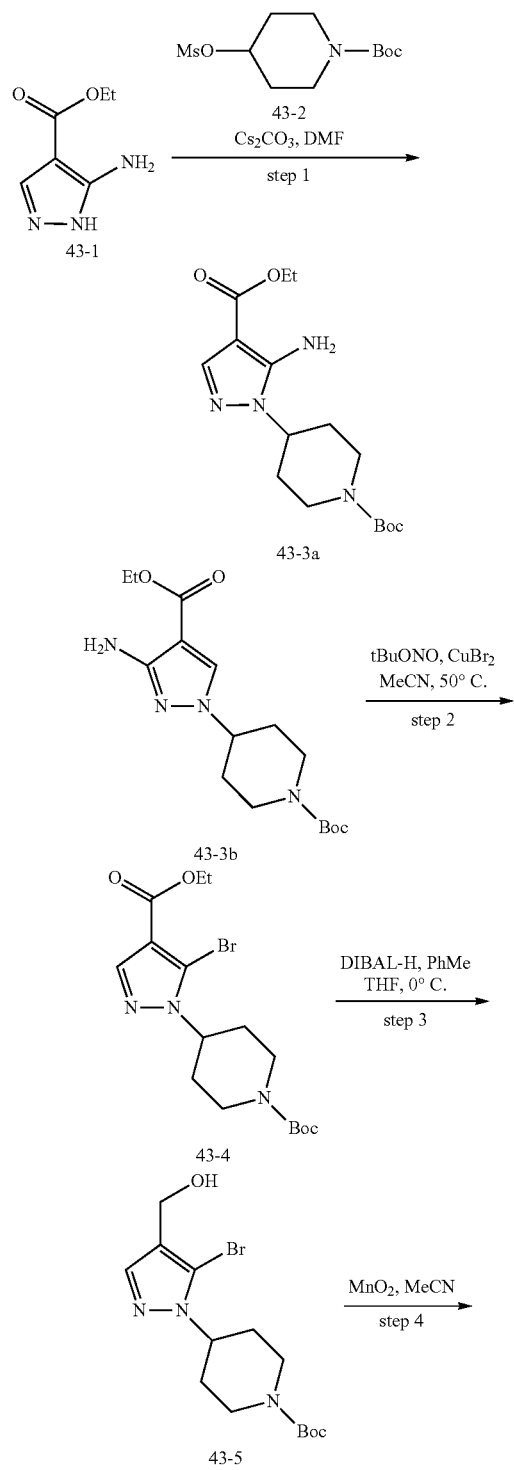
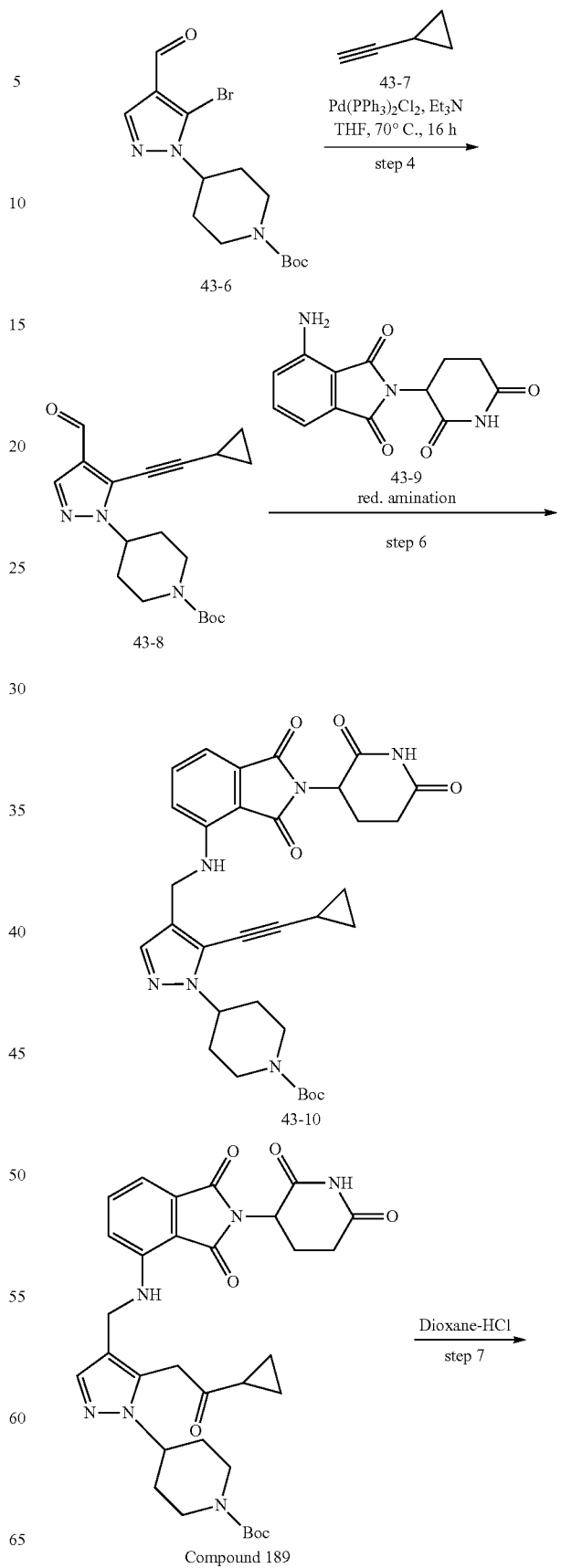

-continued

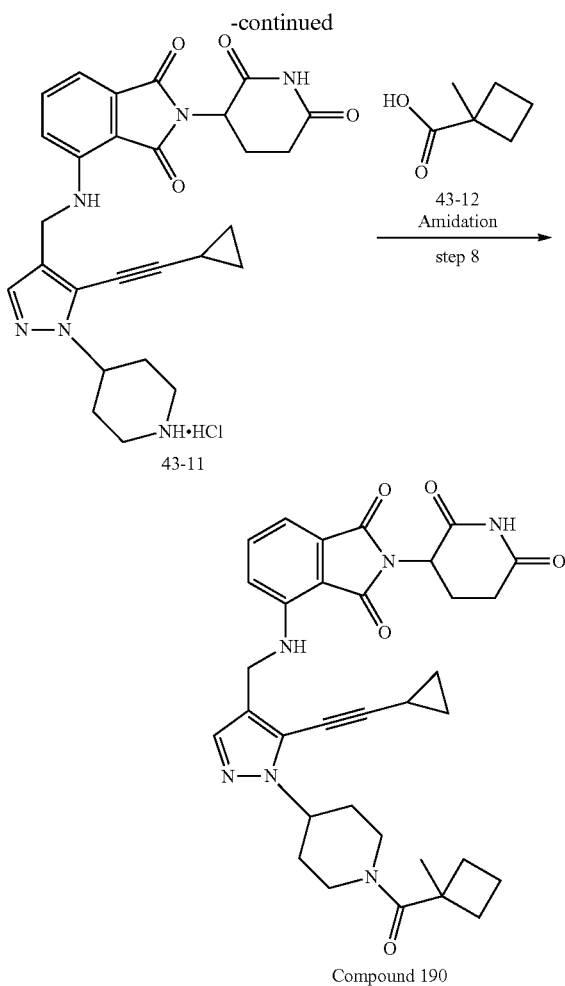

Compound 190

Step-1: Preparation of tert-Butyl 4-(5-amino-4-ethoxycarbonyl-pyrazol-1-yl)piperidine-1-carboxylate To a stirred solution of ethyl 5-amino-1H-pyrazole-4-carboxylate 43-1 (10 g, 64.45 mmol) in DMF (100 mL) tert-butyl 4-methylsulfonyloxypiperidine-1-carboxylate 43-2 (25.21 g, 90.23 mmol) and cesium carbonate (42.00 g, 128.90 mmol) were added. The reaction mixture was stirred at 80° C. for 16 hours and then diluted with ethyl acetate and washed with water. The organic layer was dried over sodium sulphate and concentrated under reduced pressure. Crude material was purified by column chromatography eluting 10% ethylacetate-DCM to afford tert-butyl 4-(5-amino-4-ethoxycarbonyl-pyrazol-1-yl)piperidine-1-carboxylate 43-3a (4.8 g, 14.18 mmol, 22.01% yield) and eluting 15% ethylacetate-DCM to afford the polar isomeric spot tert-butyl 4-(3-amino-4-ethoxycarbonyl-pyrazol-1-yl)piperidine-1-carboxylate 43-3b (3.0 g, 8.87 mmol, 13.75% yield) as off white solid. LC MS: ES+ 339.1.

Step-2: Preparation of tert-Butyl 4-(5-bromo-4-ethoxycarbonyl-pyrazol-1-yl)piperidine-1-carboxylate To the stirred solution of tert-butyl nitrite (2.10 g, 20.39 mmol, 2.43 mL) and cupric bromide (3.68 g, 16.31 mmol) in acetonitrile (50 mL) was added tert-butyl 4-(5-amino-4-ethoxycarbonyl-pyrazol-1-yl)piperidine-1-carboxylate 43-3a (4.6 g, 13.59 mmol) portionwise. The reaction mixture was stirred at room temperature for 2 hours and at 65° C. for 1 hour. Reaction mixture was cooled to room temperature, quenched with water, extracted with dichloromethane, dried over sodium sulfate and concentrated under reduced pressure. Crude material was purified by combiflash chromatography eluting at 1.2% methanol in dichloromethane to afford tert-butyl 4-(5-bromo-4-ethoxycarbonyl-pyrazol-1-yl)piperidine-1-carboxylate 43-4 (3.1 g, 7.71 mmol, 56.69% yield) as colourless gum. LC MS: ES+ 402.2 and 404.2 (Bromo pattern).

Step-3: Preparation of tert-Butyl 4-[5-bromo-4-(hydroxymethyl)pyrazol-1-yl]piperidine-1-carboxylate To the stirred solution of tert-butyl 4-(5-bromo-4-ethoxycarbonyl-pyrazol-1-yl)piperidine-1-carboxylate 43-4 (4.5 g, 11.19 mmol) in THF (30 mL) was added DIBAL-H (3.18 g, 22.37 mmol, 4.54 mL) at 0° C. drop wise. The reaction mixture was stirred at 0° C. for 30 minutes. The reaction was quenched with water, extracted with ethyl acetate, washed with water and brine, dried over sodium sulphate and concentrated under reduced pressure. The crude material was purified with column chromatography eluting at 1.5% methanol in dichloromethane to afford tert-butyl 4-[5-bromo-4-(hydroxymethyl)pyrazol-1-yl]piperidine-1-carboxylate 43-5 (3.1 g, 8.61 mmol, 76.93% yield) as colourless gum. LC MS: ES+ 360.1 and 362.1 (Bromo pattern).

Step-4: Preparation of tert-Butyl 4-(5-bromo-4-formyl-pyrazol-1-yl)piperidine-1-carboxylate To the stirred solution of tert-butyl 4-[5-bromo-4-(hydroxymethyl)pyrazol-1-yl]piperidine-1-carboxylate 43-5 (3.0 g, 8.33 mmol) in acetonitrile (20 mL) was added manganese dioxide (3.62 g, 41.64 mmol). The reaction mixture was stirred at room temperature for 16 hours and then filtered through celite, concentrated under reduced pressure and purified by combiflash eluting at 1% methanol in dichloromethane to afford tert-butyl 4-(5-bromo-4-formyl-pyrazol-1-yl)piperidine-1-carboxylate 43-6 (1800 mg, 5.02 mmol, 60.34% yield) as off white solid. LC MS: ES+ 358.0.

Step-5: Preparation of tert-Butyl 4-[5-(2-cyclopropylethynyl)-4-formyl-pyrazol-1-yl]piperidine-1-carboxylate To the stirred solution of tert-butyl 4-(5-bromo-4-formyl-pyrazol-1-yl)piperidine-1-carboxylate 43-6 (1000 mg, 2.79 mmol) in THF (10 mL) in a sealed tube was added cyclopropyl acetylene 43-7 (184.52 mg, 2.79 mmol, 236.26 uL) and triethyl amine (1.13 g, 11.17 mmol, 1.56 mL). The reaction mixture was degassed with argon for 10 minutes before bis(triphenylphosphine)palladium(II) dichloride (195.94 mg, 279.15 umol) and copper (I) iodide (53.16 mg, 279.15 umol, 9.46 uL) were added. Reaction mixture was heated at 80° C. for 16 hours and then cooled to room temperature, diluted with ethyl acetate, washed with water, brine, dried over sodium sulphate, and concentrated under reduced pressure. Crude material was purified by combiflash chromatography eluting at 1.5% methanol in dichloromethane to afford tert-butyl 4-[5-(2-cyclopropylethynyl)-4-formyl-pyrazol-1-yl]piperidine-1-carboxylate 43-8 (610 mg, 1.78 mmol, 63.63% yield) as brown gum. LC MS: ES+ 344.1.

Step-6: Preparation of tert-Butyl 4-[5-(2-cyclopropyl-2-oxo-ethyl)-4-[[[2-(2,6-dioxo-3-piperidyl)-1,3-dioxo-isoindolin-4-yl]amino]methyl]pyrazol-1-yl]piperidine-1-carboxylate To a stirred solution of tert-butyl 4-[5-(2-cyclopropyl-ethynyl)-4-formyl-pyrazol-1-yl]piperidine-1-carboxylate 43-8 (100 mg, 291.19 umol) and 4-amino-2-(2,6-dioxo-3-piperidyl)isoindoline-1,3-dione 43-9 (79.57 mg, 291.19 umol) were added phenylsilane (31.51 mg, 291.19 umol, 35.89 uL) and dibutyltin dichloride (106.17 mg, 349.43 umol, 78.07 uL) and the reaction mixture was heated at 80° C. for 16 hours. Reaction mixture was concentrated and crude material was purified by column chromatography using (0%-1.5% MeOH/DCM) to afford tert-butyl 4-[5-(2-cyclopropylethynyl)-4-[[[2-(2,6-dioxo-3-piperidyl)-1,3-dioxo-isoindolin-4-yl]amino]methyl]pyrazol-1-yl]piperidine-1-carboxylate 43-10 (30.0 mg, 49.94 umol, 17.15% yield) as yellow solid, LC MS: ES+ 601.4, along with one by-product tert-butyl 4-[5-(2-cyclopropyl-2-oxo-ethyl)-4-[[[2-(2,6-dioxo-3-piperidyl)-1,3-dioxo-isoindolin-4-yl]amino]methyl]pyrazol-1-yl]piperidine-1-carboxylate (Compound 189) (10 mg, 13.41 umol, 13.16% yield) as yellow solid. $^1$H NMR (d6-DMSO, 400 MHZ) δ 11.08 (s, 1H), 7.56 (t, J=7.78 Hz, 1H), 7.47 (s, 1H), 7.14 (d, J=8.56 Hz, 1H), 7.03 (d, J=7.04 Hz, 1H), 6.67 (t, J=5.44 Hz, 1H), 5.03 (dd, J=12.68, 5.48 Hz, 1H), 4.30-4.28 (m, 2H), 4.23 (s, 2H), 4.15-4.10 (m, 1H), 4.03-4.00 (m, 2H), 2.90-2.81 (m, 3H), 2.60-2.50 (m, 2H), 2.07-1.98 (m, 3H), 1.82-1.70 (m, 3H), 1.40 (s, 9H), 0.88-0.82 (m 4H); LC MS: ES+ 619.4.

Step-7: Preparation of 4-(((5-(Cyclopropylethynyl)-1-(piperidin-4-yl)-1H-pyrazol-4-yl)methyl)amino)-2-(2,6-dioxopiperidin-3-yl)isoindoline-1,3-dione hydrochloride To a stirred solution of tert-butyl 4-[5-(2-cyclopropylethynyl)-4-[[[2-(2,6-dioxo-3-piperidyl)-1,3-dioxo-isoindolin-4-yl]amino]methyl]pyrazol-1-yl]piperidine-1-carboxylate 43-10 (30 mg, 49.94 umol) in DCM (2 mL) was added TFA (740.00 mg, 6.49 mmol, 0.5 mL) slowly at 0° C. Reaction mixture was then stirred at room temperature for 2 hours. Volatiles were evaporated under reduced pressure triturated with ether to afford 4-(((5-(cyclopropylethynyl)-1-(piperidin-4-yl)-1H-pyrazol-4-yl)methyl)amino)-2-(2,6-dioxopiperidin-3-yl)isoindoline-1,3-dione hydrochloride (24 mg, 47.95 umol, 96.00% yield, 101) as off white solid that was used without further purification in the next step.

Step-8: Preparation of 4-(((5-(Cyclopropylethynyl)-1-(1-(1-methylcyclobutane-1-carbonyl)piperidin-4-yl)-1H-pyrazol-4-yl)methyl)amino)-2-(2,6-dioxopiperidin-3-yl)isoindoline-1,3-dione To a stirred solution of 1-methylcyclobutanecarboxylic acid 43-11(6.14 mg, 53.78 umol, 5.48 uL) in DMF (2 mL) was added 4-(((5-(cyclopropylethynyl)-1-(piperidin-4-yl)-1H-pyrazol-4-yl)methyl)amino)-2-(2,6-dioxopiperidin-3-yl)isoindoline-1,3-dione hydrochloride (30 mg, 48.89 umol). The reaction mixture was cooled 0° C. HATU (27.89 mg, 73.34 umol) and DIPEA (31.60 mg, 244.47 umol, 42.58 uL) were added. Reaction mixture was stirred at room temperature for 16 hours and then diluted with water and extracted with ethyl acetate. Organic layer was dried with sodium sulphate and evaporated under reduced pressure. Crude material was purified by preparative TLC (eluted with 4% MEOH/DCM to afford 4-[[5-(2-cyclopropylethynyl)-1-[1-(1-methylcyclobutanecarbonyl)-4-piperidyl]pyrazol-4-yl]methylamino]-2-(2,6-dioxo-3-piperidyl)isoindoline-1,3-dione (Compound 190) (10 mg, 16.73 umol, 34.22% yield, 99.82% purity, 000). 1H NMR (d6-DMSO, 400 MHZ) δ 11.09 (s, 1H), 7.57 (t, J=7.74 Hz, 1H), 7.49 (s, 1H), 7.12 (d, J=8.56 Hz, 1H), 7.04 (d, J=7.04 Hz, 1H), 6.86-6.84 (m, 1H), 5.05 (dd, J=12.04, 4.72 Hz, 1H), 4.56-4.50 (m, 1H), 4.45-4.44 (m, 1H), 4.39-4.36 (m, 2H), 3.65-3.63 (m, 1H), 3.15-3.13 (m, 1H), 2.92-2.85 (m, 1H), 2.72-2.70 (m, 1H), 2.60-2.55 (m, 2H), 2.40-2.32 (m, 2H), 2.02-2.00 (m, 1H), 1.96-1.78 (m, 6H), 1.66-1.63 (m 2H), 1.35 (s, 3H), 0.95-0.93 (m, 2H), 0.79-0.78 (m, 2H); LC MS: ES+ 597.8.

Example 44. Synthesis of 3-(4-(((3-Chloro-1-(1-(1-methylcyclobutane-1-carbonyl)piperidin-4-yl)-1H-pyrazol-4-yl)methyl)amino)-1,3-dioxo-2,3-dihydro-1H-inden-2-yl)piperidine-2,6-dione (Compound 191)

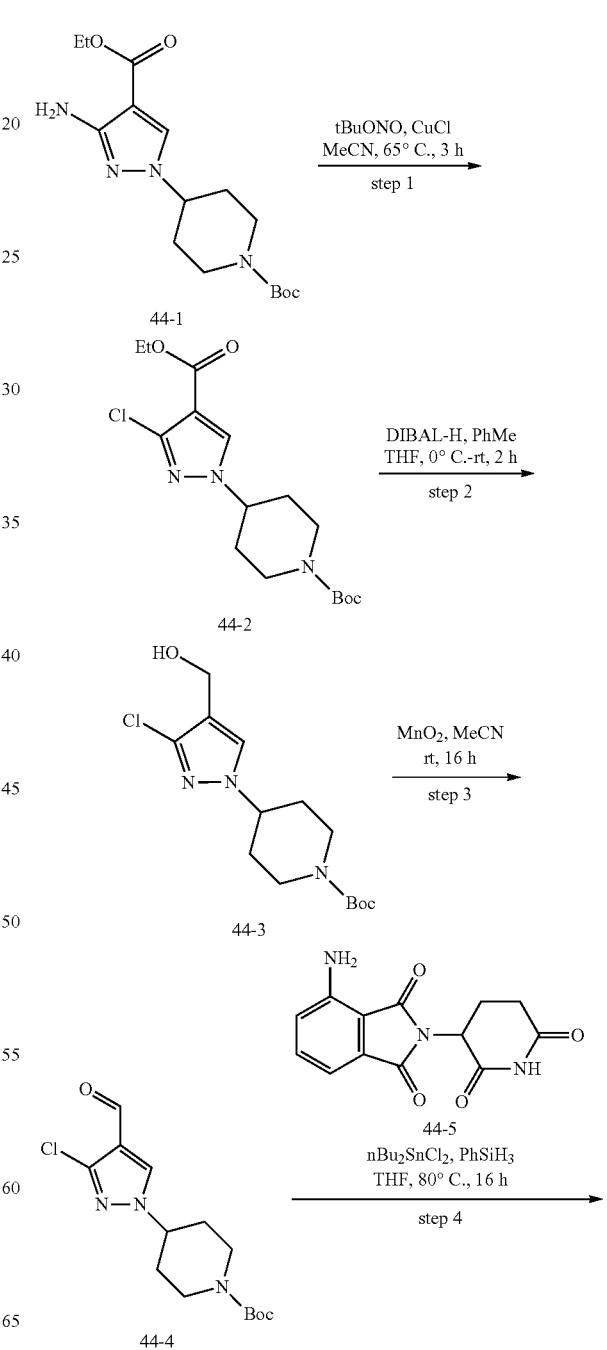

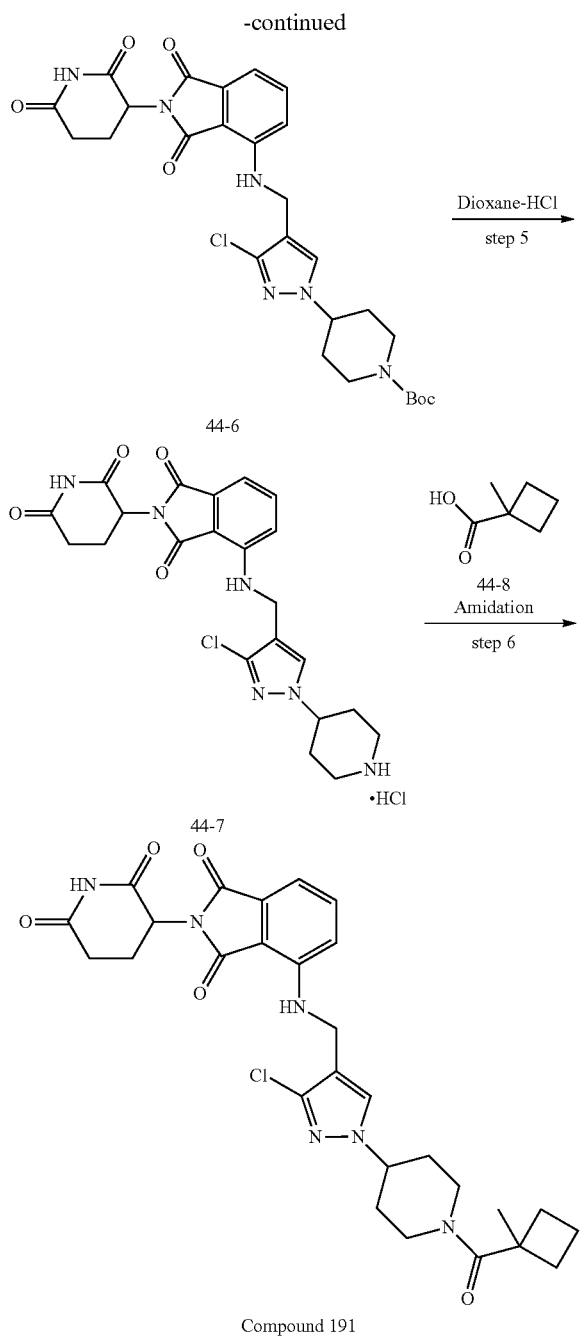

Compound 191

Step-1: Preparation of tert-Butyl 4-(3-chloro-4-(ethoxycarbonyl)-1H-pyrazol-1-yl)piperidine-1-carboxylate To a stirred solution of tert-butyl 4-(3-amino-4-ethoxycarbonyl-pyrazol-1-yl)piperidine-1-carboxylate 44-1 (2.1 g, 6.21 mmol) in acetonitrile (10.0 mL) was added tert-butyl nitrite, tech. 90% (959.89 mg, 9.31 mmol, 1.11 mL) at 0° C. and followed by CuCl (921.53 mg, 9.31 mmol). The reaction mixture was stirred at room temperature for 1 hour and then stirred for 2 hours at 65° C. Reaction mixture was then cooled to room temperature and diluted with ethyl acetate. Organic layer was separated and washed with water, saturated sodium bicarbonate solution, and brine solution, dried over sodium sulfate and concentrated under reduced pressure to afford the crude product. The crude material was then purified by column chromatography (eluting 1-1.5% MeOH-DCM) to afford tert-butyl 4-(3-chloro-4-ethoxycarbonyl-pyrazol-1-yl)piperidine-1-carboxylate 44-2 (1 g, 2.79 mmol, 45.03% yield) as gummy green liquid. LC MS: ES+ 358.3.

Step-2: Preparation of tert-Butyl 4-(3-chloro-4-(hydroxymethyl)-1H-pyrazol-1-yl)piperidine-1-carboxylate To a solution of tert-butyl 4-(3-chloro-4-ethoxycarbonyl-pyrazol-1-yl)piperidine-1-carboxylate 44-2 (2.73 g, 7.63 mmol) in THF (25.0 mL) at 0° C., DIBAL (13.02 g, 22.89 mmol, 18.57 mL, 25% purity) was added dropwise. The reaction mixture was stirred at room temperature for 2 hours. Reaction mixture was then quenched with water (20.0 ml) at 0° C. and the mixture was stirred at room temperature for 1 hour before being filtered through celite bed. The filtrate was separated and the organic part was dried over sodium sulfate and concentrated under reduced pressure. The crude material was purified by column chromatography (eluting 2-2.5% MeOH-DCM) to afford tert-butyl 4-[3-chloro-4-(hydroxymethyl)pyrazol-1-yl]piperidine-1-carboxylate 44-3 (800 mg, 2.53 mmol, 33.20% yield) as colourless liquid. LC MS: ES+ 316.2.

Step-3: Preparation of tert-Butyl 4-(3-chloro-4-formyl-1H-pyrazol-1-yl)piperidine-1-carboxylate To a stirred solution of tert-butyl 4-[3-chloro-4-(hydroxymethyl)pyrazol-1-yl]piperidine-1-carboxylate 44-3 (800 mg, 2.53 mmol) in DCM (10.0 mL) was added $MnO_2$ (2.20 g, 25.33 mmol) and the reaction mixture was stirred at room temperature for 16 hours. Reaction mixture was filtered through celite bed and the filtrate was concentrated under reduced pressure to afford the crude compound. The crude material was purified by column chromatography (eluting 2-2.5% MeOH in DCM) to afford tert-butyl 4-(3-chloro-4-formyl-pyrazol-1-yl)piperidine-1-carboxylate 44-4 (600 mg, 1.91 mmol, 75.48% yield) as white solid. LC MS: ES+ 314.2.

Step-4: Preparation of tert-Butyl 4-(3-chloro-4-(((2-(2,6-dioxopiperidin-3-yl)-1,3-dioxo-2,3-dihydro-1H-inden-4-yl)amino)methyl)-1H-pyrazol-1-yl)piperidine-1-carboxylate To a solution of tert-butyl 4-(3-chloro-4-formyl-pyrazol-1-yl)piperidine-1-carboxylate 44-4 (300 mg, 956.09 umol) in THF (5.0 mL) was added 4-amino-2-(2,6-dioxo-3-piperidyl)isoindoline-1,3-dione 44-5 (261.25 mg, 956.09 umol). Phenylsilane (103.46 mg, 956.09 umol, 117.97 uL) and dibutyltindichloride (348.60 mg, 1.15 mmol, 256.33 uL) were added to the reaction mixture and the reaction mixture was heated at 80° C. for 16 hours. Reaction mixture was cooled to room temperature, filtered through a celite bed and the filtrate was concentrated under reduced pressure to afford the crude product. The crude material was purified by column chromatography (eluting 1.5-2% MeOH in DCM) to afford tert-butyl 4-[3-chloro-4-[[[2-(2,6-dioxo-3-piperidyl)-1,3-dioxo-isoindolin-4-yl]amino]methyl]pyrazol-1-yl]piperidine-1-carboxylate 44-6 (140 mg, 245.17 umol, 25.64% yield) as yellow solid. LC MS: ES+ 571.3.

Step-5: Preparation of 3-(4-(((3-Chloro-1-(piperidin-4-yl)-1H-pyrazol-4-yl)methyl)amino)-1,3-dioxo-2,3-dihydro-1H-inden-2-yl)piperidine-2,6-dione hydrochloride To a solution of tert-butyl 4-[3-chloro-4-[[[2-(2,6-dioxo-3-piperidyl)-1,3-dioxo-isoindolin-4-yl]amino]methyl]pyrazol-1-yl]piperidine-1-carboxylate 44-6 (130 mg, 227.66 umol) in dioxane (3.0 mL) was added dioxane-HCl (227.66 umol, 6 mL) and the reaction mixture was stirred at room temperature for 2 hours. Reaction mixture was concentrated under reduced pressure and triturated with diethyl ether to afford 3-(4-(((3-chloro-1-(piperidin-4-yl)-1H-pyrazol-4-yl)methyl)amino)-1,3-dioxo-2,3-dihydro-1H-inden-2-yl)piperidine-2,6-dione hydrochloride 44-7 (140 mg, 275.93 umol, 121.20% yield, Crude purity). LC MS: ES+ 471.5.

Step-6: Preparation of 3-(4-(((3-Chloro-1-(1-(1-methylcyclobutane-1-carbonyl)piperidin-4-yl)-1H-pyrazol-4-yl)methyl)amino)-1,3-dioxo-2,3-dihydro-1H-inden-2-yl)piperidine-2,6-dione To the stirred solution of 4-[[3-chloro-1-(1-chloro-4-piperidyl)pyrazol-4-yl]methylamino]-2-(2,6-dioxo-3-piperidyl)isoindoline-1,3-dione 44-7 (140.28 mg, 276.48 umol) and 1-methylcyclobutanecarboxylic acid (31.56 mg, 276.48 umol) in DMF (8.0 mL) was added HATU (157.69 mg, 414.72 umol) followed by DIPEA (178.67 mg, 1.38 mmol, 240.79 uL) at 0° C. Reaction mixture was stirred at room temperature for 16 hours and was then diluted with ethyl acetate, washed with water, saturated aqueous sodium bicarbonate solution, dried over sodium sulfate, and concentrated under reduced pressure to afford the crude compound. Crude was then purified by column chromatography (eluting 2-2.5% MeOH in DCM) to afford 4-[[3-chloro-1-[1-(1-methylcyclobutanecarbonyl)-4-piperidyl]pyrazol-4-yl]methylamino]-2-(2,6-dioxo-3-piperidyl)isoindoline-1,3-dione (Compound 191) (50 mg, 83.77 umol, 30.30% yield, 95% purity, 000) as yellow solid. 1H NMR (d6-DMSO, 400 MHZ) 11.08 (s, 1H), 7.90 (s, 1H), 7.59 (t, J=7.82 Hz, 1H), 7.11 (d, J=8.6 Hz, 1H), 7.06 (d, J=7.04 Hz, 1H), 6.80 (t, J=5.94 Hz, 1H), 5.05 (dd, J=12.88, 5.52 Hz, 1H), 4.39-4.32 (m, 4H), 3.62-3.58 (m, 1H), 3.07-3.05 (m, 1H), 2.92-2.83 (m, 1H), 2.66-2.55 (m, 2H), 2.42-2.30 (m, 2H), 2.03-1.87 (m, 4H), 1.81-1.78 (m, 3H), 1.65-1.57 (m, 2H), 1.34 (s, 3H); LC MS: ES+ 567.4.

Example 45. Synthesis of 2-(2,6-Dioxopiperidin-3-yl)-4-(((5-ethynyl-1-(1-(1-methylcyclobutane-1-carbonyl)piperidin-4-yl)-1H-pyrazol-4-yl)methyl)amino)isoindoline-1,3-dione (Compound 192)

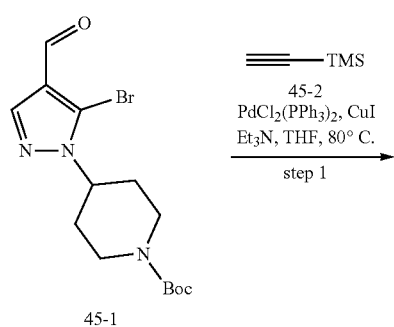

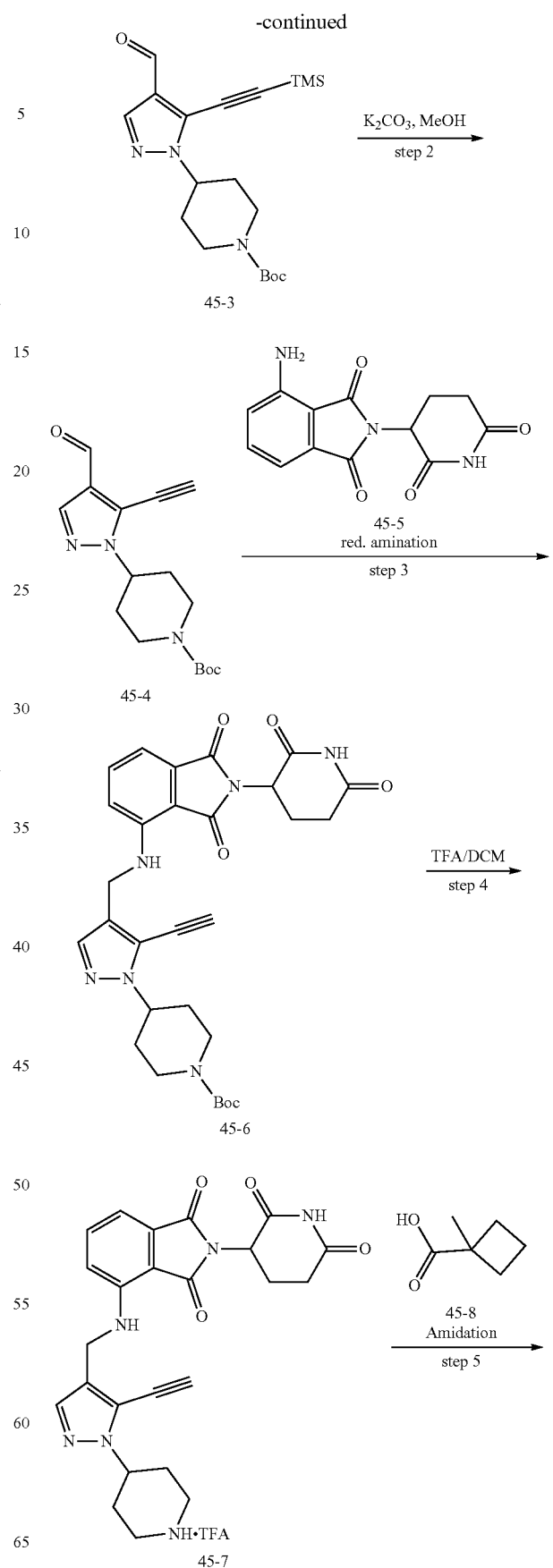

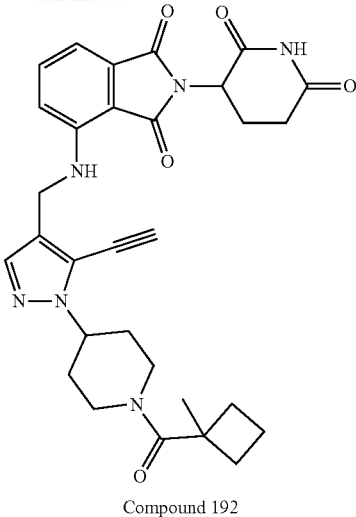

Compound 192

Step-1: Preparation of tert-Butyl 4-(4-formyl-5-((trimethylsilyl)ethynyl)-1H-pyrazol-1-yl)piperidine-1-carboxylate To the stirred solution of tert-butyl 4-(5-bromo-4-formyl-pyrazol-1-yl)piperidine-1-carboxylate 45-1 (500 mg, 1.40 mmol) in THF (5 mL) in a sealed tube was added TMS acetylene 45-2 (137.09 mg, 1.40 mmol, 197.25 uL) and triethylamine (564.94 mg, 5.58 mmol, 778.16 uL). The reaction mixture was degassed with argon for 10 minutes before bis(triphenylphosphine)palladium(II) dichloride (97.97 mg, 139.58 umol) and copper (I) iodide (26.58 mg, 139.58 umol, 4.73 uL) were added to the reaction mixture and reaction mixture was heated at 80° C. for 16 hours. Reaction mixture was cooled to room temperature, diluted with ethyl acetate and water. Layers were separated and the organic part was washed with water, brine, dried over sodium sulfate, and concentrated under reduced pressure. Crude material was purified by combiflash chromatography (eluting at 20-30% EtOAc-Hexane) to afford tert-butyl 4-[4-formyl-5-(2-trimethylsilylethynyl)pyrazol-1-yl]piperidine-1-carboxylate 45-3 (380 mg, 1.01 mmol, 72.50% yield) as brown gum. LC MS: ES+ 376.0.

Step-2: Preparation of tert-Butyl 4-(5-ethynyl-4-formyl-1H-pyrazol-1-yl)piperidine-1-carboxylate To a stirred solution of tert-butyl 4-[4-formyl-5-(2-trimethylsilylethynyl)pyrazol-1-yl]piperidine-1-carboxylate 45-3 (700 mg, 1.86 mmol) in methanol (5 mL) was added potassium carbonate (515.25 mg, 3.73 mmol, 225.00 uL) at 0° C. Reaction mixture was stirred at room temperature for 2 hours. Reaction mixture was diluted with EtOAc and water and layers were separated. The organic layer was washed with water, brine, dried over $Na_2SO_4$ and concentrated under reduced pressure to afford crude mass which was purified by column chromatography (using 30-40% EtOAc-Hexane) as eluent to afford tert-butyl 4-(5-ethynyl-4-formyl-pyrazol-1-yl)piperidine-1-carboxylate 45-4 (400 mg, 1.32 mmol, 70.74% yield) as brown semi solid. LC MS: ES+ 248.4 (−56 fragment for tertbutyl).

Step-3: Preparation of tert-Butyl 4-(4-(((2-(2,6-di-oxopiperidin-3-yl)-1,3-dioxoisoindolin-4-yl)amino)methyl)-5-ethynyl-1H-pyrazol-1-yl)piperidine-1-carboxylate To a stirred solution of 4-amino-2-(2,6-dioxo-3-piperidyl)isoindoline-1,3-dione 45-5 (270.22 mg, 988.94 umol) in THF (8 mL) in a sealed tube was added tert-butyl 4-(5-ethynyl-4-formyl-pyrazol-1-yl)piperidine-1-carboxylate 45-4 (300 mg, 988.94 umol) followed by dibutyltin dichloride (360.59 mg, 1.19 mmol, 265.14 uL) and phenylsilane (107.01 mg, 988.94 umol, 122.02 uL). The reaction mixture was then heated at 80° C. for 16 hours. Reaction mixture was concentrated under reduced pressure to afford crude mass which was purified by column chromatography (using 10% EtOAc in DCM) as eluent to afford tert-butyl 4-[4-[[[2-(2,6-dioxo-3-piperidyl)-1,3-dioxo-isoindolin-4-yl]amino]methyl]-5-ethynyl-pyrazol-1-yl]piperidine-1-carboxylate 45-6 (150 mg, 267.57 umol, 27.06% yield) as yellow solid. LC MS: ES+ 561.5.

Step-4: Preparation of 2,2,2-Trifluoroacetaldehyde compound with 2-(2,6-dioxopiperidin-3-yl)-4-(((5-ethynyl-1-(piperidin-4-yl)-1H-pyrazol-4-yl)methyl)amino)isoindoline-1,3-dione (1:1)

To a stirred solution of tert-butyl 4-[4-[[[2-(2,6-dioxo-3-piperidyl)-1,3-dioxo-isoindolin-4-yl]amino]methyl]-5-ethynyl-pyrazol-1-yl]piperidine-1-carboxylate 45-6 (150 mg, 267.57 umol) in DCM (6 mL) was added TFA (2 mL) at 0° C. Reaction mixture was then stirred for 3 hours at room temperature. Reaction mixture was concentrated under reduced pressure and washed with ether and dried to afford 2-(2,6-dioxo-3-piperidyl)-4-[[5-ethynyl-1-(4-piperidyl)pyrazol-4-yl]methylamino]isoindoline-1,3-dione, TFA salt 7 (120 mg, 260.60 umol, 97.39% yield) as yellow solid. LC MS: ES+ 461.2.

Step-5: Preparation of 2-(2,6-Dioxopiperidin-3-yl)-4-(((5-ethynyl-1-(1-(1-methylcyclobutane-1-carbonyl)piperidin-4-yl)-1H-pyrazol-4-yl)methyl)amino)isoindoline-1,3-dione To a stirred solution of 2-(2,6-dioxo-3-piperidyl)-4-[[5-ethynyl-1-(4-piperidyl)pyrazol-4-yl]methylamino]isoindoline-1,3-dione; 2,2,2-trifluoroacetic acid 45-7 (120 mg, 208.87 umol) in DMF (3 mL) was added 1-methylcyclobutanecarboxylic acid (23.84 mg, 208.87 umol, 21.29 uL) followed by HATU (119.13 mg, 313.31 umol) and the reaction mixture was cooled to 0° C. DIPEA (107.98 mg, 835.50 umol, 145.53 uL) was added to the reaction mixture and stirred at room temperature for 16 hours. Reaction mixture was diluted with water and was extracted with ethyl acetate. Organic layer was washed with saturated sodium bicarbonate solution, water and brine, dried over sodium sulphate, and concentrated under reduced pressure to afford the crude product. The crude material thus obtained was purified by preparative TLC (eluting with 2% of MeOH in DCM) to afford 2-(2,6-dioxo-3-piperidyl)-4-[[5-ethynyl-1-[1-(1-methylcyclobutanecarbonyl)-4-piperidyl]pyrazol-4-yl]methylamino]isoindoline-1,3-dione (Compound 192) (40 mg, 68.27 umol, 32.68% yield, 95% purity, 000) as yellow solid. 1H NMR (d6-DMSO, 400 MHZ) δ 11.08 (s, 1H), 7.59-7.54 (m, 2H), 7.12 (d, J=8.6 Hz, 1H), 7.05 (d, J=7.08 Hz, 1H), 6.86 (t, J=5.58 Hz, 1H), 5.09 (s, 1H), 5.04 (dd, J=12.76, 5.32 Hz, 1H), 4.60-4.58 (m, 1H), 4.43-4.41 (m, 3H), 3.63-3.61 (m, 1H), 3.16-3.15 (m, 1H), 2.92-2.84 (m, 1H), 2.73-2.71 (m, 1H), 2.66-2.55 (m, 2H), 2.43-2.32 (m, 2H), 2.04-2.01 (m, 1H), 1.95-1.85 (m, 4H), 1.82-1.77 (m, 3H), 1.66-1.60 (m, 1H), 1.35 (s, 3H); LC MS: ES+ 557.5.

Example 46. Synthesis of 4-(((1-(1-Benzylpiperidin-4-yl)-1H-pyrazol-4-yl)methyl)amino)-2-(2,6-dioxopiperidin-3-yl)isoindoline-1,3-dione (Compound 193)

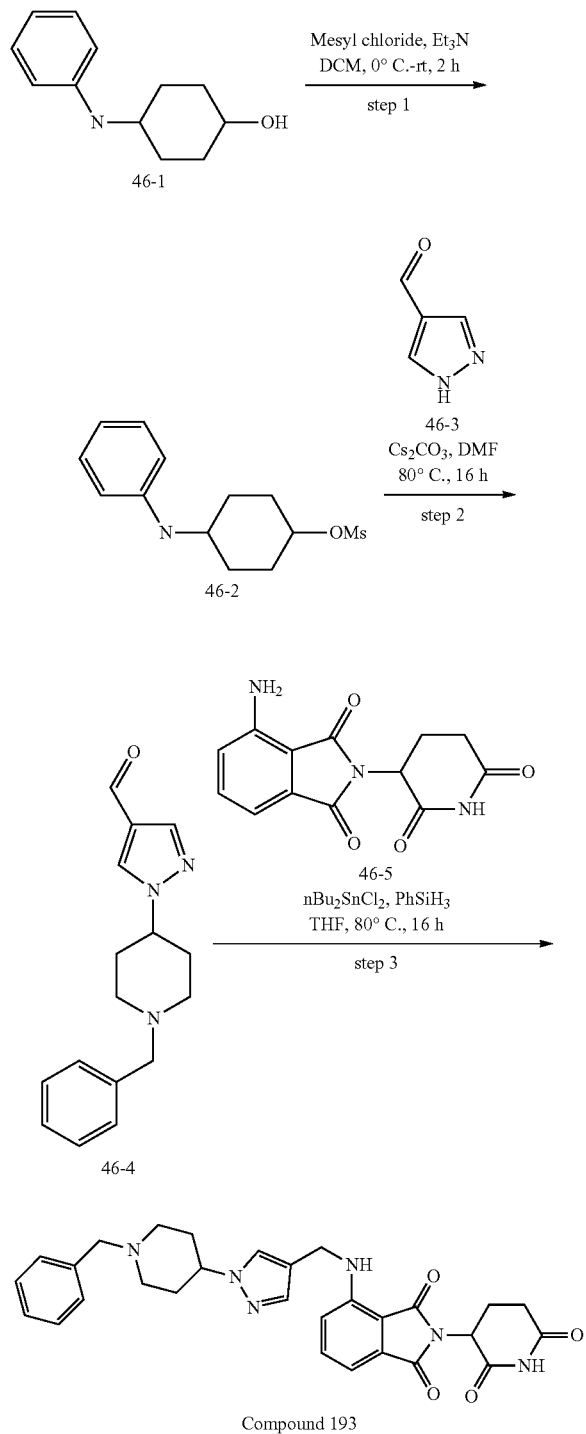

Step-1: Preparation of 1-Benzylpiperidin-4-yl methanesulfonate

To the stirred solution of 1-benzylpiperidin-4-ol 46-1 (1 g, 5.23 mmol) in DCM (20 mL) was added triethyl amine (1.32 g, 13.07 mmol, 1.82 mL) followed by methanesulfonyl chloride (718.67 mg, 6.27 mmol, 485.59 uL) at 0° C. The reaction mixture was stirred at room temperature for 4 hours. Reaction mixture was diluted with DCM, washed with water and brine, dried over sodium sulfate and concentrated under reduced pressure to afford (1-benzyl-4-piperidyl) methanesulfonate 46-2 (1.35 g, 5.01 mmol, 95.86% yield) as gum. LC MS: ES+ 269.9.

Step-2: Preparation of 1-(1-Benzyl-piperidin-4-yl)-1H-pyrazole-4-carbaldehyde

To the stirred solution of 1H-pyrazole-4-carbaldehyde 46-3 (461.54 mg, 4.80 mmol) and (1-benzyl-4-piperidyl) methanesulfonate 46-2 (1.2 g, 4.46 mmol) in DMF (20 mL) was added cesium carbonate (3.35 g, 10.28 mmol). Reaction mixture was heated at 80° C. for 16 hours and was then cooled to room temperature, diluted with ethyl acetate, washed with water and brine, dried over sodium sulfate and concentrated under reduced pressure. Crude material was purified by combiflash chromatography eluting at 0.1% methanol in dichloromethane to afford 1-(1-benzyl-4-piperidyl)pyrazole-4-carbaldehyde 46-4 (650 mg, 2.41 mmol, 70.42% yield) as brown gum. LC MS: ES+ 269.8.

Step-3: Preparation of 4-(((1-(1-Benzylpiperidin-4-yl)-1H-pyrazol-4-yl)methyl)amino)-2-(2,6-dioxopiperidin-3-yl)isoindoline-1,3-dione To the stirred solution of 1-(1-benzyl-4-piperidyl)pyrazole-4-carbaldehyde 46-4 (100 mg, 371.28 umol) and 4-amino-2-(2,6-dioxo-3-piperidyl)isoindoline-1,3-dione 46-5 (92.23 mg, 337.52 umol) in THF (5 mL) was added dibutyltindichloride (153.84 mg, 506.29 umol, 113.11 uL) followed by phenylsilane (109.57 mg, 1.01 mmol, 124.80 uL) and the reaction mixture was heated at 80° C. in a sealed tube for 16 hours. The reaction was diluted with water, extracted with ethyl acetate, washed with water and brine and dried over sodium sulfate. Crude material was purified by combiflash chromatography eluting at 1.5% methanol in dichloromethane and further purified by preparative TLC (3.5% methanol in dichloromethane) to afford 4-[[1-(1-benzyl-4-piperidyl)pyrazol-4-yl]methylamino]-2-(2,6-dioxo-3-piperidyl)isoindoline-1,3-dione (Compound 193) (6.0 mg, 11.06 umol, 3.28% yield, 97.05% purity, 000) as yellow solid. $^1$H NMR (d6-DMSO, 400 MHZ) δ 11.07 (s, 1H), 7.77 (s, 1H), 7.57 (t, J=7.64 Hz, 1H), 7.44 (s, 1H), 7.31-7.29 (br s, 4H), 7.25-7.23 (m, 1H), 7.15 (d, J=8.6 Hz, 1H), 7.03 (d, J=6.8 Hz, 1H), 6.79-6.78 (m, 1H), 5.05-5.03 (m, 1H), 4.36-4.34 (m, 2H), 4.10-4.08 (m, 1H), 3.48 (s, 2H), 2.88-2.84 (m, 3H), 2.59-2.55 (m, 2H), 2.10-2.00 (m, 3H), 1.92-1.86 (m, 4H); LC MS: ES+ 526.8.

Example 47. Synthesis of Preparation of 4-(((2-(2,6-Dioxopiperidin-3-yl)-1,3-dioxoisoindolin-4-yl)amino)methyl)-1-(1-(1-methylcyclobutane-1-carbonyl)piperidin-4-yl)-1H-pyrazole-5-carbonitrile (Compou 194)

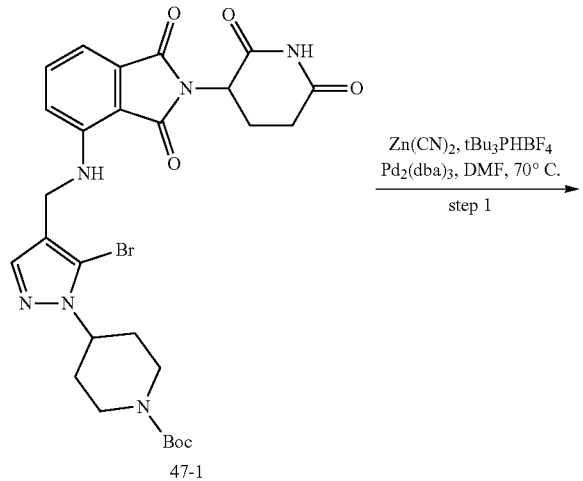

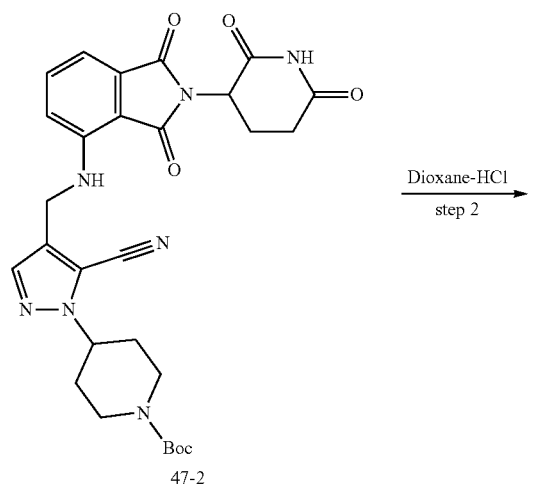

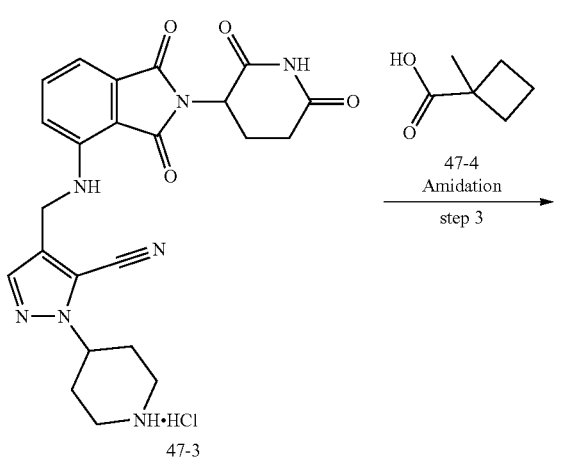

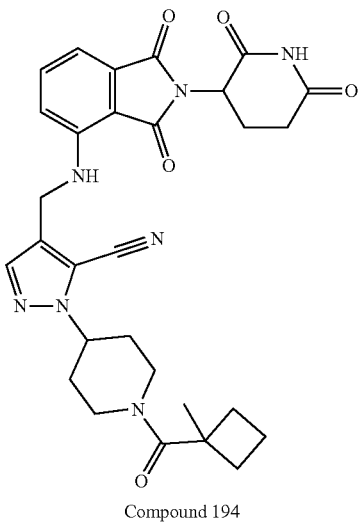 [SMILES: CC1(C(=O)N2CCC(n3ncc(CNc4cccc5c4C(=O)N(C4CCC(=O)NC4=O)C5=O)c3C#N)CC2)CCC1]

Compound 194

Step-1: Preparation of tert-Butyl 4-(5-cyano-4-(((2-(2,6-dioxopiperidin-3-yl)-1,3-dioxoisoindolin-4-yl)amino)methyl)-1H-pyrazol-1-yl)piperidine-1-carboxylate To a stirred solution of tert-butyl 4-[4-bromo-5-[[[2-(2,6-dioxo-3-piperidyl)-1,3-dioxo-isoindolin-4-yl]amino]methyl]-1H-imidazol-2-yl]piperidine-1-carboxylate 47-1 (170 mg, 276.21 umol) in DMF (1 mL) was added zinc cyanide (64.87 mg, 552.42 umol, 35.06 uL). Reaction mixture was degassed with argon followed by the addition of (1E,4E)-1,5-diphenylpenta-1,4-dien-3-one palladium (25.29 mg, 27.62 umol) and [[(CH₃)₃C]₃Ph]BF₄ (16.03 mg, 55.24 umol). Then the reaction mass was stirred at 70° C. for 16 hours. Crude LCMS confirmed product formation. Reaction mixture was filtered through celite bed and extracted with ethyl acetate. The organic layer was washed with brine, dried over sodium sulphate, concentrated under reduced pressure to afford crude tert-butyl 4-[4-cyano-5-[[[2-(2,6-dioxo-3-piperidyl)-1,3-dioxo-isoindolin-4-yl]amino]methyl]-1H-imidazol-2-yl]piperidine-1-carboxylate 47-2 (150 mg, 267.10 umol, 96.70% yield). Crude mass was forwarded to next step. LC MS: ES+ 561.4.

Step-2: Preparation of 4-(((2-(2,6-Dioxopiperidin-3-yl)-1,3-dioxoisoindolin-4-yl)amino)methyl)-1-(piperidin-4-yl)-1H-pyrazole-5-carbonitrile hydrochloride To a stirred solution of tert-butyl 4-[5-cyano-4-[[[2-(2,6-dioxo-3-piperidyl)-1,3-dioxo-isoindolin-4-yl]amino]methyl]pyrazol-1-yl]piperidine-1-carboxylate 47-2 (220 mg, 391.75 umol) in 1,4 dioxane (1 mL) was added dioxane-HCl (4M) (1 mL) and the reaction mass was stirred at room temperature for 2 hours. Reaction mass was evaporated under reduced pressure and washed with diethyl ether to afford 4-[[[2-(2,6-dioxo-3-piperidyl)-1,3-dioxo-isoindolin-4-yl]amino]methyl]-2-(4-piperidyl)pyrazole-3-carbonitrile; hydrochloride 47-3 (180 mg, 361.49 umol, 92.28% yield) as yellow solid. Crude was forwarded to next step.

Step-3: Preparation of 4-(((2-(2,6-Dioxopiperidin-3-yl)-1,3-dioxoisoindolin-4-yl)amino)methyl)-1-(1-(1-methylcyclobutane-1-carbonyl)piperidin-4-yl)-1H-pyrazole-5-carbonitrile To a stirred solution of 4-[[[2-(2,6-dioxo-3-piperidyl)-1,3-dioxo-isoindolin-4-yl]amino]methyl]-2-(4-piperidyl)pyrazole-3-carbonitrile; hydrochloride 47-3 (180.36 mg, 362.21 umol) in DMF (2 mL) were added 1-methylcyclobutanecarboxylic acid 47-4 (45.48 mg, 398.43 umol), HATU (206.58 mg, 543.31 umol) and DIPEA (234.06 mg, 1.81 mmol, 315.44 uL) at 0° C. and the reaction mixture was stirred at room temperature for 16 hours. Reaction mixture was diluted with ethyl acetate and water. Layers were separated and the organic layer was washed with saturated NaHCO₃ solution, water, and brine, dried over sodium sulfate, and concentrated to afford the crude material that was purified by preparative TLC Plate (eluting with 3% Methanol/DCM) to afford 4-[[[2-(2,6-dioxo-3-piperidyl)-1,3-dioxo-isoindolin-4-yl]amino]methyl]-2-[1-(1-methylcyclobutanecarbonyl)-4-piperidyl]pyrazole-3-carbonitrile Compound 194 (25.0 mg, 44.84 umol, 12.38% yield, 100% purity, 000) as yellow solid. $^1$H NMR (d6-DMSO, 400 MHZ) δ 11.08 (br s, 1H), 7.74 (s, 1H), 7.57 (t, J=7.82 Hz, 1H), 7.12-7.06 (m, 3H), 5.06 (dd, J=12.8, 5.0 Hz, 1H), 4.69-4.62 (m, 1H), 4.58-4.57 (m, 2H), 4.45-4.42 (m, 1H), 3.64-3.62 (m, 1H), 3.18-3.16 (m, 1H), 2.93-2.85 (m, 1H), 2.75-2.73 (m, 1H), 2.60-2.53 (m, 2H), 2.44-2.32 (m, 2H), 2.06-1.97 (m, 3H), 1.95-1.85 (m, 2H), 1.82-1.77 (m, 3H), 1.63-1.60 (m, 1H), 1.35 (s, 3H); LC MS: ES+ 558.3.

Example 48. Synthesis of 4-[[1-[1-(Cubane-1-carbonyl)-4-methyl-4-piperidyl]pyrazol-4-yl]methylamino]-2-(2,6-dioxo-3-piperidyl)isoindoline-1,3-dione (Compound 195)

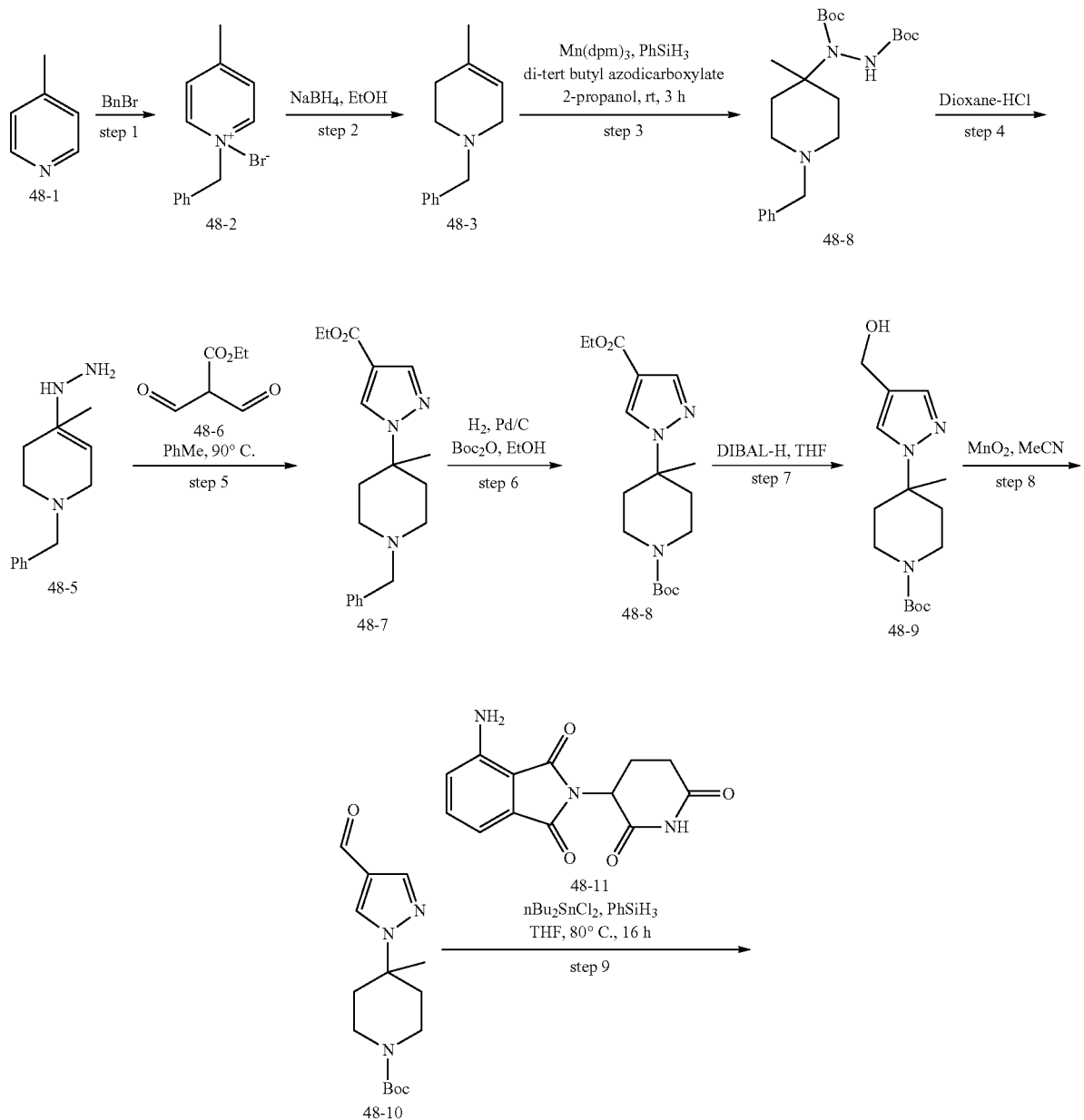

-continued

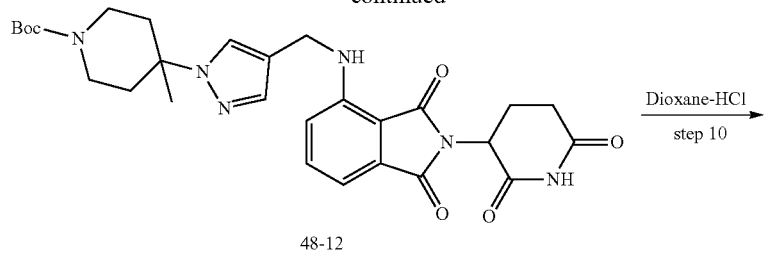

48-12

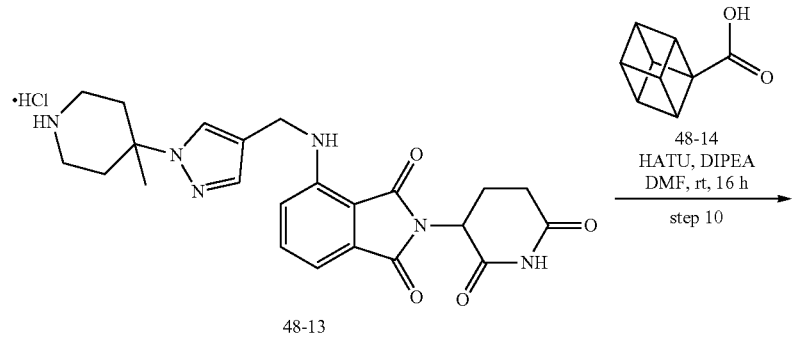

48-13

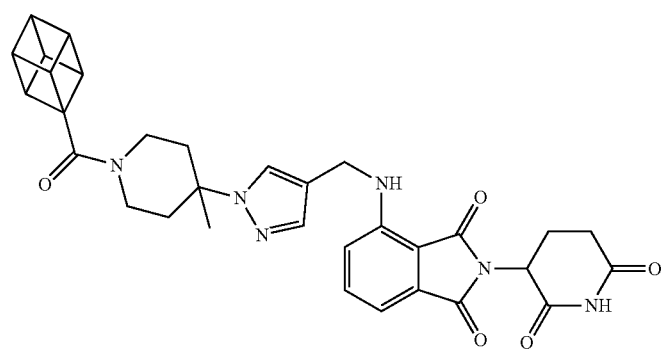

Compound 195

Step 1: Preparation of 1-Benzyl-1-bromo-4-methyl-pyridinium bromide

To a solution of 4-methylpyridine (20 g, 214.76 mmol, 20.90 mL) in dry grade acetonitrile (100 mL), benzyl bromide (44.08 g, 257.71 mmol, 30.61 mL) was added at room temperature and the resultant reaction mixture was heated at 100° C. for 12 hours. After completion of reaction (monitored by TLC), volatiles were removed under vacuum and the solid thus obtained was triturated with ethyl acetate and ether to obtain 1-benzyl-1-bromo-4-methyl-pyridine 48-2 (56 g, 211.99 mmol, 98.71% yield) as yellowish solid. LC MS: ES+ 183.9.

Step 2: Preparation of 1-Benzyl-4-methyl-3,6-dihydro-2H-pyridine

To the stirred solution of 1-benzyl-1-bromo-4-methyl-pyridinium bromide 48-2 (56.0 g, 211.99 mmol) in a mixed solvent of EtOH (72 mL) and water (8 mL), sodium borohydride (20.05 g, 529.98 mmol, 18.74 mL) was added portionwise at 0° C. After complete addition, the reaction mass was stirred for 12 hours at ambient temperature. After completion of the reaction as monitored by LCMS, the reaction mixture was quenched with water (30 mL) and the ethanol was removed under reduced pressure. The aqueous part was extracted with ethyl acetate (2×200 ml). The combined organic parts were dried over anhydrous Na$_2$SO$_4$ and concentrated under vacuum. The crude residue was purified by column chromatography (100-200 silica; 2% EtOAc in hexane) to afford 1-benzyl-4-methyl-3,6-dihydro-2H-pyridine 48-3 (39.3 g, 209.85 mmol, 98.99% yield) yellow oil. LC MS: ES+ 187.8.

Step 3: Preparation of tert-Butyl N-(1-benzyl-4-methyl-4-piperidyl)-N-(tert-butoxycarbonylamino) carbamate To a degassed stirred solution of 1-benzyl-4-methyl-3,6-dihydro-2H-pyridine 48-3 (25.0 g, 133.49 mmol) in 2-propanol (20 mL), phenylsilane (14.44 g, 133.49 mmol, 16.45 mL) and [(Z)-1-tert-butyl-3-hydroxy-4,4-dimethyl-pent-2-enylidene]oxonium manganese (1.61 g, 2.67 mmol) was added at 0° C. followed by tert-butyl-N-tert-butoxycarbonyliminocarbamate (46.11 g, 200.23 mmol) under nitrogen atmosphere. After complete addition, the reaction mixture was stirred at same temperature for 6 hours. After completion of the reaction (monitored by TLC), the reaction mass was evaporated and the crude thus obtained was purified by column chromatography (100-200 silica; 30% EtOAc in hexane) to afford tert-butyl N-(1-benzyl-4-methyl-4-piperidyl)-N-(tert-butoxycarbonylamino)carbamate 48-4 (15 g, 35.75 mmol, 26.78% yield) as yellow sticky solid. LC MS: ES+ 420.0.

Step 4: Preparation of (1-Benzyl-4-methyl-4-piperidyl)hydrazine

4M Dioxane-HCl (30 mL) was added to tert-butyl N-(1-benzyl-4-methyl-4-piperidyl)-N-(tert-butoxycarbonylamino)carbamate 48-4 (15.0 g, 35.75 mmol) at 0° C. and the reaction was stirred for 8 hours at room temperature. After completion of the reaction as evidenced from LCMS, the volatiles were removed under vacuum. The crude thus obtained was dissolved in 10% MeOH in DCM and neutralized with Amberlyst-A21 resin. The solid polymer was filtered off and washed with 10% MeOH in DCM several times. The combined filtrate was concentrated under reduced pressure to afford (1-benzyl-4-methyl-4-piperidyl) hydrazine 48-5 (7.4 g, 33.74 mmol, 94.37% yield, 90% purity) as yellow solid. LC MS: ES+ 220.0.

Step 5: Preparation of ethyl 1-(1-Benzyl-4-methyl-4-piperidyl)pyrazole-4-carboxylate To a stirred solution of ethyl 2-formyl-3-oxo-propanoate 48-6 (4.73 g, 32.83 mmol) in toluene (15 mL) crude (1-benzyl-4-methyl-4-piperidyl)hydrazine 48-5 (6.0 g, 27.36 mmol) was added at 0° C. and the reaction was heated for 12 hours at 90° C. After completion of the reaction (monitored by LC MS) all the volatiles were evaporated and crude thus obtained was purified by column chromatography (100-200 Silica; 30% EtOAc in hexane as eluent) to afford ethyl 1-(1-benzyl-4-methyl-4-piperidyl)pyrazole-4-carboxylate 48-7 (4.36 g, 13.33 mmol, 48.72% yield) as light yellow gum. LC MS: ES+ 328.3.

Step 6: Preparation of tert-Butyl 4-(4-ethoxycarbonylpyrazol-1-yl)-4-methyl-piperidine-1-carboxylate To the stirred solution of ethyl 1-(1-benzyl-4-methyl-4-piperidyl)pyrazole-4-carboxylate 48-7 (6.0 g, 18.33 mmol) in EtOH (20 mL), tert-butoxycarbonyl tert-butyl carbonate (10.85 g, 49.73 mmol, 11.41 mL) and triethylamine (7.55 g, 74.59 mmol, 10.40 mL) were added. The reaction mixture was degassed with argon for 15 minutes followed by the addition of 20% palladium on carbon (moist) (2.93 g, 27.49 mmol) and the resultant reaction mixture was stirred under hydrogen atmosphere for 16 hours at room temperature. After completion of the reaction (monitored by TLC and LCMS), the reaction mixture was filtered through celite. The filtrate was then concentrated and purified by column chromatography (100-200 Silica; 2% methanol in DCM) to afford tert-butyl 4-(4-ethoxycarbonylpyrazol-1-yl)-4-methyl-piperidine-1-carboxylate 48-8 (4.8 g, 14.23 mmol, 57.22% yield, 99% purity) as brown gum. LC MS: ES+ 338.3.

Step 7: Preparation of tert-Butyl 4-[4-(hydroxymethyl)pyrazol-1-yl]-4-methyl-piperidine-1-carboxylate To the stirred solution of tert-butyl 4-(4-ethoxycarbonylpyrazol-1-yl)-4-methyl-piperidine-1-carboxylate 48-8 (4.8 g, 10.67 mmol) in THF (50 mL), diisobutylaluminum hydride (10.12 g, 71.13 mmol, 60 mL) was added dropwise at −78° C. and the reaction was stirred for 1 hour at room temperature under N$_2$ atmosphere. After complete consumption, as evidenced from TLC, the reaction mass was diluted with ethyl acetate (300 mL) and quenched with water (50 mL). Organic phase was separated, dried over anhydrous Na$_2$SO$_4$ and concentrated under reduced pressure to afford tert-butyl 4-[4-(hydroxymethyl)pyrazol-1-yl]-4-methyl-piperidine-1-carboxylate 48-9 (4.05 g, 13.72 mmol, 96.43% yield) as brown gum which was carried forward to the next step without any further purification. LC MS: ES+ 296.2.

Step 8: Preparation of tert-Butyl 4-(4-formylpyrazol-1-yl)-4-methyl-piperidine-1-carboxylate To a stirred solution of tert-butyl 4-[4-(hydroxymethyl) pyrazol-1-yl]-4-methyl-piperidine-1-carboxylate 48-9 (4.0 g, 13.54 mmol) in acetonitrile (20 mL) was added activated MnO$_2$ (9.42 g, 108.34 mmol) and the reaction was stirred at room temperature for 24 hours. After completion of the reaction (monitored by TLC and LC MS), the reaction mass was filtered through celite and the filtrate was concentrated under reduced pressure. Crude mass was purified by column chromatography (100-200 silica; 2-3% MeOH in DCM as eluent) to afford tert-butyl 4-(4-formylpyrazol-1-yl)-4-methyl-piperidine-1-carboxylate 48-10 (3.0 g, 10.23 mmol, 75.52% yield) as colorless sticky solid. LC MS: ES+ 294.3.

Step 9: Preparation of tert-Butyl-4-[4-[[[2-(2,6-dioxo-3-piperidyl)-1,3-dioxo-isoindolin-4 yl]amino] methyl]pyrazol-1-yl]-4-methyl-piperidine-1-carboxylate To a stirred solution of crude 4-amino-2-(2,6-dioxo-3-piperidyl)isoindoline-1,3-dione 48-11 (60 mg, 219.58 umol) and tert-butyl 4-(4-formylpyrazol-1-yl)-4-methyl-piperidine-1-carboxylate 48-10 (64.42 mg, 219.58 umol) in THF (5 mL), dibutyltindichloride (80.06 mg, 263.50 umol, 58.87 uL) was added followed by phenylsilane (23.76 mg, 219.58 umol) at room temperature. The resultant reaction mixture was heated at 80° C. for 12 hours in a sealed tube. After completion of the reaction (monitored by LC MS), the reaction mixture was concentrated under reduced pressure. The crude thus obtained was purified by column chromatography (100-200 silica; 2-3% MeOH in DCM as eluent) to afford tert-butyl-4-[4-[[[2-(2,6-dioxo-3-piperidyl)-1,3-dioxo-isoindolin-4-yl]amino]methyl]pyrazol-1-yl]-4-methyl-piperidine-1-carboxylate 48-12 (56 mg, 101.71 umol, 46.32% yield) as yellow solid. LC MS: ES+ 551.1.

Step 10: Preparation of 2-(2,6-Dioxo-3-piperidyl)-4-[[1-(4-methyl-4-piperidyl)pyrazol-4 yl]methylamino] isoindoline-1,3-dione; hydrochloride 4M Dioxane-HCl (2 mL) was added to tert-butyl 4-[4-[[[2-(2,6-dioxo-3-piperidyl)-1,3-dioxo-isoindolin-4-yl] amino]methyl]pyrazol-1-yl]-4-methyl-piperidine-1-carboxylate 48-12 (50 mg, 90.81 umol) at 0° C. and the reaction mixture was stirred for 1 hour at room temperature. After completion of the reaction, volatiles were evaporated to afford 2-(2,6-dioxo-3-piperidyl)-4-[[1-(4-methyl-4-piperidyl)pyrazol-4-yl]methylamino]isoindoline-1,3-dione; hydrochloride 48-13 (32 mg, 65.72 umol, 72.37% yield). LC MS: ES+ 451.3.

Step 11: Preparation of 4-[[1-[1-(Cubane-1-carbonyl)-4-methyl-4-piperidyl]pyrazol-4-yl]methylamino]-2-(2,6-dioxo-3-piperidyl)isoindoline-1,3-dione To the stirred solution of cubane-1-carboxylic acid 48-14 (9.74 mg, 65.72 umol) in dry DMF (1 mL), HATU (37.48 mg, 98.57 umol) was added at 0° C. and the reaction was stirred for 15 minutes at room temperature under argon atmosphere. To this reaction mixture, solution of 4-[[1-(1-chloro-4-methyl-4-piperidyl)pyrazol-4-yl]methylamino]-2-(2,6-dioxo-3-piperidyl)isoindoline-1,3-dione (32 mg, 65.72 umol) and N,N-diisopropylethylamine (25.48 mg, 197.15 umol, 34.34 uL) in DMF (0.5 mL) was added and resulting reaction mixture was stirred at room temperature for 12 hours. After completion of the reaction as evidenced from LC MS, ice-cooled water (2 mL) was added to the reaction mixture and the organics were extracted with ethyl acetate (3×10 mL). The combined extract was separated, dried over anhydrous $Na_2SO_4$ and concentrated. Crude reaction mass was purified over preparative TLC plate (5% MeOH in DCM) to afford 4-[[1-[1-(cubane-1-carbonyl)-4-methyl-4-piperidyl]pyrazol-4-yl]methylamino]-2-(2,6-dioxo-3-piperidyl)isoindoline-1,3-dione (Compound 195) (10 mg, 16.31 umol, 24.83% yield) as yellow solid. LC MS: ES+ 580.9.

Example 49. Synthesis of 4-[[1-[(4R)-1-(Cubane-1-carbonyl)-2,2-dimethyl-4-piperidyl]pyrazol-4-yl]methylamino]-2-(2,6-dioxo-3-piperidyl)isoindoline-1,3-dione (Compound 196) and 4-[[1-[(4S)-1-(Cubane-1-carbonyl)-2,2-dimethyl-4-piperidyl]pyrazol-4-yl]methylamino]-2-(2,6-dioxo-3-piperidyl)isoindoline-1,3-dione (Compound 197)

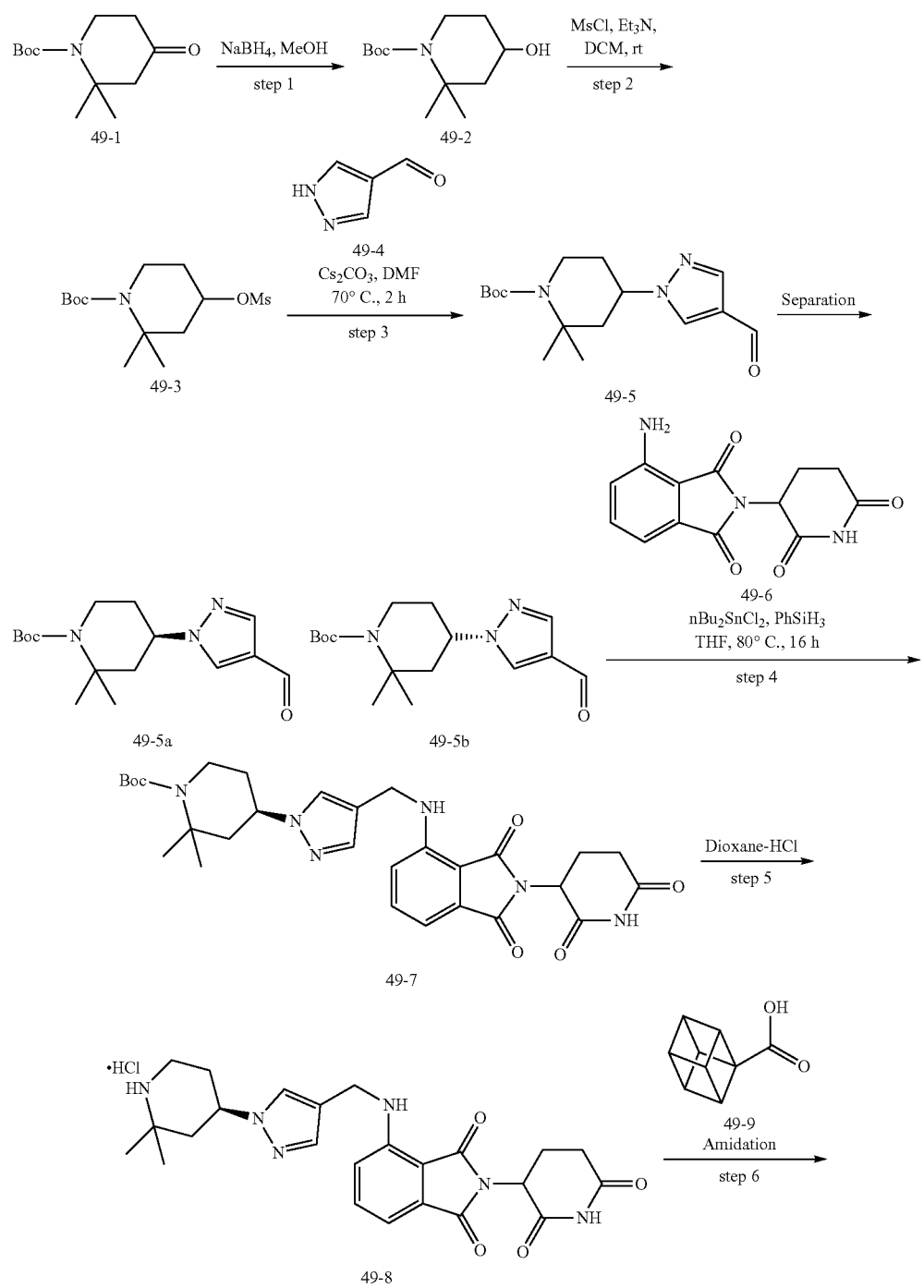

-continued
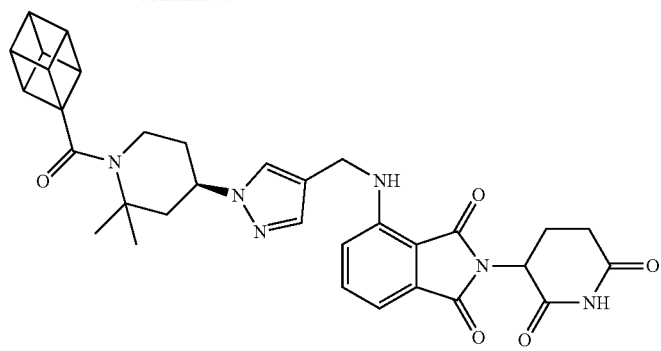
Compound 196
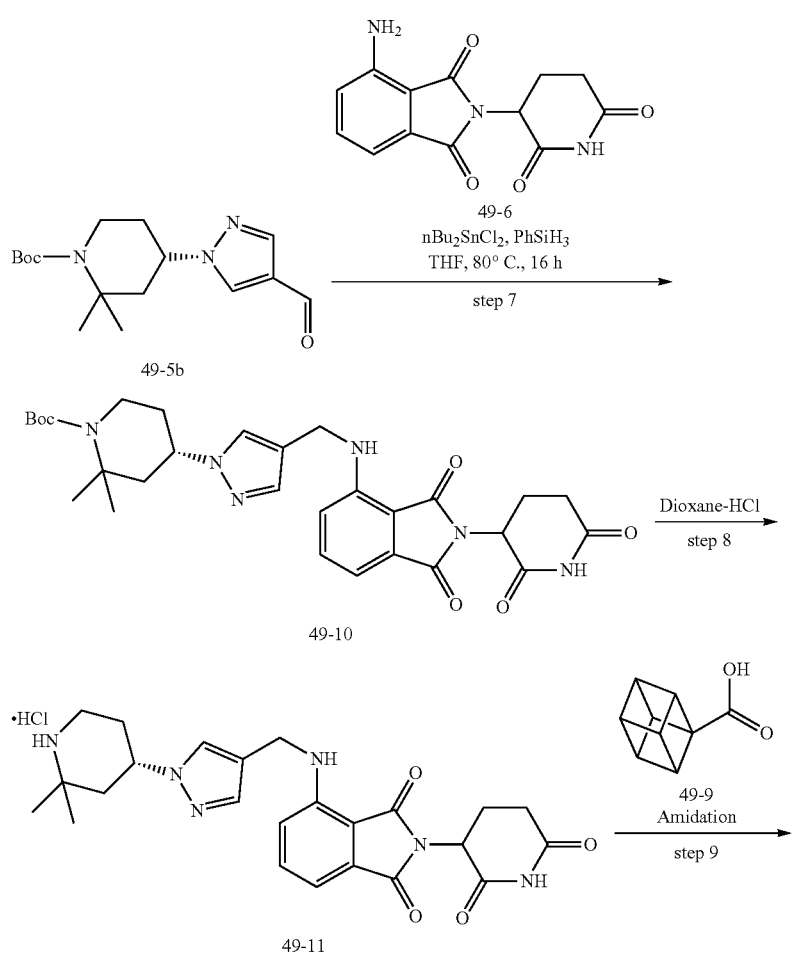
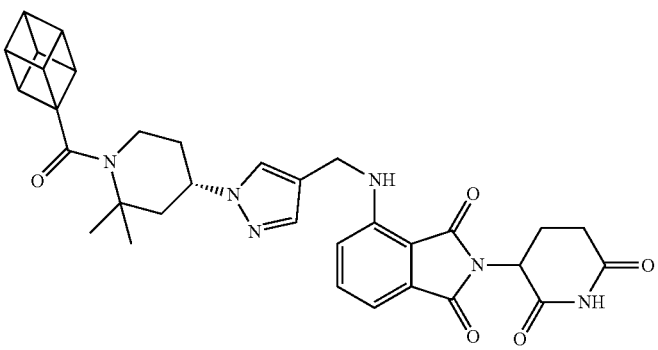
Compound 197

Step 1: Preparation of tert-Butyl 4-hydroxy-2,2-dimethylpiperidine-1-carboxylate To a stirred solution of tert-butyl 2,2-dimethyl-4-oxo-piperidine-1-carboxylate 49-1 (4 g, 17.60 mmol) in methanol (25.0 mL), sodium borohydride (998.66 mg, 26.40 mmol, 933.33 uL) was added portion-wise into the reaction mixture under 0° C. and the mixture was stirred at room temperature for 2 hours. Reaction mixture was concentrated under reduced pressure, quenched with water, and diluted with ethyl acetate. The layers were separated and the organic part was washed with water and concentrated under reduced pressure to afford tert-butyl 4-hydroxy-2,2-dimethyl-piperidine-1-carboxylate 49-2 (4.04 g, 17.62 mmol, 100.00% yield) that was carried forward without further purification. LC MS: ES+ 230.2.

Step 2: Preparation of tert-Butyl 2,2-dimethyl-4-((methylsulfonyl)oxy)piperidine-1-carboxylate To a stirred solution of tert-butyl 4-hydroxy-2,2-dimethyl-piperidine-1-carboxylate 49-2 (2.02 g, 8.81 mmol) in DCM (10.0 mL), triethyl amine (1.78 g, 17.62 mmol, 2.46 mL) was added at 0° C. Mesyl chloride (1.51 g, 13.21 mmol, 1.02 mL) was then added to the reaction mixture and the reaction was stirred at room temperature for 2 hours. The reaction mixture was diluted with DCM and washed with water. Organic part was washed with saturated sodium bicarbonate solution, dried over sodium sulfate, and concentrated under reduced pressure to afford tert-butyl 2,2-dimethyl-4-methylsulfonyloxy-piperidine-1-carboxylate 49-3 (2.71 g, 8.82 mmol, 100.00% yield) that was carried forward without purification. LC MS: ES+ 308.1.

Step 3: Preparation of tert-Butyl (R)-4-(4-formyl-1H-pyrazol-1-yl)-2,2-dimethylpiperidine-1-carboxylate and tert-Butyl (S)-4-(4-formyl-1H-pyrazol-1-yl)-2,2-dimethylpiperidine-1-carboxylate To a stirred solution of tert-butyl 2,2-dimethyl-4-methylsulfonyloxy-piperidine-1-carboxylate (1.46 g, 4.74 mmol) in DMF (10.0 mL) were added 1H-pyrazole-4-carbaldehyde (350.0 mg, 3.64 mmol) and cesium carbonate (2.37 g, 7.29 mmol). The reaction mixture was stirred at 80° C. for 16 hours. Reaction mixture was cooled to room temperature and was diluted with ethyl acetate and water. The organic part was then separated, washed with saturated sodium bicarbonate solution, dried over sodium sulfate and concentrated under reduced pressure to afford the crude compound. The crude compound was dissolved in MeOH and preparative HPLC separation using a Chiralpak IC (4.6×250 mm), 5 column with a flow rate of 1.0 mL/min and a mobile phase of hexane/EtOH (75:25) was performed to afford tert-butyl (4R)-4-(4-formylpyrazol-1-yl)-2,2-dimethyl-piperidine-1-carboxylate 49-5a (300 mg, 975.97 umol, 26.79% yield, % ee-97.02) (eluted first) and tert-butyl (4S)-4-(4-formylpyrazol-1-yl)-2,2-dimethyl-piperidine-1-carboxylate 49-5b (160 mg, 520.52 umol, 14.29% yield, % ee-99.20)(eluted second) as white solid. LC MS: ES+ 308.3.

Step 4: Preparation of tert-Butyl (4R)-4-(4-(((2-(2,6-dioxopiperidin-3-yl)-1,3-dioxoisoindolin-4-yl)amino)methyl)-1H-pyrazol-1-yl)-2,2-dimethylpiperidine-1-carboxylate To a stirred solution of tert-butyl (4R)-4-(4-formylpyrazol-1-yl)-2,2-dimethyl-piperidine-1-carboxylate 49-5a (150.00 mg, 487.98 umol) and 4-amino-2-(2,6-dioxo-3-piperidyl)isoindoline-1,3-dione 49-6 (133.34 mg, 487.98 umol) in THF (5.0 mL) were added phenylsilane (52.81 mg, 487.98 umol, 60.21 uL) and dibutyltindichloride (177.93 mg, 585.58 umol, 130.83 uL) and the reaction mixture was stirred at 80° C. for 16 hours. Reaction mixture was filtered through celite bed and the filtrate was concentrated under reduced pressure to afford the crude compound. Crude material was purified by combiflash chromatography (eluting 25-30% ethyl acetate in DCM) to afford tert-butyl (4R)-4-[4-[[[2-(2,6-dioxo-3-piperidyl)-1,3-dioxo-isoindolin-4-yl]amino]methyl]pyrazol-1-yl]-2,2-dimethyl-piperidine-1-carboxylate 49-7 (100 mg, 177.11 umol, 36.29% yield) as yellow solid. LC MS: ES+ 565.4.

Step 5: Preparation of 4-(((1-((R)-2,2-Dimethylpiperidin-4-yl)-1H-pyrazol-4-yl)methyl)amino)-2-(2,6-dioxopiperidin-3-yl)isoindoline-1,3-dione hydrochloride To the stirred solution of tert-butyl (4R)-4-[4-[[[2-(2,6-dioxo-3-piperidyl)-1,3-dioxo-isoindolin-4-yl]amino]methyl]pyrazol-1-yl]-2,2-dimethyl-piperidine-1-carboxylate 49-7 (50.0 mg, 88.55 umol) in dioxane (1 mL) was added hydrochloric acid in dioxane (88.55 umol, 5 mL) and the reaction was stirred at room temperature for 2 hours. The solvent in the reaction mixture was evaporated under reduced pressure to obtain a yellow solid which was washed with ether and pentane to afford 4-[[1-[(4R)-1-chloro-2,2-dimethyl-4-piperidyl]pyrazol-4-yl]methylamino]-2-(2,6-dioxo-3-piperidyl)isoindoline-1,3-dione 49-8 (44.0 mg, 87.83 umol, 99.18% yield) as yellow solid. LC MS: ES+ 465.1.

Step 6: Preparation of 4-[[1-[(4R)-1-(Cubane-1-carbonyl)-2,2-dimethyl-4-piperidyl]pyrazol-4-yl]methylamino]-2-(2,6-dioxo-3-piperidyl)isoindoline-1,3-dione To the stirred solution of 4-[[1-[(4R)-1-chloro-2,2-dimethyl-4-piperidyl]pyrazol-4-yl]methylamino]-2-(2,6-dioxo-3-piperidyl)isoindoline-1,3-dione 49-8 (44.00 mg, 87.83 umol) was added N,N-diisopropylethylamine (34.05 mg, 263.49 umol, 45.89 uL) under cold conditions and the reaction was stirred for 10 minutes. Then to the reaction mixture was added cubane-1-carboxylic acid 49-9 (13.01 mg, 87.83 umol) and HATU (50.09 mg, 131.74 umol). Reaction mixture was continued for 16 hours at room temperature. The reaction mixture was diluted with ethyl acetate and water. Layers were separated and organic part was washed with saturated aqueous sodium bicarbonate solution, water, and brine solution. The organics were was then dried over anhydrous sodium sulphate and evaporated under reduced pressure to obtain the crude compound that was purified by preparative TLC plate (eluting with 3% MeOH-DCM) to afford 4-[[1-[(4R)-1-(cubane-1-carbonyl)-2,2-dimethyl-4-piperidyl]pyrazol-4-yl]methylamino]-2-(2,6-dioxo-3-piperidyl)isoindoline-1,3-dione (Compound 196) (10.0 mg, 16.37 umol, 18.64% yield, 97.36% purity, 000) as yellow solid. $^1$H NMR (d6-DMSO, 400 HZ) δ 11.08 (s, 1H), 7.80 (s, 1H), 7.57 (t, J=7.56 Hz, 1H), 7.47 (s, 1H), 7.15 (d, J=8.0 Hz, 1H), 7.04 (d, J=7.84 Hz, 1H), 6.84-6.82 (m, 1H), 5.06-5.03 (m, 1H), 4.54-4.53 (m, 1H), 4.37-4.36 (m, 2H), 4.13 (br s, 3H), 3.95 (br s, 4H), 3.44-3.40 (m, 1H), 3.10-3.08 (m, 1H), 2.91-2.75 (m, 1H), 2.66-2.55 (m, 2H), 2.27-2.21 (m, 1H), 2.14-2.02 (m, 3H), 1.90-1.79 (m, 1H), 1.49 (s, 3H), 1.39 (s, 3H); LC MS: ES+ 595.3.

Step 7: Preparation of tert-Butyl (4S)-4-(4-(((2-(2, 6-dioxopiperidin-3-yl)-1,3-dioxoisoindolin-4-yl) amino)methyl)-1H-pyrazol-1-yl)-2,2-dimethylpiperidine-1-carboxylate To the stirred solution of tert-butyl (4S)-4-(4-formylpyrazol-1-yl)-2,2-dimethyl-piperidine-1-carboxylate 49-5b (57.00 mg, 185.43 umol) and 4-amino-2-(2,6-dioxo-3-piperidyl)isoindoline-1,3-dione 49-6 (50.67 mg, 185.43 umol) in THF (2 mL) were added phenylsilane (20.07 mg, 185.43 umol, 22.88 uL) and dibutyltindichloride (67.61 mg, 222.52 umol, 49.72 uL) and the reaction mixture was then stirred at 80° C. for 16 hours. The reaction mixture was evaporated under reduced pressure to obtain the crude compound that was purified by flash chromatography (eluting 25-30% ethyl acetate in DCM) to afford tert-butyl (4S)-4-[4-[[[2-(2,6-dioxo-3-piperidyl)-1,3-dioxo-isoindolin-4-yl]amino] methyl]pyrazol-1-yl]-2,2-dimethyl-piperidine-1-carboxylate 49-10 (60.0 mg, 106.26 umol, 57.31% yield) as yellow solid. LC MS: ES+ 565.6.

Step 8: Preparation of 4-(((1-((S)-2,2-Dimethylpiperidin-4-yl)-1H-pyrazol-4-yl)methyl)amino)-2-(2,6-dioxopiperidin-3-yl)isoindoline-1,3-dione hydrochloride To the stirred solution of tert-butyl 4-[(1R)-4-[[[2-(2,6-dioxo-3-piperidyl)-1,3-dioxo-isoindolin-4-yl]amino] methyl]pyrazol-1-yl]-2,2-dimethyl-piperidine-1-carboxylate 49-10 (60.00 mg, 106.26 umol) in dioxane (1 mL) was added hydrochloric acid in dioxane (106.26 umol, 5 mL) and the reaction was stirred at room temperature for 2 hours. The solvent in the reaction mixture was evaporated under reduced pressure to obtain a yellow solid that was washed with ether and pentane to afford 4-[[(1R)-1-(1-chloro-2,2-dimethyl-4-piperidyl)pyrazol-4-yl]methylamino]-2-(2,6-dioxo-3-piperidyl)isoindoline-1,3-dione 49-11 (53.0 mg, 105.79 umol, 99.56% yield) as yellow solid. LC MS: ES+ 465.2.

Step 9: Preparation of 4-[[1-[(4S)-1-(Cubane-1-carbonyl)-2,2-dimethyl-4-piperidyl]pyrazol-4-yl] methylamino]-2-(2,6-dioxo-3-piperidyl)isoindoline-1,3-dione To the stirred solution of 4-[[1-[(4S)-1-chloro-2,2-dimethyl-4-piperidyl]pyrazol-4-yl]methylamino]-2-(2,6-dioxo-3-piperidyl)isoindoline-1,3-dione 49-11 (53.00 mg, 105.79 umol) was added N,N-diisopropylethylamine (41.02 mg, 317.38 umol, 55.28 uL) under cold conditions and the reaction was stirred for 10 minutes. Then to the reaction mixture was added cubane-1-carboxylic acid 49-9 (15.67 mg, 105.79 umol) and HATU (60.34 mg, 158.69 umol) and the reaction was stirred for 16 hours at room temperature. The reaction mixture was diluted with ethyl acetate and water. Layers were separated and organic part was washed with saturated aqueous sodium bicarbonate solution, water, and brine solution. The organics were then dried over anhydrous sodium sulphate and evaporated under reduced pressure to obtain the crude compound that was purified by preparative TLC plate (eluting with 3% MeOH-DCM) to afford 4-[[1-[(4S)-1-(cubane-1-carbonyl)-2,2-dimethyl-4-piperidyl]pyrazol-4-yl]methylamino]-2-(2,6-dioxo-3-piperidyl)isoindoline-1,3-dione (Compound 197) (30.0 mg, 47.89 umol, 45.27% yield, 94.93% purity, 000) as yellow solid. $^1$H NMR (d6-DMSO, 400 MHZ) δ 11.08 (s, 1H), 7.80 (s, 1H), 7.57 (t, J=7.82 Hz, 1H), 7.47 (s, 1H), 7.15 (d, J=8.6 Hz, 1H), 7.04 (d, J=7.48 Hz, 1H), 6.83-6.81 (m, 1H), 5.04 (dd, J=12.76, 4.92 Hz, 1H), 4.54-4.52 (m, 1H), 4.37-4.36 (m, 2H), 4.13 (br s, 3H), 3.95-3.94 (m, 4H), 3.39-3.37 (m, 1H), 3.10-3.07 (m, 1H), 2.89-2.84 (m, 1H), 2.64-2.60 (m, 2H), 2.15-2.08 (m, 1H), 2.07-2.01 (m, 2H), 1.92-1.90 (m, 1H), 1.79-1.75 (m, 1H), 1.49 (s, 3H), 1.39 (s, 3H); LC MS: ES+ 595.5.

Example 50. Synthesis of 4-(((3-Chloro-1-(1-(cubane-1-carbonyl)piperidin-4-yl)-1H-pyrazol-4-yl) methyl)amino)-2-(2,6-dioxopiperidin-3-yl)isoindoline-1,3-dione (Compound 198)

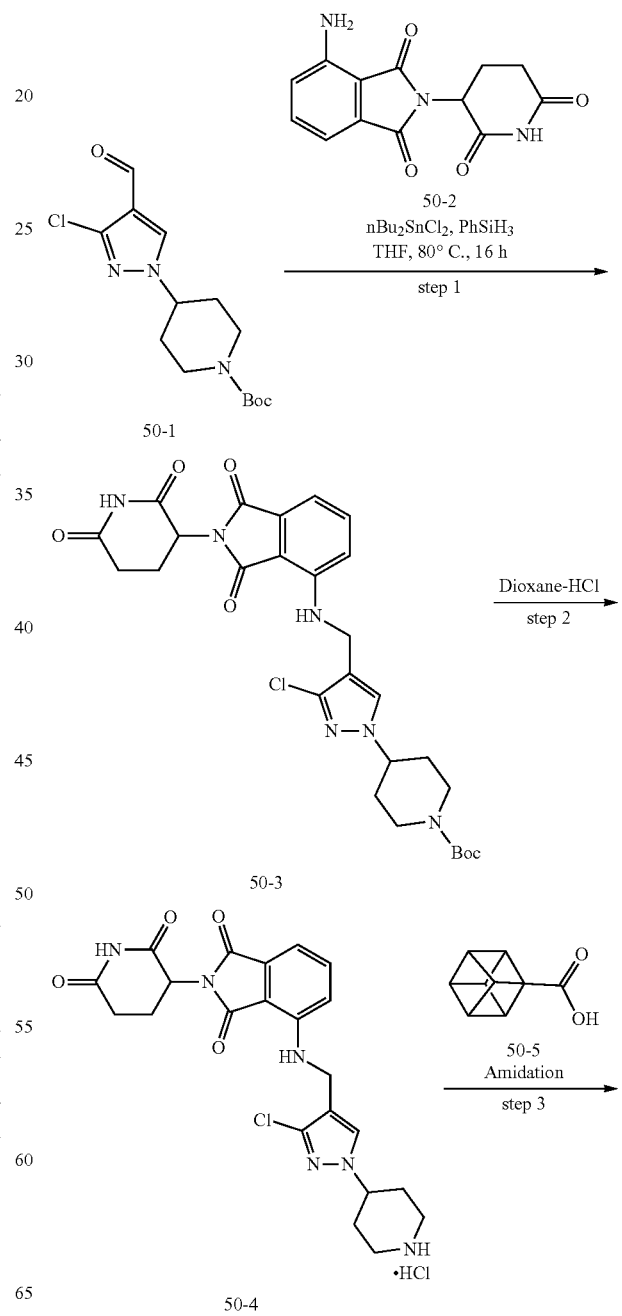

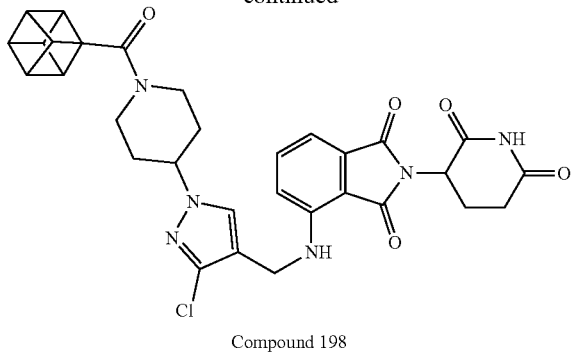

Compound 198

Step-1: Preparation of tert-Butyl 4-(3-chloro-4-(((2-(2,6-dioxopiperidin-3-yl)-1,3-dioxoisoindolin-4-yl)amino)methyl)-1H-pyrazol-1-yl)piperidine-1-carboxylate To the stirred solution of tert-butyl 4-(3-chloro-4-formyl-pyrazol-1-yl)piperidine-1-carboxylate 50-1 (300 mg, 956.09 umol) in THF (5.0 mL) was added 4-amino-2-(2,6-dioxo-3-piperidyl)isoindoline-1,3-dione 50-2 (261.25 mg, 956.09 umol). Phenylsilane (103.46 mg, 956.09 umol, 117.97 uL) and dibutyltindichloride (348.60 mg, 1.15 mmol, 256.33 uL) were then added to the reaction mixture. Reaction mixture was then heated at 80° C. for 16 hours and then cooled to room temperature and concentrated under reduced pressure. The crude material was purified by column chromatography (eluting with 1.5%-2% MeOH in DCM) to afford tert-butyl 4-[3-chloro-4-[[[2-(2,6-dioxo-3-piperidyl)-1,3-dioxo-isoindolin-4-yl]amino]methyl]pyrazol-1-yl]piperidine-1-carboxylate 50-3 (140 mg, 245.17 umol, 25.64% yield) as yellow solid. LC MS: ES+ 571.3.

Step-2: Preparation of 4-(((3-Chloro-1-(piperidin-4-yl)-1H-pyrazol-4-yl)methyl)amino)-2-(2,6-dioxopiperidin-3-yl)isoindoline-1,3-dione hydrochloride To the stirred solution of tert-butyl 4-[3-chloro-4-[[[2-(2,6-dioxo-3-piperidyl)-1,3-dioxo-isoindolin-4-yl]amino]methyl]pyrazol-1-yl]piperidine-1-carboxylate 50-3 (100 mg, 175.12 umol) in dioxane (3.0 mL) was added dioxane-HCl (175.12 umol, 6 mL) and reaction mixture was stirred at room temperature for 2 hours. Volatiles were removed and resulting solid was triturated with diethyl ether to afford 4-[[3-chloro-1-(1-chloro-4-piperidyl)pyrazol-4-yl]methylamino]-2-(2,6-dioxo-3-piperidyl)isoindoline-1,3-dione 50-4 (88.85 mg, 175.12 umol, 100.00% yield) as yellow solid. LC MS: ES+ 471.5.

Step-3: Preparation of 4-(((3-Chloro-1-(1-(cubane-1-carbonyl)piperidin-4-yl)-1H-pyrazol-4-yl)methyl)amino)-2-(2,6-dioxopiperidin-3-yl)isoindoline-1,3-dione To the stirred solution of 4-[[3-chloro-1-(1-chloro-4-piperidyl)pyrazol-4-yl]methylamino]-2-(2,6-dioxo-3-piperidyl)isoindoline-1,3-dione 50-4 (88.85 mg, 175.12 umol) and cubane-1-carboxylic acid 50-5 (25.95 mg, 175.12 umol) in DMF (5.0 mL) was added HATU (99.88 mg, 262.68 umol), followed by DIPEA (113.16 mg, 875.60 umol, 152.51 uL) at 0° C. Reaction mixture was stirred at room temperature for 16 hours. Reaction mixture was diluted with ethyl acetate and water. Layers were separated and the organic part was washed with water and saturated sodium bicarbonate solution, dried over sodium sulfate and concentrated under reduced pressure. The crude material was then purified by Prep-TLC Plate (eluting 2.5%-3% MeOH in DCM) to afford 4-[[3-chloro-1-[1-(cubane-1-carbonyl)-4-piperidyl]pyrazol-4-yl]methylamino]-2-(2,6-dioxo-3-piperidyl)isoindoline-1,3-dione (Compound 198) (40 mg, 66.55 umol, 38.00% yield, 100.0% purity, 000) as yellow solid $^1$H NMR (d6-DMSO, 400 MHZ) δ 11.09 (S, 1H), 7.91 (s, 1H), 7.59 (t, J=7.8 Hz, 1H), 7.11 (d, J=8.56 Hz, 1H), 7.06 (d, J=7.04 Hz, 1H), 6.82-6.80 (m, 1H), 5.05 (dd, J=12.8, 5.28 Hz), 4.41-4.33 (m, 4H), 4.19-4.18 (m, 3H), 3.98 (br s, 4H), 3.38-3.33 (m, 1H), 3.20-3.14 (m, 1H), 2.93-2.84 (m, 1H), 2.73-2.67 (m, 1H), 2.60-2.56 (m, 2H), 2.07-1.95 (m, 3H), 1.87-1.81 (m, 1H), 1.70-1.63 (m, 1H); LC MS: ES+ 601.3.

Example 51. Synthesis of 2-(2,6-Dioxopiperidin-3-yl)-4-(((1-(1-(4-methyl-1-(6-methylpyrazin-2-yl)piperidine-4-carbonyl)piperidin-4-yl)-1H-pyrazol-4-yl)methyl)amino)isoindoline-1,3-dione (Compound 199)

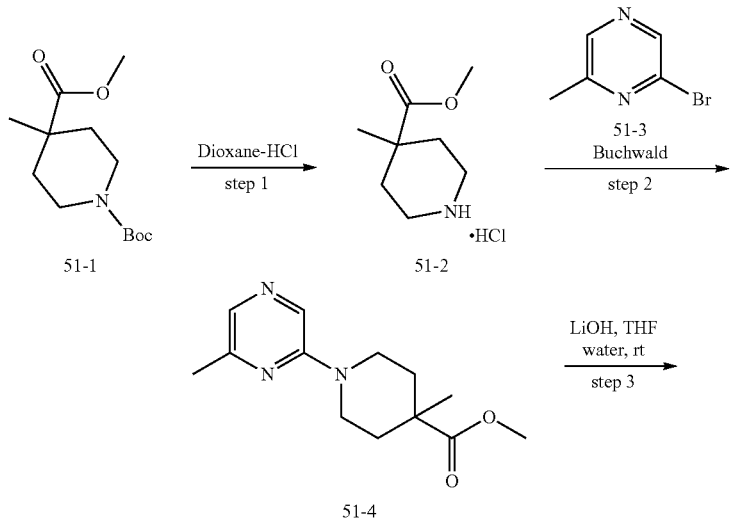

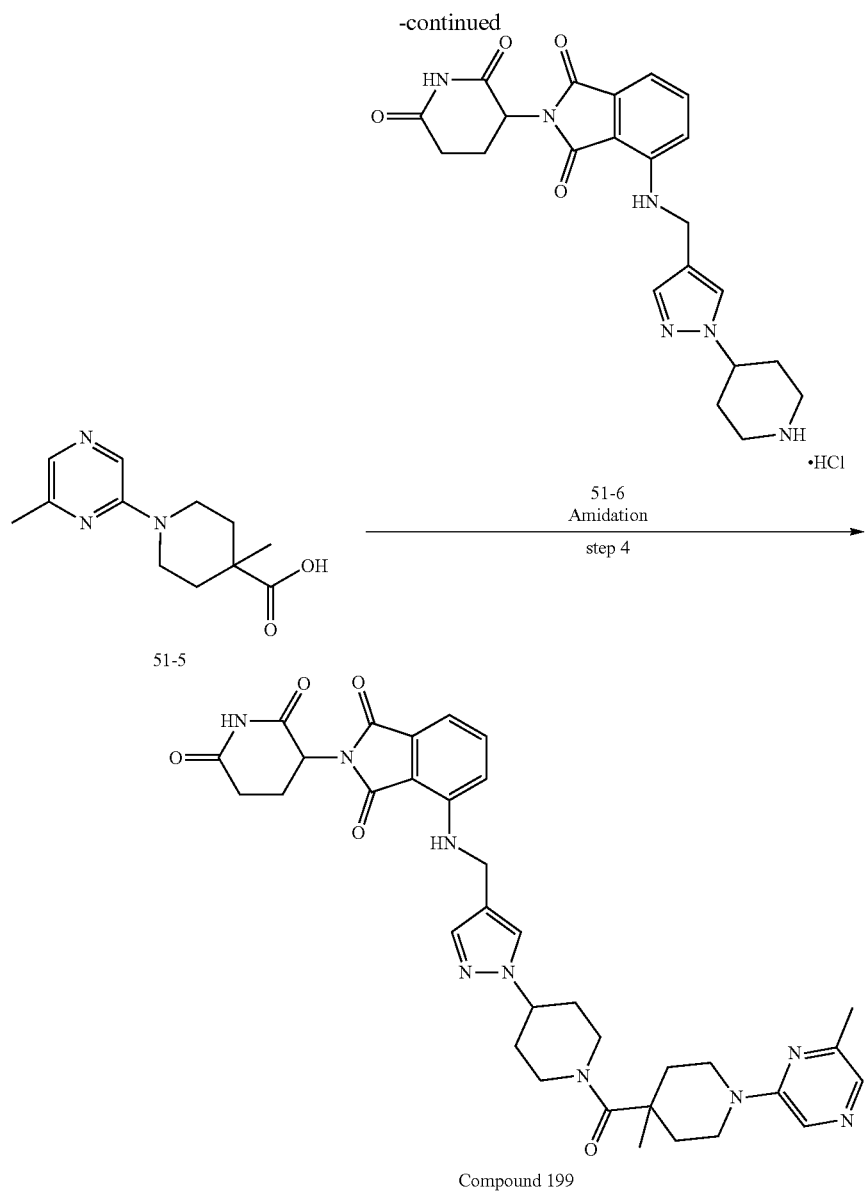

Compound 199

Step-1: Preparation of Methyl 4-methylpiperidine-4-carboxylate hydrochloride To a solution of O1-tert-butyl O4-methyl 4-methylpiperidine-1,4-dicarboxylate 51-1 (3.0 g, 11.66 mmol) in dioxane (25 mL) was added 4M dioxane-HCl (4 M, 14.57 mL). Reaction mixture was stirred at room temperature for 4 hours and then concentrated under reduced pressure to afford methyl 4-methylpiperidine-4-carboxylate 51-2 (1.8 g, 11.45 mmol, 98.21% yield) as off white solid. Crude material was forwarded to next step.

Step-2: Preparation of Methyl 4-methyl-1-(6-methylpyrazin-2-yl)piperidine-4-carboxylate To the stirred solution of 2-bromo-6-methyl-pyrazine 51-3 (812.11 mg, 4.69 mmol) and methyl 1-chloro-4-methyl-piperidine-4-carboxylate 51-2 (1000 mg, 5.16 mmol) in toluene (25 mL) was added cesium carbonate (4.59 g, 14.08 mmol). The reaction was degassed with argon for 10 minutes. Xanthphos (135.80 mg, 234.70 umol) and $Pd_2(dba)_3$ (214.92 mg, 234.70 umol) were added to the reaction mixture and the reaction mixture was heated at 90° C. for 16 hours. Reaction mixture was cooled to room temperature and diluted with ethyl acetate and water. Layers were separated and the organic layer was washed with water and brine, dried over sodium sulfate and concentrated under reduced pressure. The crude material was purified by combiflash chromatography (eluting at 2% methanol in dichloromethane) to afford methyl 4-methyl-1-(6-methylpyrazin-2-yl)piperidine-4-carboxylate 51-4 (630 mg, 2.53 mmol, 53.83% yield) as brown gum. LC MS: ES+ 250.3.

Step-3: Preparation of 4-Methyl-1-(6-methylpyrazin-2-yl)piperidine-4-carboxylic acid To the stirred solution of methyl 4-methyl-1-(6-methylpyrazin-2-yl)piperidine-4-carboxylate 51-4 (650 mg, 2.61 mmol) in THF (8 mL) and water (2 mL) was added lithium;

hydroxide hydrate (218.82 mg, 5.21 mmol, 144.91 uL). The reaction was stirred at room temperature for 16 hours and diluted with water and washed with ethyl acetate. The aqueous part was acidified with 1N HCl and was extracted with ethyl acetate. The organic part was washed with brine, dried over sodium sulfate, and concentrated under reduced pressure to afford 4-methyl-1-(6-methylpyrazin-2-yl)piperidine-4-carboxylic acid 51-5 (310 mg, 1.32 mmol, 50.54% yield) as brown solid. LC MS: ES+ 236.1.

Step-4: Preparation of 2-(2,6-Dioxopiperidin-3-yl)-4-(((1-(1-(4-methyl-1-(6-methylpyrazin-2-yl)piperidine-4-carbonyl)piperidin-4-yl)-1H-pyrazol-4-yl)methyl)amino)isoindoline-1,3-dione To the stirred solution of 4-[[1-(1-chloro-4-piperidyl)pyrazol-4-yl]methylamino]-2-(2,6-dioxo-3-piperidyl)isoindoline-1,3-dione 51-6 (60.0 mg, 126.87 umol) in DMF (1 mL) was added N,N-diisopropylethylamine (49.19 mg, 380.61 umol, 66.30 uL) under cold conditions followed by 4-methyl-1-(6-methylpyrazin-2-yl)piperidine-4-carboxylic acid 51-5 (29.85 mg, 126.87 umol) and HATU (72.36 mg, 190.31 umol). The reaction was stirred at room temperature for 16 hours. The reaction mixture was diluted with ethyl acetate and water. The organic layer was washed with sodium bicarbonate solution, water and brine solution, dried over anhydrous sodium sulphate and evaporated under reduced pressure to obtain the crude compound which was purified by preparative TLC plate (eluting with 3% MeOH-DCM) to afford 2-(2,6-dioxo-3-piperidyl)-4-[[1-[1-[4-methyl-1-(6-methylpyrazin-2-yl)piperidine-4-carbonyl]-4-piperidyl]pyrazol-4-yl]methylamino]isoindoline-1,3-dione (Compound 199) (15 mg, 22.70 umol, 17.89% yield, 98.92% purity, 000) as yellow solid. $^1$H NMR (d6-DMSO, 400 MHZ) δ 11.08 (s, 1H), 8.05 (s, 1H), 7.80 (s, 1H), 7.67 (s, 1H), 7.57 (t, J=7.74 Hz, 1H), 7.46 (s, 1H), 7.15 (d, J=8.72 Hz, 1H), 7.03 (d, J=6.96 Hz, 1H), 6.81-6.80 (m, 1H), 5.04 (dd, J=13.0, 5.36 Hz, 1H), 4.38-4.35 (m, 4H), 3.77-3.75 (m, 2H), 3.32-3.30 (m, 2H), 3.10-2.84 (m, 3H), 2.60-2.55 (m, 2H), 2.50-2.48 (m, 2H), 2.27 (s, 3H), 2.11-1.99 (m, 4H), 1.79-1.72 (m, 2H), 1.55-1.50 (m, 2H), 1.27 (s, 3H); LC MS: ES+ 654.6.

Example 52. Synthesis of 4-(((1-((1r,3r)-3-(Benzyloxy)cyclobutyl)-1H-pyrazol-4-yl)methyl)amino)-2-(2,6-dioxopiperidin-3-yl)isoindoline-1,3-dione (Compound 200)

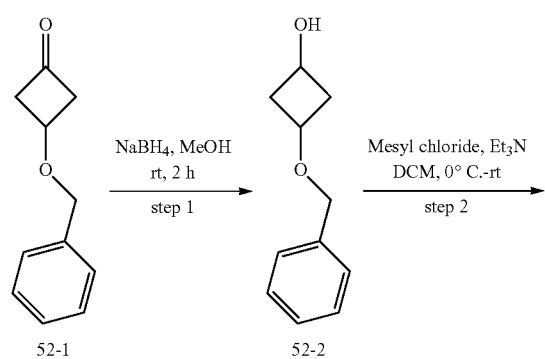

Step-1: Preparation of 3-(Benzyloxy)cyclobutan-1-ol

To a stirred a solution of 3-benzyloxycyclobutanone 52-1 (500 mg, 2.84 mmol) in methanol (5 mL) was added sodium borohydride (161.02 mg, 4.26 mmol, 150.49 uL) at 0° C. and the reaction mixture was stirred for 2 hours. The reaction mixture was concentrated under reduced pressure and EtOAc and water were added to the residue. The layers were separated and the organic layer was washed with water and brine, dried over Na$_2$SO$_4$ to afford crude product 3-benzyloxycyclobutanol 52-2 (500 mg, 2.81 mmol, 98.87% yield) as colourless oil that was used in next step without further purification. LC MS: ES+ 179.0.

Step-2: Preparation of 3-(Benzyloxy)cyclobutyl methanesulfonate

To a stirred solution of 3-benzyloxycyclobutanol 52-2 (500 mg, 2.81 mmol) in DCM (10 mL) was added triethylamine (567.76 mg, 5.61 mmol, 782.04 uL) and the reaction was cooled to 0° C. followed by the dropwise addition of methane sulfonyl chloride (385.63 mg, 3.37 mmol, 260.56 uL). The reaction mixture was stirred at room temperature for 1 hour and then diluted with water and extracted with DCM. Organic layer was washed with saturated solution of $NaHCO_3$ and brine, dried over anhydrous sodium sulphate, and evaporated under reduced pressure to afford crude compound (3-benzyloxycyclobutyl) methanesulfonate 52-3 (700 mg, 2.73 mmol, 97.35% yield) as orange liquid, that was used in next step without further purification. LC MS: ES+ 257.0.

Step-3: Preparation of 1-((1r,3r)-3-(Benzyloxy)cyclobutyl)-1H-pyrazole-4-carbaldehyde To the stirred solution of 1H-pyrazole-4-carbaldehyde 52-4 (300 mg, 3.12 mmol) and (3-benzyloxycyclobutyl) methanesulfonate 52-3 (800.26 mg, 3.12 mmol) in DMF (10 mL) was added cesium carbonate (2.03 g, 6.24 mmol) and the reaction mixture was heated at 80° C. for 16 hours. The reaction mixture was diluted with ethyl acetate, washed with water and the organic fraction was separated. The organics were then dried over anhydrous sodium sulphate and evaporated under reduced pressure to obtain the crude which was purified by flash chromatography (using 0-20% ethyl acetate-hexane) to afford 1-(3-benzyloxycyclobutyl)pyrazole-4-carbaldehyde 52-5 (520 mg, 2.03 mmol, 64.98% yield) as colorless gum. LC MS: ES+ 257.3.

Step-4: Preparation of 4-(((1-((1r,3r)-3-(Benzyloxy)cyclobutyl)-1H-pyrazol-4-yl)methyl)amino)-2-(2,6-dioxopiperidin-3-yl)isoindoline-1,3-dione To the stirred solution of 4-amino-2-(2,6-dioxo-3-piperidyl)isoindoline-1,3-dione 52-6 (106.61 mg, 390.17 umol) in THF (4 mL) in a sealed tube was added 1-(3-benzyloxycyclobutyl)pyrazole-4-carbaldehyde 52-5 (100.00 mg, 390.17 umol) followed by phenylsilane (42.22 mg, 390.17 umol, 48.14 uL) and dibutyltin dichloride (142.26 mg, 468.20 umol, 104.61 uL). Reaction mixture was heated at 80° C. for 16 hours. The reaction mixture was concentrated under reduced pressure to afford the crude mass that was purified by column chromatography (using 10% EtOAc in DCM as eluent) to afford 4-[[1-(3-benzyloxycyclobutyl)pyrazol-4-yl]methylamino]-2-(2,6-dioxo-3-piperidyl)isoindoline-1,3-dione (Compound 200) (80.0 mg, 140.20 umol, 35.93% yield, 90% purity, 000) as yellow solid. $^1$H NMR (d6-DMSO, 400 MHZ) δ 11.07 (s, 1H), 7.78 (s, 1H), 7.56 (t, J=7.82 Hz, 1H), 7.49 (s, 1H), 7.34-7.28 (m, 5H), 7.14 (d, J=8.56 Hz, 1H), 7.03 (d, J=7.0 Hz, 1H), 6.83-6.80 (m, 1H), 5.04 (dd, J=12.96, 5.44 Hz, 1H), 4.94-4.91 (m, 1H), 4.41 (s, 2H), 4.36-4.32 (m, 3H), 2.88-2.84 (m, 1H), 2.60-2.55 (m, 4H), 2.49-2.45 (m, 2H), 2.03-2.00 (m, 1H); LC MS: ES+ 514.3.

Example 53. Synthesis of 4-(((3-Chloro-1-(1-(1-(6-methylpyrazin-2-yl)piperidine-4-carbonyl)piperidin-4-yl)-1H-pyrazol-4-yl)methyl)amino)-2-(2,6-dioxopiperidin-3-yl)isoindoline-1,3-dione (Compound 201)

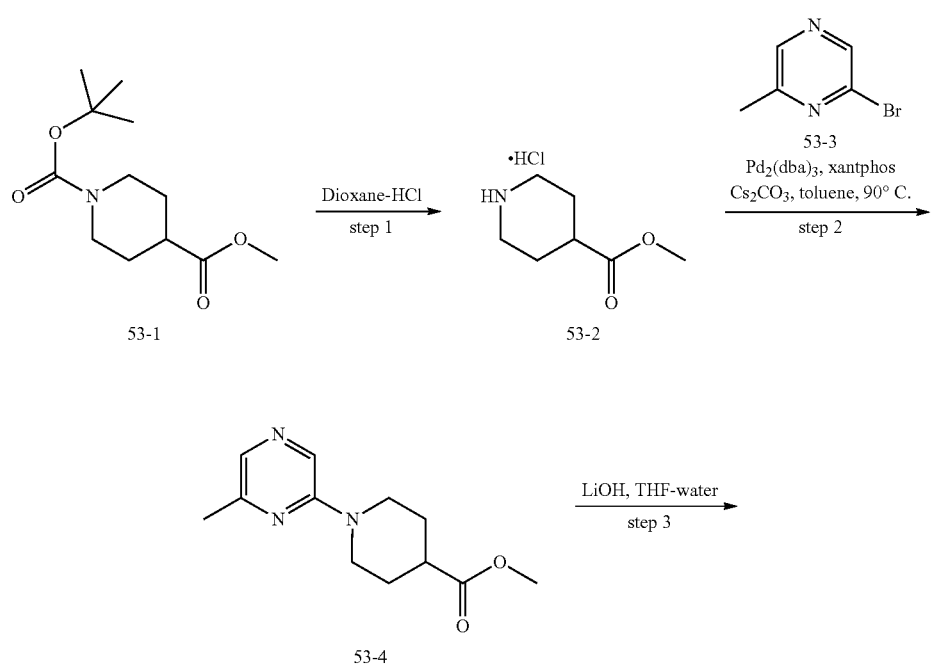

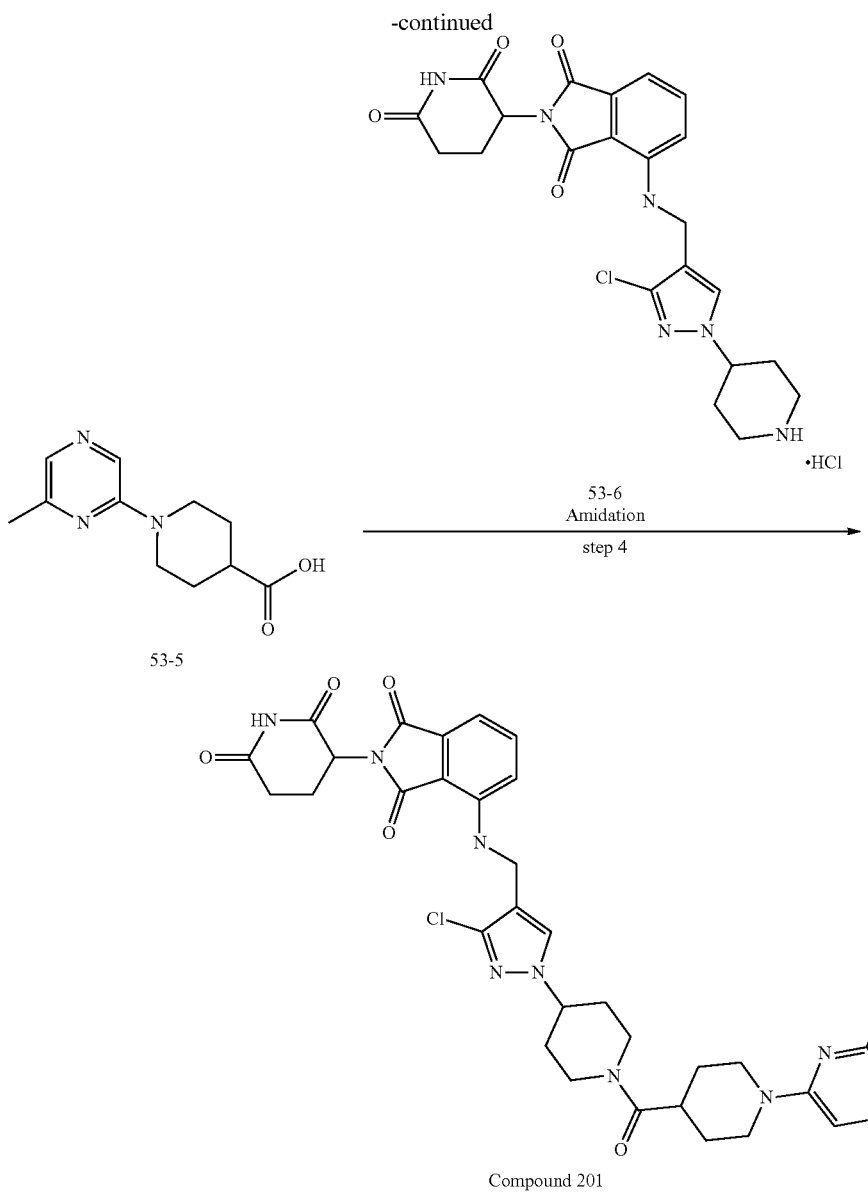

Compound 201

Step-1: Preparation of Methyl piperidine-4-carboxylate hydrochloride

To the stirred solution of O1-tert-butyl O4-methyl piperidine-1,4-dicarboxylate 53-1 (5 g, 20.55 mmol) in dioxane (25 mL) was added 4M dioxane-HCl (4 M, 25.69 mL). The reaction was stirred at room temperature for 4 hours and then concentrated under reduced pressure to afford methyl piperidine-4-carboxylate 53-2 (2.93 g, 20.46 mmol, 99.57% yield) as off white solid that was carried forward to the next step.

Step-2: Preparation of Methyl 1-(6-methylpyrazin-2-yl)piperidine-4-carboxylate To a solution of 2-bromo-6-methyl-pyrazine 53-3 (875.52 mg, 5.06 mmol) and methyl 1-chloropiperidine-4-carboxylate 53-2 (1000 mg, 5.57 mmol) in toluene (25 mL) was added cesium carbonate (4.95 g, 15.18 mmol). The reaction was degassed with argon for 10 minutes. Xanthphos (146.40 mg, 253.03 umol) and $Pd_2(dba)_3$ (231.70 mg, 253.03 umol) were added and the mixture was heated at 90° C. for 16 hours. The reaction was then cooled to room temperature and diluted with ethyl acetate. Organic layer was washed with water and brine, dried over sodium sulfate, concentrated under reduced pressure, and purified by combiflash chromatography (eluting with 2% methanol in dichloromethane) to afford methyl 1-(6-methylpyrazin-2-yl)piperidine-4-carboxylate 53-4 (750 mg, 3.19 mmol, 62.99% yield) as brown solid. LC MS: ES+ 235.9.

Step-3: Preparation of 1-(6-Methylpyrazin-2-yl)piperidine-4-carboxylic acid

To the stirred solution of methyl 1-(6-methylpyrazin-2-yl)piperidine-4-carboxylate 53-4 (750 mg, 3.19 mmol) in THF (8 mL) and water (2 mL) was added lithium hydroxide hydrate (267.53 mg, 6.38 mmol, 177.17 uL). Reaction mixture was stirred at room temperature for 4 hours and diluted with water and washed with ethyl acetate. The aqueous part was acidified with 1N HCl and was extracted with ethyl acetate. Organic part was washed with brine, dried over sodium sulfate and concentrated under reduced pressure to afford 1-(6-methylpyrazin-2-yl)piperidine-4-carboxylic acid 53-5 (450 mg, 2.03 mmol, 63.80% yield) as brown solid. LC MS: ES+ 222.1

Step-4: Preparation of 4-(((3-Chloro-1-(1-(1-(6-methylpyrazin-2-yl)piperidine-4-carbonyl)piperidin-4-yl)-1H-pyrazol-4-yl)methyl)amino)-2-(2,6-dioxopiperidin-3-yl)isoindoline-1,3-dione In a round bottomed flask under nitrogen atmosphere 4-[[3-chloro-1-(1-chloro-4-piperidyl)pyrazol-4-yl]methylamino]-2-(2,6-dioxo-3-piperidyl)isoindoline-1,3-dione 53-6 (75 mg, 147.82 umol) and 1-(6-methylpyrazin-2-yl)piperidine-4-carboxylic acid 53-5 (32.71 mg, 147.82 umol) were taken up in DMF (3.0 mL) and at 0° C. DIPEA (95.52 mg, 739.11 umol, 128.74 uL) and HATU (84.31 mg, 221.73 umol) were added. The reaction mixture was stirred at room temperature for 16 hours. The reaction mixture was extracted with ethyl acetate and the organic part was washed with water and saturated sodium bicarbonate solution. The organic part was then dried over sodium sulfate and concentrated under reduced pressure to afford the crude material. The crude was then purified by prep-TLC Plate (eluting with 3% MeOH in DCM) to afford 4-[[3-chloro-1-[1-[1-(6-methylpyrazin-2-yl)piperidine-4-carbonyl]-4-piperidyl]pyrazol-4-yl]methylamino]-2-(2,6-dioxo-3-piperidyl)isoindoline-1,3-dione (Compound 202) (40 mg, 56.37 umol, 38.13% yield, 95% purity, 000) as yellow solid. $^1$H NMR (d6-DMSO, 400 MHZ) δ 11.10 (s, 1H), 8.10 (s, 1H), 7.90 (s, 1H), 7.69 (s, 1H), 7.59 (t, J=7.74 Hz, 1H), 7.12 (d, J=8.44 Hz, 1H), 7.06 (d, J=7.08 Hz, 1H), 6.82-6.81 (m, 1H), 5.05 (dd, J=12.92, 5.48 Hz, 1H), 4.48-4.34 (m, 6H), 4.13-4.09 (m, 1H), 3.19-3.13 (m, 1H), 2.96-2.84 (m, 4H), 2.70-2.56 (m, 3H), 2.28 (s, 3H), 2.07-1.90 (m, 3H), 1.81-1.78 (m, 1H), 1.67-1.52 (m, 5H); LC MS: ES+ 674.5.

Example 54. Synthesis of 2-(2,6-Dioxopiperidin-3-yl)-4-(((1-(4-methyl-1-(4-methyl-1-(6-methylpyrazin-2-yl)piperidine-4-carbonyl)piperidin-4-yl)-1H-pyrazol-4-yl)methyl)amino)isoindoline-1,3-dione (Compound 202)

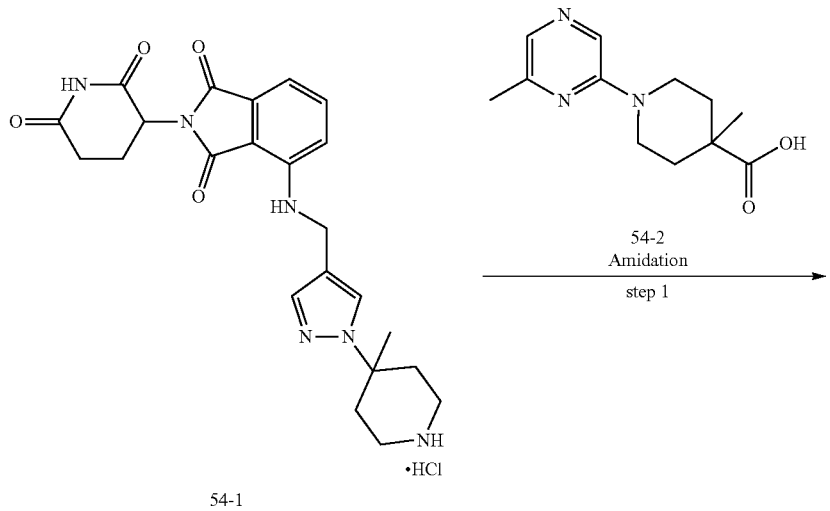

54-1

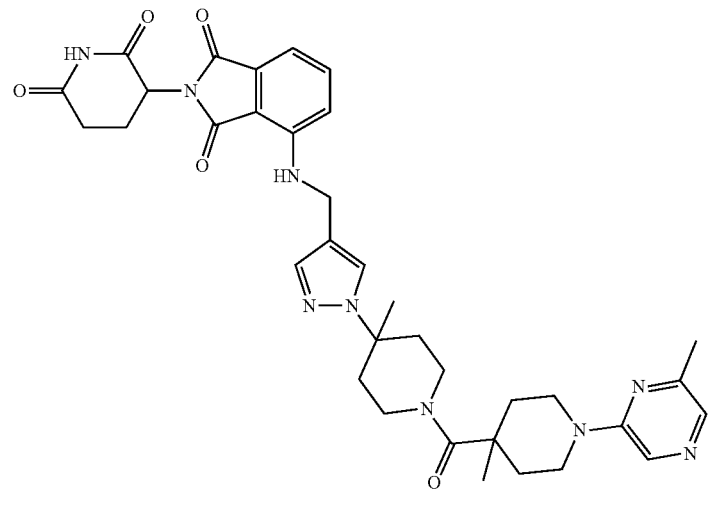

Compound 202

Step-1: Preparation of 2-(2,6-Dioxopiperidin-3-yl)-4-(((1-(4-methyl-1-(4-methyl-1-(6-methylpyrazin-2-yl)piperidine-4-carbonyl)piperidin-4-yl)-1H-pyrazol-4-yl)methyl)amino)isoindoline-1,3-dione To a stirred solution of 4-methyl-1-(6-methylpyrazin-2-yl)piperidine-4-carboxylic acid 54-2 (28.99 mg, 123.22 umol) in DMF (2.0 mL), HATU (51.54 mg, 135.54 umol) was added at 0° C. under $N_2$ atmosphere and the reaction was stirred for 15 minutes. N-Ethyl-N-isopropyl-propan-2-amine (31.85 mg, 246.43 umol, 42.92 uL) and 2-(2,6-dioxo-3-piperidyl)-4-[[1-(4-methyl-4-piperidyl)pyrazol-4-yl]methylamino]isoindoline-1,3-dione; hydrochloride 54-1 (60 mg, 123.22 umol) were added and the resultant reaction mixture was stirred for an additional 12 hours. Ice-cold water (2 mL) was added and the aqueous part was extracted with ethyl acetate. Organic portion was separated, dried over sodium sulfate and concentrated under vacuum. Crude residue was purified by preparative TLC Plate (eluting with 3% methanol/DCM) to afford 2-(2,6-dioxo-3-piperidyl)-4-[[1-[4-methyl-1-[4-methyl-1-(6-methylpyrazin-2-yl)piperidine-4-carbonyl]-4-piperidyl]pyrazol-4-yl]methylamino]isoindoline-1,3-dione (Compound 202) (23 mg, 32.49 umol, 26.37% yield, 94.32% purity, 000). $^1$H NMR (d6-DMSO, 400 MHZ) δ 11.08 (s, 1H), 8.04 (s, 1H), 7.93 (s, 1H), 7.67 (s, 1H), 7.55 (t, J=8.04 Hz, 1H), 7.50 (s, 1H), 7.17 (d, J=8.56 Hz, 1H), 7.04 (d, J=7.12 Hz, 1H), 6.80-6.78 (m, 1H), 5.05-5.01 (m, 1H), 4.39-4.37 (m, 2H), 3.75-3.73 (m, 4H), 2.92-2.85 (m, 1H), 2.60-2.55 (s, 2H), 2.49-2.48 (m, 4H), 2.32-2.27 (m, 5H), 2.10-2.07 (m, 3H), 1.81-1.79 (m, 2H), 1.53-1.48 (m, 2H), 1.40 (s, 3H), 1.25 (s, 3H); LC MS: ES+ 668.4.

Example 55. Synthesis of tert-Butyl 4-[4-[[1-(1-tert-butoxycarbonyl-4-piperidyl)triazol-4-yl]-[[2-(2,6-dioxo-3-piperidyl)-1,3-dioxo-isoindolin-4-yl]amino]methyl]triazol-1-yl]piperidine-1-carboxylate (Compound 203)

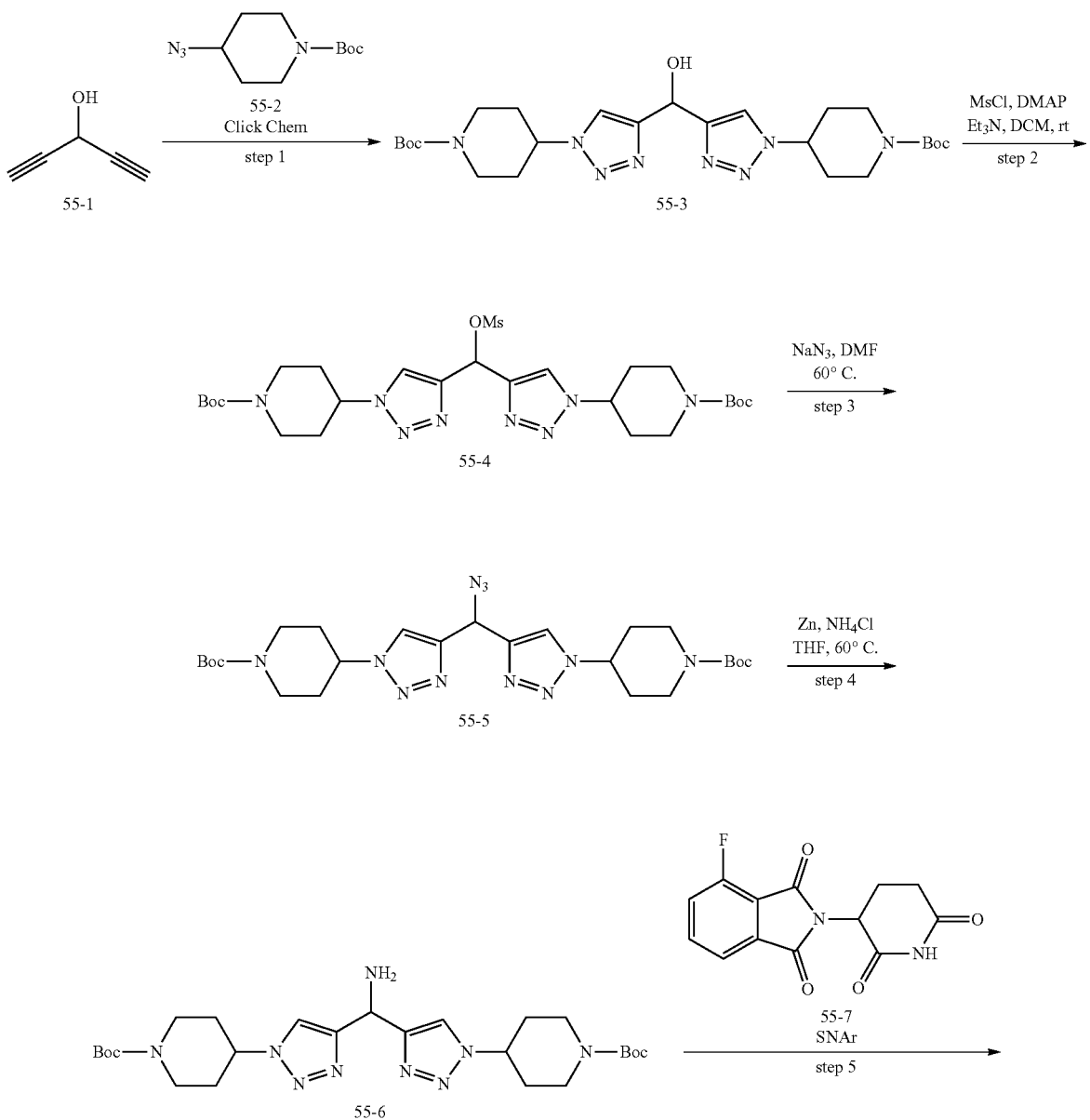

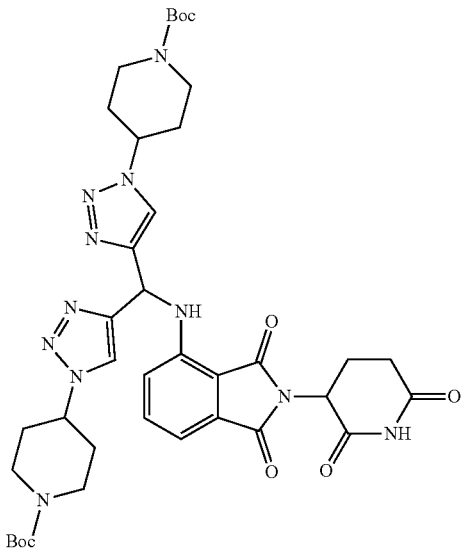

Compound 203

Step 1: Preparation of tert-Butyl 4-[4-[[1-(1-tert-butoxycarbonyl-4-piperidyl)triazol-4-yl]-hydroxy-methyl]triazol-1-yl]piperidine-1-carboxylate To the stirred solution of penta-1,4-diyn-3-ol 55-1 (100 mg, 1.25 mmol, 733.94 uL) and tert-butyl 4-azidopiperidine-1-carboxylate 55-2 (565.09 mg, 2.50 mmol) in THF (20 mL), 5 mL aqueous solution of copper sulfate pentahydrate (31.18 mg, 124.87 umol) was added and the reaction was stirred for 15 minutes at room temperature. Sodium (2R)-2-[(1S)-1,2-dihydroxyethyl]-4-hydroxy-5-oxo-2H-furan-3-olate (98.95 mg, 499.47 umol) was added to the resultant reaction mixture and stirring was continued for 16 hours at the same temperature. After completion of the reaction as monitored by LCMS, the reaction mass was filtered through a celite bed that was washed with ethyl acetate several times. The filtrate was collected and evaporated and the resulting crude residue was purified by column chromatography (100-200 silica; 30% ethyl acetate in hexane to 80% ethyl acetate in hexane as eluent) to afford tert-butyl 4-[4-[[1-(1-tert-butoxycarbonyl-4-piperidyl)triazol-4-yl]-hydroxy-methyl]triazol-1-yl]piperidine-1-carboxylate 55-3 (250 mg, 422.43 umol, 33.83% yield, 90% purity, 000) as brown sticky solid. LC MS: ES+ 533.4.

Step 2: Preparation of tert-Butyl 4-[4-[[1-(1-tert-butoxycarbonyl-4-piperidyl)triazol-4-yl]-methylsulfonyloxy-methyl]triazol-1-yl]piperidine-1-carboxylate To the stirred solution of tert-butyl 4-[4-[[1-(1-tert-butoxycarbonyl-4-piperidyl)triazol-4-yl]-hydroxy-methyl]triazol-1-yl]piperidine-1-carboxylate 55-3 (200 mg, 375.49 umol) in dry DCM (4 mL), triethyl amine (75.99 mg, 750.98 umol, 104.67 uL) and N,N-dimethylpyridin-4-amine (4.59 mg, 37.55 umol) were added followed by the dropwise addition of methanesulfonyl chloride (64.52 mg, 563.24 umol, 43.59 uL) at 0° C. under N2 atmosphere. The reaction was stirred for 12 hours at room temperature. After complete consumption of starting material as evidenced from LCMS, the reaction mass was quenched with saturated sodium bicarbonate solution and extracted with DCM (2×30 mL). Organic portion was separated, dried over sodium sulfate and concentrated under reduced pressure to afford tert-butyl 4-[4-[[1-(1-tert-butoxycarbonyl-4-piperidyl)triazol-4-yl]-methylsulfonyloxy-methyl]triazol-1-yl]piperidine-1-carboxylate 55-4 (150 mg, 245.61 umol, 65.41% yield) as brown sticky solid that was carried forward in the next step.

Step 3: Preparation of tert-Butyl 4-[4-[azido-[1-(1-tert-butoxycarbonyl-4-piperidyl)triazol-4-yl]methyl]triazol-1-yl]piperidine-1-carboxylate To the stirred solution of tert-butyl 4-[4-[[1-(1-tert-butoxycarbonyl-4-piperidyl)triazol-4-yl]-methylsulfonyloxy-methyl]triazol-1-yl]piperidine-1-carboxylate 55-4 (600 mg, 982.44 umol) in DMF (3 mL), sodium azide (319.34 mg, 4.91 mmol, 172.62 uL) was added and the resulting reaction mass was heated at 80° C. for 12 hours. After formation of desired product as confirmed by LCMS, ice cooled water (5 mL) was added to the reaction mass and extracted with ethyl acetate (2×25 mL). Organic phase was separated, dried over sodium sulfate and concentrated under reduced pressure. Crude residual part was purified by column chromatography (100-200 silica; 30% ethylacetate in hexane to 70% ethyl acetate in hexane) to afford tert-butyl 4-[4-[azido-[1-(1-tert-butoxycarbonyl-4-piperidyl)triazol-4-yl]methyl]triazol-1-yl]piperidine-1-carboxylate 55-5 (400 mg, 717.30 umol, 73.01% yield) as yellowish solid. LC MS: ES+ 558.4.

Step 4: Preparation of tert-Butyl 4-[4-[amino-[1-(1-tert-butoxycarbonyl-4-piperidyl)triazol-4-yl]methyl]triazol-1-yl]piperidine-1-carboxylate To the stirred solution of tert-butyl 4-[4-[azido-[1-(1-tert-butoxycarbonyl-4-piperidyl)triazol-4-yl]methyl]triazol-1-yl]piperidine-1-carboxylate 55-5 (700 mg, 1.26 mmol) in THF (10 mL), zinc (410.41 mg, 6.28 mmol, 57.48 uL) was added followed by an aqueous solution of ammonium chloride (3 mL, 268.59 mg, 5.02 mmol, 175.55 uL). The resultant solution was then heated at 60° C. for 6 hours. After complete consumption of starting material as evidenced by TLC and LCMS, the reaction mixture was filtered through a celite bed and washed with 5% MeOH-DCM 3 times. Filtrate was collected and concentrated under vacuum. The crude reaction mass was purified by column chromatography (100-200 silica; DCM to 5% MeOH in DCM as eluent) to afford tert-butyl 4-[4-[amino-[1-(1-tert-butoxycarbonyl-4-piperidyl)triazol-4-yl]methyl]triazol-1-yl]piperidine-1-carboxylate 55-6 (350 mg, 658.33 umol, 52.44% yield) as yellow solid. LC MS: ES+ 532.2.

Step 5: Preparation of tert-Butyl 4-[4-[[1-(1-tert-butoxycarbonyl-4-piperidyl)triazol-4-yl]-[[2-(2,6-dioxo-3-piperidyl)-1,3-dioxo-isoindolin-4-yl]amino]methyl]triazol-1-yl]piperidine-1-carboxylate To the well degassed solution of 2-(2,6-dioxo-3-piperidyl)-4-fluoro-isoindoline-1,3-dione 55-7 (70 mg, 253.42 umol) in 1-methylpyrrolidin-2-one (1 mL), tert-butyl 4-[4-[amino-[1-(1-tert-butoxycarbonyl-4-piperidyl)triazol-4-yl]methyl]triazol-1-yl]piperidine-1-carboxylate 55-6 (134.73 mg, 253.42 umol) was added and the reaction was heated to 120° C. in a sealed tube for 12 hours. After completion of reaction, as evidenced by LCMS, ice-cooled water (2 mL) was added to the reaction mass and extracted with ethyl acetate (2×30 mL). Organic portion was separated, dried over sodium sulfate and concentrated. Crude material was purified by prep-TLC (5% MeOH in DCM) to afford tert-butyl 4-[4-[[1-(1-tert-butoxycarbonyl-4-piperidyl)triazol-4-yl]-[[2-(2,6-dioxo-3-piperidyl)-1,3-dioxo-isoindolin-4-yl]amino]methyl]triazol-1-yl]piperidine-1-carboxylate (Compound 203) (28 mg, 31.99 umol, 12.62% yield, 90% purity, 000) as yellow solid. $^1$H NMR (d6-DMSO, 400 MHZ) δ 11.11 (s, 1H), 8.20 (s, 2H), 7.59 (t, J=7.82 Hz, 1H), 7.28 (d, J=7.04 Hz, 1H), 7.20 (d, J=8.68 Hz, 1H), 7.11 (d, J=7.04 Hz, 1H), 6.32 (d, J=7.28 Hz, 1H), 5.08-5.05 (m, 1H), 4.72-4.66 (m, 2H), 4.04-4.01 (m, 4H), 2.93-2.82 (m, 5H), 2.60-2.49 (m, 2H), 2.05-2.01 (m, 5H), 1.85-1.78 (m, 4H), 1.40 (s, 18H); LC MS: ES+ 788.2.

Example 56. Synthesis of 4-({1-[1-(1-Cyclopropyl-ethynyl-cyclobutylmethyl)-piperidin-4-yl]-1H-pyrazol-4-ylme-thyl}-amino)-2-(2,6-dioxo-piperidin-3-yl)-isoindole-1,3-dione (Compound 204)

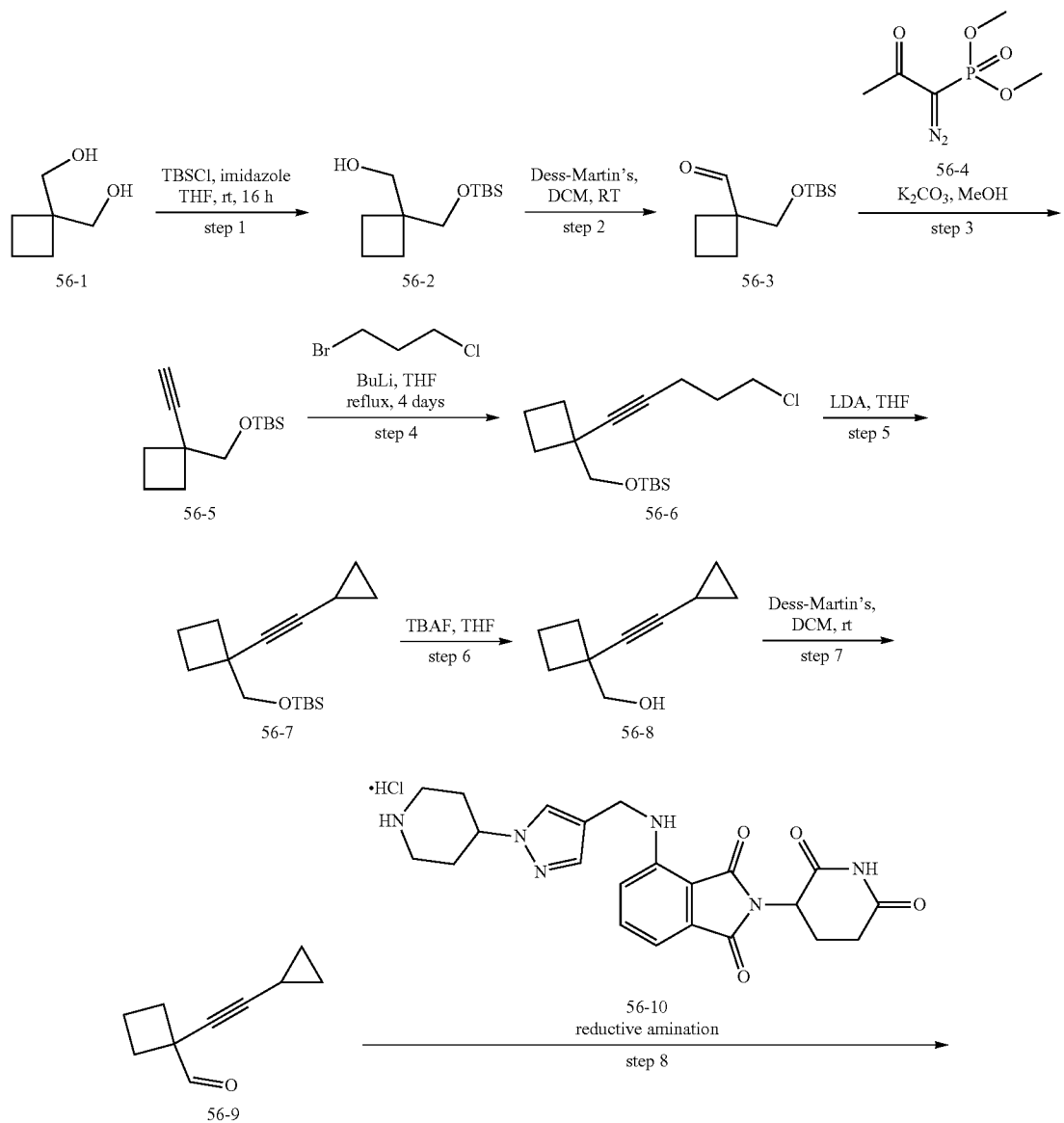

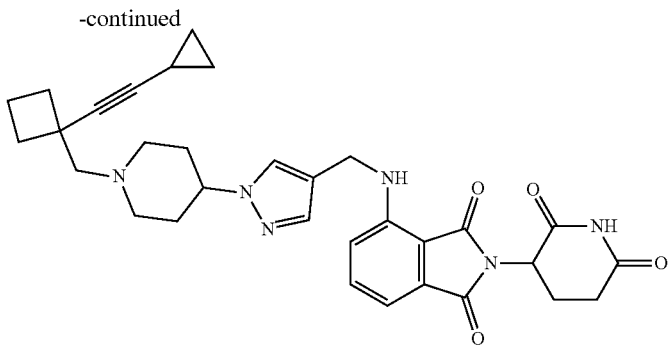

Compound 204

Step-1: Preparation of [1-(tert-Butyl-dimethyl-silanyloxym ethyl)-cyclobutyl]-methanol To a stirred solution of [1-(hydroxymethyl)cyclobutyl] methanol 56-1 (10 g, 86.09 mmol) and imidazole (11.72 g, 172.18 mmol) in DCM (200 mL) was added tert-butyldimethylchlorosilane (12.98 g, 86.09 mmol) at 0-25° C. The mixture was stirred at room temperature for 16 hr and then quenched by adding a $NaHCO_3$ solution (60 mL). The mixture was extracted using DCM, dried over MgSO4, filtered and then concentrated. The residue was purified by silica gel column chromatography (EtOAc/hexane, 1:10) to get [1-[[tert-butyl(dimethyl)silyl]oxymethyl]cyclobutyl] methanol 56-2 (8 g, 34.72 mmol, 40.33% yield) as a colorless liquid. 1H NMR (400 MHz, $CDCl_3$): δ 3.70-3.67 (m, 4H), 2.83-2.80 (m, 1H), 1.93-1.67 (m, 6H), 0.90 (s, 9H), 0.086 (s, 6H).

Step-2: Preparation of 1-(tert-Butyl-dimethyl-silanyloxymethyl)-cyclobutanecarbaldehyde Dess-Martin Periodinane (17.67 g, 41.66 mmol) was added to a heterogeneous mixture of [1-[[tert-butyl (dimethyl)silyl]ox methyl]cyclobutyl]methanol 56-2 (8 g, 34.72 mmol) and sodium bicarbonate (29.17 g, 347.19 mmol, 13.50 mL) in DCM (300 mL). After stirring for 24 hr, the heterogeneous mixture was diluted with saturated aqueous sodium sulfite and water and then extracted with DCM. The combined organic extracts were dried over anhydrous magnesium sulfate, filtered and concentrated. The residue was triturated by 2-5% ether in hexanes and filtered. The filtrate was evaporated to dryness to get 1-[[tert-butyl (dimethyl) silyl]oxymethyl]cyclobutanecarbaldehyde 56-3 (4.2 g, 18.39 mmol, 52.96% yield) as clear liquid. 1H NMR (400 MHZ, CDCl3): δ 9.66 (s, 1H), 3.85-3.76 (m, 3H), 2.29-2.19 (m, 2.7H), 1.99-1.84 (m, 5.8H), 0.92-0.86 (m, 14H, 0.046 (s, 7H).

Step-3: Preparation of tert-Butyl-(1-ethynyl-cyclobutylmethoxy)-dimethyl-silane To a stirred solution of 1-[[tert-butyl(dimethyl)silyl] oxymethyl]cyclobutanecarbaldehyde 56-3 (5 g, 21.89 mmol) in methanol (30 mL) was added potassium carbonate (6.05 g, 43.78 mmol, 2.64 mL) followed by 1-diazo-1-dimethoxyphosphoryl-propan-2-one 56-4 (4.21 g, 21.89 mmol) and stirred at 25° C. for 16 h. A new non polar spot was formed in TLC. The reaction was filtered through celite and diluted with EtOAc and washed with water followed by brine and dried over sodium sulphate. The crude was evaporated to dryness to afford tert-butyl-[(1-ethynylcyclobutyl) methoxy]-dimethyl-silane 56-5 (4.2 g, 18.72 mmol, 85.49% yield) as clear liquid. 1H NMR (400 MHZ, CDCl3): δ 3.57 (s, 2H), 2.22 (s, 1H), 2.20-2.09 (m, 3H), 2.04-1.96 (m, 1H), 1.87-1.83 (m, 1H), 0.91 (s, 9H), 0.069 (s, 6H).

Step-4: Preparation of tert-Butyl-[1-(5-chloro-pent-1-ynyl)-cyclobutylmethoxy]-dimethyl-silane A solution of tert-butyl-[(1-ethynylcyclobutyl) methoxy]-dimethyl-silane 56-5 (3.4 g, 15.15 mmol) in THE (5 mL) was added with n-butyl lithium (2.2 M, 6.89 mL) at −78° C. within 60 min. The mixture was warmed to 0° C. and stirred at the same temperature for 1 hr. Then 1-bromo-3-chloropropane (2.39 g, 15.15 mmol, 1.50 mL) was added drop wise and the reaction mixture was heated to reflux for 4 days. After completion of the reaction, $NH_4Cl$ (200 mL) was added and extracted with EtOAc. The crude was dried over sodium sulphate and evaporated to dryness. It was then purified by column with eluting solvent 1-10% EtOAc in hexane to get tert-butyl-[[1-(5-chloropent-1-ynyl)cyclobutyl]methoxy]-dimethyl-silane 56-6 (1.8 g, 5.98 mmol, 39.48% yield) as clear liquid. 1H NMR (400 MHZ, $CDCl_3$): δ 3.65 (t, J=8 Hz, 2H), 3.52 (s, 2H), 2.38 (t, J=8 Hz, 2H), 2.16-2.12 (m, 2H), 2.09-2.02 (m, 1H), 1.95-1.90 (m, 2.4H), 1.83-1.79 (m, 1H), 0.90 (s, 9H), 0.063 (s, 6H).

Step-5: Preparation of 2-tert-Butyl-(1-cyclopropyl-ethynyl-cyclobutylmethoxy)-dimethyl-silane A solution of tert-butyl-[[1-(5-chloropent-1-ynyl)cyclobutyl]methoxy]-dimethyl-silane 56-6 (2.1 g, 6.98 mmol) in THE (60 mL) was added drop wise to an LDA solution (2 M, 7.68 mL) at 0° C. and the reaction mixture was heated for 4 hr at 70° C. After completion of the reaction it was diluted with water and after phase separation the aqueous phase was extracted with ether (2×20 mL). The combined organic phases were washed with $H_2O$ and saturated NaCl (30 mL) and dried over $MgSO_4$. The solvent was removed and the residue was purified by combi-flash with eluting solvent 1-10% EtOAc in hexane to afford tert-butyl-[[1-(2-cyclopropylethynyl)-cyclobutyl]methoxy]-dimethyl-silane 56-7 (1.3 g, 4.92 mmol, 70.44% yield) as clear oil. 1H NMR (400 MHZ, CDCl3): δ 3.50 (s, 2H), 2.17-2.11 (m, 2H), 2.08-2.01 (m, 2H), 1.94-1.90 (m, 1H), 1.82-1.77 (m, 1H), 1.25-1.19 (m, 2H), 0.90 (s, 10H), 0.72-0.68 (m, 2H), 0.61-0.58 (m, 2H), 0.01 (s, 6H).

Step-6: Preparation of 2-tert-Butyl-(1-cyclopropyl-ethynyl-cyclobutylmethoxy)-dimethyl-silane A mixture of the tert-butyl-[[1-(2-cyclopropylethynyl) cyclobutyl]methoxy]-dimethyl-silane 56-7 (98 mg, 370.54 umol) and tetra butyl ammonium fluoride (1 M, 555.81 uL) in THE (2 mL) was stirred at room temperature for 2 h. After completion of the reaction, the solvent was removed and the residue was chromatographed by combi-flash using EtOAc/ hexane (3-35%) to get the [1-(2-cyclopropylethynyl)cyclobutyl]methanol 56-8 (30 mg, 199.71 umol, 53.90% yield) as clear gel. 1H NMR (400 MHZ, CDCl3): δ 3.57 (d, J=8 Hz, 2H), 2.21-2.14 (m, 2H), 2.02-1.83 (m, 4H), 1.71 (d, J=8 Hz, 1H), 1.26-1.20 (m, 2H), 0.76-0.74 (m, 2H), 0.73-0.72 (m, 2H).

Step-7: Preparation of 1-Cyclopropylethynyl-cyclobutanecarbaldehyde

Dess-Martin Periodinane (211.76 mg, 499.28 umol) was added to a heterogeneous mixture of [1-(2-cyclopropylethynyl) cyclobutyl] methanol 56-8 (50 mg, 332.85 umol) and sodium bicarbonate (167.77 mg, 2.00 mmol, 77.67 uL) in DCM (10 mL). After stirring for 16 hr, the hetero-geneous mixture was diluted with saturated aqueous sodium sulfite and water and then extracted with DCM. The combined organic extracts were dried over anhydrous magnesium sulfate, filtered and concentrated. The residue was triturated by 2-5% ether in hexanes and filtered. The filtrate was evaporated to dryness to get 1-(2-cyclopropylethynyl) cyclobutanecarbaldehyde 56-9 (45 mg, 303.64 umol, 91.22% yield) as clear liquid.

1H NMR (400 MHZ, CDCl3): δ 9.52 (s, 1H), 2.50-2.43 (m, 2H), 2.24-2.17 (m, 2H), 2.03-1.97 (m, 2H), 1.89-1.82 (m, 1H), 0.94-0.79 (m, 6.5H), 0.77-0.75 (m, 2.4H), 0.68-0.66 (m, 2H).

Step-8: Preparation of 4-({1-[1-(1-Cyclopropylethynyl-cyclobutylmethyl)-piperidin-4-yl]-1H-pyrazol-4-ylme-thyl}-amino)-2-(2,6-dioxo-piperidin-3-yl)-isoindole-1,3-dione To the stirred solution of hydrochloride salt of 2-(2,6-dioxo-3-piperidyl)-4-[[1-(4-piperidyl)pyrazol-4-yl]me-thylamino]isoindoline-1,3-dione 56-10 (140 mg, 320.76 umol) and triethylamine (35.70 mg, 352.84 umol, 49.18 uL) in THE (25 mL) was added 1-(2-cyclopropylethynyl)cy-clobutanecarbaldehyde 56-9 (47.54 mg, 320.76 umol) and dibutyltindichloride (116.96 mg, 384.91 umol, 86.00 uL) followed by the addition of phenylsilane (34.71 mg, 320.76 umol, 39.53 uL) and the reaction was heated at reflux temperature for 16 hours. TLC showed formation of new spot with some starting material. Crude LCMS showed formation of product. The reaction was cooled and evaporated to dryness. Crude was purified by combi-flash with eluting solvent 30-100% EtOAc in hexane to get 4-[[1-[1-[[1-(2-cyclopropylethynyl) cyclobutyl] methyl]-4-piperidyl] pyrazol-4-yl] me-thylamino]-2-(2,6-dioxo-3-piperidyl) isoindoline-1,3-dione (Compound 204) (54 mg, 94.96 umol, 29.60% yield, 000) (CFT-00012828-000-01) as yellow solid. 1H NMR (400 MHz, DMSO-d6): δ 11.10 (s, 1H), 7.78 (s, 1H), 7.59 (t, J=8 Hz, 1H), 7.44 (s, 1H), 7.17 (d, J=12 Hz, 1H), 7.04 (d, J=8 Hz, 1H), 6.81-6.78 (m, 1H), 5.06-5.02 (m, 1H), 4.36 (d, J=8 Hz, 2H), 4.06-4.01 (m, 1H), 3.02 (bd, J=12 Hz, 2H), 2.92-2.84 (m, 1H), 2.67-2.57 (m, 1H), 2.45 (s, 2H), 2.23-2.17 (m, 2H), 1.97-1.80 (m, 12H), 1.21-1.19 (m, 1H), 0.71-0.69 (m, 2H), 0.49 (m, 2H). LCMS (ES+)=569.3 [M+H]$^+$.

Example 57. Synthesis of 4-({1-[1-(1-Cyclopropylethynyl-cyclobutanecarbonyl)-piperidin-4-yl]-1H-pyrazol-4-yl-methyl}-amino)-2-(2,6-dioxo-piperidin-3-yl)-isoindole-1,3-dione (Compound 205)

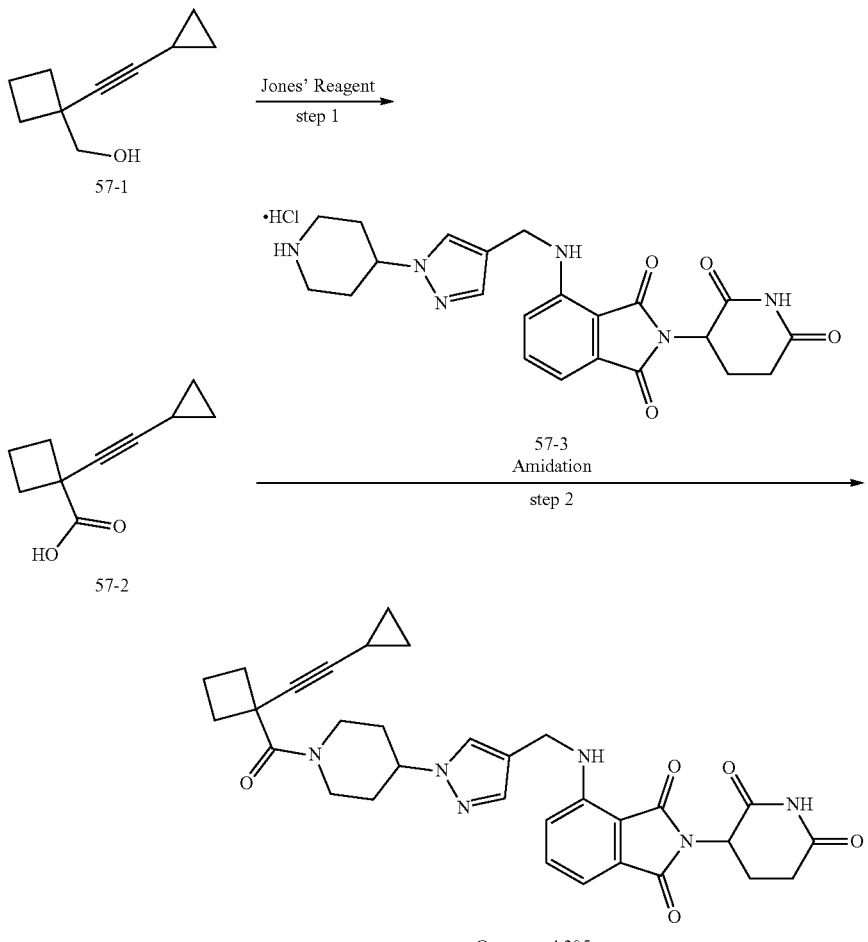

Compound 205

Step-1: Preparation of 1-Cyclopropylethynyl-cyclobutanecarboxylic acid

To a stirred solution of [1-(2-cyclopropylethynyl)cyclobutyl]methanol 57-1 (50 mg, 332.85 umol) in acetone (5 mL) at 0° C. was added Jones reagent (2.5 M, 266.28 uL) drop wise and the obtained reaction mixture was stirred for 3 hours at 0° C. Then it was quenched by adding i-PrOH (8 mL). Then the reaction mixture was filtered off and the organic phase was concentrated by evaporation. Water (10 mL) was added and the aqueous phase was extracted with $CH_2Cl_2$ (5×10 mL). Then the combined organic layers were dried over anhydrous $Na_2SO_4$ and concentrated in vacuum to get 1-(2-cyclopropylethynyl)cyclobutanecarboxylic acid 57-2 (51 mg, 310.60 umol, 93.31% yield) as off white solid. m/z=164.
NOTE: Jones reagent was prepared by dissolving 7.5 g of $CrO_3$ in conc. $H_2SO_4$ (7.5 mL). This solution was added drop wise to water (22.5 mL) at 0° C., which yielded the Jones reagent (2.5 M, 30 ml).

Step-2: Preparation of 4-({1-[1-(1-Cyclopropylethynyl-cyclobutanecarbonyl)-piperidin-4-yl]-1H-pyrazol-4-yl-methyl}-amino)-2-(2,6-dioxo-piperidin-3-yl)-isoindole-1,3-dione To a stirred solution of 2-(2,6-dioxo-3-piperidyl)-4-[[1-(4-piperidyl)pyrazol-4-yl]methylamino]isoindoline-1,3-dione 57-3 (40 mg, 91.65 umol) and 1-(2-cyclopropylethynyl)cyclobutanecarboxylic acid 57-2 (15.05 mg, 91.65 umol) in DMF (3 mL) was added DIPEA (11.84 mg, 91.65 umol, 15.96 uL) and stirred for few minutes at 25° C. HATU (34.85 mg, 91.65 umol) was added to the reaction mass and continued for 16 hr. Crude LCMS showed formation of product. Water was added to the reaction mixture and extracted with EtOAc. The organic layer was washed with water, brine and dried over $Na_2SO_4$. The crude was evaporated to dryness and purified by Prep-TLC with eluting solvent 3% MeOH in DCM to afford 4-[[1-[1-[1-(2-cyclopropyl-ethynyl)cyclobutanecarbonyl]-4-piperidyl]pyrazol-4-yl]methylamino]-2-(2,6-dioxo-3-piperidyl)isoindoline-1,3-dione (Compound 205) (12 mg, 19.67 umol, 21.47% yield, 95.52% purity, 000) (CFT-00013062-000-01) as yellow solid. $^1$H NMR (400 MHz, DMSO-d6): δ 11.08 (s, 1H), 7.77 (s, 1H), 7.58 (t, J=8 Hz, 1H), 7.46 (s, 1H), 7.16 (d, J=8 Hz, 1H), 7.04 (d, J=8 Hz, 1H), 6.83 (t, J=8 Hz, 1H), 5.06-5.02 (m, 1H), 4.40-4.36 (m, 4H), 3.85 (m, 1H), 3.11 (m, 1H), 2.88-2.87 (m, 1H), 2.75 (s, 2H), 2.68-2.47 (m, 3H), 2.17-2.13 (bs, 2H), 2.02-1.96 (m, 4H), 1.80 (m, 1H), 1.72-1.68 (m, 2H), 1.33-1.25 (m, 3H), 0.76-0.74 (m, 2H), 0.56 (m, 2H). LCMS (ES+)=583.4 [M+H]$^+$.

Example 58. Synthesis of 4-{4-[2-(2,6-Dioxo-piperidin-3-yl)-1,3-dioxo-2,3-dihydro-1H-isoindol-4-ylamino]-5,6-dihydro-4H-cyclopentapyrazol-1-yl}-piperidine-1-carboxylic acid tert-butyl ester (Compound 206) and 2-(2,6-Dioxo-piperidin-3-yl)-4-{1-[1-(1-methyl-cyclobutanecarbonyl)-piperidin-4-yl]-1,4,5,6-tetrahydro-cyclopentapyrazol-4-ylamino}-isoindole-1,3-dione (Compound 207)

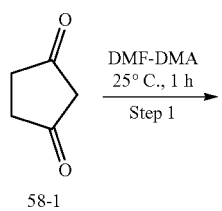

58-1

DMF-DMA
25° C., 1 h
Step 1

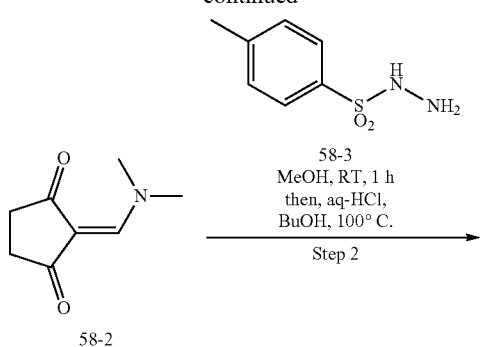

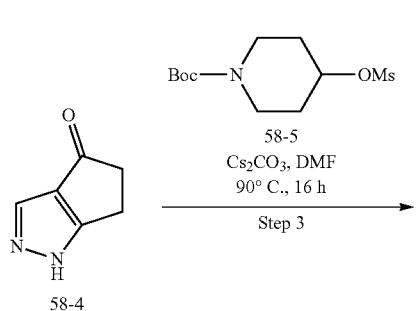

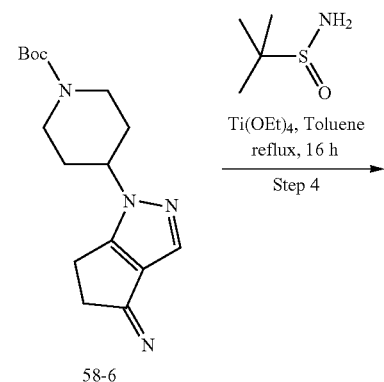

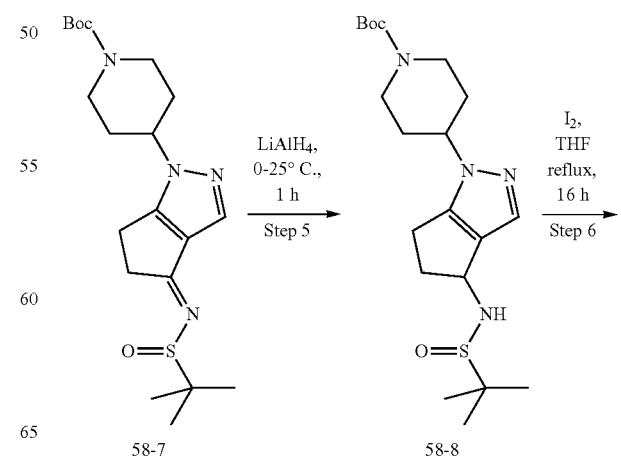

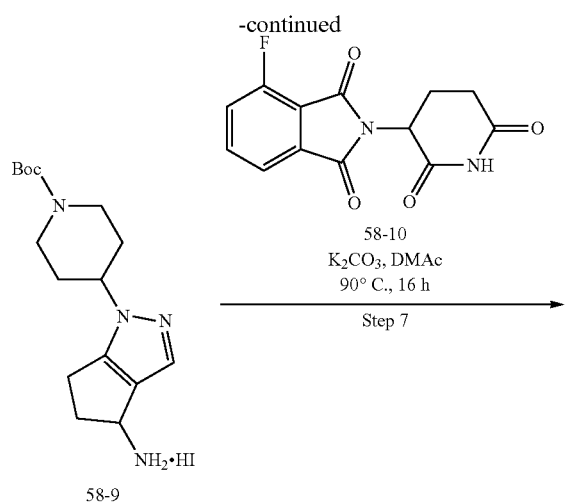

58-10

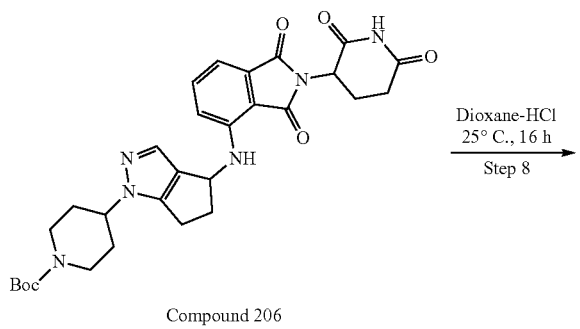

Compound 206

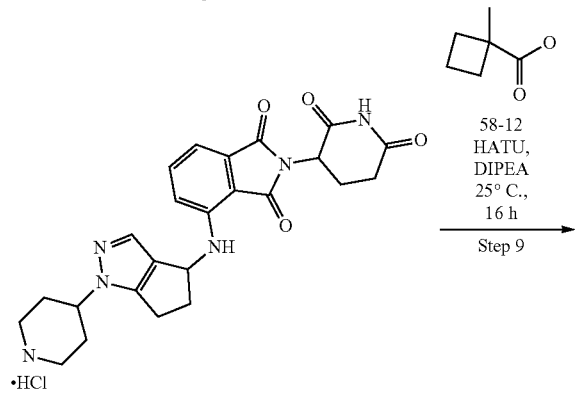

58-11

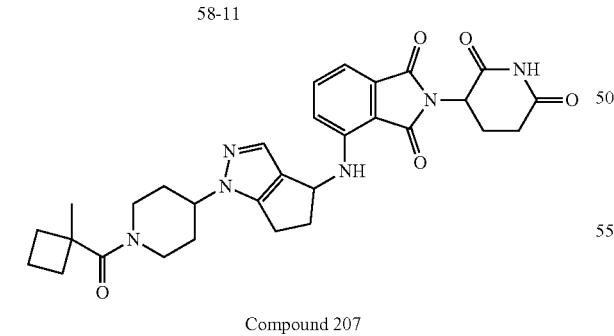

Compound 207

Step-1: Preparation of 2-Dimethylaminomethylene-cyclopentane-1,3-Dione

A solution of cyclopentane-1,3-dione 58-1 (5 g, 50.97 mmol) in DMF-DMA (50 mL) was stirred at 25° C. for 1 hr. After completion of the reaction, reaction mixture was concentrated in vacuum and the solid was washed with pentane and then dried to give the title compound 2-Dimethylaminomethylene-cyclopentane-1,3-dione 58-2 (7.5 g, 47.98 mmol, 94.14% yield, crude) as brown solid. LCMS (ES+)=154.1 [M+H]+.

Step-2: Preparation of 5,6-Dihydro-1H-cyclopentapyrazol-4-one

To a stirred solution of 2-(dimethylaminomethylene)cyclopentane-1,3-dione 58-2 (5 g, 32.64 mmol) in MeOH (12 mL) was added 4-methylbenzenesulfonohydrazide 58-3 (6.38 g, 34.27 mmol, 4.56 mL) and the mixture was stirred at RT for 1 hr. The mixture was then concentrated in vacuum to give the crude product. This crude product was taken up in butanol (15 mL) and then HCl (37% in H2O) (16.66 g, 456.98 mmol, 20.83 mL) was added and the reaction mixture was heated to 110° C. for 2 hr. After that the reaction mixture was then concentrated in vacuum to give the crude which was purified by combi-flash column chromatography (70% ethyl acetate in hexane) to give the title compound 5,6-Dihydro-1H-cyclopentapyrazol-4-one 58-4 (500 mg, 3.48 mmol, 10.66% yield, 85% purity) as brown solid. LCMS (ES+)=122.9 [M+H]+.

Step-3: Preparation of 4-(4-Oxo-5,6-dihydro-4H-cyclopentapyrazol-1-yl)-piperidine-1-carboxylic acid tert-butyl ester In a sealed tube the stirred solution of tert-butyl 4-methylsulfonyloxypiperidine-1-carboxylate 58-5 (10 g, 35.80 mmol) and 5,6-dihydro-1H-cyclopenta[c]pyrazol-4-one 58-4 (5.25 g, 42.96 mmol) in DMF (15 mL) was added cesium carbonate (17.50 g, 53.70 mmol) then the reaction mixture was heated to 90° C. for 16 hr. After completion of the reaction, it was diluted with ice cold water and extracted with ethyl acetate, washed with brine, dried over anhydrous sodium sulphate and evaporate under reduced pressure. It was then purified by combi-flash column chromatography (using 50% ethyl acetate in n-hexane) to give the mixture of two isomers 4-(4-Oxo-5,6-dihydro-4H-cyclopentapyrazol-1-yl)-piperidine-1-carboxylic acid tert-butyl ester 58-6 (8 g, 26.20 mmol, 73.18% yield) as colorless sticky solid. LCMS (ES+)=306.3 [M+H]+.

Step-4: Preparation of 4-{4-[(E)-2-Methyl-propane-2-sulfinylimino]-5,6-dihydro-4H-cyclopentapyrazol-1-yl}-piperidine-1-carboxylic acid tert-butyl ester To a stirred solution of tert-butyl 4-(4-oxo-5,6-dihydrocyclopenta[c]pyrazol-1-yl)piperidine-1-carboxylate 58-6 (5.2 g, 17.03 mmol) and 2-methylpropane-2-sulfinamide (2.27 g, 18.73 mmol) in toluene (50 mL) was added titanium (IV) ethoxide (5.83 g, 25.54 mmol, 5.35 mL) and then the reaction mixture was heated to refluxed for 16 hr. After completion of the reaction, reaction mixture was quenched with water and extracted with ethyl acetate, dried over sodium sulphate, concentrated under reduced pressure to give the mixture of two isomers as a crude material. It was then purified by combi-flash column chromatography (eluted by 80% ethyl acetate in hexane) and isolate the desired isomer tert-butyl 4-[(4Z)-4-tert-butylsulfinylimino-5,6-dihydrocyclopenta[c]pyrazol-1-yl]piperidine-1-carboxylate 58-7 (2.5 g, 6.12 mmol, 35.93% yield) as brown sticky solid. LC-MS: (ES+)=409.2 [M+H]$^+$

Step-5: Preparation of 4-[4-(2-Methyl-propane-2-sulfinylamino)-5,6-dihydro-4H-cyclopentapyrazol-1-yl]-piperidine-1-carboxylic acid tert-butyl ester To a stirred solution of tert-butyl 4-[(4E)-4-tert-butylsulfinylimino-5,6-dihydrocyclopenta[c]pyrazol-1-yl]piperidine-1-carboxylate 58-7 (1.5 g, 3.67 mmol) in THF (10 mL) was added lithium aluminum hydride (1 M in THF, 4.41 mL) at 0° C. slowly drop wise and then temperature was slowly rise to RT, then it was stirred at 25° C. for 1 hr. After completion of the reaction, it was quenched by sodium sulphate decahydrate. It was then filtered through a celite bed and filtrate was concentrated under reduced pressure to get the title compound tert-butyl 4-[4-(tert-butylsulfinylamino)-5,6-dihydro-4H-cyclopenta[c]pyrazol-1-yl]piperidine-1-carboxylate 58-8 (1.5 g, 3.65 mmol, 99.51% yield) as colorless sticky liquid. LC-MS: (ES+)=411.2 [M+H]+.

Step-6: Preparation of 4-(4-Amino-5,6-dihydro-4H-cyclopentapyrazol-1-yl)-piperidine-1-carboxylic acid tert-butyl ester. HI Salt To a stirred solution of tert-butyl 4-[4-(tert-butylsulfinylamino)-5,6-dihydro-4H-cyclopenta[c]pyrazol-1-yl]piperidine-1-carboxylate 58-8 (1.5 g, 3.65 mmol) in THF (10 mL) was added iodine (927.27 mg, 3.65 mmol), then reaction mixture was refluxed for 16 hr. After completion of the reaction, it was concentrated under reduced pressure and the crude was washed by 30% ethyl acetate in hexane and then dried to give the title compound tert-butyl 4-(4-amino-5,6-dihydro-4H-cyclopenta[c]pyrazol-1-yl)piperidine-1-carboxylate (500 mg, 1.63 mmol, 44.67% yield) 58-9 as brown solid. LC-MS: (ES+)=307.4 [M+H]+.

Step-7: Preparation of 4-{4-[2-(2,6-Dioxo-piperidin-3-yl)-1,3-dioxo-2,3-dihydro-1H-isoindol-4-ylamino]-5,6-dihydro-4H-cyclopentapyrazol-1-yl}-piperidine-1-carboxylic acid tert-butyl ester In a sealed tube the stirred solution of tert-butyl 4-(4-amino-5,6-dihydro-4H-cyclopenta[c]pyrazol-1-yl)piperidine-1-carboxylate. HI salt 58-9 (500 mg, 1.62 mmol) and 2-(2,6-dioxo-3-piperidyl)-4-fluoro-isoindoline-1,3-dione 58-10 (455.35 mg, 1.62 mmol) in dimethylacetamide (5 mL) was added potassium carbonate (273.40 mg, 1.94 mmol, 119.39 uL, 98% purity) and reaction mixture was heated to 90° C. for 16 hr. LCMS showed desired mass and the reaction mixture was diluted with ethyl acetate and extracted with EtOAc. Combined organic layer washed with water, organic layer separated, dried over sodium sulphate and concentrated under reduced pressure to give the crude. This crude was purified by combi-flash column chromatography (using 50% ethyl acetate in n-hexane) to give the title compound 4-{4-[2-(2,6-Dioxo-piperidin-3-yl)-1,3-dioxo-2,3-dihydro-1H-isoindol-4-ylamino]-5,6-dihydro-4H-cyclopentapyrazol-1-yl}-piperidine-1-carboxylic acid tert-butyl ester (Compound 206) (130 mg, 218.40 umol, 13.52% yield, 94.52% purity) (CFT-00013123-000-01) as yellow solid. 1H NMR (400 MHz, DMSO-d6): δ 11.07 (s, 1H), 7.65 (t, 1H), 7.27-7.23 (m, 2H), 7.10-7.08 (d, 1H), 6.36-6.35 (d, 1H), 5.05-5.00 (m, 2H), 4.29-4.23 (m, 1H), 4.04-4.01 (d, 2H), 3.05-3.02 (m, 1H), 2.98-2.86 (m, 4H), 2.83-2.76 (m, 1H), 2.58 (s, 2H), 2.37-2.32 (m, 1H), 2.02-1.94 (m, 3H), 1.77 (brs, 2H), 1.42 (s, 9H); LCMS (ES+)=563.5 [M+H]+.

Step-8: Preparation of 2-(2,6-Dioxo-piperidin-3-yl)-4-(1-piperidin-4-yl-1,4,5,6-tetrahydro-cyclopentapyrazol-4-ylamino)-isoindole-1,3-dione. HCl Salt To a stirred solution of tert-butyl 4-[4-[[2-(2,6-dioxo-3-piperidyl)-1,3-dioxo-isoindolin-4-yl]amino]-5,6-dihydro-4H-cyclopenta[c]pyrazol-1-yl]piperidine-1-carboxylate (Compound 206) (50 mg, 88.87 umol) in 1,4 dioxane (5 mL) was added HCl in dioxane (4 M, 888.68 uL) slowly drop wise at 0° C., and the reaction mixture was stirred at 25° C. for 16 hr. After completion of the reaction, it was concentrated under reduced pressure, washed with pentane, and dried to get the title compound 2-(2,6-dioxo-3-piperidyl)-4-[[1-(4-piperidyl)-5,6-dihydro-4H-cyclopenta[c]pyrazol-4-yl]amino]isoindoline-1,3-dione 58-11 (40 mg, 86.49 umol, 97.32% yield, HCl salt) as yellow solid. LCMS (ES+)=463.2 [M+H]+.

Step-9: Preparation of 2-(2,6-Dioxo-piperidin-3-yl)-4-{1-[1-(1-methyl-cyclobutanecarbonyl)-piperidin-4-yl]-1,4,5,6-tetrahydro-cyclopentapyrazol-4-ylamino}-isoindole-1,3-dione To a stirred solution of 2-(2,6-dioxo-3-piperidyl)-4-[[1-(4-piperidyl)-5,6-dihydro-4H-cyclopenta[c]pyrazol-4-yl]amino]isoindoline-1,3-dione 58-11 (50 mg, 108.11 umol) and 1-methylcyclobutanecarboxylic acid 58-12 (12.34 mg, 108.11 umol) in DMF (2 mL) was added HATU (61.66 mg, 162.16 umol) and DIPEA (41.92 mg, 324.32 umol, 56.49 uL) and stirred at 25° C. for 16 hr. LCMS showed desired mass and the reaction mixture was diluted with ethyl acetate and water and then extracted with EtOAc. The combined organic layer was washed with water, dried over sodium sulphate and concentrated under reduced pressure to get the crude product. It was then purified by Prep-TLC (using 100% ethyl acetatye) to get the title compound 2-(2,6-dioxo-3-piperidyl)-4-[[1-[1-(1-methylcyclobutanecarbonyl)-4-piperidyl]-5,6-dihydro-4H-cyclopenta[c]pyrazol-4 yl]amino]isoin-doline-1,3-dione (Compound 207) (5 mg, 8.13 umol, 7.52% yield, 90.85% purity) (CFT-00013187-000-01) as yellow solid. 1H NMR (400 MHz, DMSO-d6): δ 11.07 (s, 1H), 7.67-7.63 (t, 1H), 7.27-7.23 (m, 2H), 7.10-7.09 (d, 1H), 6.36-6.35 (d, 1H), 5.05-5.00 (m, 2H), 4.43 (m, 1H), 4.33 (m, 1H), 3.63 (m, 1H), 3.49-3.46 (m, 1H), 3.42-3.41 (m, 1H), 3.20-3.12 (m, 1H), 3.09-3.06 (m, 2H), 2.81-2.79 (m, 2H), 2.53-2.50 (m, 1H), 2.42-2.37 (m, 4H), 2.01-1.98 (m, 3H), 1.93-1.90 (m, 1H), 2.82-2.78 (m, 3H), 1.36-1.33 (m, 3H); LCMS (ES+)=557.3 [M−H]+.

Example 59. Cell Viability Assay

Materials

RPMI 1640 medium, fetal bovine serum (FBS) and 2-mercaptoethanol were purchased from Gibco (Grand Island, N.Y., USA). CellTiter-Glo® 2.0 Assay was purchased from Promega (Madison, Wis., USA). NCIH929.1 cell line was purchased from ATCC (Manassas, Va., USA). Cell culture flasks and 384-well microplates were acquired from VWR (Radnor, Pa., USA).

Cell Viability Analysis

NCIH929.1 cell viability was determined based on quantification of ATP using CellTiter-Glo® 2.0 luminescent Assay kit, which signals the presence of metabolically-active cells. Briefly, the test compound was added to 384-well plates at a top concentration of 1 μM with 10 points, half log titration in duplicates. NCIH929.1 cells were seeded into the 384-well plates in RPMI medium containing 10% FBS and 0.05 mM 2-mercaptoethanol at a cell density of 750 cells per well. Cells treated in the absence of the test compound were the negative control and cells treated in the absence of CellTiter-Glo® 2.0 were the positive control. At the same day of compound treatment, CellTiter-Glo® 2.0 was added to a plate with cells treated in the absence of the test compound to establish Cytostatic control value ($C_{T0}$). Cells treated with the test compound were incubated at 37° C. with 5% CO2 for 96 hr. CellTiter-Glo reagent was then added to the cells and luminescence was acquired on EnVision™ Multilabel Reader (PerkinElmer, Santa Clara, Calif., USA).
Results
Using the above assay GI50 data was determined for representative compounds in Table 2 below.
TABLE 2
| Compound # | Structure | GI50 |
|---|---|---|
| 5 | 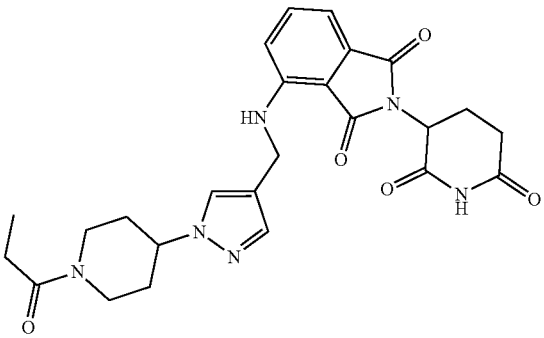 [SMILES: CCC(=O)N1CCC(n2cc(CNc3cccc4c3C(=O)N(C3CCC(=O)NC3=O)C4=O)cn2)CC1] | ND |
| 6 | 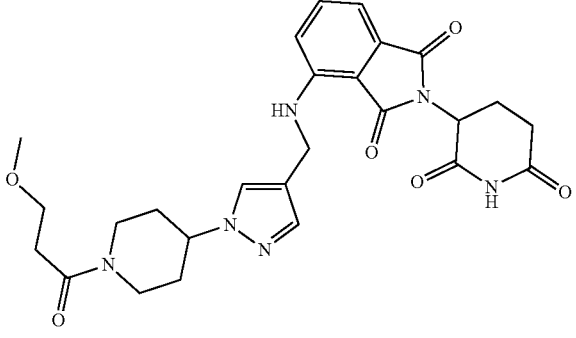 [SMILES: COCCC(=O)N1CCC(n2cc(CNc3cccc4c3C(=O)N(C3CCC(=O)NC3=O)C4=O)cn2)CC1] | ++ |
| 7 | 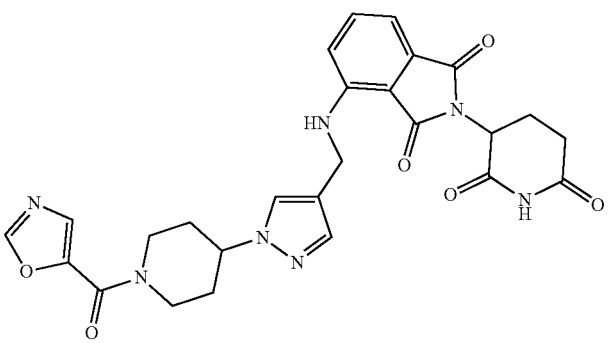 [SMILES: O=C1CCC(N2C(=O)c3cccc(NCc4cnn(C5CCN(C(=O)c6cnco6)CC5)c4)c3C2=O)C(=O)N1] | ++ |
| 8 | 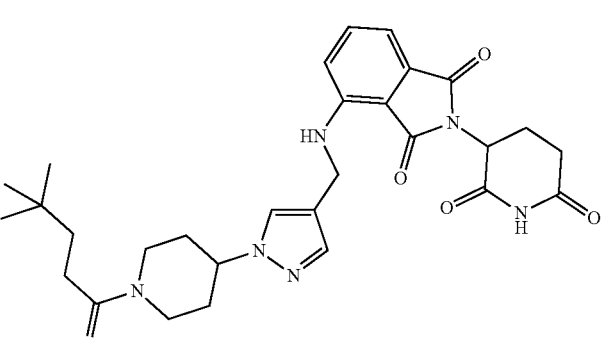 | +++ |

TABLE 2-continued

| Compound # | Structure | GI50 |
|---|---|---|
| 9 | 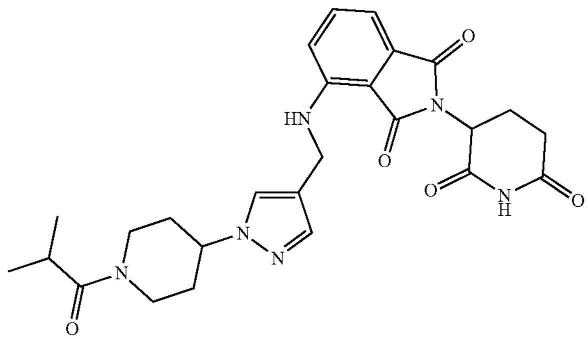 [SMILES: CC(C)C(=O)N1CCC(n2cc(CNc3cccc4c3C(=O)N(C3CCC(=O)NC3=O)C4=O)cn2)CC1] | ++ |
| 10 | 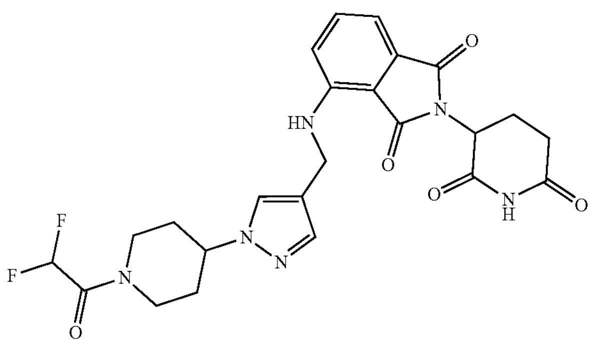 [SMILES: O=C1CCC(N2C(=O)c3cccc(NCc4cnn(C5CCN(C(=O)C(F)F)CC5)c4)c3C2=O)C(=O)N1] | ++ |
| 11 | 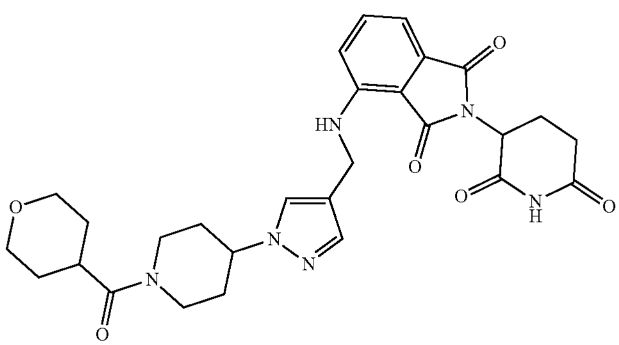 | ++ |
| 12 | 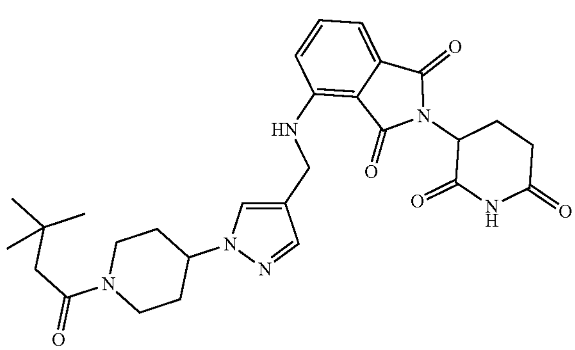 [SMILES: CC(C)(C)CC(=O)N1CCC(n2cc(CNc3cccc4c3C(=O)N(C3CCC(=O)NC3=O)C4=O)cn2)CC1] | ++ |

TABLE 2-continued

| Compound # | Structure | GI50 |
|---|---|---|
| 13 | 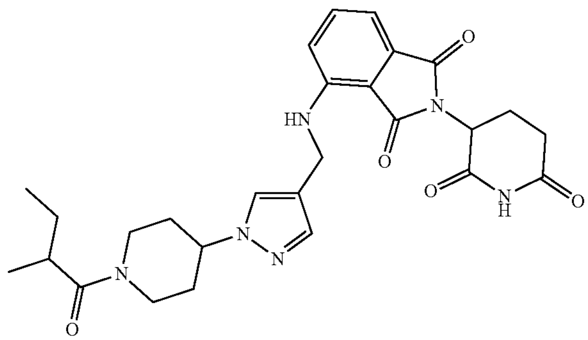 [SMILES: CCC(C)C(=O)N1CCC(n2cc(CNc3cccc4c3C(=O)N(C3CCC(=O)NC3=O)C4=O)cn2)CC1] | ++ |
| 14 | 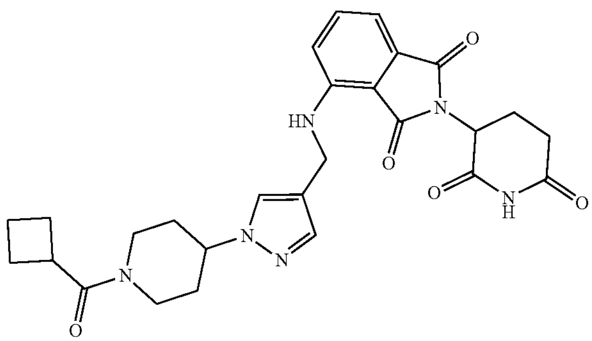 [SMILES: O=C1CCC(N2C(=O)c3cccc(NCc4cnn(C5CCN(C(=O)C6CCC6)CC5)c4)c3C2=O)C(=O)N1] | ++ |
| 15 | 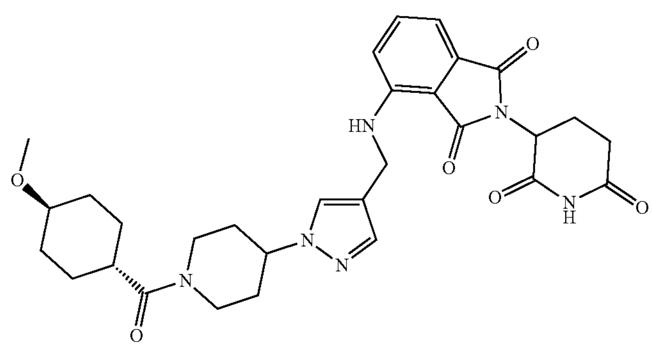 [SMILES: CO[C@H]1CC[C@H](C(=O)N2CCC(n3cc(CNc4cccc5c4C(=O)N(C4CCC(=O)NC4=O)C5=O)cn3)CC2)CC1] | ++ |
| 16 | 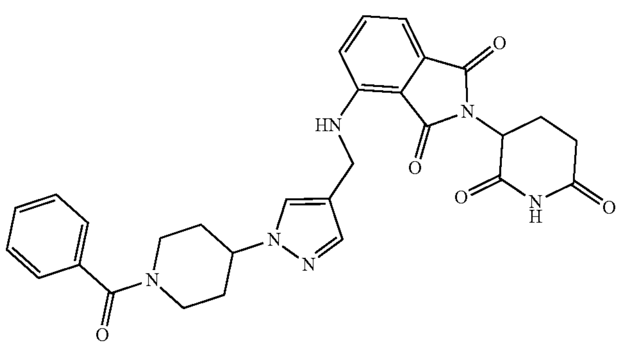 [SMILES: O=C1CCC(N2C(=O)c3cccc(NCc4cnn(C5CCN(C(=O)c6ccccc6)CC5)c4)c3C2=O)C(=O)N1] | ++ |

TABLE 2-continued

| Compound # | Structure | GI50 |
|---|---|---|
| 17 | 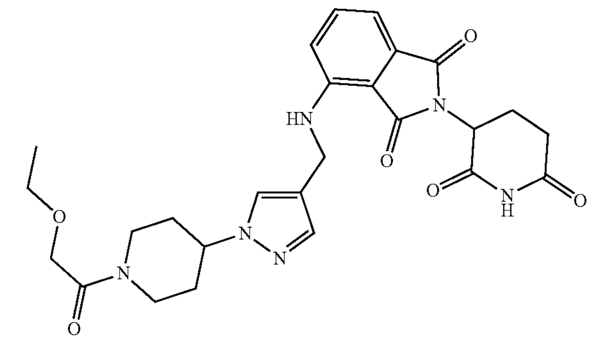 [SMILES: CCOCC(=O)N1CCC(n2cc(CNc3cccc4c3C(=O)N(C3CCC(=O)NC3=O)C4=O)cn2)CC1] | ++ |
| 18 | 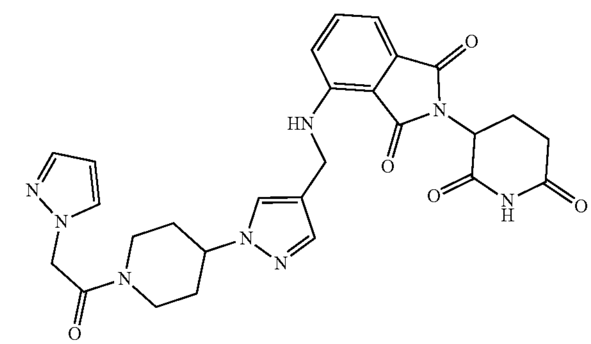 [SMILES: O=C1CCC(N2C(=O)c3cccc(NCc4cnn(C5CCN(C(=O)Cn6cccn6)CC5)c4)c3C2=O)C(=O)N1] | ++ |
| 19 | 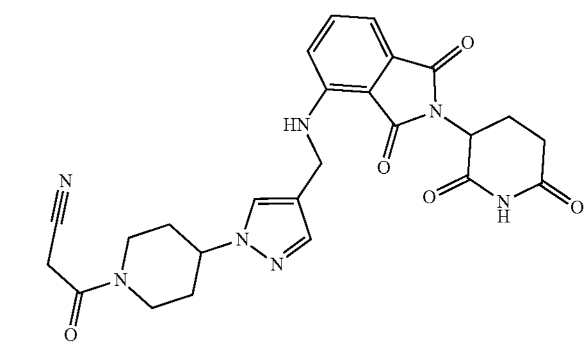 [SMILES: N#CCC(=O)N1CCC(n2cc(CNc3cccc4c3C(=O)N(C3CCC(=O)NC3=O)C4=O)cn2)CC1] | ++ |
| 20 | 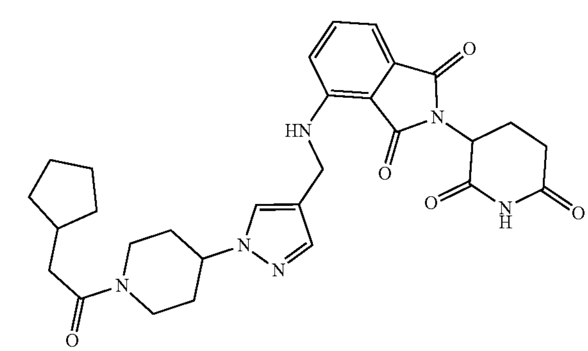 [SMILES: O=C1CCC(N2C(=O)c3cccc(NCc4cnn(C5CCN(C(=O)CC6CCCC6)CC5)c4)c3C2=O)C(=O)N1] | ++ |

TABLE 2-continued
| Compound # | Structure | GI50 |
|---|---|---|
| 21 | 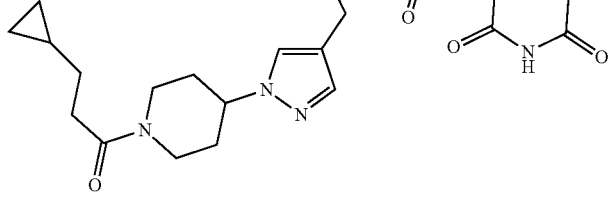 | ++ |
| 22 | 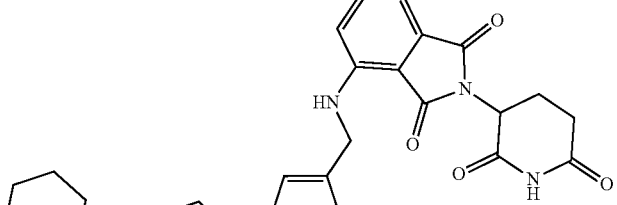 | ++ |
| 23 | 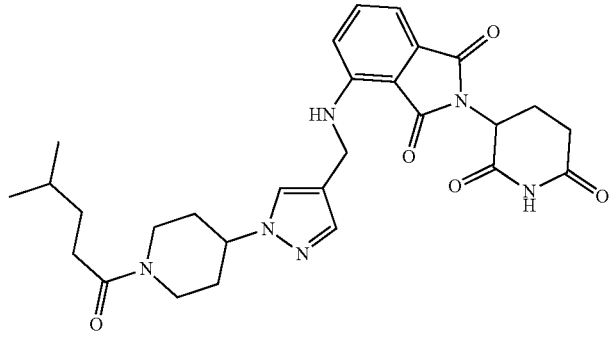 [SMILES: CC(C)CCC(=O)N1CCC(n2cc(CNc3cccc4c3C(=O)N(C3CCC(=O)NC3=O)C4=O)cn2)CC1] | +++ |
| 24 | 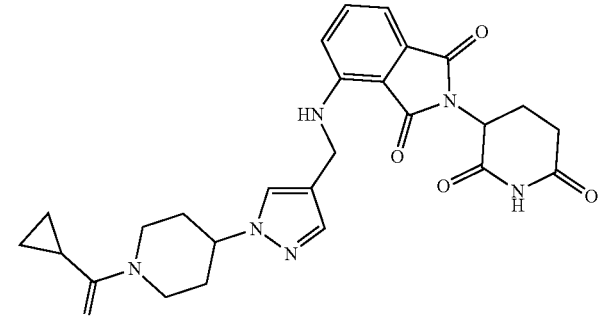 | ++ |

TABLE 2-continued

| Compound # | Structure | GI50 |
|---|---|---|
| 25 | 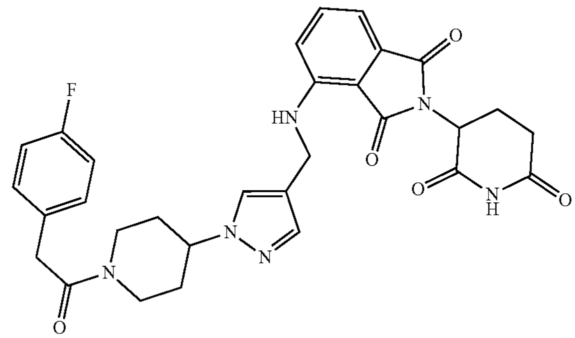 [SMILES: O=C1CCC(N2C(=O)c3cccc(NCc4cnn(C5CCN(C(=O)Cc6ccc(F)cc6)CC5)c4)c3C2=O)C(=O)N1] | ++ |
| 26 | 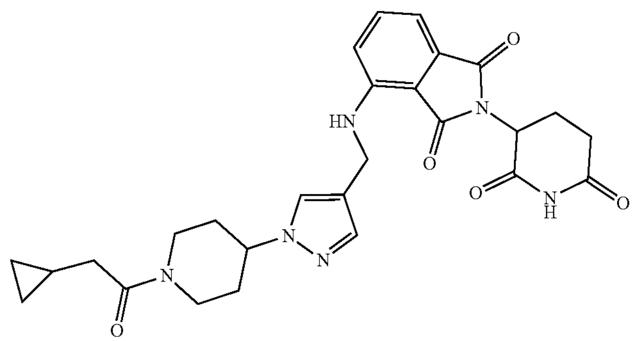 [SMILES: O=C1CCC(N2C(=O)c3cccc(NCc4cnn(C5CCN(C(=O)CC6CC6)CC5)c4)c3C2=O)C(=O)N1] | ++ |
| 27 | 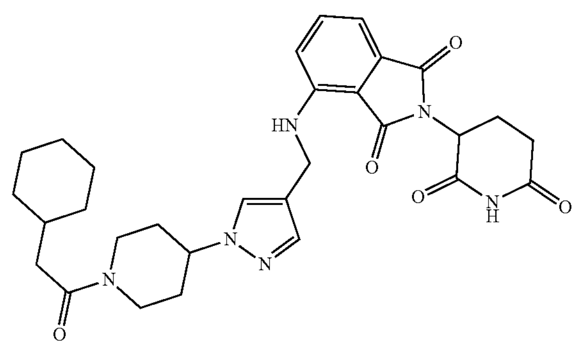 [SMILES: O=C1CCC(N2C(=O)c3cccc(NCc4cnn(C5CCN(C(=O)CC6CCCCC6)CC5)c4)c3C2=O)C(=O)N1] | +++ |
| 28 | 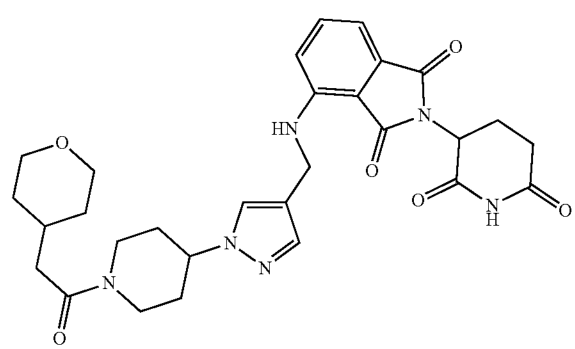 [SMILES: O=C1CCC(N2C(=O)c3cccc(NCc4cnn(C5CCN(C(=O)CC6CCOCC6)CC5)c4)c3C2=O)C(=O)N1] | ++ |

TABLE 2-continued

| Compound # | Structure | GI50 |
|---|---|---|
| 29 | 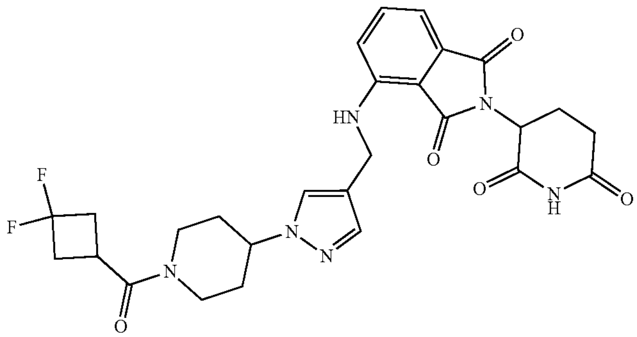 [SMILES: O=C1CCC(N2C(=O)c3cccc(NCc4cnn(C5CCN(C(=O)C6CC(F)(F)C6)CC5)c4)c3C2=O)C(=O)N1] | ++ |
| 30 | 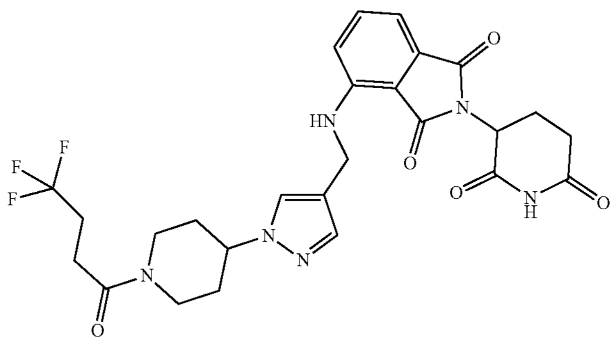 [SMILES: O=C1CCC(N2C(=O)c3cccc(NCc4cnn(C5CCN(C(=O)CCC(F)(F)F)CC5)c4)c3C2=O)C(=O)N1] | ++ |
| 31 | 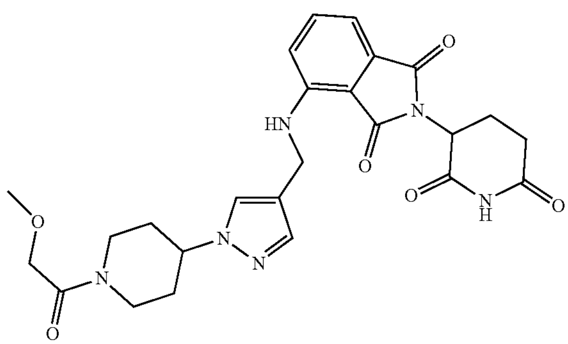 [SMILES: COCC(=O)N1CCC(n2cc(CNc3cccc4c3C(=O)N(C3CCC(=O)NC3=O)C4=O)cn2)CC1] | ++ |
| 32 | 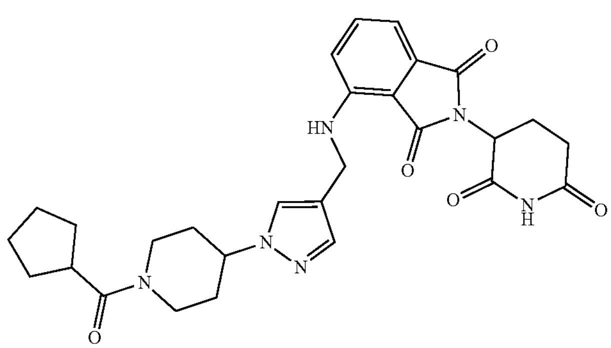 [SMILES: O=C1CCC(N2C(=O)c3cccc(NCc4cnn(C5CCN(C(=O)C6CCCC6)CC5)c4)c3C2=O)C(=O)N1] | ++ |

TABLE 2-continued
| Compound # | Structure | GI50 |
|---|---|---|
| 33 | 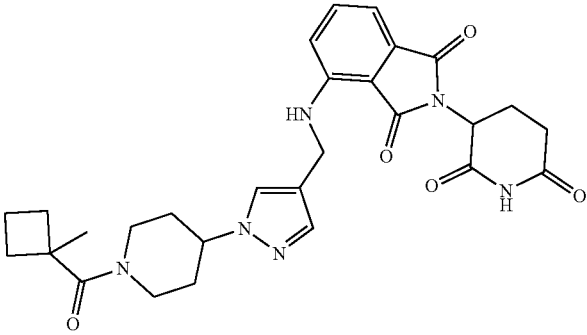 [SMILES: CC1(C(=O)N2CCC(n3cc(CNc4cccc5c4C(=O)N(C4CCC(=O)NC4=O)C5=O)cn3)CC2)CCC1] | +++ |
| 34 | 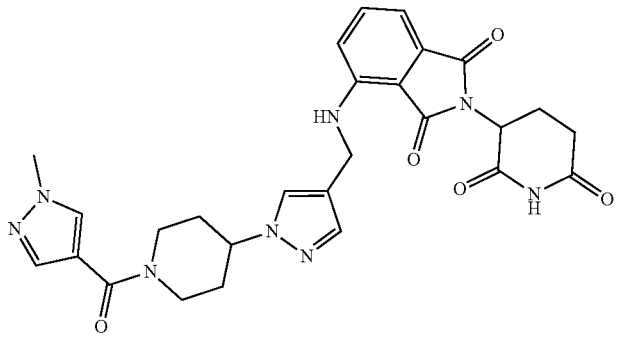 [SMILES: Cn1cc(C(=O)N2CCC(n3cc(CNc4cccc5c4C(=O)N(C4CCC(=O)NC4=O)C5=O)cn3)CC2)cn1] | ++ |
| 35 | 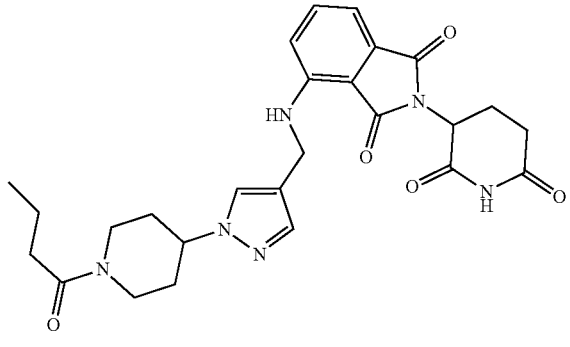 [SMILES: CCCC(=O)N1CCC(n2cc(CNc3cccc4c3C(=O)N(C3CCC(=O)NC3=O)C4=O)cn2)CC1] | ++ |
| 36 | 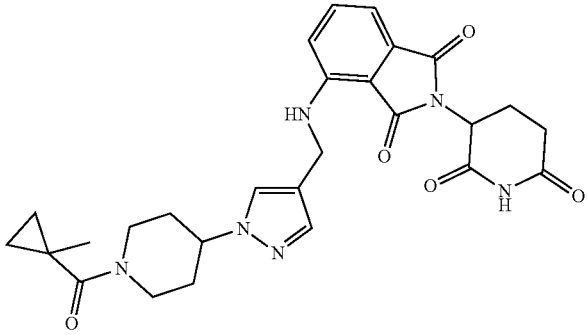 [SMILES: CC1(C(=O)N2CCC(n3cc(CNc4cccc5c4C(=O)N(C4CCC(=O)NC4=O)C5=O)cn3)CC2)CC1] | ++ |

TABLE 2-continued
| Compound # | Structure | GI50 |
|---|---|---|
| 37 | 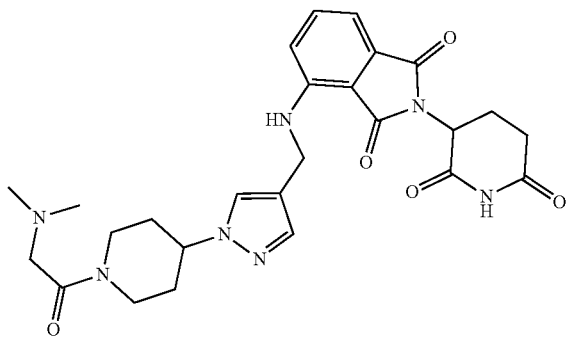 | ++ |
| 38 | 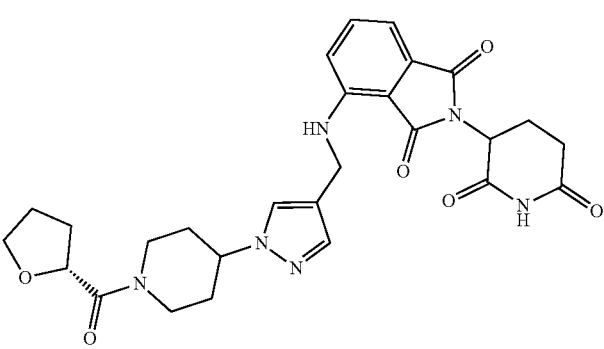 [SMILES: O=C1CCC(N2C(=O)c3cccc(NCc4cnn(C5CCN(C(=O)[C@H]6CCCO6)CC5)c4)c3C2=O)C(=O)N1] | ++ |
| 39 | 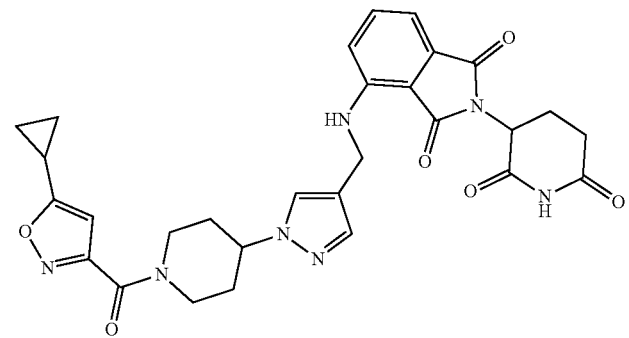 [SMILES: O=C1CCC(N2C(=O)c3cccc(NCc4cnn(C5CCN(C(=O)c6cc(C7CC7)on6)CC5)c4)c3C2=O)C(=O)N1] | ++ |
| 40 | 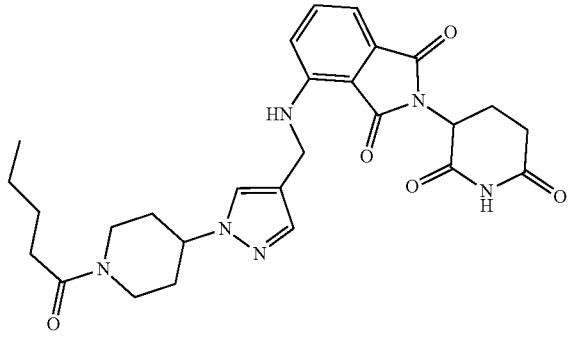 [SMILES: CCCCC(=O)N1CCC(n2cc(CNc3cccc4c3C(=O)N(C3CCC(=O)NC3=O)C4=O)cn2)CC1] | ++ |

TABLE 2-continued
| Compound # | Structure | GI50 |
|---|---|---|
| 41 | 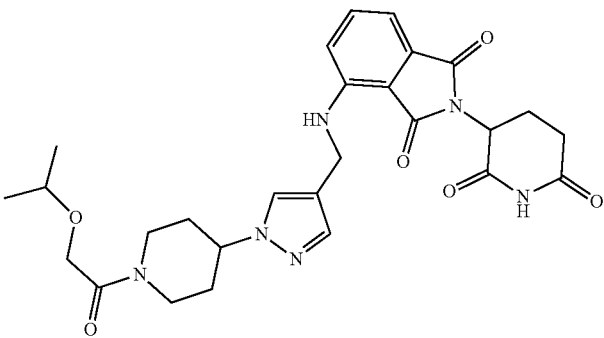 [SMILES: CC(C)OCC(=O)N1CCC(n2cc(CNc3cccc4c3C(=O)N(C3CCC(=O)NC3=O)C4=O)cn2)CC1] | ++ |
| 42 | 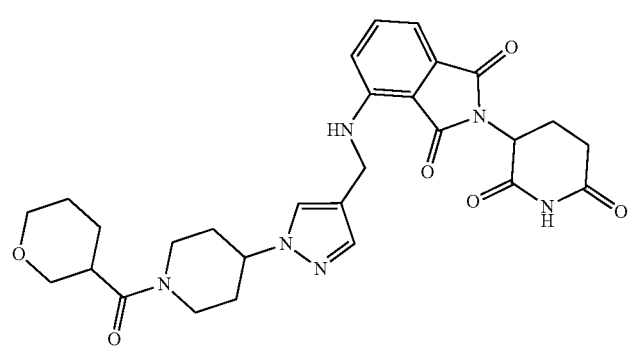 [SMILES: O=C1CCC(N2C(=O)c3cccc(NCc4cnn(C5CCN(C(=O)C6CCCOC6)CC5)c4)c3C2=O)C(=O)N1] | ++ |
| 43 | 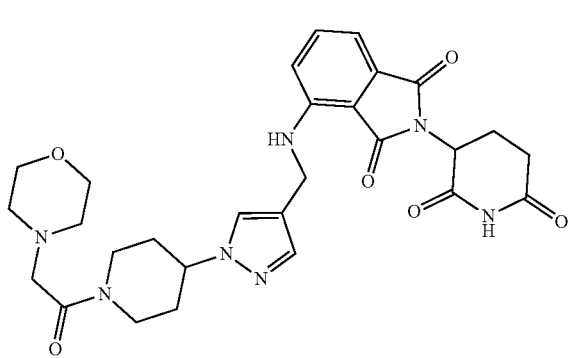 | ++ |
| 44 | 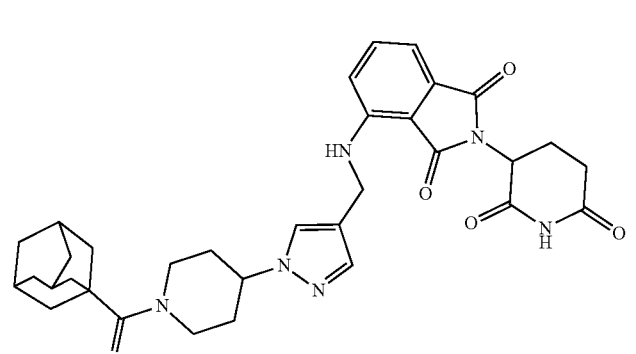 | +++ |

TABLE 2-continued

| Compound # | Structure | GI50 |
|---|---|---|
| 45 | 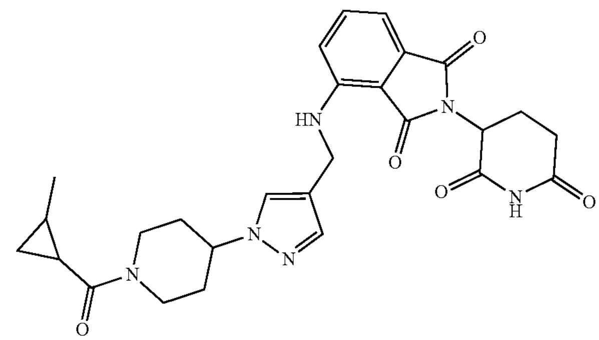 [SMILES: CC1CC1C(=O)N1CCC(n2cc(CNc3cccc4c3C(=O)N(C3CCC(=O)NC3=O)C4=O)cn2)CC1] | ++ |
| 46 | 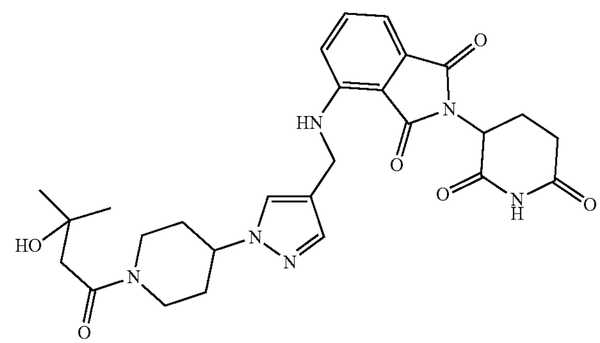 [SMILES: CC(C)(O)CC(=O)N1CCC(n2cc(CNc3cccc4c3C(=O)N(C3CCC(=O)NC3=O)C4=O)cn2)CC1] | ++ |
| 47 | 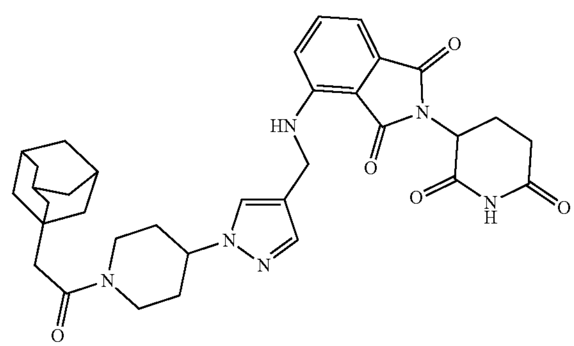 [SMILES: O=C1CCC(N2C(=O)c3cccc(NCc4cnn(C5CCN(C(=O)CC67CC8CC(CC(C8)C6)C7)CC5)c4)c3C2=O)C(=O)N1] | +++ |
| 48 | 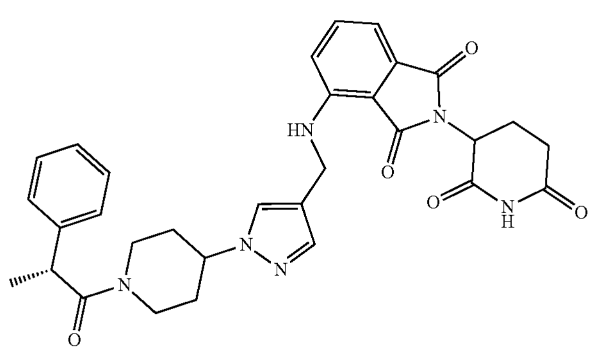 [SMILES: C[C@@H](C(=O)N1CCC(n2cc(CNc3cccc4c3C(=O)N(C3CCC(=O)NC3=O)C4=O)cn2)CC1)c1ccccc1] | ++ |

TABLE 2-continued

| Compound # | Structure | GI50 |
|---|---|---|
| 49 | 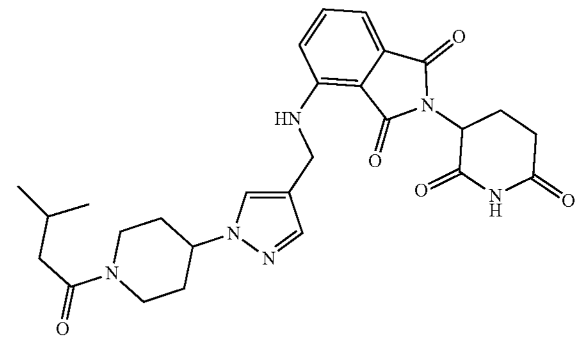 [SMILES: CC(C)CC(=O)N1CCC(n2cc(CNc3cccc4c3C(=O)N(C3CCC(=O)NC3=O)C4=O)cn2)CC1] | ++ |
| 50 | 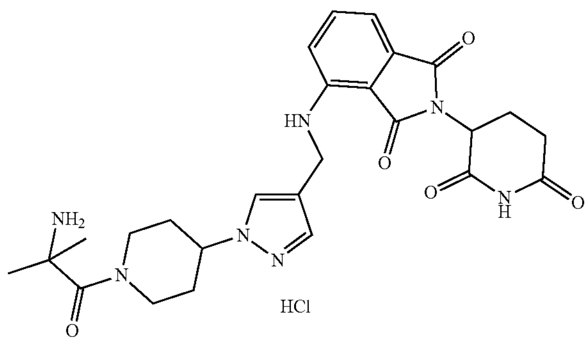 [SMILES: CC(C)(N)C(=O)N1CCC(n2cc(CNc3cccc4c3C(=O)N(C3CCC(=O)NC3=O)C4=O)cn2)CC1 ; Cl] | ++ |
| 51 | 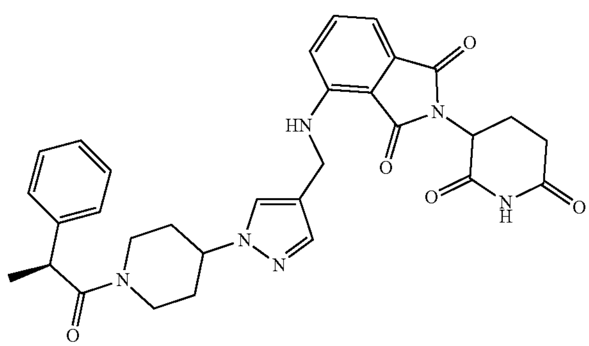 [SMILES: C[C@H](C(=O)N1CCC(n2cc(CNc3cccc4c3C(=O)N(C3CCC(=O)NC3=O)C4=O)cn2)CC1)c1ccccc1] | ++ |
| 52 | 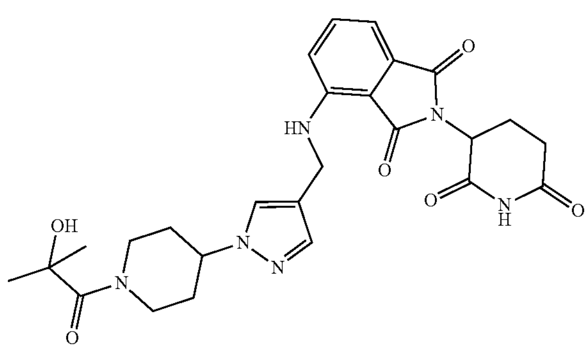 [SMILES: CC(C)(O)C(=O)N1CCC(n2cc(CNc3cccc4c3C(=O)N(C3CCC(=O)NC3=O)C4=O)cn2)CC1] | ++ |

TABLE 2-continued

| Compound # | Structure | GI50 |
|---|---|---|
| 53 | 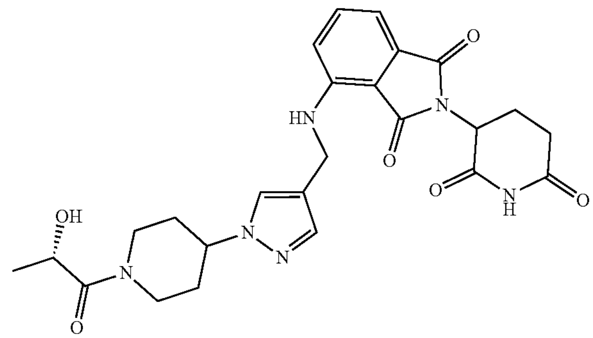 [SMILES: C[C@H](O)C(=O)N1CCC(n2cc(CNc3cccc4c3C(=O)N(C3CCC(=O)NC3=O)C4=O)cn2)CC1] | ++ |
| 54 | 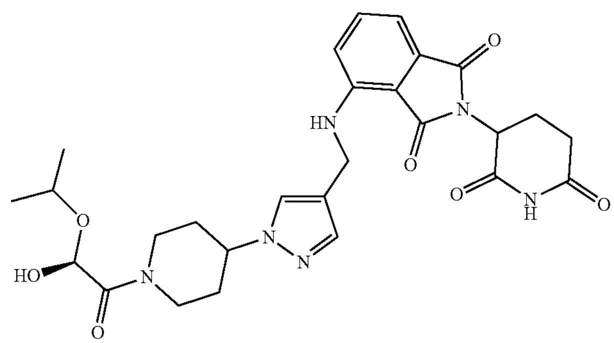 [SMILES: CC(C)O[C@H](O)C(=O)N1CCC(n2cc(CNc3cccc4c3C(=O)N(C3CCC(=O)NC3=O)C4=O)cn2)CC1] | ++ |
| 55 | 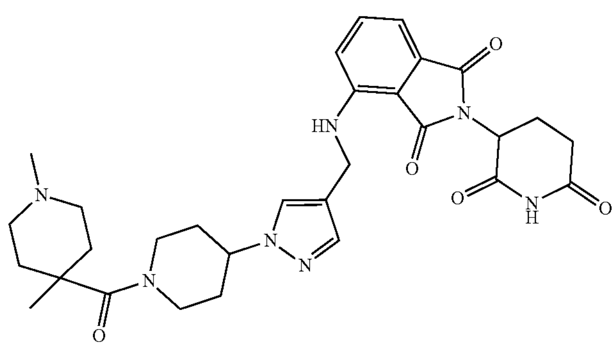 [SMILES: CN1CCC(C)(C(=O)N2CCC(n3cc(CNc4cccc5c4C(=O)N(C4CCC(=O)NC4=O)C5=O)cn3)CC2)CC1] | ++ |
| 56 | 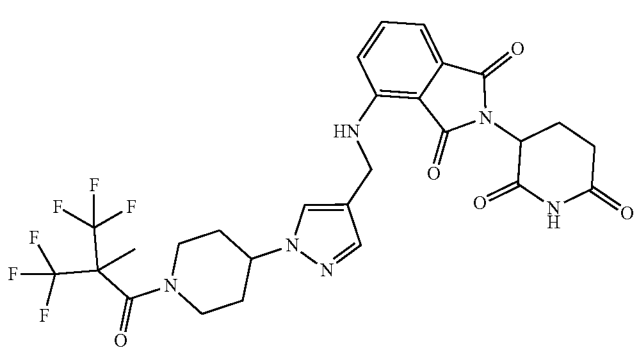 [SMILES: CC(C(=O)N1CCC(n2cc(CNc3cccc4c3C(=O)N(C3CCC(=O)NC3=O)C4=O)cn2)CC1)(C(F)(F)F)C(F)(F)F] | ++ |

TABLE 2-continued

| Compound # | Structure | GI50 |
|---|---|---|
| 57 | 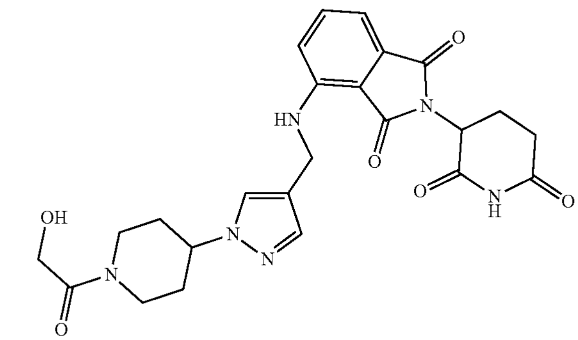 [SMILES: O=C1CCC(N2C(=O)c3cccc(NCc4cnn(C5CCN(C(=O)CO)CC5)c4)c3C2=O)C(=O)N1] | ND |
| 58 | 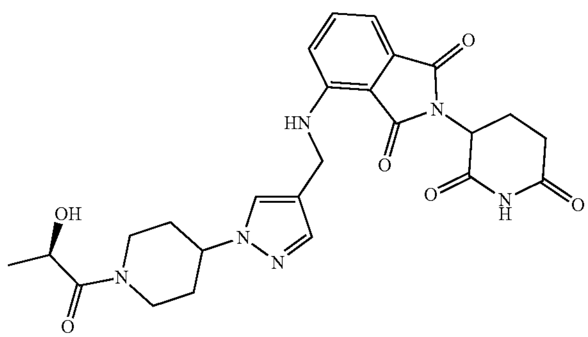 [SMILES: C[C@@H](O)C(=O)N1CCC(n2cc(CNc3cccc4c3C(=O)N(C3CCC(=O)NC3=O)C4=O)cn2)CC1] | ND |
| 59 | 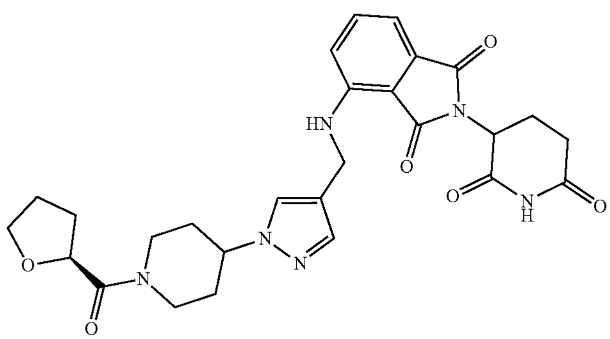 [SMILES: O=C1CCC(N2C(=O)c3cccc(NCc4cnn(C5CCN(C(=O)[C@@H]6CCCO6)CC5)c4)c3C2=O)C(=O)N1] | ++ |
| 60 | 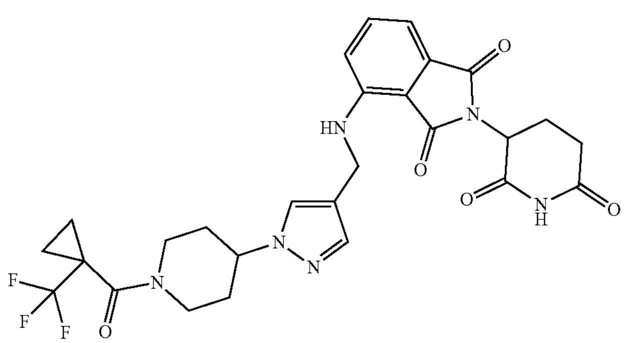 [SMILES: O=C1CCC(N2C(=O)c3cccc(NCc4cnn(C5CCN(C(=O)C6(C(F)(F)F)CC6)CC5)c4)c3C2=O)C(=O)N1] | ++ |

TABLE 2-continued

| Compound # | Structure | GI50 |
|---|---|---|
| 61 | 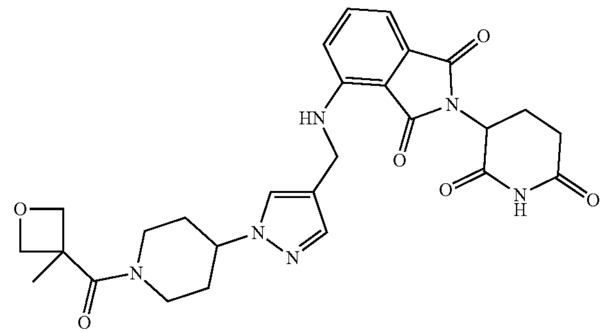 [SMILES: CC1(C(=O)N2CCC(n3cc(CNc4cccc5c4C(=O)N(C4CCC(=O)NC4=O)C5=O)cn3)CC2)COC1] | ++ |
| 62 | 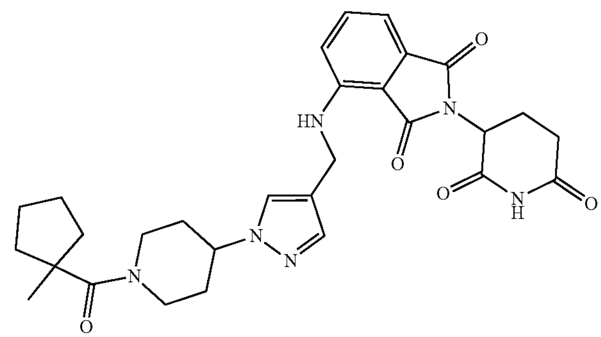 [SMILES: CC1(C(=O)N2CCC(n3cc(CNc4cccc5c4C(=O)N(C4CCC(=O)NC4=O)C5=O)cn3)CC2)CCCC1] | +++ |
| 63 | 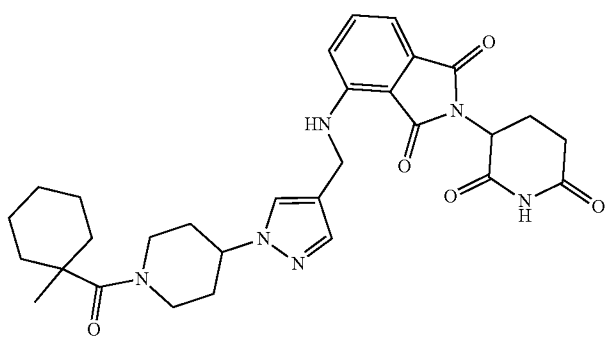 [SMILES: CC1(C(=O)N2CCC(n3cc(CNc4cccc5c4C(=O)N(C4CCC(=O)NC4=O)C5=O)cn3)CC2)CCCCC1] | +++ |
| 64 | 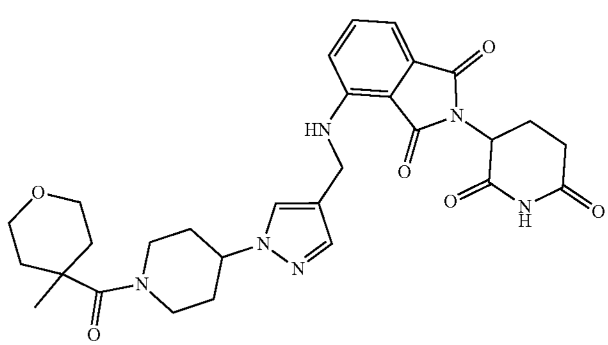 [SMILES: CC1(C(=O)N2CCC(n3cc(CNc4cccc5c4C(=O)N(C4CCC(=O)NC4=O)C5=O)cn3)CC2)CCOCC1] | ++ |

TABLE 2-continued

| Compound # | Structure | GI50 |
|---|---|---|
| 65 | 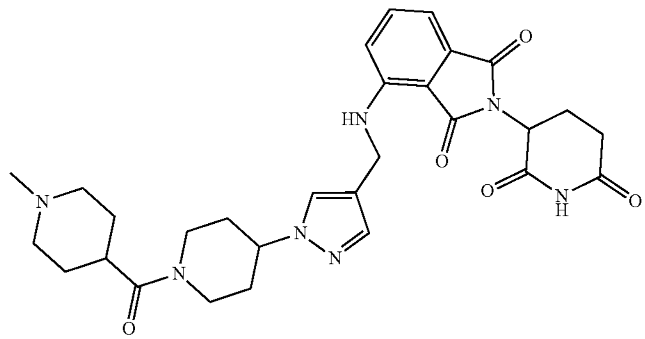 [SMILES: CN1CCC(C(=O)N2CCC(n3cc(CNc4cccc5c4C(=O)N(C4CCC(=O)NC4=O)C5=O)cn3)CC2)CC1] | ND |
| 66 | 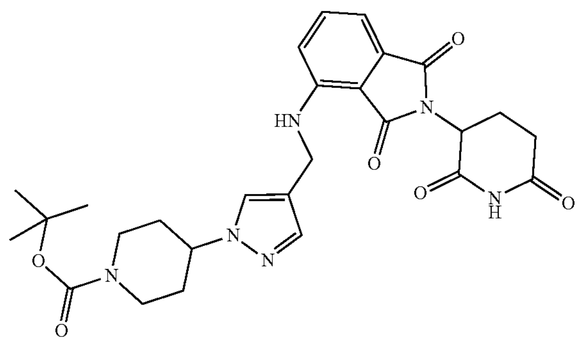 | ++ |
| 67 | 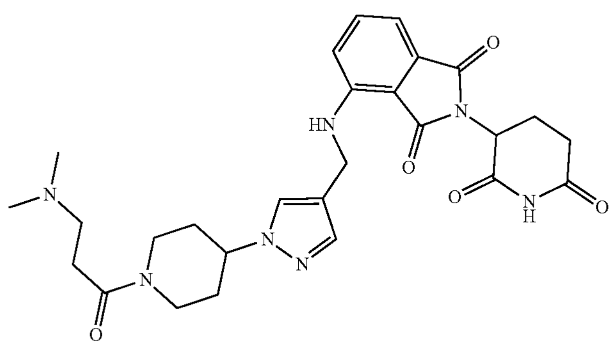 [SMILES: CN(C)CCC(=O)N1CCC(n2cc(CNc3cccc4c3C(=O)N(C3CCC(=O)NC3=O)C4=O)cn2)CC1] | ND |
| 68 | 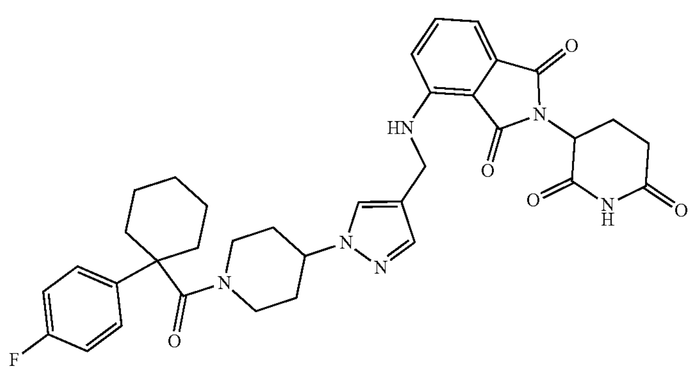 [SMILES: O=C1CCC(N2C(=O)c3cccc(NCc4cnn(C5CCN(C(=O)C6(c7ccc(F)cc7)CCCCC6)CC5)c4)c3C2=O)C(=O)N1] | ++ |

TABLE 2-continued

| Compound # | Structure | GI50 |
|---|---|---|
| 69 | 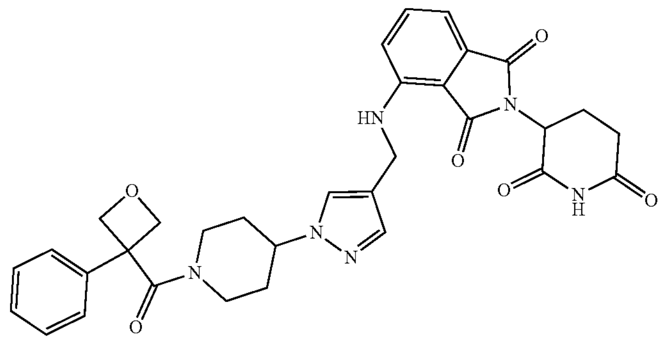 [SMILES: O=C1CCC(N2C(=O)c3cccc(NCc4cnn(C5CCN(C(=O)C6(c7ccccc7)COC6)CC5)c4)c3C2=O)C(=O)N1] | ++ |
| 70 | 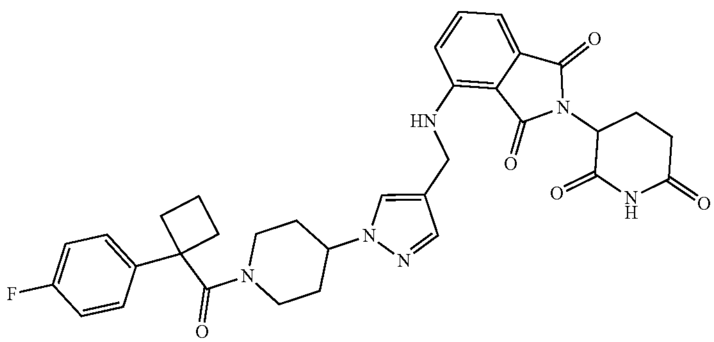 [SMILES: O=C1CCC(N2C(=O)c3cccc(NCc4cnn(C5CCN(C(=O)C6(c7ccc(F)cc7)CCC6)CC5)c4)c3C2=O)C(=O)N1] | +++ |
| 71 | 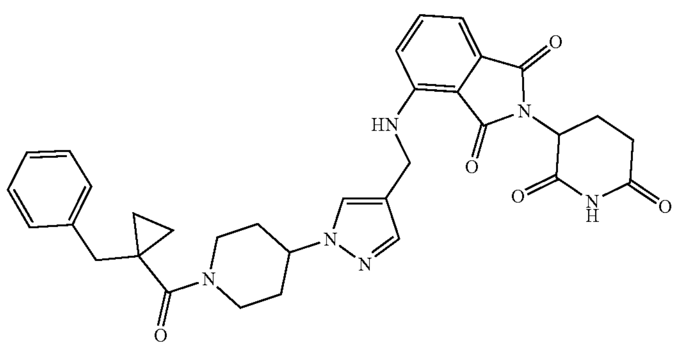 [SMILES: O=C1CCC(N2C(=O)c3cccc(NCc4cnn(C5CCN(C(=O)C6(Cc7ccccc7)CC6)CC5)c4)c3C2=O)C(=O)N1] | ++ |
| 72 | 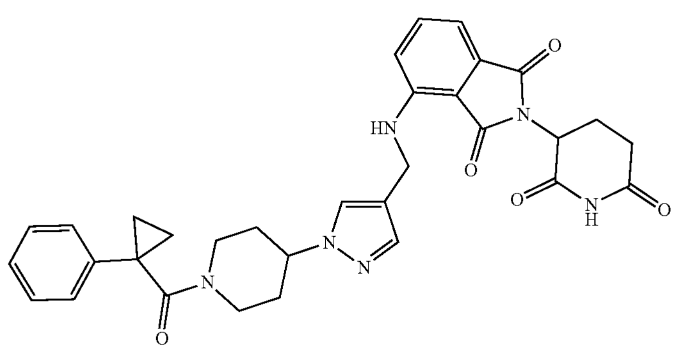 [SMILES: O=C1CCC(N2C(=O)c3cccc(NCc4cnn(C5CCN(C(=O)C6(c7ccccc7)CC6)CC5)c4)c3C2=O)C(=O)N1] | ++ |

TABLE 2-continued

| Compound # | Structure | GI50 |
|---|---|---|
| 73 | 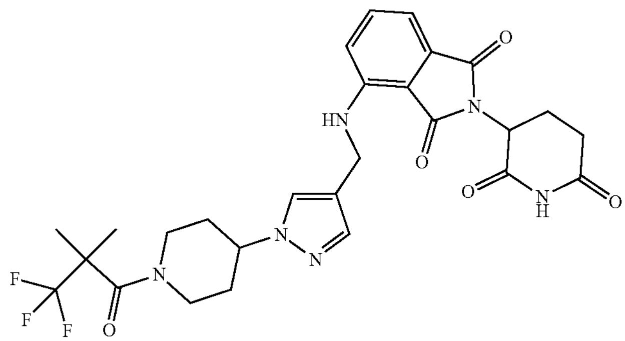 [SMILES: CC(C)(C(=O)N1CCC(n2cc(CNc3cccc4c3C(=O)N(C3CCC(=O)NC3=O)C4=O)cn2)CC1)C(F)(F)F] | ++ |
| 74 | 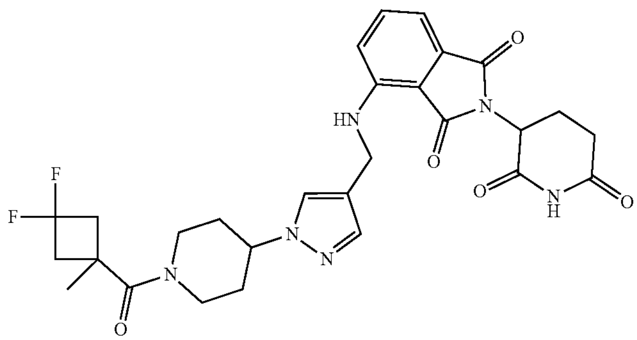 [SMILES: CC1(C(=O)N2CCC(n3cc(CNc4cccc5c4C(=O)N(C4CCC(=O)NC4=O)C5=O)cn3)CC2)CC(F)(F)C1] | ++ |
| 75 | 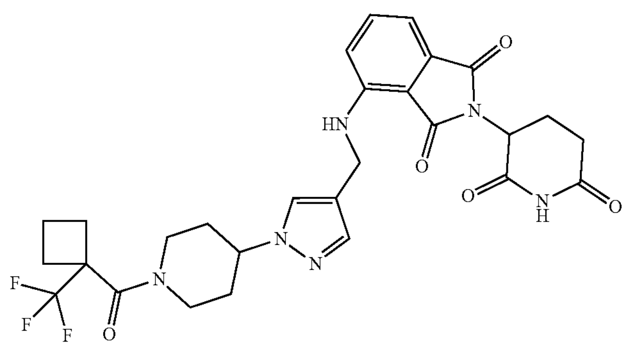 [SMILES: O=C1CCC(N2C(=O)c3cccc(NCc4cnn(C5CCN(C(=O)C6(C(F)(F)F)CCC6)CC5)c4)c3C2=O)C(=O)N1] | +++ |
| 76 | 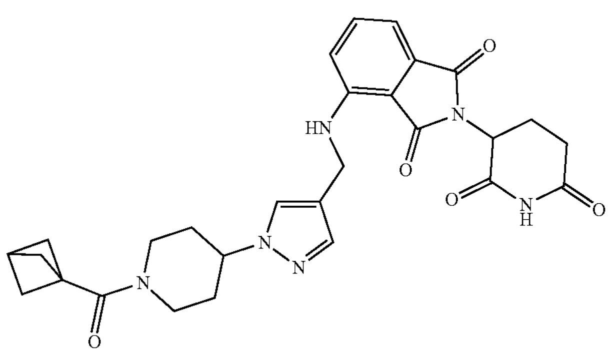 [SMILES: O=C1CCC(N2C(=O)c3cccc(NCc4cnn(C5CCN(C(=O)C67CC(C6)C7)CC5)c4)c3C2=O)C(=O)N1] | ++ |

TABLE 2-continued

| Compound # | Structure | GI50 |
|---|---|---|
| 77 | 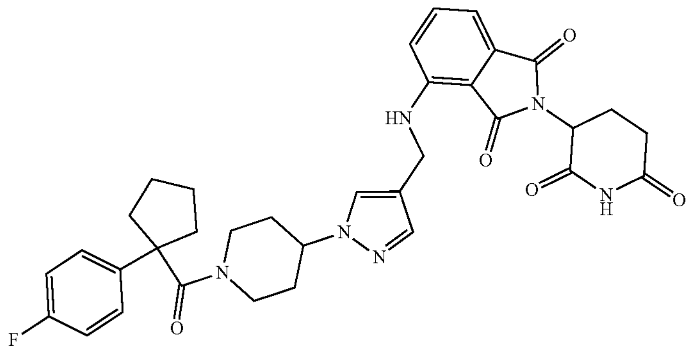 [SMILES: O=C1CCC(N2C(=O)c3cccc(NCc4cnn(C5CCN(C(=O)C6(c7ccc(F)cc7)CCCC6)CC5)c4)c3C2=O)C(=O)N1] | +++ |
| 78 | 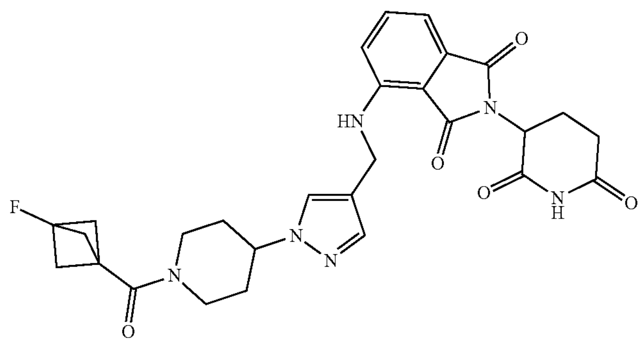 [SMILES: O=C1CCC(N2C(=O)c3cccc(NCc4cnn(C5CCN(C(=O)C67CC(F)(C6)C7)CC5)c4)c3C2=O)C(=O)N1] | ++ |
| 79 | 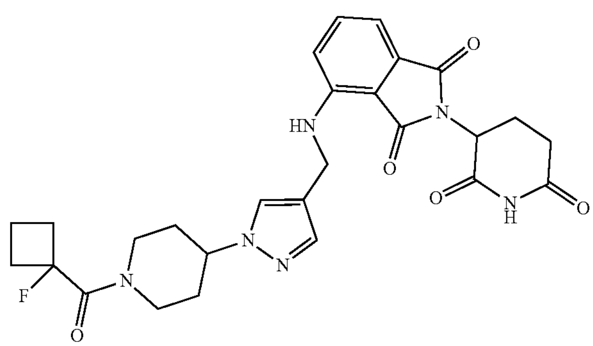 [SMILES: O=C1CCC(N2C(=O)c3cccc(NCc4cnn(C5CCN(C(=O)C6(F)CCC6)CC5)c4)c3C2=O)C(=O)N1] | ++ |
| 80 | 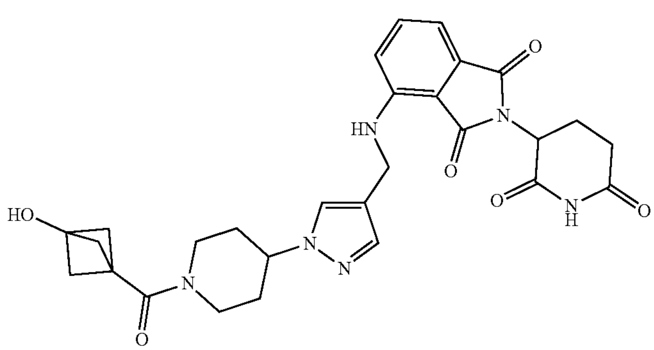 [SMILES: O=C1CCC(N2C(=O)c3cccc(NCc4cnn(C5CCN(C(=O)C67CC(O)(C6)C7)CC5)c4)c3C2=O)C(=O)N1] | ND |

TABLE 2-continued

| Compound # | Structure | GI50 |
|---|---|---|
| 81 | 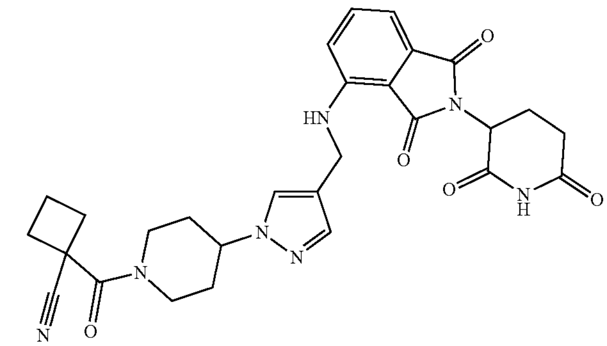 [SMILES: N#CC1(C(=O)N2CCC(n3cc(CNc4cccc5c4C(=O)N(C4CCC(=O)NC4=O)C5=O)cn3)CC2)CCC1] | ++ |
| 82 | 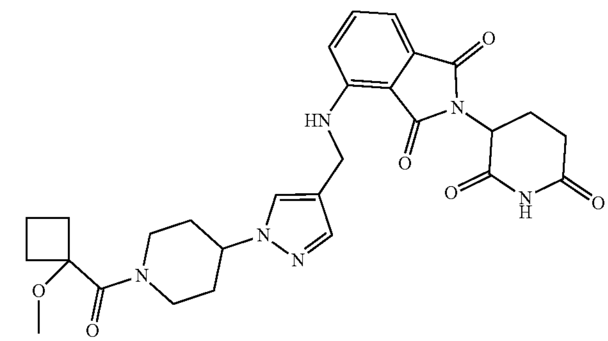 | ++ |
| 83 | 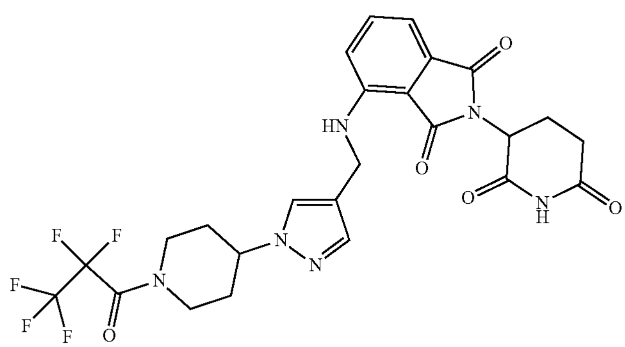 [SMILES: O=C1CCC(N2C(=O)c3cccc(NCc4cnn(C5CCN(C(=O)C(F)(F)C(F)(F)F)CC5)c4)c3C2=O)C(=O)N1] | ++ |
| 84 | 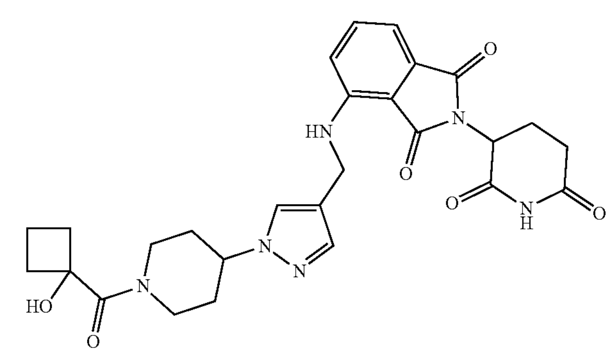 | ++ |

TABLE 2-continued
| Compound # | Structure | GI50 |
|---|---|---|
| 85 | 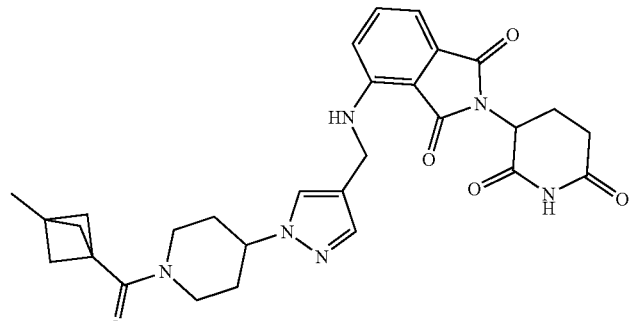 | ++ |
| 86 | 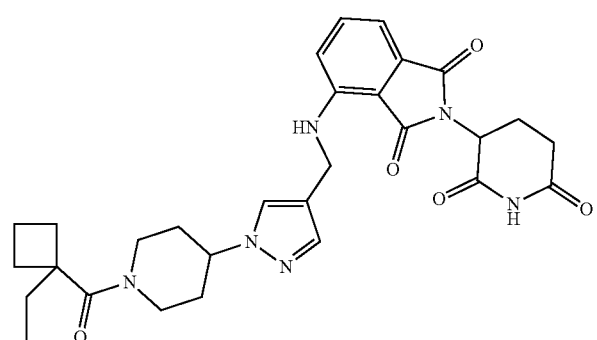 | ++ |
| 87 | 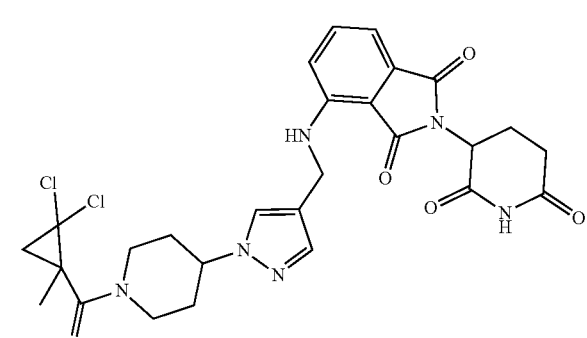 | +++ |
| 88 | 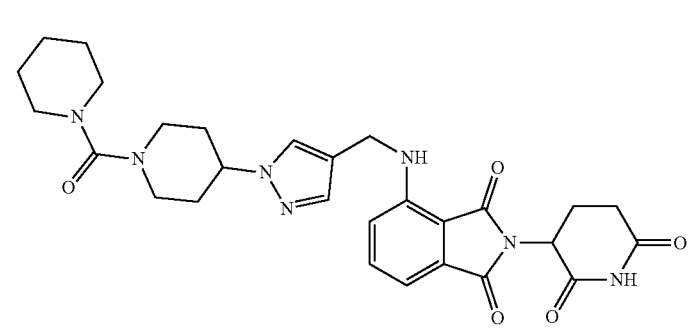 [SMILES: O=C1CCC(N2C(=O)c3cccc(NCc4cnn(C5CCN(C(=O)N6CCCCC6)CC5)c4)c3C2=O)C(=O)N1] | ++ |

TABLE 2-continued

| Compound # | Structure | GI50 |
|---|---|---|
| 89 | 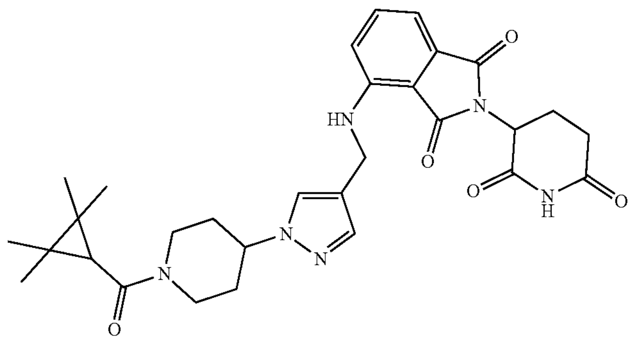 [SMILES: CC1(C)C(C(=O)N2CCC(n3cc(CNc4cccc5c4C(=O)N(C4CCC(=O)NC4=O)C5=O)cn3)CC2)C1(C)C] | +++ |
| 90 | 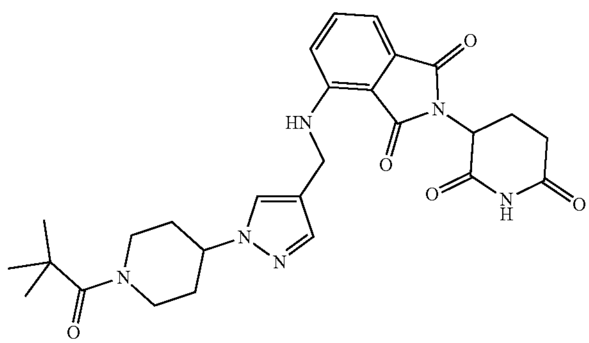 [SMILES: CC(C)(C)C(=O)N1CCC(n2cc(CNc3cccc4c3C(=O)N(C3CCC(=O)NC3=O)C4=O)cn2)CC1] | +++ |
| 91 | 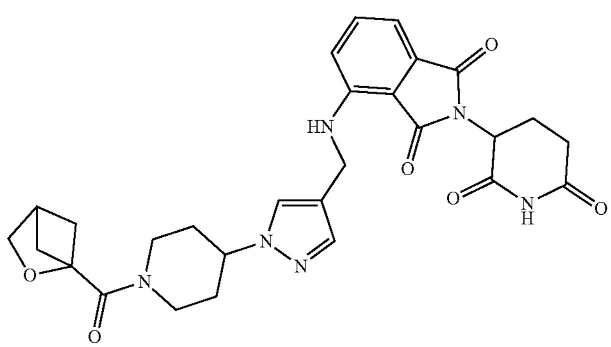 [SMILES: O=C1CCC(N2C(=O)c3cccc(NCc4cnn(C5CCN(C(=O)C67CC(CO6)C7)CC5)c4)c3C2=O)C(=O)N1] | ++ |
| 92 | 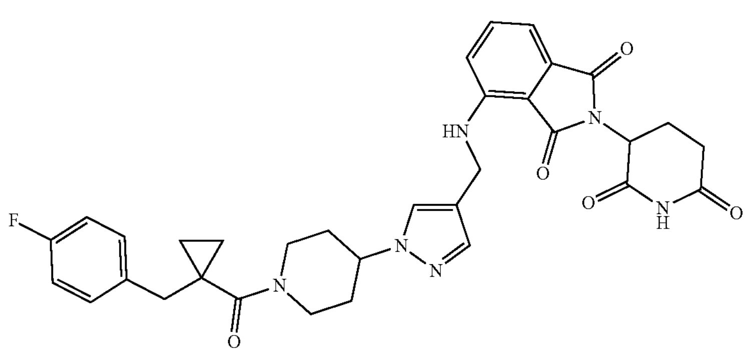 [SMILES: O=C1CCC(N2C(=O)c3cccc(NCc4cnn(C5CCN(C(=O)C6(Cc7ccc(F)cc7)CC6)CC5)c4)c3C2=O)C(=O)N1] | ++ |

TABLE 2-continued
| Compound # | Structure | GI50 |
|---|---|---|
| 93 | 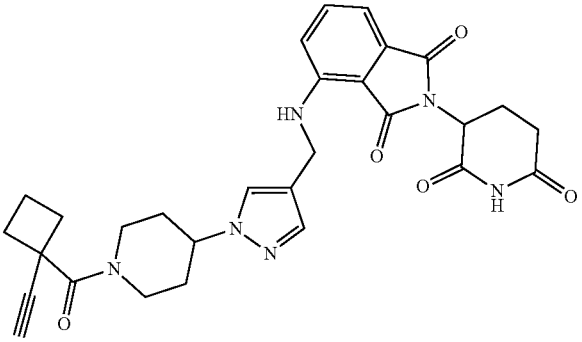 [SMILES: C#CC1(C(=O)N2CCC(n3cc(CNc4cccc5c4C(=O)N(C4CCC(=O)NC4=O)C5=O)cn3)CC2)CCC1] | +++ |
| 94 | 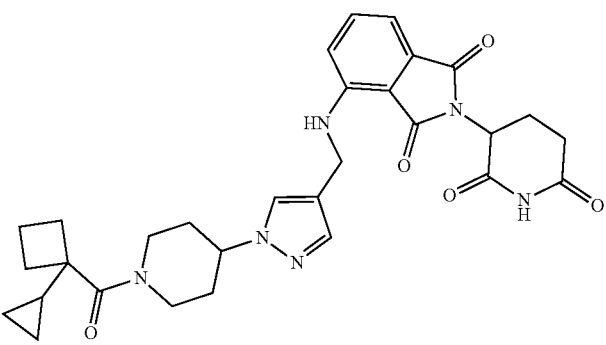 [SMILES: O=C1CCC(N2C(=O)c3cccc(NCc4cnn(C5CCN(C(=O)C6(C7CC7)CCC6)CC5)c4)c3C2=O)C(=O)N1] | +++ |
| 95 | 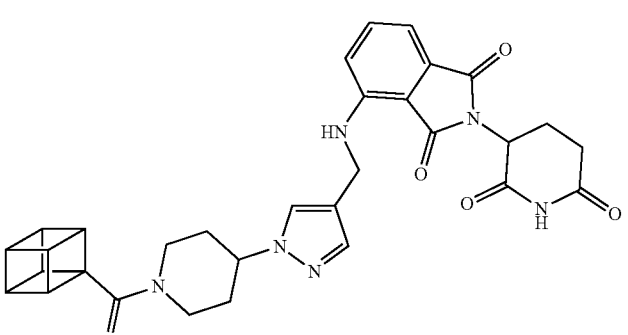 | +++ |
| 96 | 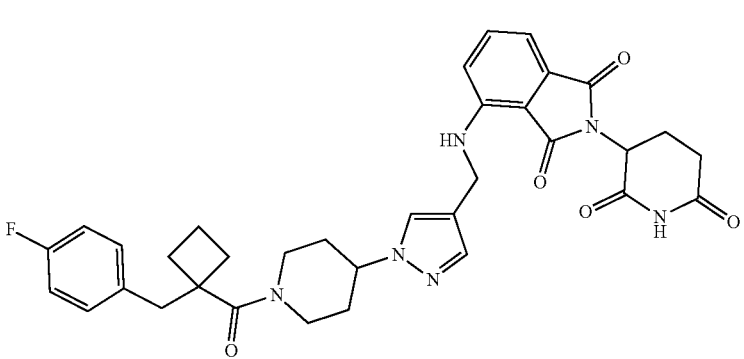 [SMILES: O=C1CCC(N2C(=O)c3cccc(NCc4cnn(C5CCN(C(=O)C6(Cc7ccc(F)cc7)CCC6)CC5)c4)c3C2=O)C(=O)N1] | +++ |

TABLE 2-continued
| Compound # | Structure | GI50 |
|---|---|---|
| 97 | 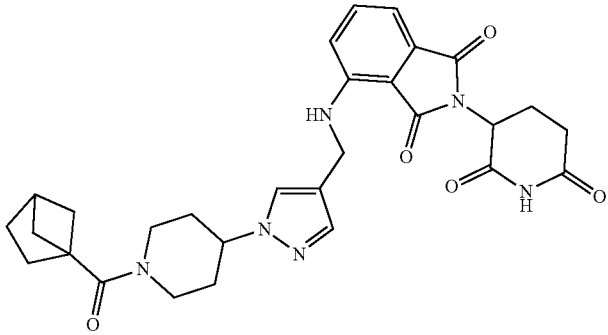 [SMILES: O=C1CCC(N2C(=O)c3cccc(NCc4cnn(C5CCN(C(=O)C67CCC(C6)C7)CC5)c4)c3C2=O)C(=O)N1] | ++ |
| 98 | 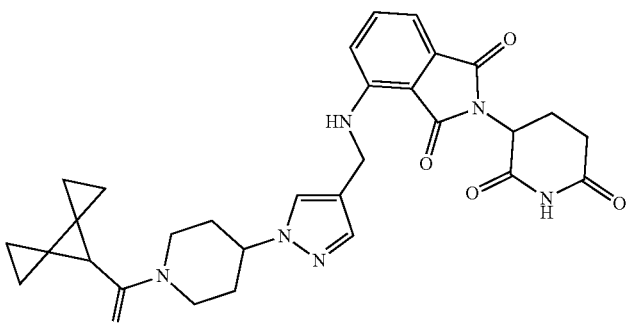 | +++ |
| 99 | 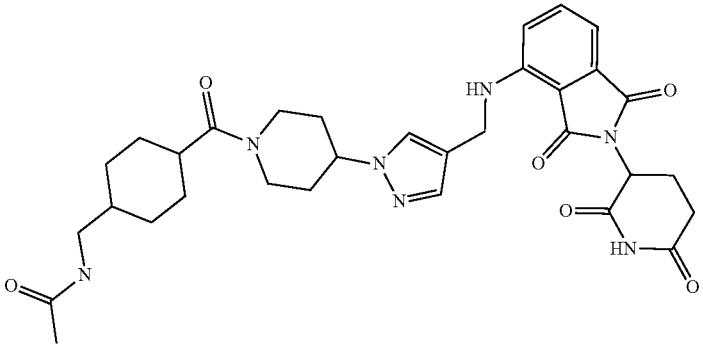 [SMILES: CC(=O)NCC1CCC(C(=O)N2CCC(n3cc(CNc4cccc5c4C(=O)N(C4CCC(=O)NC4=O)C5=O)cn3)CC2)CC1] | ++ |
| 100 | 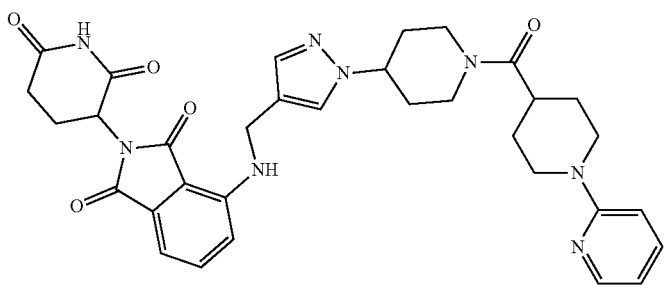 [SMILES: O=C1CCC(N2C(=O)c3cccc(NCc4cnn(C5CCN(C(=O)C6CCN(c7ccccn7)CC6)CC5)c4)c3C2=O)C(=O)N1] | +++ |

TABLE 2-continued

| Compound # | Structure | GI50 |
|---|---|---|
| 101 | 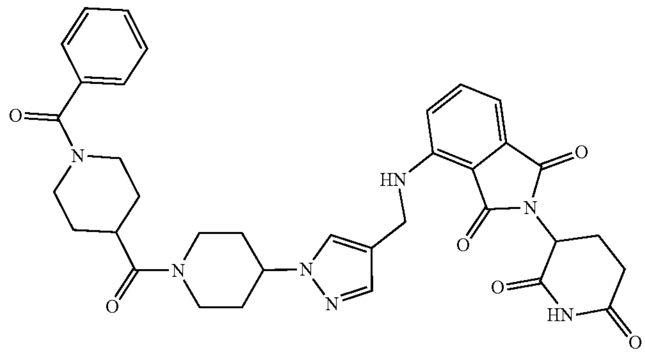 [SMILES: O=C1CCC(N2C(=O)c3cccc(NCc4cnn(C5CCN(C(=O)C6CCN(C(=O)c7ccccc7)CC6)CC5)c4)c3C2=O)C(=O)N1] | ++ |
| 102 | 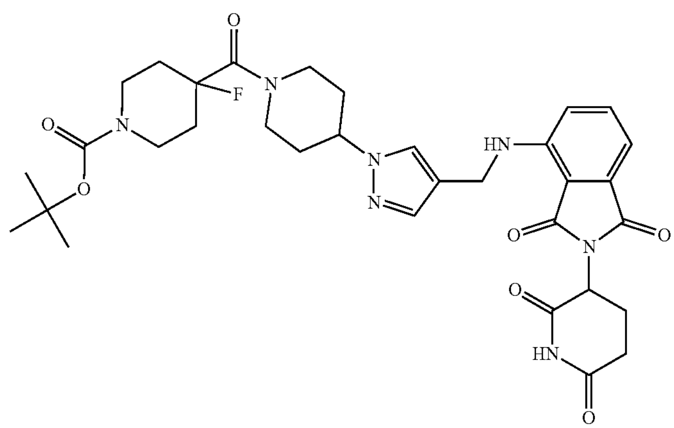 [SMILES: CC(C)(C)OC(=O)N1CCC(F)(C(=O)N2CCC(n3cc(CNc4cccc5c4C(=O)N(C4CCC(=O)NC4=O)C5=O)cn3)CC2)CC1] | ++ |
| 103 | 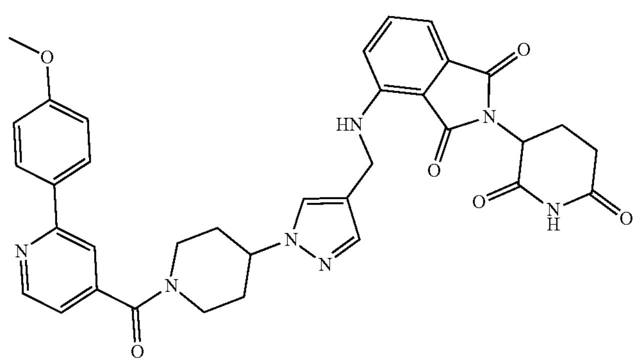 [SMILES: COc1ccc(-c2cc(C(=O)N3CCC(n4cc(CNc5cccc6c5C(=O)N(C5CCC(=O)NC5=O)C6=O)cn4)CC3)ccn2)cc1] | ++ |
| 104 | 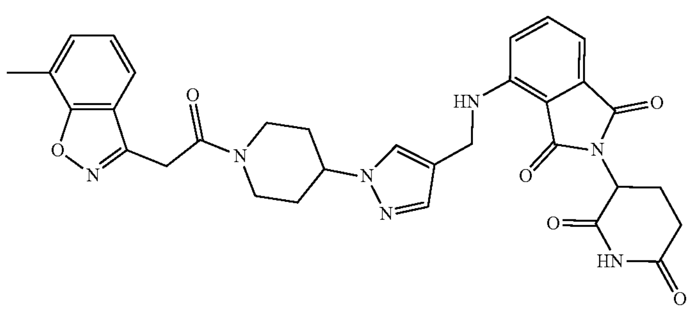 [SMILES: Cc1cccc2c(CC(=O)N3CCC(n4cc(CNc5cccc6c5C(=O)N(C5CCC(=O)NC5=O)C6=O)cn4)CC3)noc12] | +++ |

TABLE 2-continued

| Compound # | Structure | GI50 |
|---|---|---|
| 105 | 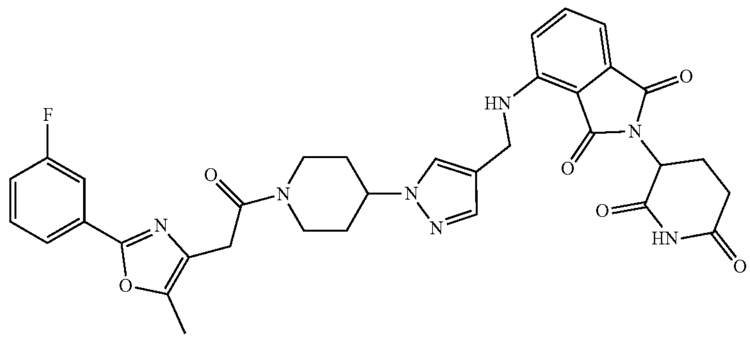 [SMILES: Cc1oc(-c2cccc(F)c2)nc1CC(=O)N1CCC(n2cc(CNc3cccc4c3C(=O)N(C3CCC(=O)NC3=O)C4=O)cn2)CC1] | ++ |
| 106 | 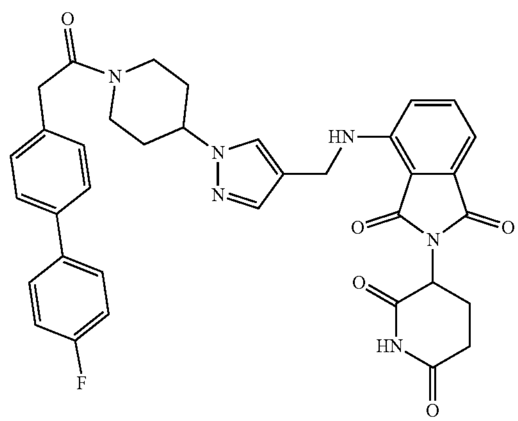 [SMILES: O=C1CCC(N2C(=O)c3cccc(NCc4cnn(C5CCN(C(=O)Cc6ccc(-c7ccc(F)cc7)cc6)CC5)c4)c3C2=O)C(=O)N1] | ++ |
| 107 | 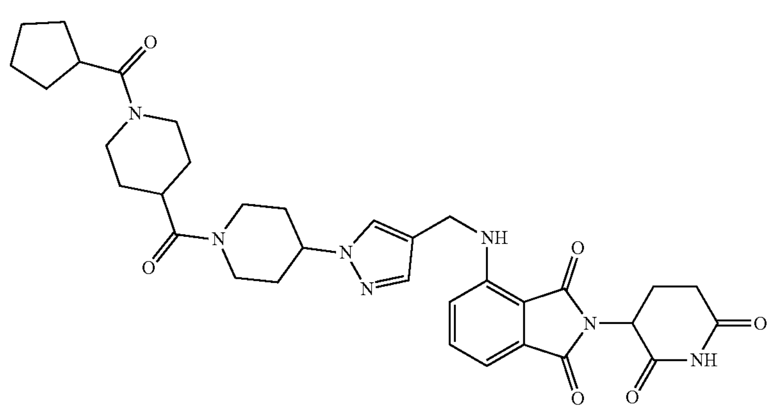 [SMILES: O=C1CCC(N2C(=O)c3cccc(NCc4cnn(C5CCN(C(=O)C6CCN(C(=O)C7CCCC7)CC6)CC5)c4)c3C2=O)C(=O)N1] | ++ |

TABLE 2-continued
| Compound # | Structure | GI50 |
|---|---|---|
| 108 | 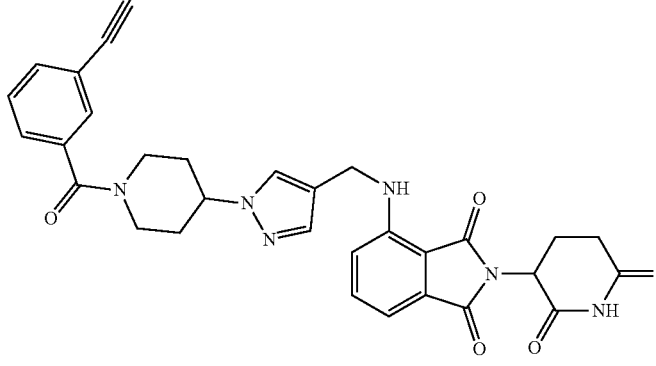 | ++ |
| 109 | 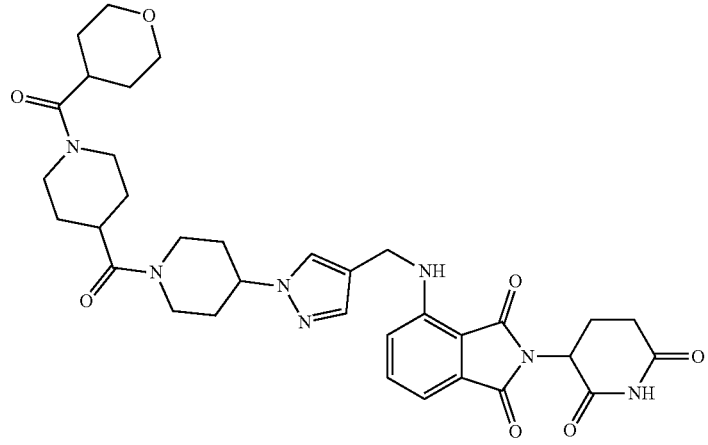 [SMILES: O=C1CCC(N2C(=O)c3cccc(NCc4cnn(C5CCN(C(=O)C6CCN(C(=O)C7CCOCC7)CC6)CC5)c4)c3C2=O)C(=O)N1] | ++ |
| 110 | 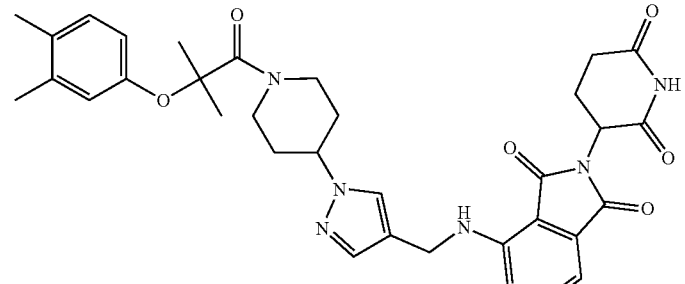 | ++ |

TABLE 2-continued

| Compound # | Structure | GI50 |
|---|---|---|
| 111 | 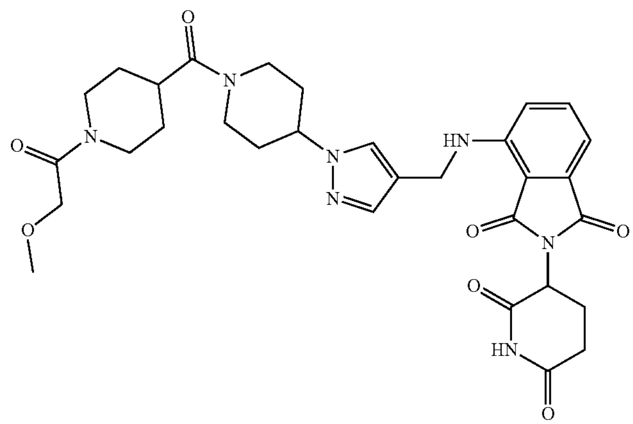 [SMILES: COCC(=O)N1CCC(C(=O)N2CCC(n3cc(CNc4cccc5c4C(=O)N(C4CCC(=O)NC4=O)C5=O)cn3)CC2)CC1] | ++ |
| 112 | 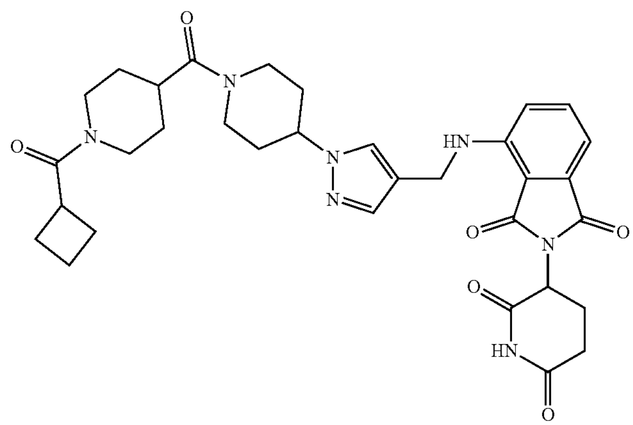 [SMILES: O=C1CCC(N2C(=O)c3cccc(NCc4cnn(C5CCN(C(=O)C6CCN(C(=O)C7CCC7)CC6)CC5)c4)c3C2=O)C(=O)N1] | ++ |
| 113 | 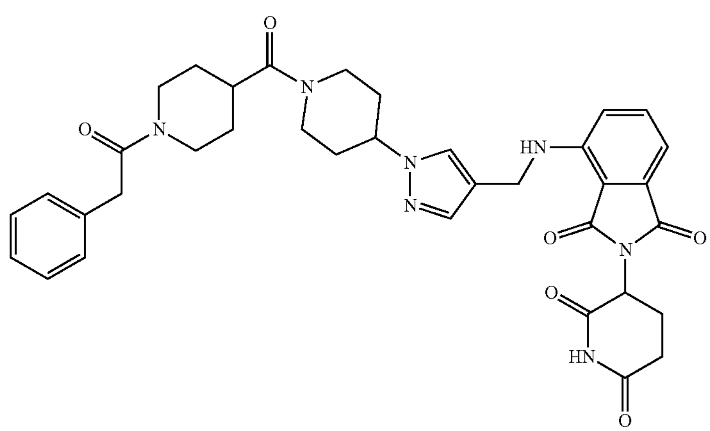 [SMILES: O=C1CCC(N2C(=O)c3cccc(NCc4cnn(C5CCN(C(=O)C6CCN(C(=O)Cc7ccccc7)CC6)CC5)c4)c3C2=O)C(=O)N1] | ++ |
| 114 | 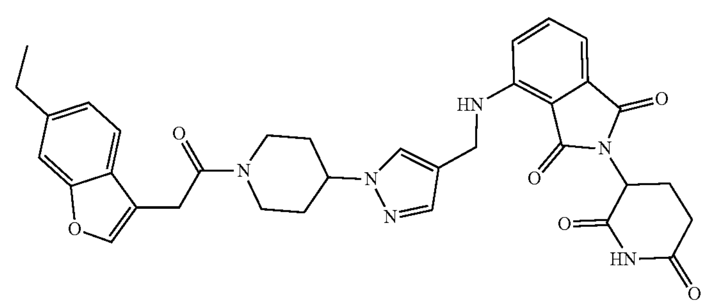 [SMILES: CCc1ccc2c(CC(=O)N3CCC(n4cc(CNc5cccc6c5C(=O)N(C5CCC(=O)NC5=O)C6=O)cn4)CC3)coc2c1] | ++ |

TABLE 2-continued

| Compound # | Structure | GI50 |
|---|---|---|
| 115 | 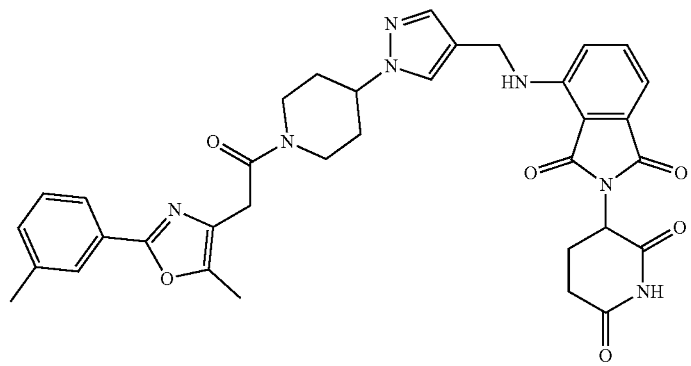 [SMILES: Cc1cccc(-c2nc(CC(=O)N3CCC(n4cc(CNc5cccc6c5C(=O)N(C5CCC(=O)NC5=O)C6=O)cn4)CC3)c(C)o2)c1] | ++ |
| 116 | 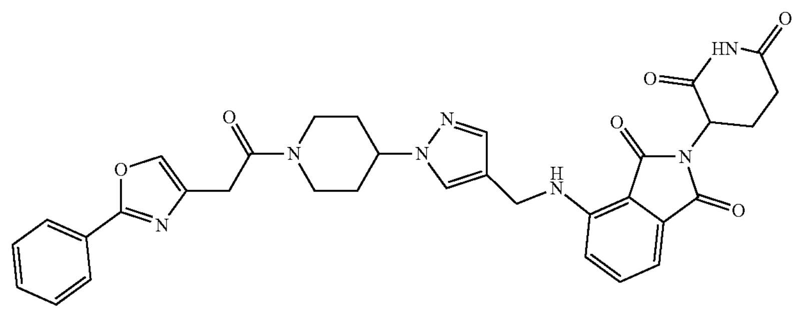 [SMILES: O=C1CCC(N2C(=O)c3cccc(NCc4cnn(C5CCN(C(=O)Cc6coc(-c7ccccc7)n6)CC5)c4)c3C2=O)C(=O)N1] | ++ |
| 117 | 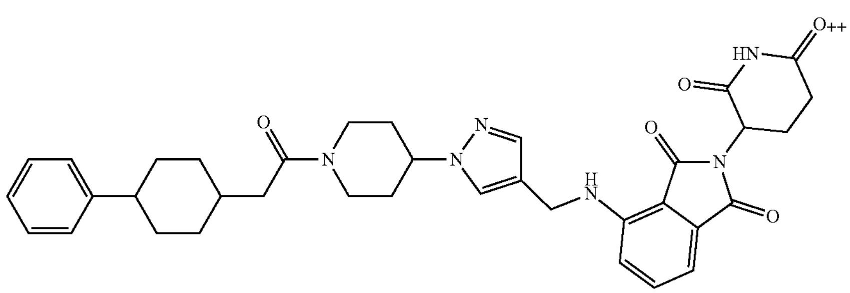 | ++ |
| 118 | 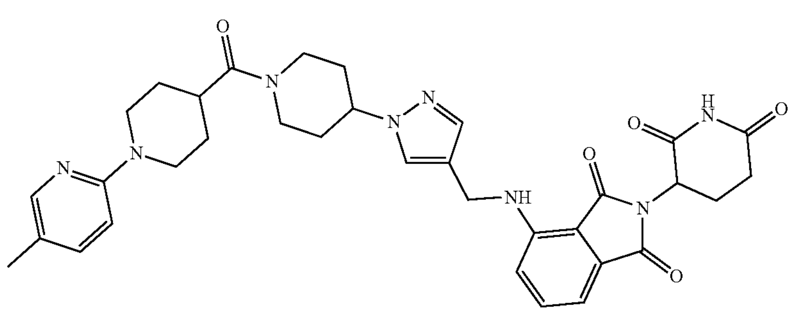 [SMILES: Cc1ccc(N2CCC(C(=O)N3CCC(n4cc(CNc5cccc6c5C(=O)N(C5CCC(=O)NC5=O)C6=O)cn4)CC3)CC2)nc1] | +++ |

TABLE 2-continued

| Compound # | Structure | GI50 |
|---|---|---|
| 119 | 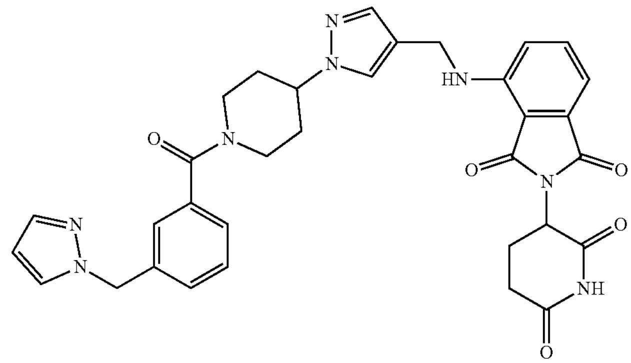 [SMILES: O=C1CCC(N2C(=O)c3cccc(NCc4cnn(C5CCN(C(=O)c6cccc(Cn7cccn7)c6)CC5)c4)c3C2=O)C(=O)N1] | ++ |
| 120 | 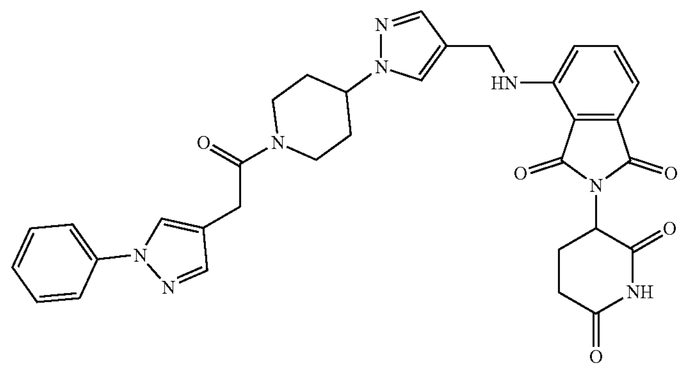 [SMILES: O=C1CCC(N2C(=O)c3cccc(NCc4cnn(C5CCN(C(=O)Cc6cnn(-c7ccccc7)c6)CC5)c4)c3C2=O)C(=O)N1] | ++ |
| 121 | 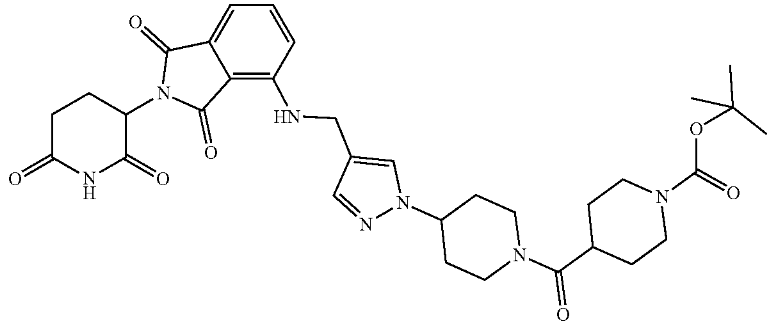 [SMILES: CC(C)(C)OC(=O)N1CCC(C(=O)N2CCC(n3cc(CNc4cccc5c4C(=O)N(C4CCC(=O)NC4=O)C5=O)cn3)CC2)CC1] | ++ |
| 122 | 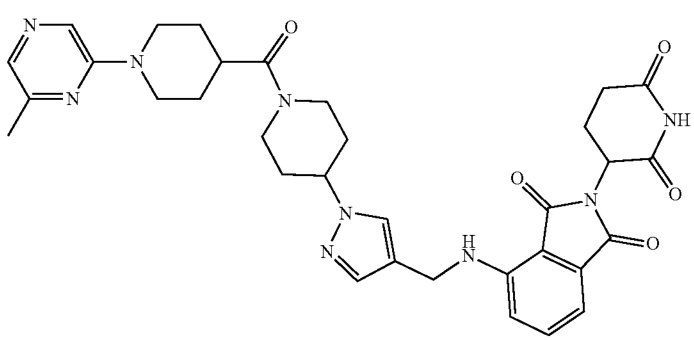 [SMILES: Cc1cncc(N2CCC(C(=O)N3CCC(n4cc(CNc5cccc6c5C(=O)N(C5CCC(=O)NC5=O)C6=O)cn4)CC3)CC2)n1] | +++ |

TABLE 2-continued
| Compound # | Structure | GI50 |
|---|---|---|
| 123 | 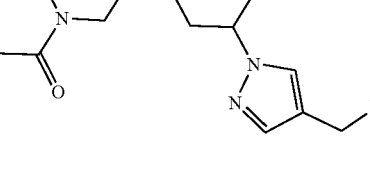 | ++ |
| 124 | 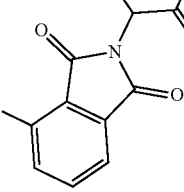 | ++ |
| 125 | 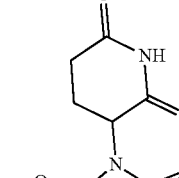 | ++ |
| 126 | 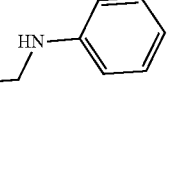 | ++ |

TABLE 2-continued

| Compound # | Structure | GI50 |
|---|---|---|
| 127 | 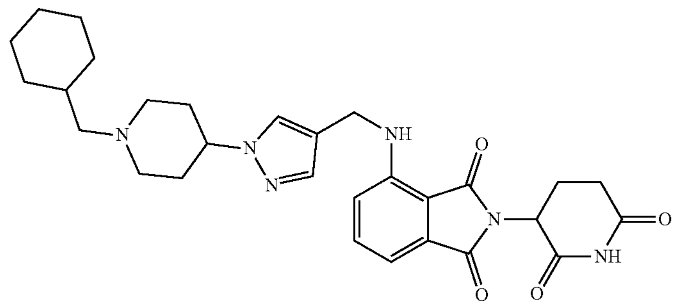 [SMILES: O=C1CCC(N2C(=O)c3cccc(NCc4cnn(C5CCN(CC6CCCCC6)CC5)c4)c3C2=O)C(=O)N1] | ++ |
| 128 | 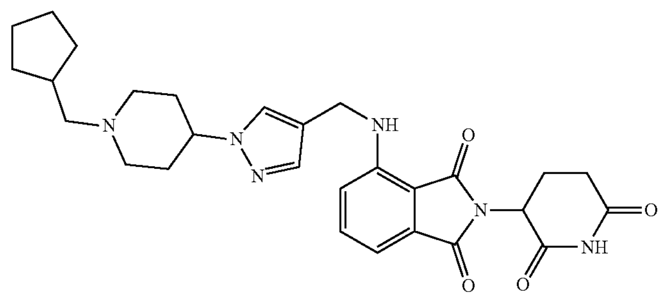 [SMILES: O=C1CCC(N2C(=O)c3cccc(NCc4cnn(C5CCN(CC6CCCC6)CC5)c4)c3C2=O)C(=O)N1] | ++ |
| 129 | 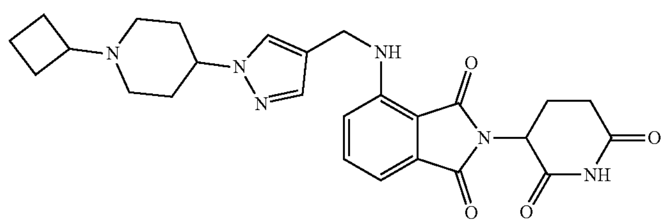 [SMILES: O=C1CCC(N2C(=O)c3cccc(NCc4cnn(C5CCN(C6CCC6)CC5)c4)c3C2=O)C(=O)N1] | ++ |
| 130 | 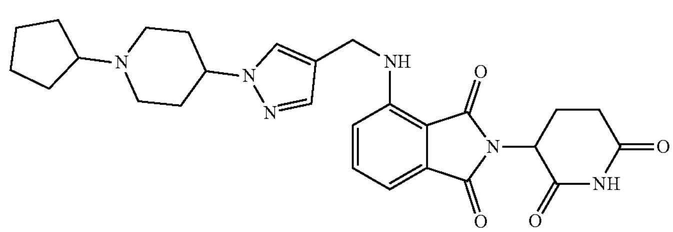 | ++ |
| 131 | 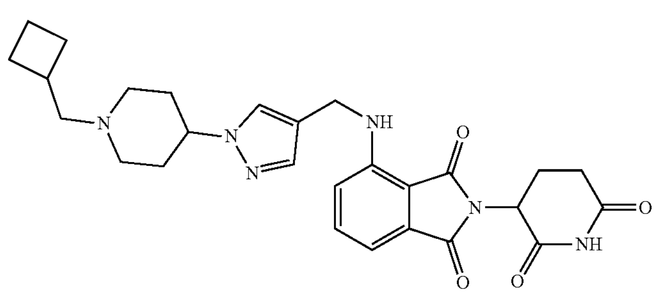 [SMILES: O=C1CCC(N2C(=O)c3cccc(NCc4cnn(C5CCN(CC6CCC6)CC5)c4)c3C2=O)C(=O)N1] | ++ |

TABLE 2-continued

| Compound # | Structure | GI50 |
|---|---|---|
| 132 | 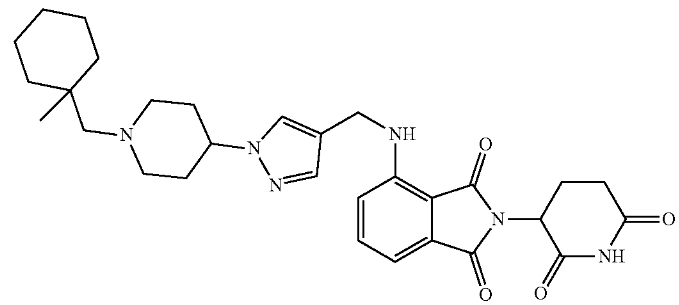 [SMILES: CC1(CN2CCC(n3cc(CNc4cccc5c4C(=O)N(C4CCC(=O)NC4=O)C5=O)cn3)CC2)CCCCC1] | ++ |
| 133 | 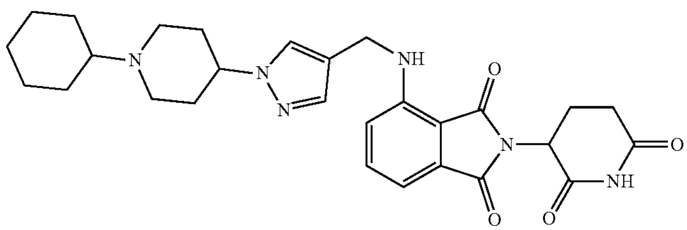 [SMILES: O=C1CCC(N2C(=O)c3cccc(NCc4cnn(C5CCN(C6CCCCC6)CC5)c4)c3C2=O)C(=O)N1] | ++ |
| 134 | 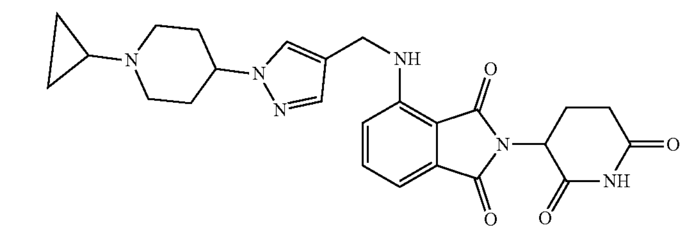 [SMILES: O=C1CCC(N2C(=O)c3cccc(NCc4cnn(C5CCN(C6CC6)CC5)c4)c3C2=O)C(=O)N1] | ++ |
| 135 | 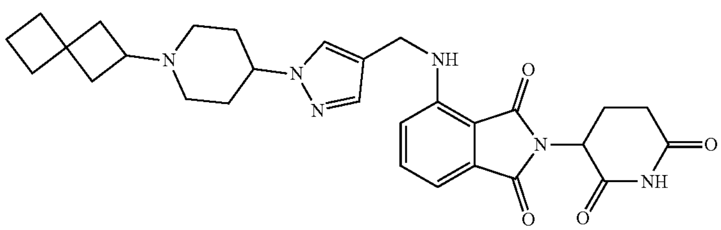 [SMILES: O=C1CCC(N2C(=O)c3cccc(NCc4cnn(C5CCN(C6CC7(CCC7)C6)CC5)c4)c3C2=O)C(=O)N1] | ++ |
| 136 | 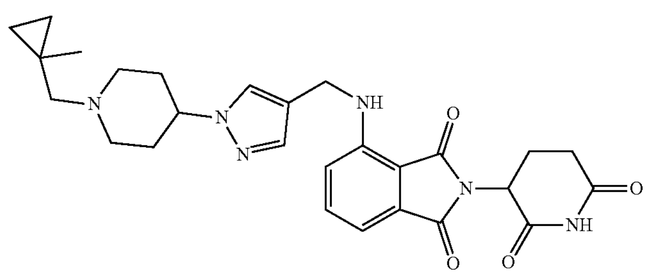 [SMILES: CC1(CN2CCC(n3cc(CNc4cccc5c4C(=O)N(C4CCC(=O)NC4=O)C5=O)cn3)CC2)CC1] | +++ |
| 137 | 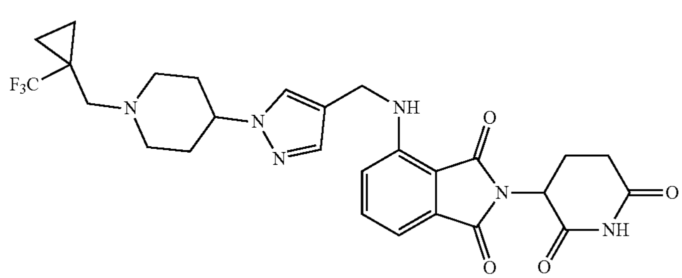 [SMILES: O=C1CCC(N2C(=O)c3cccc(NCc4cnn(C5CCN(CC6(C(F)(F)F)CC6)CC5)c4)c3C2=O)C(=O)N1] | ++ |

TABLE 2-continued

| Compound # | Structure | GI50 |
|---|---|---|
| 138 | 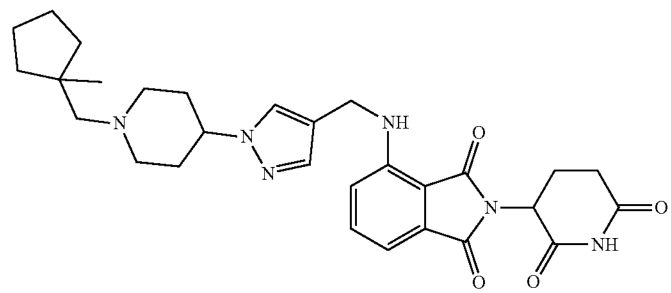 [SMILES: CC1(CN2CCC(n3cc(CNc4cccc5c4C(=O)N(C4CCC(=O)NC4=O)C5=O)cn3)CC2)CCCC1] | +++ |
| 139 | 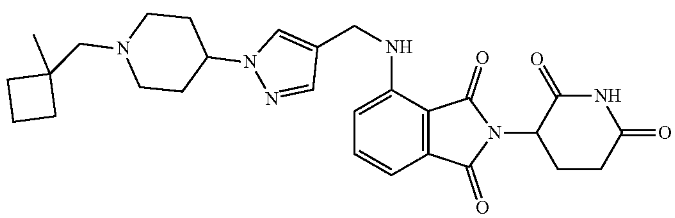 [SMILES: CC1(CN2CCC(n3cc(CNc4cccc5c4C(=O)N(C4CCC(=O)NC4=O)C5=O)cn3)CC2)CCC1] | ++ |
| 140 | 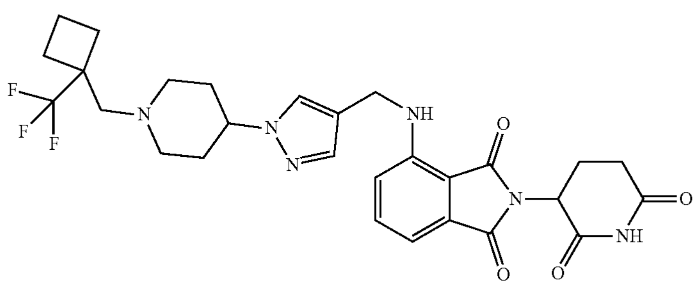 [SMILES: O=C1CCC(N2C(=O)c3cccc(NCc4cnn(C5CCN(CC6(C(F)(F)F)CCC6)CC5)c4)c3C2=O)C(=O)N1] | ++ |
| 141 | 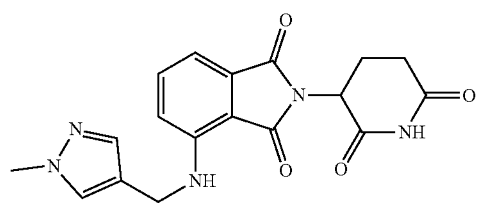 [SMILES: Cn1cc(CNc2cccc3c2C(=O)N(C2CCC(=O)NC2=O)C3=O)cn1] | ++ |
| 142 | 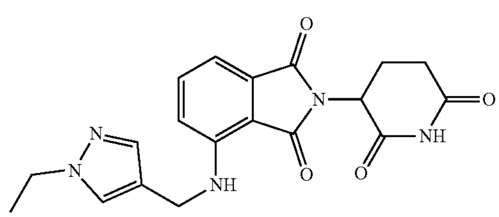 [SMILES: CCn1cc(CNc2cccc3c2C(=O)N(C2CCC(=O)NC2=O)C3=O)cn1] | ++ |
| 143 | 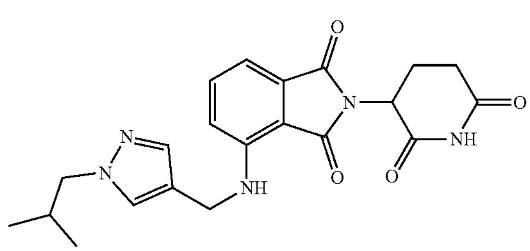 [SMILES: CC(C)Cn1cc(CNc2cccc3c2C(=O)N(C2CCC(=O)NC2=O)C3=O)cn1] | + |

TABLE 2-continued

| Compound # | Structure | GI50 |
|---|---|---|
| 144 | 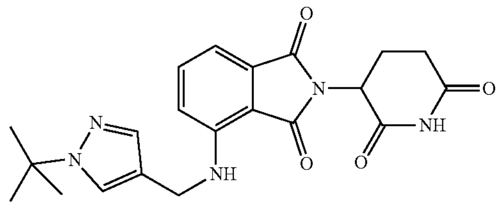 [SMILES: CC(C)(C)n1cc(CNc2cccc3c2C(=O)N(C2CCC(=O)NC2=O)C3=O)cn1] | ++ |
| 145 | 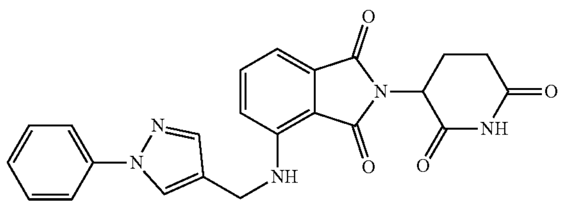 [SMILES: O=C1CCC(N2C(=O)c3cccc(NCc4cnn(-c5ccccc5)c4)c3C2=O)C(=O)N1] | ++ |
| 146 | 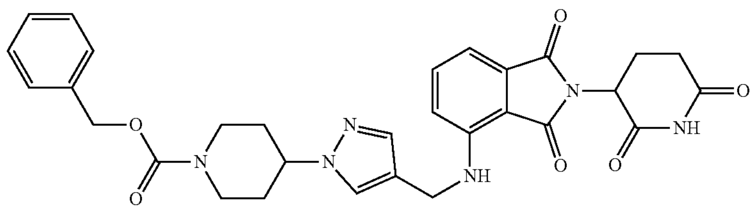 [SMILES: O=C1CCC(N2C(=O)c3cccc(NCc4cnn(C5CCN(C(=O)OCc6ccccc6)CC5)c4)c3C2=O)C(=O)N1] | ++ |
| 147 | 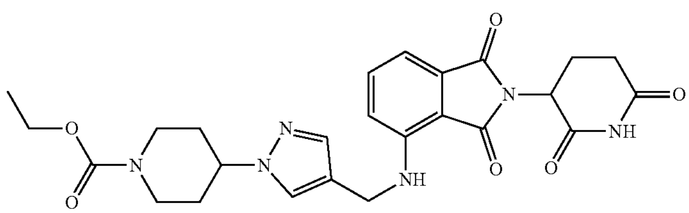 [SMILES: CCOC(=O)N1CCC(n2cc(CNc3cccc4c3C(=O)N(C3CCC(=O)NC3=O)C4=O)cn2)CC1] | ++ |
| 148 | 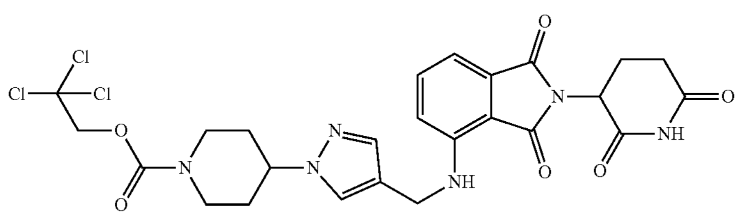 [SMILES: O=C1CCC(N2C(=O)c3cccc(NCc4cnn(C5CCN(C(=O)OCC(Cl)(Cl)Cl)CC5)c4)c3C2=O)C(=O)N1] | ++ |
| 149 | 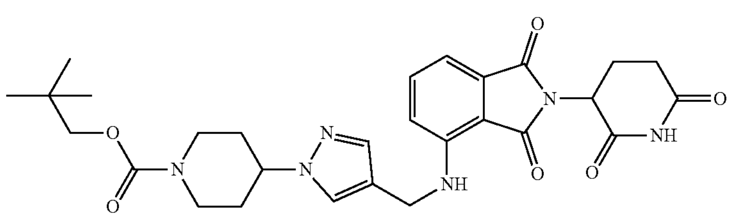 [SMILES: CC(C)(C)COC(=O)N1CCC(n2cc(CNc3cccc4c3C(=O)N(C3CCC(=O)NC3=O)C4=O)cn2)CC1] | +++ |
| 150 | 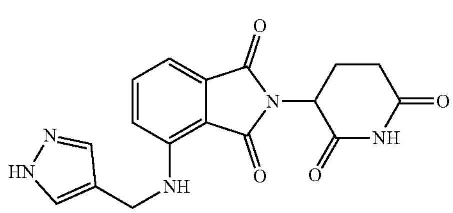 [SMILES: O=C1CCC(N2C(=O)c3cccc(NCc4cn[nH]c4)c3C2=O)C(=O)N1] | ND |

TABLE 2-continued
| Compound # | Structure | GI50 |
|---|---|---|
| 151 | 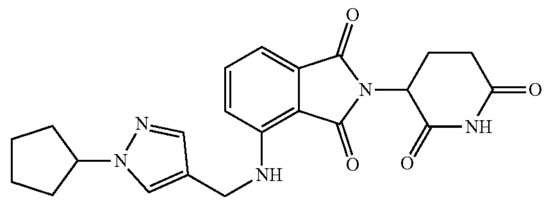 [SMILES: O=C1CCC(N2C(=O)c3cccc(NCc4cnn(C5CCCC5)c4)c3C2=O)C(=O)N1] | ++ |
| 152 | 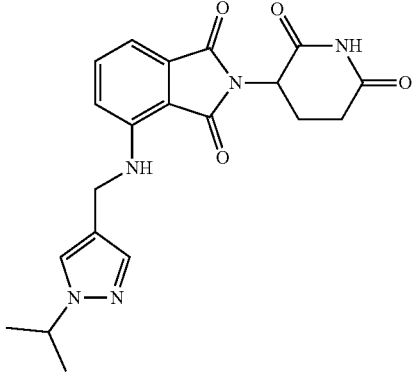 [SMILES: CC(C)n1cc(CNc2cccc3c2C(=O)N(C2CCC(=O)NC2=O)C3=O)cn1] | ++ |
| 153 | 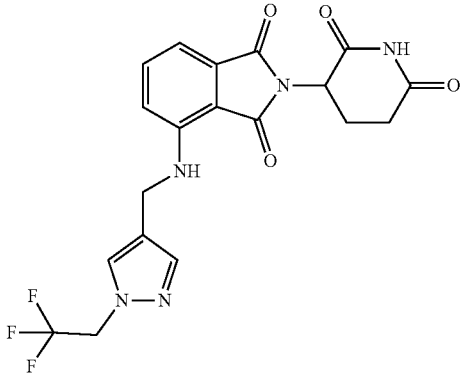 [SMILES: O=C1CCC(N2C(=O)c3cccc(NCc4cnn(CC(F)(F)F)c4)c3C2=O)C(=O)N1] | ++ |
| 154 | 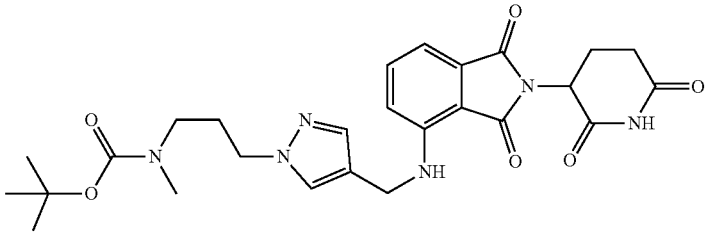 [SMILES: CN(CCCn1cc(CNc2cccc3c2C(=O)N(C2CCC(=O)NC2=O)C3=O)cn1)C(=O)OC(C)(C)C] | ++ |
| 155 | 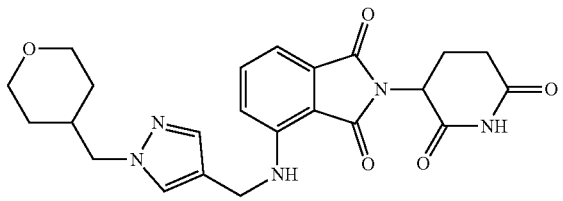 [SMILES: O=C1CCC(N2C(=O)c3cccc(NCc4cnn(CC5CCOCC5)c4)c3C2=O)C(=O)N1] | ++ |

TABLE 2-continued

| Compound # | Structure | GI50 |
|---|---|---|
| 156 | 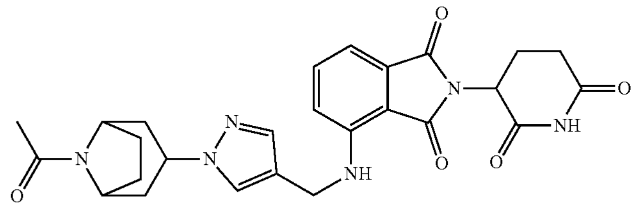 [SMILES: CC(=O)N1C2CCC1CC(n1cc(CNc3cccc4c3C(=O)N(C3CCC(=O)NC3=O)C4=O)cn1)C2] | ++ |
| 157 | (HCl) | ++ |
| 158 | 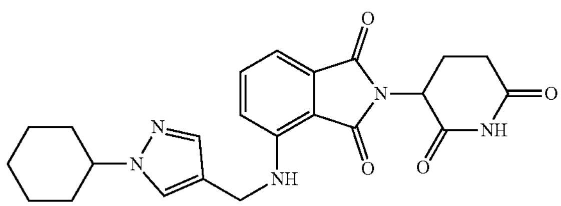 [SMILES: O=C1CCC(N2C(=O)c3cccc(NCc4cnn(C5CCCCC5)c4)c3C2=O)C(=O)N1] | ++ |
| 159 | 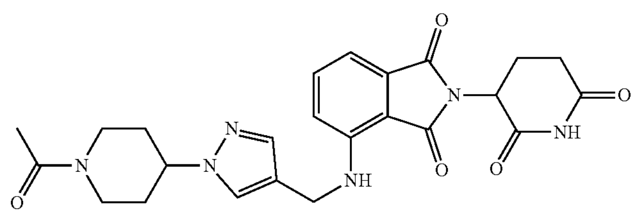 [SMILES: CC(=O)N1CCC(n2cc(CNc3cccc4c3C(=O)N(C3CCC(=O)NC3=O)C4=O)cn2)CC1] | ++ |
| 160 | 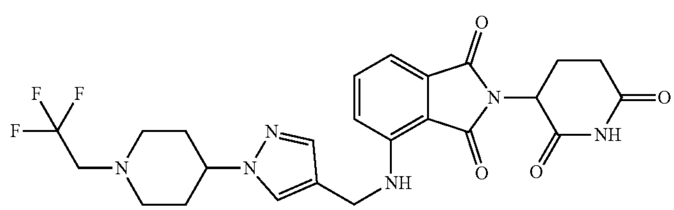 [SMILES: O=C1CCC(N2C(=O)c3cccc(NCc4cnn(C5CCN(CC(F)(F)F)CC5)c4)c3C2=O)C(=O)N1] | ++ |
| 161 | 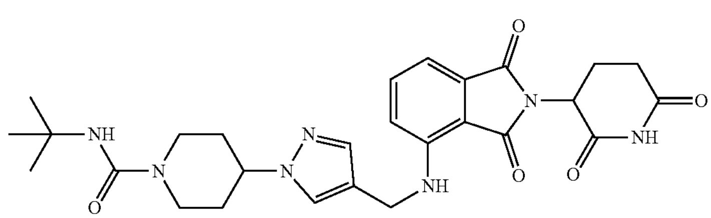 [SMILES: CC(C)(C)NC(=O)N1CCC(n2cc(CNc3cccc4c3C(=O)N(C3CCC(=O)NC3=O)C4=O)cn2)CC1] | ++ |

| Compound # | Structure | GI50 |
|---|---|---|
| 162 | 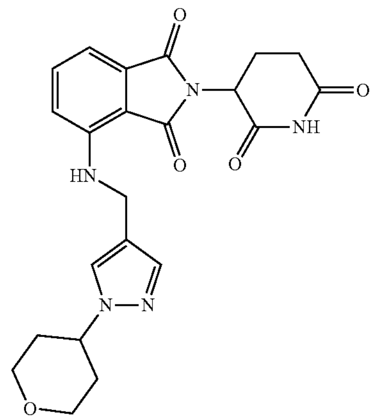 [SMILES: O=C1CCC(N2C(=O)c3cccc(NCc4cnn(C5CCOCC5)c4)c3C2=O)C(=O)N1] | ND |
| 163 | 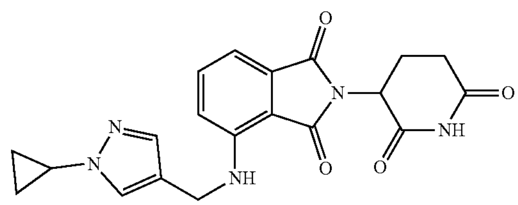 [SMILES: O=C1CCC(N2C(=O)c3cccc(NCc4cnn(C5CC5)c4)c3C2=O)C(=O)N1] | ++ |
| 164 | 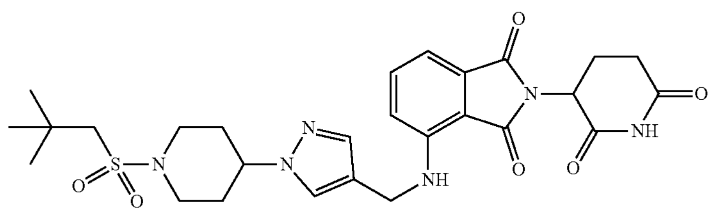 [SMILES: CC(C)(C)CS(=O)(=O)N1CCC(n2cc(CNc3cccc4c3C(=O)N(C3CCC(=O)NC3=O)C4=O)cn2)CC1] | ND |
| 165 | 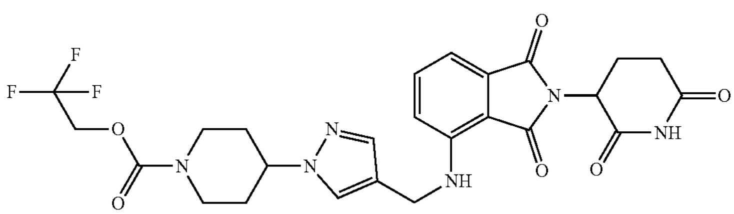 [SMILES: O=C1CCC(N2C(=O)c3cccc(NCc4cnn(C5CCN(C(=O)OCC(F)(F)F)CC5)c4)c3C2=O)C(=O)N1] | ++ |
| 166 | 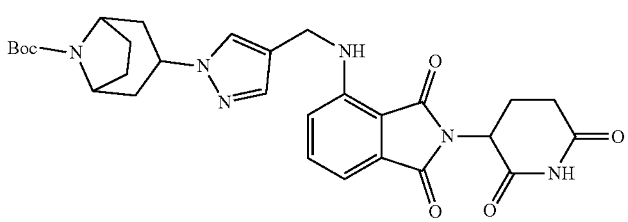 [SMILES: CC(C)(C)OC(=O)N1C2CCC1CC(n1cc(CNc3cccc4c3C(=O)N(C3CCC(=O)NC3=O)C4=O)cn1)C2] | ++ |
| 167 | 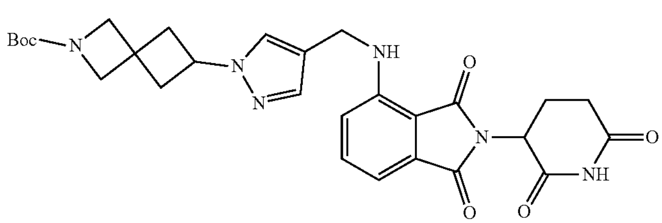 [SMILES: CC(C)(C)OC(=O)N1CC2(CC(n3cc(CNc4cccc5c4C(=O)N(C4CCC(=O)NC4=O)C5=O)cn3)C2)C1] | ++ |

TABLE 2-continued

| Compound # | Structure | GI50 |
|---|---|---|
| 168 | 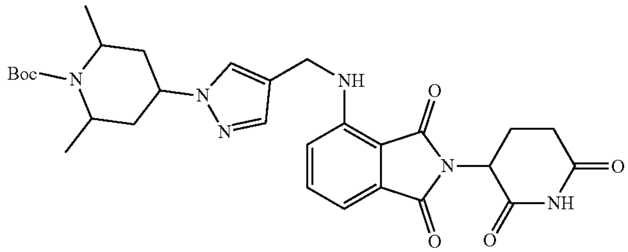 [SMILES: CC1CC(n2cc(CNc3cccc4c3C(=O)N(C3CCC(=O)NC3=O)C4=O)cn2)CC(C)N1C(=O)OC(C)(C)C] | ++ |
| 169 | 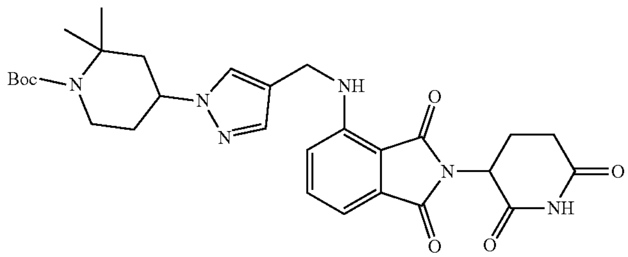 [SMILES: CC(C)(C)OC(=O)N1CCC(n2cc(CNc3cccc4c3C(=O)N(C3CCC(=O)NC3=O)C4=O)cn2)CC1(C)C] | +++ |
| 170 | 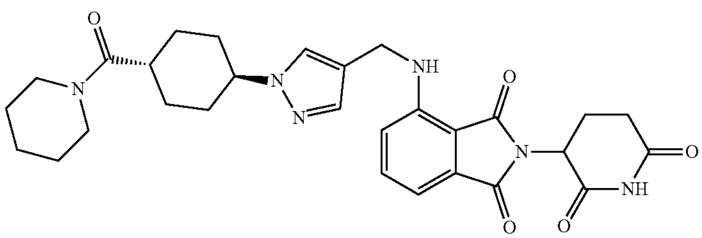 [SMILES: O=C1CCC(N2C(=O)c3cccc(NCc4cnn([C@H]5CC[C@H](C(=O)N6CCCCC6)CC5)c4)c3C2=O)C(=O)N1] | ++ |
| 171 | 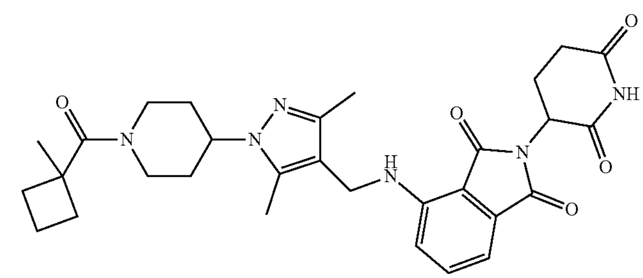 [SMILES: Cc1nn(C2CCN(C(=O)C3(C)CCC3)CC2)c(C)c1CNc1cccc2c1C(=O)N(C1CCC(=O)NC1=O)C2=O] | ++ |
| 172 | 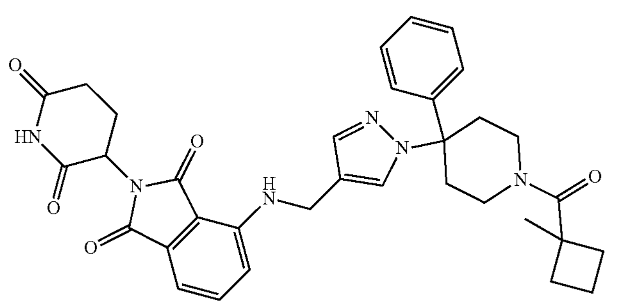 [SMILES: CC1(C(=O)N2CCC(c3ccccc3)(n3cc(CNc4cccc5c4C(=O)N(C4CCC(=O)NC4=O)C5=O)cn3)CC2)CCC1] | ++ |
| 173 | 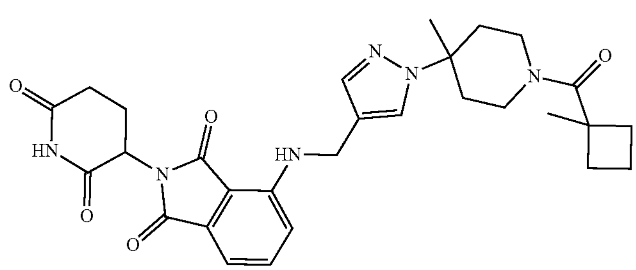 [SMILES: CC1(C(=O)N2CCC(C)(n3cc(CNc4cccc5c4C(=O)N(C4CCC(=O)NC4=O)C5=O)cn3)CC2)CCC1] | ++ |

TABLE 2-continued

| Compound # | Structure | GI50 |
|---|---|---|
| 174 | 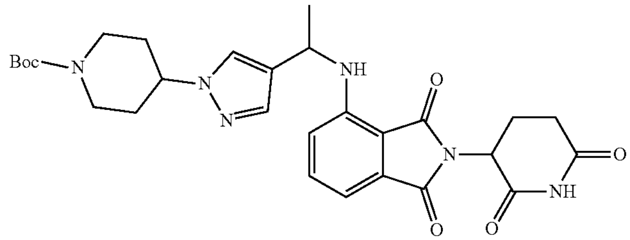 [SMILES: CC(Nc1cccc2c1C(=O)N(C1CCC(=O)NC1=O)C2=O)c1cnn(C2CCN(C(=O)OC(C)(C)C)CC2)c1] | ++ |
| 175 | 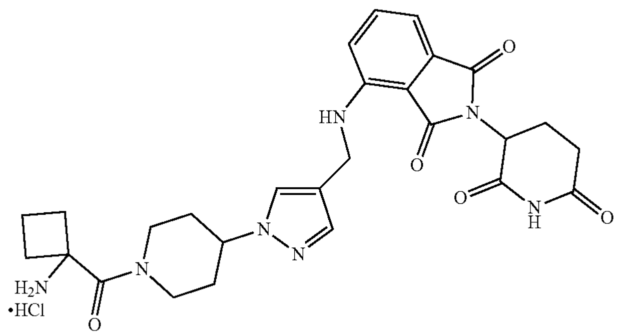 [SMILES: Cl ; NC1(C(=O)N2CCC(n3cc(CNc4cccc5c4C(=O)N(C4CCC(=O)NC4=O)C5=O)cn3)CC2)CCC1] | ++ |
| 176 | 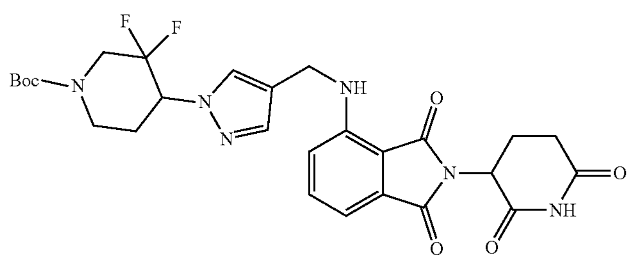 [SMILES: CC(C)(C)OC(=O)N1CCC(n2cc(CNc3cccc4c3C(=O)N(C3CCC(=O)NC3=O)C4=O)cn2)C(F)(F)C1] | ++ |
| 177 | 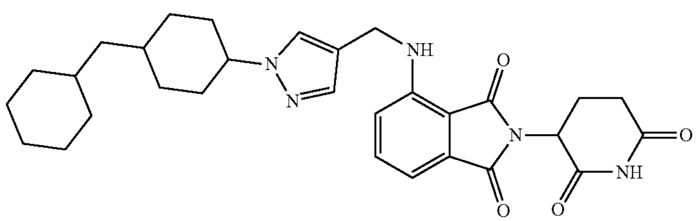 [SMILES: O=C1CCC(N2C(=O)c3cccc(NCc4cnn(C5CCC(CC6CCCCC6)CC5)c4)c3C2=O)C(=O)N1] | ++ |
| 178 | 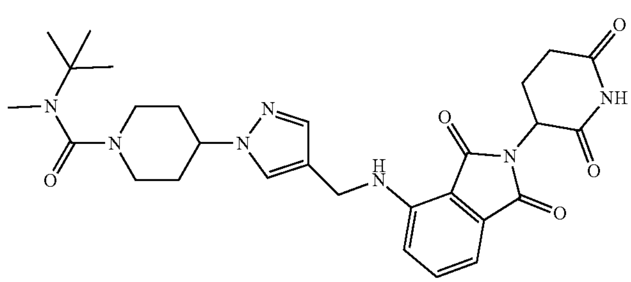 [SMILES: CN(C(=O)N1CCC(n2cc(CNc3cccc4c3C(=O)N(C3CCC(=O)NC3=O)C4=O)cn2)CC1)C(C)(C)C] | ++ |

TABLE 2-continued
| Compound # | Structure | GI50 |
|---|---|---|
| 179 | 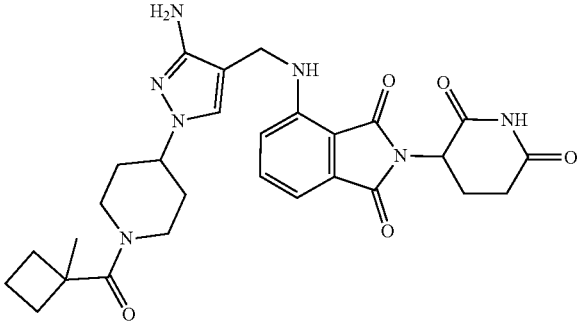 [SMILES: CC1(C(=O)N2CCC(n3cc(CNc4cccc5c4C(=O)N(C4CCC(=O)NC4=O)C5=O)c(N)n3)CC2)CCC1] | ++ |
| 180 | 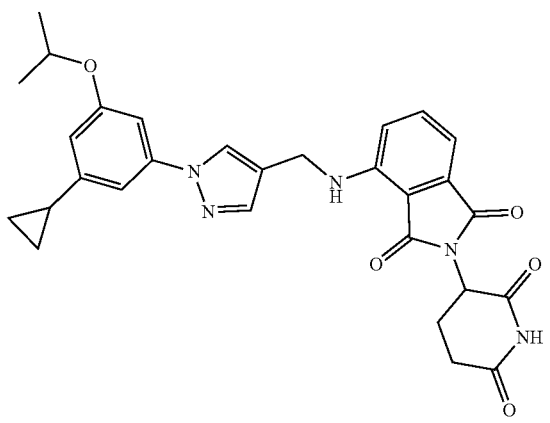 [SMILES: CC(C)Oc1cc(C2CC2)cc(-n2cc(CNc3cccc4c3C(=O)N(C3CCC(=O)NC3=O)C4=O)cn2)c1] | ++ |
| 181 | 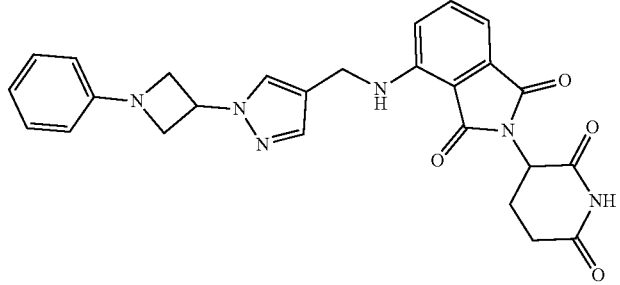 [SMILES: O=C1CCC(N2C(=O)c3cccc(NCc4cnn(C5CN(c6ccccc6)C5)c4)c3C2=O)C(=O)N1] | ++ |
| 182 | 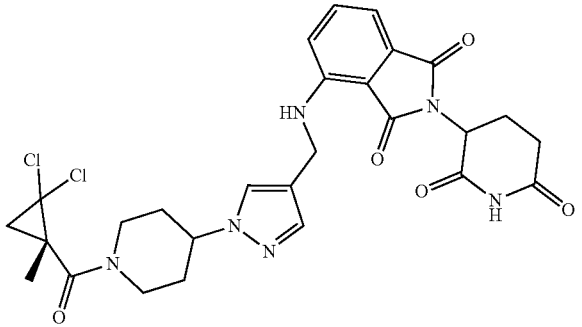 [SMILES: C[C@@]1(C(=O)N2CCC(n3cc(CNc4cccc5c4C(=O)N(C4CCC(=O)NC4=O)C5=O)cn3)CC2)CC1(Cl)Cl] | ++ |

TABLE 2-continued
| Compound # | Structure | GI50 |
|---|---|---|
| 183 | 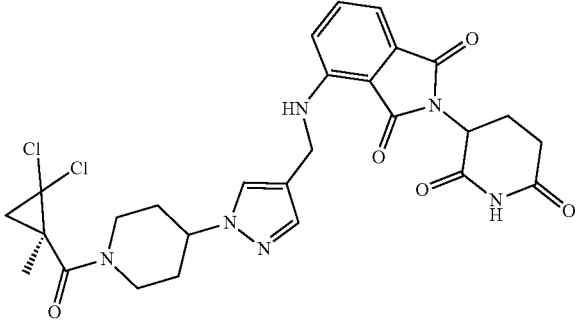 [SMILES: C[C@]1(C(=O)N2CCC(n3cc(CNc4cccc5c4C(=O)N(C4CCC(=O)NC4=O)C5=O)cn3)CC2)CC1(Cl)Cl] | +++ |
| 184 | 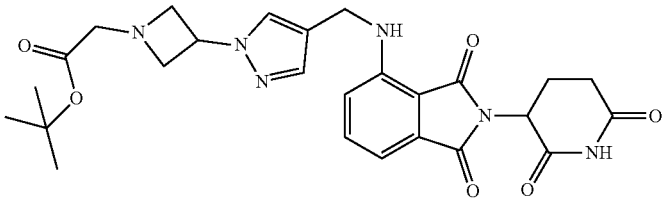 [SMILES: CC(C)(C)OC(=O)CN1CC(n2cc(CNc3cccc4c3C(=O)N(C3CCC(=O)NC3=O)C4=O)cn2)C1] | ++ |
| 185 | 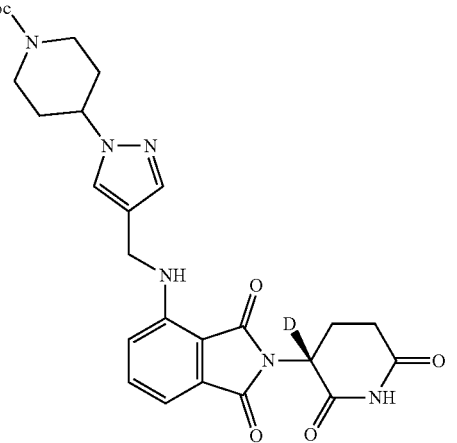 | ++ |
| 186 | 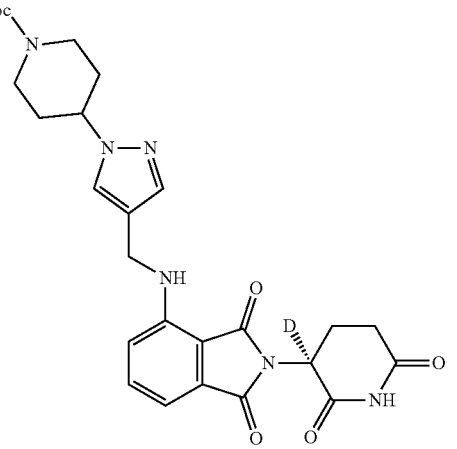 | ++ |

TABLE 2-continued

| Compound # | Structure | GI50 |
|---|---|---|
| 187 | 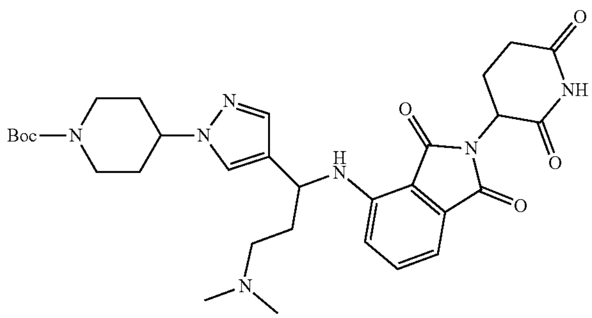 [SMILES: CN(C)CCC(Nc1cccc2c1C(=O)N(C1CCC(=O)NC1=O)C2=O)c1cnn(C2CCN(C(=O)OC(C)(C)C)CC2)c1] | + |
| 188 | 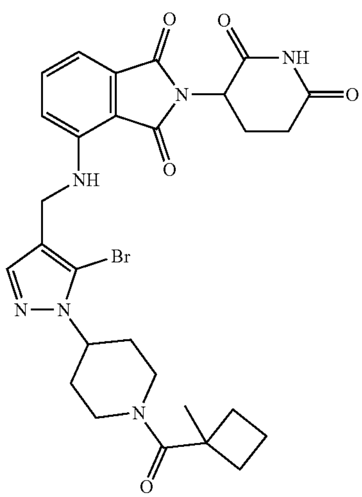 [SMILES: CC1(C(=O)N2CCC(n3ncc(CNc4cccc5c4C(=O)N(C4CCC(=O)NC4=O)C5=O)c3Br)CC2)CCC1] | ++ |
| 189 | 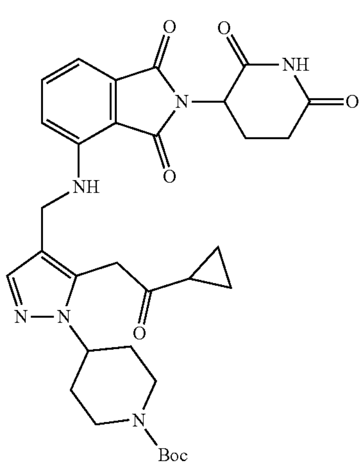 [SMILES: CC(C)(C)OC(=O)N1CCC(n2ncc(CNc3cccc4c3C(=O)N(C3CCC(=O)NC3=O)C4=O)c2CC(=O)C2CC2)CC1] | ++ |

TABLE 2-continued
| Compound # | Structure | GI50 |
|---|---|---|
| 190 | 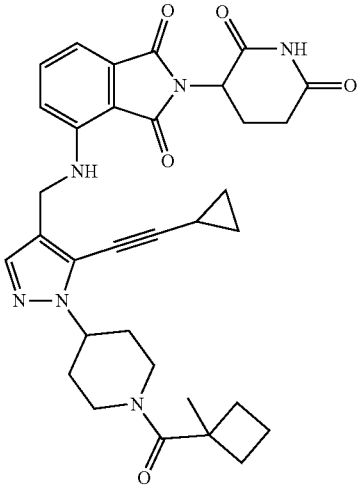 [SMILES: CC1(C(=O)N2CCC(n3ncc(CNc4cccc5c4C(=O)N(C4CCC(=O)NC4=O)C5=O)c3C#CC3CC3)CC2)CCC1] | ++ |
| 191 | 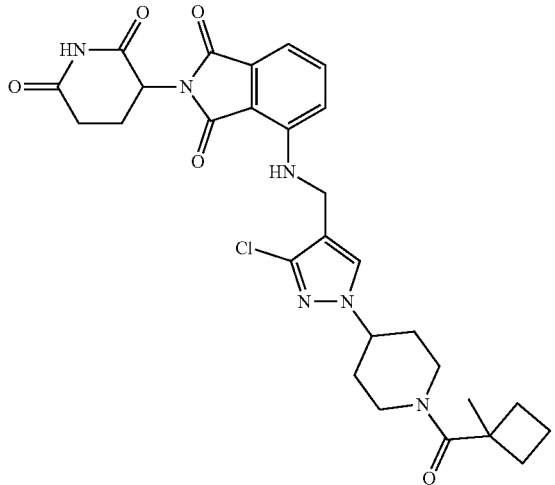 [SMILES: CC1(C(=O)N2CCC(n3cc(CNc4cccc5c4C(=O)N(C4CCC(=O)NC4=O)C5=O)c(Cl)n3)CC2)CCC1] | +++ |
| 192 | 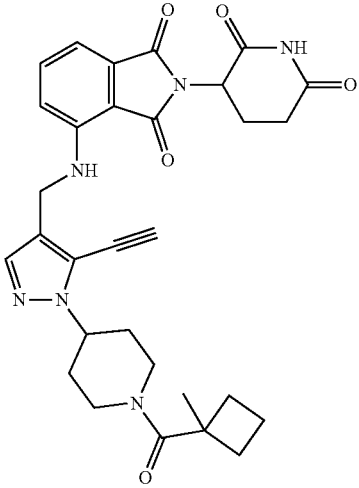 [SMILES: C#Cc1c(CNc2cccc3c2C(=O)N(C2CCC(=O)NC2=O)C3=O)cnn1C1CCN(C(=O)C2(C)CCC2)CC1] | ++ |

TABLE 2-continued
| Compound # | Structure | GI50 |
|---|---|---|
| 193 | 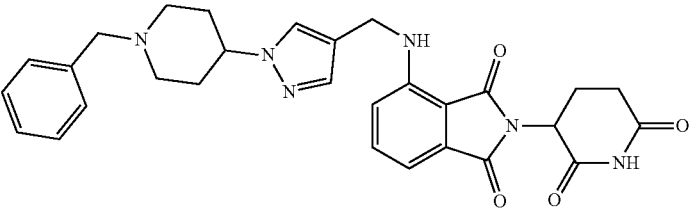 [SMILES: O=C1CCC(N2C(=O)c3cccc(NCc4cnn(C5CCN(Cc6ccccc6)CC5)c4)c3C2=O)C(=O)N1] | ND |
| 194 | 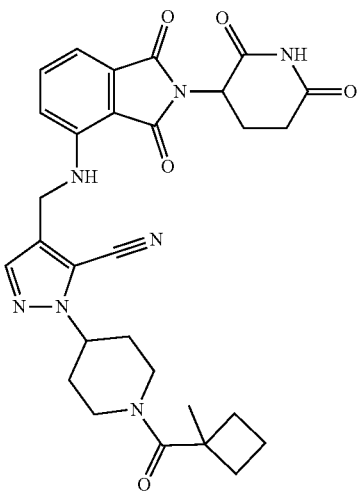 [SMILES: CC1(C(=O)N2CCC(n3ncc(CNc4cccc5c4C(=O)N(C4CCC(=O)NC4=O)C5=O)c3C#N)CC2)CCC1] | ++ |
| 195 | 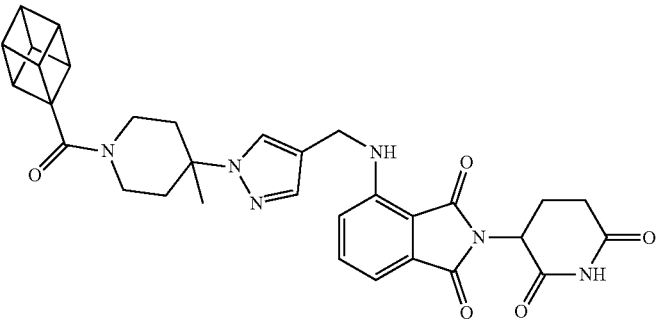 [SMILES: CC1(n2cc(CNc3cccc4c3C(=O)N(C3CCC(=O)NC3=O)C4=O)cn2)CCN(C(=O)C23C4C5C6C4C2C6C53)CC1] | ND |
| 196 | 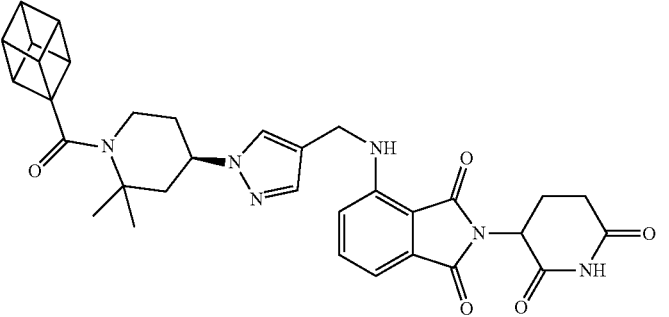 [SMILES: CC1(C)C[C@H](n2cc(CNc3cccc4c3C(=O)N(C3CCC(=O)NC3=O)C4=O)cn2)CCN1C(=O)C12C3C4C5C3C1C5C42] | +++ |

TABLE 2-continued

| Compound # | Structure | GI50 |
|---|---|---|
| 197 | 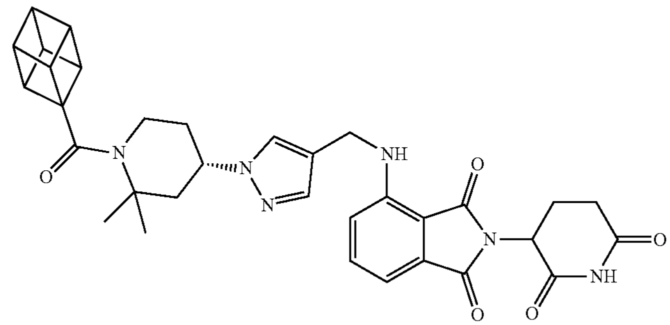 [SMILES: CC1(C)C[C@@H](n2cc(CNc3cccc4c3C(=O)N(C3CCC(=O)NC3=O)C4=O)cn2)CCN1C(=O)C12C3C4C5C3C1C5C42] | ++ |
| 198 | 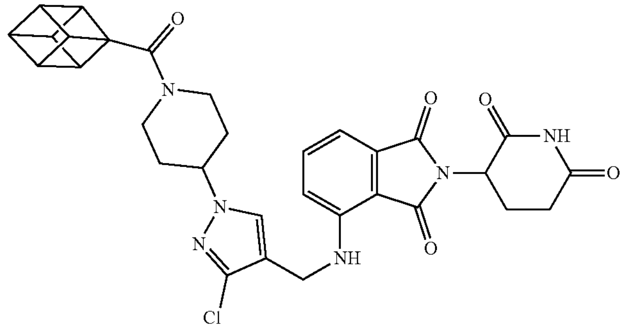 [SMILES: O=C1CCC(N2C(=O)c3cccc(NCc4cn(C5CCN(C(=O)C67C8C9C%10C8C6C%10C97)CC5)nc4Cl)c3C2=O)C(=O)N1] | ND |
| 199 | 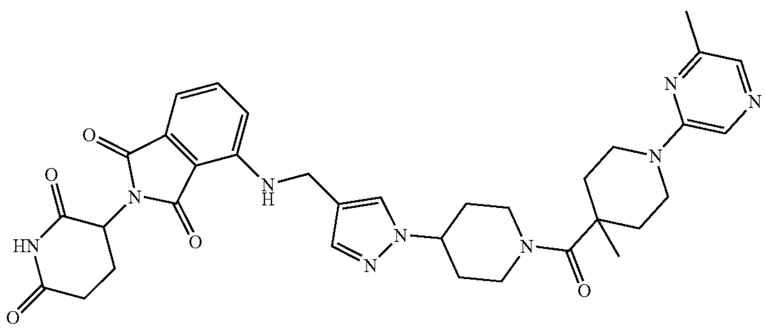 [SMILES: Cc1cncc(N2CCC(C)(C(=O)N3CCC(n4cc(CNc5cccc6c5C(=O)N(C5CCC(=O)NC5=O)C6=O)cn4)CC3)CC2)n1] | ND |
| 200 | 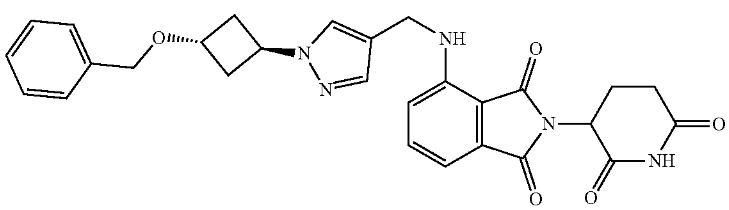 [SMILES: O=C1CCC(N2C(=O)c3cccc(NCc4cnn([C@H]5C[C@H](OCc6ccccc6)C5)c4)c3C2=O)C(=O)N1] | ND |
| 201 | 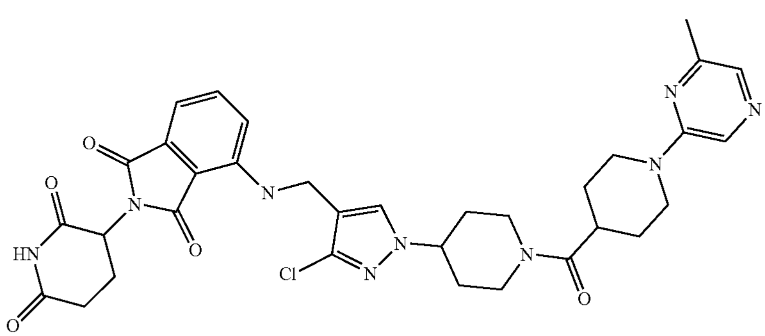 [SMILES: Cc1cncc(N2CCC(C(=O)N3CCC(n4cc(CNc5cccc6c5C(=O)N(C5CCC(=O)NC5=O)C6=O)c(Cl)n4)CC3)CC2)n1] | ND |

TABLE 2-continued

| Compound # | Structure | GI50 |
|---|---|---|
| 202 | 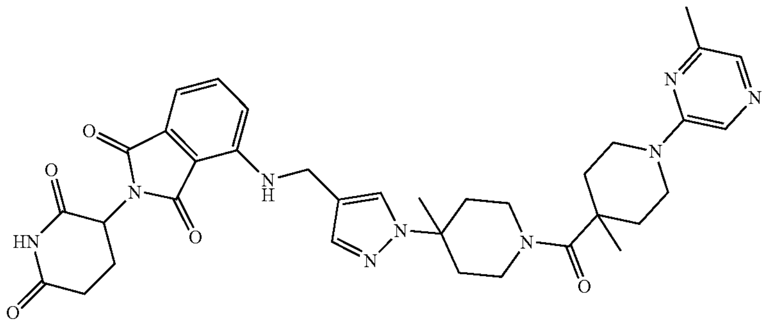 [SMILES: Cc1cncc(N2CCC(C)(C(=O)N3CCC(C)(n4cc(CNc5cccc6c5C(=O)N(C5CCC(=O)NC5=O)C6=O)cn4)CC3)CC2)n1] | ND |
| 203 | 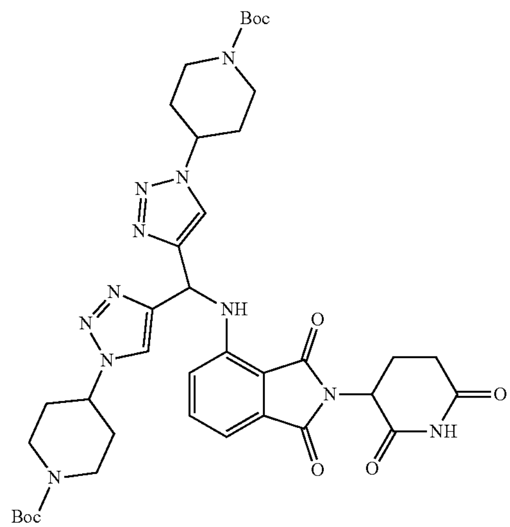 [SMILES: CC(C)(C)OC(=O)N1CCC(n2cc(C(Nc3cccc4c3C(=O)N(C3CCC(=O)NC3=O)C4=O)c3cn(C4CCN(C(=O)OC(C)(C)C)CC4)nn3)nn2)CC1] | + |
| 204 | 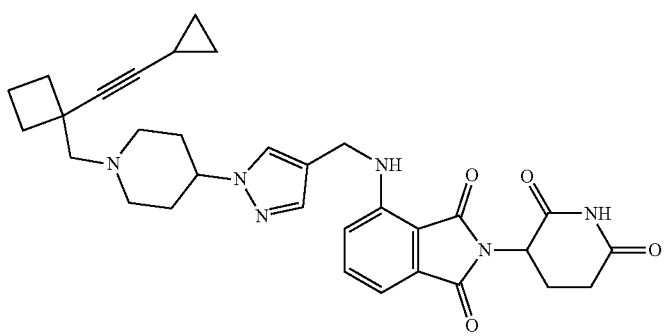 [SMILES: O=C1CCC(N2C(=O)c3cccc(NCc4cnn(C5CCN(CC6(C#CC7CC7)CCC6)CC5)c4)c3C2=O)C(=O)N1] | ++ |
| 205 | 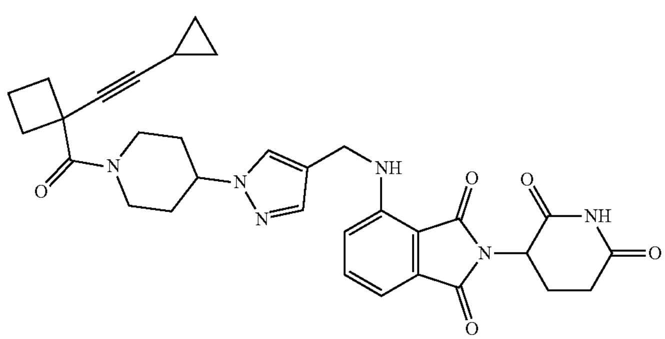 [SMILES: O=C1CCC(N2C(=O)c3cccc(NCc4cnn(C5CCN(C(=O)C6(C#CC7CC7)CCC6)CC5)c4)c3C2=O)C(=O)N1] | ++ |

TABLE 2-continued

| Compound # | Structure | GI50 |
|---|---|---|
| 206 | 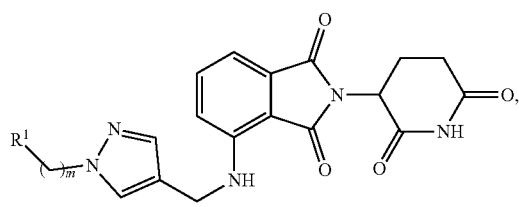 | ND |
| 207 | 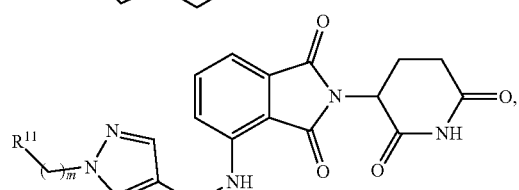 | ++ |

In the above table:
+++ is <1 nM;
++ is <100 nM; + is >100 nM;
ND is not determined.

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the claims.

We claim:

1. A compound selected from the following Formulas:

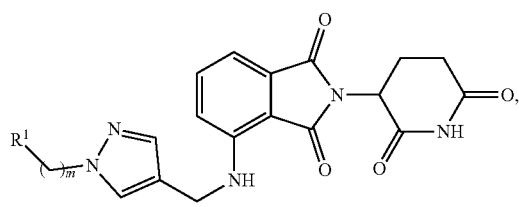

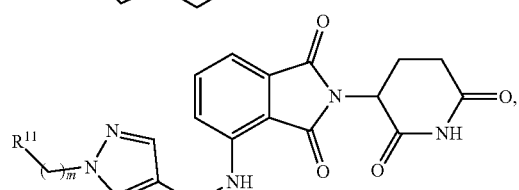

-continued

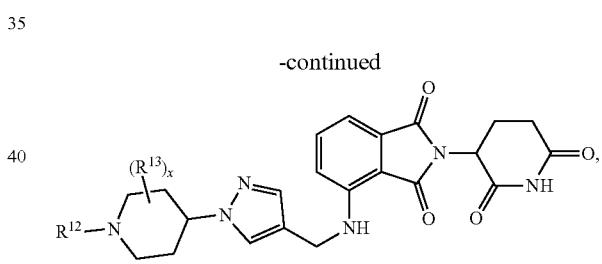

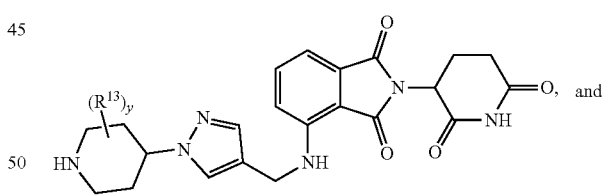

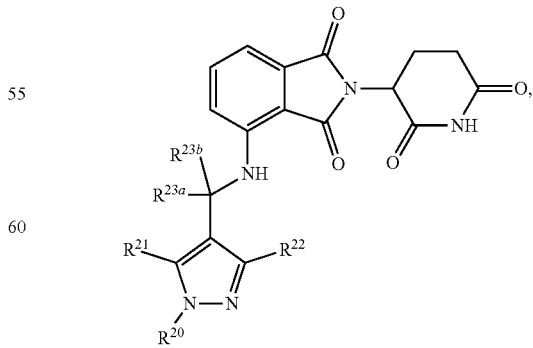

or a pharmaceutically acceptable salt thereof;

wherein:
R$^1$ is selected from:
  a. haloalkyl and alkyl; either of which is optionally substituted with 1, 2, or 3 substituents independently selected from aryl, cycloalkyl, heteroaryl, —SO$_2$R$^5$, —NR$^2$—C(O)—R$^3$, —C(O)OR$^4$, and —C(O)—R$^3$; wherein when the haloalkyl or alkyl group has two or more carbons it can additionally be optionally substituted with 1, 2, 3, or 4 substituents independently selected from —OC(O)—R$^3$, —NR$^4$R$^4$, and —OR$^4$, wherein these additional substituents are not on the carbon alpha to the pyrazole;
  b. cycloalkyl and aryl; either of which is optionally substituted with 1, 2, 3, or 4 substituents independently selected from alkyl, alkenyl, alkynyl, halogen, cyano, heteroaryl, aryl, cycloalkyl, heterocycle, —NR$^2$R$^2$, —OR$^2$, —NR$^2$—C(O)—R$^3$, —O—C(O)—R$^3$, and —C(O)—R$^3$;
  c. heteroaryl optionally substituted with 1, 2, 3, or 4 substituents independently selected from alkyl, alkenyl, halogen, cyano, heteroaryl, aryl, cycloalkyl, —NR$^4$R$^4$, —OR$^4$, —NR$^2$—C(O)—R$^3$, —O—C(O)—R$^3$, and —C(O)—R$^3$; wherein the heteroaryl group is only substituted such that no N—O or N—N bonds are formed;
  d. heterocycle substituted with 1, 2, 3, or 4 substituents independently selected from alkyl, alkenyl, alkynyl, halogen, cyano, heteroaryl, aryl, cycloalkyl, heterocycle, —NR$^2$R$^2$, —OR$^2$, —NR$^2$—C(O)—R$^3$, —O—C(O)—R$^3$, —C(O)—R$^3$, —SO$_2$R$^5$, —C(O)—R$^5$, and R$^5$; wherein the heterocycle group is only substituted such that no N—O or N—N bonds are formed;
  e. (CR$^4$R$^2$)—(CR$^2$R$^2$)$_o$-heterocycle optionally substituted with 1, 2, 3, or 4 substituents independently selected from alkyl, alkenyl, alkynyl, halogen, cyano, heteroaryl, aryl, cycloalkyl, heterocycle, —NR$^2$R$^2$, —OR$^2$, —NR$^2$—C(O)—R$^3$, —O—C(O)—R$^3$, —C(O)—R$^3$, —SO$_2$R$^5$, —C(O)—R$^5$, and R$^5$; wherein the heterocycle group is only substituted such that no N—O or N—N bonds are formed; and
  f. bicyclic heterocycle or multicyclic heterocycle optionally substituted with 1, 2, 3, or 4 substituents independently selected from alkyl, alkenyl, alkynyl, halogen, cyano, heteroaryl, aryl, cycloalkyl, heterocycle, —NR$^2$R$^2$, —OR$^2$, —NR$^2$—C(O)—R$^3$, —O—C(O)—R$^3$, —C(O)—R$^3$, —SO$_2$R$^5$, —C(O)—R$^5$, and R$^5$; wherein the bicyclic heterocycle group is only substituted such that no N—O or N—N bonds are formed;
R$^2$ at each instance is independently selected from hydrogen, alkyl, alkenyl, alkynyl, aryl, heterocycle, heteroaryl, and cycloalkyl;
R$^3$ is selected from hydrogen, alkyl, alkenyl, alkynyl, haloalkyl, cycloalkyl, aryl, heterocycle, heteroaryl, —NR$^2$R$^2$, and —OR$^4$;
R$^4$ at each instance is independently selected from hydrogen, alkyl, alkenyl, cycloalkyl, haloalkyl, aryl, heterocycle, heteroaryl, and alkynyl;
R$^5$ is selected from hydrogen, alkyl, alkenyl, alkynyl, haloalkyl, cycloalkyl, heteroaryl, heterocycle, aryl, —O-cycloalkyl, —O-aryl, —O-heteroaryl, —O-heterocycle, —O-alkyl, —NR$^2$— cycloalkyl, —NR$^2$-aryl, —NR$^2$-heteroaryl, —NR$^2$-heterocycle, —NR$^2$-alkyl, —CH$_2$-cycloalkyl, —CH$_2$-aryl, —CH$_2$-heteroaryl, —CH$_2$-heterocycle, —OR$^2$, and —NR$^2$R$^2$; each of which except for hydrogen is optionally substituted with 1, 2, 3, or 4 substituents independently selected from alkyl, alkenyl, alkynyl, haloalkyl, cycloalkyl, heterocycle, aryl, heteroaryl, cyano, halogen, —OR$^2$, and —NR$^2$R$^2$;
m and o are independently selected from 0, 1, 2, 3, 4, and 5;
x is 0, 1, 2, 3, or 4;
n is 0, 1, 2, 3, or 4;
y is 1, 2, 3, 4, 5, or 6;
R$^{11}$ is selected from
  a. haloalkyl and alkyl; each of which is optionally substituted with 1, 2, 3, or 4 substituents independently selected from —NR$^2$—C(O)—R$^3$, —O—C(O)—R$^3$, and —C(O)—R$^3$; wherein when the haloalkyl or alkyl group has two or more carbons it can additionally be optionally substituted with 1, 2, 3, or 4 substituents independently selected from —OC(O)—R$^3$, —NR$^4$R$^4$, and —OR$^4$, wherein these additional substituents are not on the carbon alpha to the pyrazole;
  b. cycloalkyl, heteroaryl, and aryl; each of which is optionally substituted with 1, 2, 3, or 4 substituents independently selected from alkyl, alkenyl, F, Cl, Br, I, cyano, heteroaryl, aryl, cycloalkyl, —NR$^4$R$^4$, —OR$^4$, —NR$^2$—C(O)—R$^3$, —O—C(O)—R$^3$, and —C(O)—R$^3$;
  c. (CR$^2$R$^2$)$_n$-heterocycle substituted with 1, 2, 3, or 4 substituents independently selected from alky, alkenyl, halogen, cyano, heteroaryl, aryl, cycloalkyl, —NR$^4$R$^4$, —OR$^4$, —NR$^2$—C(O)—R$^3$, —O—C(O)—R$^3$, —C(O)—R$^3$, and —SO$_2$R$^5$; wherein the heterocycle group is only substituted such that no N—O or N—N bonds are formed; and
  d. bicyclic heterocycle optionally substituted with 1, 2, 3, or 4 substituents independently selected from alkyl, alkenyl, alkynyl, halogen, cyano, heteroaryl, aryl, cycloalkyl, heterocycle, —NR$^2$R$^2$, —OR$^2$, —NR$^2$—C(O)—R$^3$, —O—C(O)—R$^3$, —C(O)—R$^3$, —SO$_2$R$^5$, —C(O)—R$^5$, and R$^5$; wherein the bicyclic heterocycle group is only substituted such that no N—O or N—N bonds are formed;
R$^{12}$ is selected from alkyl, haloalkyl, alkenyl, alkynyl, heteroaryl, aryl, cycloalkyl, heterocycle, —C(O)—R$^3$, —SO$_2$R$^5$, and —C(O)—R$^5$;
R$^{13}$ at each instance is independently selected from alkyl, alkenyl, alkynyl, halogen, cyano, heteroaryl, aryl, cycloalkyl, heterocycle, —NR$^2$R$^2$, —OR$^2$, —NR$^2$—C(O)—R$^3$, —O—C(O)—R$^3$, —C(O)—R$^3$, —SO$_2$R$^5$, —C(O)—R$^5$, and R$^5$; or two R$^{13}$s may together with the carbon(s) to which they are attached be replaced with a spiro or fused, heterocycle or carbocycle ring, or two R$^{13}$s may together with the carbon to which they are attached be replaced with an aryl ring;
R$^{20}$ is heterocycle substituted with 1, 2, 3, or 4 substituents independently selected from alkyl, alkenyl, alkynyl, halogen, cyano, heteroaryl, aryl, cycloalkyl, heterocycle, —NR$^2$R$^2$, —OR$^2$, —NR$^2$—C(O)—R$^{24}$, —O—C(O)—R$^{24}$, —C(O)—R$^{24}$, —SO$_2$R$^{24}$, and R$^{24}$; wherein the heterocycle group is only substituted such that no N—O or N—N bonds are formed;

$R^{21}$ and $R^{22}$ are independently selected from hydrogen, alkyl, cycloalkyl, alkenyl, alkynyl, —($C_2$-$C_6$alkenylene)-cycloalkyl, —($C_2$-$C_6$alkynylene)-cycloalkyl, halogen, and cyano;

$R^{23a}$ and $R^{23b}$ are independently selected from hydrogen, alkyl, cycloalkyl, and —($C_1$-$C_6$alkylene)-$NR^2R^2$;

or $R^{21}$ and $R^{23a}$ are joined together with the carbons to which they are attached to form a 5- to 6-membered carbocyclic ring;

or $R^{22}$ and $R^{23a}$ are joined together with the carbons to which they are attached to form a 5- to 6-membered carbocyclic ring;

$R^{24}$ is selected at each occurrence from alkyl, alkenyl, alkynyl, haloalkyl, cycloalkyl, heteroaryl, heterocycle, aryl, —O-cycloalkyl, —O-aryl, —O-heteroaryl, —O-heterocycle, —O-alkyl, —$NR^2$-cycloalkyl, —$NR^2$-aryl, —$NR^2$-heteroaryl, —$NR^2$-heterocycle, —$NR^2$-alkyl, —$CH_2$-cycloalkyl, —$CH_2$-aryl, —$CH_2$-heteroaryl, —$CH_2$-heterocycle, —$OR^2$, and —$NR^2R^2$; wherein each $R^{24}$ is optionally substituted with 1, 2, 3, or 4 groups independently selected from $R^{25}$; and $R^{25}$ is selected at each occurrence from: alkyl; alkenyl; alkynyl; haloalkyl; cycloalkyl; heterocycle; aryl optionally substituted with 1, 2, or 4 groups independently selected from alkyl, alkoxy, or halogen; heteroaryl optionally substituted with 1, 2, or 3 groups independently selected from alkyl, alkoxy, or halogen; —$CH_2$-cycloalkyl; —$CH_2$-aryl optionally substituted with 1, 2, or 3 groups independently selected from alkyl, alkoxy, or halogen; —$CH_2$-heteroaryl optionally substituted with 1, 2, or 3 groups independently selected from alkyl, alkoxy, or halogen; —$CH_2$-heterocycle; —$CH_2$—NH—C(O)$CH_3$; —C(O)-cycloalkyl; —C(O)-aryl optionally substituted with 1, 2, or 3 groups independently selected from alkyl, alkoxy, or halogen; —C(O)-heteroaryl optionally substituted with 1, 2, or 3 groups independently selected from alkyl, alkoxy, or halogen; —C(O)-heterocycle; —C(O)-alkyl; —($C_2$-$C_6$alkenylene)-aryl; —($C_2$-$C_6$alkynylene)-aryl; —($C_2$-$C_6$alkenylene)-cycloalkyl; —($C_2$-$C_6$alkynylene)-cycloalkyl; —C(O)—($C_1$-$C_6$alkylene)-O-alkyl; —C(O)—($C_1$-$C_6$alkylene)-aryl; cyano; halogen; —$OR^2$; and —$NR^2R^2$; or two $R^{25}$ groups may join together with the atoms to which they are attached to form a 3- to 7-membered carbocyclic ring.

2. The compound of claim 1, wherein m is 0.

3. The compound of claim 1, wherein $R^1$ is heterocycle substituted with 1, 2, 3, or 4 substituents independently selected from alkyl, alkenyl, alkynyl, halogen, cyano, heteroaryl, aryl, cycloalkyl, heterocycle, —$NR^2R^2$, —$OR^2$, —$NR^2$—C(O)—$R^3$, —O—C(O)—$R^3$, —C(O)—$R^3$, —$SO_2R^5$, —C(O)—$R^5$, and $R^5$; and wherein the heterocycle group is only substituted such that no N—O or N—N bonds are formed.

4. The compound of claim 1, wherein the compound is of formula:

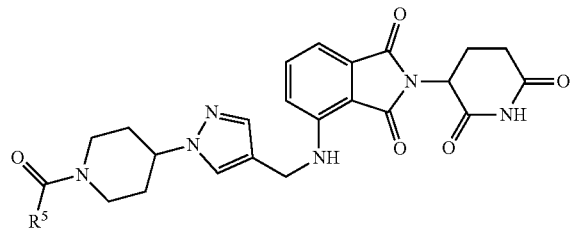

or a pharmaceutically acceptable salt thereof.

5. The compound of claim 1, wherein the compound is of formula:

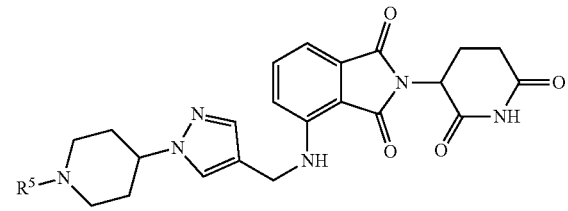

or a pharmaceutically acceptable salt thereof.

6. The compound of claim 1, wherein the compound is of formula:

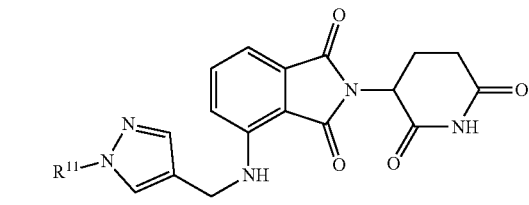

or a pharmaceutically acceptable salt thereof.

7. The compound of claim 1, wherein the compound is selected from:

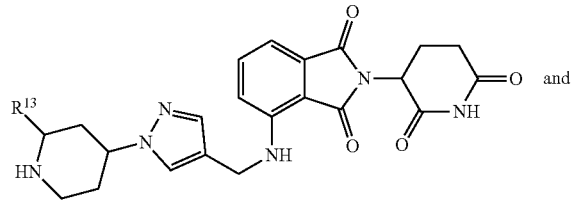

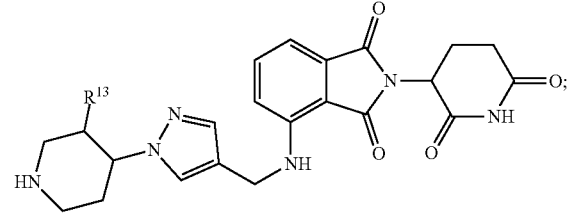

or a pharmaceutically acceptable salt thereof.

8. The compound of claim 1, wherein $R^5$ is alkyl optionally substituted with 1, 2, 3, or 4 substituents independently selected from alkyl, alkenyl, alkynyl, haloalkyl, cycloalkyl, heterocycle, aryl, heteroaryl, cyano, halogen, —$OR^2$, and —$NR^2R^2$.

9. The compound of claim 1, wherein $R^5$ is cycloalkyl optionally substituted with 1, 2, 3, or 4 substituents independently selected from alkyl, alkenyl, alkynyl, haloalkyl, cycloalkyl, heterocycle, aryl, heteroaryl, cyano, halogen, —$OR^2$, and —$NR^2R^2$.

10. The compound of claim 1, wherein $R^5$ is —$CH_2$-cycloalkyl optionally substituted with 1, 2, 3, or 4 substituents independently selected from alkyl, alkenyl, alkynyl, haloalkyl, cycloalkyl, heterocycle, aryl, heteroaryl, cyano, halogen, —$OR^2$, and —$NR^2R^2$.

11. The compound of claim 1, wherein $R^5$ is heterocycle optionally substituted with 1, 2, 3, or 4 substituents independently selected from alkyl, alkenyl, alkynyl, haloalkyl, cycloalkyl, heterocycle, aryl, heteroaryl, cyano, halogen, —$OR^2$, and —$NR^2R^2$.

12. The compound of claim 1, wherein $R^5$ is —$CH_2$-heterocycle optionally substituted with 1, 2, 3, or 4 substituents independently selected from alkyl, alkenyl, alkynyl, haloalkyl, cycloalkyl, heterocycle, aryl, heteroaryl, cyano, halogen, —$OR^2$, and —$NR^2R^2$.

13. The compound of claim 1, wherein $R^5$ is —$OR^2$.

14. The compound of claim 1, wherein x is 0, 1, or 2.

15. The compound of claim 1, wherein $R^{13}$ is alkyl.

16. A compound selected from:

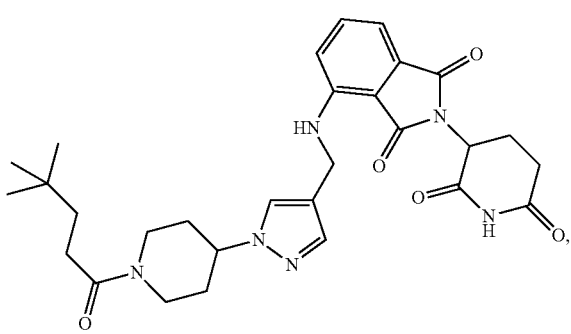

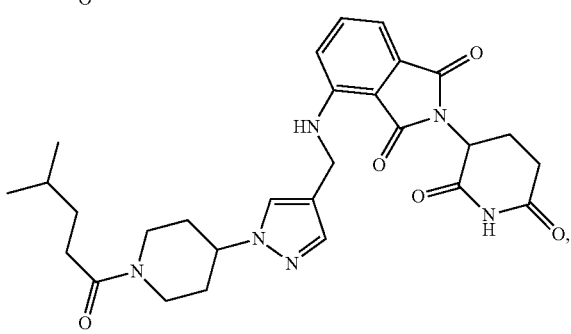

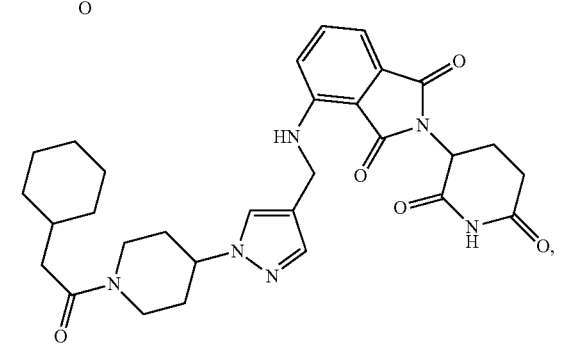

-continued

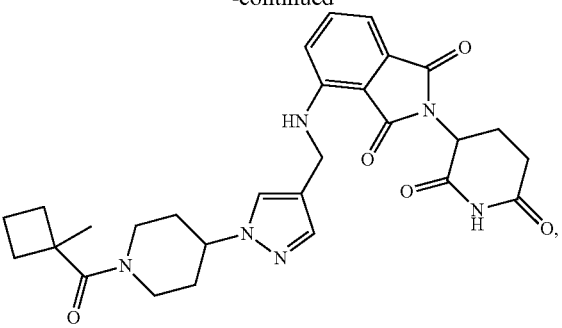

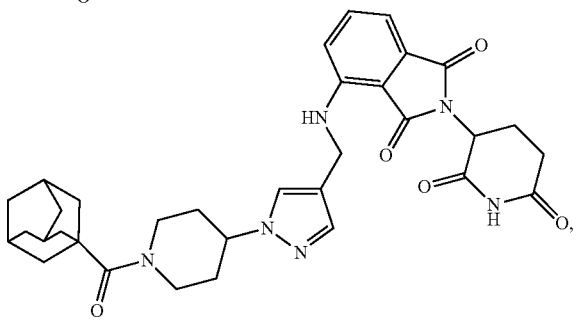

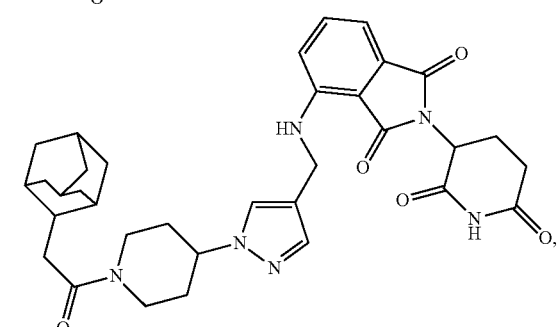

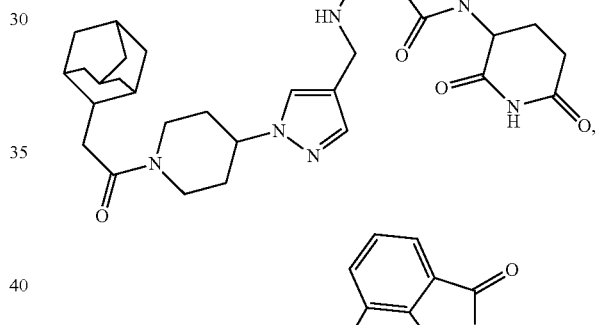

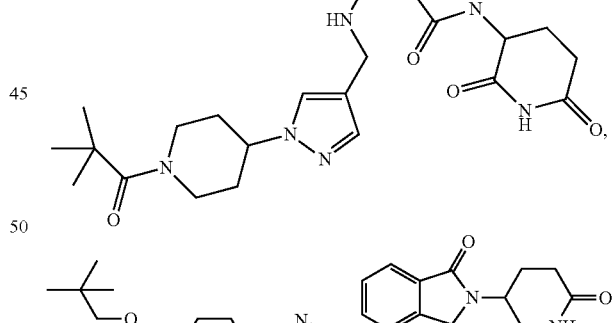

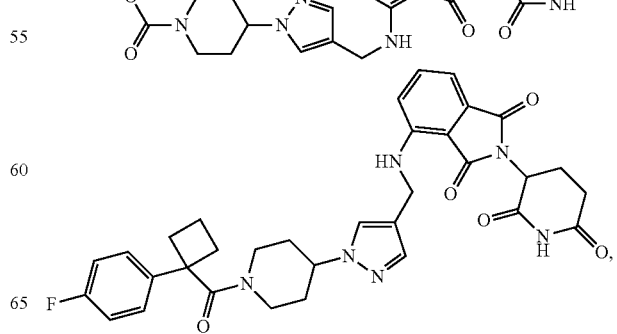

-continued
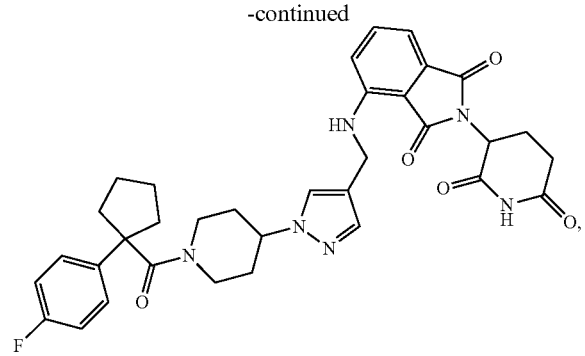
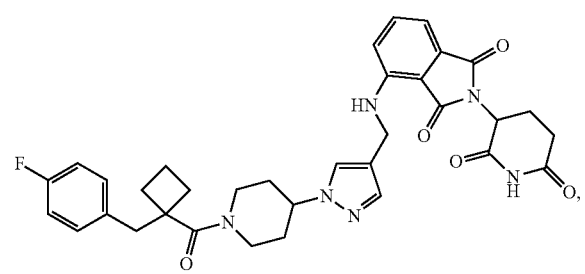
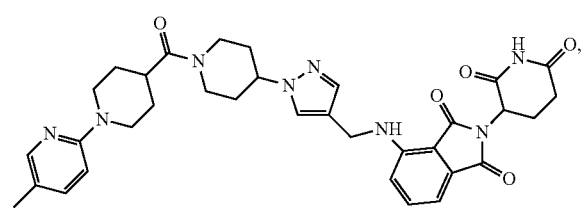
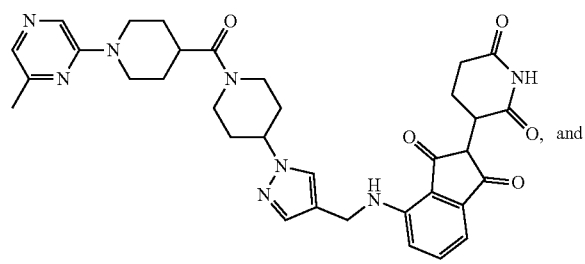
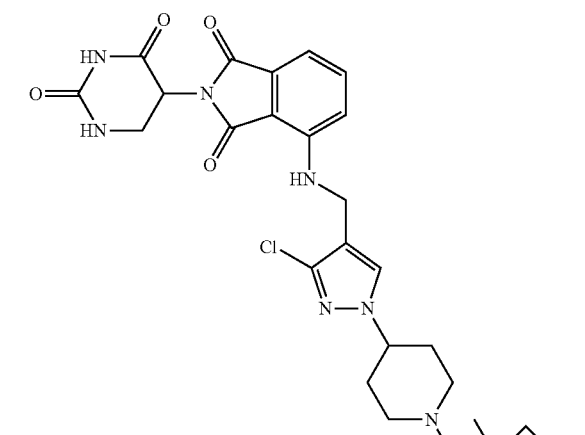
or a pharmaceutically acceptable salt thereof.
17. A compound of claim 1 selected from:
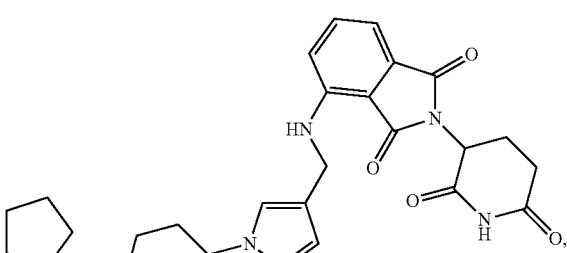
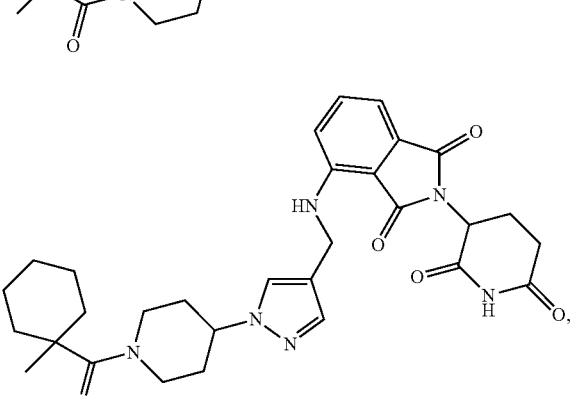
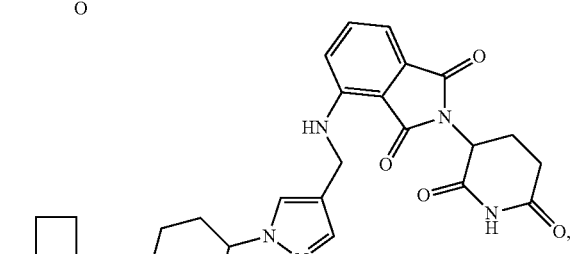
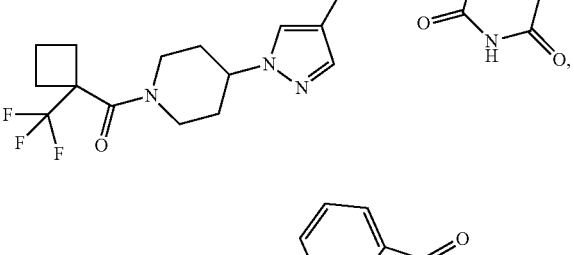
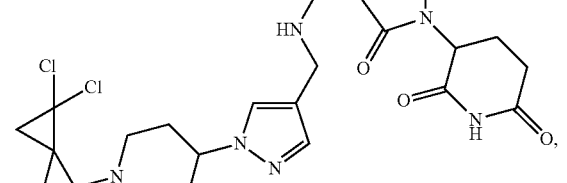
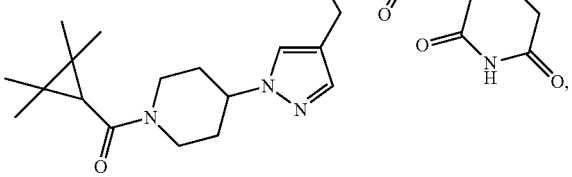

677
-continued
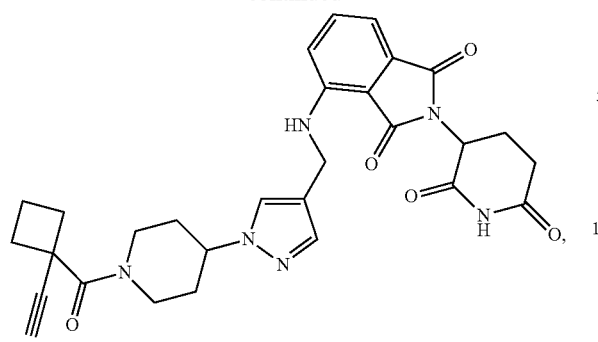
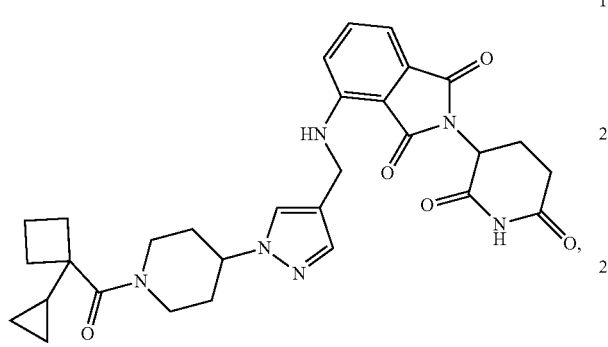
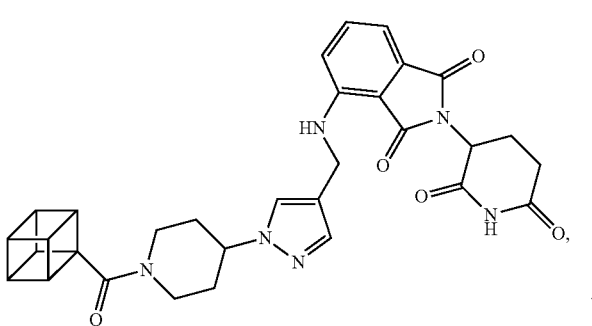
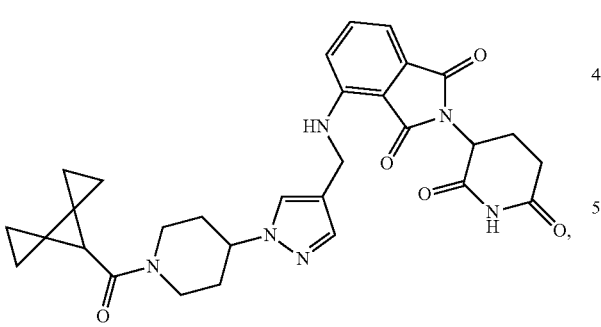
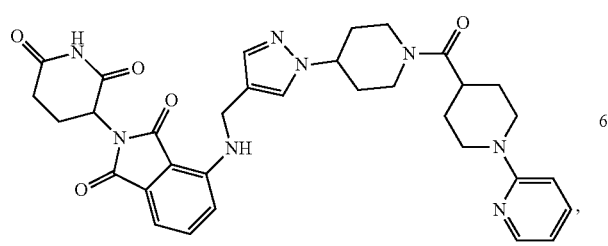
678
-continued
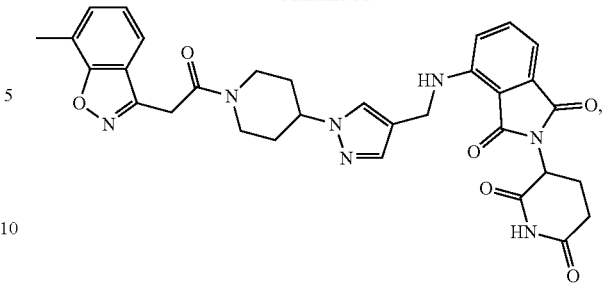
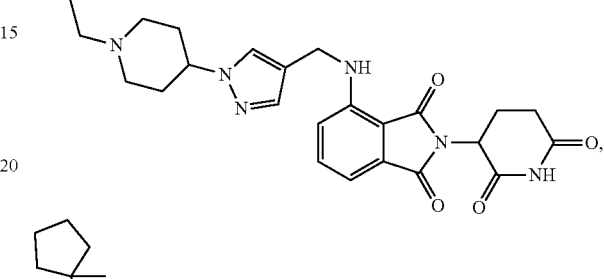
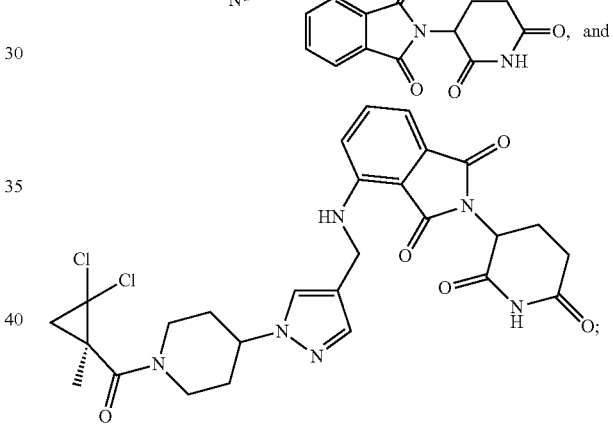
or a pharmaceutically acceptable salt thereof.
18. A pharmaceutical composition comprising a compound of claim 1 with a pharmaceutically acceptable carrier or diluent.
19. A compound of claim 1 of formula:
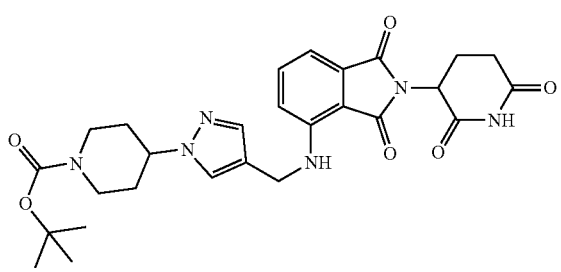 [SMILES: CC(C)(C)OC(=O)N1CCC(n2cc(CNc3cccc4c3C(=O)N(C3CCC(=O)NC3=O)C4=O)cn2)CC1]
or a pharmaceutically acceptable salt thereof.
* * * * *